US012570610B2

(12) United States Patent
Ackerman et al.

(10) Patent No.: US 12,570,610 B2
(45) **Date of Patent: *Mar. 10, 2026**

(54) MACROMOLECULE-SUPPORTED AMINOBENZAZEPINE COMPOUNDS

(71) Applicant: Bolt Biotherapeutics, Inc., Redwood City, CA (US)

(72) Inventors: Shelley Erin Ackerman, Redwood City, CA (US); Michael N. Alonso, Redwood City, CA (US); Romas Kudirka, Redwood City, CA (US); Arthur Lee, Redwood City, CA (US); Brian Safina, Redwood City, CA (US); Matthew Zhou, Redwood City, CA (US)

(73) Assignee: BOLT BIOTHERAPEUTICS, INC., Redwood City, CA (US)

( * ) Notice: Subject to any disclaimer, the term of this patent is extended or adjusted under 35 U.S.C. 154(b) by 1065 days.

This patent is subject to a terminal disclaimer.

(21) Appl. No.: 17/618,729

(22) PCT Filed: Jun. 12, 2020

(86) PCT No.: PCT/US2020/037423

§ 371 (c)(1),
(2) Date: Dec. 13, 2021

(87) PCT Pub. No.: WO2020/252254

PCT Pub. Date: Dec. 17, 2020

(65) Prior Publication Data

US 2022/0315537 A1 Oct. 6, 2022

Related U.S. Application Data

(60) Provisional application No. 62/963,884, filed on Jan. 21, 2020, provisional application No. 62/861,139, filed on Jun. 13, 2019, provisional application No. 62/861,117, filed on Jun. 13, 2019.

(51) Int. Cl.

| | |
|---|---|
| ***C07D 223/16*** | (2006.01) |
| ***C07D 403/10*** | (2006.01) |
| ***C07D 403/12*** | (2006.01) |
| ***C07H 15/203*** | (2006.01) |

(52) U.S. Cl.

CPC ......... *C07D 223/16* (2013.01); *C07D 403/10* (2013.01); *C07D 403/12* (2013.01); *C07H 15/203* (2013.01)

(58) Field of Classification Search

CPC .. C07D 223/16; C07D 403/10; C07D 403/12; C07D 403/02; C07H 15/203; A61K 47/60

See application file for complete search history.

(56) References Cited

U.S. PATENT DOCUMENTS

| | | | | |
|---|---|---|---|---|
| 2014/0142086 A1* | 5/2014 | Howbert | ................. | A61P 31/00 540/593 |
| 2014/0234376 A1* | 8/2014 | Howbert | ................. | A61P 11/06 424/277.1 |

FOREIGN PATENT DOCUMENTS

| | | | |
|---|---|---|---|
| JP | 2017538723 | A | 12/2017 |
| JP | 2018508535 | A | 3/2018 |
| JP | 2018532803 | A | 11/2018 |
| WO | 2016096778 | A1 | 6/2016 |
| WO | 2016142250 | A1 | 9/2016 |
| WO | 2017079283 | A1 | 5/2017 |
| WO | 2017202703 | A1 | 11/2017 |
| WO | 2017202704 | A1 | 11/2017 |
| WO | 2017216054 | A1 | 12/2017 |
| WO | WO 2018/140831 | A2 | 8/2018 |
| WO | WO 2018/170179 | A1 | 9/2018 |
| WO | WO 2019/084060 | A1 | 5/2019 |
| WO | WO 2019/118884 | A1 | 6/2019 |
| WO | WO 2020/056008 | A1 | 3/2020 |
| WO | WO 2020/056194 | A1 | 3/2020 |
| WO | WO 2020/056198 | A2 | 3/2020 |

OTHER PUBLICATIONS

Wiktorowska-Owczarek, A; et al. "PUFAs: Structures, Metabolism and Functions" 2015, Advanced Clinical and Experimental Medicine, vol. 24, pp. 931-941. (Year: 2015).*
Du, X.; et al. "Advances in Base-Metal-Catalyzed Alkene Hydrosilylation" 2017, ACS Catalysis, vol. 7, pp. 1227-1243. (Year: 2017).*
Hang, H. C.; et al. "Bioorthogonal Chemical Reporters for Analyzing Protein Lipidation and Lipid Trafficking" 2011, Accounts of Chemical Research, vol. 44, pp. 699-708. (Year: 2011).*
Roy, D.; et al. "Stimuli-Responsive Polymer-Antibody Conjugates via RAFT and Tetrafluorophenyl Active Ester Chemistry" 2013, ACS Macro Letters, vol. 2, pp. 132-136. (Year: 2013).*
European Patent Office, International Search Report for International Patent Application PCT/US2020/037423 (Sep. 29, 2020).
European Patent Office, Written Opinion for International Patent Application PCT/US2020/037423 (Sep. 29, 2020).

* cited by examiner

*Primary Examiner* — Eric Olson
*Assistant Examiner* — Benjamin M Brandsen
(74) *Attorney, Agent, or Firm* — Viksnins Harris Padys Malen LLP

(57) ABSTRACT

The application provides macromolecule-supported compounds of Formula I or III comprising a macromolecular support linked by conjugation to one or more aminobenzazepine derivatives. The application also provides aminobenzazepine derivative intermediate compositions of Formula II comprising a reactive functional group. Such intermediate compositions are suitable substrates for formation of the macromolecule-supported compounds through a linker or linking moiety. The application further provides compositions comprising the macromolecule-supported compounds, as well as methods of treating cancer with the macromolecule-supported compounds.

10 Claims, No Drawings

MACROMOLECULE-SUPPORTED AMINOBENZAZEPINE COMPOUNDS

CROSS-REFERENCE TO RELATED APPLICATIONS

This patent application is the U.S. national phase of International Patent Application PCT/US2020/037423, filed Jun. 12, 2020, which claims the benefit of U.S. Provisional Patent Application No. 62/861,117, filed Jun. 13, 2019, U.S. Provisional Patent Application No. 62/861,139, filed Jun. 13, 2019, and U.S. Provisional Patent Application No. 62/963,884, filed Jan. 21, 2020, each of which is incorporated by reference in their entirety herein.

FIELD OF THE INVENTION

The invention relates generally to a macromolecule-supported compound comprising a macromolecular support conjugated to one or more aminobenzazepine molecules.

BACKGROUND OF THE INVENTION

New conjugates and compositions are needed for diagnostic assays, pharmacokinetic detection, antibody generation, and treatment of disease (e.g., cancer). The conjugates and compositions can be used directly in methods for the delivery of immune adjuvants to reach inaccessible tumors and/or the development of other immunoconjugates to expand treatment options for cancer patients and other subjects. The invention provides such immune adjuvants, conjugates, compositions, and methods.

SUMMARY OF THE INVENTION

The invention is generally directed to macromolecule-supported compounds comprising a macromolecular support linked by conjugation to one or more aminobenzazepine derivatives. The invention is further directed to aminobenzazepine derivative intermediate compositions comprising a reactive functional group. Such intermediate compositions are suitable substrates for formation of macromolecule-supported compounds wherein a macromolecular support may be covalently bound to one or more aminobenzazepine derivatives, through a linker or linking moiety. The invention is further directed to use of such macromolecule-supported compounds in the treatment of an illness, in particular cancer.

An aspect of the invention is a macromolecule-supported compound comprising a macromolecular support covalently attached to a linker which is covalently attached to one or more aminobenzazepine moieties.

Another aspect of the invention is an aminobenzazepine-linker compound.

Another aspect of the invention is a method for treating cancer comprising administering a therapeutically effective amount of a macromolecule-supported compound comprising a macromolecular support linked by conjugation to one or more aminobenzazepine moieties.

Another aspect of the invention is a use of a macromolecule-supported compound comprising a macromolecular support linked by conjugation to one or more aminobenzazepine moieties for treating cancer.

Another aspect of the invention is a use of a macromolecule-supported compound or a composition of macromolecule-supported compounds for a chemical assay for TLR engagement and/or activity (e.g., TLR7 and/or TLR8 engagement and/or activity).

Another aspect of the invention is a method of preparing a macromolecule-supported compound by conjugation of one or more aminobenzazepine moieties with a macromolecular support.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that the enumerated embodiments are not intended to limit the invention to those embodiments. On the contrary, the invention is intended to cover all alternatives, modifications, and equivalents, which may be included within the scope of the invention as defined by the claims.

One skilled in the art will recognize many methods and materials similar or equivalent to those described herein, which could be used in the practice of the present invention. The invention is in no way limited to the methods and materials described.

Definitions

As used herein, the phrase "macromolecule-supported compound" refers to a macromolecular support that is covalently bonded to a TLR agonist via a linking moiety.

As used herein, the terms "macromolecule support," "macromolecular support," or "macromolecule" can be used interchangeably to refer to an organic or inorganic structure having a chemical moiety on a surface of the structure that can be modified. In some embodiments, the macromolecular support is a resin, bead, probe, tag, well, plate, or any other surface that can be used for therapeutics, diagnostics, or chemical assays. The resin, bead, probe, tag, well, plate, or any other surface can be made of any suitable material so long as the material can be surface modified. In some embodiments, the macromolecular support is a chemical structure (e.g., a biological structure or an inorganic framework) having a molecular weight of at least about 200 Da (e.g., at least about 500 Da, at least about 1,000 Da, at least about 2,000 Da, at least about 5,000 Da, or at least about 10,000 Da). As a singular entity, the macromolecular support can be biologically active or biologically inactive relative to the TLR agonist described herein. However, when used in combination with the TLR agonist, the biological activity of the TLR agonist desirably is enhanced, for example, by providing a targeted effect (i.e., TLR activity), beneficial off-target effects (i.e., biological activity other than TLR activity), improved pharmacokinetic properties (e.g., half-life extension), enhanced biological delivery (e.g., tumor penetration), or additional biological stimulation, differentiation, up-regulation, and/or down-regulation. In certain embodiments, the biological effect of the macromolecular support and the TLR agonist is synergistic, i.e., greater than the sum of the biological activity of each of the macromolecular support and TLR agonist as singular entities. For example, the macromolecular support can be a biopolymer (e.g., a glycopolymer, a cellulosic polymer, etc.), a nanoparticle (e.g., a carbon nanotube, a quantum dot, a metal nanoparticle (e.g., silver, gold, titanium dioxide, silicon dioxide, zirconium dioxide, aluminum oxide, or ytterbium trifluoride), etc.), a lipid (e.g., lipid vesicles, micelles, liposomes, etc.), a carbohydrate (e.g., sugar, starch, cellulose, glycogen, etc.), a peptide (e.g., a polypeptide, a protein, a peptide mimetic, a glycopeptide, etc.), an antibody construct (e.g., antibody, an antibody-derivative (including Fc fusions, Fab fragments and scFvs), etc.), a nucleotide (e.g., RNA, DNA, antisense, siRNA, an aptamer, etc.), or any combination thereof. In some embodiments, the macromolecular support is a peptide, a nucleotide, a sugar, a lipid, or an antibody. In certain embodiments, the macromolecular support is an immune checkpoint inhibitor.

As used herein, the term "biopolymer" refers to any polymer produced by a living organism. For example, biopolymer can include peptides, polypeptides, proteins, oligonucleotides, nucleic acids (e.g., RNA and DNA) antibodies, polysaccharides, carbohydrates, sugars, peptide hormones, glycoproteins, glycogen, etc. Alternatively, a subunit of a biopolymer, such as a fatty acid, glucose, an amino acid, a succinate, a ribonucleotide, a ribonucleoside, a deoxyribonucleotide, and a deoxyribonucleoside can be used. Illustrative examples include antibodies or fragments thereof, extracellular matrix proteins such as laminin, fibronectin, growth factors, peptide hormones, and other polypeptides. In some embodiments, the biopolymer comprises suberin, melanin, lignin, or cellulose, or the biopolymer is glycosidic.

As used herein, the term "nanoparticle" refers to a support structure having a diameter of about 1 nm to about 100 nm. Exemplary structure types include nanopowders, nanoparticles, nanoclusters, nanorods, nanotubes, nanocrystals, nanospheres, nanochains, nanoreefs, nanoboxes, and quantum dots. The nanoparticles can contain an inorganic material (e.g., silver, gold, hydroxyapatite, clay, titanium dioxide, silicon dioxide, zirconium dioxide, carbon (graphite), diamond, aluminum oxide, ytterbium trifluoride, etc.) or an organic material (e.g., micelles, dendrimers, vesicles, liposomes, etc.). Alternatively, the nanoparticle can have a mixture of organic and inorganic material.

As used herein the term "lipid" refers to a hydrophobic or amphiphilic biomolecule. Exemplary lipids include fatty acids, waxes, sterols, fat-soluble vitamins, monoglycerides, diglycerides, triglycerides, phospholipids, sphingolipids, saccharolipids, polyketides, sterol lipids, glycerophospholipids, prenol lipids, etc. The lipid can exist in any suitable macromolecular structure, for example, a vesicle, a micelle, a liposome, etc.

As used herein, the term "carbohydrate" refers to any chemical entity comprising a monosaccharide, disaccharide, oligosaccharide, or polysaccharide. For example, the chemical entity can comprise a sugar (e.g., fructose, glucose, sucrose, lactose, galactose, etc.), starch, glycogen, or cellulose.

The terms "polypeptide," "peptide," and "protein" are used interchangeably herein to refer to a polymer of amino acid residues. The terms also apply to amino acid polymers in which one or more amino acid residues is an artificial chemical mimetic of a corresponding naturally occurring amino acid, as well as to naturally occurring amino acid polymers and non-naturally occurring amino acid polymers. The peptide can have any suitable posttranslational modification (e.g., phosphorylation, hydroxylation, sulfonation, palmitoylation, glycosylation, disulfide formation, galactosylation, fucosylation, etc.).

As used herein, the phrase "alternative protein scaffold" refers to a non-immunoglobulin derived protein or peptide. Such proteins and peptides are generally amenable to engineering and can be designed to confer monospecificity against a given antigen, bispecificity, or multispecificity. Engineering of an alternative protein scaffold can be conducted using several approaches. A loop grafting approach can be used where sequences of known specificity are grafted onto a variable loop of a scaffold. Sequence randomization and mutagenesis can be used to develop a library of mutants, which can be screened using various display platforms (e.g., phage display) to identify a novel binder. Site-specific mutagenesis can also be used as part of a similar approach. Alternative protein scaffolds exist in a variety of sizes, ranging from small peptides with minimal secondary structure to large proteins of similar size to a full-sized antibody. Examples of scaffolds include, but are not limited to, cystine knotted miniproteins (also known as knottins), cyclic cystine knotted miniproteins (also known as cyclotides), avimers, affibodies, the tenth type III domain of human fibronectin, DARPins (designed ankyrin repeats), and anticalins (also known as lipocalins). Naturally occurring ligands with known specificity can also be engineered to confer novel specificity against a given target. Examples of naturally occurring ligands that may be engineered include the EGF ligand and VEGF ligand. Engineered proteins can either be produced as monomeric proteins or as multimers, depending on the desired binding strategy and specificities. Protein engineering strategies can be used to fuse alternative protein scaffolds to Fc domains.

As used herein, the term "nucleotide" refers to any chemical entity comprising deoxyribonucleic acid ("DNA"), ribonucleic acid ("RNA"), a deoxyribonucleic acid derivative, or a ribonucleic acid derivative. Exemplary nucleotide-based structures include RNA, DNA, antisense oligonucleotides, siRNA, aptamers, etc. As used herein, the terms "deoxyribonucleic acid derivative" and "ribonucleic acid derivative" refer to DNA and RNA, respectively, that have been modified, such as, for example, by removing the phosphate backbone, methylating a hydroxyl group, or replacing a hydroxyl group with a thiol group.

As used herein, the phrase "antibody construct" refers to polypeptide comprising an antigen binding domain and an Fc domain. An antibody construct can comprise or be an antibody.

As used herein, the phrase "antigen binding domain" refers to a protein, or a portion of a protein, that specifically binds a specified antigen (e.g., a paratope), for example, that portion of an antigen-binding protein that contains the amino acid residues that interact with an antigen and confer on the antigen-binding protein its specificity and affinity for the antigen.

As used herein, the phrase "Fe domain" refers to the fragment crystallizable region, or the tail region of an antibody. The Fe domain interacts with Fc receptors on cell surfaces.

As used herein, the phrase "targeting binding domain" refers to a protein, or a portion of a protein, that specifically binds a second antigen that is distinct from the antigen bound by the antigen binding domain of an antibody construct. The targeting binding domain can be conjugated to the antibody construct at a C-terminal end of the Fe domain.

As used herein, the term "antibody" refers to a polypeptide comprising an antigen binding region (including the complementarity-determining regions (CDRs)) from an immunoglobulin gene or fragments thereof that specifically binds and recognizes an antigen. The recognized immunoglobulin genes include the kappa, lambda, alpha, gamma, delta, epsilon, and mu constant region genes, as well as numerous immunoglobulin variable region genes.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively. Light chains are classified as either kappa or lambda. Heavy chains are classified as gamma, mu, alpha, delta, or epsilon, which in turn define the immunoglobulin classes IgG, IgM, IgA, IgD, and IgE, respectively.

IgG antibodies are large molecules of about 150 kDa composed of four peptide chains. IgG antibodies contain two identical class γ heavy chains of about 50 kDa and two identical light chains of about 25 kDa, forming a tetrameric quaternary structure. The two heavy chains are linked to each other and to a light chain each by disulfide bonds. The resulting tetramer has two identical halves, which together form the Y-like shape. Each end of the fork contains an identical antigen binding site. There are four IgG subclasses (IgG1, 2, 3, and 4) in humans, named in order of their abundance in serum (IgG1 being the most abundant). Typically, the antigen-binding region of an antibody will be most critical in specificity and affinity of binding.

Dimeric IgA antibodies are about 320 kDa. IgA has two subclasses (IgA1 and IgA2) and can be produced as a monomeric as well as a dimeric form. The IgA dimeric form (secretory or sIgA) is the most abundant.

Antibodies can exist, for examples, as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region, thereby converting the $F(ab)'_2$ dimer into a Fab' monomer. The Fab' monomer is essentially Fab with part of the hinge region (see, e.g., *Fundamental Immunology* (Paul, editor, 7th edition, 2012)). While various antibody fragments are defined in terms of the digestion of an intact antibody, such fragments may be synthesized de novo either chemically or by using recombinant DNA methodology. Thus, the term antibody, as used herein, also includes antibody fragments produced by the modification of whole antibodies, synthesized de novo using recombinant DNA methodologies (e.g., single chain Fv), or identified using phage display libraries (see, e.g., McCafferty et al., *Nature,* 348: 552-554 (1990)).

The term "antibody" is used in the broadest sense and specifically encompasses monoclonal antibodies (including full length monoclonal antibodies), polyclonal antibodies, multispecific antibodies (e.g., bispecific antibodies), and antibody fragments so long as they exhibit the desired biological activity. "Antibody fragment" and all grammatical variants thereof as used herein are defined as a portion of an intact antibody comprising the antigen binding site or variable region of the intact antibody, wherein the portion is free of the constant heavy chain domains (i.e., CH2, CH3, and CH4, depending on antibody isotype) of the Fc region of the intact antibody. Examples of antibody fragments include Fab, Fab', Fab'-SH, $F(ab')_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules; (2) single chain polypeptides containing only one light chain variable domain, or a fragment thereof that contains the three CDRs of the light chain variable domain, without an associated heavy chain moiety; (3) single chain polypeptides containing only one heavy chain variable region, or a fragment thereof containing the three CDRs of the heavy chain variable region, without an associated light chain moiety; (4) nanobodies comprising single Ig domains from non-human species or other specific single-domain binding modules; and (5) multispecific or multivalent structures formed from antibody fragments. In an antibody fragment comprising one or more heavy chains, the heavy chain(s) can contain any constant domain sequence (e.g., CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

As used herein, the term "biosimilar" in reference to a biological product means that the biological product is highly similar to the reference product notwithstanding minor differences in clinically inactive components, and there are no clinically meaningful differences between the biological product and the reference product in terms of the safety, purity, and potency of the product.

As used herein, the term "epitope" means any antigenic determinant on an antigen to which binds the antigen-binding site, also referred to as the paratope, of an antibody. Epitopic determinants usually consist of chemically active surface groupings of molecules such as amino acids or sugar side chains and usually have specific three-dimensional structural characteristics, as well as specific charge characteristics.

The terms "polypeptide," "peptide," and "protein" are used interchangeably herein to refer to a polymer of amino acid residues. The terms also apply to amino acid polymers in which one or more amino acid residues are artificial chemical mimetics of a corresponding naturally occurring amino acids, as well as to naturally occurring amino acid polymers and non-naturally occurring amino acid polymer.

As used herein, the term "immune checkpoint inhibitors" refers to any modulator that inhibits the activity of the immune checkpoint molecule. Immune checkpoint inhibitors can include, but are not limited to, immune checkpoint molecule binding proteins, antibodies, antibody-derivatives (including Fc fusions, Fab fragments and scFvs), antisense oligonucleotides, siRNA, aptamers, peptides and peptide mimetics.

"Adjuvant" refers to a substance capable of eliciting an immune response in a subject exposed to the adjuvant. The phrase "adjuvant moiety" refers to an adjuvant that is covalently bonded to a macromolecular support, e.g., through a linker, as described herein. The adjuvant moiety can elicit the immune response while bonded to the macromolecular support or after cleavage (e.g., enzymatic cleavage) from the macromolecular support following administration of a macromolecule-supported compound to the subject.

The terms "Toll-like receptor" and "TLR" refer to any member of a family of highly-conserved mammalian proteins which recognizes pathogen-associated molecular patterns and acts as key signaling elements in innate immunity. TLR polypeptides share a characteristic structure that includes an extracellular domain that has leucine-rich repeats, a transmembrane domain, and an intracellular domain that is involved in TLR signaling.

The terms "Toll-like receptor 7" and "TLR7" refer to nucleic acids or polypeptides sharing at least about 70%, about 80%, about 90%, about 95%, about 96%, about 97%, about 98%, about 99%, or more sequence identity to a publicly-available TLR7 sequence, e.g., GenBank accession number AAZ99026 for human TLR7 polypeptide, or GenBank accession number AAK62676 for murine TLR7 polypeptide.

The terms "Toll-like receptor 8" and "TLR8" refer to nucleic acids or polypeptides sharing at least about 70%, about 80%, about 90%, about 95%, about 96%, about 97%, about 98%, about 99%, or more sequence identity to a publicly-available TLR7 sequence, e.g., GenBank accession number AAZ95441 for human TLR8 polypeptide, or GenBank accession number AAK62677 for murine TLR8 polypeptide.

A "TLR agonist" is a substance that binds, directly or indirectly, to a TLR (e.g., TLR7 and/or TLR8) to induce TLR signaling. Any detectable difference in TLR signaling can indicate that an agonist stimulates or activates a TLR. Signaling differences can be manifested, for example, as changes in the expression of target genes, in the phosphorylation of signal transduction components, in the intracellular localization of downstream elements such as nuclear factor-κB (NF-κB), in the association of certain components (such as TL-1 receptor associated kinase (IRAK)) with other proteins or intracellular structures, or in the biochemical activity of components such as kinases (such as mitogen-activated protein kinase (MAPK)).

"Amino acid" refers to any monomeric unit that can be incorporated into a peptide, polypeptide, or protein. Amino acids include naturally-occurring α-amino acids and their stereoisomers, as well as unnatural (non-naturally occurring) amino acids and their stereoisomers. "Stereoisomers" of a given amino acid refer to isomers having the same molecular formula and intramolecular bonds but different three-dimensional arrangements of bonds and atoms (e.g., an L-amino acid and the corresponding D-amino acid). The amino acids can be glycosylated (e.g., N-linked glycans, O-linked glycans, phosphoglycans, C-linked glycans, or glypication) or deglycosylated. Amino acids may be referred to herein by either the commonly known three letter symbols or by the one-letter symbols recommended by the IUPAC-IUB Biochemical Nomenclature Commission.

Naturally-occurring amino acids are those encoded by the genetic code, as well as those amino acids that are later modified, e.g., hydroxyproline, 7-carboxyglutamate, and O-phosphoserine. Naturally-occurring α-amino acids include, without limitation, D and L stereoisomers where they exist of alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof stereoisomers of naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Naturally-occurring amino acids include those formed in proteins by posttranslational modification, such as citrulline (Cit).

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" can be unnatural amino acids that have the same basic chemical structure as naturally-occurring amino acids (i.e., a carbon that is bonded to a hydrogen, a carboxyl group, an amino group) but have modified side-chain groups or modified peptide backbones, e.g., homoserine, norleucine, methionine sulfoxide, and methionine methyl sulfonium. "Amino acid mimetics" refer to chemical compounds that have a structure that is different from the general chemical structure of an amino acid, but that functions in a manner similar to a naturally-occurring amino acid.

"Linker" refers to a functional group that covalently bonds two or more moieties in a compound or material. For example, the linking moiety can serve to covalently bond an adjuvant moiety to a macromolecular support in a macromolecule-supported compound.

"Linking moiety" refers to a functional group that covalently bonds two or more moieties in a compound or material. For example, the linking moiety can serve to covalently bond an adjuvant moiety to a macromolecular support in a macromolecule-supported compound. Useful bonds for connecting linking moieties to proteins and other materials include, but are not limited to, amides, amines, esters, carbamates, ureas, thioethers, thiocarbamates, thiocarbonates, and thioureas.

"Divalent" refers to a chemical moiety that contains two points of attachment for linking two functional groups; polyvalent linking moieties can have additional points of attachment for linking further functional groups. Divalent radicals may be denoted with the suffix "diyl". For example, divalent linking moieties include divalent polymer moieties such as divalent poly(ethylene glycol), divalent cycloalkyl, divalent heterocycloalkyl, divalent aryl, and divalent heteroaryl group. A "divalent cycloalkyl, heterocycloalkyl, aryl, or heteroaryl group" refers to a cycloalkyl, heterocycloalkyl, aryl, or heteroaryl group having two points of attachment for covalently linking two moieties in a molecule or material. Cycloalkyl, heterocycloalkyl, aryl, or heteroaryl groups can be substituted or unsubstituted. Cycloalkyl, heterocycloalkyl, aryl, or heteroaryl groups can be substituted with one or more groups selected from halo, hydroxy, amino, alkylamino, amido, acyl, nitro, cyano, and alkoxy.

A wavy line ( ) or an asterisk (*) represents a point of attachment of the specified chemical moiety. If the specified chemical moiety has two wavy lines ( ) present, it will be understood that a divalent chemical moiety can be used bilaterally, i.e., as read from left to right or from right to left. In some embodiments, a specified moiety having two wavy lines ( ) present is considered to be used as read from left to right.

"Alkyl" refers to a straight or branched, saturated, aliphatic radical having the number of carbon atoms indicated. Alkyl can include any number of carbons. For example, $C_1$-$C_4$ alkyl includes, but is not limited to, methyl, ethyl, propyl, isopropyl, butyl, isobutyl, sec-butyl, and tert-butyl. Alkyl can also refer to alkyl groups having up to 30 carbons atoms, such as, but not limited to heptyl, octyl, nonyl, decyl, etc. Alkyl groups can be substituted or unsubstituted. "Substituted alkyl" groups can be substituted with one or more groups selected from halo, hydroxy, amino, oxo (=O), alkylamino, amido, acyl, nitro, cyano, and alkoxy.

The term "alkyldiyl" refers to a divalent alkyl radical.

"Cycloalkyl" refers to a saturated or partially unsaturated, monocyclic, fused bicyclic, or bridged polycyclic ring assembly containing from 3 to 12 ring atoms, or the number of atoms indicated. Saturated monocyclic carbocyclic rings include, for example, cyclopropyl, cyclobutyl, cyclopentyl, cyclohexyl, and cyclooctyl. Saturated bicyclic and polycyclic carbocyclic rings include, for example, norbornane, [2.2.2] bicyclooctane, decahydronaphthalene and adamantane. Carbocyclic groups can also be partially unsaturated, having one or more double or triple bonds in the ring. Representative carbocyclic groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene.

The term "cycloalkyldiyl" refers to a divalent cycloalkyl radical.

"Aryl" refers to an aromatic ring system having any suitable number of ring atoms and any suitable number of rings. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl.

"Heterocycloalkyl" and "heteroaryl" refer to a "cycloalkyl" or "aryl" group as described herein, wherein one or more carbon atoms are optionally and independently replaced with heteroatom selected from N, O, and S. "Heteroaryl," by itself or as part of another substituent, refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can be oxidized to form moieties such as, but not limited to, —S(O)— and —$S(O)_2$—. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. "Substituted heteroaryl" groups can be substituted with one or more groups selected from halo, hydroxy, amino, oxo (═O), alkylamino, amido, acyl, nitro, cyano, and alkoxy.

The term "heterocycloalkyldiyl" refers to a divalent heterocycloalkyl radical.

Heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

The term "heteroaryldiyl" refers to a divalent heteroaryl radical.

"Heterocycloalkyl," by itself or as part of another substituent, refers to a saturated ring system having from 3 to 12 ring members and from 1 to 4 heteroatoms of N, O and S. Additional heteroatoms can also be useful, including, but not limited to, B, Al, Si and P. The heteroatoms can be oxidized to form moieties such as, but not limited to, —S(O)— and —$S(O)_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted.

Heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

The term "heterocycloalkyldiyl" refers to a divalent heterocycloalkyl radical.

The terms "halo" and "halogen," by themselves or as part of another substituent, refer to a fluorine, chlorine, bromine, or iodine atom.

The term "carbonyl," by itself or as part of another substituent, refers to C(═O) or —C(═O)—, i.e., a carbon atom double-bonded to oxygen and bound to two other groups in the moiety having the carbonyl.

As used herein, the phrase "quaternary ammonium salt" refers to a tertiary amine that has been quaternized with an alkyl substituent (e.g., a $C_1$-$C_4$ alkyl such as methyl, ethyl, propyl, or butyl).

The terms "treat," "treatment," and "treating" refer to any indicia of success in the treatment or amelioration of an injury, pathology, condition (e.g., cancer), or symptom (e.g., cognitive impairment), including any objective or subjective parameter such as abatement; remission; diminishing of symptoms or making the symptom, injury, pathology, or condition more tolerable to the patient; reduction in the rate of symptom progression; decreasing the frequency or duration of the symptom or condition; or, in some situations, preventing the onset of the symptom. The treatment or amelioration of symptoms can be based on any objective or subjective parameter, including, for example, the result of a physical examination.

The terms "cancer," "neoplasm," and "tumor" are used herein to refer to cells which exhibit autonomous, unregulated growth, such that the cells exhibit an aberrant growth phenotype characterized by a significant loss of control over cell proliferation. Cells of interest for detection, analysis, and/or treatment in the context of the invention include cancer cells (e.g., cancer cells from an individual with cancer), malignant cancer cells, pre-metastatic cancer cells, metastatic cancer cells, and non-metastatic cancer cells. Cancers of virtually every tissue are known. The phrase "cancer burden" refers to the quantum of cancer cells or cancer volume in a subject. Reducing cancer burden accordingly refers to reducing the number of cancer cells or the cancer cell volume in a subject. The term "cancer cell" as used herein refers to any cell that is a cancer cell (e.g., from any of the cancers for which an individual can be treated, e.g., isolated from an individual having cancer) or is derived from a cancer cell, e.g., clone of a cancer cell. For example, a cancer cell can be from an established cancer cell line, can be a primary cell isolated from an individual with cancer, can be a progeny cell from a primary cell isolated from an individual with cancer, and the like. In some embodiments, the term can also refer to a portion of a cancer cell, such as a sub-cellular portion, a cell membrane portion, or a cell lysate of a cancer cell. Many types of cancers are known to those of skill in the art, including solid tumors such as carcinomas, sarcomas, glioblastomas, melanomas, lymphomas, and myelomas, and circulating cancers such as leukemias.

As used herein, the term "cancer" includes any form of cancer, including but not limited to, solid tumor cancers (e.g., skin, lung, prostate, breast, gastric, bladder, colon, ovarian, pancreas, kidney, liver, glioblastoma, medulloblastoma, leiomyosarcoma, head & neck squamous cell carcinomas, melanomas, and neuroendocrine) and liquid cancers (e.g., hematological cancers); carcinomas; soft tissue tumors; sarcomas; teratomas; melanomas; leukemias; lymphomas; and brain cancers, including minimal residual disease, and including both primary and metastatic tumors.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, and invasion of surrounding or distant tissues or organs, such as lymph nodes.

As used herein, the phrases "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs, therefore, tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part that is not directly connected to the organ of the original cancerous tumor. Metastasis can also be defined as several steps of a process, such as the departure of cancer cells from an original tumor site, and migration and/or invasion of cancer cells to other parts of the body.

The phrases "effective amount" and "therapeutically effective amount" refer to a dose or amount of a substance such as a macromolecule-supported compound that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); *Goodman & Gilman's The Pharmacological Basis of Therapeutics,* $11^{th}$ Edition (McGraw-Hill, 2006); and *Remington: The Science and Practice of Pharmacy,* $22^{nd}$ Edition, (Pharmaceutical Press, London, 2012)). In the case of cancer, the therapeutically effective amount of the macromolecule-supported compound may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the macromolecule-supported compound may prevent growth and/or kill existing cancer cells, it may be cytostatic and/or cytotoxic. For cancer therapy, efficacy can, for example, be measured by assessing the time to disease progression (TTP) and/or determining the response rate (RR)

"Recipient," "individual," "subject," "host," and "patient" are used interchangeably and refer to any mammalian subject for whom diagnosis, treatment, or therapy is desired (e.g., humans). "Mammal" for purposes of treatment refers to any animal classified as a mammal, including humans, domestic and farm animals, and zoo, sports, or pet animals, such as dogs, horses, cats, cows, sheep, goats, pigs, camels, etc. In certain embodiments, the mammal is human.

As used herein, the term "administering" refers to parenteral, intravenous, intraperitoneal, intramuscular, intratumoral, intralesional, intranasal, or subcutaneous administration, oral administration, administration as a suppository, topical contact, intrathecal administration, or the implantation of a slow-release device, e.g., a mini-osmotic pump, to the subject.

The terms "about" and "around," as used herein to modify a numerical value, indicate a close range surrounding the numerical value. Thus, if "X" is the value, "about X" or "around X" indicates a value of from 0.9X to 1.1X, e.g., from 0.95X to 1.05X or from 0.99X to 1.01X. A reference to "about X" or "around X" specifically indicates at least the values X, 0.95X, 0.96X, 0.97X, 0.98X, 0.99X, 1.01X, 1.02X, 1.03X, 1.04X, and 1.05X. Accordingly, "about X" and "around X" are intended to teach and provide written description support for a claim limitation of, e.g., "0.98X."

Aminobenzazepine Adjuvant Compounds

The macromolecule-supported compound of the invention comprises an aminobenzazepine adjuvant moiety. The adjuvant moiety described herein is a compound that elicits an immune response (i.e., an immunostimulatory agent). Generally, the adjuvant moiety described herein is a TLR agonist. TLRs are type-I transmembrane proteins that are responsible for the initiation of innate immune responses in vertebrates. TLRs recognize a variety of pathogen-associated molecular patterns from bacteria, viruses, and fungi and act as a first line of defense against invading pathogens. TLRs elicit overlapping yet distinct biological responses due to differences in cellular expression and in the signaling pathways that they initiate. Once engaged (e.g., by a natural stimulus or a synthetic TLR agonist), TLRs initiate a signal transduction cascade leading to activation of nuclear factor-κB (NF-κB) via the adapter protein myeloid differentiation primary response gene 88 (MyD88) and recruitment of the IL-1 receptor associated kinase (IRAK). Phosphorylation of IRAK then leads to recruitment of TNF-receptor associated factor 6 (TRAF6), which results in the phosphorylation of the NF-κB inhibitor I-κB. As a result, NF-κB enters the cell nucleus and initiates transcription of genes whose promoters contain NF-κB binding sites, such as cytokines. Additional modes of regulation for TLR signaling include TIR-domain containing adapter-inducing interferon-β (TRIF)-dependent induction of TNF-receptor associated factor 6 (TRAF6) and activation of MyD88 independent pathways via TRIF and TRAF3, leading to the phosphorylation of interferon response factor three (IRF3). Similarly, the MyD88 dependent pathway also activates several IRF family members, including IRF5 and IRF7 whereas the TRIF dependent pathway also activates the NF-κB pathway.

Typically, the adjuvant moiety described herein is a TLR7 and/or TLR8 agonist. TLR7 and TLR8 are both expressed in cells of myeloid lineage (e.g., monocytes and dendritic cells). In humans, TLR7 is also expressed in plasmacytoid dendritic cells (pDCs) and B cells. TLR8 is expressed mostly in cells of myeloid origin, i.e., monocytes, granulocytes, and myeloid dendritic cells. TLR7 and TLR8 are capable of detecting the presence of "foreign" single-stranded RNA within a cell, as a means to respond to viral invasion. Treatment of TLR8-expressing cells, with TLR8 agonists can result in production of high levels of IL-12, IFN-γ, IL-1, TNF-α, IL-6, and other inflammatory cytokines. Similarly, stimulation of TLR7-expressing cells, such as pDCs, with TLR7 agonists can result in production of high levels of IFN-α and other inflammatory cytokines. TLR7/TLR8 engagement and resulting cytokine production can activate dendritic cells and other antigen-presenting cells, driving diverse innate and acquired immune response mechanisms leading to tumor destruction.

Exemplary aminobenzazepine compounds (Bz) of the invention are shown in Tables 1a, 1b, and 1c. Each compound was synthesized and purified by the methods in the Examples provided herein, characterized by mass spectrometry, and shown to have the mass indicated. Activity against HEK293 NFKB reporter cells expressing human TLR7 or human TLR8 was measured according to method described in Example 67. The aminobenzazepine compounds of Tables 1a, 1b, and 1c demonstrate the surprising and unexpected property of TLR8 agonist selectivity which may predict useful therapeutic activity to treat cancer and other disorders.

TABLE 1a

| Aminobenzazepine Compounds (Bz) | | | | |
|---|---|---|---|---|
| Bz No. | Structure | MW | HEK293 hTLR7 EC50 (nM) | HEK293 hTLR8 EC50 (nM) |
| Bz-1 | 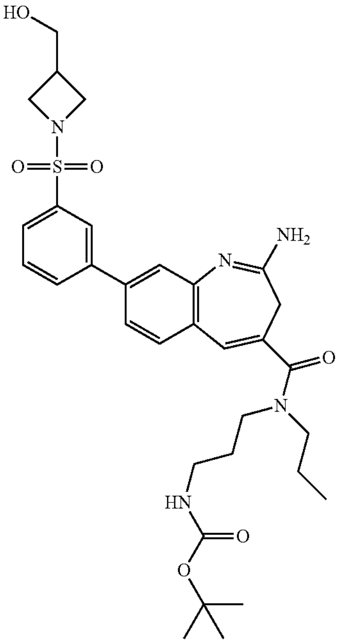 [SMILES: CCCN(CCCNC(=O)OC(C)(C)C)C(=O)C1=Cc2ccc(-c3cccc(S(=O)(=O)N4CC(CO)C4)c3)cc2N=C(N)C1] | 625.8 | 571 | 106 |

TABLE 1a-continued
| Aminobenzazepine Compounds (Bz) | | | | |
|---|---|---|---|---|
| Bz No. | Structure | MW | HEK293 hTLR7 EC50 (nM) | HEK293 hTLR8 EC50 (nM) |
| Bz-2 | 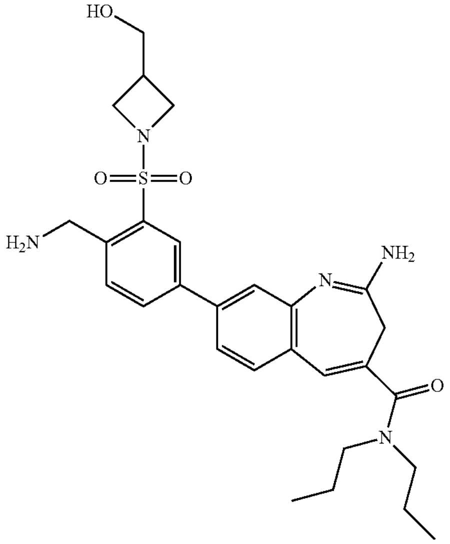 [SMILES: CCCN(CCC)C(=O)C1=Cc2ccc(-c3ccc(CN)c(S(=O)(=O)N4CC(CO)C4)c3)cc2N=C(N)C1] | 538.7 | >9000 | 9760 |
| Bz-3 | 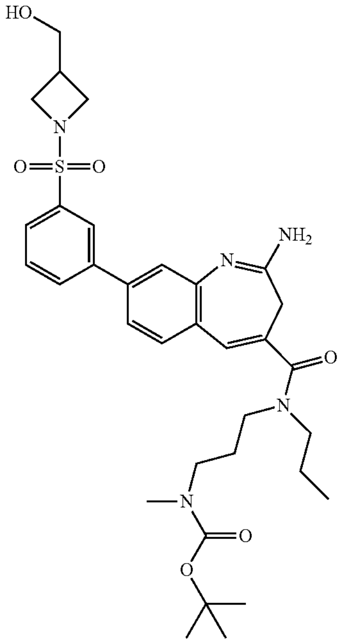 [SMILES: CCCN(CCCN(C)C(=O)OC(C)(C)C)C(=O)C1=Cc2ccc(-c3cccc(S(=O)(=O)N4CC(CO)C4)c3)cc2N=C(N)C1] | 639.8 | 545.2 | 4306 |

TABLE 1a-continued
| Aminobenzazepine Compounds (Bz) | | | | |
|---|---|---|---|---|
| Bz No. | Structure | MW | HEK293 hTLR7 EC50 (nM) | HEK293 hTLR8 EC50 (nM) |
| Bz-4 | 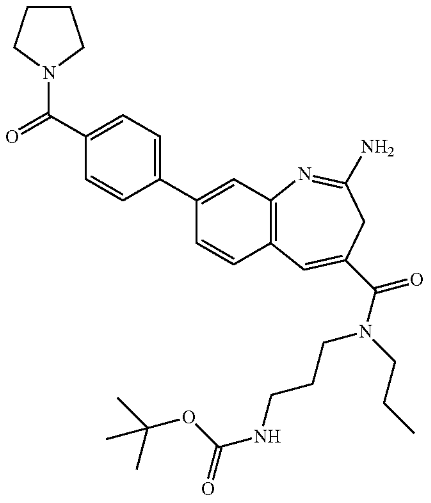 [SMILES: CCCN(CCCNC(=O)OC(C)(C)C)C(=O)C1=Cc2ccc(-c3ccc(C(=O)N4CCCC4)cc3)cc2N=C(N)C1] | 573.7 | 1484 | 1681 |
| Bz-5 | 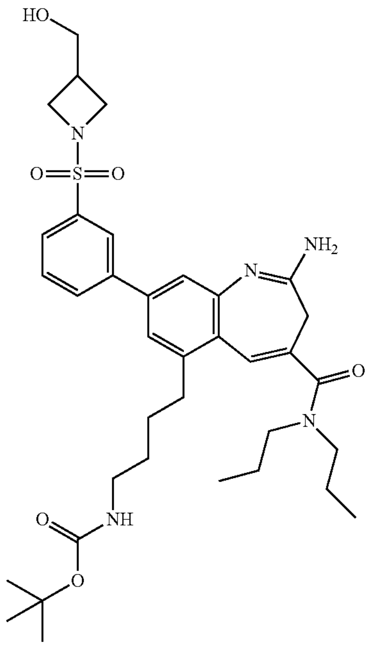 [SMILES: CCCN(CCC)C(=O)C1=Cc2c(CCCCNC(=O)OC(C)(C)C)cc(-c3cccc(S(=O)(=O)N4CC(CO)C4)c3)cc2N=C(N)C1] | 681.9 | 155.2 | 255.5 |

TABLE 1a-continued
Aminobenzazepine Compounds (Bz)
| Bz No. | Structure | MW | HEK293 hTLR7 EC50 (nM) | HEK293 hTLR8 EC50 (nM) |
|---|---|---|---|---|
| Bz-6 | 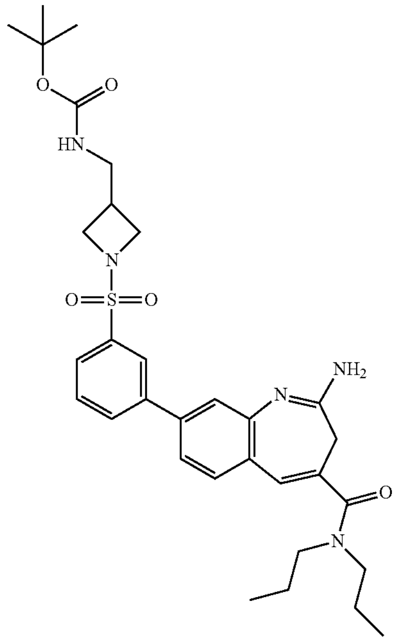 [SMILES: CCCN(CCC)C(=O)C1=Cc2ccc(-c3cccc(S(=O)(=O)N4CC(CNC(=O)OC(C)(C)C)C4)c3)cc2N=C(N)C1] | 609.8 | >9000 | 264.7 |
| Bz-7 | 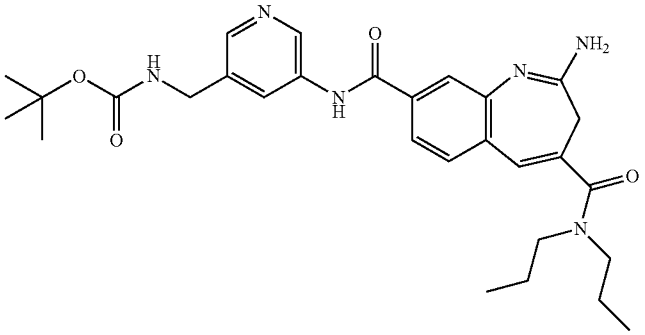 [SMILES: CCCN(CCC)C(=O)C1=Cc2ccc(C(=O)Nc3cncc(CNC(=O)OC(C)(C)C)c3)cc2N=C(N)C1] | 534.7 | >9000 | 4.283 |
| Bz-8 | 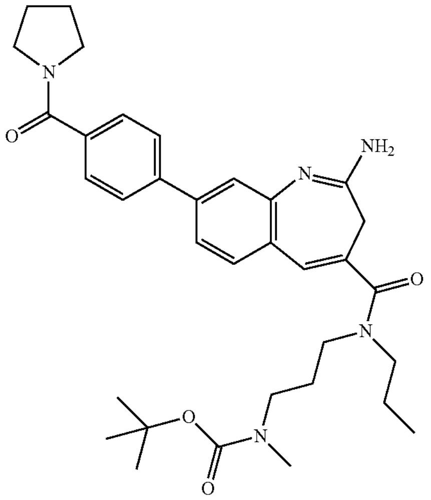 [SMILES: CCCN(CCCN(C)C(=O)OC(C)(C)C)C(=O)C1=Cc2ccc(-c3ccc(C(=O)N4CCCC4)cc3)cc2N=C(N)C1] | 587.8 | 3367 | >9000 |

TABLE 1a-continued
| Aminobenzazepine Compounds (Bz) | | | | |
|---|---|---|---|---|
| Bz No. | Structure | MW | HEK293 hTLR7 EC50 (nM) | HEK293 hTLR8 EC50 (nM) |
| Bz-9 | 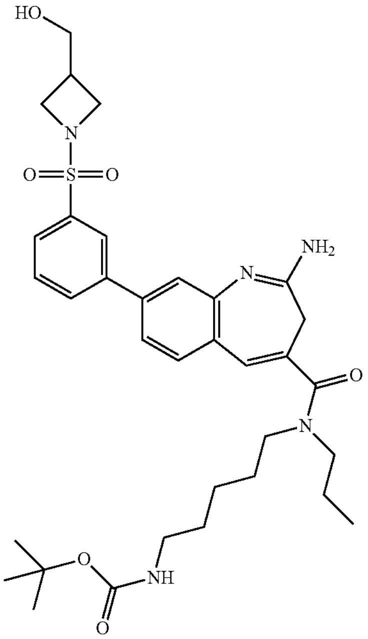 [SMILES: CCCN(CCCCCNC(=O)OC(C)(C)C)C(=O)C1=Cc2ccc(-c3cccc(S(=O)(=O)N4CC(CO)C4)c3)cc2N=C(N)C1] | 653.8 | 8647 | 629.1 |
| Bz-10 | 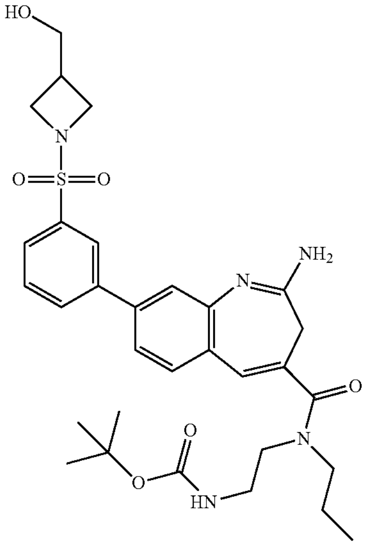 [SMILES: CCCN(CCNC(=O)OC(C)(C)C)C(=O)C1=Cc2ccc(-c3cccc(S(=O)(=O)N4CC(CO)C4)c3)cc2N=C(N)C1] | 611.8 | >9000 | >9000 |

TABLE 1a-continued
| Aminobenzazepine Compounds (Bz) | | | | |
|---|---|---|---|---|
| Bz No. | Structure | MW | HEK293 hTLR7 EC50 (nM) | HEK293 hTLR8 EC50 (nM) |
| Bz-11 | 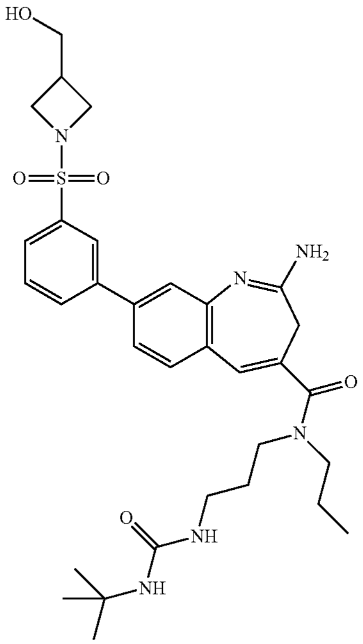 [SMILES: CCCN(CCCNC(=O)NC(C)(C)C)C(=O)C1=Cc2ccc(-c3cccc(S(=O)(=O)N4CC(CO)C4)c3)cc2N=C(N)C1] | 624.8 | 7843 | 1387 |
| Bz-12 | 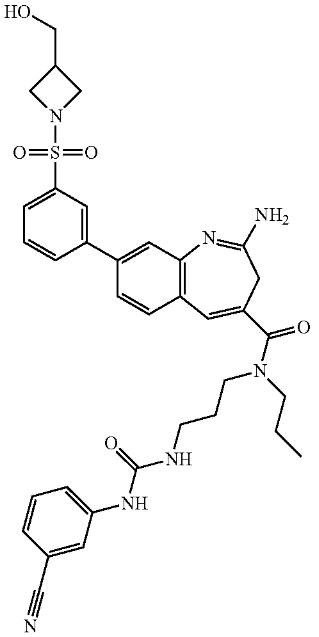 [SMILES: CCCN(CCCNC(=O)Nc1cccc(C#N)c1)C(=O)C1=Cc2ccc(-c3cccc(S(=O)(=O)N4CC(CO)C4)c3)cc2N=C(N)C1] | 669.8 | 2487 | 2375 |

TABLE 1a-continued
| Aminobenzazepine Compounds (Bz) | | | | |
|---|---|---|---|---|
| Bz No. | Structure | MW | HEK293 hTLR7 EC50 (nM) | HEK293 hTLR8 EC50 (nM) |
| Bz-13 | 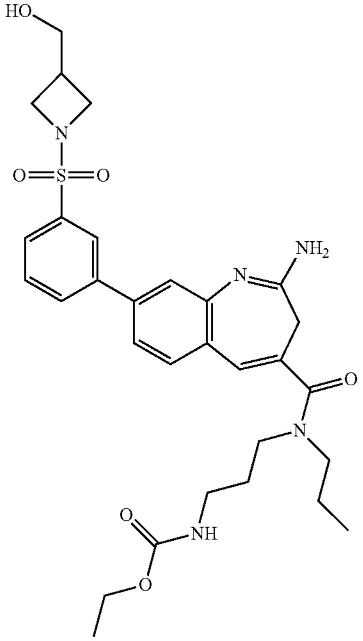 [SMILES: CCCN(CCCNC(=O)OCC)C(=O)C1=Cc2ccc(-c3cccc(S(=O)(=O)N4CC(CO)C4)c3)cc2N=C(N)C1] | 597.7 | 1371 | 134 |
| Bz-14 | 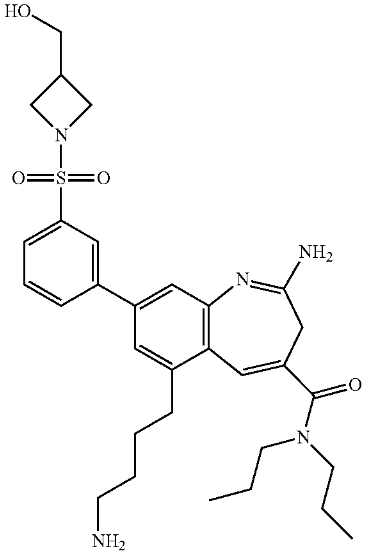 [SMILES: CCCN(CCC)C(=O)C1=Cc2c(CCCCN)cc(-c3cccc(S(=O)(=O)N4CC(CO)C4)c3)cc2N=C(N)C1] | 581.8 | >9000 | 1700 |

TABLE 1a-continued
| Aminobenzazepine Compounds (Bz) | | | | |
|---|---|---|---|---|
| Bz No. | Structure | MW | HEK293 hTLR7 EC50 (nM) | HEK293 hTLR8 EC50 (nM) |
| Bz-15 | 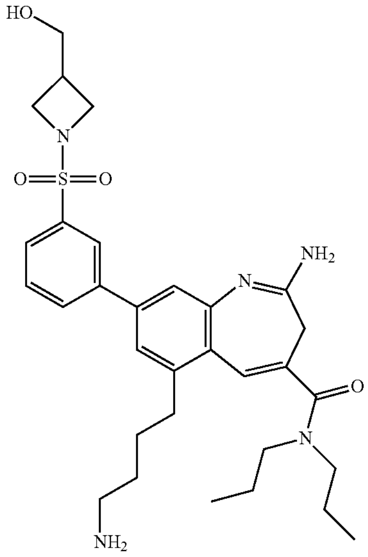 [SMILES: CCCN(CCC)C(=O)C1=Cc2c(CCCCN)cc(-c3cccc(S(=O)(=O)N4CC(CO)C4)c3)cc2N=C(N)C1] | 509.7 | >9000 | 103 |
| Bz-16 | 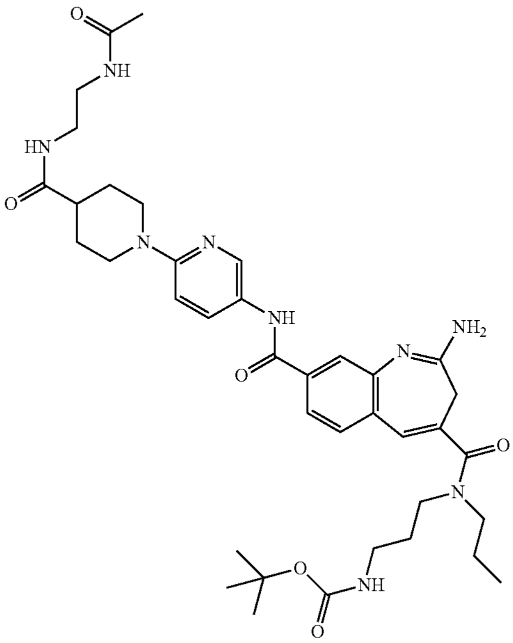 [SMILES: CCCN(CCCNC(=O)OC(C)(C)C)C(=O)C1=Cc2ccc(C(=O)Nc3ccc(N4CCC(C(=O)NCCNC(C)=O)CC4)nc3)cc2N=C(N)C1] | 731.9 | >9000 | 1047 |

TABLE 1B
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-17 | 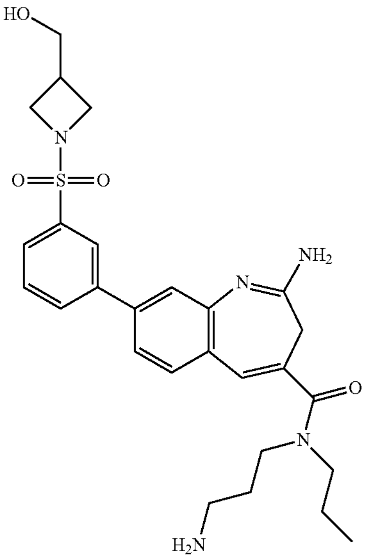 [SMILES: CCCN(CCCN)C(=O)C1=Cc2ccc(-c3cccc(S(=O)(=O)N4CC(CO)C4)c3)cc2N=C(N)C1] | 525.7 | >9000 | >9000 |
| Bz-18 | 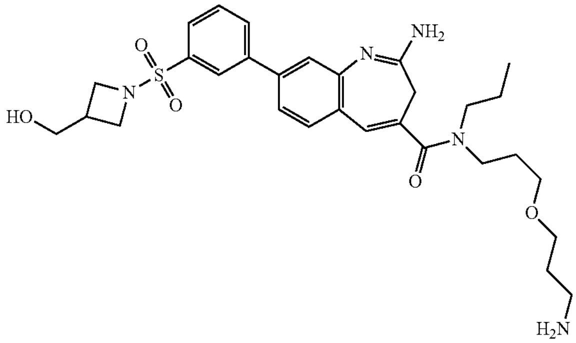 [SMILES: CCCN(CCCOCCCN)C(=O)C1=Cc2ccc(-c3cccc(S(=O)(=O)N4CC(CO)C4)c3)cc2N=C(N)C1] | 583.7 | 1994 | 3403 |
| Bz-19 | 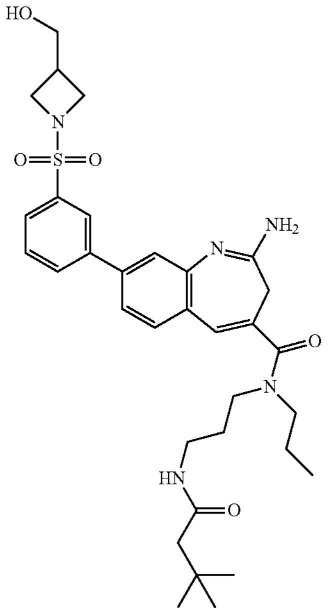 | 623.8 | 1067 | 3168 |

TABLE 1B-continued
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-20 | 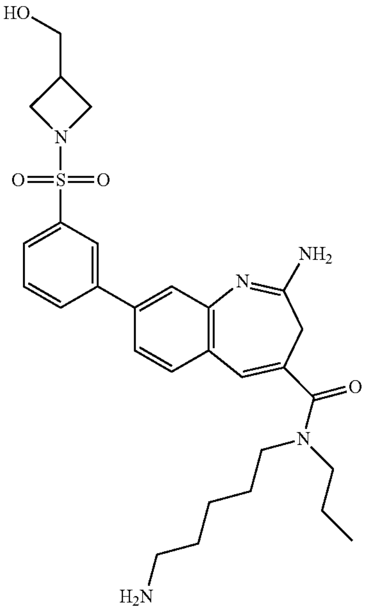 [SMILES: CCCN(CCCCCN)C(=O)C1=Cc2ccc(-c3cccc(S(=O)(=O)N4CC(CO)C4)c3)cc2N=C(N)C1] | 553.7 | >9000 | >9000 |
| Bz-21 | 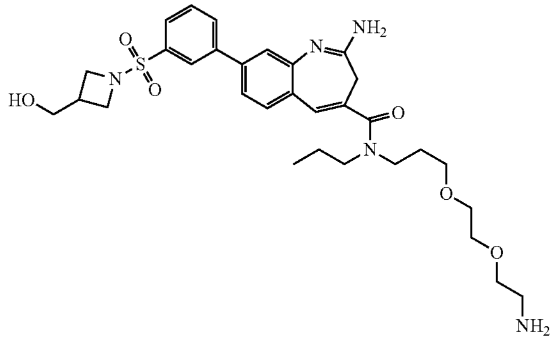 [SMILES: CCCN(CCCOCCOCCN)C(=O)C1=Cc2ccc(-c3cccc(S(=O)(=O)N4CC(CO)C4)c3)cc2N=C(N)C1] | 613.8 | >9000 | >9000 |
| Bz-22 | 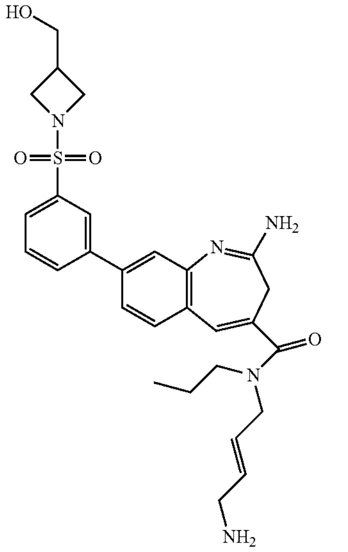 [SMILES: CCCN(C/C=C/CN)C(=O)C1=Cc2ccc(-c3cccc(S(=O)(=O)N4CC(CO)C4)c3)cc2N=C(N)C1] | 537.7 | >9000 | >9000 |

TABLE 1B-continued
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-23 | 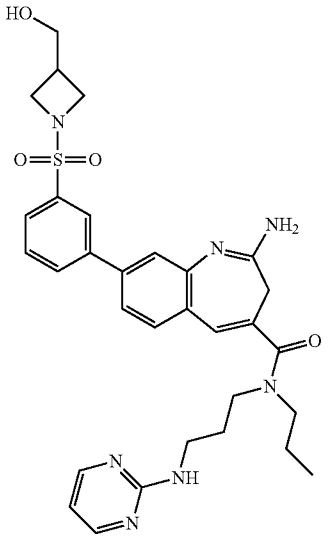 [SMILES: CCCN(CCCNc1ncccn1)C(=O)C1=Cc2ccc(-c3cccc(S(=O)(=O)N4CC(CO)C4)c3)cc2N=C(N)C1] | 603.7 | 2427 | 1162 |
| Bz-24 | 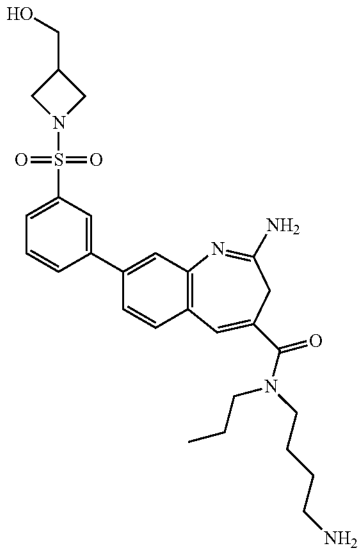 [SMILES: CCCN(CCCCN)C(=O)C1=Cc2ccc(-c3cccc(S(=O)(=O)N4CC(CO)C4)c3)cc2N=C(N)C1] | 539.7 | >9000 | >9000 |

TABLE 1B-continued
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-25 | 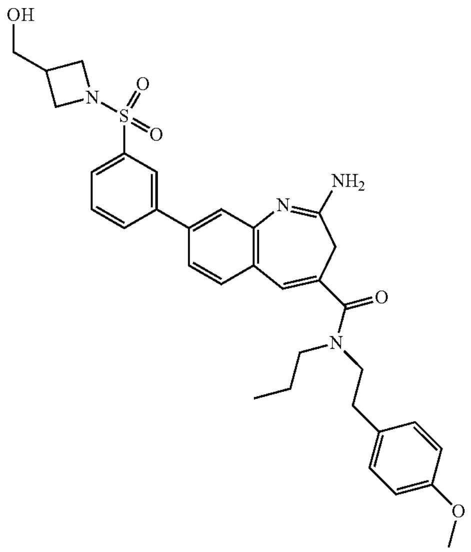 [SMILES: CCCN(CCc1ccc(OC)cc1)C(=O)C1=Cc2ccc(-c3cccc(S(=O)(=O)N4CC(CO)C4)c3)cc2N=C(N)C1] | 602.8 | >9000 | 1403 |
| Bz-26 | 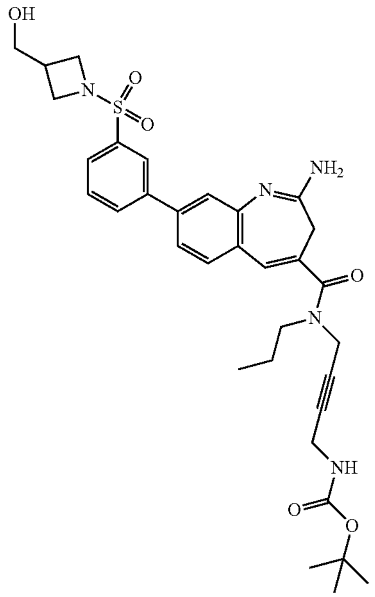 [SMILES: CCCN(CC#CCNC(=O)OC(C)(C)C)C(=O)C1=Cc2ccc(-c3cccc(S(=O)(=O)N4CC(CO)C4)c3)cc2N=C(N)C1] | 635.8 | >9000 | 318 |

TABLE 1B-continued
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-27 | 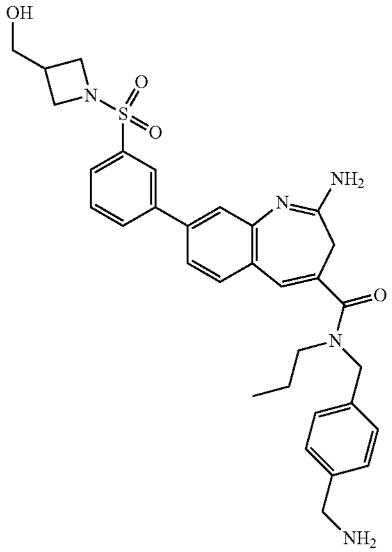 [SMILES: CCCN(Cc1ccc(CN)cc1)C(=O)C1=Cc2ccc(-c3cccc(S(=O)(=O)N4CC(CO)C4)c3)cc2N=C(N)C1] | 587.7 | >9000 | 138 |
| Bz-28 | 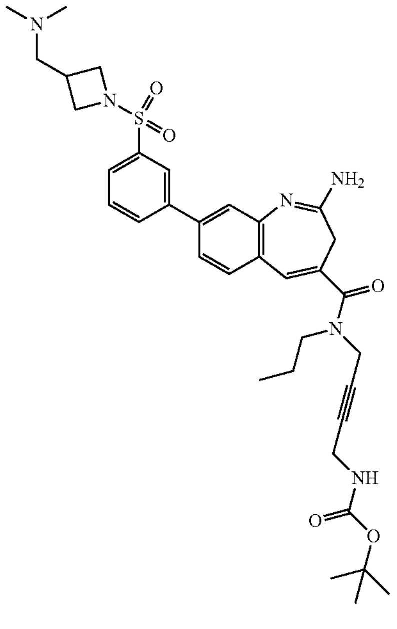 [SMILES: CCCN(CC#CCNC(=O)OC(C)(C)C)C(=O)C1=Cc2ccc(-c3cccc(S(=O)(=O)N4CC(CN(C)C)C4)c3)cc2N=C(N)C1] | 662.9 | 4253.9 | 42.8 |

TABLE 1B-continued
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-29 | 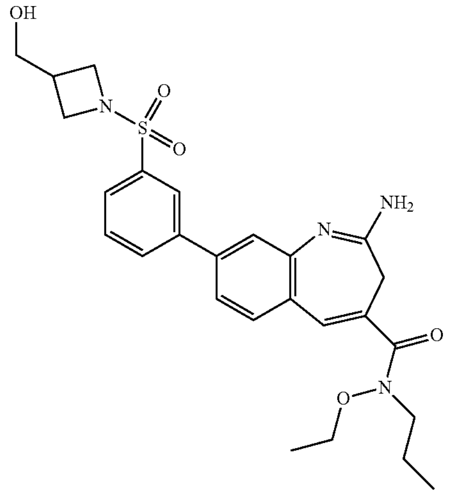 [SMILES: CCCN(OCC)C(=O)C1=Cc2ccc(-c3cccc(S(=O)(=O)N4CC(CO)C4)c3)cc2N=C(N)C1] | 512.6 | >9000 | 32 |
| Bz-30 | 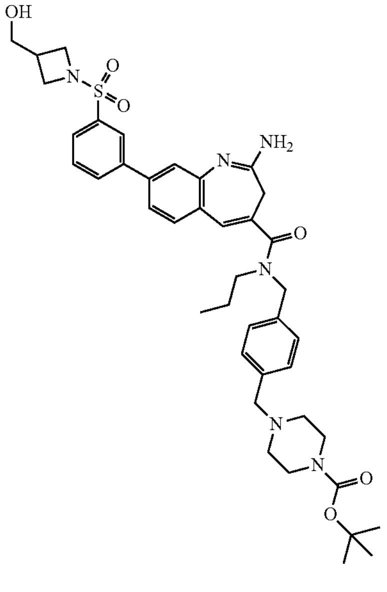 [SMILES: CCCN(Cc1ccc(CN2CCN(C(=O)OC(C)(C)C)CC2)cc1)C(=O)C1=Cc2ccc(-c3cccc(S(=O)(=O)N4CC(CO)C4)c3)cc2N=C(N)C1] | 757.0 | >9000 | 1022.3 |

TABLE 1B-continued
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-31 | 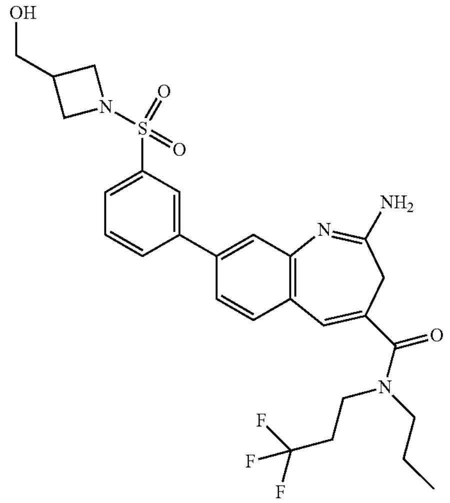 [SMILES: CCCN(CCC(F)(F)F)C(=O)C1=Cc2ccc(-c3cccc(S(=O)(=O)N4CC(CO)C4)c3)cc2N=C(N)C1] | 564.6 | >9000 | 341 |
| Bz-32 | 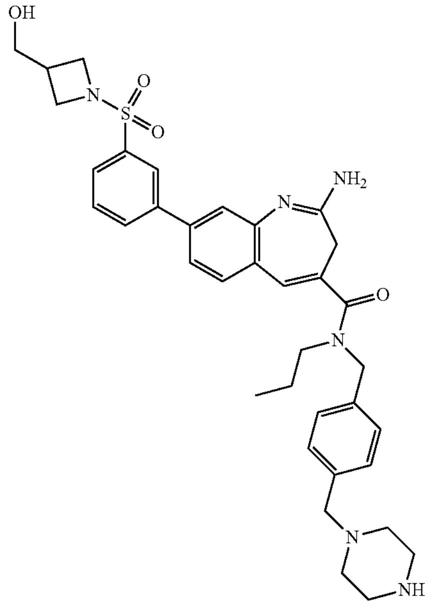 [SMILES: CCCN(Cc1ccc(CN2CCNCC2)cc1)C(=O)C1=Cc2ccc(-c3cccc(S(=O)(=O)N4CC(CO)C4)c3)cc2N=C(N)C1] | 656.8 | >9000 | >9000 |

TABLE 1B-continued
Aminobenzazepine compounds (Bz)
| Bz No. | Structure | MW | HEK293 hTLR7 EC50 (nM) | HEK293 hTLR8 EC50 (nM) |
|---|---|---|---|---|
| Bz-33 | 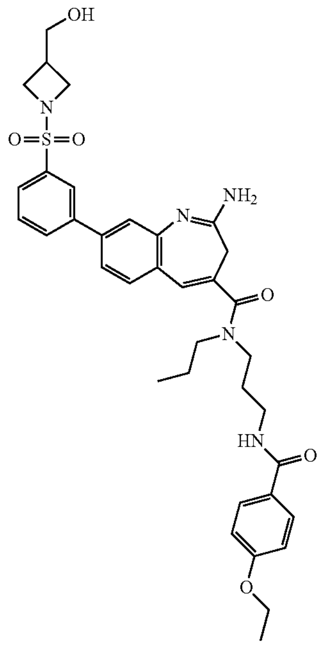 [SMILES: CCCN(CCCNC(=O)c1ccc(OCC)cc1)C(=O)C1=Cc2ccc(-c3cccc(S(=O)(=O)N4CC(CO)C4)c3)cc2N=C(N)C1] | 673.8 | 1428 | 1919 |
| Bz-34 | 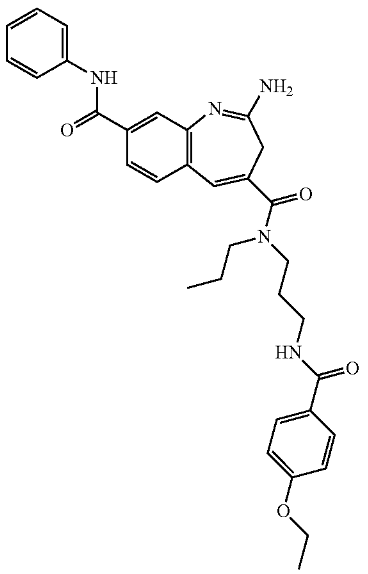 [SMILES: CCCN(CCCNC(=O)c1ccc(OCC)cc1)C(=O)C1=Cc2ccc(C(=O)Nc3ccccc3)cc2N=C(N)C1] | 567.7 | >9000 | 1040 |

TABLE 1C
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-35 | 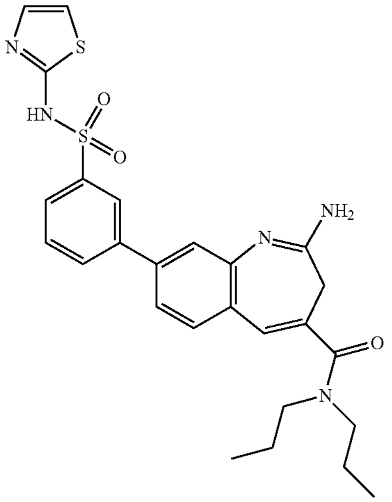 [SMILES: CCCN(CCC)C(=O)C1=Cc2ccc(-c3cccc(S(=O)(=O)Nc4nccs4)c3)cc2N=C(N)C1] | 523.7 | >9000 | >9000 |
| Bz-36 | 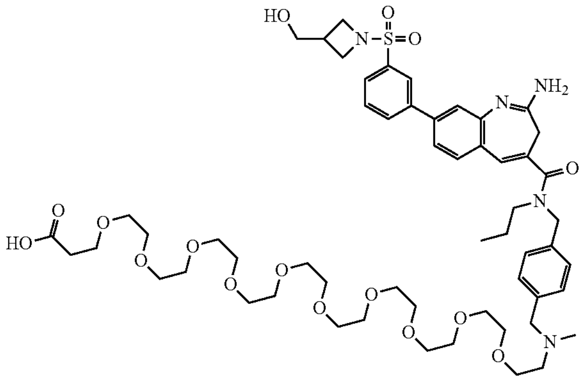 [SMILES: CCCN(Cc1ccc(CN(C)CCOCCOCCOCCOCCOCCOCCOCCOCCOCCOCCC(=O)O)cc1)C(=O)C1=Cc2ccc(-c3cccc(S(=O)(=O)N4CC(CO)C4)c3)cc2N=C(N)C1] | 1114.4 | ND | ND |
| Bz-37 | 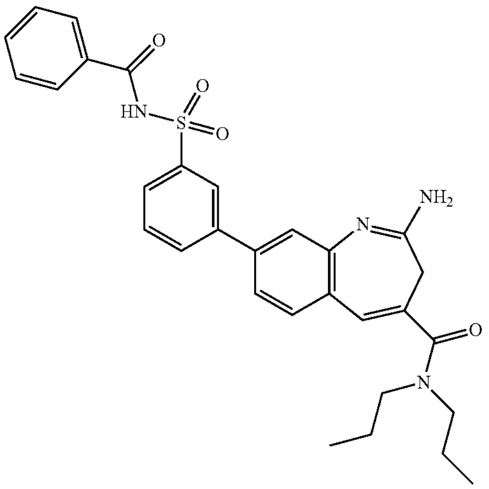 [SMILES: CCCN(CCC)C(=O)C1=Cc2ccc(-c3cccc(S(=O)(=O)NC(=O)c4ccccc4)c3)cc2N=C(N)C1] | 544.7 | >9000 | >9000 |

TABLE 1C-continued
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-38 | 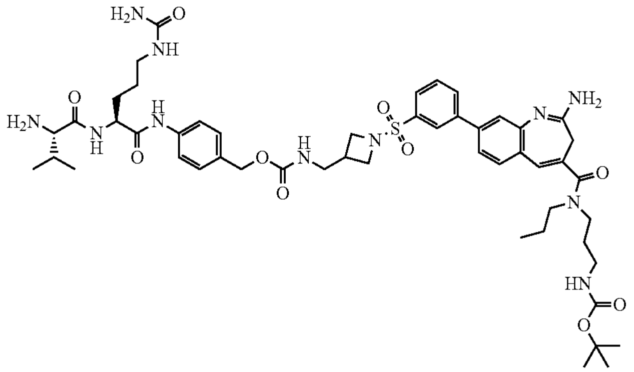 [SMILES: CCCN(CCCNC(=O)OC(C)(C)C)C(=O)C1=Cc2ccc(-c3cccc(S(=O)(=O)N4CC(CNC(=O)OCc5ccc(NC(=O)[C@H](CCCNC(N)=O)NC(=O)[C@@H](N)C(C)C)cc5)C4)c3)cc2N=C(N)C1] | 1030.2 | ND | ND |
| Bz-39 | 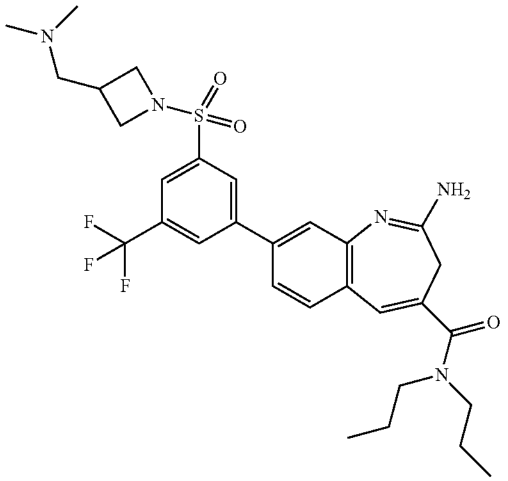 [SMILES: CCCN(CCC)C(=O)C1=Cc2ccc(-c3cc(C(F)(F)F)cc(S(=O)(=O)N4CC(CN(C)C)C4)c3)cc2N=C(N)C1] | 605.7 | 42 | 728 |
| Bz-40 | 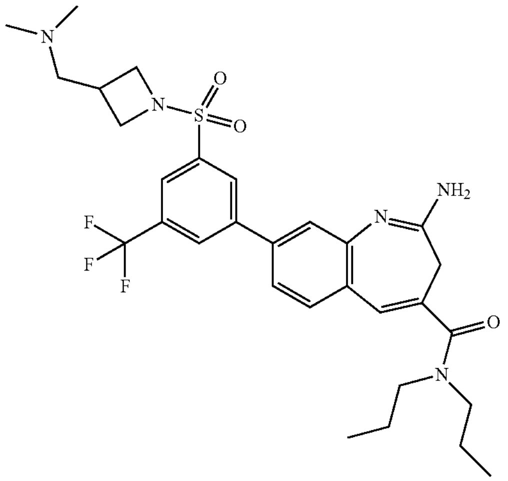 [SMILES: CCCN(CCC)C(=O)C1=Cc2ccc(-c3cc(C(F)(F)F)cc(S(=O)(=O)N4CC(CN(C)C)C4)c3)cc2N=C(N)C1] | 509.8 | 332 | >9000 |

TABLE 1C-continued
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-41 | 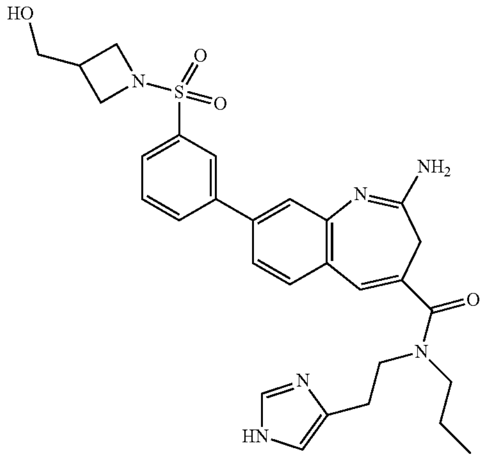 [SMILES: CCCN(CCc1c[nH]cn1)C(=O)C1=Cc2ccc(-c3cccc(S(=O)(=O)N4CC(CO)C4)c3)cc2N=C(N)C1] | 562.7 | >9000 | >9000 |
| Bz-42 | 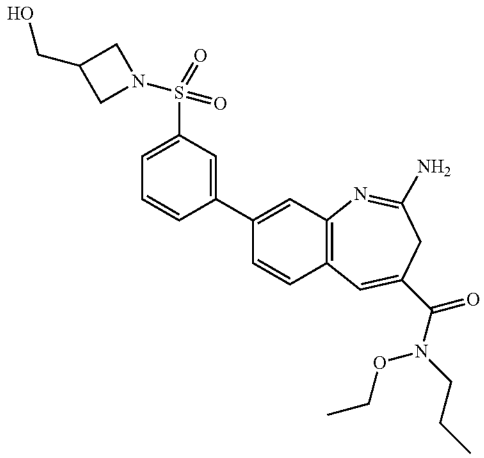 [SMILES: CCCN(OCC)C(=O)C1=Cc2ccc(-c3cccc(S(=O)(=O)N4CC(CO)C4)c3)cc2N=C(N)C1] | 512.6 | >9000 | 49 |
| Bz-43 | 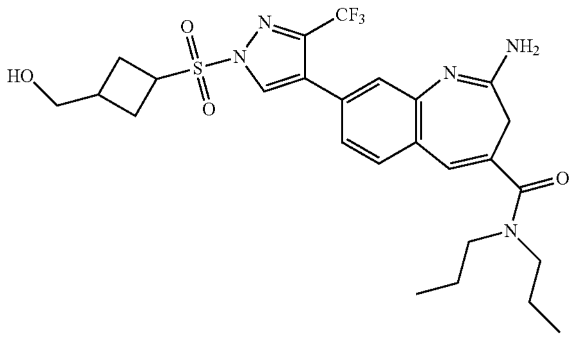 [SMILES: CCCN(CCC)C(=O)C1=Cc2ccc(-c3cn(S(=O)(=O)C4CC(CO)C4)nc3C(F)(F)F)cc2N=C(N)C1] | 568.6 | >9000 | 7005 |

TABLE 1C-continued
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-44 | 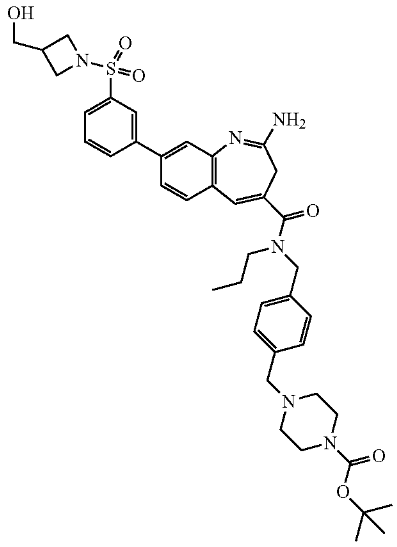 [SMILES: CCCN(Cc1ccc(CN2CCN(C(=O)OC(C)(C)C)CC2)cc1)C(=O)C1=Cc2ccc(-c3cccc(S(=O)(=O)N4CC(CO)C4)c3)cc2N=C(N)C1] | 757.0 | >9000 | 1022 |
| Bz-45 | 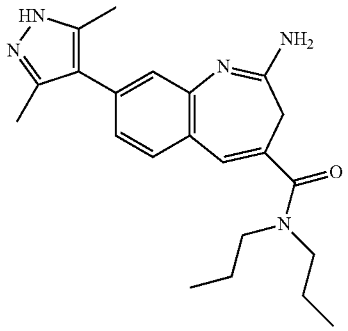 [SMILES: CCCN(CCC)C(=O)C1=Cc2ccc(-c3c(C)n[nH]c3C)cc2N=C(N)C1] | 379.5 | >9000 | 345 |
| Bz-46 | 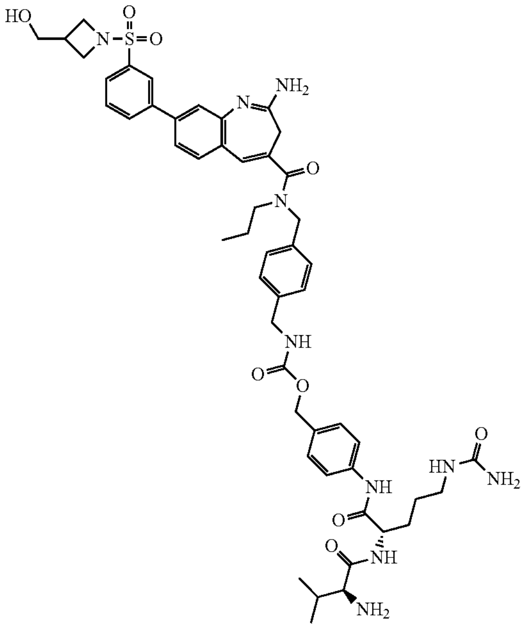 [SMILES: CCCN(Cc1ccc(CNC(=O)OCc2ccc(NC(=O)[C@H](CCCNC(N)=O)NC(=O)[C@@H](N)C(C)C)cc2)cc1)C(=O)C1=Cc2ccc(-c3cccc(S(=O)(=O)N4CC(CO)C4)c3)cc2N=C(N)C1] | 993.2 | ND | ND |

TABLE 1C-continued
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-47 | 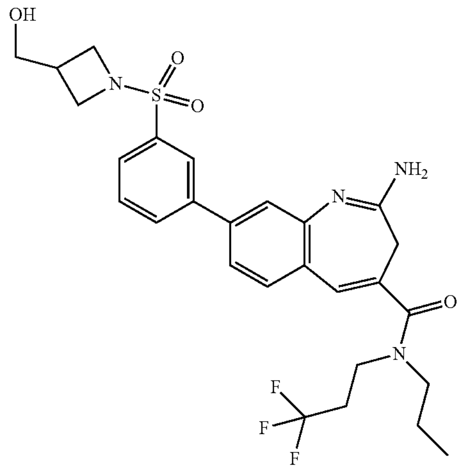 [SMILES: CCCN(CCC(F)(F)F)C(=O)C1=Cc2ccc(-c3cccc(S(=O)(=O)N4CC(CO)C4)c3)cc2N=C(N)C1] | 564.6 | >9000 | 341 |
| Bz-48 | 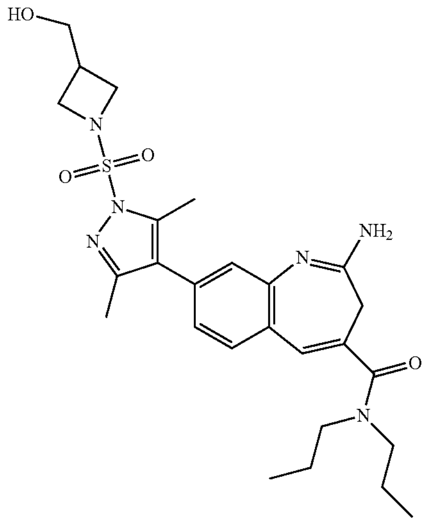 [SMILES: CCCN(CCC)C(=O)C1=Cc2ccc(-c3c(C)nn(S(=O)(=O)N4CC(CO)C4)c3C)cc2N=C(N)C1] | 528.7 | ND | 499 |

TABLE 1C-continued
Aminobenzazepine compounds (Bz)
| Bz No. | Structure | MW | HEK293 hTLR7 EC50 (nM) | HEK293 hTLR8 EC50 (nM) |
|---|---|---|---|---|
| Bz-49 | 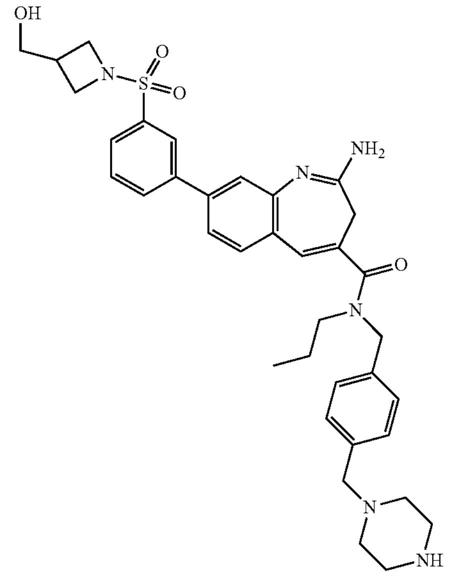 [SMILES: CCCN(Cc1ccc(CN2CCNCC2)cc1)C(=O)C1=Cc2ccc(-c3cccc(S(=O)(=O)N4CC(CO)C4)c3)cc2N=C(N)C1] | 656.8 | >9000 | >9000 |
| Bz-50 | 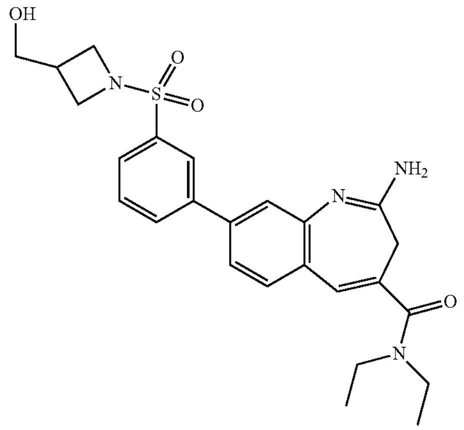 [SMILES: CCN(CC)C(=O)C1=Cc2ccc(-c3cccc(S(=O)(=O)N4CC(CO)C4)c3)cc2N=C(N)C1] | 482.6 | ND | >9000 |

TABLE 1C-continued
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-51 | 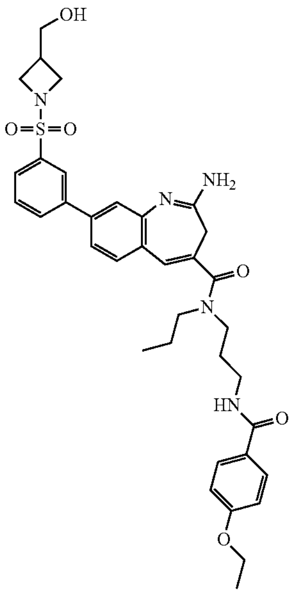 [SMILES: CCCN(CCCNC(=O)c1ccc(OCC)cc1)C(=O)C1=Cc2ccc(-c3cccc(S(=O)(=O)N4CC(CO)C4)c3)cc2N=C(N)C1] | 673.8 | 1428 | 1919 |
| Bz-52 | 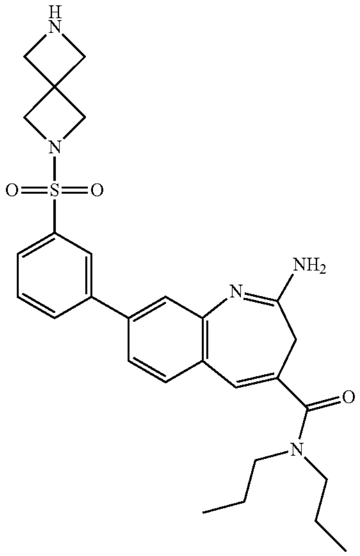 [SMILES: CCCN(CCC)C(=O)C1=Cc2ccc(-c3cccc(S(=O)(=O)N4CC5(CNC5)C4)c3)cc2N=C(N)C1] | 521.7 | ND | 1320 |

TABLE 1C-continued
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-53 | 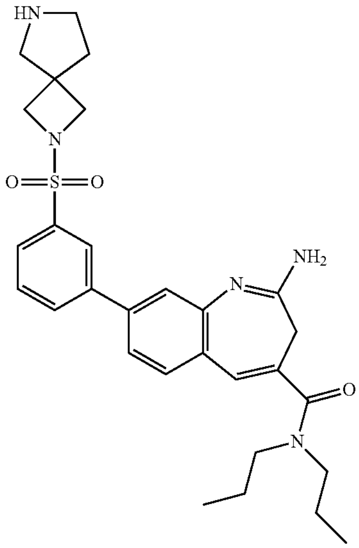 [SMILES: CCCN(CCC)C(=O)C1=Cc2ccc(-c3cccc(S(=O)(=O)N4CC5(CCNC5)C4)c3)cc2N=C(N)C1] | 535.7 | ND | 249 |
| Bz-54 | 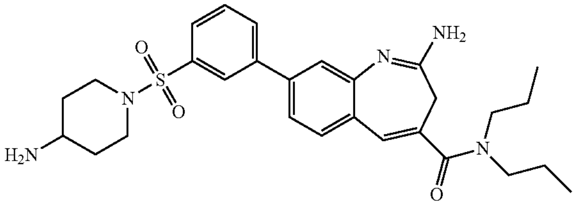 [SMILES: CCCN(CCC)C(=O)C1=Cc2ccc(-c3cccc(S(=O)(=O)N4CCC(N)CC4)c3)cc2N=C(N)C1] | 523.7 | ND | 198 |
| Bz-55 | 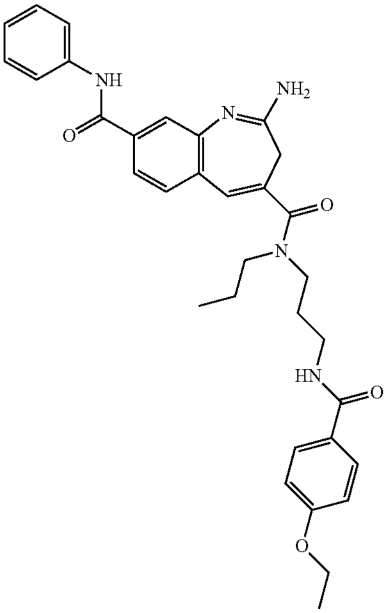 [SMILES: CCCN(CCCNC(=O)c1ccc(OCC)cc1)C(=O)C1=Cc2ccc(C(=O)Nc3ccccc3)cc2N=C(N)C1] | 567.7 | >9000 | 1040 |

TABLE 1C-continued
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-56 | 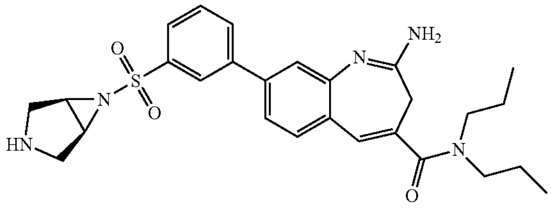 [SMILES: CCCN(CCC)C(=O)C1=Cc2ccc(-c3cccc(S(=O)(=O)N4[C@@H]5CNC[C@@H]54)c3)cc2N=C(N)C1] | 507.7 | ND | 111 |
| Bz-57 | 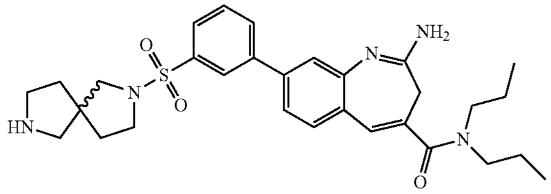 [SMILES: CCCN(CCC)C(=O)C1=Cc2ccc(-c3cccc(S(=O)(=O)N4CCC5(CCNC5)C4)c3)cc2N=C(N)C1] | 549.7 | ND | 741 |
| Bz-58 | 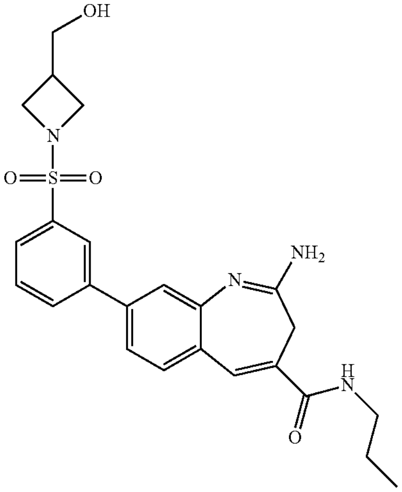 [SMILES: CCCNC(=O)C1=Cc2ccc(-c3cccc(S(=O)(=O)N4CC(CO)C4)c3)cc2N=C(N)C1] | 468.6 | >9000 | >9000 |
| Bz-59 | 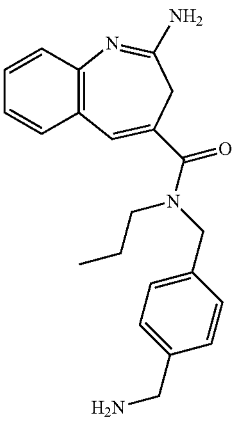 [SMILES: CCCN(Cc1ccc(CN)cc1)C(=O)C1=Cc2ccccc2N=C(N)C1] | 362.5 | >9000 | 870 |

TABLE 1C-continued
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-60 | 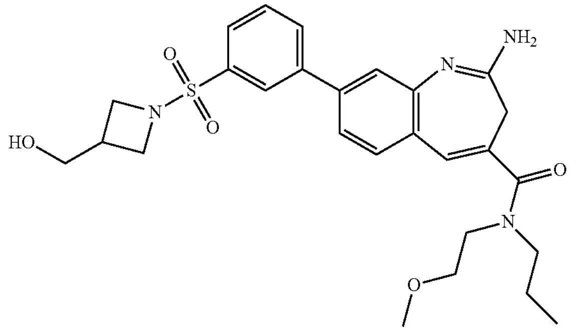 [SMILES: CCCN(CCOC)C(=O)C1=Cc2ccc(-c3cccc(S(=O)(=O)N4CC(CO)C4)c3)cc2N=C(N)C1] | 562.7 | >9000 | 288 |
| Bz-61 | 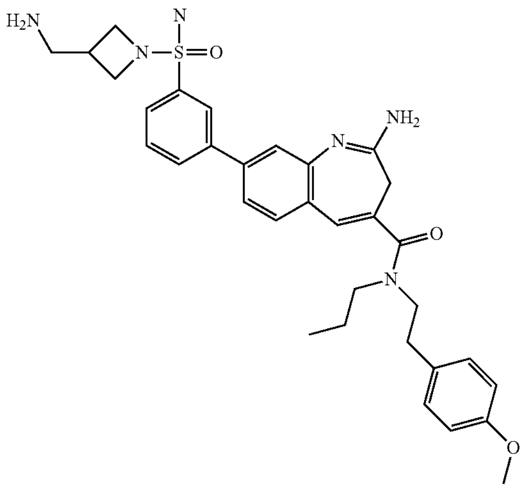 | 601.8 | >9000 | 5846 |
| Bz-62 | 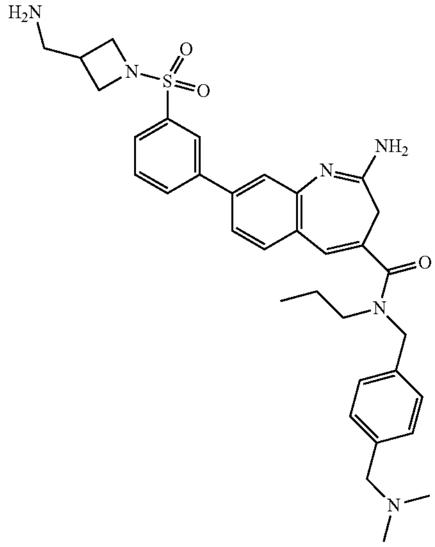 [SMILES: CCCN(Cc1ccc(CN(C)C)cc1)C(=O)C1=Cc2ccc(-c3cccc(S(=O)(=O)N4CC(CN)C4)c3)cc2N=C(N)C1] | 614.8 | >9000 | >9000 |

TABLE 1C-continued
| Bz No. | Structure | MW | HEK293 hTLR7 EC50 (nM) | HEK293 hTLR8 EC50 (nM) |
|---|---|---|---|---|
| | Aminobenzazepine compounds (Bz) | | | |
| Bz-63 | 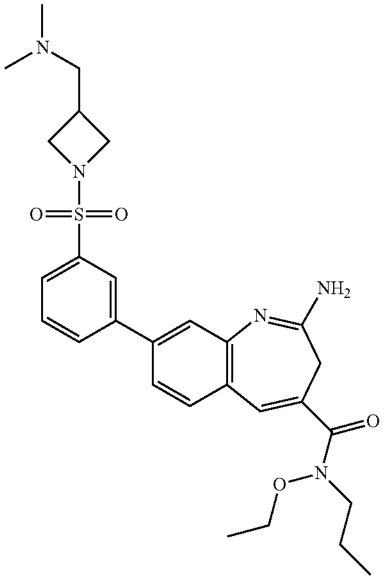 [SMILES: CCCN(OCC)C(=O)C1=Cc2ccc(-c3cccc(S(=O)(=O)N4CC(CN(C)C)C4)c3)cc2N=C(N)C1] | 539.7 | 1270 | 8 |
| Bz-64 | 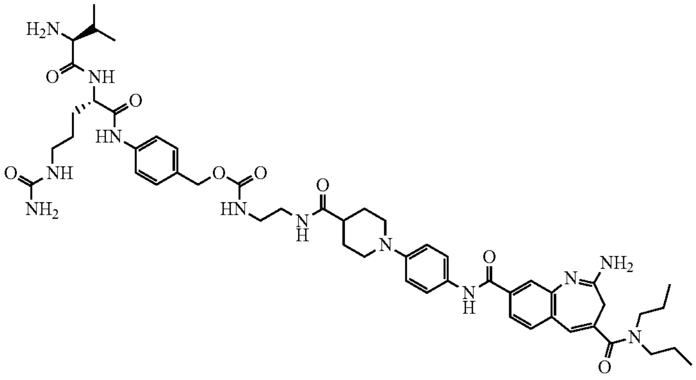 [SMILES: CCCN(CCC)C(=O)C1=Cc2ccc(C(=O)Nc3ccc(N4CCC(C(=O)NCCNC(=O)OCc5ccc(NC(=O)[C@H](CCCNC(N)=O)NC(=O)[C@@H](N)C(C)C)cc5)CC4)cc3)cc2N=C(N)C1] | 980.2 | ND | ND |
| Bz-65 | 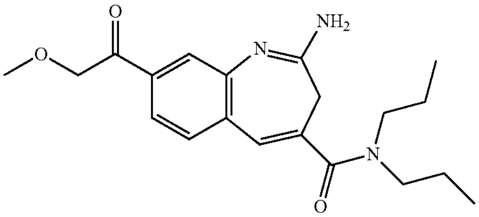 [SMILES: CCCN(CCC)C(=O)C1=Cc2ccc(C(=O)COC)cc2N=C(N)C1] | 357.5 | 3929 | 5902 |

TABLE 1C-continued
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-66 | 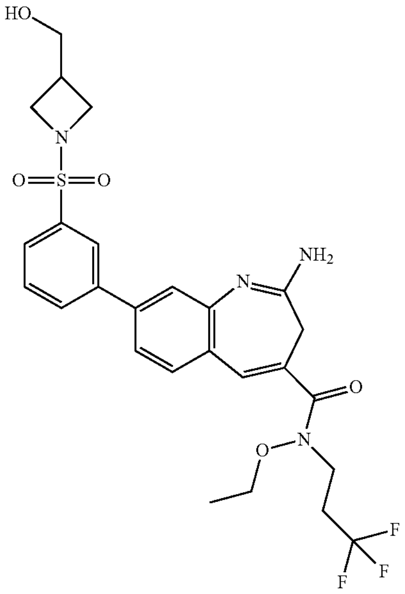 [SMILES: CCON(CCC(F)(F)F)C(=O)C1=Cc2ccc(-c3cccc(S(=O)(=O)N4CC(CO)C4)c3)cc2N=C(N)C1] | 566.6 | 4614 | 26 |
| Bz-67 | 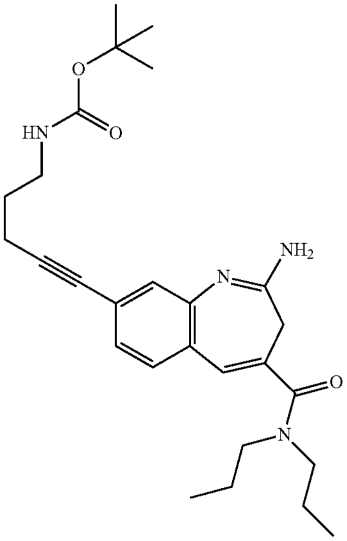 [SMILES: CCCN(CCC)C(=O)C1=Cc2ccc(C#CCCCNC(=O)OC(C)(C)C)cc2N=C(N)C1] | 466.6 | 3926 | 2053 |

TABLE 1C-continued
| Bz No. | Structure | MW | HEK293 hTLR7 EC50 (nM) | HEK293 hTLR8 EC50 (nM) |
|---|---|---|---|---|
| | Aminobenzazepine compounds (Bz) | | | |
| Bz-68 | 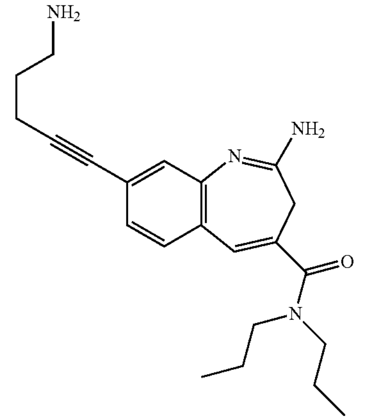 [SMILES: CCCN(CCC)C(=O)C1=Cc2ccc(C#CCCCN)cc2N=C(N)C1] | 366.5 | 4595 | 3070 |
| Bz-69 | 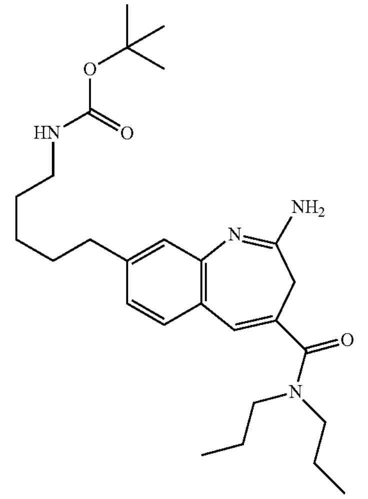 [SMILES: CCCN(CCC)C(=O)C1=Cc2ccc(CCCCCNC(=O)OC(C)(C)C)cc2N=C(N)C1] | 470.7 | 3205 | 6670 |
| Bz-70 | 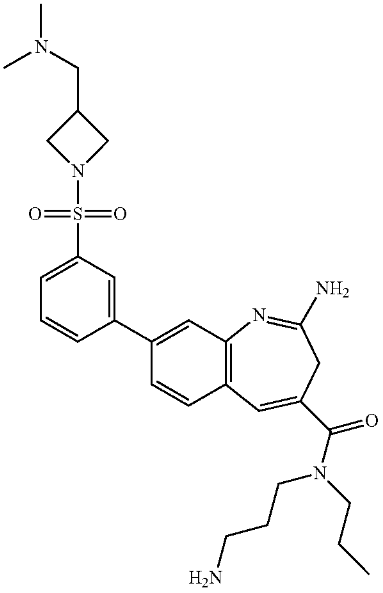 [SMILES: CCCN(CCCN)C(=O)C1=Cc2ccc(-c3cccc(S(=O)(=O)N4CC(CN(C)C)C4)c3)cc2N=C(N)C1] | 552.7 | ND | ND |

TABLE 1C-continued
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-71 | 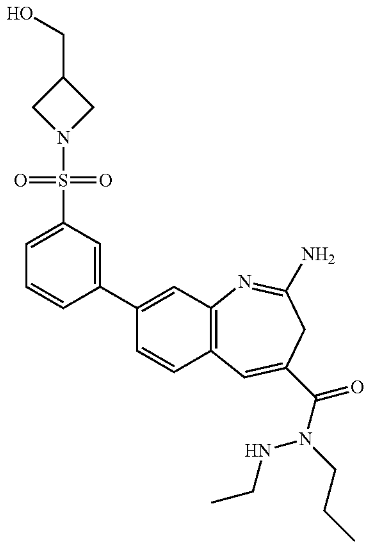 [SMILES: CCCN(NCC)C(=O)C1=Cc2ccc(-c3cccc(S(=O)(=O)N4CC(CO)C4)c3)cc2N=C(N)C1] | 511.6 | >9000 | 2752 |
| Bz-72 | 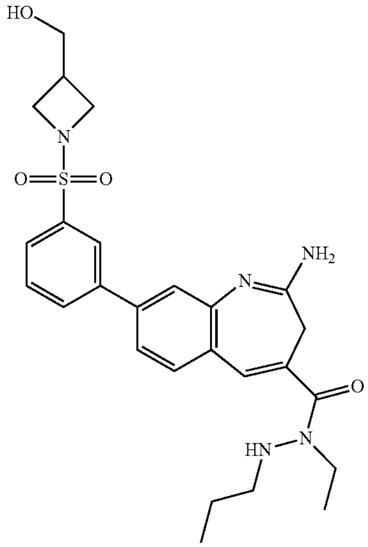 [SMILES: CCCNN(CC)C(=O)C1=Cc2ccc(-c3cccc(S(=O)(=O)N4CC(CO)C4)c3)cc2N=C(N)C1] | 511.6 | ND | 4253 |

TABLE 1C-continued
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-73 | 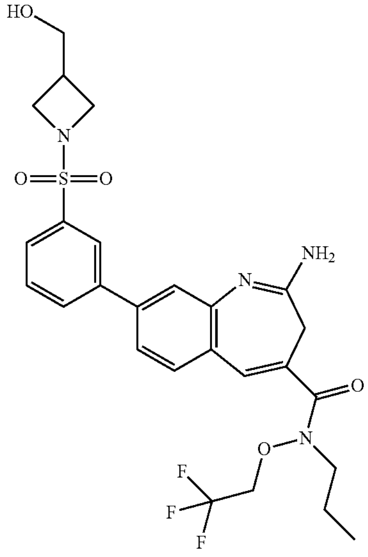 [SMILES: CCCN(OCC(F)(F)F)C(=O)C1=Cc2ccc(-c3cccc(S(=O)(=O)N4CC(CO)C4)c3)cc2N=C(N)C1] | 566.6 | 4478 | 120 |
| Bz-74 | 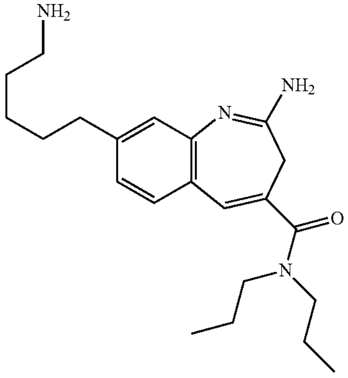 [SMILES: CCCN(CCC)C(=O)C1=Cc2ccc(CCCCCN)cc2N=C(N)C1] | 370.5 | >9000 | 2555 |
| Bz-75 | 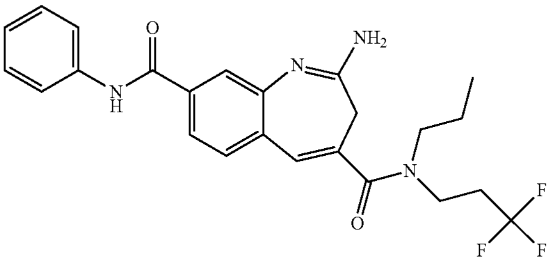 [SMILES: CCCN(CCC(F)(F)F)C(=O)C1=Cc2ccc(C(=O)Nc3ccccc3)cc2N=C(N)C1] | 458.5 | >9000 | 246 |

TABLE 1C-continued
| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-76 | 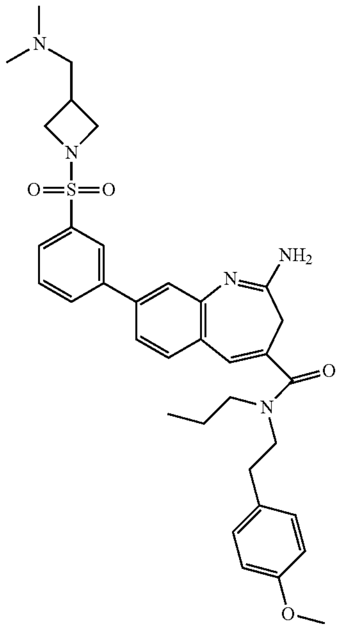 [SMILES: CCCN(CCc1ccc(OC)cc1)C(=O)C1=Cc2ccc(-c3cccc(S(=O)(=O)N4CC(CN(C)C)C4)c3)cc2N=C(N)C1] | 629.8 | 969 | 786 |
| Bz-77 | 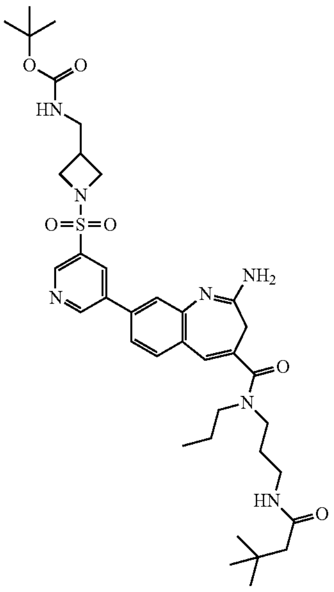 [SMILES: CCCN(CCCNC(=O)CC(C)(C)C)C(=O)C1=Cc2ccc(-c3cncc(S(=O)(=O)N4CC(CNC(=O)OC(C)(C)C)C4)c3)cc2N=C(N)C1] | 723.9 | ND | ND |

TABLE 1C-continued

| Aminobenzazepine compounds (Bz) | | | | |
|---|---|---|---|---|
| Bz No. | Structure | MW | HEK293 hTLR7 EC50 (nM) | HEK293 hTLR8 EC50 (nM) |
| Bz-78 | 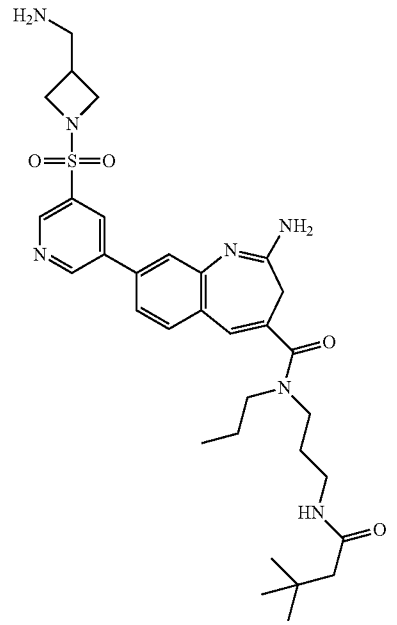 [SMILES: CCCN(CCCNC(=O)CC(C)(C)C)C(=O)C1=Cc2ccc(-c3cncc(S(=O)(=O)N4CC(CN)C4)c3)cc2N=C(N)C1] | 623.8 | MD | MD |
| Bz-79 | 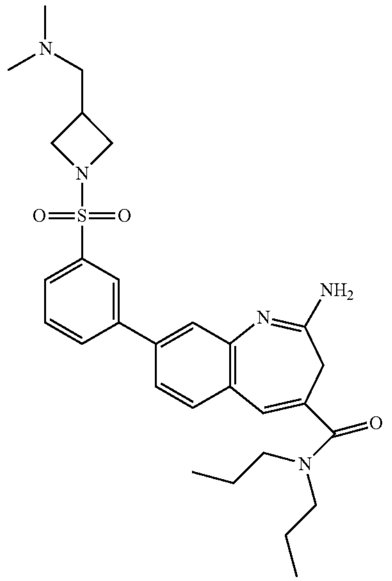 [SMILES: CCCN(CCC)C(=O)C1=Cc2ccc(-c3cccc(S(=O)(=O)N4CC(CN(C)C)C4)c3)cc2N=C(N)C1] | 537.7 | ND | ND |

Aminobenzazepine-Linker Compounds

The macromolecule-supported compounds of the invention are prepared by conjugation of a macromolecular support with an aminobenzazepine-linker compound. The aminobenzazepine-linker compounds comprise an aminobenzazepine moiety covalently attached to a linker unit. The linker units comprise functional groups and subunits which affect stability, permeability, solubility, and other pharmacokinetic, safety, and efficacy properties of the macromolecule-supported compounds. One of skill in the art will appreciate that the aminobenzazepine-linker compounds in the macromolecule-support compound can be covalently bonded to the macromolecular support using various chemistries and that the functional group linking moieties described herein can react with any free functional group of the macromolecular support (e.g., amino acid side chains, surface alcohols, thiols, carbonyls, acids, or amines, nucleic acids, etc.). For example, a nucleophilic group such as a lysine side chain amino of the macromolecular support reacts with an electrophilic reactive functional group of the aminobenzazepine-linker compound to form the macromolecule-supported compound. Also, for example, a cysteine thiol of the macromolecular support reacts with a maleimide or bromoacetamide group of the aminobenzazepine-linker compound to form the macromolecule-supported compound.

Electrophilic reactive functional groups suitable for the aminobenzazepine-linker compounds include, but are not limited to, N-hydroxysuccinimidyl (NHS) esters and N-hydroxysulfosuccinimidyl (sulfo-NHS) esters (amine reactive); carbodiimides (amine and carboxyl reactive); hydroxymethyl phosphines (amine reactive); maleimides (thiol reactive); halogenated acetamides such as N-iodoacetamides (thiol reactive); aryl azides (primary amine reactive); fluorinated aryl azides (reactive via carbon-hydrogen (C—H) insertion); pentafluorophenyl (PFP) esters (amine reactive); tetrafluorophenyl (TFP) esters (amine reactive); imidoesters (amine reactive); isocyanates (hydroxyl reactive); vinyl sulfones (thiol, amine, and hydroxyl reactive); pyridyl disulfides (thiol reactive); and benzophenone derivatives (reactive via C—H bond insertion). Further reactive functional groups include, but are not limited, to those described in Hermanson, *Bioconjugate Techniques* 2nd Edition, Academic Press, 2008.

In some embodiments, the invention provides solutions to the limitations and challenges to the design, preparation and use of conjugates. Some linkers may be labile in the blood stream, thereby releasing unacceptable amounts of the adjuvant/drug prior to internalization in a target cell (Khot, A. et al., *Bioanalysis,* 7(13): 1633-1648 (2015)). Other linkers may provide stability in the bloodstream, but intracellular release effectiveness may be negatively impacted. Linkers that provide for desired intracellular release typically have poor stability in the bloodstream. Alternatively stated, bloodstream stability and intracellular release are typically inversely related. In addition, in standard conjugation processes, the amount of adjuvant/drug moiety loaded on the macromolecule, i.e. drug loading, the amount of aggregate that is formed in the conjugation reaction, and the yield of final purified conjugate that can be obtained are interrelated. For example, aggregate formation is generally positively correlated to the number of equivalents of adjuvant/drug moiety and derivatives thereof conjugated to the macromolecule. Under high drug loading, formed aggregates must be removed for therapeutic applications. As a result, drug loading-mediated aggregate formation decreases conjugate yield and can render process scale-up difficult.

Exemplary embodiments of aminobenzazepine-linker compounds include an aminobenzazepine-linker compound of Formula II:

II

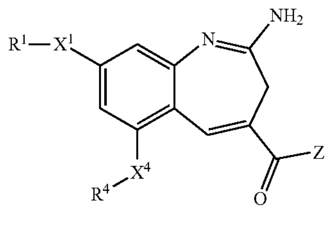

wherein

Z is selected from H, —O($C_1$-$C_8$ alkyl), and N($X^2R^2$)($X^3R^3$);

$R^1$, $R^2$, $R^3$, and $R^4$ are independently selected from the group consisting of H, $C_1$-$C_{12}$ alkyl, $C_2$-$C_6$ alkenyl, $C_2$-$C_6$ alkynyl, $C_3$-$C_{12}$ carbocyclyl, $C_6$-$C_{20}$ aryl, $C_2$-$C_9$ heterocyclyl, and $C_1$-$C_{20}$ heteroaryl, where alkyl, alkenyl, alkynyl, carbocyclyl, aryl, heterocyclyl, and heteroaryl are independently and optionally substituted with one or more groups selected from:

—($C_1$-$C_{12}$ alkyldiyl)-N($R^5$)—*;
—($C_1$-$C_{12}$ alkyldiyl)-N($R^5$)$_2$;
—($C_3$-$C_{12}$ carbocyclyl);
—($C_3$-$C_{12}$ carbocyclyl)-*;
—($C_3$-$C_{12}$ carbocyclyl)-($C_1$-$C_{12}$ alkyldiyl)-N$R^5$—*;
—($C_3$-$C_{12}$ carbocyclyl)-($C_1$-$C_{12}$ alkyldiyl)-N($R^5$)$_2$;
—($C_3$-$C_{12}$ carbocyclyl)-N$R^5$—C(═N$R^5$)N$R^5$—*;
—($C_6$-$C_{20}$ aryl);
—($C_6$-$C_{20}$ aryl)-*;
—($C_6$-$C_{20}$ aryldiyl)-N($R^5$)—*;
—($C_6$-$C_{20}$ aryldiyl)-($C_1$-$C_{12}$ alkyldiyl)-N($R^5$)—*;
—($C_6$-$C_{20}$ aryldiyl)-($C_1$-$C_{12}$ alkyldiyl)-N($R^5$)$_2$;
—($C_6$-$C_{20}$ aryldiyl)-($C_1$-$C_{12}$ alkyldiyl)-N$R^5$—C(═N$R^{5a}$)N($R^5$)—*;
—($C_2$-$C_{20}$ heterocyclyl);
—($C_2$-$C_{20}$ heterocyclyl)-*;
—($C_2$-$C_9$ heterocyclyl)-($C_1$-$C_{12}$ alkyldiyl)-N$R^5$—*;
—($C_2$-$C_9$ heterocyclyl)-($C_1$-$C_{12}$ alkyldiyl)-N($R^5$)$_2$;
—($C_2$-$C_9$ heterocyclyl)-N$R^5$—C(═N$R^{5a}$)N$R^5$—*;
—($C_1$-$C_{20}$ heteroaryl);
—($C_1$-$C_{20}$ heteroaryl)-*;
—($C_1$-$C_{20}$ heteroaryl)-($C_1$-$C_{12}$ alkyldiyl)-N($R^5$)—*;
—($C_1$-$C_{20}$ heteroaryl)-($C_1$-$C_{12}$ alkyldiyl)-N($R^5$)$_2$;
—($C_1$-$C_{20}$ heteroaryl)-N$R^5$—C(═N$R^{5a}$)N($R^5$)—*;
—C(═O)—*;
—C(═O)—($C_2$-$C_{20}$ heterocyclyldiyl)-*;
—C(═O)N($R^5$)$_2$;
—C(═O)N($R^5$)—*;
—C(═O)N($R^5$)—($C_1$-$C_{12}$ alkyldiyl)-N($R^5$)C(═O)$R^5$;
—C(═O)N($R^5$)—($C_1$-$C_{12}$ alkyldiyl)-N($R^5$)C(═O)N($R^5$)$_2$;
—C(═O)N$R^5$—($C_1$-$C_{12}$ alkyldiyl)-N($R^5$)$CO_2R^5$;
—C(═O)N$R^5$—($C_1$-$C_{12}$ alkyldiyl)-N($R^5$)C(═N$R^{5a}$)N($R^5$)$_2$;
—C(═O)N$R^5$—($C_1$-$C_{12}$ alkyldiyl)-N$R^5$C(═N$R^{5a}$)$R^5$;
—C(═O)N$R^5$—($C_1$-$C_8$ alkyldiyl)-N$R^5$($C_2$-$C_5$ heteroaryl);
—C(═O)N$R^5$—($C_1$-$C_{20}$ heteroaryldiyl)-N($R^5$)—*;
—C(═O)N$R^5$—($C_1$-$C_{20}$ heteroaryldiyl)-*;
—C(═O)N$R^5$—($C_1$-$C_{20}$ heteroaryldiyl)-($C_1$-$C_{12}$ alkyldiyl)-N($R^5$)$_2$;
—C(═O)N$R^5$—($C_1$-$C_{20}$ heteroaryldiyl)-($C_2$-$C_{20}$ heterocyclyldiyl)-C(═O)N$R^5$—($C_1$-$C_{12}$ alkyldiyl)-N$R^5$—*;
—N($R^5$)$_2$;
—N($R^5$)—*;
—N($R^5$)C(═O)$R^5$;
—N($R^5$)C(═O)—*;
—N($R^5$)C(═O)N($R^5$)$_2$;
—N($R^5$)C(═O)N($R^5$)—*;
—N($R^5$)$CO_2R^5$;
—N$R^5$C(═N$R^{5a}$)N($R^5$)$_2$;
—N$R^5$C(═N$R^{5a}$)N($R^5$)—*;
—N$R^5$C(═N$R^{5a}$)$R^5$;
—N($R^5$)—($C_2$-$C_5$ heteroaryl);
—O—($C_1$-$C_{12}$ alkyl);
—O—($C_1$-$C_{12}$ alkyldiyl)-N($R^5$)$_2$;
—O—($C_1$-$C_{12}$ alkyldiyl)-N($R^5$)—*;
—S(═O)$_2$—($C_2$-$C_{20}$ heterocyclyldiyl)-*;
—S(═O)$_2$—($C_2$-$C_{20}$ heterocyclyldiyl)-($C_1$-$C_{12}$ alkyldiyl)-N($R^5$)$_2$;
—S(═O)$_2$—($C_2$-$C_{20}$ heterocyclyldiyl)-($C_1$-$C_{12}$ alkyldiyl)-N$R^5$—*; and
—S(═O)$_2$—($C_2$-$C_{20}$ heterocyclyldiyl)-($C_1$-$C_{12}$ alkyldiyl)-OH;

or $R^2$ and $R^3$ together form a 5- or 6-membered heterocyclyl ring;

$X^1$, $X^2$, $X^3$, and $X^4$ are independently selected from the group consisting of a bond, C(═O), C(═O)N($R^5$), O, N($R^5$), S, $S(O)_2$, and $S(O)_2N(R^5)$;

$R^5$ is selected from the group consisting of H, $C_6$-$C_{20}$ aryl, $C_6$-$C_{20}$ aryldiyl, $C_1$-$C_{12}$ alkyl, and $C_1$-$C_{12}$ alkyldiyl, or two $R^5$ groups together form a 5- or 6-membered heterocyclyl ring;

$R^{5a}$ is selected from the group consisting of $C_6$-$C_{20}$ aryl and $C_1$-$C_{20}$ heteroaryl;

where the asterisk * indicates the attachment site of L, and where one of $R^1$, $R^2$, $R^3$ and $R^4$ is attached to L;

L is the linker selected from the group consisting of:

Q-C(═O)—(PEG)-;

Q-C(═O)—(PEG)-C(═O)—;

Q-C(═O)—(PEG)-O—;

Q-C(═O)—(PEG)-C(═O)—(PEP)—;

Q-C(═O)—(PEG)-C(═O)N($R^5$)—($C_1$-$C_{12}$ alkyldiyl)-;

Q-C(═O)—(PEG)-C(═O)N($R^5$)—($C_1$-$C_{12}$ alkyldiyl)-N($R^5$)C(═O)—($C_2$-$C_5$ monoheterocyclyldiyl)-;

Q-C(═O)—(PEG)-C(═O)N($R^5$)—($C_1$-$C_{12}$ alkyldiyl)-(MCgluc)-;

Q-C(═O)—(PEG)-C(═O)-(MCgluc)-;

Q-C(═O)—(PEG)-C(═O)—(PEP)—N($R^5$)—($C_1$-$C_{12}$ alkyldiyl)-;

Q-C(═O)—(PEG)-C(═O)—(PEP)—N($R^5$)—($C_1$-$C_{12}$ alkyldiyl)-N($R^5$)C(═O)—($C_2$-$C_5$ monoheterocyclyldiyl)-;

Q-C(═O)—(PEG)-N($R^5$)—;

Q-C(═O)—(PEG)-N($R^5$)—(PEG)-C(═O)—(PEP)—;

Q-C(═O)—(PEG)-$N^+(R^5)_2$—(PEG)-C(═O)—(PEP)—;

Q-C(═O)—(PEG)-C(═O)—N($R^5$)CH($AA_1$)C(═O)—(PEG)-C(═O)—(PEP)—;

Q-C(═O)—(PEG)-C(═O)—N($R^5$)CH($AA_1$)C(═O)—N($R^5$)—($C_1$-$C_{12}$ alkyldiyl)-;

Q-C(═O)—(PEG)-SS—($C_1$-$C_{12}$ alkyldiyl)-OC(═O)—;

Q-C(═O)—(PEG)-SS—($C_1$-$C_{12}$ alkyldiyl)-C(═O)—;

Q-C(═O)—($C_1$-$C_{12}$ alkyldiyl)-C(═O)—(PEP)—;

Q-C(═O)—($C_1$-$C_{12}$ alkyldiyl)-C(═O)—(PEP)—N($R^5$)—($C_1$-$C_{12}$ alkyldiyl)-;

Q-C(═O)—($C_1$-$C_{12}$ alkyldiyl)-C(═O)—(PEP)—N($R^5$)—($C_1$-$C_{12}$ alkyldiyl)-N($R^5$)—C(═O);

Q-C(═O)—($C_1$-$C_{12}$ alkyldiyl)-C(═O)—(PEP)—N($R^5$)—($C_1$-$C_{12}$ alkyldiyl)-N($R^5$)C(═O)—($C_2$-$C_5$ monoheterocyclyldiyl)-;

Q-C(═O)—$CH_2CH_2OCH_2CH_2$—($C_1$-$C_{20}$ heteroaryldiyl)-$CH_2O$—(PEG)-C(═O)-(MCgluc)-;

Q-C(═O)—$CH_2CH_2OCH_2CH_2$—($C_1$-$C_{20}$ heteroaryldiyl)-$CH_2O$—(PEG)-C(═O)-(MCgluc)-N($R^5$)—($C_1$-$C_{12}$ alkyldiyl)-N($R^5$)C(═O)—($C_2$-$C_5$ monoheterocyclyldiyl)-; and Q-$(CH_2)_m$—C(═O)—(PEP)—N($R^5$)—($C_1$-$C_{12}$ alkyldiyl)-N($R^5$)C(═O)—($C_2$-$C_5$ monoheterocyclyldiyl)-;

where PEG has the formula: —$(CH_2CH_2O)_n$—$(CH_2)_m$—; m is an integer from 1 to 5, and n is an integer from 2 to 50;

PEP has the formula:

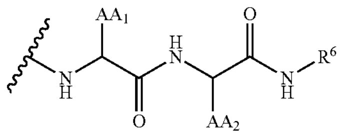

where $AA_1$ and $AA_2$ are independently selected from an amino acid side chain, or $AA_1$ or $AA_2$ and an adjacent nitrogen atom form a 5-membered ring proline amino acid, and the wavy line indicates a point of attachment and;

$R^6$ is selected from the group consisting of $C_6$-$C_{20}$ aryldiyl and $C_1$-$C_{20}$ heteroaryldiyl, substituted with —$CH_2O$—C(═O)— and optionally with:

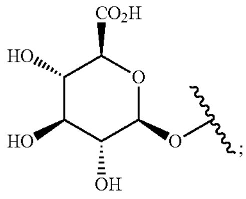 [SMILES: *O[C@@H]1O[C@H](C(=O)O)[C@@H](O)[C@H](O)[C@H]1O]

;

and

MCgluc is selected from the groups:

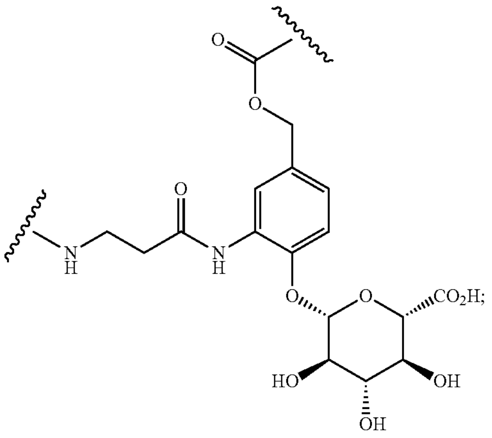

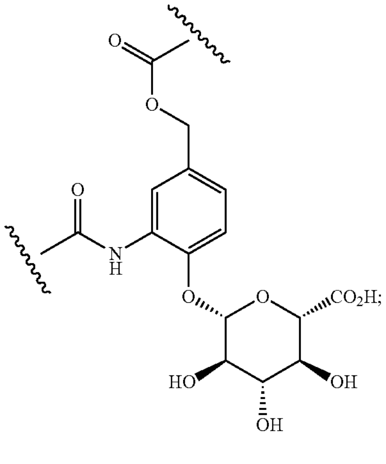

and

-continued

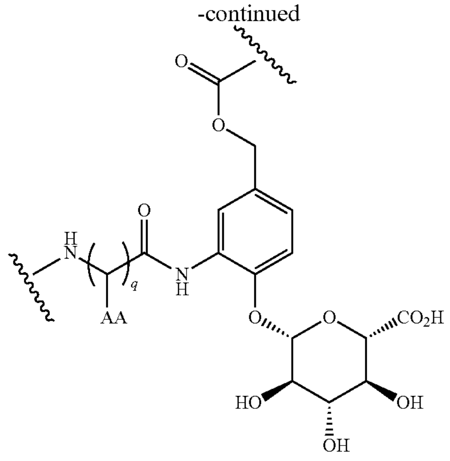

where q is 1 to 8, and AA is an amino acid side chain; and

Q is selected from the group consisting of N-hydroxysuccinimidyl, N-hydroxysulfosuccinimidyl, maleimide, and phenoxy substituted with one or more groups independently selected from F, Cl, $NO_2$, and $SO_3^-$;

where alkyl, alkyldiyl, alkenyl, alkenyldiyl, alkynyl, alkynyldiyl, aryl, aryldiyl carbocyclyl, carbocyclyldiyl, heterocyclyl, heterocyclyldiyl, heteroaryl, and heteroaryldiyl are optionally substituted with one or more groups independently selected from F, Cl, Br, I, —CN, $—CH_3$, $—CH_2CH_3$, $—CH{=}CH_2$, $—C{\equiv}CH$, $—C{\equiv}CCH_3$, $—CH_2CH_2CH_3$, $—CH(CH_3)_2$, $—CH_2CH(CH_3)_2$, $—CH_2OH$, $—CH_2OCH_3$, $—CH_2CH_2OH$, $—C(CH_3)_2OH$, $—CH(OH)CH(CH_3)_2$, $—C(CH_3)_2CH_2OH$, $—CH_2CH_2SO_2CH_3$, $—CH_2OP(O)(OH)_2$, $—CH_2F$, $—CHF_2$, $—CF_3$, $—CH_2CF_3$, $—CH_2CHF_2$, $—CH(CH_3)CN$, $—C(CH_3)_2CN$, $—CH_2CN$, $—CH_2NH_2$, $—CH_2NHSO_2CH_3$, $—CH_2NHCH_3$, $—CH_2N(CH_3)_2$, $—CO_2H$, $—COCH_3$, $—CO_2CH_3$, $—CO_2C(CH_3)_3$, $—COCH(OH)CH_3$, $—CONH_2$, $—CONHCH_3$, $—CON(CH_3)_2$, $—C(CH_3)_2CONH_2$, $—NH_2$, $—NHCH_3$, $—N(CH_3)_2$, $—NHCOCH_3$, $—N(CH_3)COCH_3$, $—NHS(O)_2CH_3$, $—N(CH_3)C(CH_3)_2CONH_2$, $—N(CH_3)CH_2CH_2S(O)_2CH_3$, $—NHC({=}NH)H$, $—NHC({=}NH)CH_3$, $—NHC({=}NH)NH_2$, $—NHC({=}O)NH_2$, $—NO_2$, $={O}$, —OH, $—OCH_3$, $—OCH_2CH_3$, $—OCH_2CH_2OCH_3$, $—OCH_2CH_2OH$, $—OCH_2CH_2N(CH_3)_2$, $—O(CH_2CH_2O)_n—(CH_2)_mCO_2H$, $—O(CH_2CH_2O)_nH$, $—OP(O)(OH)_2$, $—S(O)_2N(CH_3)_2$, $—SCH_3$, $—S(O)_2CH_3$, and $—S(O)_3H$.

An exemplary embodiment of the aminobenzazepine-linker compound of Formula II includes wherein PEP is selected from the groups:

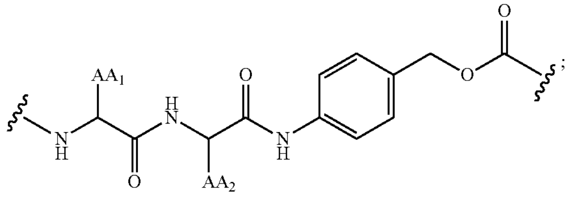

-continued

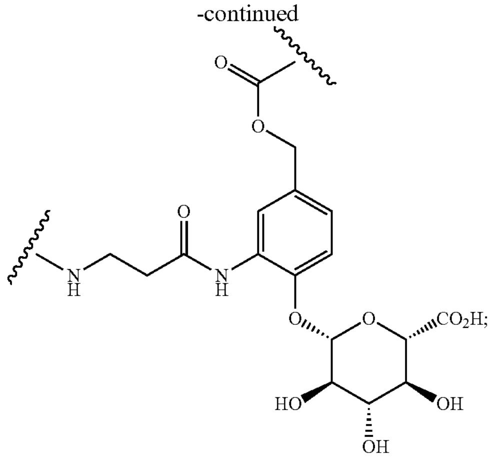

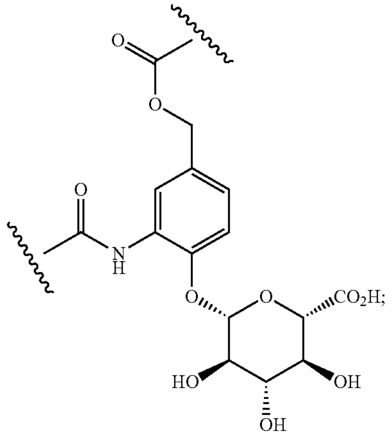

and

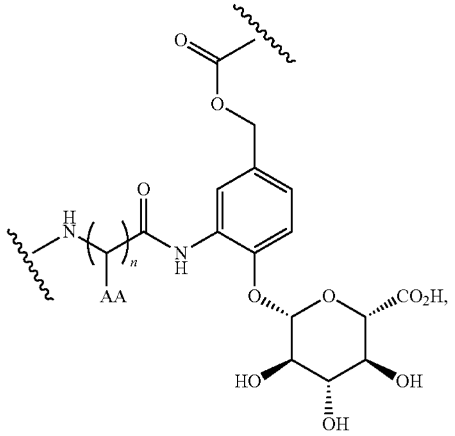

where n is 1 or more, and AA is an amino acid side chain.

An exemplary embodiment of the aminobenzazepine-linker compound of Formula II includes wherein each $AA_1$ and $AA_2$ are independently selected from a side chain of a naturally-occurring amino acid.

An exemplary embodiment of the aminobenzazepine-linker compound of Formula II includes wherein $AA_1$ and $AA_2$ are independently selected from H, $—CH_3$, $—CH(CH_3)_2$, $—CH_2(C_6H_5)$, $—CH_2CH_2CH_2CH_2NH_2$, $—CH_2CH_2CH_2NHC(NH)NH_2$, $—CH_2CH(CH_3)_2$, $—CH_2SO_3H$, and $—CH_2CH_2CH_2NHC(O)NH_2$.

An exemplary embodiment of the aminobenzazepine-linker compound of Formula II includes wherein each $AA_1$ is $—CH(CH_3)_2$, and $AA_2$ is $—CH_2CH_2CH_2NHC(O)NH_2$.

An exemplary embodiment of the aminobenzazepine-linker compound of Formula II includes wherein each $AA_1$ and $AA_2$ are independently selected from GlcNAc aspartic acid, —$CH_2SO_3H$, and —$CH_2OPO_3H$.

An exemplary embodiment of the aminobenzazepine-linker compound of Formula II is selected from Formulas IIa-d:

IIa

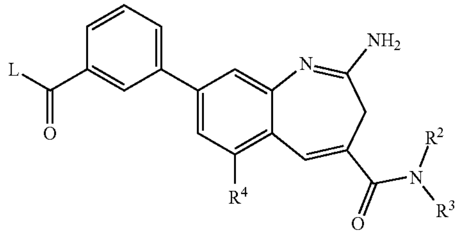

IIb

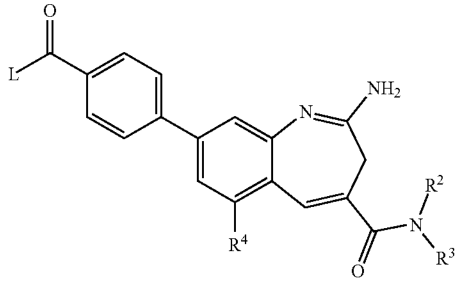

IIc

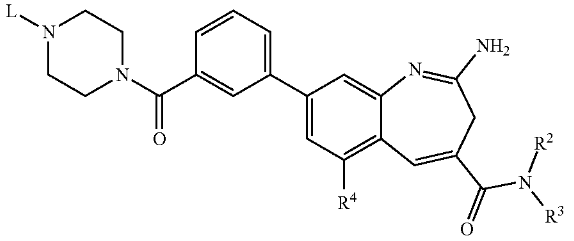

IId

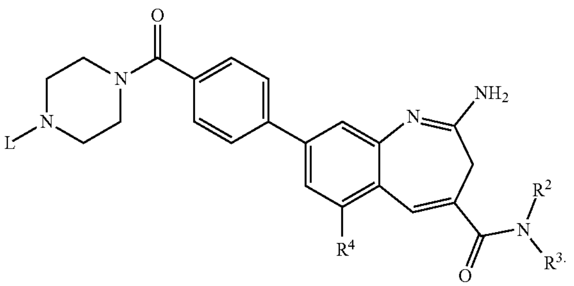

An exemplary embodiment of the aminobenzazepine-linker compound of Formula II is selected from Formulas IIe and IIf:

IIe

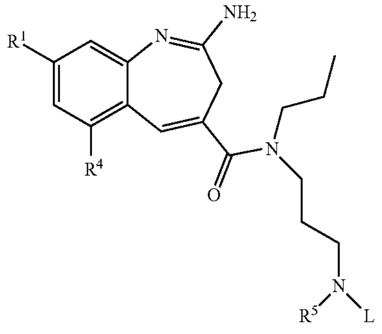

IIf

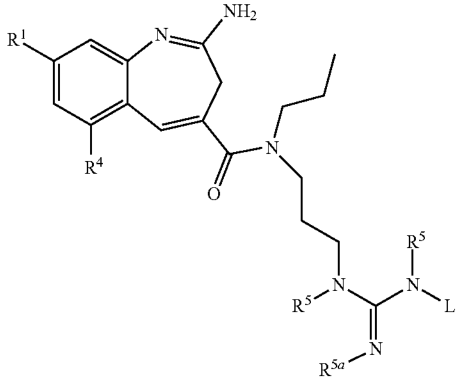

where $R^{5a}$ of formula IIf is phenyl, optionally substituted with one or more groups selected from F, Cl, Br, I, —CN, and —$NO_2$.

An exemplary embodiment of the aminobenzazepine-linker compound of Formula II includes wherein L is Q-C(═O)—(PEG)- or Q-C(═O)—(PEG)-C(═O)—.

An exemplary embodiment of the aminobenzazepine-linker compound of Formula II is selected from Formulas IIg and IIh:

IIg

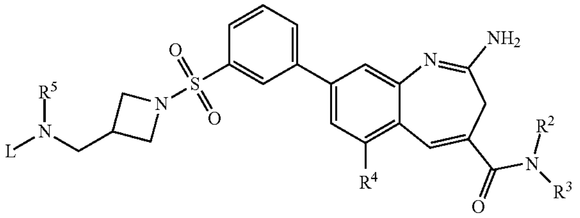

-continued

IIh

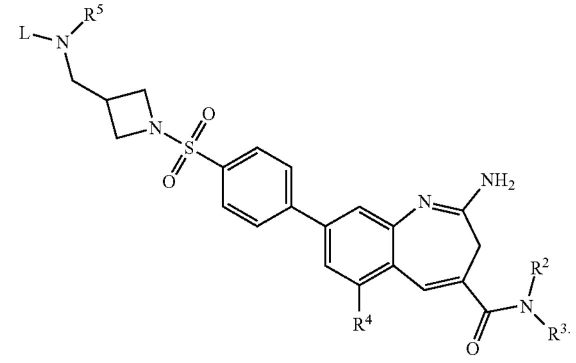

An exemplary embodiment of the aminobenzazepine-linker compound of Formula II includes wherein L is —C(═O)—(PEG)-C(═O)—(PEP)-.

An exemplary embodiment of the aminobenzazepine-linker compound of Formula TT includes wherein $R^2$ and $R^3$ are each $C_1$-$C_8$ alkyl.

An exemplary embodiment of the aminobenzazepine-linker compound of Formula II includes wherein $R^2$ and $R^3$ are each —$CH_2CH_2CH_3$.

An exemplary embodiment of the aminobenzazepine-linker compound of Formula II includes wherein $X^2$ and $X^3$ are each a bond, and $R^2$ or $R^3$ is —O—($C_1$-$C_{12}$ alkyl).

An exemplary embodiment of the aminobenzazepine-linker compound of Formula II includes wherein $X^2$ and $X^3$ are each a bond, and $R^2$ or $R^3$ is —$OCH_2CH_3$.

An exemplary embodiment of the aminobenzazepine-linker compound of Formula II includes wherein one of $R^1$ and $R^4$ is selected from —($C_6$-$C_{20}$ aryldiyl)-S(═O)$_2$—($C_2$-$C_{20}$ heterocyclyldiyl)-($C_1$-$C_{12}$ alkyldiyl)-N($R^5$)$_2$ and —($C_6$-$C_{20}$ aryldiyl)-S(═O)$_2$—($C_2$-$C_{20}$ heterocyclyldiyl)-($C_1$-$C_{12}$ alkyldiyl)-OH.

An exemplary embodiment of the aminobenzazepine-linker compound of Formula II includes wherein $C_6$-$C_{20}$ aryldiyl is phenyldiyl and $C_2$-$C_{20}$ heterocyclyldiyl is azetidindiyl.

An exemplary embodiment of the aminobenzazepine-linker compound of Formula II is selected from the formulas:

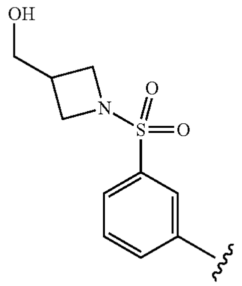

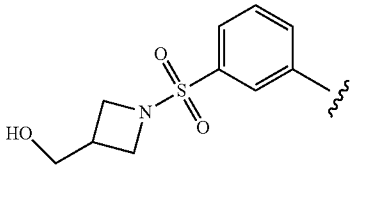

-continued

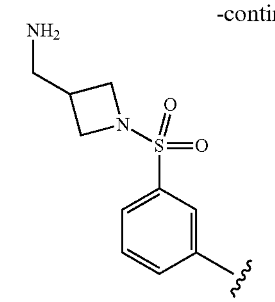

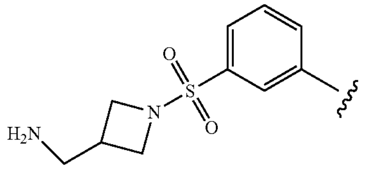.

An exemplary embodiment of the aminobenzazepine-linker compound of Formula II includes wherein one of $R^1$ and $R^4$ is —C(═O)$NR^5$—($C_1$-$C_{20}$ heteroaryldiyl)-($C_2$-$C_{20}$ heterocyclyldiyl)-C(═O)$NR^5$—($C_1$-$C_{12}$ alkyldiyl)-$NR^5$-L.

An exemplary embodiment of the aminobenzazepine-linker compound of Formula II includes wherein $C_1$-$C_{20}$ heteroaryldiyl is pyridindiyl and $C_2$-$C_{20}$ heterocyclyldiyl is piperidinyl.

An exemplary embodiment of the aminobenzazepine-linker compound of Formula II includes wherein Q is selected from:

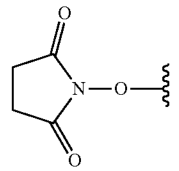,

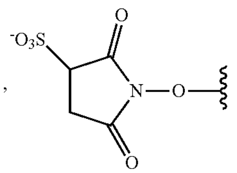,

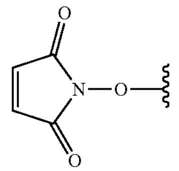,

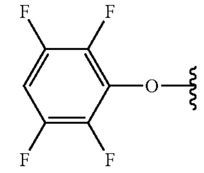,

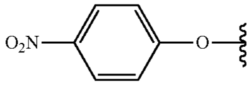,

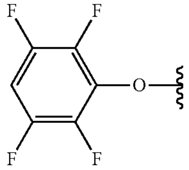, and

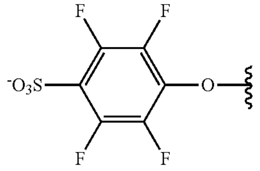.

The invention includes all reasonable combinations, and permutations of the features, of the Formula II embodiments.

An exemplary embodiment of the aminobenzazepine-linker compound of Formula II is selected from the Table 2a, 2b, and 2c compounds. Each compound was synthesized and purified by the methods in the Examples provided herein, characterized by mass spectrometry, and shown to have the mass indicated. The aminobenzazepine-linker compounds of Tables 2a, 2b, and 2c demonstrate the surprising and unexpected property of TLR8 agonist selectivity which may predict useful therapeutic activity to treat cancer and other disorders.

TABLE 2A

Aminobenzazepine-linker Formula II compounds (BzL) and intermediates

| BzL No. | Structure | MW |
|---|---|---|
| BzL-1 | 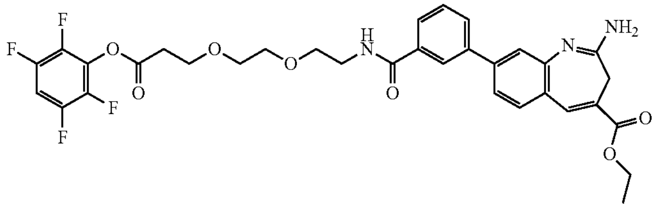 [SMILES: CCOC(=O)C1=Cc2ccc(-c3cccc(C(=O)NCCOCCOCCC(=O)Oc4c(F)c(F)cc(F)c4F)c3)cc2N=C(N)C1] | 657.6 |
| BzL-2 | 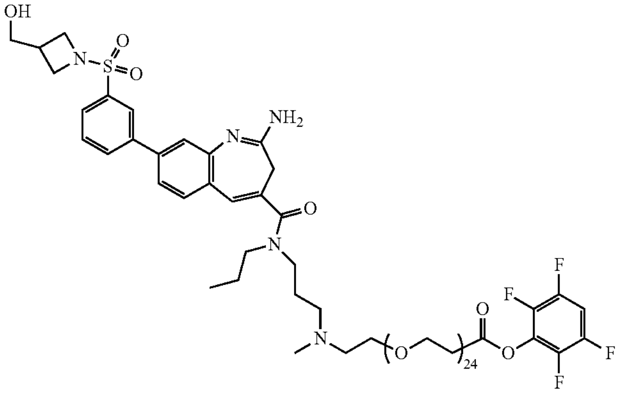 | 1817.1 |
| BzL-3 | 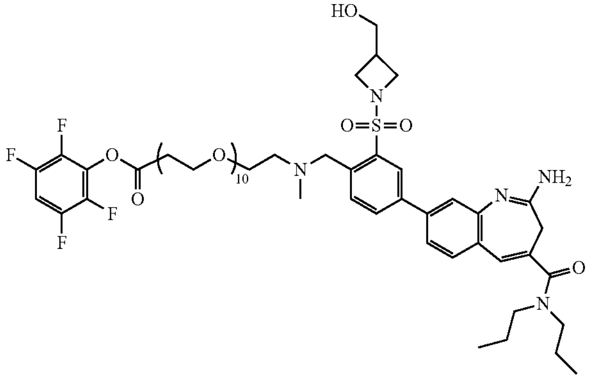 | 1214.4 |
| BzL-4 | 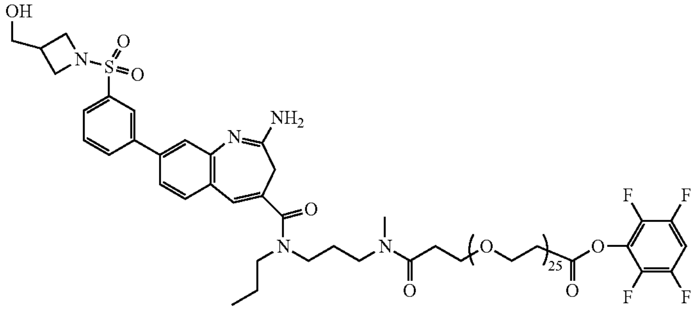 | 1889.1 |

TABLE 2A-continued
| Aminobenzazepine-linker Formula II compounds (BzL) and intermediates | | |
|---|---|---|
| BzL No. | Structure | MW |
| BzL-5 | 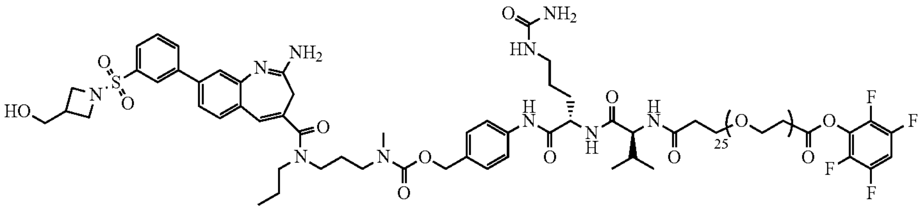 | 2294.6 |
| BzL-6 | 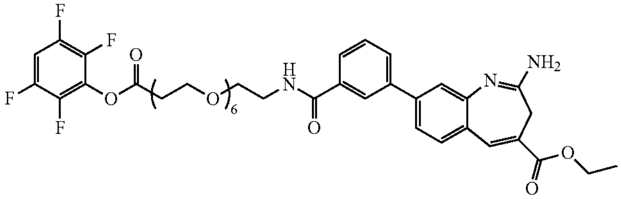 | 833.82 |
| BzL-7 | 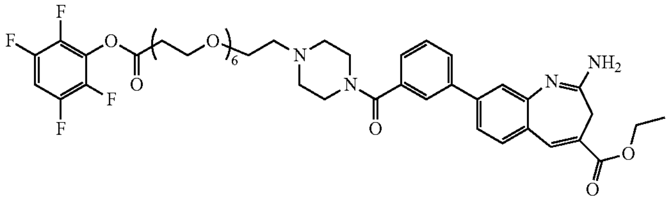 | 902.9 |
| BzL-8 | 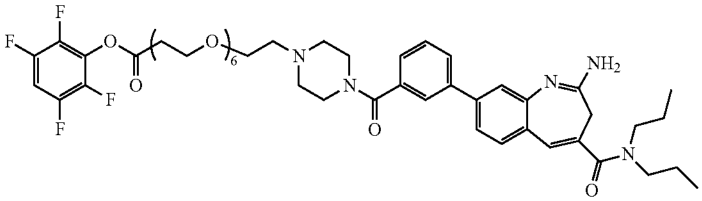 | 958.1 |
| BzL-9 | 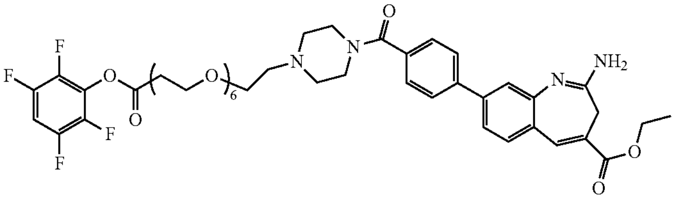 | 958.1 |
| BzL-10 | 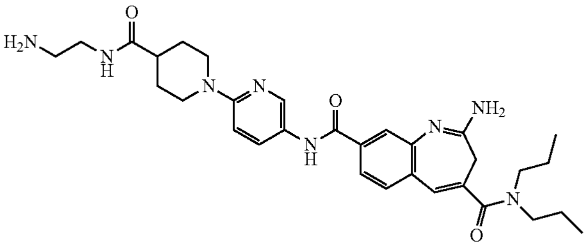 [SMILES: CCCN(CCC)C(=O)C1=Cc2ccc(C(=O)Nc3ccc(N4CCC(C(=O)NCCN)CC4)nc3)cc2N=C(N)C1] | 574.7 |

TABLE 2A-continued
| Aminobenzazepine-linker Formula II compounds (BzL) and intermediates | | |
|---|---|---|
| BzL No. | Structure | MW |
| BzL-11 | 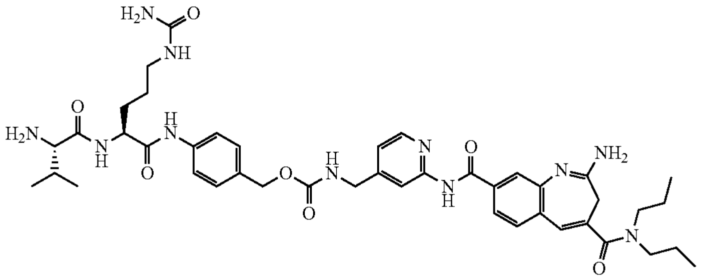 [SMILES: CCCN(CCC)C(=O)C1=Cc2ccc(C(=O)Nc3cc(CNC(=O)OCc4ccc(NC(=O)[C@H](CCCNC(N)=O)NC(=O)[C@@H](N)C(C)C)cc4)ccn3)cc2N=C(N)C1] | 840.0 |
| BzL-12 | 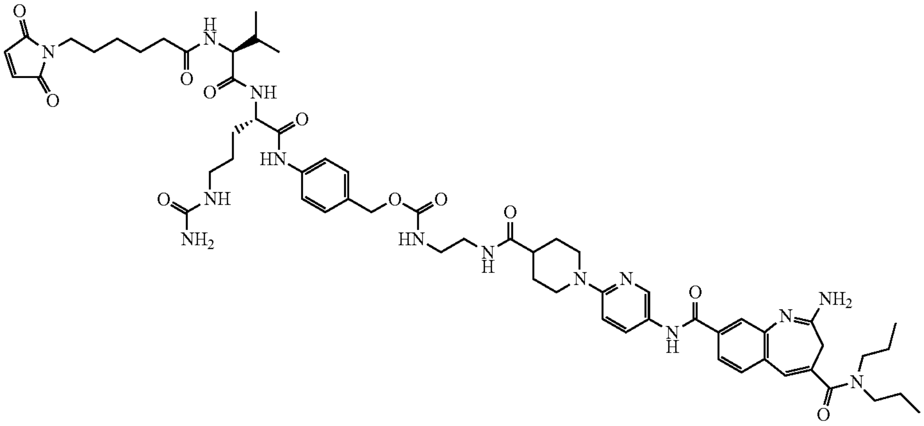 [SMILES: CCCN(CCC)C(=O)C1=Cc2ccc(C(=O)Nc3ccc(N4CCC(C(=O)NCCNC(=O)OCc5ccc(NC(=O)[C@H](CCCNC(N)=O)NC(=O)[C@@H](NC(=O)CCCCCN6C(=O)C=CC6=O)C(C)C)cc5)CC4)nc3)cc2N=C(N)C1] | 1173.4 |
| BzL-13 | 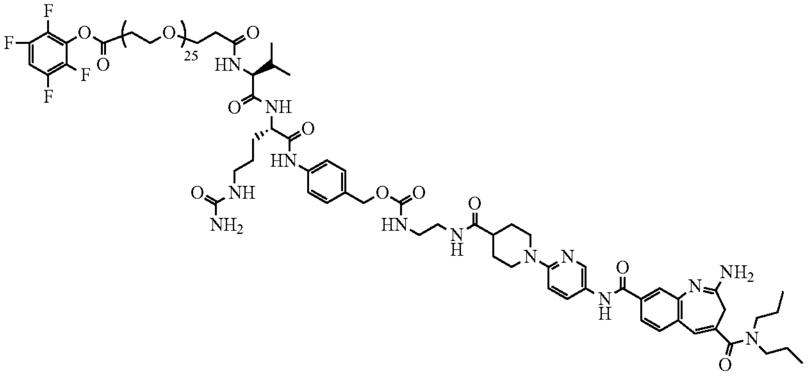 | 2329.6 |
| BzL-14 | 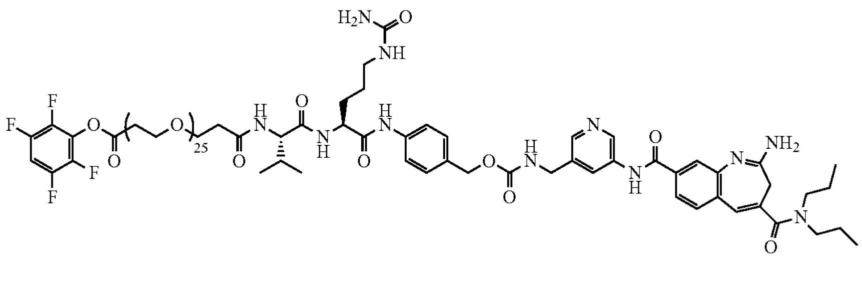 | 2189.4 |

TABLE 2A-continued
Aminobenzazepine-linker Formula II compounds (BzL) and intermediates
| BzL No. | Structure | MW |
| --- | --- | --- |
| BzL-15 | 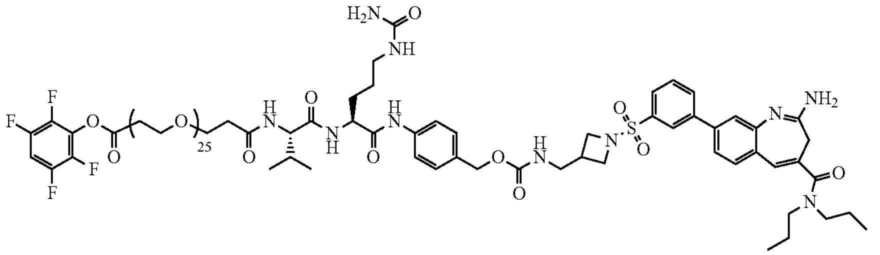 | 2264.6 |
| BzL-16 | 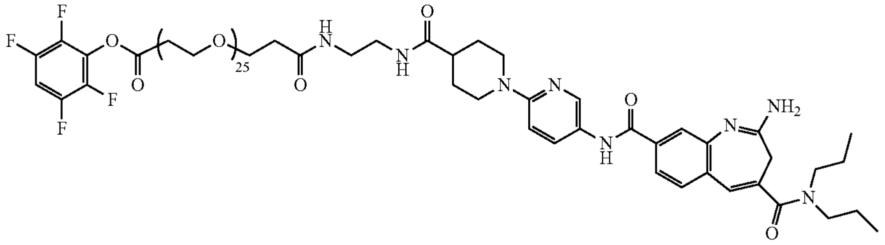 | 1924.2 |
| BzL-17 | 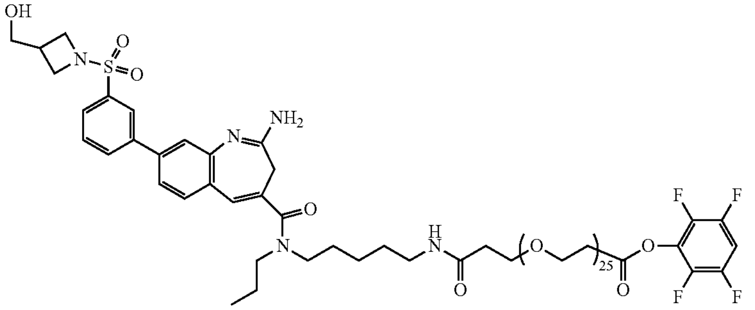 | 1903.2 |
| BzL-18 | 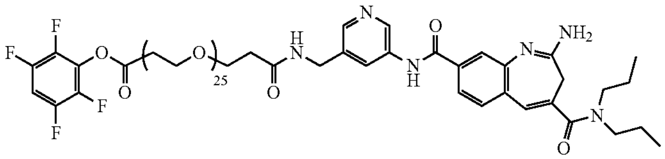 | 1784 |
| BzL-19 | 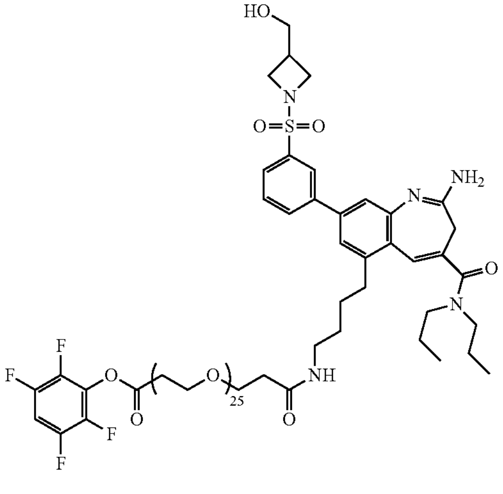 | 1931.2 |

TABLE 2A-continued
Aminobenzazepine-linker Formula II compounds (BzL) and intermediates
| BzL No. | Structure | MW |
|---|---|---|
| BzL-20 | 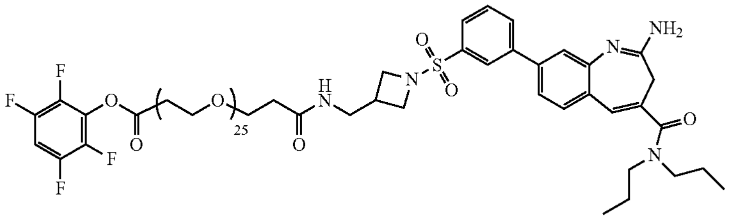 | 1859.1 |
| BzL-21 | 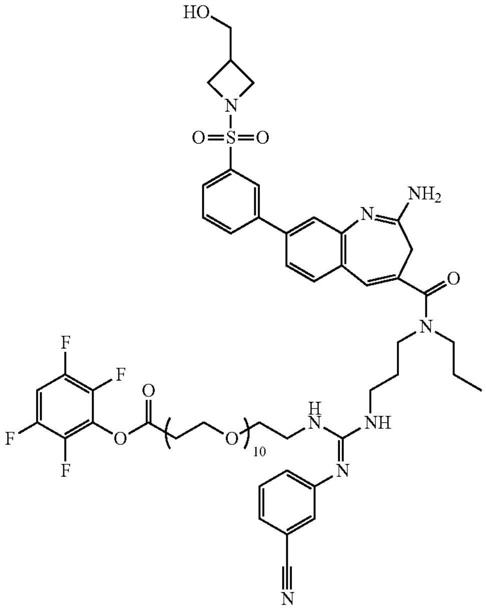 | 1329.5 |
| BzL-22 | 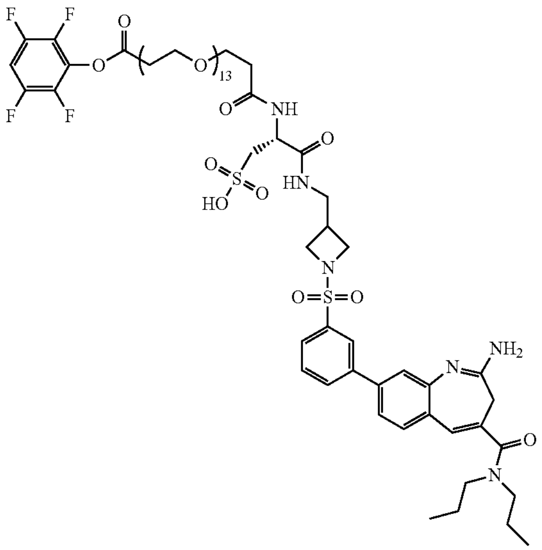 | 1481.6 |

TABLE 2A-continued
| BzL No. | Structure | MW |
|---|---|---|
| Aminobenzazepine-linker Formula II compounds (BzL) and intermediates | | |
| BzL-23 | 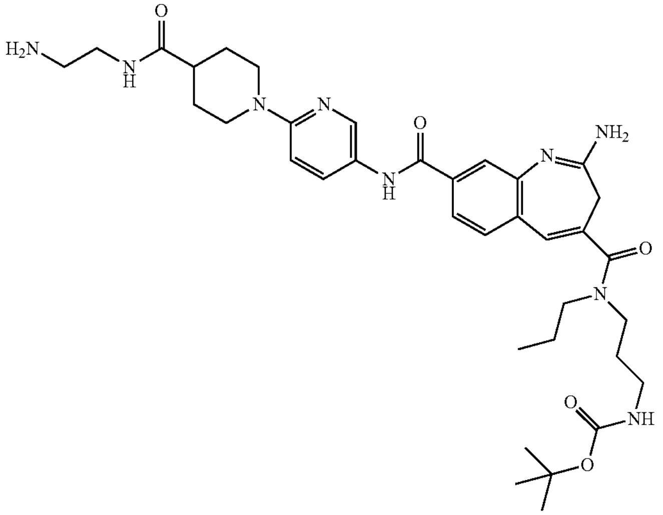 [SMILES: CCCN(CCCNC(=O)OC(C)(C)C)C(=O)C1=Cc2ccc(C(=O)Nc3ccc(N4CCC(C(=O)NCCN)CC4)nc3)cc2N=C(N)C1] | 689.9 |
| BzL-24 | 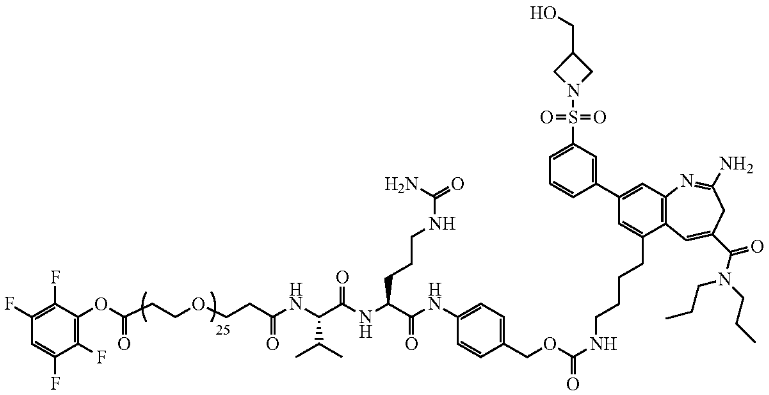 | 2336.7 |
| BzL-25 | 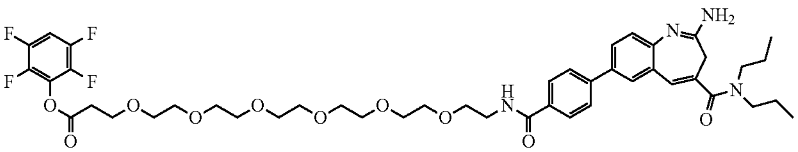 [SMILES: CCCN(CCC)C(=O)C1=Cc2cc(-c3ccc(C(=O)NCCOCCOCCOCCOCCOCCOCCC(=O)Oc4c(F)c(F)cc(F)c4F)cc3)ccc2N=C(N)C1] | 888.95 |
| BzL-26 | 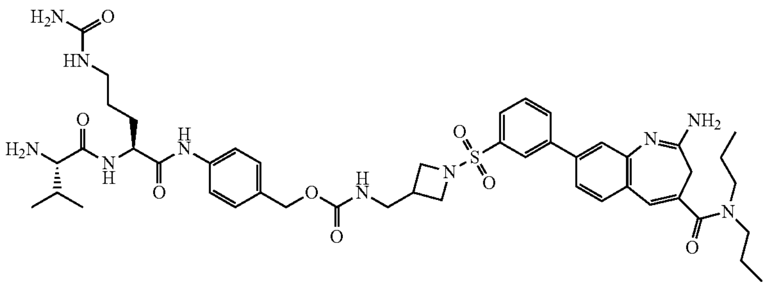 [SMILES: CCCN(CCC)C(=O)C1=Cc2ccc(-c3cccc(S(=O)(=O)N4CC(CNC(=O)OCc5ccc(NC(=O)[C@H](CCCNC(N)=O)NC(=O)[C@@H](N)C(C)C)cc5)C4)c3)cc2N=C(N)C1] | 915.1 |

TABLE 2A-continued
| Aminobenzazepine-linker Formula II compounds (BzL) and intermediates | | |
|---|---|---|
| BzL No. | Structure | MW |
| BzL-27 | 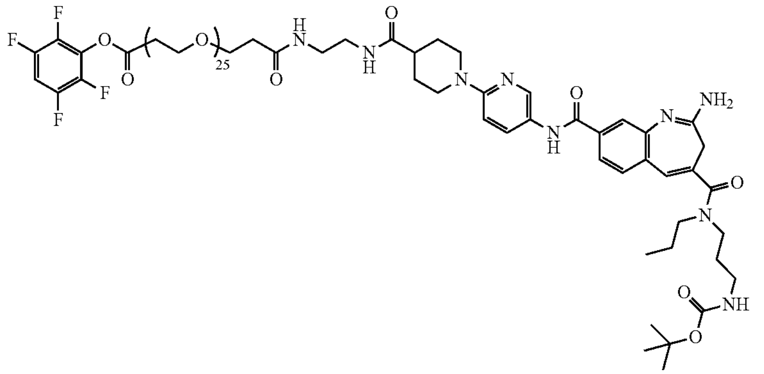 | 2039.3 |
| BzL-28 | 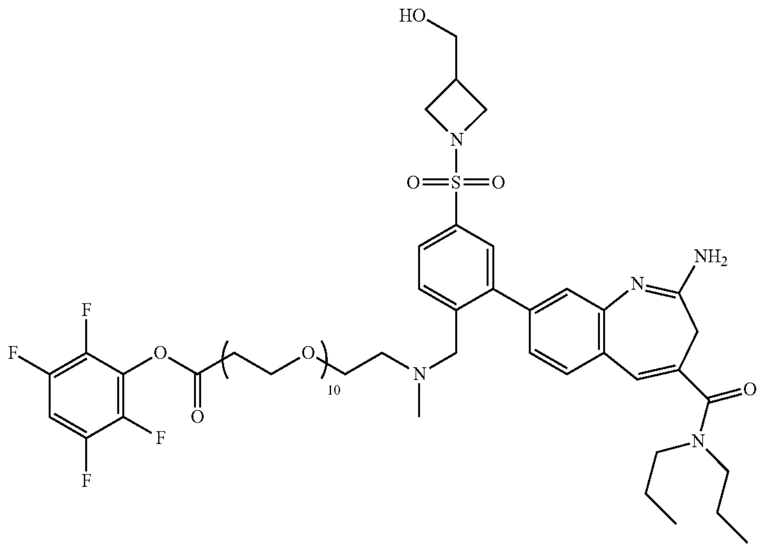 | 1214.4 |
| BzL-29 | 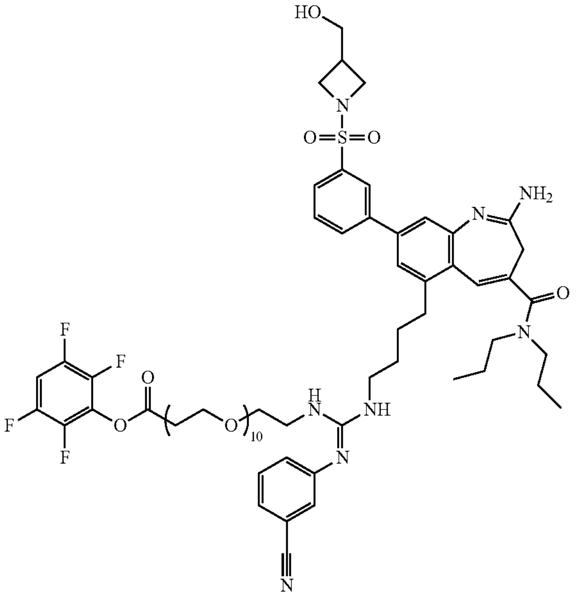 | 1385.6 |

TABLE 2A-continued
| Aminobenzazepine-linker Formula II compounds (BzL) and intermediates | | |
|---|---|---|
| BzL No. | Structure | MW |
| BzL-30 | 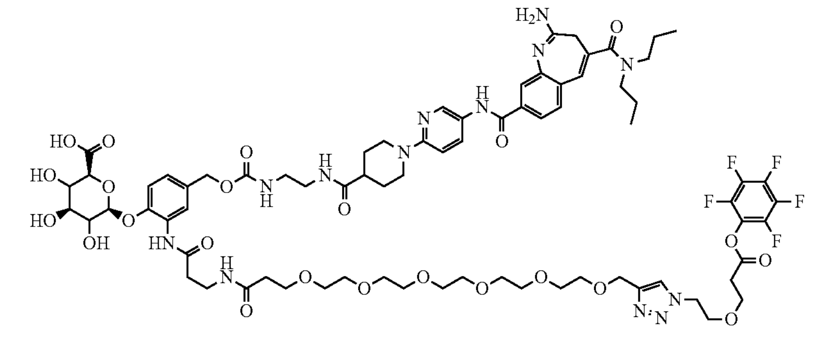 [SMILES: CCCN(CCC)C(=O)C1=Cc2ccc(C(=O)Nc3ccc(N4CCC(C(=O)NCCNC(=O)OCc5ccc(O[C@@H]6O[C@H](C(=O)O)C(O)[C@H](O)C6O)c(NC(=O)CCNC(=O)CCOCCOCCOCCOCCOCCOCc6cn(CCOCCC(=O)Oc7c(F)c(F)c(F)c(F)c7F)nn6)c5)CC4)nc3)cc2N=C(N)C1] | 1642.6 |
| BzL-31 | 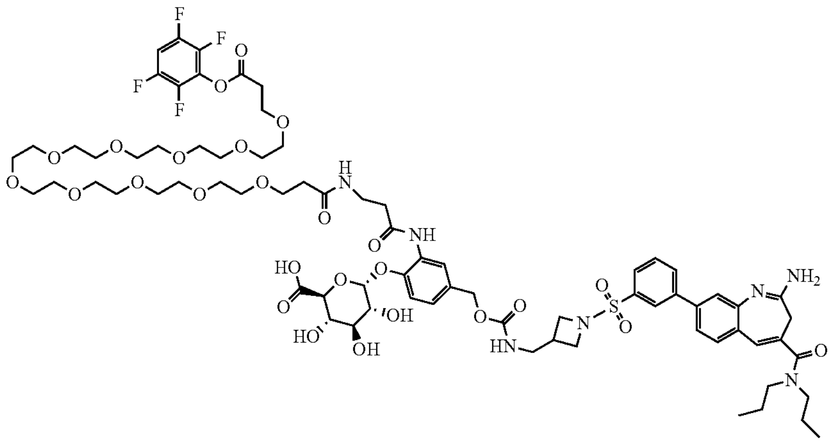 [SMILES: CCCN(CCC)C(=O)C1=Cc2ccc(-c3cccc(S(=O)(=O)N4CC(CNC(=O)OCc5ccc(O[C@H]6O[C@H](C(=O)O)[C@@H](O)[C@H](O)[C@H]6O)c(NC(=O)CCNC(=O)CCOCCOCCOCCOCCOCCOCCOCCOCCOCCOCCC(=O)Oc6c(F)c(F)cc(F)c6F)c5)C4)c3)cc2N=C(N)C1] | 1610.7 |
| BzL-32 | 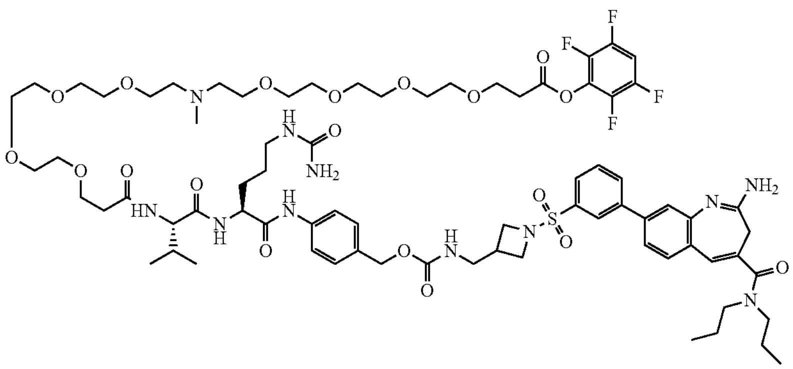 [SMILES: CCCN(CCC)C(=O)C1=Cc2ccc(-c3cccc(S(=O)(=O)N4CC(CNC(=O)OCc5ccc(NC(=O)[C@H](CCCNC(N)=O)NC(=O)[C@@H](NC(=O)CCOCCOCCOCCOCCN(C)CCOCCOCCOCCOCCC(=O)Oc6c(F)c(F)cc(F)c6F)C(C)C)cc5)C4)c3)cc2N=C(N)C1] | 1572.8 |

TABLE 2b
| Aminobenzazepine-linker Formula II compounds (BzL) and intermediates | | |
|---|---|---|
| BzL No. | Structure | MW |
| BzL-33 | 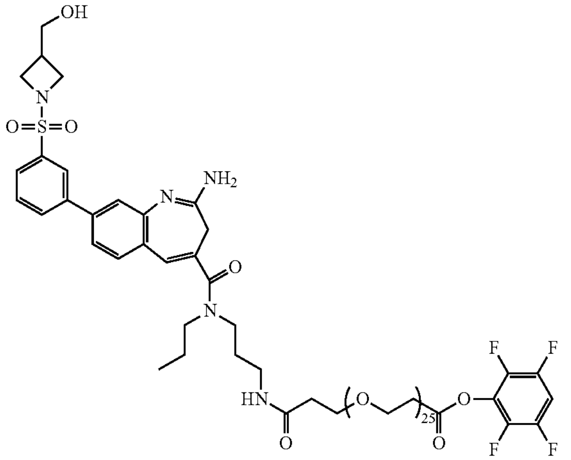 | 1875.1 |
| BzL-34 | 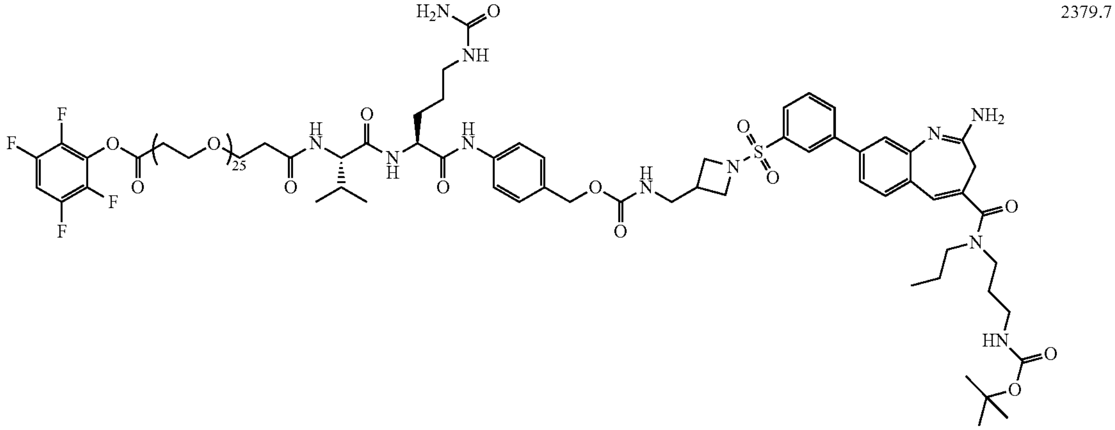 | 2379.7 |
| BzL-35 | 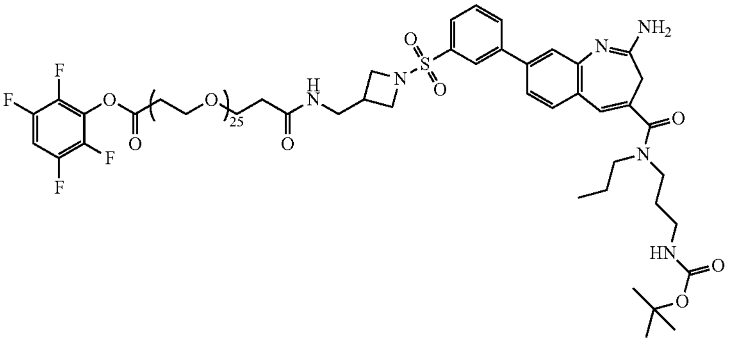 | 1974.2 |
| BzL-36 | 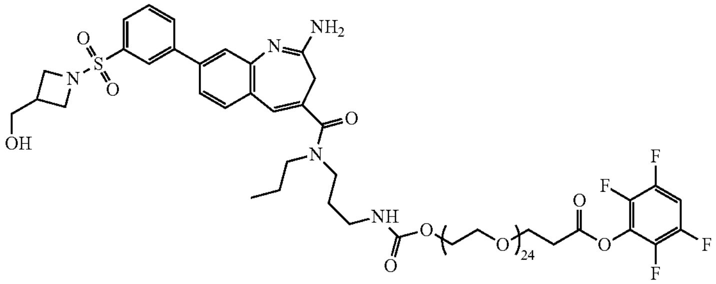 | 1847.1 |

TABLE 2b-continued
| Aminobenzazepine-linker Formula II compounds (BzL) and intermediates | | |
|---|---|---|
| BzL No. | Structure | MW |
| BzL-37 | 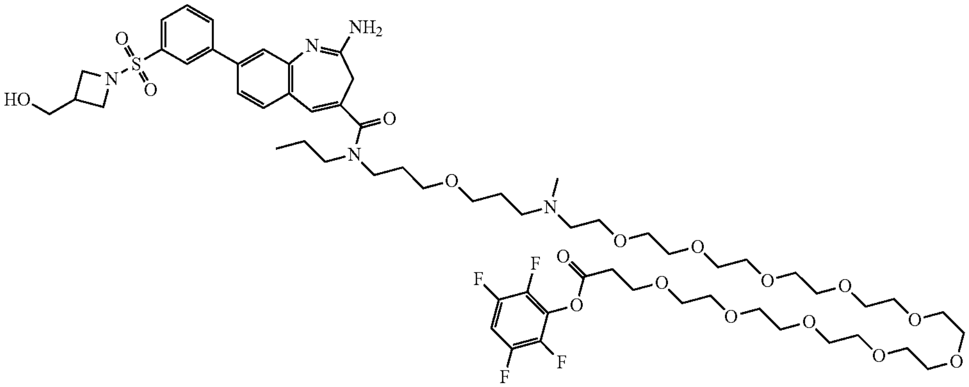 [SMILES: CCCN(CCCOCCCN(C)CCOCCOCCOCCOCCOCCOCCOCCOCCOCCOCCC(=O)Oc1c(F)c(F)cc(F)c1F)C(=O)C1=Cc2ccc(-c3cccc(S(=O)(=O)N4CC(CO)C4)c3)cc2N=C(N)C1] | 1258.4 |
| BzL-38 | 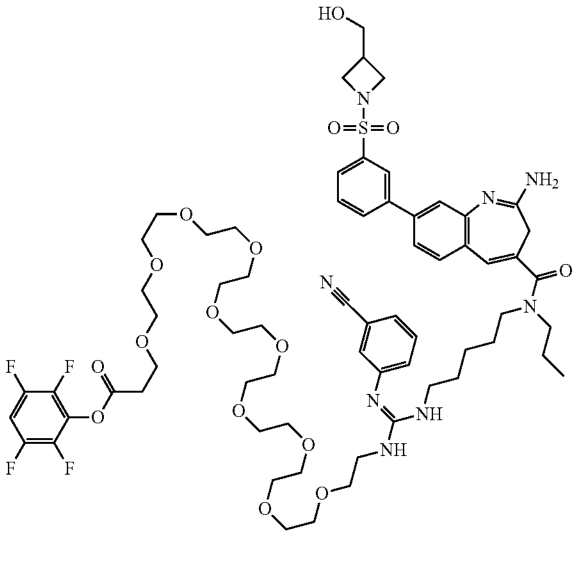 [SMILES: CCCN(CCCCCN/C(=N\c1cccc(C#N)c1)NCCOCCOCCOCCOCCOCCOCCOCCOCCOCCOCCC(=O)Oc1c(F)c(F)cc(F)c1F)C(=O)C1=Cc2ccc(-c3cccc(S(=O)(=O)N4CC(CO)C4)c3)cc2N=C(N)C1] | 1357.5 |

TABLE 2b-continued
| Aminobenzazepine-linker Formula II compounds (BzL) and intermediates | | |
|---|---|---|
| BzL No. | Structure | MW |
| BzL-39 | 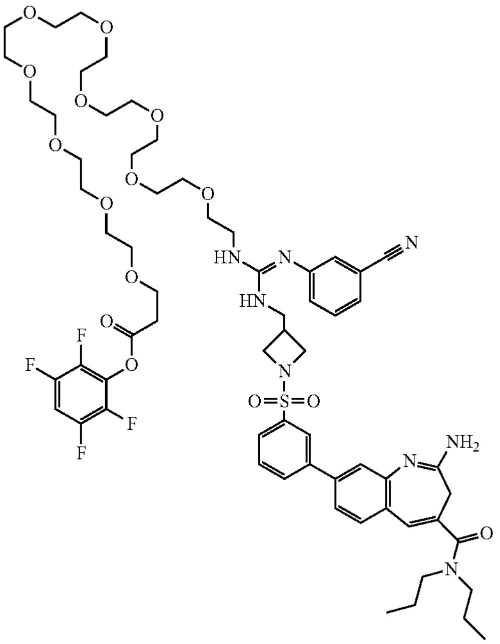 [SMILES: CCCN(CCC)C(=O)C1=Cc2ccc(-c3cccc(S(=O)(=O)N4CC(CN/C(=N\c5cccc(C#N)c5)NCCOCCOCCOCCOCCOCCOCCOCCOCCOCCOCCC(=O)Oc5c(F)c(F)cc(F)c5F)C4)c3)cc2N=C(N)C1] | 1313.5 |
| BzL-40 | 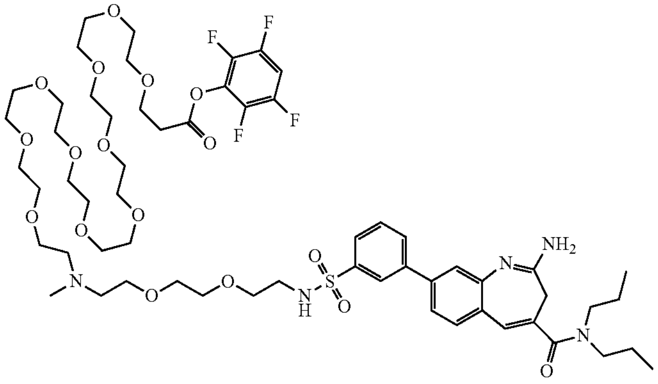 [SMILES: CCCN(CCC)C(=O)C1=Cc2ccc(-c3cccc(S(=O)(=O)NCCOCCOCCN(C)CCOCCOCCOCCOCCOCCOCCOCCOCCOCCOCCC(=O)Oc4c(F)c(F)cc(F)c4F)c3)cc2N=C(N)C1] | 1246.4 |
| BzL-41 | 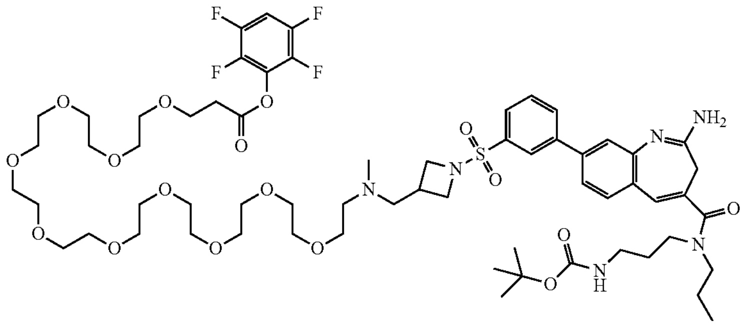 [SMILES: CCCN(CCCNC(=O)OC(C)(C)C)C(=O)C1=Cc2ccc(-c3cccc(S(=O)(=O)N4CC(CN(C)CCOCCOCCOCCOCCOCCOCCOCCOCCOCCOCCC(=O)Oc5c(F)c(F)cc(F)c5F)C4)c3)cc2N=C(N)C1] | 1299.5 |

TABLE 2b-continued
Aminobenzazepine-linker Formula II compounds (BzL) and intermediates
| BzL No. | Structure | MW |
|---|---|---|
| BzL-42 | 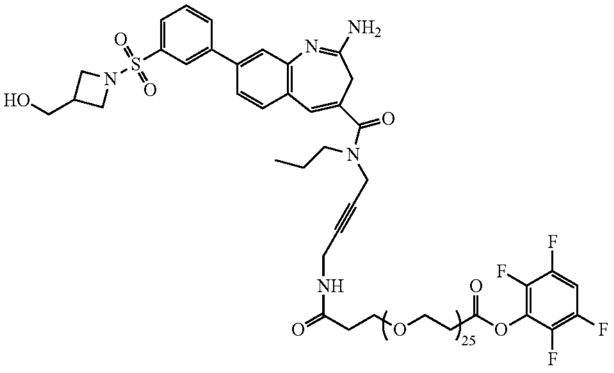 | 1885.1 |
| BzL-43 | 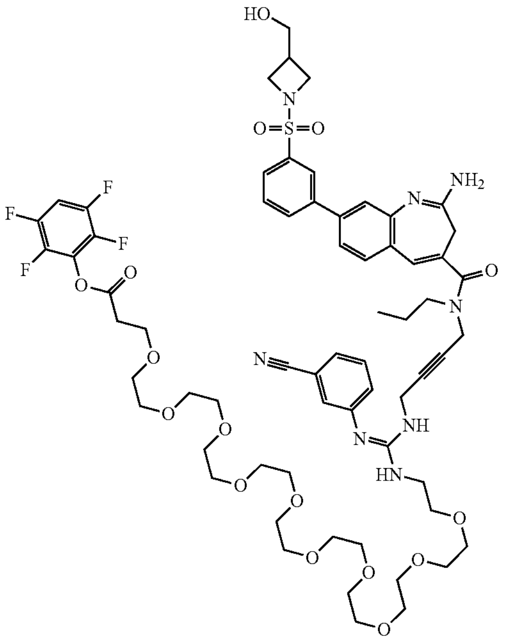 [SMILES: CCCN(CC#CCN/C(=N\c1cccc(C#N)c1)NCCOCCOCCOCCOCCOCCOCCOCCOCCOCCOCCC(=O)Oc1c(F)c(F)cc(F)c1F)C(=O)C1=Cc2ccc(-c3cccc(S(=O)(=O)N4CC(CO)C4)c3)cc2N=C(N)C1] | 1339.5 |
| BzL-44 | 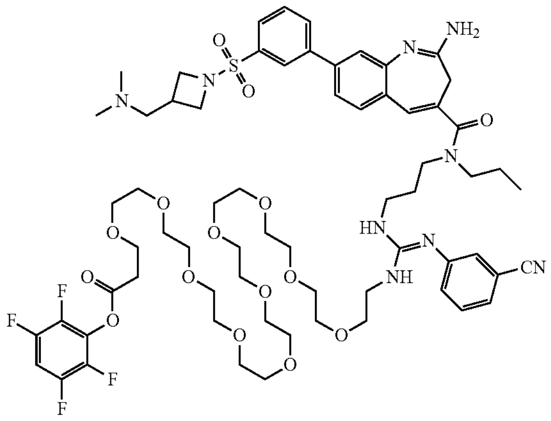 [SMILES: CCCN(CCCN/C(=N/c1cccc(C#N)c1)NCCOCCOCCOCCOCCOCCOCCOCCOCCOCCOCCC(=O)Oc1c(F)c(F)cc(F)c1F)C(=O)C1=Cc2ccc(-c3cccc(S(=O)(=O)N4CC(CN(C)C)C4)c3)cc2N=C(N)C1] | 1356.5 |

TABLE 2b-continued
| Aminobenzazepine-linker Formula II compounds (BzL) and intermediates | | |
|---|---|---|
| BzL No. | Structure | MW |
| BzL-45 | 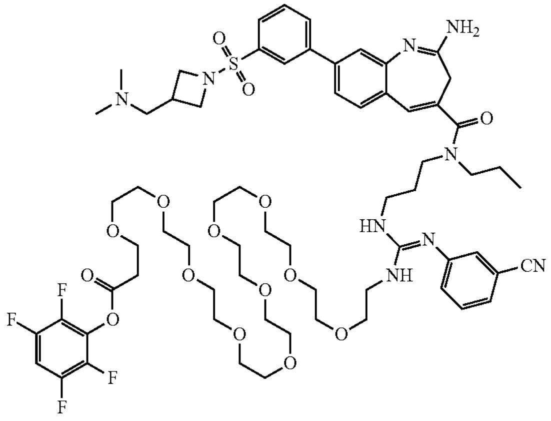 [SMILES: CCCN(CCCN/C(=N/c1cccc(C#N)c1)NCCOCCOCCOCCOCCOCCOCCOCCOCCOCCOCCC(=O)Oc1c(F)c(F)cc(F)c1F)C(=O)C1=Cc2ccc(-c3cccc(S(=O)(=O)N4CC(CN(C)C)C4)c3)cc2N=C(N)C1] | 1210.3 |
| BzL-46 | 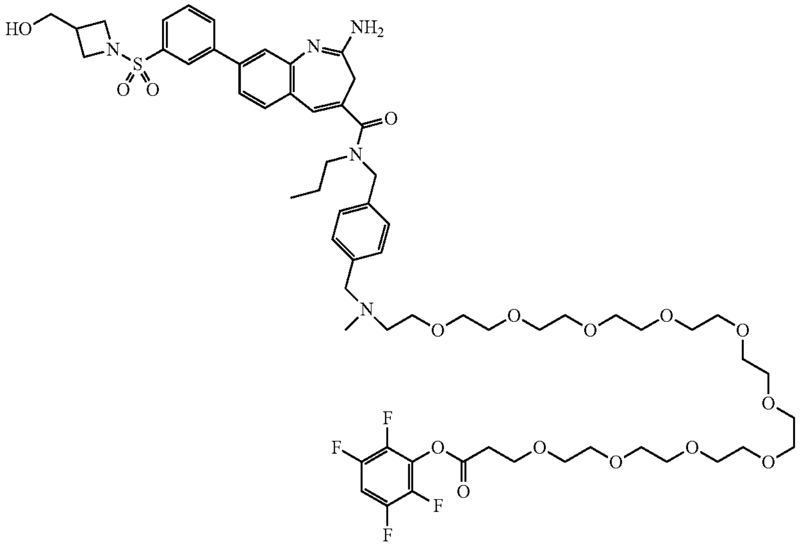 [SMILES: CCCN(Cc1ccc(CN(C)CCOCCOCCOCCOCCOCCOCCOCCOCCOCCOCCC(=O)Oc2c(F)c(F)cc(F)c2F)cc1)C(=O)C1=Cc2ccc(-c3cccc(S(=O)(=O)N4CC(CO)C4)c3)cc2N=C(N)C1] | 1262.4 |

TABLE 2b-continued
| Aminobenzazepine-linker Formula II compounds (BzL) and intermediates | | |
|---|---|---|
| BzL No. | Structure | MW |
| BzL-47 | 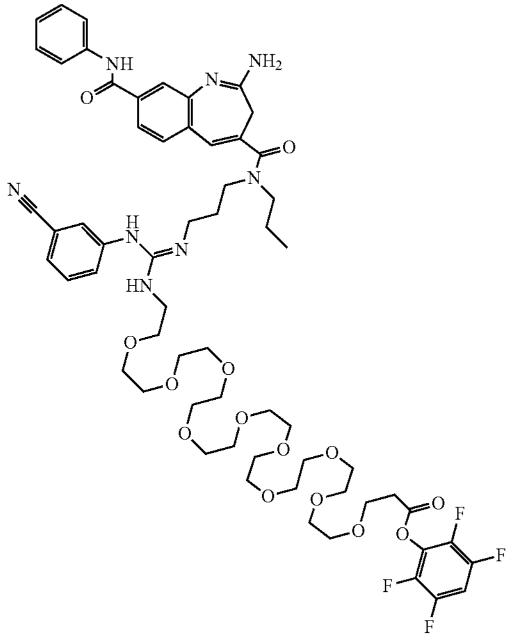 [SMILES: CCCN(CCC/N=C(/NCCOCCOCCOCCOCCOCCOCCOCCOCCOCCOCCC(=O)Oc1c(F)c(F)cc(F)c1F)Nc1cccc(C#N)c1)C(=O)C1=Cc2ccc(C(=O)Nc3ccccc3)cc2N=C(N)C1] | 1223.3 |
| BzL-48 | 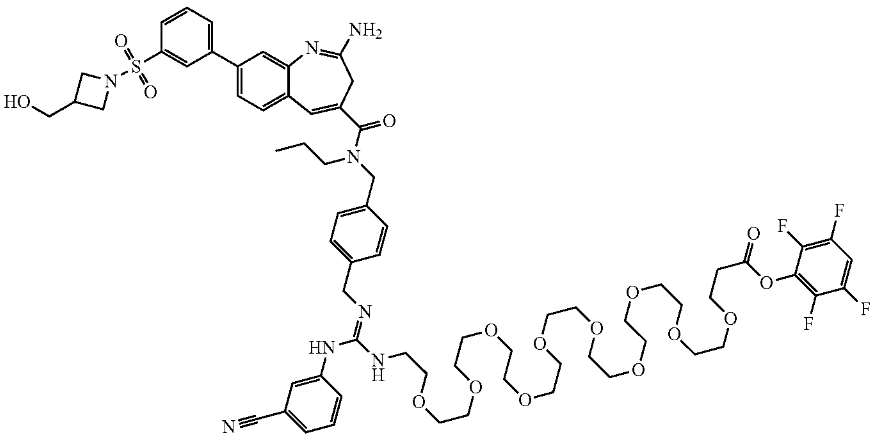 [SMILES: CCCN(Cc1ccc(C/N=C(/NCCOCCOCCOCCOCCOCCOCCOCCOCCOCCOCCC(=O)Oc2c(F)c(F)cc(F)c2F)Nc2cccc(C#N)c2)cc1)C(=O)C1=Cc2ccc(-c3cccc(S(=O)(=O)N4CC(CO)C4)c3)cc2N=C(N)C1] | 1391.5 |

TABLE 2c
| BzL No. | Structure | MW |
|---|---|---|
| | Aminobenzazepine-linker Formula II compounds (BzL) and intermediates | |
| BzL-49 | 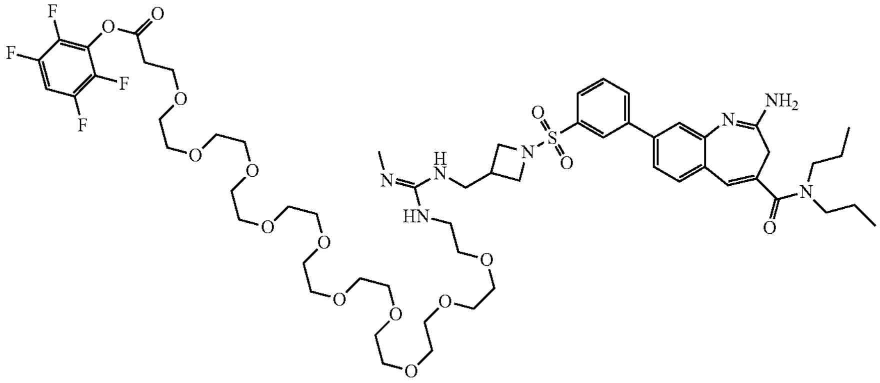 [SMILES: CCCN(CCC)C(=O)C1=Cc2ccc(-c3cccc(S(=O)(=O)N4CC(CN/C(=N\C)NCCOCCOCCOCCOCCOCCOCCOCCOCCOCCOCCC(=O)Oc5c(F)c(F)cc(F)c5F)C4)c3)cc2N=C(N)C1] | 1226.4 |
| BzL-50 | 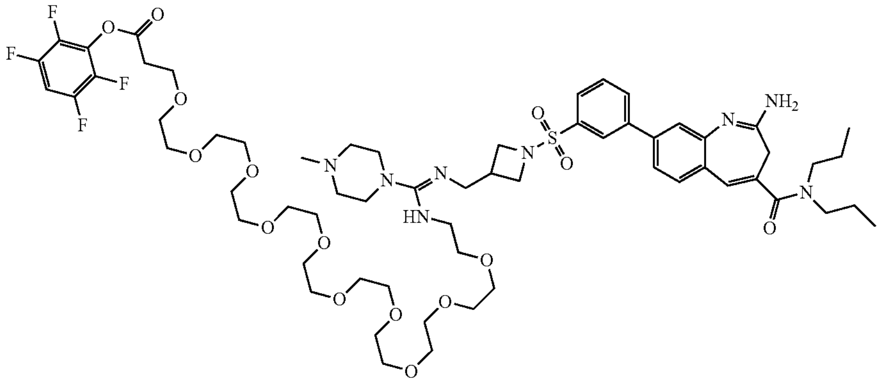 [SMILES: CCCN(CCC)C(=O)C1=Cc2ccc(-c3cccc(S(=O)(=O)N4CC(C/N=C(\NCCOCCOCCOCCOCCOCCOCCOCCOCCOCCOCCC(=O)Oc5c(F)c(F)cc(F)c5F)N5CCN(C)CC5)C4)c3)cc2N=C(N)C1] | 1295.5 |
| BzL-51 | 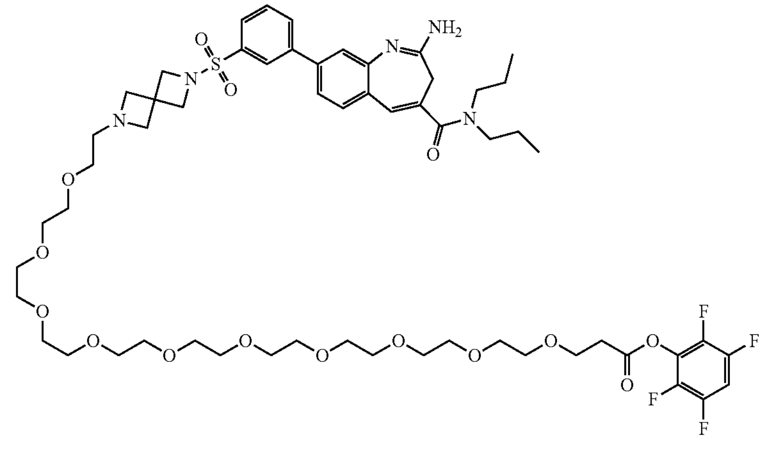 [SMILES: CCCN(CCC)C(=O)C1=Cc2ccc(-c3cccc(S(=O)(=O)N4CC5(CN(CCOCCOCCOCCOCCOCCOCCOCCOCCOCCOCCC(=O)Oc6c(F)c(F)cc(F)c6F)C5)C4)c3)cc2N=C(N)C1] | 1182.3 |

TABLE 2c-continued
| Aminobenzazepine-linker Formula II compounds (BzL) and intermediates | | |
|---|---|---|
| BzL No. | Structure | MW |
| BzL-52 | 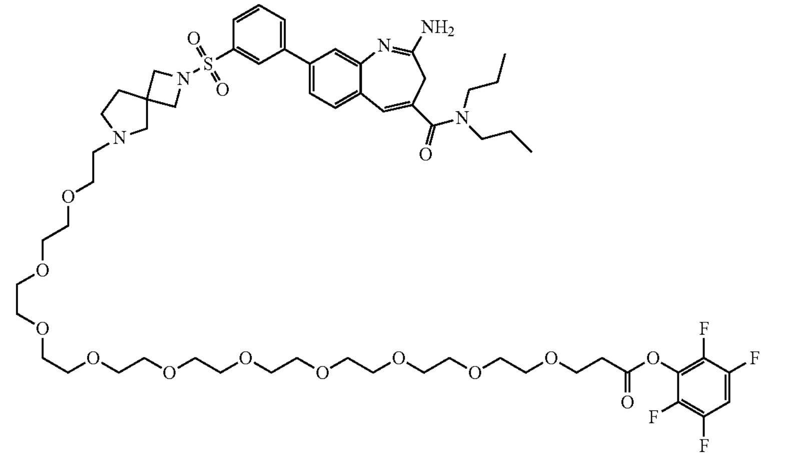 [SMILES: CCCN(CCC)C(=O)C1=Cc2ccc(-c3cccc(S(=O)(=O)N4CC5(CCN(CCOCCOCCOCCOCCOCCOCCOCCOCCOCCOCCC(=O)Oc6c(F)c(F)cc(F)c6F)C5)C4)c3)cc2N=C(N)C1] | 1196.4 |
| BzL-53 | 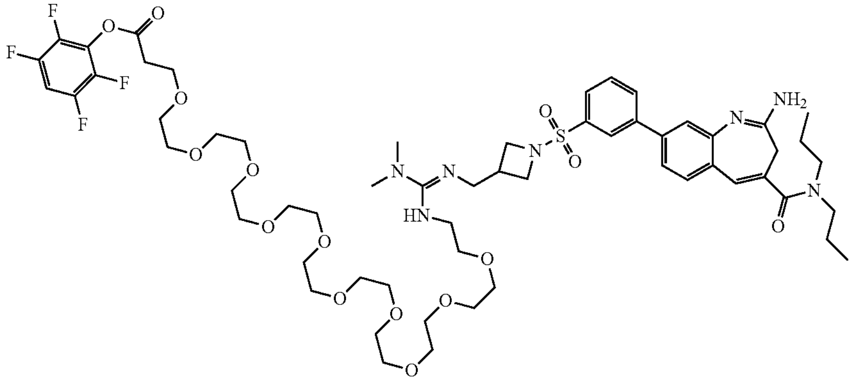 [SMILES: CCCN(CCC)C(=O)C1=Cc2ccc(-c3cccc(S(=O)(=O)N4CC(C/N=C(\NCCOCCOCCOCCOCCOCCOCCOCCOCCOCCOCCC(=O)Oc5c(F)c(F)cc(F)c5F)N(C)C)C4)c3)cc2N=C(N)C1] | 1240.4 |
| BzL-54 | 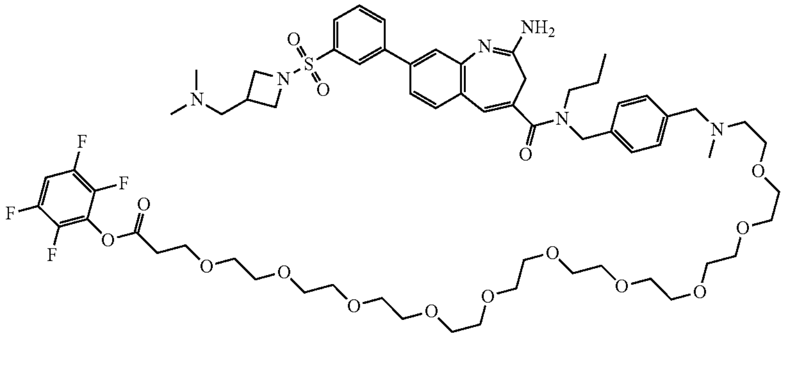 [SMILES: CCCN(Cc1ccc(CN(C)CCOCCOCCOCCOCCOCCOCCOCCOCCOCCOCCC(=O)Oc2c(F)c(F)cc(F)c2F)cc1)C(=O)C1=Cc2ccc(-c3cccc(S(=O)(=O)N4CC(CN(C)C)C4)c3)cc2N=C(N)C1] | 1289.5 |

TABLE 2c-continued
| BzL No. | Structure | MW |
|---|---|---|
| Aminobenzazepine-linker Formula II compounds (BzL) and intermediates | | |
| BzL-55 | 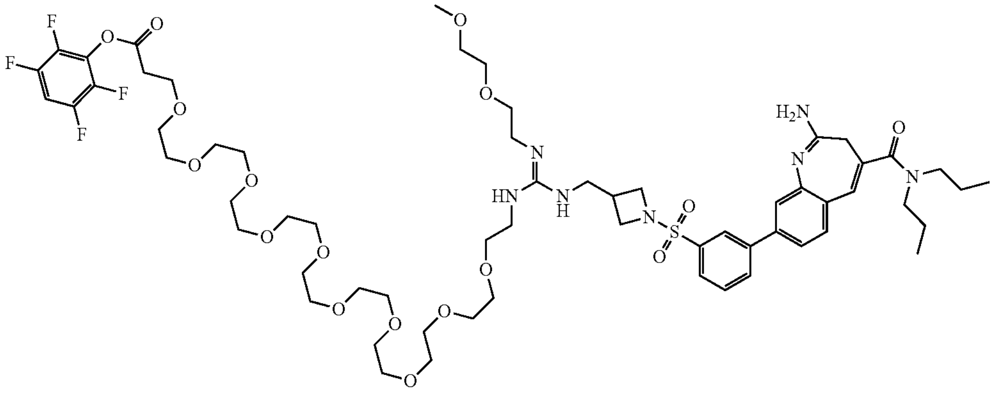 [SMILES: CCCN(CCC)C(=O)C1=Cc2ccc(-c3cccc(S(=O)(=O)N4CC(CN/C(=N/CCOCCOC)NCCOCCOCCOCCOCCOCCOCCOCCOCCOCCOCCC(=O)Oc5c(F)c(F)cc(F)c5F)C4)c3)cc2N=C(N)C1] | 1314.5 |
| BzL-56 | 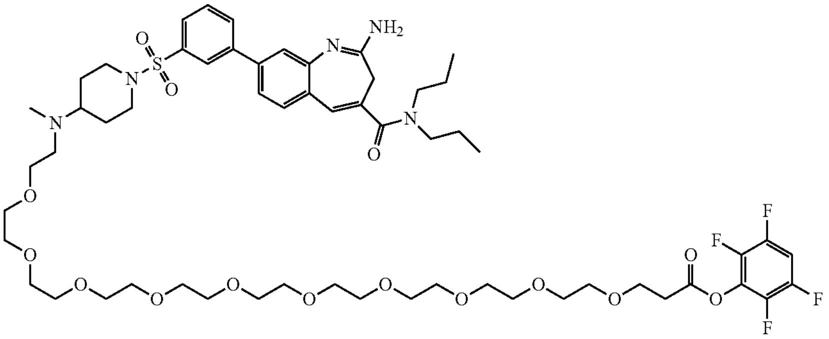 [SMILES: CCCN(CCC)C(=O)C1=Cc2ccc(-c3cccc(S(=O)(=O)N4CCC(N(C)CCOCCOCCOCCOCCOCCOCCOCCOCCOCCOCCC(=O)Oc5c(F)c(F)cc(F)c5F)CC4)c3)cc2N=C(N)C1] | 1198.4 |
| BzL-57 | 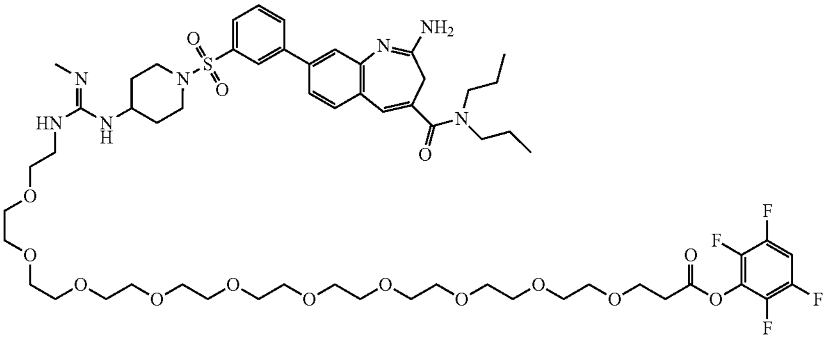 [SMILES: CCCN(CCC)C(=O)C1=Cc2ccc(-c3cccc(S(=O)(=O)N4CCC(N/C(=N/C)NCCOCCOCCOCCOCCOCCOCCOCCOCCOCCOCCC(=O)Oc5c(F)c(F)cc(F)c5F)CC4)c3)cc2N=C(N)C1] | 1240.4 |
| BzL-58 | 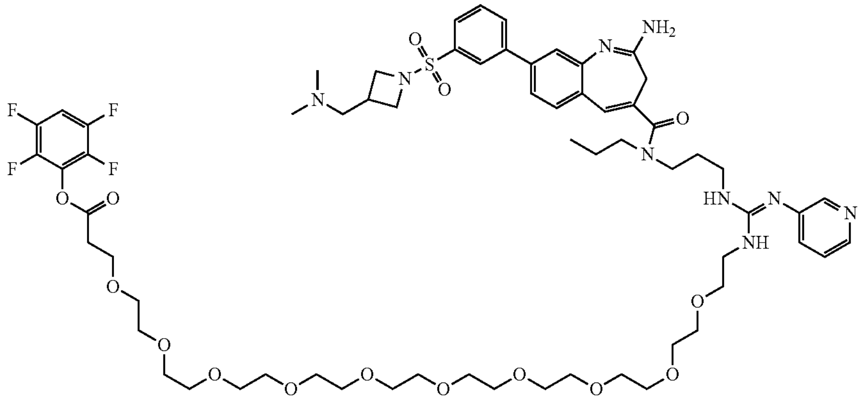 [SMILES: CCCN(CCCN/C(=N/c1cccnc1)NCCOCCOCCOCCOCCOCCOCCOCCOCCOCCOCCC(=O)Oc1c(F)c(F)cc(F)c1F)C(=O)C1=Cc2ccc(-c3cccc(S(=O)(=O)N4CC(CN(C)C)C4)c3)cc2N=C(N)C1] | 1332.5 |

TABLE 2c-continued
Aminobenzazepine-linker Formula II compounds (BzL) and intermediates
| BzL No. | Structure | MW |
| --- | --- | --- |
| BzL-59 | 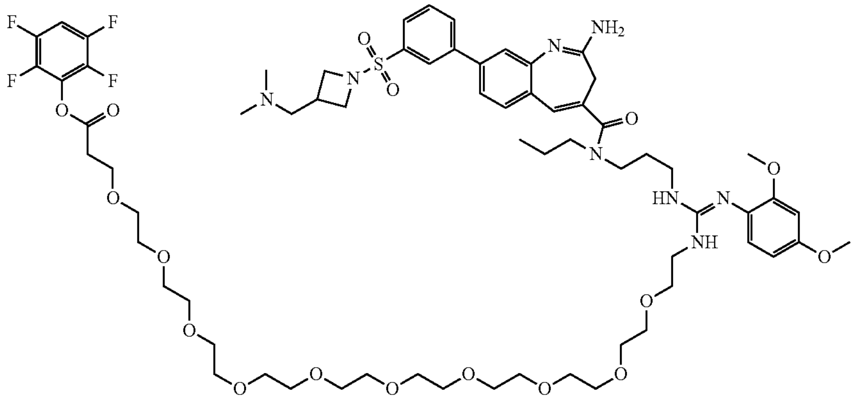 [SMILES: CCCN(CCCN/C(=N/c1ccc(OC)cc1OC)NCCOCCOCCOCCOCCOCCOCCOCCOCCOCCOCCC(=O)Oc1c(F)c(F)cc(F)c1F)C(=O)C1=Cc2ccc(-c3cccc(S(=O)(=O)N4CC(CN(C)C)C4)c3)cc2N=C(N)C1] | 1391.6 |
| BzL-60 | 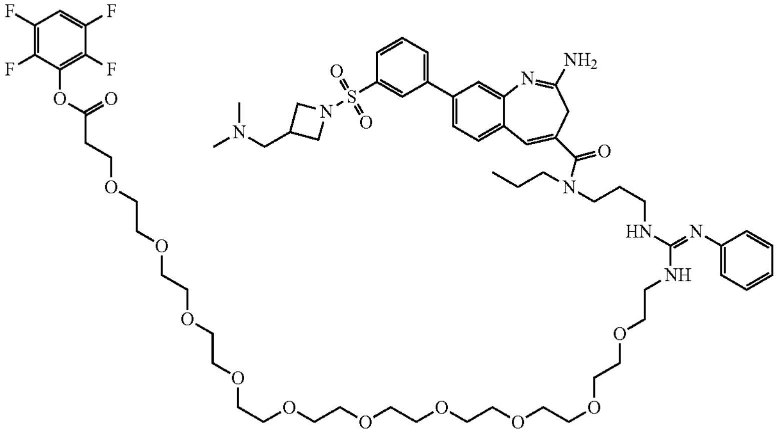 [SMILES: CCCN(CCCN/C(=N/c1ccccc1)NCCOCCOCCOCCOCCOCCOCCOCCOCCOCCOCCC(=O)Oc1c(F)c(F)cc(F)c1F)C(=O)C1=Cc2ccc(-c3cccc(S(=O)(=O)N4CC(CN(C)C)C4)c3)cc2N=C(N)C1] | 1331.5 |
| BzL-61 | 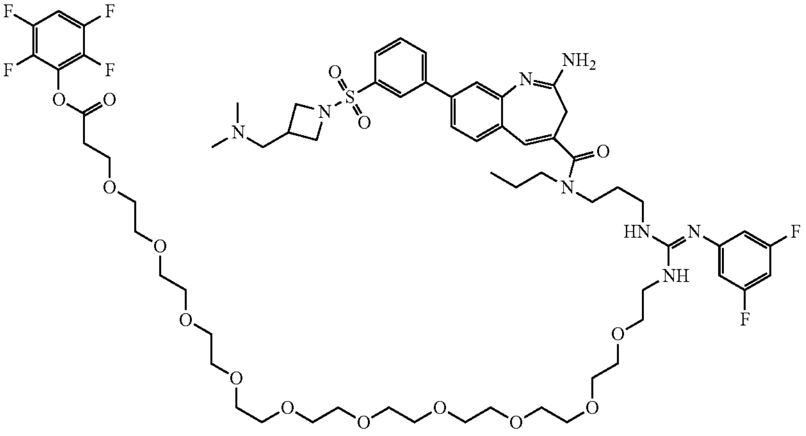 [SMILES: CCCN(CCCN/C(=N/c1cc(F)cc(F)c1)NCCOCCOCCOCCOCCOCCOCCOCCOCCOCCOCCC(=O)Oc1c(F)c(F)cc(F)c1F)C(=O)C1=Cc2ccc(-c3cccc(S(=O)(=O)N4CC(CN(C)C)C4)c3)cc2N=C(N)C1] | 1367.5 |

TABLE 2c-continued
| Aminobenzazepine-linker Formula II compounds (BzL) and intermediates | | |
|---|---|---|
| BzL No. | Structure | MW |
| BzL-62 | 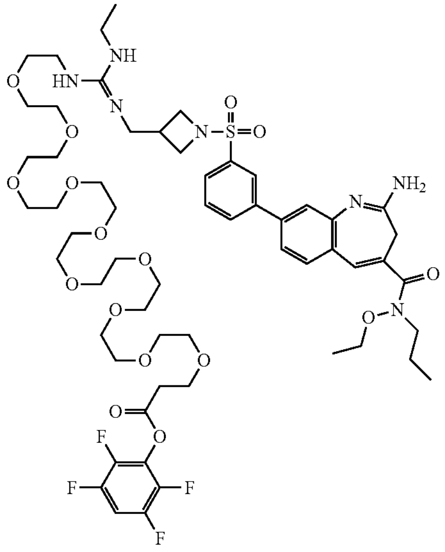 [SMILES: CCCN(OCC)C(=O)C1=Cc2ccc(-c3cccc(S(=O)(=O)N4CC(CN=C(NCC)NCCOCCOCCOCCOCCOCCOCCOCCOCCOCCOCCC(=O)Oc5c(F)c(F)cc(F)c5F)C4)c3)cc2N=C(N)C1] | 1242.4 |
| BzL-63 | 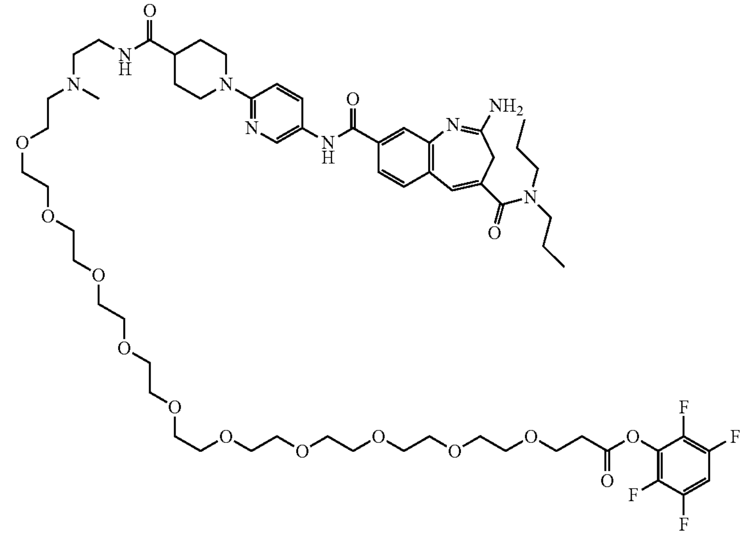 [SMILES: CCCN(CCC)C(=O)C1=Cc2ccc(C(=O)Nc3ccc(N4CCC(C(=O)NCCN(C)CCOCCOCCOCCOCCOCCOCCOCCOCCOCCOCCC(=O)Oc5c(F)c(F)cc(F)c5F)CC4)nc3)cc2N=C(N)C1] | 1249.4 |

TABLE 2c-continued
| Aminobenzazepine-linker Formula II compounds (BzL) and intermediates | | |
|---|---|---|
| BzL No. | Structure | MW |
| BzL-64 | 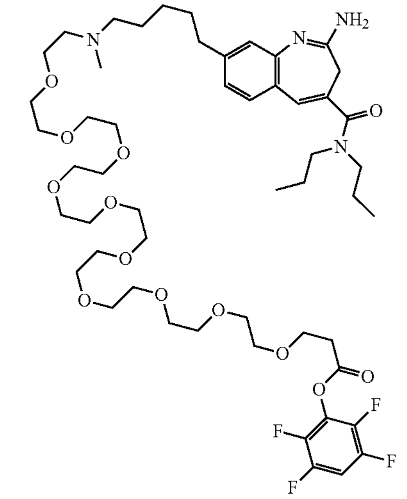 [SMILES: CCCN(CCC)C(=O)C1=Cc2ccc(CCCCCN(C)CCOCCOCCOCCOCCOCCOCCOCCOCCOCCOCCC(=O)Oc3c(F)c(F)cc(F)c3F)cc2N=C(N)C1] | 1045.2 |
| BzL-65 | 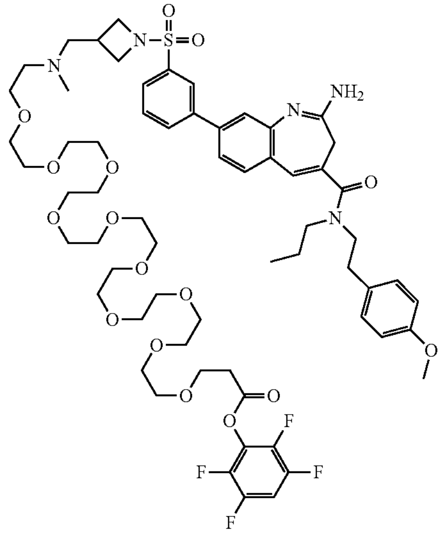 [SMILES: CCCN(CCc1ccc(OC)cc1)C(=O)C1=Cc2ccc(-c3cccc(S(=O)(=O)N4CC(CN(C)CCOCCOCCOCCOCCOCCOCCOCCOCCOCCOCCC(=O)Oc5c(F)c(F)cc(F)c5F)C4)c3)cc2N=C(N)C1] | 1276.4 |

TABLE 2c-continued
| Aminobenzazepine-linker Formula II compounds (BzL) and intermediates | | |
|---|---|---|
| BzL No. | Structure | MW |
| BzL-66 | 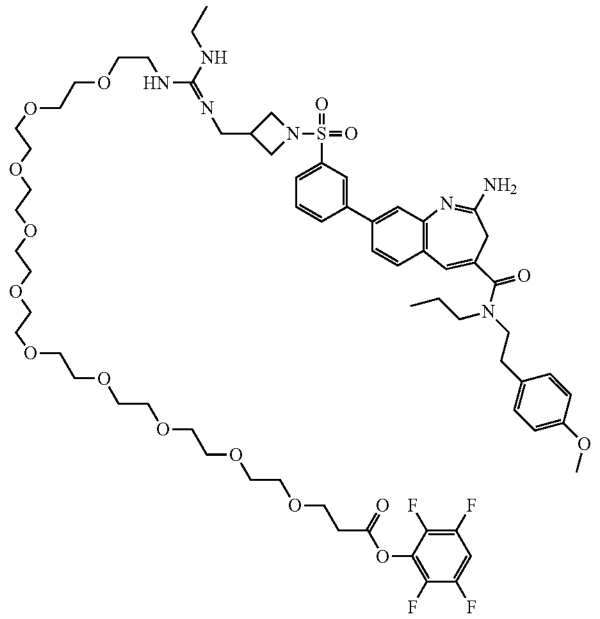 [SMILES: CCCN(CCc1ccc(OC)cc1)C(=O)C1=Cc2ccc(-c3cccc(S(=O)(=O)N4CC(CN=C(NCC)NCCOCCOCCOCCOCCOCCOCCOCCOCCOCCOCCC(=O)Oc5c(F)c(F)cc(F)c5F)C4)c3)cc2N=C(N)C1] | 1332.5 |
| BzL-67 | 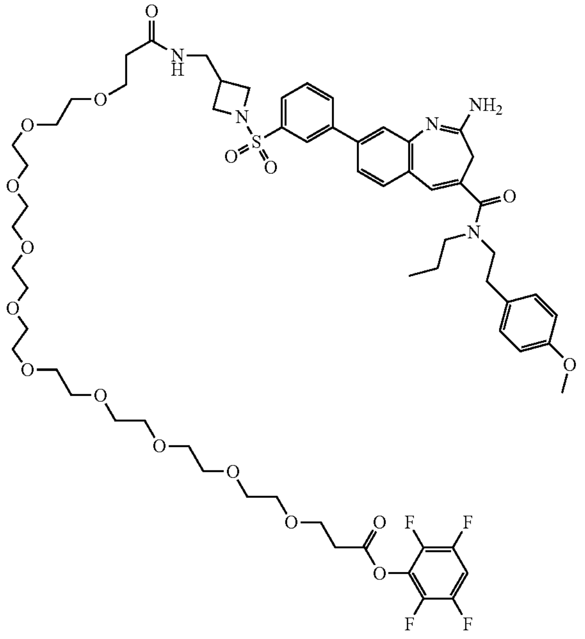 [SMILES: CCCN(CCc1ccc(OC)cc1)C(=O)C1=Cc2ccc(-c3cccc(S(=O)(=O)N4CC(CNC(=O)CCOCCOCCOCCOCCOCCOCCOCCOCCOCCOCCC(=O)Oc5c(F)c(F)cc(F)c5F)C4)c3)cc2N=C(N)C1] | 1290.4 |

TABLE 2c-continued
| Aminobenzazepine-linker Formula II compounds (BzL) and intermediates | | |
|---|---|---|
| BzL No. | Structure | MW |
| BzL-68 | 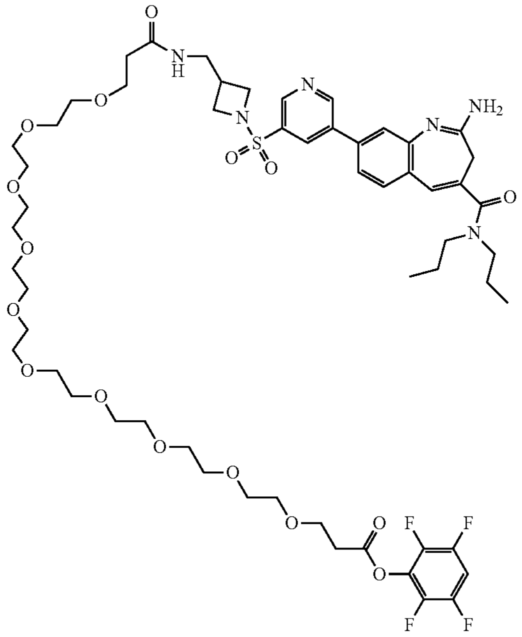 [SMILES: CCCN(CCC)C(=O)C1=Cc2ccc(-c3cncc(S(=O)(=O)N4CC(CNC(=O)CCOCCOCCOCCOCCOCCOCCOCCOCCOCCOCCC(=O)Oc5c(F)c(F)cc(F)c5F)C4)c3)cc2N=C(N)C1] | 1199.3 |
| BzL-69 | 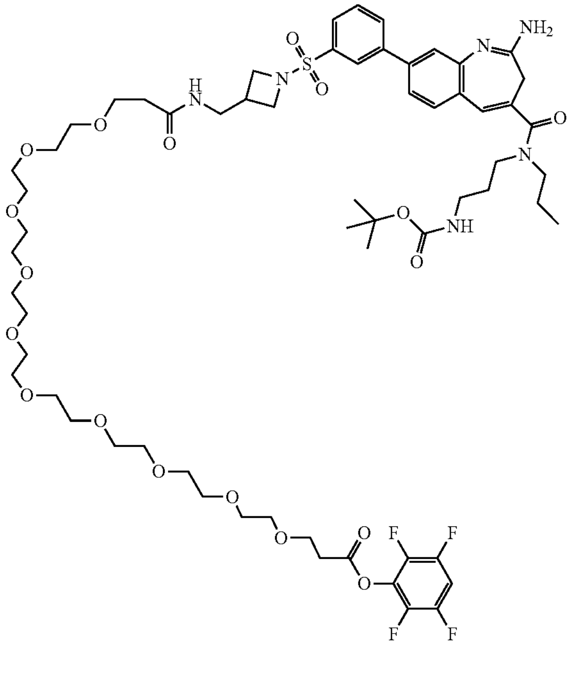 [SMILES: CCCN(CCCNC(=O)OC(C)(C)C)C(=O)C1=Cc2ccc(-c3cccc(S(=O)(=O)N4CC(CNC(=O)CCOCCOCCOCCOCCOCCOCCOCCOCCOCCOCCC(=O)Oc5c(F)c(F)cc(F)c5F)C4)c3)cc2N=C(N)C1] | 1313.5 |

TABLE 2c-continued
| Aminobenzazepine-linker Formula II compounds (BzL) and intermediates | | |
|---|---|---|
| BzL No. | Structure | MW |
| BzL-70 | 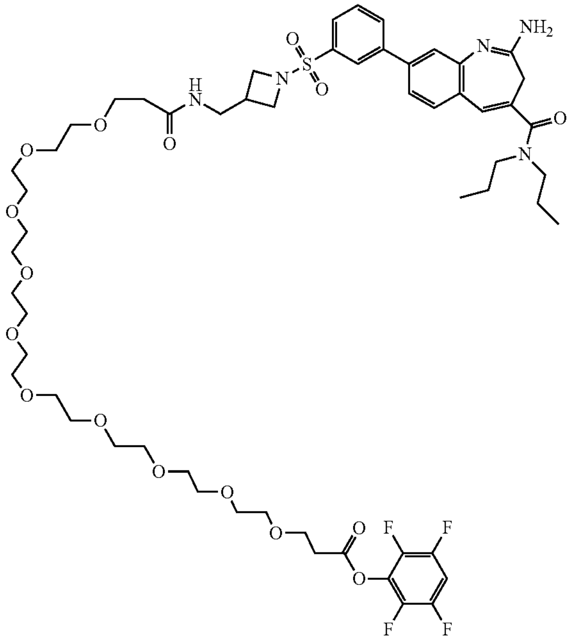 [SMILES: CCCN(CCC)C(=O)C1=Cc2ccc(-c3cccc(S(=O)(=O)N4CC(CNC(=O)CCOCCOCCOCCOCCOCCOCCOCCOCCOCCOCCC(=O)Oc5c(F)c(F)cc(F)c5F)C4)c3)cc2N=C(N)C1] | 1198.3 |
| BzL-71 | 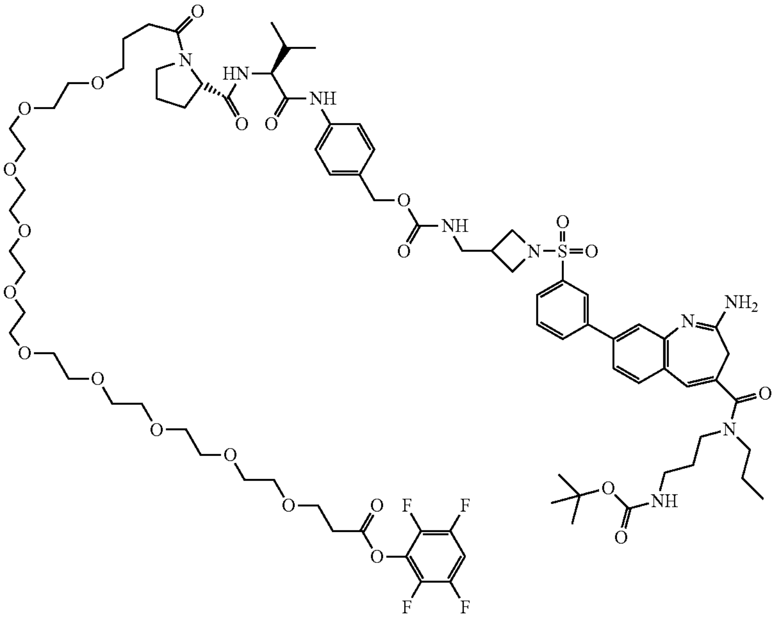 | 1658.9 |

TABLE 2c-continued
| Aminobenzazepine-linker Formula II compounds (BzL) and intermediates | | |
|---|---|---|
| BzL No. | Structure | MW |
| BzL-72 | 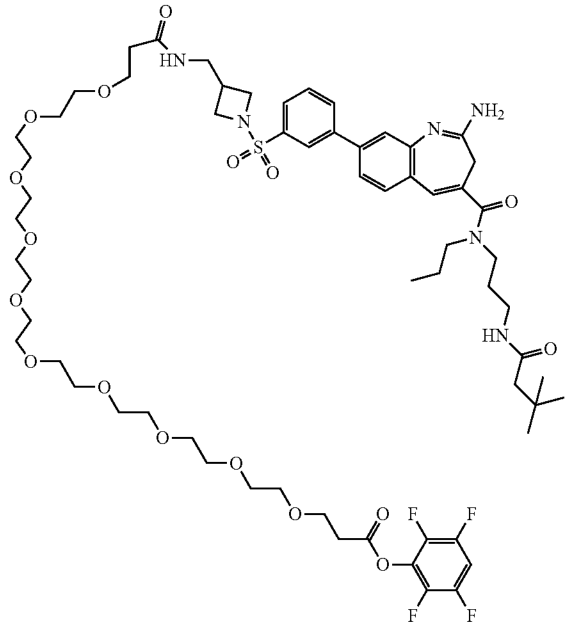 [SMILES: CCCN(CCCNC(=O)CC(C)(C)C)C(=O)C1=Cc2ccc(-c3cccc(S(=O)(=O)N4CC(CNC(=O)CCOCCOCCOCCOCCOCCOCCOCCOCCOCCOCCC(=O)Oc5c(F)c(F)cc(F)c5F)C4)c3)cc2N=C(N)C1] | 1311.5 |
| BzL-73 | 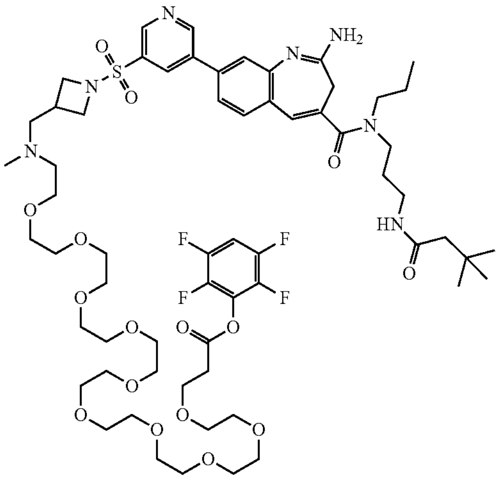 [SMILES: CCCN(CCCNC(=O)CC(C)(C)C)C(=O)C1=Cc2ccc(-c3cncc(S(=O)(=O)N4CC(CN(C)CCOCCOCCOCCOCCOCCOCCOCCOCCOCCOCCC(=O)Oc5c(F)c(F)cc(F)c5F)C4)c3)cc2N=C(N)C1] | 1298.5 |

TABLE 2c-continued
| Aminobenzazepine-linker Formula II compounds (BzL) and intermediates | | |
|---|---|---|
| BzL No. | Structure | MW |
| BzL-74 | 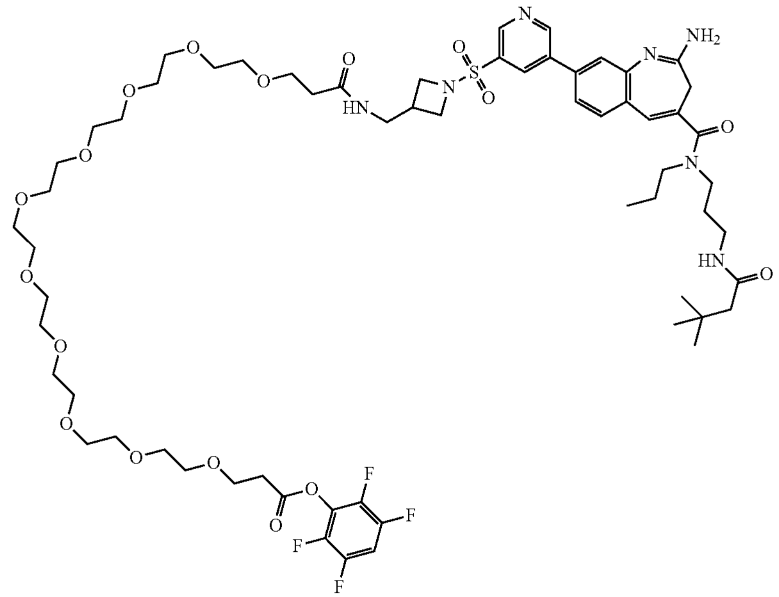 [SMILES: CCCN(CCCNC(=O)CC(C)(C)C)C(=O)C1=Cc2ccc(-c3cncc(S(=O)(=O)N4CC(CNC(=O)CCOCCOCCOCCOCCOCCOCCOCCOCCOCCOCCC(=O)Oc5c(F)c(F)cc(F)c5F)C4)c3)cc2N=C(N)C1] | 1312.5 |
| BzL-75 | 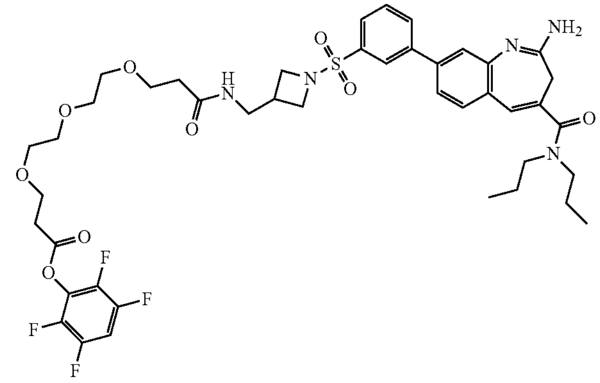 [SMILES: CCCN(CCC)C(=O)C1=Cc2ccc(-c3cccc(S(=O)(=O)N4CC(CNC(=O)CCOCCOCCOCCC(=O)Oc5c(F)c(F)cc(F)c5F)C4)c3)cc2N=C(N)C1] | 890.0 |
| BzL-76 | 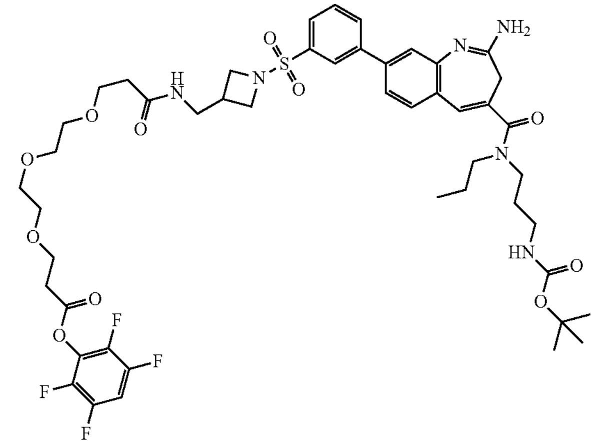 [SMILES: CCCN(CCCNC(=O)OC(C)(C)C)C(=O)C1=Cc2ccc(-c3cccc(S(=O)(=O)N4CC(CNC(=O)CCOCCOCCOCCC(=O)Oc5c(F)c(F)cc(F)c5F)C4)c3)cc2N=C(N)C1] | 1005.1 |

TABLE 2c-continued
| Aminobenzazepine-linker Formula II compounds (BzL) and intermediates | | |
|---|---|---|
| BzL No. | Structure | MW |
| BzL-77 | 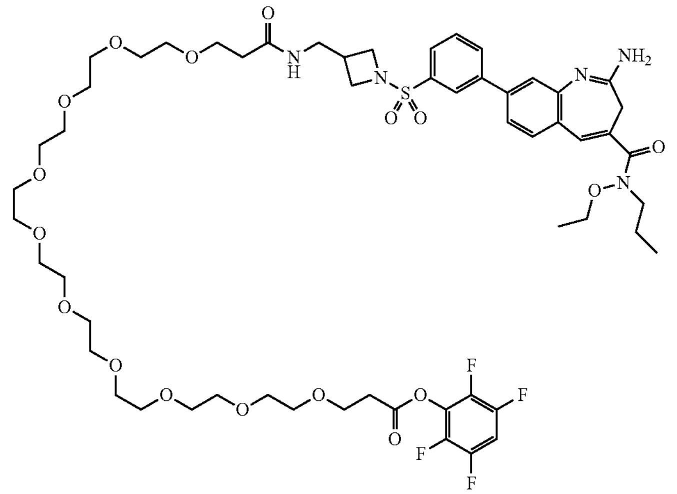 [SMILES: CCCN(OCC)C(=O)C1=Cc2ccc(-c3cccc(S(=O)(=O)N4CC(CNC(=O)CCOCCOCCOCCOCCOCCOCCOCCOCCOCCOCCC(=O)Oc5c(F)c(F)cc(F)c5F)C4)c3)cc2N=C(N)C1] | 1200.3 |
| BzL-78 | 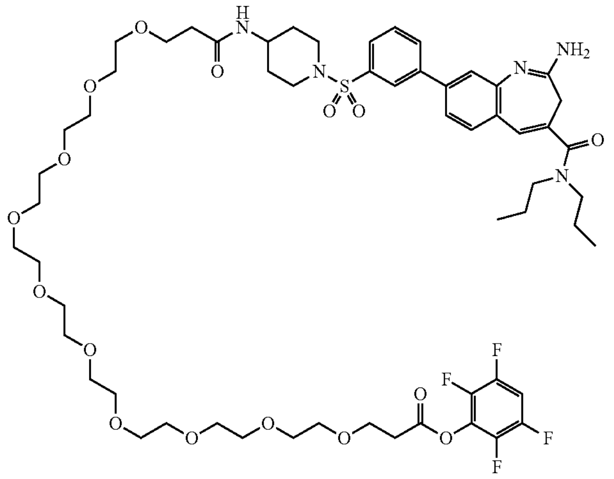 [SMILES: CCCN(CCC)C(=O)C1=Cc2ccc(-c3cccc(S(=O)(=O)N4CCC(NC(=O)CCOCCOCCOCCOCCOCCOCCOCCOCCOCCOCCC(=O)Oc5c(F)c(F)cc(F)c5F)CC4)c3)cc2N=C(N)C1] | 1212.4 |
| BzL-79 | 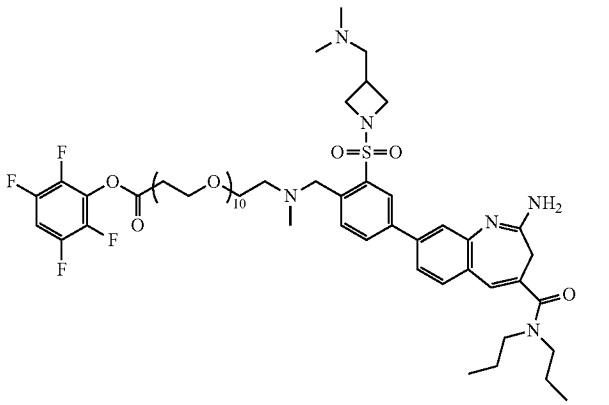 | 1241.4 |

Macromolecule-Supported Compounds

Exemplary embodiments of macromolecule-supported compounds comprise a macromolecular support covalently attached to a divalent linker which is covalently attached to one or more aminobenzazepine moieties, and having Formula I:

Ms-[L-Bza]$_p$ I or a pharmaceutically acceptable salt thereof, wherein:

"$M_S$" is the macromolecular support;

p is an integer from 1 to 50;

Bza is the aminobenzazepine moiety having the formula:

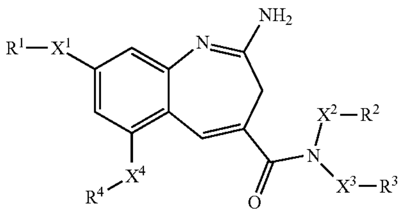

$R^1$, $R^2$, $R^3$, and $R^4$ are independently selected from the group consisting of H, $C_1$-$C_{12}$ alkyl, $C_2$-$C_6$ alkenyl, $C_2$-$C_6$ alkynyl, $C_3$-$C_{12}$ carbocyclyl, $C_6$-$C_{20}$ aryl, $C_2$-$C_9$ heterocyclyl, and $C_1$-$C_{20}$ heteroaryl, where alkyl, alkenyl, alkynyl, carbocyclyl, aryl, heterocyclyl, and heteroaryl are independently and optionally substituted with one or more groups selected from:

—($C_1$-$C_{12}$ alkyldiyl)-N($R^5$)—*;

—($C_1$-$C_{12}$ alkyldiyl)-N($R^5$)$_2$;

—($C_3$-$C_{12}$ carbocyclyl);

—($C_3$-$C_{12}$ carbocyclyl)-*;

—($C_3$-$C_{12}$ carbocyclyl)-($C_1$-$C_{12}$ alkyldiyl)-N$R^5$—*;

—($C_3$-$C_{12}$ carbocyclyl)-($C_1$-$C_{12}$ alkyldiyl)-N($R^5$)$_2$;

—($C_3$-$C_{12}$ carbocyclyl)-N$R^5$—C(═N$R^5$)N$R^5$—*;

—($C_6$-$C_{20}$ aryl);

—($C_6$-$C_{20}$ aryl)-*;

—($C_6$-$C_{20}$ aryldiyl)-N($R^5$)—*;

—($C_6$-$C_{20}$ aryldiyl)-($C_1$-$C_{12}$ alkyldiyl)-N($R^5$)—*;

—($C_6$-$C_{20}$ aryldiyl)-($C_1$-$C_{12}$ alkyldiyl)-N($R^5$)$_2$;

—($C_6$-$C_{20}$ aryldiyl)-($C_1$-$C_{12}$ alkyldiyl)-N$R^5$—C(═N$R^{5a}$)N($R^5$)—*;

—($C_2$-$C_{20}$ heterocyclyl);

—($C_2$-$C_{20}$ heterocyclyl)-*;

—($C_2$-$C_9$ heterocyclyl)-($C_1$-$C_{12}$ alkyldiyl)-N$R^5$—*;

—($C_2$-$C_9$ heterocyclyl)-($C_1$-$C_{12}$ alkyldiyl)-N($R^5$)$_2$;

—($C_2$-$C_9$ heterocyclyl)-N$R^5$—C(═N$R^{5a}$)N$R^5$—*;

—($C_1$-$C_{20}$ heteroaryl);

—($C_1$-$C_{20}$ heteroaryl)-*;

—($C_1$-$C_{20}$ heteroaryl)-($C_1$-$C_{12}$ alkyldiyl)-N($R^5$)—*;

—($C_1$-$C_{20}$ heteroaryl)-($C_1$-$C_{12}$ alkyldiyl)-N($R^5$)$_2$;

—($C_1$-$C_{20}$ heteroaryl)-N$R^5$—C(═N$R^{5a}$)N($R^5$)—*;

—C(═O)—*;

—C(═O)—($C_2$-$C_{20}$ heterocyclyldiyl)-*;

—C(═O)N($R^5$)$_2$;

—C(═O)N($R^5$)—*;

—C(═O)N($R^5$)—($C_1$-$C_{12}$ alkyldiyl)-N($R^5$)C(═O)$R^5$;

—C(═O)N($R^5$)—($C_1$-$C_{12}$ alkyldiyl)-N($R^5$)C(═O)N($R^5$)$_2$;

—C(═O)N$R^5$—($C_1$-$C_{12}$ alkyldiyl)-N($R^5$)$CO_2R^5$;

—C(═O)N$R^5$—($C_1$-$C_{12}$ alkyldiyl)-N($R^5$)C(═N$R^{5a}$)N($R^5$)$_2$;

—C(═O)N$R^5$—($C_1$-$C_{12}$ alkyldiyl)-N$R^5$C(═N$R^{5a}$)$R^5$;

—C(═O)N$R^5$—($C_1$-$C_8$ alkyldiyl)-N$R^5$($C_2$-$C_5$ heteroaryl);

—C(═O)N$R^5$—($C_1$-$C_{20}$ heteroaryldiyl)-N($R^5$)—*;

—C(═O)N$R^5$—($C_1$-$C_{20}$ heteroaryldiyl)-*;

—C(═O)N$R^5$—($C_1$-$C_{20}$ heteroaryldiyl)-($C_1$-$C_{12}$ alkyldiyl)-N($R^5$)$_2$;

—C(═O)N$R^5$—($C_1$-$C_{20}$ heteroaryldiyl)-($C_2$-$C_{20}$ heterocyclyldiyl)-C(═O)N$R^5$—($C_1$-$C_{12}$ alkyldiyl)-N$R^5$—*;

—N($R^5$)$_2$;

—N($R^5$)—*;

—N($R^5$)C(═O)$R^5$;

—N($R^5$)C(═O)—*;

—N($R^5$)C(═O)N($R^5$)$_2$;

—N($R^5$)C(═O)N($R^5$)—*;

—N($R^5$)$CO_2R^5$;

—N$R^5$C(═N$R^{5a}$)N($R^5$)$_2$,

—N$R^5$C(═N$R^{5a}$)N($R^5$)—*;

—N$R^5$C(═N$R^{5a}$)$R^5$;

—N($R^5$)—($C_2$-$C_5$ heteroaryl);

—O—($C_1$-$C_{12}$ alkyl);

—O—($C_1$-$C_{12}$ alkyldiyl)-N($R^5$)$_2$;

—O—($C_1$-$C_{12}$ alkyldiyl)-N($R^5$)—*;

—S(═O)$_2$—($C_2$-$C_{20}$ heterocyclyldiyl)-*;

—S(═O)$_2$—($C_2$-$C_{20}$ heterocyclyldiyl)-($C_1$-$C_{12}$ alkyldiyl)-N($R^5$)$_2$;

—S(═O)$_2$—($C_2$-$C_{20}$ heterocyclyldiyl)-($C_1$-$C_{12}$ alkyldiyl)-N$R^5$—*; and —S(═O)$_2$—($C_2$-$C_{20}$ heterocyclyldiyl)-($C_1$-$C_{12}$ alkyldiyl)-OH;

or $R^2$ and $R^3$ together form a 5- or 6-membered heterocyclyl ring;

$X^1$, $X^2$, $X^3$, and $X^4$ are independently selected from the group consisting of a bond, C(═O), C(═O)N($R^5$), O, N($R^5$), S, S(O)$_2$, and S(O)$_2$N($R^5$);

$R^5$ is selected from the group consisting of H, $C_6$-$C_{20}$ aryl, $C_6$-$C_{20}$ aryldiyl, $C_1$-$C_{12}$ alkyl, and $C_1$-$C_{12}$ alkyldiyl, or two $R^5$ groups together form a 5- or 6-membered heterocyclyl ring;

$R^{5a}$ is selected from the group consisting of $C_6$-$C_{20}$ aryl and $C_1$-$C_{20}$ heteroaryl;

where the asterisk * indicates the attachment site of L, and where one of $R^1$, $R^2$, $R^3$ and $R^4$ is attached to L;

L is the linker selected from the group consisting of:

—C(═O)—(PEG)-;

—C(═O)—(PEG)-C(═O)—;

—C(═O)—(PEG)-O—;

—C(═O)—(PEG)-C(═O)—(PEP)—;

—C(═O)—(PEG)-C(═O)N($R^5$)—($C_1$-$C_{12}$ alkyldiyl)-;

—C(═O)—(PEG)-C(═O)N($R^5$)—($C_1$-$C_{12}$ alkyldiyl)-N($R^5$)C(═O)—($C_2$-$C_5$ monoheterocyclyldiyl)-;

—C(═O)—(PEG)-C(═O)N($R^5$)—($C_1$-$C_{12}$ alkyldiyl)-(MCgluc)-;

—C(═O)—(PEG)-C(═O)-(MCgluc)-;

—C(═O)—(PEG)-C(═O)—(PEP)—N($R^5$)—($C_1$-$C_{12}$ alkyldiyl)-;

—C(═O)—(PEG)-C(═O)—(PEP)—N($R^5$)—($C_1$-$C_{12}$ alkyldiyl)-N($R^5$)C(═O)—($C_2$-$C_5$ monoheterocyclyldiyl)-;

—C(═O)—(PEG)-N($R^5$)—;

—C(═O)—(PEG)-N($R^5$)—(PEG)-C(═O)—(PEP)—;

—C(═O)—(PEG)-N$^+$($R^5$)$_2$—(PEG)-C(═O)—(PEP)—;

—C(═O)—(PEG)-C(═O)—N($R^5$)CH($AA_1$)C(═O)—(PEG)-C(═O)—(PEP)—;

—C(═O)—(PEG)-C(═O)—N($R^5$)CH($AA_1$)C(═O)—N($R^5$)—($C_1$-$C_{12}$ alkyldiyl)-;

—C(═O)—(PEG)-SS—($C_1$-$C_{12}$ alkyldiyl)-OC(═O)—;

—C(═O)—(PEG)-SS—($C_1$-$C_{12}$ alkyldiyl)-C(═O)—;

—C(═O)—($C_1$-$C_{12}$ alkyldiyl)-C(═O)—(PEP)—;

—C(═O)—($C_1$-$C_{12}$ alkyldiyl)-C(═O)—(PEP)—N($R^5$)—($C_1$-$C_{12}$ alkyldiyl)-;

—C(═O)—($C_1$-$C_{12}$ alkyldiyl)-C(═O)—(PEP)—N($R^5$)—($C_1$-$C_{12}$ alkyldiyl)-N($R^5$)—C(═O);

—C(═O)—($C_1$-$C_{12}$ alkyldiyl)-C(═O)—(PEP)—N($R^5$)—($C_1$-$C_{12}$ alkyldiyl)-N($R^5$)C(═O)—($C_2$-$C_5$ monoheterocyclyldiyl)-;

—C(═O)—$CH_2CH_2O$ $CH_2CH_2$—($C_1$-$C_{20}$ heteroaryldiyl)-$CH_2O$—(PEG)-C(═O)-(MCgluc)-;

—C(═O)—$CH_2CH_2OCH_2CH_2$—($C_1$-$C_{20}$ heteroaryldiyl)-$CH_2O$—(PEG)-C(═O)-(MCgluc)-N($R^5$)—($C_1$-$C_{12}$ alkyldiyl)-N($R^5$)C(═O)—($C_2$-$C_5$ monoheterocyclyldiyl)-; and -(succinimidyl)-$(CH_2)_m$—C(═O)—(PEP)—N($R^5$)—($C_1$-$C_{12}$ alkyldiyl)-N($R^5$)C(═O)—($C_2$-$C_5$ monoheterocyclyldiyl)-;

PEG has the formula: —$(CH_2CH_2O)_n$—$(CH_2)_m$—; m is an integer from 1 to 5, and n is an integer from 2 to 50;

PEP has the formula:

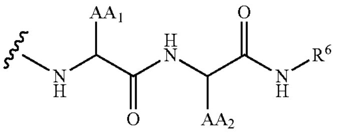

where $AA_1$ and $AA_2$ are independently selected from an amino acid side chain, or $AA_1$ or $AA_2$ and an adjacent nitrogen atom form a 5-membered ring proline amino acid, and the wavy line indicates a point of attachment;

$R^6$ is selected from the group consisting of $C_6$-$C_{20}$ aryldiyl and $C_1$-$C_{20}$ heteroaryldiyl, substituted with —$CH_2O$—C(═O)— and optionally with:

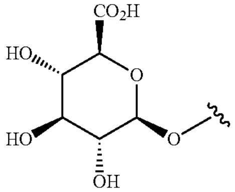

;

and

MCgluc is selected from the groups:

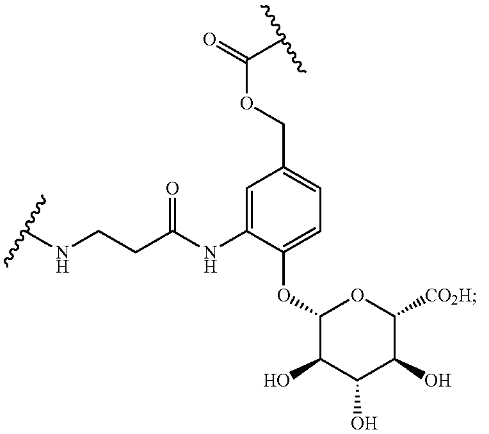

-continued

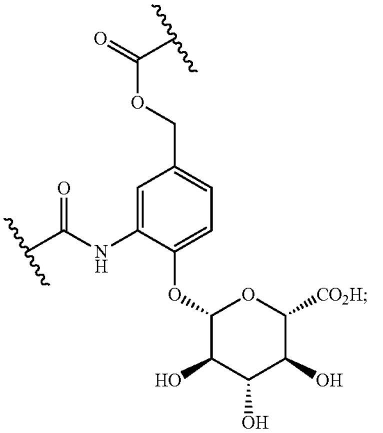

and

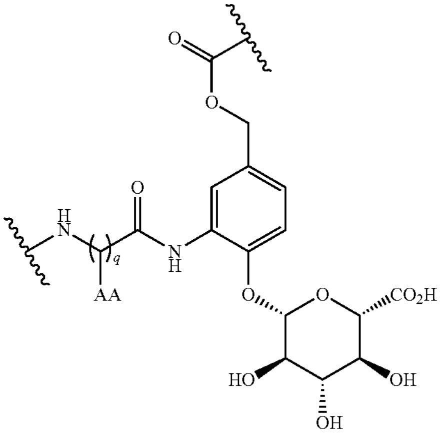

where q is 1 to 8, and AA is an amino acid side chain; and alkyl, alkyldiyl, alkenyl, alkenyldiyl, alkynyl, alkynyldiyl, aryl, aryldiyl, carbocyclyl, carbocyclyldiyl, heterocyclyl, heterocyclyldiyl, heteroaryl, and heteroaryldiyl are independently and optionally substituted with one or more groups independently selected from F, Cl, Br, I, —CN, —$CH_3$, —$CH_2CH_3$, —CH═$CH_2$, —C≡CH, —C≡$CCH_3$, —$CH_2CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —CH(OH)$CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CF_3$, —$CH_2CF_3$, —$CH_2CHF_2$, —CH($CH_3$)CN, —$C(CH_3)_2CN$, —$CH_2CN$, —$CH_2NH_2$, —$CH_2NHSO_2CH_3$, —$CH_2NHCH_3$, —$CH_2N(CH_3)_2$, —$CO_2H$, —$COCH_3$, —$CO_2CH_3$, —$CO_2C(CH_3)_3$, —COCH(OH)$CH_3$, —$CONH_2$, —$CONHCH_3$, —CON$(CH_3)_2$, —$C(CH_3)_2CONH_2$, —$NH_2$, —$NHCH_3$, —$N(CH_3)_2$, —$NHCOCH_3$, —N($CH_3$)$COCH_3$, —NHS$(O)_2CH_3$, —N($CH_3$)$C(CH_3)_2CONH_2$, —N($CH_3$)$CH_2CH_2S(O)_2CH_3$, —NHC(═NH)H, —NHC(═NH)$CH_3$, —NHC(═NH)$NH_2$, —NHC(═O)$NH_2$, —$NO_2$, ═O, —OH, —$OCH_3$, —$OCH_2CH_3$, —$OCH_2CH_2OCH_3$, —$OCH_2CH_2OH$, —$OCH_2CH_2N(CH_3)_2$, —$O(CH_2CH_2O)_n$—$(CH_2)_mCO_2H$, —$O(CH_2CH_2O)_nH$, —$OP(O)(OH)_2$, —$S(O)_2N(CH_3)_2$, —$SCH_3$, —$S(O)_2CH_3$, and —$S(O)_3H$.

An exemplary embodiment of the macromolecule-supported compound of Formula I includes wherein PEP is selected from the groups:

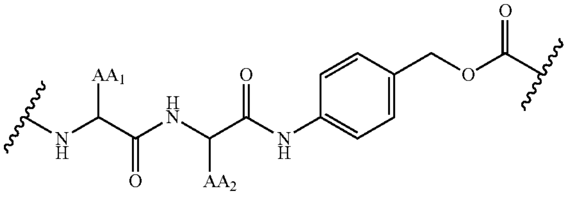

;

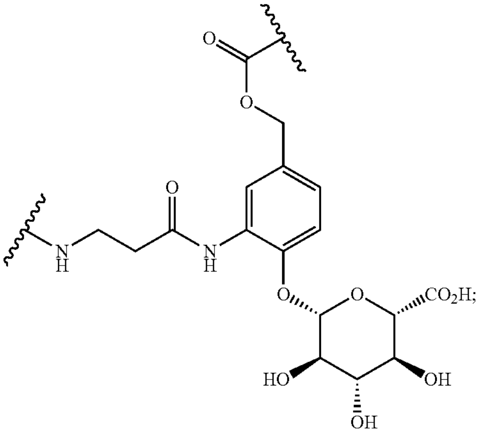

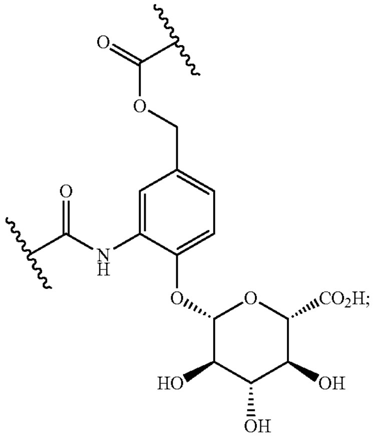

and

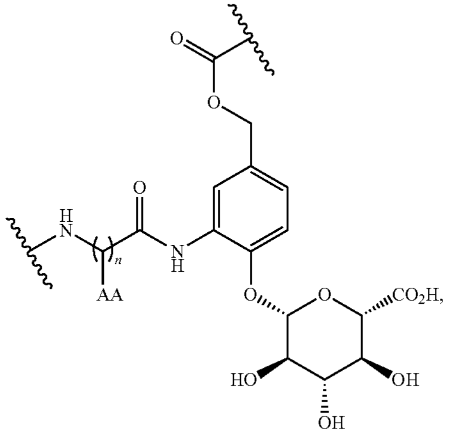

where n is 1 or more, and AA is an amino acid side chain.

An exemplary embodiment of the macromolecule-supported compound of Formula I includes wherein each $AA_1$ and $AA_2$ are independently selected from a side chain of a naturally-occurring amino acid.

An exemplary embodiment of the macromolecule-supported compound of Formula I includes wherein each $AA_1$ and $AA_2$ are independently selected from H, $—CH_3$, $—CH(CH_3)_2$, $—CH_2(C_6H_5)$, $—CH_2CH_2CH_2CH_2NH_2$, $—CH_2CH_2CH_2NHC(NH)NH_2$, $—CH_2CH(CH_3)_2$, $—CH_2SO_3H$, and $—CH_2CH_2CH_2NHC(O)NH_2$.

An exemplary embodiment of the macromolecule-supported compound of Formula I includes wherein each $AA_1$ is $—CH(CH_3)_2$, and $AA_2$ is $—CH_2CH_2CH_2NHC(O)NH_2$.

An exemplary embodiment of the macromolecule-supported compound of Formula I includes wherein each $AA_1$ and $AA_2$ are independently selected from GlcNAc aspartic acid, $—CH_2SO_3H$, and $—CH_2OPO_3H$.

An exemplary embodiment of the macromolecule-supported compound of Formula I includes wherein L-Bza is selected from Formulas Ia-d:

Ia

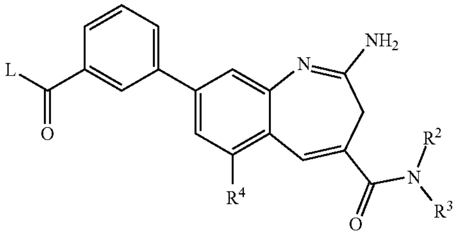

Ib

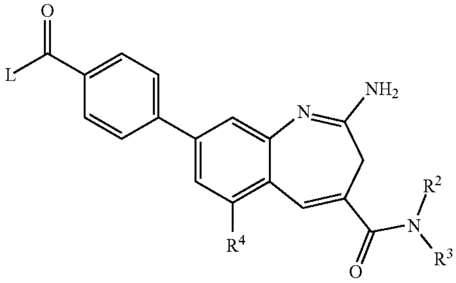

Ic

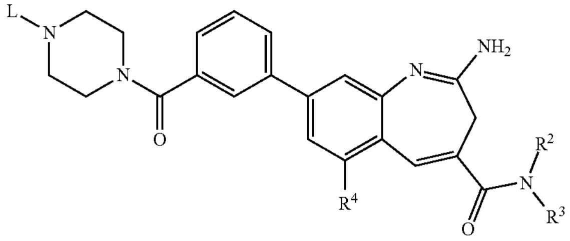

Id

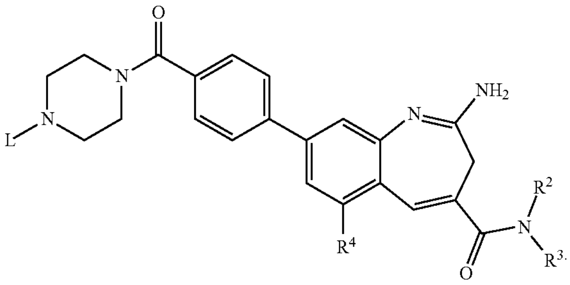

An exemplary embodiment of the macromolecule-supported compound of Formula I includes wherein L-Bza is selected from Formulas Ie and If:

Ie

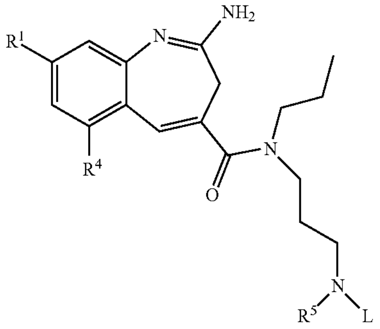

If

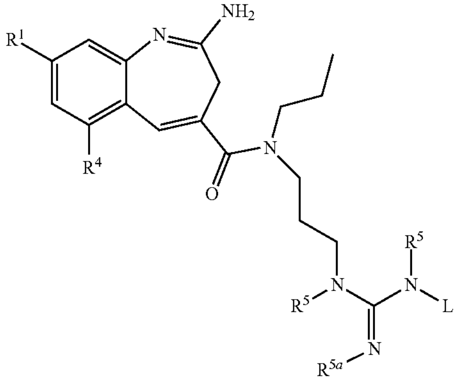

where $R^{5a}$ of Formula If is phenyl, optionally substituted with one or more groups selected from F, Cl, Br, I, —CN, and —$NO_2$.

An exemplary embodiment of the macromolecule-supported compound of Formula I includes wherein L is —C(═O)—(PEG)- or —C(═O)—(PEG)-C(═O)—.

An exemplary embodiment of the macromolecule-supported compound of Formula I includes wherein L-Bza is selected from Formulas Ig and Ih:

Ig

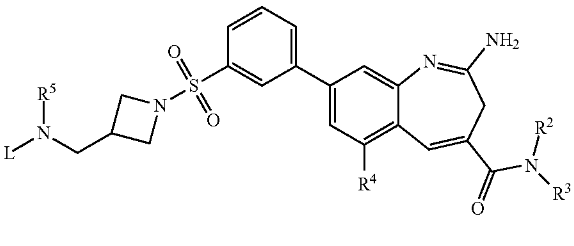

-continued

Ih

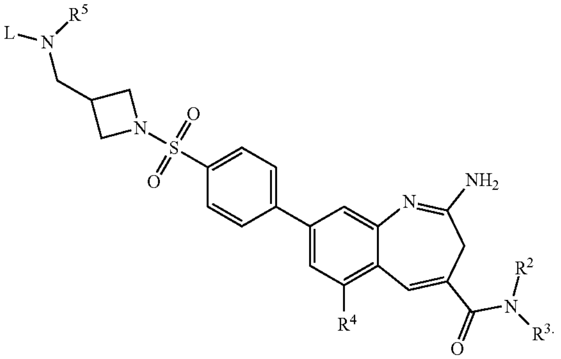

An exemplary embodiment of the macromolecule-supported compound of Formula I includes wherein L is —C(═O)—(PEG)-C(═O)—(PEP)-.

An exemplary embodiment of the macromolecule-supported compound of Formula I includes wherein $R^2$ and $R^3$ are each $C_1$-$C_8$ alkyl.

An exemplary embodiment of the macromolecule-supported compound of Formula I includes wherein $R^2$ and $R^3$ are each —$CH_2CH_2CH_3$.

An exemplary embodiment of the immunoconjugate of Formula I includes wherein $X^2$ and $X^3$ are each a bond, and $R^2$ or $R^3$ is —O—($C_1$-$C_{12}$ alkyl).

An exemplary embodiment of the immunoconjugate of Formula I includes wherein $X^2$ and $X^3$ are each a bond, and $R^2$ or $R^3$ is —$OCH_2CH_3$.

An exemplary embodiment of the immunoconjugate of Formula I includes wherein one of $R^1$ and $R^4$ is selected from:

—($C_1$-$C_{12}$ alkyldiyl)-N($R^5$)—*;
—($C_1$-$C_{12}$ alkyldiyl)-N($R^5$)C(═N$R^5$)N($R^5$)—*;
—($C_6$-$C_{20}$ aryldiyl)-S(═O)$_2$—($C_2$-$C_{20}$ heterocyclyldiyl)-*;
—($C_6$-$C_{20}$ aryldiyl)-S(═O)$_2$—($C_2$-$C_{20}$ heterocyclyldiyl)-($C_1$-$C_{12}$ alkyldiyl)-N($R^5$)—*;
—($C_6$-$C_{20}$ aryldiyl)-C(═O)—*;
—($C_6$-$C_{20}$ aryldiyl)-($C_1$-$C_{12}$ alkyldiyl)-N($R^5$)—*;
—($C_6$-$C_{20}$ aryldiyl)-C(═O)—($C_2$-$C_{20}$ heterocyclyldiyl)-*;
—C(═O)N$R^5$—($C_1$-$C_{20}$ heteroaryldiyl)-*; and
—C(═O)N$R^5$—($C_1$-$C_{20}$ heteroaryldiyl)-($C_2$-$C_{20}$ heterocyclyldiyl)-C(═O)N$R^5$—($C_1$-$C_{12}$ alkyldiyl)-N$R^5$—*.

An exemplary embodiment of the immunoconjugate of Formula I includes wherein one of $R^2$ and $R^3$ is selected from:

—($C_1$-$C_{12}$ alkyldiyl)-N($R^5$)—*;
—($C_1$-$C_{12}$ alkyldiyl)-O—($C_1$-$C_{12}$ alkyldiyl)-N($R^5$)—*;
—($C_1$-$C_{12}$ alkyldiyl)-N($R^5$)C(═N$R^5$)—N($R^5$)—*;
—($C_1$-$C_{12}$ alkyldiyl)-($C_6$-$C_{20}$ aryldiyl)-($C_1$-$C_{12}$ alkyldiyl)-N($R^5$)—*;
—($C_1$-$C_{12}$ alkyldiyl)-($C_6$-$C_{20}$ aryldiyl)-($C_1$-$C_{12}$ alkyldiyl)-N($R^5$)—C(═N$R^5$)N($R^5$)—*;
—($C_2$-$C_6$ alkynyldiyl)-N($R^5$)—*; and
—($C_2$-$C_6$ alkynyldiyl)-N($R^5$)C(═N$R^5$)N($R^5$)—*;

$X^2$ and $X^3$ are a bond, and where the asterisk * indicates the attachment site of L.

An exemplary embodiment of the macromolecule-supported compound of Formula I includes wherein one of $R^1$ and $R^4$ is selected from —($C_6$-$C_{20}$ aryldiyl)-S(═O)$_2$—($C_2$-

$C_{20}$ heterocyclyldiyl)-($C_1$-$C_{12}$ alkyldiyl)-N($R^5$)$_2$ and —($C_6$-$C_{20}$ aryldiyl)-S(═O)$_2$—($C_2$-$C_{20}$ heterocyclyldiyl)-($C_1$-$C_{12}$ alkyldiyl)-OH.

An exemplary embodiment of the macromolecule-supported compound of Formula I includes wherein $C_6$-$C_{20}$ aryldiyl is phenyldiyl and $C_2$-$C_{20}$ heterocyclyldiyl is azetidindiyl.

An exemplary embodiment of the macromolecule-supported compound of Formula I includes wherein one of $R^1$ and $R^4$ is selected from the formulas:

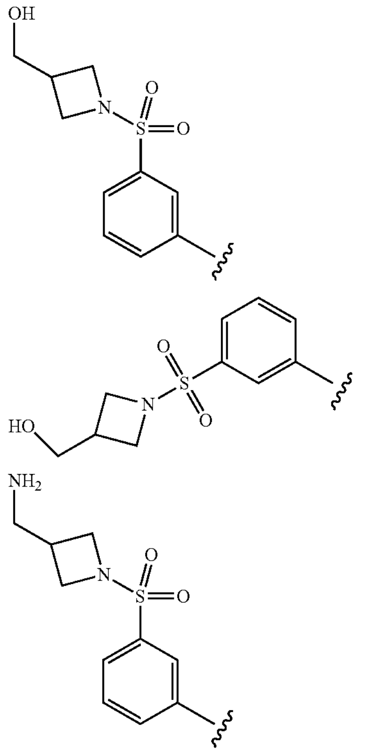

-continued

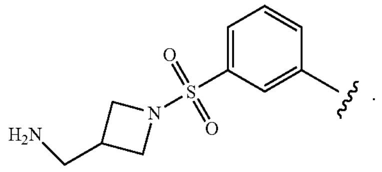

An exemplary embodiment of the macromolecule-supported compound of Formula I includes wherein one of $R^1$ and $R^4$ is —C(═O)NR$^5$—($C_1$-$C_{20}$ heteroaryldiyl)-($C_2$-$C_{20}$ heterocyclyldiyl)-C(═O)NR$^5$—($C_1$-$C_{12}$ alkyldiyl)-NR$^5$-L.

An exemplary embodiment of the macromolecule-supported compound of Formula I includes wherein $C_1$-$C_{20}$ heteroaryldiyl is pyridinediyl and $C_2$-$C_{20}$ heterocyclyldiyl is piperidinyl.

Exemplary embodiments of macromolecule-supported compounds comprise a macromolecular support covalently attached to a linker which is covalently attached to one or more aminobenzazepine moieties, and having Formula III:

III

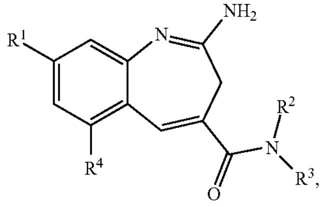

a pharmaceutically acceptable salt thereof, or a quaternary ammonium salt thereof, wherein $R^1$, $R^2$, $R^3$, and $R^4$ are independently Y or Z, wherein one of $R^1$, $R^2$, $R^3$, and $R^4$ is Y, having the formula:

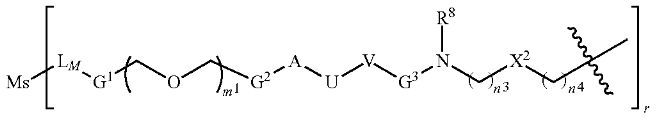

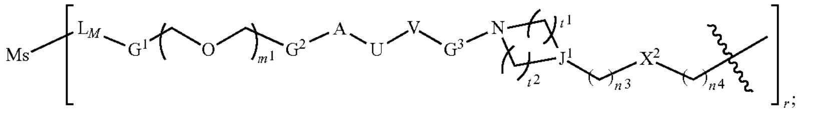

each Z independently is hydrogen or selected from the formulas:

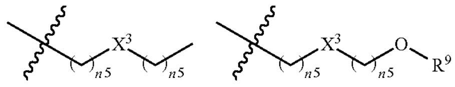

-continued

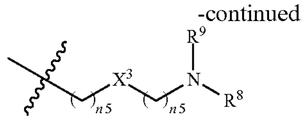

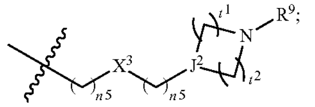

U is optionally present and is $CH_2$, C(═O), $CH_2C$(═O), or C(═O)$CH_2$,

A is optionally present and is $NR^{10}$ or selected from the formulas:

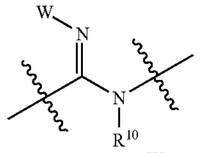
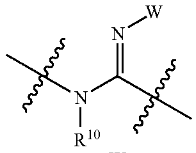
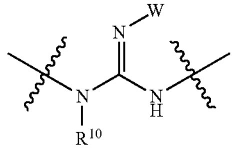
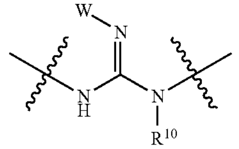
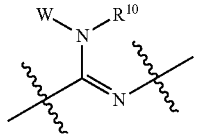
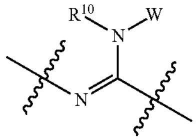
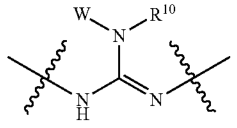

$R^{10}$ and W independently are hydrogen, $Ar^1$, or of formula:

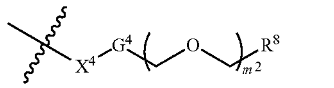
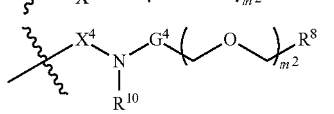

V is optionally present and is of formula:

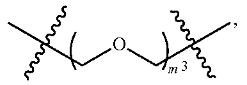

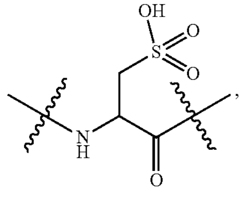 or 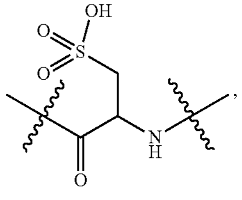

$J^1$ and $J^2$ independently are CH or N, $m^1$, $m^2$, and $m^3$ independently are an integer from 0 to 25, except that at least one of $m^1$, $m^2$, and $m^3$ is a non-zero integer, $n^1$, $n^2$, $n^3$, $n^4$, $n^5$, and $n^6$ independently are an integer from 0 to 10, $t^1$ and $t^2$ independently are an integer from 1 to 3, $G^1$, $G^2$, $G^3$, and $G^4$ independently are $CH_2$, C(═O), $CH_2C$(═O), C(═O)$CH_2$, or a bond, $X^1$, $X^2$, $X^3$, and $X^4$ are each optionally present and independently are O, $NR^7$, $CHR^7$, $SO_2$, S, or one or two cycloalkyldiyl, heterocycloalkyldiyl, aryldiyl, or heteroaryldiyl groups, and when more than one cycloalkyldiyl, heterocycloalkyldiyl, aryldiyl, or heteroaryldiyl group is present, the more than one cycloalkyldiyl, heterocycloalkyldiyl, aryldiyl, or heteroaryldiyl groups are linked or fused, wherein linked cycloalkyldiyl, heterocycloalkyldiyl, aryldiyl, or heteroaryldiyl groups are linked through a bond or —CO—, $R^9$ is hydrogen, $C_1$-$C_4$ alkyl, or selected from the formulas:

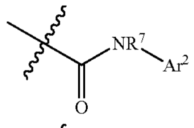
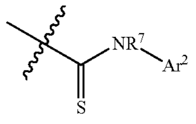
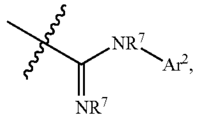

$R^8$ is independently hydrogen or $C_1$-$C_4$ alkyl, $Ar^1$ and $Ar^2$ independently are an aryl or heteroaryl group, optionally substituted with one or more halogens (e.g., fluorine, chlorine, bromine, or iodine), nitriles, hydroxyls, $C_1$-$C_4$ alkyl groups, or a combination thereof, $L_M$ is a linking moiety that comprises a functional group selected from an amide, amine, ester, carbamate, urea, thioether, thiocarbamate, thiocarbonate, and thiourea, r is an integer from 1 to 50, "$M_S$" is a macromolecular support, and each wavy line ( ) represents a point of attachment.

Generally, the macromolecule-supported compounds of the invention comprise about 1 to about 50 aminobenzazepine compounds (e.g., about 1 to about 25 or about 1 to about 10), each aminobenzazepine compound linked to the macromolecular support, as designated with subscript "p" or "r". In an embodiment, p or r is 1, such that there is a single aminobenzazepine compound linked to the macromolecular support. In some embodiments, p or r is an integer from about 2 to about 10 (e.g., about 2 to about 9, about 3 to about 9, about 4 to about 9, about 5 to about 9, about 6 to about 9, about 3 to about 8, about 3 to about 7, about 3 to about 6, about 4 to about 8, about 4 to about 7, about 4 to about 6, about 5 to about 6, about 1 to about 6, about 1 to about 4, about 2 to about 4, or about 1 to about 3). Accordingly, the macromolecule-supported compounds can have (i.e., subscript "p" or "r" can be) 1, 2, 3, 4, 5, 6, 7, 8, 9, or 10 aminobenzazepine compounds linked to the macromolecular support. In preferred embodiments, the macromolecule-supported compounds have (i.e., subscript "p" or "r" can be) 1, 2, 3, or 4 aminobenzazepine compounds linked to the macromolecular support. The desirable aminobenzazepine compound to macromolecular support ratio (i.e., the value of the subscript "r") can be determined by a skilled artisan depending on the desired effect of the treatment.

The invention includes all reasonable combinations, and permutations of the features, of the Formula I and III embodiments.

The loading (drug/macromolecular support ratio) of a macromolecule-supported compound may be controlled in different ways, and for example, by: (i) limiting the molar excess of the aminobenzazepine-linker intermediate compound relative to macromolecular support or (ii) limiting the conjugation reaction time or temperature.

It is to be understood that where more than one nucleophilic group of the macromolecular support reacts with a drug, then the resulting product is a mixture of macromolecule-supported compounds with a distribution of one or more drug moieties attached to a macromolecular support. Individual macromolecule-supported compound molecules may be identified in the mixture by mass spectroscopy and separated by HPLC, e.g., hydrophobic interaction chromatography (see, e.g., McDonagh et al., *Prot. Engr. Design & Selection,* 19(7): 299-307 (2006); Hamblett et al., *Clin. Cancer Res.,* 10: 7063-7070 (2004); Hamblett et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous macromolecule-supported compound with a single loading value may be isolated from the conjugation mixture by electrophoresis or chromatography.

In certain embodiments, the macromolecule-supported compounds of the invention include those with immunostimulatory activity. The macromolecule-supported compounds of the invention can selectively deliver an effective dose of an aminobenzazepine drug to tumor tissue, whereby greater selectivity (i.e., a lower efficacious dose) may be achieved while increasing the therapeutic index ("therapeutic window") relative to unconjugated aminobenzazepine.

Macromolecular Support

The macromolecule-supported compound of the invention comprises a macromolecular support. As a singular entity, the macromolecular support can be biologically active or biologically inactive relative to the aminobenzazepine compound described herein. However, when used in combination with the aminobenzazepine compound, the biological activity of the aminobenzazepine compound is enhanced, for example, by providing a targeting effect, by providing beneficial off-target effects (i.e., biological activity other than TLR activity), improved pharmacokinetic properties (e.g., half-life extension), enhanced biological delivery (e.g., tumor penetration), or by providing additional biological stimulation, differentiation, up-regulation, and/or down-regulation. In certain embodiments, the biological effect of the macromolecular support and the aminobenzazepine compound is synergistic, i.e., greater than the sum of the biological activity of each of the macromolecular support and aminobenzazepine compound as a singular entity.

In some embodiments, the macromolecular support is a resin, bead, probe, tag, well, plate, or any other surface that can be used for therapeutics, diagnostics, or chemical assays. The resin, bead, probe, tag, well, plate, or any other surface can be made of any suitable material so long as the material can be surface modified. For example, the resin, bead, probe, tag, well, plate, or any other surface can polymer-based such as, for example, polyacrylates, polyacrylamides, polystyrenes, polyethylenes, polypropylenes, polyethylene glycols, or polypropylene glycols.

In some embodiments, the macromolecular support is a chemical structure (e.g., a biological structure or an inorganic framework) that can be used for therapeutics, diagnostics, or chemical assays. The macromolecular support can have any suitable structure and size. The macromolecular support can be an organic or inorganic structure having a molecular weight of at least about 200 Da (e.g., at least about 500 Da, at least about 1,000 Da, at least about 2,000 Da, at least about 5,000 Da, or at least about 10,000 Da). For example, the macromolecular support can be a biopolymer (e.g., a glycopolymer, a cellulosic polymer, etc.), a nanoparticle (e.g., a carbon nanotube, a quantum dot, a metal nanoparticle (e.g., silver, gold, titanium dioxide, silicon dioxide, zirconium dioxide, aluminum oxide, or ytterbium trifluoride), etc.), a lipid (e.g., lipid vesicles, micelles, liposomes, etc.), a carbohydrate (e.g., sugar, starch, cellulose, glycogen, etc.), a peptide (e.g., a polypeptide, a protein, a peptide mimetic, a glycopeptide, etc.), an alternative protein scaffold, an antibody construct (e.g., antibody, an antibody-derivative (including Fc fusions, Fab fragments and scFvs), etc.), a nucleotide (e.g., RNA, DNA, antisense, siRNA, an aptamer, etc.), or any combination thereof. In some embodiments, the macromolecular support is a peptide, a nucleotide, a sugar, a lipid, or an antibody. In certain embodiments, the macromolecular support is an immune checkpoint inhibitor.

Macromolecule-Supported Compound Composition

The invention provides a composition, e.g., a pharmaceutically acceptable composition or formulation, comprising a plurality of macromolecule-supported compounds as described herein and optionally a carrier therefor, e.g., a pharmaceutically acceptable carrier. The macromolecule-supported compounds can be the same or different in the composition, i.e., the composition can comprise macromolecule-supported compounds that have the same number of aminobenzazepine compounds linked to the same chemical entity of the macromolecule-supported compound, macromolecule-supported compounds that have the same number of aminobenzazepine compounds linked to different chemical entities of the macromolecule-supported compound, that have different numbers of aminobenzazepine compounds linked to the same chemical entity of the macromolecule-supported compound, and/or that have different numbers of aminobenzazepine compounds linked to different chemical entities of the macromolecule-supported compound.

The composition can have any suitable average aminobenzazepine compound to macromolecular support ratio (e.g., about 0.1 to about 50, about 1 to about 10, about 1 to about 6, or about 1 to about 4). For example, a composition of macromolecule-supported compounds of the invention can have an average aminobenzazepine compound to macromolecular support ratio of about 0.4, 0.6, 0.8, 1, 1.2, 1.4, 1.6, 1.8, 2, 2.2, 2.4, 2.6, 2.8, 3, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, or 10, or within a range bounded by any two of the aforementioned values. A skilled artisan will recognize that the number of aminobenzazepine compound conjugated to the macromolecular support may vary from macromolecule-supported compound to macromolecule-supported compound in a composition comprising multiple macromolecule-supported compounds of the invention, and, thus, the aminobenzazepine compound to macromolecule-supported ratio can be measured as an average. The aminobenzazepine compound to macromolecule-supported ratio can be assessed by any suitable means, many of which are known in the art.

The average number of adjuvant moieties per macromolecular support (DAR) in preparations of macromolecule-supported compounds from conjugation reactions may be characterized by conventional means such as mass spectrometry, ELISA assay, UV-Vis, and HPLC. The quantitative distribution of macromolecule-supported compounds in a composition in terms of p may also be determined. In some instances, separation, purification, and characterization of homogeneous macromolecule-supported compounds where p or r is a certain value from macromolecule-supported compounds with other drug loadings may be achieved by means such as reverse phase HPLC or electrophoresis.

In some embodiments, the composition further comprises one or more pharmaceutically or pharmacologically acceptable excipients. For example, the macromolecule-supported compounds of the invention can be formulated for parenteral administration, such as IV administration or administration into a body cavity or lumen of an organ. Alternatively, the macromolecule-supported compounds can be injected intratumorally. Compositions for injection will commonly comprise a solution of the macromolecule-supported compound dissolved in a pharmaceutically acceptable carrier. Among the acceptable vehicles and solvents that can be employed are water and an isotonic solution of one or more salts such as sodium chloride, e.g., Ringer's solution. In addition, sterile fixed oils can conventionally be employed as a solvent or suspending medium. For this purpose, any bland fixed oil can be employed, including synthetic monoglycerides or diglycerides. In addition, fatty acids such as oleic acid can likewise be used in the preparation of injectables. These compositions desirably are sterile and generally free of undesirable matter. These compositions can be sterilized by conventional, well known sterilization techniques. The compositions can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like.

The composition can contain any suitable concentration of the macromolecule-supported compound. The concentration of the macromolecule-supported compound in the composition can vary widely, and will be selected primarily based on fluid volumes, viscosities, body weight, and the like, in accordance with the particular mode of administration selected and the patient's needs. In certain embodiments, the concentration of a macromolecule-supported compound in a solution formulation for injection will range from about 0.1% (w/w) to about 10% (w/w).

Methods of Using the Macromolecule-Supported Compound

The invention provides a method of recognizing TLR (e.g., TLR7 and/or TLR8) for use in therapeutics, diagnostics, or chemical assays. Without wishing to be bound by any particular theory, TLR has a high affinity for the adjuvant/linker combinations described herein, such that the macromolecule-supported compounds described herein are useful in assessing the presence and/or abundance of TLR. In certain embodiments, the macromolecule-supported compound is used as a chemical assay for TLR engagement and/or activity. In such embodiments, the macromolecular support can be a resin, bead, probe, tag, well, or plate. In certain embodiments, the macromolecule-supported compound is used as a therapeutic or diagnostic for diseases associated with TLR. In such embodiments, the macromolecular support is typically a chemical structure (e.g., a biological structure or an inorganic framework) having a molecular weight of at least about 200 Da (e.g., at least about 500 Da, at least about 1,000 Da, at least about 2,000 Da, at least about 5,000 Da, or at least about 10,000 Da).

The invention also provides a method for treating cancer. The method comprises administering a therapeutically effective amount of a macromolecule-supported compound (e.g., as a composition as described above) to a subject in need thereof. For example, the method can include administering the macromolecule-supported compound to provide a dose of from about 100 ng/kg to about 50 mg/kg to the subject. The macromolecule-supported compound dose can range from about 5 mg/kg to about 50 mg/kg, from about 10 μg/kg to about 5 mg/kg, or from about 100 μg/kg to about 1 mg/kg. The macromolecule-supported compound dose can be about 100, 200, 300, 400, or 500 μg/kg. The macromolecule-supported compound dose can be about 1, 2, 3, 4, 5, 6, 7, 8, 9, or 10 mg/kg. The macromolecule-supported compound dose can also be outside of these ranges, depending on the particular compound as well as the type and severity of the cancer being treated. Frequency of administration can range from a single dose to multiple doses per week, or more frequently. In some embodiments, the macromolecule-supported compound is administered from about once per month to about five times per week. In some embodiments, the macromolecule-supported compound is administered once per week.

In a further aspect, the invention provides a method for curing cancer. The method comprises administering a therapeutically effective amount of a macromolecule-supported compound (e.g., as a composition as described above) to a subject. For example, the methods can include administering the macromolecule-supported compound to provide a dose of from about 100 ng/kg to about 50 mg/kg to the subject. The macromolecule-supported compound dose can range from about 5 mg/kg to about 50 mg/kg, from about 10 μg/kg to about 5 mg/kg, or from about 100 μg/kg to about 1 mg/kg. The macromolecule-supported compound dose can be about 100, 200, 300, 400, or 500 μg/kg. The macromolecule-supported compound dose can be about 1, 2, 3, 4, 5, 6, 7, 8, 9, or 10 mg/kg. The macromolecule-supported compound dose can also be outside of these ranges, depending on the particular conjugate as well as the type and severity of the cancer being cured. Frequency of administration can range from a single dose to multiple doses per week, or more frequently. In some embodiments, the macromolecule-supported compound is administered from about once per month to about five times per week. In some embodiments, the macromolecule-supported compound is administered once per week.

In another aspect, the invention provides a method for preventing cancer. The method comprises administering a therapeutically effective amount of a macromolecule-supported compound (e.g., as a composition as described above) to a subject. In certain embodiments, the subject is susceptible to a certain cancer to be prevented. For example, the methods can include administering the macromolecule-supported compound to provide a dose of from about 100 ng/kg to about 50 mg/kg to the subject. The macromolecule-supported compound dose can range from about 5 mg/kg to about 50 mg/kg, from about 10 μg/kg to about 5 mg/kg, or from about 100 μg/kg to about 1 mg/kg. The macromolecule-supported compound dose can be about 100, 200, 300, 400, or 500 μg/kg. The macromolecule-supported compound dose can be about 1, 2, 3, 4, 5, 6, 7, 8, 9, or 10 mg/kg. The macromolecule-supported compound dose can also be outside of these ranges, depending on the particular conjugate as well as the type and severity of the cancer being treated. Frequency of administration can range from a single dose to multiple doses per week, or more frequently. In some embodiments, the macromolecule-supported compound is administered from about once per month to about five times per week. In some embodiments, the macromolecule-supported compound is administered once per week.

Some embodiments of the invention provide methods for treating cancer as described above, wherein the cancer is a head and neck cancer. Head and neck cancer (as well as head and neck squamous cell carcinoma) refers to a variety of cancers characterized by squamous cell carcinomas of the oral cavity, pharynx and larynx, salivary glands, paranasal sinuses, and nasal cavity, as well as the lymph nodes of the upper part of the neck. Head and neck cancers account for approximately 3 to 5 percent of all cancers in the United States. These cancers are more common in men and in people over age 50. Tobacco (including smokeless tobacco) and alcohol use are the most important risk factors for head and neck cancers, particularly those of the oral cavity, oropharynx, hypopharynx and larynx. Eighty-five percent of head and neck cancers are linked to tobacco use.

In the methods of the invention, the macromolecule-supported compounds can be used to target a number of malignant cells. For example, the macromolecule-supported compounds can be used to target squamous epithelial cells of the lip, oral cavity, pharynx, larynx, nasal cavity, or paranasal sinuses. The macromolecule-supported compounds can be used to target mucoepidermoid carcinoma cells, adenoid cystic carcinoma cells, adenocarcinoma cells, small-cell undifferentiated cancer cells, esthesioneuroblastoma cells, Hodgkin lymphoma cells, and Non-Hodgkin lymphoma cells.

Some embodiments of the invention provide methods for treating cancer as described above, wherein the cancer is breast cancer. Breast cancer can originate from different areas in the breast, and a number of different types of breast cancer have been characterized. For example, the macromolecule-supported compounds of the invention can be used for treating ductal carcinoma in situ; invasive ductal carcinoma (e.g., tubular carcinoma; medullary carcinoma; mucinous carcinoma; papillary carcinoma; or cribriform carcinoma of the breast); lobular carcinoma in situ; invasive lobular carcinoma; inflammatory breast cancer; and other forms of breast cancer.

It is contemplated that the macromolecule-supported compounds of the present invention may be used to treat various hyperproliferative diseases or disorders, e.g., characterized by the overexpression of a tumor antigen. Exemplary hyperproliferative disorders include benign or malignant solid tumors and hematological disorders such as leukemia and lymphoid malignancies.

In another aspect, a macromolecule-supported compound for use as a medicament is provided. In certain embodiments, the invention provides a macromolecule-supported compound for use in a method of treating an individual comprising administering to the individual an effective amount of the macromolecule-supported compound. In one such embodiment, the method further comprises administering to the individual an effective amount of at least one additional therapeutic agent, e.g., as described herein.

In a further aspect, the invention provides for the use of a macromolecule-supported compound in the manufacture or preparation of a medicament. In one embodiment, the medicament is for treatment of cancer, the method comprising administering to an individual having cancer an effective amount of the medicament. In one such embodiment, the method further comprises administering to the individual an effective amount of at least one additional therapeutic agent, e.g., as described herein.

Carcinomas are malignancies that originate in the epithelial tissues. Epithelial cells cover the external surface of the body, line the internal cavities, and form the lining of glandular tissues. Examples of carcinomas include, but are not limited to, adenocarcinoma (cancer that begins in glandular (secretory) cells such as cancers of the breast, pancreas, lung, prostate, stomach, gastroesophageal junction, and colon) adrenocortical carcinoma; hepatocellular carcinoma; renal cell carcinoma; ovarian carcinoma; carcinoma in situ; ductal carcinoma; carcinoma of the breast; basal cell carcinoma; squamous cell carcinoma; transitional cell carcinoma; colon carcinoma; nasopharyngeal carcinoma; multilocular cystic renal cell carcinoma; oat cell carcinoma; large cell lung carcinoma; small cell lung carcinoma; non-small cell lung carcinoma; and the like. Carcinomas may be found in prostrate, pancreas, colon, brain (usually as secondary metastases), lung, breast, and skin.

Soft tissue tumors are a highly diverse group of rare tumors that are derived from connective tissue. Examples of soft tissue tumors include, but are not limited to, alveolar soft part sarcoma; angiomatoid fibrous histiocytoma; chondromyxoid fibroma; skeletal chondrosarcoma; extraskeletal myxoid chondrosarcoma; clear cell sarcoma; desmoplastic small round-cell tumor; dermatofibrosarcoma protuberans; endometrial stromal tumor; Ewing's sarcoma; fibromatosis (Desmoid); fibrosarcoma, infantile; gastrointestinal stromal tumor; bone giant cell tumor; tenosynovial giant cell tumor; inflammatory myofibroblastic tumor; uterine leiomyoma; leiomyosarcoma; lipoblastoma; typical lipoma; spindle cell or pleomorphic lipoma; atypical lipoma; chondroid lipoma; well-differentiated liposarcoma; myxoid/round cell liposarcoma; pleomorphic liposarcoma; myxoid malignant fibrous histiocytoma; high-grade malignant fibrous histiocytoma; myxofibrosarcoma; malignant peripheral nerve sheath tumor; mesothelioma; neuroblastoma; osteochondroma; osteosarcoma; primitive neuroectodermal tumor; alveolar rhabdomyosarcoma; embryonal rhabdomyosarcoma; benign or malignant schwannoma; synovial sarcoma; Evan's tumor; nodular fasciitis; desmoid-type fibromatosis; solitary fibrous tumor; dermatofibrosarcoma protuberans (DFSP); angiosarcoma; epithelioid hemangioendothelioma; tenosynovial giant cell tumor (TGCT); pigmented villonodular synovitis (PVNS); fibrous dysplasia; myxofibrosarcoma; fibrosarcoma; synovial sarcoma; malignant peripheral nerve sheath tumor; neurofibroma; pleomorphic adenoma of soft tissue; and neoplasias derived from fibroblasts, myofibroblasts, histiocytes, vascular cells/endothelial cells, and nerve sheath cells.

A sarcoma is a rare type of cancer that arises in cells of mesenchymal origin, e.g., in bone or in the soft tissues of the body, including cartilage, fat, muscle, blood vessels, fibrous tissue, or other connective or supportive tissue. Different types of sarcoma are based on where the cancer forms. For example, osteosarcoma forms in bone, liposarcoma forms in fat, and rhabdomyosarcoma forms in muscle. Examples of sarcomas include, but are not limited to, askin's tumor; sarcoma botryoides; chondrosarcoma; ewing's sarcoma; malignant hemangioendothelioma; malignant schwannoma;

osteosarcoma; and soft tissue sarcomas (e.g., alveolar soft part sarcoma; angiosarcoma; cystosarcoma phyllodesdermatofibrosarcoma protuberans (DFSP); desmoid tumor; desmoplastic small round cell tumor; epithelioid sarcoma; extraskeletal chondrosarcoma; extraskeletal osteosarcoma; fibrosarcoma; gastrointestinal stromal tumor (GIST); hemangiopericytoma; hemangiosarcoma (more commonly referred to as "angiosarcoma"); kaposi's sarcoma; leiomyosarcoma; liposarcoma; lymphangiosarcoma; malignant peripheral nerve sheath tumor (MPNST); neurofibrosarcoma; synovial sarcoma; and undifferentiated pleomorphic sarcoma).

A teratoma is a type of germ cell tumor that may contain several different types of tissue (e.g., can include tissues derived from any and/or all of the three germ layers: endoderm, mesoderm, and ectoderm), including, for example, hair, muscle, and bone. Teratomas occur most often in the ovaries in women, the testicles in men, and the tailbone in children.

Melanoma is a form of cancer that begins in melanocytes (cells that make the pigment melanin). Melanoma may begin in a mole (skin melanoma), but can also begin in other pigmented tissues, such as in the eye or in the intestines.

Merkel cell carcinoma is a rare type of skin cancer that usually appears as a flesh-colored or bluish-red nodule on the face, head or neck. Merkel cell carcinoma is also called neuroendocrine carcinoma of the skin. In some embodiments, methods for treating Merkel cell carcinoma include administering a macromolecule-supported compound containing a macromolecular support. In some embodiments, the Merkel cell carcinoma has metastasized when administration occurs.

Leukemias are cancers that start in blood-forming tissue, such as the bone marrow, and cause large numbers of abnormal blood cells to be produced and enter the bloodstream. For example, leukemias can originate in bone marrow-derived cells that normally mature in the bloodstream. Leukemias are named for how quickly the disease develops and progresses (e.g., acute versus chronic) and for the type of white blood cell that is affected (e.g., myeloid versus lymphoid). Myeloid leukemias are also called myelogenous or myeloblastic leukemias. Lymphoid leukemias are also called lymphoblastic or lymphocytic leukemia. Lymphoid leukemia cells may collect in the lymph nodes, which can become swollen. Examples of leukemias include, but are not limited to, Acute myeloid leukemia (AML), Acute lymphoblastic leukemia (ALL), Chronic myeloid leukemia (CML), and Chronic lymphocytic leukemia (CLL).

Lymphomas are cancers that begin in cells of the immune system. For example, lymphomas can originate in bone marrow-derived cells that normally mature in the lymphatic system. There are two basic categories of lymphomas. One category of lymphoma is Hodgkin lymphoma (HL), which is marked by the presence of a type of cell called the Reed-Sternberg cell. There are currently 6 recognized types of HL. Examples of Hodgkin lymphomas include nodular sclerosis classical Hodgkin lymphoma (CHL), mixed cellularity CHL, lymphocyte-depletion CHL, lymphocyte-rich CHL, and nodular lymphocyte predominant HL.

The other category of lymphoma is non-Hodgkin lymphomas (NHL), which includes a large, diverse group of cancers of immune system cells. Non-Hodgkin lymphomas can be further divided into cancers that have an indolent (slow-growing) course and those that have an aggressive (fast-growing) course. There are currently 61 recognized types of NHL. Examples of non-Hodgkin lymphomas include, but are not limited to, AIDS-related Lymphomas, anaplastic large-cell lymphoma, angioimmunoblastic lymphoma, blastic NK-cell lymphoma, Burkitt's lymphoma, Burkitt-like lymphoma (small non-cleaved cell lymphoma), chronic lymphocytic leukemia/small lymphocytic lymphoma, cutaneous T-Cell lymphoma, diffuse large B-Cell lymphoma, enteropathy-type T-Cell lymphoma, follicular lymphoma, hepatosplenic gamma-delta T-Cell lymphomas, T-Cell leukemias, lymphoblastic lymphoma, mantle cell lymphoma, marginal zone lymphoma, nasal T-Cell lymphoma, pediatric lymphoma, peripheral T-Cell lymphomas, primary central nervous system lymphoma, transformed lymphomas, treatment-related T-Cell lymphomas, and Waldenstrom's macroglobulinemia.

Brain cancers include any cancer of the brain tissues. Examples of brain cancers include, but are not limited to, gliomas (e.g., glioblastomas, astrocytomas, oligodendrogliomas, ependymomas, and the like), meningiomas, pituitary adenomas, and vestibular schwannomas, primitive neuroectodermal tumors (medulloblastomas).

Macromolecule-supported compounds of the invention can be used either alone or in combination with other agents in a therapy. For instance, a macromolecule-supported compound may be co-administered with at least one additional therapeutic agent, such as a chemotherapeutic agent. Such combination therapies encompass combined administration (where two or more therapeutic agents are included in the same or separate formulations), and separate administration, in which case, administration of the macromolecule-supported compound can occur prior to, simultaneously, and/or following, administration of the additional therapeutic agent and/or adjuvant. Macromolecule-supported compounds can also be used in combination with radiation therapy.

The macromolecule-supported compounds of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

In some embodiments, the cancer is susceptible to a pro-inflammatory response induced by TLR7 and/or TLR8.

Examples of Non-Limiting Aspects of the Disclosure

Aspects, including embodiments, of the invention described herein may be beneficial alone or in combination, with one or more other aspects or embodiments. Without limiting the foregoing description, certain non-limiting aspects of the disclosure numbered 1-49 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A macromolecule-supported compound comprising a macromolecular support covalently attached to one or more aminobenzazepine moieties by a linker, and having Formula I:

$$\text{Ms-[L-Bza]}_p \quad \text{I}$$

or a pharmaceutically acceptable salt thereof, wherein:

"$M_S$" is the macromolecular support;

p is an integer from 1 to 50;

Bza is the aminobenzazepine moiety having the formula:

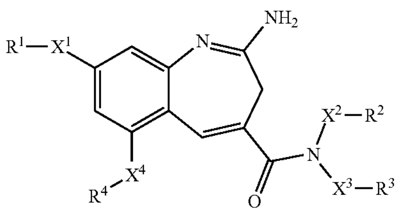

$R^1$, $R^2$, $R^3$, and $R^4$ are independently selected from the group consisting of H, $C_1$-$C_{12}$ alkyl, $C_2$-$C_6$ alkenyl, $C_2$-$C_6$ alkynyl, $C_3$-$C_{12}$ carbocyclyl, $C_6$-$C_{20}$ aryl, $C_2$-$C_9$ heterocyclyl, and $C_1$-$C_{20}$ heteroaryl, where alkyl, alkenyl, alkynyl, carbocyclyl, aryl, heterocyclyl, and heteroaryl are independently and optionally substituted with one or more groups selected from:

—($C_1$-$C_{12}$ alkyldiyl)-N($R^5$)—*;

—($C_1$-$C_{12}$ alkyldiyl)-N($R^5$)$_2$;

—($C_3$-$C_{12}$ carbocyclyl);

—($C_3$-$C_{12}$ carbocyclyl)-*;

—($C_3$-$C_{12}$ carbocyclyl)-($C_1$-$C_{12}$ alkyldiyl)-N$R^5$—*;

—($C_3$-$C_{12}$ carbocyclyl)-($C_1$-$C_{12}$ alkyldiyl)-N($R^5$)$_2$;

—($C_3$-$C_{12}$ carbocyclyl)-N$R^5$—C(=N$R^5$)N$R^5$—*;

—($C_6$-$C_{20}$ aryl);

—($C_6$-$C_{20}$ aryl)-*;

—($C_6$-$C_{20}$ aryldiyl)-N($R^5$)—*;

—($C_6$-$C_{20}$ aryldiyl)-($C_1$-$C_{12}$ alkyldiyl)-N($R^5$)—*;

—($C_6$-$C_{20}$ aryldiyl)-($C_1$-$C_{12}$ alkyldiyl)-N($R^5$)$_2$;

—($C_6$-$C_{20}$ aryldiyl)-($C_1$-$C_{12}$ alkyldiyl)-N$R^5$—C(=N$R^{5a}$)N($R^5$)—*;

—($C_2$-$C_{20}$ heterocyclyl);

—($C_2$-$C_{20}$ heterocyclyl)-*;

—($C_2$-$C_9$ heterocyclyl)-($C_1$-$C_{12}$ alkyldiyl)-N$R^5$—*;

—($C_2$-$C_9$ heterocyclyl)-($C_1$-$C_{12}$ alkyldiyl)-N($R^5$)$_2$;

—($C_2$-$C_9$ heterocyclyl)-N$R^5$—C(=N$R^{5a}$)N$R^5$—*;

—($C_1$-$C_{20}$ heteroaryl);

—($C_1$-$C_{20}$ heteroaryl)-*;

—($C_1$-$C_{20}$ heteroaryl)-($C_1$-$C_2$ alkyldiyl)-N($R^5$)—*;

—($C_1$-$C_{20}$ heteroaryl)-($C_1$-$C_{12}$ alkyldiyl)-N($R^5$)$_2$;

—($C_1$-$C_{20}$ heteroaryl)-N$R^5$—C(=N$R^{5a}$)N($R^5$)—*;

—C(=O)—*;

—C(=O)—($C_2$-$C_{20}$ heterocyclyldiyl)-*;

—C(=O)N($R^5$)$_2$;

—C(=O)N($R^5$)—*;

—C(=O)N($R^5$)—($C_1$-$C_{12}$ alkyldiyl)-N($R^5$)C(=O)$R^5$;

—C(=O)N($R^5$)—($C_1$-$C_{12}$ alkyldiyl)-N($R^5$)C(=O)N($R^5$)$_2$;

—C(=O)N$R^5$—($C_1$-$C_{12}$ alkyldiyl)-N($R^5$)C$O_2R^5$;

—C(=O)N$R^5$—($C_1$-$C_{12}$ alkyldiyl)-N($R^5$)C(=N$R^{5a}$)N($R^5$)$_2$;

—C(=O)N$R^5$—($C_1$-$C_{12}$ alkyldiyl)-N$R^5$C(=N$R^{5a}$)$R^5$;

—C(=O)N$R^5$—($C_1$-$C_8$ alkyldiyl)-N$R^5$($C_2$-$C_5$ heteroaryl);

—C(=O)N$R^5$—($C_1$-$C_{20}$ heteroaryldiyl)-N($R^5$)—*;

—C(=O)N$R^5$—($C_1$-$C_{20}$ heteroaryldiyl)-*;

—C(=O)N$R^5$—($C_1$-$C_{20}$ heteroaryldiyl)-($C_1$-$C_{12}$ alkyldiyl)-N($R^5$)$_2$;

—C(=O)N$R^5$—($C_1$-$C_{20}$ heteroaryldiyl)-($C_2$-$C_{20}$ heterocyclyldiyl)-C(=O)N$R^5$—($C_1$-$C_{12}$ alkyldiyl)-N$R^5$—*;

—N($R^5$)$_2$;

—N($R^5$)—*;

—N($R^5$)C(=O)$R^5$;

—N($R^5$)C(=O)—*;

—N($R^5$)C(=O)N($R^5$)$_2$;

—N($R^5$)C(=O)N($R^5$)—*;

—N($R^5$)C$O_2R^5$;

—N$R^5$C(=N$R^{5a}$)N($R^5$)$_2$;

—N$R^5$C(=N$R^{5a}$)N($R^5$)—*;

—N$R^5$C(=N$R^{5a}$)$R^5$;

—N($R^5$)—($C_2$-$C_5$ heteroaryl);

—O—($C_1$-$C_{12}$ alkyl);

—O—($C_1$-$C_{12}$ alkyldiyl)-N($R^5$)$_2$;

—O—($C_1$-$C_2$ alkyldiyl)-N($R^5$)—*;

—S(=O)$_2$—($C_2$-$C_{20}$ heterocyclyldiyl)-*;

—S(=O)$_2$—($C_2$-$C_{20}$ heterocyclyldiyl)-($C_1$-$C_{12}$ alkyldiyl)-N($R^5$)$_2$;

—S(=O)$_2$—($C_2$-$C_{20}$ heterocyclyldiyl)-($C_1$-$C_{12}$ alkyldiyl)-N$R^5$—*; and —S(=O)$_2$—($C_2$-$C_{20}$ heterocyclyldiyl)-($C_1$-$C_{12}$ alkyldiyl)-OH;

or $R^2$ and $R^3$ together form a 5- or 6-membered heterocyclyl ring;

$X^1$, $X^2$, $X^3$, and $X^4$ are independently selected from the group consisting of a bond, C(=O), C(=O)N($R^5$), O, N($R^5$), S, S(O)$_2$, and S(O)$_2$N($R^5$);

$R^5$ is selected from the group consisting of H, $C_6$-$C_{20}$ aryl, $C_6$-$C_{20}$ aryldiyl, $C_1$-$C_{12}$ alkyl, and $C_1$-$C_{12}$ alkyldiyl, or two $R^5$ groups together form a 5- or 6-membered heterocyclyl ring;

$R^{5a}$ is selected from the group consisting of $C_6$-$C_{20}$ aryl and $C_1$-$C_{20}$ heteroaryl;

where the asterisk * indicates the attachment site of L, and where one of $R^1$, $R^2$, $R^3$ and $R^4$ is attached to L;

L is the linker selected from the group consisting of:

—C(=O)—(PEG)-;

—C(=O)—(PEG)-C(=O)—;

—C(=O)—(PEG)-O—;

—C(=O)—(PEG)-C(=O)—(PEP)—;

—C(=O)—(PEG)-C(=O)N($R^5$)—($C_1$-$C_{12}$ alkyldiyl)-;

—C(=O)—(PEG)-C(=O)N($R^5$)—($C_1$-$C_{12}$ alkyldiyl)-N($R^5$)C(=O)—($C_2$-$C_5$ monoheterocyclyldiyl)-;

—C(=O)—(PEG)-C(=O)N($R^5$)—($C_1$-$C_{12}$ alkyldiyl)-(MCgluc)-;

—C(=O)—(PEG)-C(=O)-(MCgluc)-;

—C(=O)—(PEG)-C(=O)—(PEP)—N($R^5$)—($C_1$-$C_{12}$ alkyldiyl)-;

—C(=O)—(PEG)-C(=O)—(PEP)—N($R^5$)—($C_1$-$C_{12}$ alkyldiyl)-N($R^5$)C(=O)—($C_2$-$C_5$ monoheterocyclyldiyl)-;

—C(=O)—(PEG)-N($R^5$)—;

—C(=O)—(PEG)-N($R^5$)—(PEG)-C(=O)—(PEP)—;

—C(=O)—(PEG)-$N^+$($R^5$)$_2$—(PEG)-C(=O)—(PEP)—;

—C(=O)—(PEG)-C(=O)—N($R^5$)CH($AA_1$)C(=O)—(PEG)-C(=O)—(PEP)—;

—C(=O)—(PEG)-C(=O)—N($R^5$)CH($AA_1$)C(=O)—N($R^5$)—($C_1$-$C_{12}$ alkyldiyl)-;

—C(=O)—(PEG)-SS—($C_1$-$C_{12}$ alkyldiyl)-OC(=O)—;

—C(=O)—(PEG)-SS—($C_1$-$C_{12}$ alkyldiyl)-C(=O)—;

—C(=O)—($C_1$-$C_{12}$ alkyldiyl)-C(=O)—(PEP)—;

—C(=O)—($C_1$-$C_{12}$ alkyldiyl)-C(=O)—(PEP)—N($R^5$)—($C_1$-$C_{12}$ alkyldiyl)-;

—C(=O)—($C_1$-$C_{12}$ alkyldiyl)-C(=O)—(PEP)—N($R^5$)—($C_1$-$C_{12}$ alkyldiyl)-N($R^5$)—C(=O);

—C(=O)—($C_1$-$C_{12}$ alkyldiyl)-C(=O)—(PEP)—N($R^5$)—($C_1$-$C_{12}$ alkyldiyl)-N($R^5$)C(=O)—($C_2$-$C_5$ monoheterocyclyldiyl)-;

—C(=O)—$CH_2CH_2OCH_2CH_2$—($C_1$-$C_{20}$ heteroaryldiyl)-$CH_2O$—(PEG)-C(=O)-(MCgluc)-;

—C(═O)—$CH_2CH_2OCH_2CH_2$—($C_1$-$C_{20}$ heteroaryldiyl)-$CH_2O$—(PEG)-C(═O)-(MCgluc)-N($R^5$)—($C_1$-$C_{12}$ alkyldiyl)-N($R^5$)C(═O)—($C_2$-$C_5$ monoheterocyclyldiyl)-; and -(succinimidyl)-$(CH_2)_m$—C(═O)—(PEP)—N($R^5$)—($C_1$-$C_{12}$ alkyldiyl)-N($R^5$)C(═O)—($C_2$-$C_5$ monoheterocyclyldiyl)-;

PEG has the formula: —$(CH_2CH_2O)_n$—$(CH_2)_m$—; m is an integer from 1 to 5, and n is an integer from 2 to 50;

PEP has the formula:

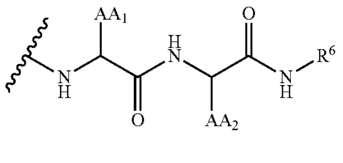

where $AA_1$ and $AA_2$ are independently selected from an amino acid side chain, or $AA_1$ or $AA_2$ and an adjacent nitrogen atom form a 5-membered ring proline amino acid, and the wavy line indicates a point of attachment;

$R^6$ is selected from the group consisting of $C_6$-$C_{20}$ aryldiyl and $C_1$-$C_{20}$ heteroaryldiyl, substituted with —$CH_2O$—C(═O)— and optionally with:

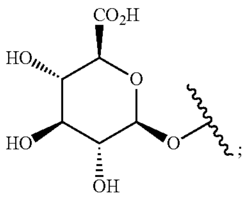 [SMILES: *O[C@@H]1O[C@H](C(=O)O)[C@@H](O)[C@H](O)[C@H]1O]

;

and

MCgluc is selected from the groups:

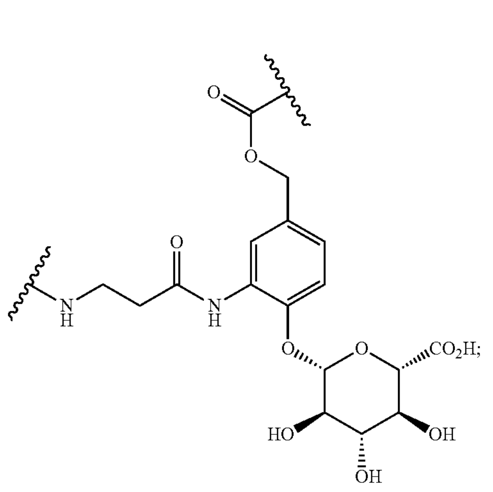

;

-continued

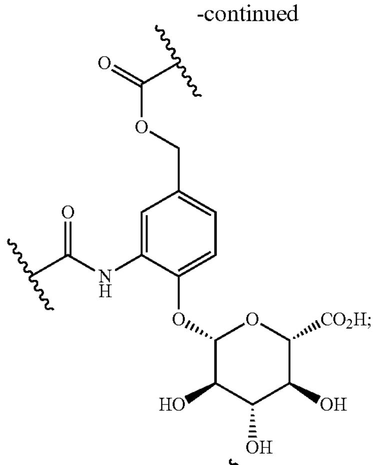

; and

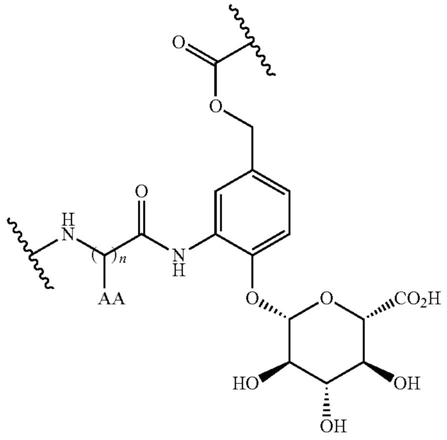

where q is 1 to 8, and AA is an amino acid side chain; and alkyl, alkyldiyl, alkenyl, alkenyldiyl, alkynyl, alkynyldiyl, aryl, aryldiyl, carbocyclyl, carbocyclyldiyl, heterocyclyl, heterocyclyldiyl, heteroaryl, and heteroaryldiyl are independently and optionally substituted with one or more groups independently selected from F, Cl, Br, I, —CN, —$CH_3$, —$CH_2CH_3$, —CH═$CH_2$, —C≡CH, —C≡C$CH_3$, —$CH_2CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —CH(OH)$CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CF_3$, —$CH_2CF_3$, —$CH_2CHF_2$, —CH($CH_3$)CN, —$C(CH_3)_2CN$, —$CH_2CN$, —$CH_2NH_2$, —$CH_2NHSO_2CH_3$, —$CH_2NHCH_3$, —$CH_2N(CH_3)_2$, —$CO_2H$, —$COCH_3$, —$CO_2CH_3$, —$CO_2C(CH_3)_3$, —COCH(OH)$CH_3$, —$CONH_2$, —$CONHCH_3$, —CON$(CH_3)_2$, —$C(CH_3)_2CONH_2$, —$NH_2$, —$NHCH_3$, —$N(CH_3)_2$, —$NHCOCH_3$, —N($CH_3$)$COCH_3$, —NHS$(O)_2CH_3$, —N($CH_3$)$C(CH_3)_2CONH_2$, —N($CH_3$)$CH_2CH_2S(O)_2CH_3$, —NHC(═NH)H, —NHC(═NH)$CH_3$, —NHC(═NH)$NH_2$, —NHC(═O)$NH_2$, —$NO_2$, ═O, —OH, —$OCH_3$, —$OCH_2CH_3$, —$OCH_2CH_2OCH_3$, —$OCH_2CH_2OH$, —$OCH_2CH_2N(CH_3)_2$, —$O(CH_2CH_2O)_n$—$(CH_2)_mCO_2H$, —$O(CH_2CH_2O)_nH$, —$OP(O)(OH)_2$, —$S(O)_2N(CH_3)_2$, —$SCH_3$, —$S(O)_2CH_3$, and —$S(O)_3H$.

2. The macromolecule-supported compound of aspect 1, wherein subscript p is an integer from 1 to 25.

3. The macromolecule-supported compound of aspect 2, wherein subscript p is an integer from 1 to 6.

4. The macromolecule-supported compound of any one of aspects 1-3, wherein the macromolecular support is a peptide.

5. The macromolecule-supported compound of any one of aspects 1-3, wherein the macromolecular support is a nucleotide.

6. The macromolecule-supported compound of any one of aspects 1-3, wherein the macromolecular support is a carbohydrate.

7. The macromolecule-supported compound of any one of aspects 1-3, wherein the macromolecular support is a lipid.

8. The macromolecule-supported compound of any one of aspects 1-3, wherein the macromolecular support is an antibody construct.

9. The macromolecule-supported compound of any one of aspects 1-3, wherein the macromolecular support is a biopolymer.

10. The macromolecule-supported compound of any one of aspects 1-3, wherein the macromolecular support is a nanoparticle.

11. The macromolecule-supported compound of any one of aspects 1-3, wherein the macromolecular support is an immune checkpoint inhibitor.

12. The macromolecule-supported compound of any one of aspects 1-11, wherein PEP has the formula:

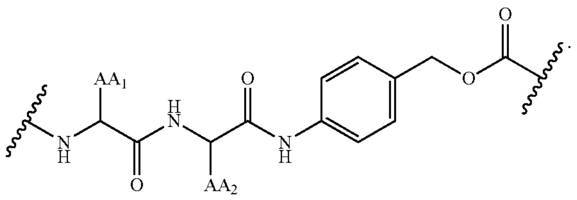

13. The macromolecule-supported compound of any one of aspects 1-11, wherein PEP is selected from the groups:

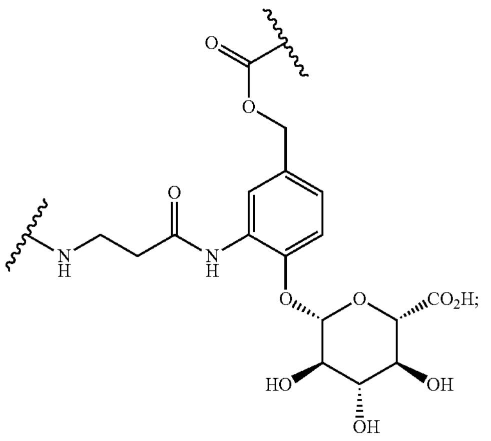

-continued

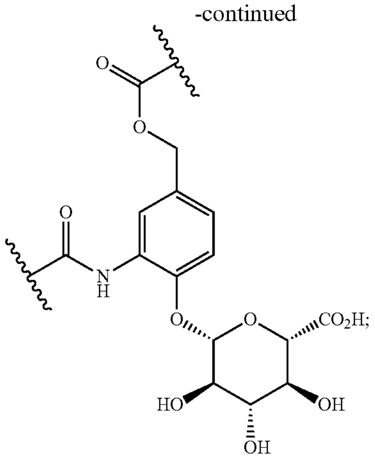

and

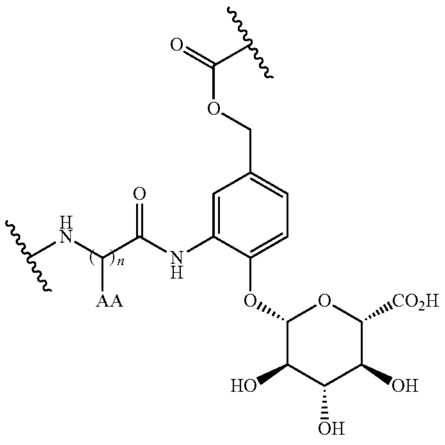

where n is 1 or more, and AA is an amino acid side chain.

14. The macromolecule-supported compound of any one of aspects 1-13, wherein each $AA_1$ and $AA_2$ are independently selected from a side chain of a naturally-occurring amino acid.

15. The macromolecule-supported compound of any one of aspects 1-13, wherein $AA_1$ and $AA_2$ are independently selected from H, $-CH_3$, $-CH(CH_3)_2$, $-CH_2(C_6H_5)$, $-CH_2CH_2CH_2CH_2NH_2$, $-CH_2CH_2CH_2NHC(NH)NH_2$, $-CH_2CH(CH_3)_2$, $-CH_2SO_3H$, and $-CH_2CH_2CH_2NHC(O)NH_2$.

16. The macromolecule-supported compound of aspect 15, wherein each $AA_1$ is $-CH(CH_3)_2$, and $AA_2$ is $-CH_2CH_2CH_2NHC(O)NH_2$.

17. The macromolecule-supported compound of any one of aspects 1-13, wherein each $AA_1$ and $AA_2$ are independently selected from GlcNAc aspartic acid, $-CH_2SO_3H$, and $-CH_2OPO_3H$.

18. The macromolecule-supported compound of any one of aspects 1-17, wherein L-Bza is selected from Formulas Ia-d:

Ia

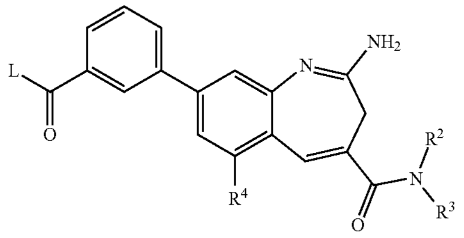

Ib

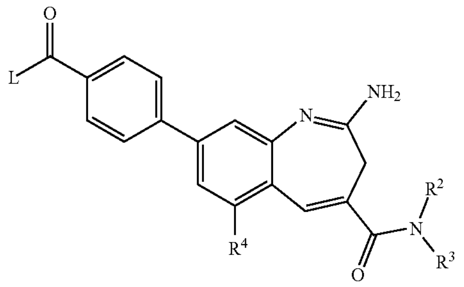

Ic

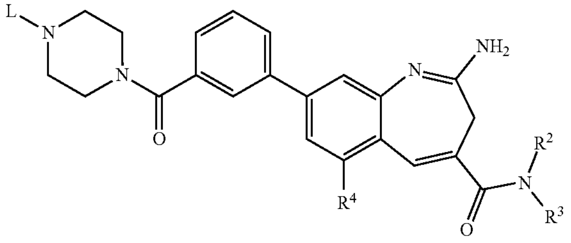

Id

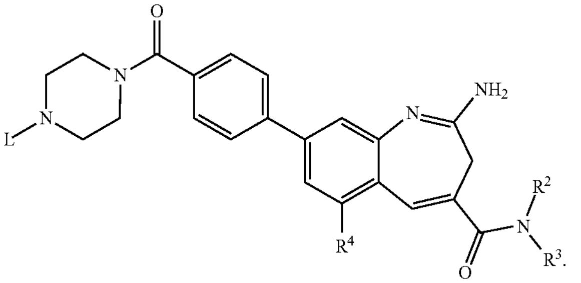

19. The macromolecule-supported compound of any one of aspects 1-17, wherein L-Bza is selected from Formulas Ie and If:

Ie

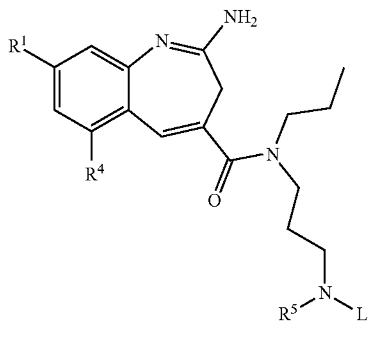

-continued

If

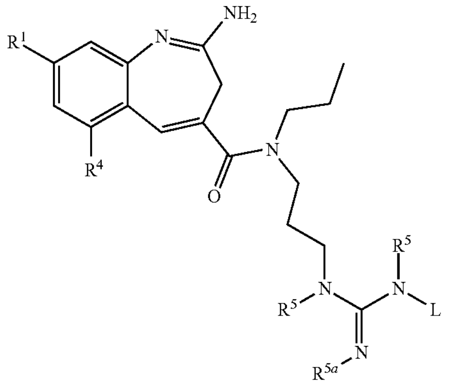

where $R^{5a}$ of Formula If is selected from the group consisting of phenyl and pyridyl, optionally substituted with one or more groups selected from F, Cl, Br, I, —CN, —$NO_2$ and —$OCH_3$.

20. The macromolecule-supported compound of any one of aspects 1-17, wherein L-Bza is selected from Formulas Ig and Ih:

Ig

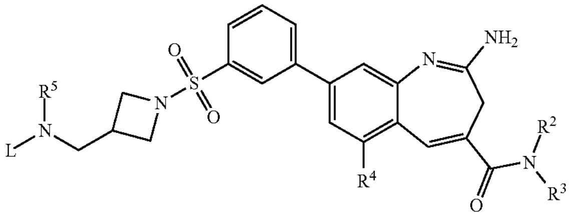

Ih

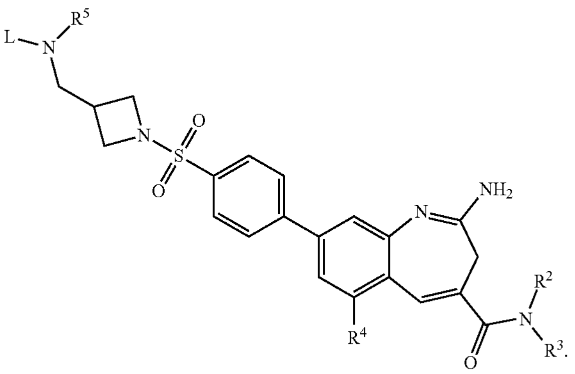

21. The macromolecule-supported compound of any one of aspects 18-20, wherein L is —C(═O)—(PEG)- or —C(═O)—(PEG)-C(═O)—.

22. The macromolecule-supported compound of any one of aspects 1-21, wherein $R^2$ and $R^3$ are each $C_1$-$C_8$ alkyl.

23. The macromolecule-supported compound of aspect 22, wherein $R^2$ and $R^3$ are each —$CH_2CH_2CH_3$.

24. The macromolecule-supported compound of any one of aspects 1-21, wherein $X^2$ and $X^3$ are each a bond, and $R^2$ or $R^3$ is —O—($C_1$-$C_{12}$ alkyl).

25. The macromolecule-supported compound of aspect 24, wherein $R^2$ or $R^3$ is —$OCH_2CH_3$.

26. The macromolecule-supported compound of any one of aspects 1-21, wherein one of $R^2$ and $R^3$ is selected from:

—($C_1$-$C_{12}$ alkyldiyl)-N($R^5$)—*;

—($C_1$-$C_{12}$ alkyldiyl)-O—($C_1$-$C_{12}$ alkyldiyl)-N($R^5$)—*;

—($C_1$-$C_{12}$ alkyldiyl)-N($R^5$)C(═$NR^5$)—N($R^5$)—*;

—($C_1$-$C_{12}$ alkyldiyl)-($C_6$-$C_{20}$ aryldiyl)-($C_1$-$C_{12}$ alkyldiyl)-N($R^5$)—*;

—($C_1$-$C_{12}$ alkyldiyl)-($C_6$-$C_{20}$ aryldiyl)-($C_1$-$C_{12}$ alkyldiyl)-N($R^5$)—C(═$NR^5$)N($R^5$)—*;

—($C_2$-$C_6$ alkynyldiyl)-N($R^5$)—*; and

—($C_2$-$C_6$ alkynyldiyl)-N($R^5$)C(═$NR^5$)N($R^5$)$_1$—*;

$X^2$ and $X^3$ are a bond, and where the asterisk * indicates the attachment site of L.

27. The macromolecule-supported compound of any one of aspects 1-25, wherein one of $R^1$ and $R^4$ is selected from:

—($C_1$-$C_{12}$ alkyldiyl)-N($R^5$)—*;

—($C_1$-$C_{12}$ alkyldiyl)-N($R^5$)C(═$NR^5$)N($R^5$)—*;

—($C_6$-$C_{20}$ aryldiyl)-S(═O)$_2$—($C_2$-$C_{20}$ heterocyclyldiyl)-*;

—($C_6$-$C_{20}$ aryldiyl)-S(═O)$_2$—($C_2$-$C_{20}$ heterocyclyldiyl)-($C_1$-$C_{12}$ alkyldiyl)-N($R^5$)—*;

—($C_6$-$C_{20}$ aryldiyl)-C(═O)—*;

—($C_6$-$C_{20}$ aryldiyl)-($C_1$-$C_{12}$ alkyldiyl)-N($R^5$)—*;

—($C_6$-$C_{20}$ aryldiyl)-C(═O)—($C_2$-$C_{20}$ heterocyclyldiyl)-*;

—C(═O)$NR^5$—($C_1$-$C_{20}$ heteroaryldiyl)-*; and

—C(═O)$NR^5$—($C_1$-$C_{20}$ heteroaryldiyl)-($C_2$-$C_{20}$ heterocyclyldiyl)-C(═O)$NR^5$—($C_1$-$C_{12}$ alkyldiyl)-$NR^5$—*;

$X^1$ and $X^4$ are a bond, and where the asterisk * indicates the attachment site of L.

28. The macromolecule-supported compound of any one of aspects 1-27, wherein one of $R^1$ and $R^4$ is selected from —($C_6$-$C_{20}$ aryldiyl)-S(═O)$_2$—($C_2$-$C_{20}$ heterocyclyldiyl)-($C_1$-$C_{12}$ alkyldiyl)-N($R^5$)$_2$ and —($C_6$-$C_{20}$ aryldiyl)-S(═O)$_2$—($C_2$-$C_{20}$ heterocyclyldiyl)-($C_1$-$C_{12}$ alkyldiyl)-OH.

29. The macromolecule-supported compound of aspect 28, wherein $C_6$-$C_{20}$ aryldiyl is phenyldiyl and $C_2$-$C_{20}$ heterocyclyldiyl is azetidindiyl.

30. The macromolecule-supported compound of aspect 29, wherein one of $R^1$ and $R^4$ is selected from the formulas:

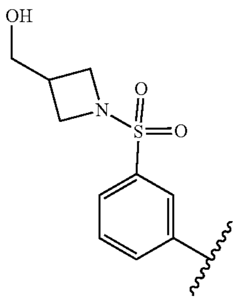

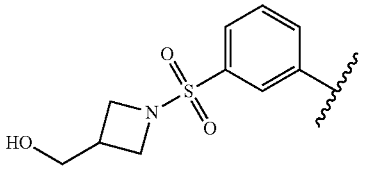

-continued

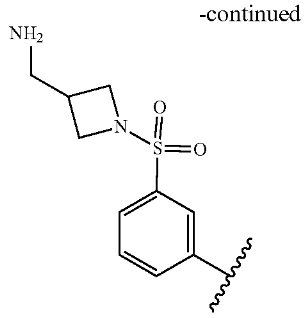

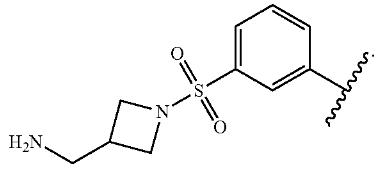

31. The macromolecule-supported compound of any one of aspects 1-27, wherein one of $R^1$ and $R^4$ is —C(═O)$NR^5$—($C_1$-$C_{20}$ heteroaryldiyl)-($C_2$-$C_{20}$ heterocyclyldiyl)-C(═O)$NR^5$—($C_1$-$C_{12}$ alkyldiyl)-$NR^5$-L.

32. The macromolecule-supported compound of aspect 31, wherein $C_1$-$C_{20}$ heteroaryldiyl is pyridindiyl and $C_2$-$C_{20}$ heterocyclyldiyl is piperidinyl.

33. A macromolecule-supported compound of Formula III:

III

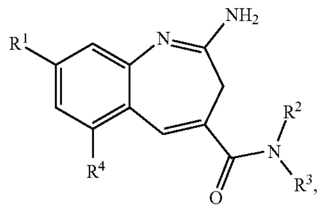

a pharmaceutically acceptable salt thereof, or a quaternary ammonium salt thereof, wherein $R^1$, $R^2$, $R^3$, and $R^4$ are independently Y or Z, wherein one of $R^1$, $R^2$, $R^3$, and $R^4$ is Y, having the formula:

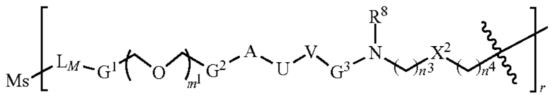

or

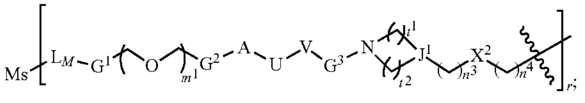

each Z independently is hydrogen or selected from the formulas:

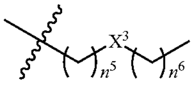

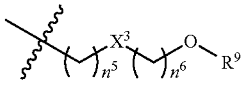

-continued

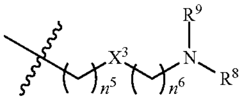 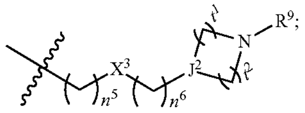

U is optionally present and is $CH_2$, C(=O), $CH_2C$(=O), or C(=O)$CH_2$,

A is optionally present and is $NR^{10}$ or selected from the formulas:

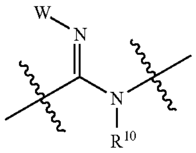 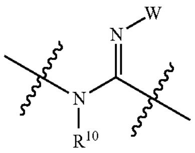

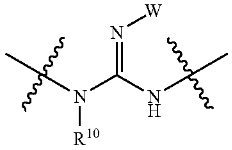 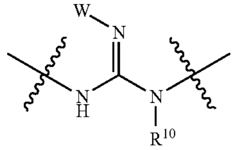

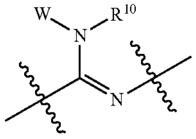 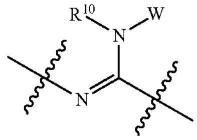

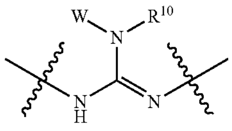

$R^{10}$ and W independently are hydrogen, $Ar^1$, or of formula:

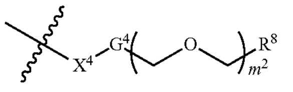

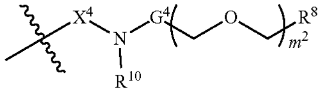

V is optionally present and is of formula:

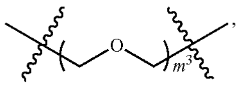, 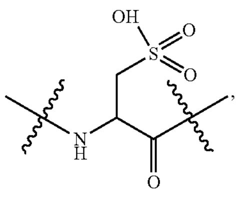, or

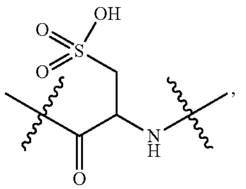, $J^1$ and $J^2$ independently are CH or N, $m^1$, $m^2$, and $m^3$ independently are an integer from 0 to 25, except that at least one of $m^1$, $m^2$, and $m^3$ is a non-zero integer, $n^1$, $n^2$, $n^3$, $n^4$, $n^5$, and $n^6$ independently are an integer from 0 to 10, $t^1$ and $t^2$ independently are an integer from 1 to 3, $G^1$, $G^2$, $G^3$, and $G^4$ independently are $CH_2$, C(O), $CH_2C$(O), C(O)$CH_2$, or a bond, $X^1$, $X^2$, $X^3$, and $X^4$ are each optionally present and independently are O, $NR^7$, $CHR^7$, $SO_2$, S, or one or two cycloalkyldiyl, heterocycloalkyldiyl, aryldiyl, or heteroaryldiyl groups, and when more than one cycloalkyldiyl, heterocycloalkyldiyl, aryldiyl, or heteroaryldiyl group is present, the more than one cycloalkyldiyl, heterocycloalkyldiyl, aryldiyl, or heteroaryldiyl groups are linked or fused, wherein linked cycloalkyldiyl, heterocycloalkyldiyl, aryldiyl, or heteroaryldiyl groups are linked through a bond or —CO—, $R^9$ is hydrogen, $C_1$-$C_4$ alkyl, or selected from the formulas:

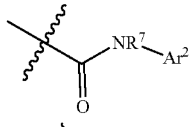 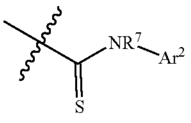

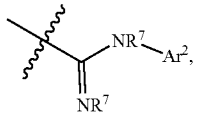

$R^8$ is independently hydrogen or $C_1$-$C_4$ alkyl, $Ar^1$ and $Ar^2$ independently are an aryl or heteroaryl group, optionally substituted with one or more halogens (e.g., fluorine, chlorine, bromine, or iodine), nitriles, hydroxyls, $C_1$-$C_4$ alkyl groups, or a combination thereof, $L_M$ is a linking moiety that comprises a functional group selected from an amide, amine, ester, carbamate, urea, thioether, thiocarbamate, thiocarbonate, and thiourea, r is an integer from 1 to 50, "$M_S$" is a macromolecular support, and each wavy line () represents a point of attachment.

34. The macromolecule-supported compound of aspect 33, wherein subscript r is an integer from 1 to 25.

35. The macromolecule-supported compound of aspect 34, wherein subscript r is an integer from 1 to 6.

36. The macromolecule-supported compound of any one of aspects 33-35, wherein the macromolecular support is a peptide.

37. The macromolecule-supported compound of any one of aspects 33-35, wherein the macromolecular support is a nucleotide.

38. The macromolecule-supported compound of any one of aspects 33-35, wherein the macromolecular support is a carbohydrate.

39. The macromolecule-supported compound of any one of aspects 33-35, wherein the macromolecular support is a lipid.

40. The macromolecule-supported compound of any one of aspects 33-35, wherein the macromolecular support is an antibody construct.

41. The macromolecule-supported compound of any one of aspects 33-35, wherein the macromolecular support is a biopolymer.

42. The macromolecule-supported compound of any one of aspects 33-35, wherein the macromolecular support is a nanoparticle.

43. The macromolecule-supported compound of any one of aspects 33-35, wherein the macromolecular support is an immune checkpoint inhibitor.

44. A macromolecule-supported compound prepared by conjugation of a macromolecular support with an amino-benzazepine-linker compound selected from any one of BzL-1 to BzL-79 provided in Tables 2a, 2b, and 2c.

45. A composition comprising a plurality of macromolecule-supported compounds according to any one of aspects 1-44.

46. The composition of aspect 45, wherein the average aminobenzazepine moiety to macromolecular support ratio is from about 0.01 to about 50.

47. The composition of aspect 46, wherein the average aminobenzazepine moiety to macromolecular support ratio is from about 1 to about 10.

48. The composition of aspect 47, wherein the average aminobenzazepine moiety to macromolecular support ratio is from about 1 to about 6.

49. The composition of aspect 48, wherein the average aminobenzazepine moiety to macromolecular support ratio is from about 1 to about 4.

50. A method for treating cancer comprising administering a therapeutically effective amount of a macromolecule-supported compound according to any one of aspects 1-44 or a composition according to any one of aspects 45-49 to a subject in need thereof.

51. The method of aspect 50, wherein the cancer is susceptible to a pro-inflammatory response induced by TLR7 and/or TLR8 agonism.

52. Use of a macromolecule-supported compound according to any one of aspects 1-44 or a composition according to any one of aspects 45-49 for treating cancer.

53. Use of a macromolecule-supported compound according to any one of aspects 1-44 or a composition according to any one of aspects 45-49 for a chemical assay for TLR engagement and/or activity.

54. The use according to aspect 53, wherein the chemical assay is for TLR7 and/or TLR8 engagement and/or activity.

EXAMPLES

The following examples further illustrate the invention but, of course, should not be construed as in any way limiting its scope.

Preparation of Aminobenzazepine Compounds (Bz) and Intermediates

Example 1: Synthesis of Bz-1

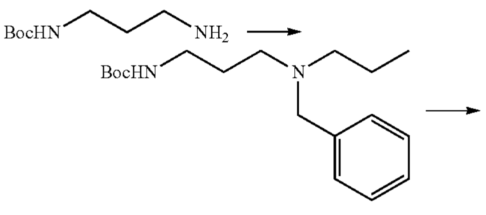

Bz-1a

-continued

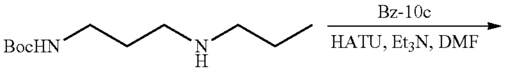

Bz-1b

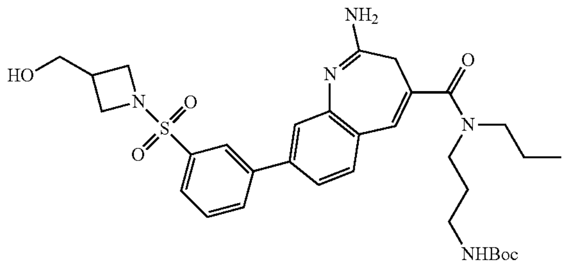

Bz-1

Synthesis of tert-butyl (3-(benzyl(propyl)amino)propyl) carbamate Bz-1a. tert-Butyl N-(3-aminopropyl)carbamate (10 g, 57.39 mmol, 10.02 mL, 1 eq) and benzaldehyde (6.09 g, 57.39 mmol, 5.80 mL, 1 eq) in DCE (100 mL) was stirred at 70° C. for 24 hours. MeOH (100 mL) and $NaBH_3CN$ (16.23 g, 258.26 mmol, 4.5 eq) was added to the mixture in portions at 0° C. The mixture was stirred at 0° C. for 2 hours, then propanal (16.67 g, 286.96 mmol, 20.89 mL, 5 eq) was added at 0° C. and stirred for 2 hours. LCMS showed the reaction was completed. The mixture was added a few drops water and concentrated in reduced pressure at 40° C. The residue was poured into ice water (200 mL) and stirred for 5 min. The aqueous phase was extracted with ethyl acetate (200 mL×3). The combined organic phase was washed with brine (300 mL), dried with anhydrous $Na_2SO_4$, filtered and concentrated in vacuum. The residue was purified by silica gel chromatography (petroleum ether/ethyl acetate=10/1, 3/1) to afford tert-butyl N-[3-[benzyl(propyl)amino]propyl] carbamate, Bz-1a (16 g, 52.21 mmol, 90.98% yield) as light yellow oil. $^1H$ NMR ($CDCl_3$, 400 MHz) δ 7.39-7.29 (m, 5H), 3.60-3.52 (m, 2H), 3.20-3.08 (m, 2H), 2.56-2.45 (m, 2H), 2.39 (s, 2H), 1.73-1.61 (m, 2H), 1.58-1.48 (m, 2H), 1.42 (s, 1H), 1.45 (s, 9H), 0.89 (t, J=7.2 Hz, 3H).

Synthesis of tert-butyl N-[3-(propylamino)propyl]carbamate, Bz-1b. To a solution of tert-butyl N-[3-[benzyl(propyl)amino]propyl]carbamate, Bz-1a (10 g, 32.63 mmol, 1 eq) in MeOH (150 mL) was added $Pd(OH)_2/C$ (10%, 3 g) under $N_2$. The suspension was degassed under vacuum and purged with $H_2$ several times. The mixture was stirred under $H_2$ (50 psi) at 50° C. for 12 hours. TLC (petroleum ether/ethyl acetate=3:1) showed the starting material was consumed completely. The reaction mixture was filtered, and the filtrate was concentrated to give tert-butyl N-[3-(propylamino)propyl]carbamate, Bz-1b (5 g, 23.11 mmol, 70.83% yield) as colorless oil which was used into the next step without further purification. $^1H$ NMR (MeOD, 400 MHz) δ 3.13-3.05 (m, 2H), 2.60 (t, J=7.2 Hz, 2H), 2.56-2.50 (m, 2H), 1.66 (m, 2H), 1.58-1.48 (m, 2H), 1.44 (s, 9H), 0.94 (t, J=7.2 Hz, 3H).

Synthesis of tert-butyl N-[3-[[2-amino-8-[3-[3-(hydroxymethyl)azetidin-1-yl]sulfonylphenyl]-3H-1-benzazepine-4-carbonyl]-propyl-amino]propyl]carbamate, Bz-1. To a mixture of tert-butyl N-[3-(propylamino)propyl] carbamate, Bz-1b (202.42 mg, 935.73 μmol (micromole), 2 eq) and 2-amino-8-[3-[3-(hydroxymethyl)azetidin-1-yl] sulfonylphenyl]-3H-1-benzazepine-4-carboxylic acid, Bz-10c from Example 6 (0.2 g, 467.87 μmol, 1 eq) in DMF (2 mL) was added HATU (213.48 mg, 561.44 μmol, 1.2 eq)

and $Et_3N$ (94.69 mg, 935.73 μmol, 130.24 μL (microliter), 2 eq) in one portion at 15° C. The mixture was stirred at 15° C. for 30 min. LCMS and HPLC showed the reaction was completed. The mixture was filtered and purified by prep-HPLC (column: Waters Xbridge 150×25 mm, 5 μm particle size; mobile phase: [water (10 mM $NH_4HCO_3$)-ACN]; B %: 30%-50%, 20 min) to afford tert-butyl N-[3-[[2-amino-8-[3-[3-(hydroxymethyl)azetidin-1-yl]sulfonylphenyl]-3H-1-benzazepine-4-carbonyl]-propyl-amino]propyl]carbamate, Bz-1 (0.087 g, 139.03 μmol, 29.72% yield) as light yellow solid. $^1H$ NMR (MeOD, 400 MHz) δ 8.07 (s, 1H), 8.03 (d, J=8.0 Hz, 1H), 7.86-7.81 (m, 1H), 7.79-7.73 (m, 1H), 7.50-7.45 (m, 2H), 7.39 (m, 1H), 6.92 (s, 1H), 3.86 (t, J=8.0 Hz, 2H), 3.61-3.58 (m, 2H), 3.52-3.48 (m, 2H), 3.45-3.41 (m, 4H), 3.10 (s, 4H), 2.62-2.52 (m, 1H), 1.86-1.79 (m, 2H), 1.71-1.65 (m, 2H), 1.42-1.50 (m, 9H), 0.87-0.95 (m, 3H). LC/MS [M+H] 626.30 (calculated); LC/MS [M+H] 626.40 (observed).

Example 2: Synthesis of Bz-3

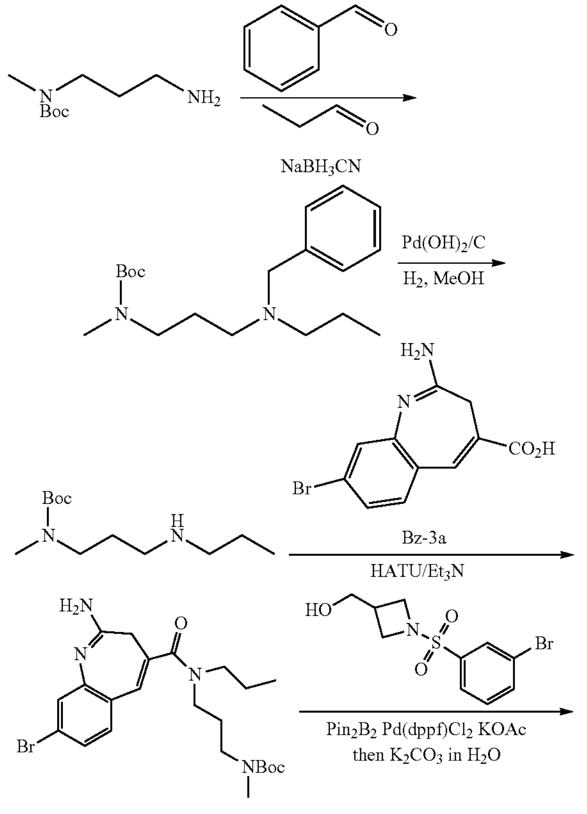

Bz-3b

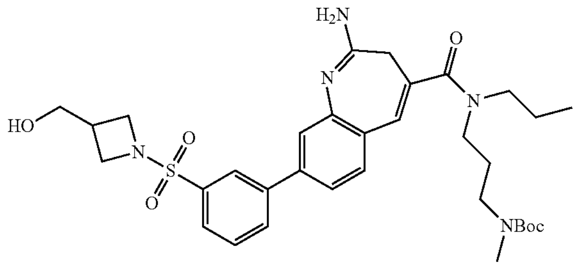

Bz-3

Synthesis of tert-butyl (3-(benzyl(propyl)amino)propyl)(methyl)carbamate. To a mixture of benzaldehyde (310.02 mg, 2.92 mmol, 295.26 μL, 1 eq) in DCE (10 mL) was added tert-butyl N-(3-aminopropyl)-N-methyl-carbamate (0.55 g, 2.92 mmol, 1 eq) at 25° C. under $N_2$. The mixture was stirred at 60° C. for 12 hours, then cooled to 0° C., MeOH (10 mL) was added to the mixture, $NaBH_3CN$ (550.48 mg, 8.76 mmol, 3 eq) was added to the mixture stirred for 1 h. Propanal (339.18 mg, 5.84 mmol, 425.04 μL, 2 eq) was added to the mixture and stirred at 0° C. for 1 h. LCMS showed the reaction was completed. The mixture was concentrated in vacuum. The residue was purified by prep-HPLC column: Luna C18 100×30 mm, 5 μm particle size; mobile phase: [water (0.1% TFA)-ACN]; B %: 10%-40%, 10 min to give tert-butyl N-[3-[benzyl(propyl)amino]propyl]-N-methyl-carbamate (0.4 g, 1.25 mmol, 42.75% yield) as colorless oil. $^1H$ NMR (MeOD, 400 MHz) δ 7.18-7.37 (m, 5H), 3.57 (s, 2H), 3.20 (t, J=7.2 Hz, 2H), 2.78 (s, 3H), 2.35-2.52 (m, 4H), 1.70 (quin, J=7.2 Hz, 2H), 1.47-1.57 (m, 2H), 1.42 (s, 9H), 0.88 (t, J=7.2 Hz, 3H).

Synthesis of tert-butyl methyl(3-(propylamino)propyl)carbamate. To a solution of tert-butyl N-[3-[benzyl(propyl)amino]propyl]-N-methyl-carbamate (0.4 g, 1.25 mmol, 1 eq) in MeOH (20 mL) was added $Pd(OH)_2/C$ (0.2 g, 5% purity) under $N_2$. The suspension was degassed under vacuum and purged with $H_2$ several times. The mixture was stirred under $H_2$ (50 psi) at 50° C. for 12 hours. LCMS showed the reactant was consumed, and the desired mass was detected. The mixture was filtered and concentrated in vacuum. Afforded tert-butyl N-methyl-N-[3-(propylamino)propyl]carbamate (0.25 g, 1.09 mmol, 86.95% yield) as colorless oil. $^1H$ NMR (MeOD, 400 MHz) δ 3.26-3.31 (m, 2H), 2.85 (s, 3H), 2.56 (q, J=8.0 Hz, 4H), 1.74 (quin, J=7.2 Hz, 2H), 1.48-1.59 (m, 2H), 1.46 (s, 9H), 0.94 (t, J=7.2 Hz, 3H)

Synthesis of tert-butyl (3-(2-amino-8-bromo-N-propyl-3H-benzo[b] azepine-4-carboxamido)propyl)(methyl)carbamate, Bz-3b. To a mixture of 2-amino-8-bromo-3H-1-benzazepine-4-carboxylic acid, Bz-3a (80 mg, 284.59 μmol, 1 eq) and tert-butyl N-methyl-N-[3-(propylamino)propyl]carbamate (78.67 mg, 341.51 μmol, 1.2 eq) in DMF (1 mL) was added HATU (162.32 mg, 426.89 μmol, 1.5 eq) $Et_3N$ (57.60 mg, 569.18 μmol, 79.22 μL, 2 eq) at 25° C. under $N_2$. The mixture was stirred at 25° C. for 1 h. LCMS showed major as desired. The mixture was poured into water (20 mL). The aqueous phase was extracted with ethyl acetate (20 mL×3). The combined organic phase was washed with brine (20 mL), dried with anhydrous $Na_2SO_4$, filtered and concentrated in vacuum. The residue was purified by prep-TLC (petroleum ether/ethyl acetate=0/1) to give Bz-3b (60 mg, 121.60 μmol, 42.73% yield) as yellow oil.

Synthesis of tert-butyl (3-(2-amino-8-(3-((3-(hydroxymethyl)azetidin-1-yl)sulfonyl)phenyl)-N-propyl-3H-benzo[b] azepine-4-carboxamido)propyl)(methyl)carbamate, Bz-3. To a mixture of [1-(3-bromophenyl)sulfonylazetidin-3-yl] methanol (155.12 mg, 506.65 μmol, 1 eq) $Pin_2B_2$ (154.39 mg, 607.98 μmol, 1.2 eq) potassium acetate, KOAc (124.31 mg, 1.27 mmol, 2.5 eq) in dioxane (30 mL) was added $Pd(dppf)Cl_2 \cdot CH_2Cl_2$ (41.38 mg, 50.67 μmol, 0.1 eq) at 25° C. under $N_2$. The mixture was stirred at 90° C. for 2 hours. tert-butyl N-[3-[(2-amino-8-bromo-3H-1-benzazepine-4-carbonyl)-propyl-amino]propyl]-N-methyl-carbamate, Bz-3b (0.25 g, 506.65 μmol, 1 eq), and $K_2CO_3$ (140.04 mg, 1.01 mmol, 2 eq) in $H_2O$ (2 mL) were added to the mixture and stirred at 90° C. for 2 hours under nitrogen gas, $N_2$. LCMS showed the reaction was completed. The mixture was filtered and concentrated in vacuum. The residue was purified by prep-TLC (EtOAc/MeOH=7:1) to give Bz-3 (112 mg, 175.05 μmol, 34.55% yield) as a light yellow solid. $^1$H NMR (MeOD, 400 MHz) δ 8.07 (s, 1H), 8.03 (d, J=7.6 Hz, 1H), 7.85 (br d, J=7.6 Hz, 1H), 7.73-7.79 (m, 1H), 7.41-7.54 (m, 3H), 6.95 (s, 1H), 3.86 (t, J=8.2 Hz, 2H), 3.60 (dd, J=8.0, 6.0 Hz, 2H), 3.39-3.52 (m, 6H), 3.17-3.29 (m, 2H), 2.82-2.90 (m, 4H), 2.53-2.67 (m, 1H), 1.89-1.92 (m, 2H), 1.66-1.72 (m, 2H), 1.42-1.46 (m, 9H), 0.80-1.05 (m, 3H). LC/MS [M+H] 640.32 (calculated); LC/MS [M+H] 640.30 (observed).
Example 3: Synthesis of Bz-5
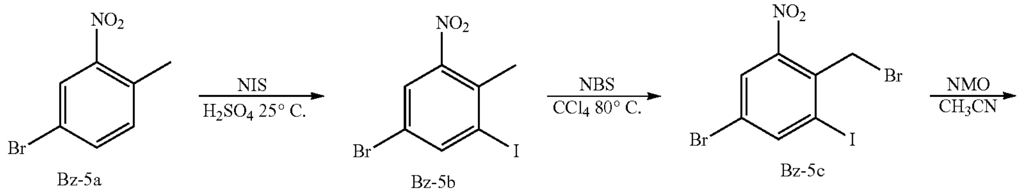
Bz-5a Bz-5b Bz-5c
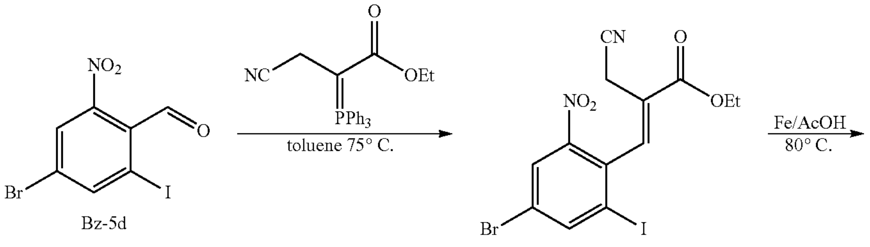
Bz-5d Bz-5e
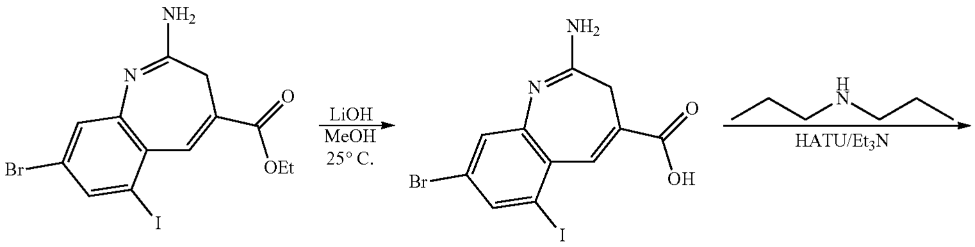
Bz-5f Bz-5g
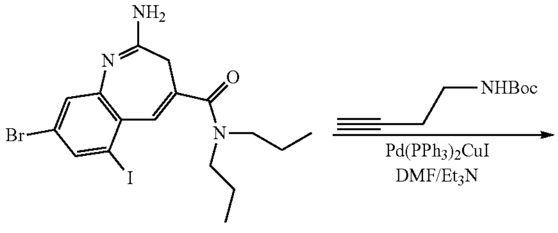
Bz-5h
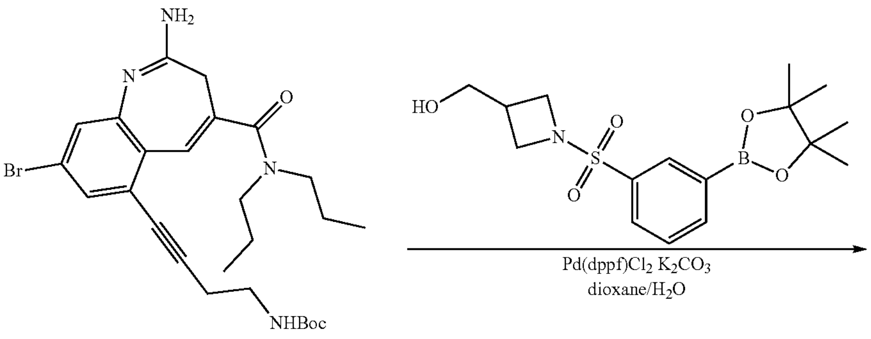
Bz-5i -continued

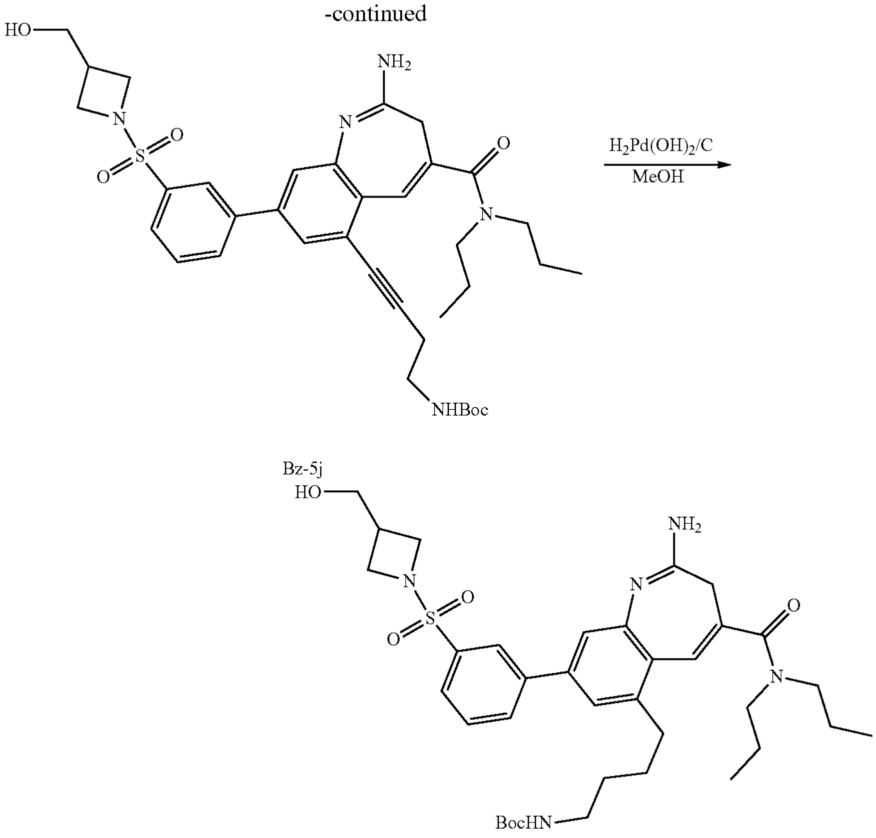

Bz-5j

Bz-5

Synthesis of 5-bromo-1-iodo-2-methyl-3-nitrobenzene, Bz-5b. To a mixture of 4-bromo-1-methyl-2-nitro-benzene, Bz-5a (20 g, 92.58 mmol, 20.00 mL, 1 eq) in $H_2SO_4$ (20 mL) was added NIS (37.49 g, 166.64 mmol, 1.8 eq) at 0° C. under $N_2$. The mixture was stirred at 0° C. for 1 hour. TLC showed the reactant was consumed and two points formed. The mixture was poured into ice-water (200 mL) slowly. The aqueous phase was extracted with ethyl acetate (150 mL×2). The combined organic phase was washed with brine (150 mL), dried with anhydrous $Na_2SO_4$, filtered and concentrated in vacuum. The residue was purified by silica gel chromatography (column height: 250 mm, diameter: 100 mm, 100-200 mesh silica gel, petroleum ether/ethyl acetate=100/1, 20/1) to afford Bz-5b (14 g, 40.94 mmol, 44.23% yield) as white solid. $^1$H NMR (CDCl3, 400 MHz) δ 8.20 (d, J=2.0 Hz, 1H), 7.87 (d, J=2.0 Hz, 1H), 2.55 (s, 3H).

Synthesis of 5-bromo-2-(bromomethyl)-1-iodo-3-nitrobenzene, Bz-5c. To a mixture of 5-bromo-1-iodo-2-methyl-3-nitro-benzene, Bz-5b (13 g, 38.02 mmol, 1 eq) in $CCl_4$ (100 mL) was added NBS (10.15 g, 57.03 mmol, 1.5 eq) BPO (920.94 mg, 3.80 mmol, 0.1 eq) at 25° C. under $N_2$. The mixture was stirred at 90° C. for 12 hours. TLC showed one new point formed, HPLC and LCMS showed about 50% as desired and about 50% the reactant remained. The mixture was concentrated in vacuum. The residue was purified by silica gel chromatography (column height: 250 mm, diameter: 100 mm, 100-200 mesh silica gel, petroleum ether/ethyl acetate=50/1, 10/1) to afford Bz-5c (7 g, 16.63 mmol, 43.75% yield) as white solid. $^1$H NMR (CDCl3-$d_6$, 400 MHz) δ 8.29 (d, J=2.0 Hz, 1H), 8.02 (d, J=2.0 Hz, 1H), 4.82 (s, 3H).

Synthesis of 4-bromo-2-iodo-6-nitrobenzaldehyde, Bz-5d. To a mixture of 5-bromo-2-(bromomethyl)-1-iodo-3-nitro-benzene, Bz-5c (7 g, 16.63 mmol, 1 eq) in $CH_3CN$ (10 mL) was added NMO (3.90 g, 33.27 mmol, 3.51 mL, 2 eq) at 25° C. under $N_2$. The mixture was stirred at 25° C. for 2 hours. TLC showed the reaction was completed. The mixture was concentrated in vacuum. The residue was purified by silica gel chromatography (column height: 250 mm, diameter: 100 mm, 100-200 mesh silica gel, petroleum ether/ethyl acetate=20/1, 4/1) to afford Bz-5d (5 g, 14.05 mmol, 84.46% yield) as white solid. $^1$H NMR (CDCl3, 400 MHz) δ 10.00 (s, 1H), 8.37 (d, J=1.6 Hz, 1H), 8.15 (d, J=1.6 Hz, 1H).

Synthesis of (E)-ethyl 3-(4-bromo-2-iodo-6-nitrophenyl)-2-(cyanomethyl)acrylate, Bz-5e. To a mixture of 4-bromo-2-iodo-6-nitro-benzaldehyde, Bz-5d (3.5 g, 9.83 mmol, 1 eq) in toluene (30 mL) was added ethyl 3-cyano-2-(triphenyl-phosphanylidene)propanoate (5.71 g, 14.75 mmol, 1.5 eq) at 25° C. under $N_2$. The mixture was stirred at 85° C. for 12 hours. TLC showed major as desired. The mixture was concentrated in vacuum. The residue was purified by silica gel chromatography (column height: 250 mm, diameter: 100 mm, 100-200 mesh silica gel, petroleum ether/ethyl acetate=10/1, 1/1) to afford Bz-5e (2 g, 4.30 mmol, 43.73% yield) as yellow oil. $^1$H NMR (CDCl3, 400 MHz) δ 8.62 (d, J=1.8 Hz, 1H), 8.42 (d, J=1.8 Hz, 1H), 7.74 (s, 1H), 4.32 (q, J=7.2 Hz, 2H), 3.33 (s, 2H), 1.31 (t, J=7.2 Hz, 3H).

Synthesis of ethyl 2-amino-8-bromo-6-iodo-3H-benzo[b]azepine-4-carboxylate, Bz-5f. To a mixture of ethyl (E)-3-(4-bromo-2-iodo-6-nitro-phenyl)-2-(cyanomethyl)prop-2-enoate, Bz-5e (2 g, 4.30 mmol, 1 eq) in acetic acid, AcOH (20 mL) was added Fe (1.20 g, 21.50 mmol, 5 eq) at 25° C. under $N_2$. The mixture was stirred at 80° C. for 5 hours. LCMS showed major as desired and the reactant was consumed. The reaction was filtered, and the filtrate was concentrated in vacuum. The residue was purified by silica gel chromatography (column height: 250 mm, diameter: 100 mm, 100-200 mesh silica gel, petroleum ether/ethyl acetate=1/1, 0/1) to afford Bz-5f (1.8 g, 4.14 mmol, 96.20% yield) as off-white solid. $^1H$ NMR (DMSO-$d_6$, 400 MHz) δ 7.71 (s, 1H), 7.69 (d, J=2.0 Hz, 1H), 7.22 (br d, J=2.0 Hz, 1H), 4.26 (q, J=7.0 Hz, 3H), 2.83 (s, 2H), 1.30 (t, J=7.2 Hz, 3H).

Synthesis of 2-amino-8-bromo-6-iodo-3H-benzo[b]azepine-4-carboxylic acid, Bz-5g. To a mixture of ethyl 2-amino-8-bromo-6-iodo-3H-1-benzazepine-4-carboxylate, Bz-5f (1.8 g, 4.14 mmol, 1 eq) in EtOH (40 mL) was added LiOH·$H_2O$ (1.04 g, 24.82 mmol, 6 eq) in $H_2O$ (10 mL) at 25° C. under $N_2$. The mixture was stirred at 35° C. for 2 hours. LCMS showed the reaction was completed. The mixture was concentrated to remove the EtOH, then adjusted PH to 5 by aq. HCl (4 M), filtered to get desired solid to afford Bz-5g (1.2 g, 2.95 mmol, 71.26% yield) as white solid. $^1H$ NMR (DMSO-$d_6$, 400 MHz) δ 7.77 (s, 1H), 7.69 (s, 1H), 7.29 (s, 1H), 2.92 (s, 2H).

Synthesis of 2-amino-8-bromo-6-iodo-N,N-dipropyl-3H-benzo[b]azepine-4-carboxamide, Bz-5h. To a mixture of N-propylpropan-1-amine (186.47 mg, 1.84 mmol, 254.04 μL, 1.5 eq) and 2-amino-8-bromo-6-iodo-3H-1-benzazepine-4-carboxylic acid, Bz-5g (0.5 g, 1.23 mmol, 1 eq) in DMF (10 mL) was added HATU (700.67 mg, 1.84 mmol, 1.5 eq) $Et_3N$ (186.47 mg, 1.84 mmol, 256.49 μL, 1.5 eq) at 25° C. The mixture was stirred at 25° C. for 30 min. LCMS showed the reaction was completed. The mixture was poured into water (50 mL), separated out from the mixture, and filtered to obtain Bz-5h (0.55 g, 1.12 mmol, 91.33% yield) as yellow solid. $^1H$ NMR (DMSO-$d_6$, 400 MHz) δ 7.74 (d, J=2.0 Hz, 1H), 7.33 (d, J=2.0 Hz, 1H), 6.81 (s, 1H), 3.43-3.47 (m, 4H), 1.66-1.72 (m, 4H), 0.93 (s, 6H).

Synthesis of tert-butyl (4-(2-amino-8-bromo-4-(dipropylcarbamoyl)-3H-benzo[b]azepin-6-yl)but-3-yn-1-yl)carbamate, Bz-5i. To a mixture of 2-amino-8-bromo-6-iodo-N,N-dipropyl-3H-1-benzazepine-4-carboxamide, Bz-5h (200 mg, 408.02 μmol, 1 eq) and tert-butyl N-but-3-ynylcarbamate (72.50 mg, 428.42 μmol, 1.05 eq) in DMF (5 mL) $Et_3N$ (1 mL) was added $Pd(PPh_3)_2Cl_2$ (14.32 mg, 20.40 μmol, 0.05 eq) $Et_3N$ (0.5 mL) CuI (15.54 mg, 81.60 μmol, 0.2 eq) at 25° C. under $N_2$. The mixture was stirred at 80° C. for 1 hour. LCMS showed major as desired. The mixture was poured into water (20 mL). The aqueous phase was extracted with ethyl acetate (20 mL×3). The combined organic phase was washed with brine (20 mL), dried with anhydrous $Na_2SO_4$, filtered and concentrated in vacuum. The residue was purified by prep-TLC (petroleum ether/ethyl acetate=0/1) to give Bz-5i (0.2 g, 376.31 μmol, 92.23% yield) as a yellow solid. $^1H$ NMR (CDCl3, 400 MHz) δ 7.40 (s, 1H), 7.35 (s, 1H), 7.13 (s, 1H), 3.46-3.52 (m, 4H), 3.35-3.40 (m, 2H), 2.65 (s, 2H), 1.58-1.78 (m, 4H), 1.46 (s, 9H), 0.93 (t, J=7.2 Hz, 6H).

Synthesis of tert-butyl (4-(2-amino-4-(dipropylcarbamoyl)-8-(3-((3-(hydroxymethyl)azetidin-1-yl)sulfonyl)phenyl)-3H-benzo[b]azepin-6-yl)but-3-yn-1-yl)carbamate, Bz-5j. To a mixture of tert-butyl N-[4-[2-amino-8-bromo-4-(dipropylcarbamoyl)-3H-1-benzazepin-6-yl]but-3-ynyl]carbamate, Bz-5i (0.18 g, 338.67 μmol, 1 eq) and [1-[3-(4,4,5,5-tetramethyl-1,3,2-dioxaborolan-2-yl)phenyl]sulfonylazetidin-3-yl]methanol (179.45 mg, 508.01 μmol, 1.5 eq) in dioxane (10 mL) $H_2O$ (1 mL) was added Pd(dppf)$Cl_2$ (12.39 mg, 16.93 μmol, 0.05 eq) $K_2CO_3$ (93.61 mg, 677.35 μmol, 2 eq) at 25° C. under $N_2$. The mixture was stirred at 90° C. for 2 hours. LCMS showed desired mass was detected. The mixture was concentrated in vacuum to give Bz-5j (0.2 g, crude) as a yellow solid.

Synthesis of tert-butyl (4-(2-amino-4-(dipropylcarbamoyl)-8-(3-((3-(hydroxymethyl)azetidin-1-yl)sulfonyl)phenyl)-3H-benzo[b]azepin-6-yl)butyl)carbamate, Bz-5. To a solution of tert-butyl N-[4-[2-amino-4-(dipropylcarbamoyl)-8-[3-[3-(hydroxymethyl)azetidin-1-yl]sulfonylphenyl]-3H-1-benzazepin-6-yl]but-3-ynyl]carbamate, Bz-5j (140 mg, 206.53 μmol, 1 eq) in MeOH (20 mL) was added $Pd(OH)_2/C$ (0.1 g, 5% purity) under $N_2$. The suspension was degassed under vacuum and purged with $H_2$ several times. The mixture was stirred under $H_2$ (50 psi) at 25° C. for 2 hours. LCMS showed the reaction was completed. The mixture was filtered and concentrated in vacuum. The residue was purified by prep-HPLC column: Xtimate C18 150×25 mm, 5 μm particle size; mobile phase: [water (0.04% $NH_3H_2O$+10 mM $NH_4HCO_3$)-ACN]; B %: 50%-60%, 10.5 min. Afforded Bz-5 (45 mg, 65.99 μmol, 31.95% yield) as a white solid. $^1H$ NMR (MeOD, 400 MHz) δ 8.00-8.08 (m, 2H), 7.83 (d, J=7.6 Hz, 1H), 7.71-7.79 (m, 1H), 7.33 (s, 1H), 7.28 (s, 1H), 6.99 (s, 1H), 3.86 (t, J=8.0 Hz, 2H), 3.57-3.66 (m, 2H), 3.38-3.51 (m, 6H), 3.06 (t, J=6.4 Hz, 2H), 2.84 (t, J=7.6 Hz, 2H), 2.52-2.63 (m, 1H), 1.50-1.77 (m, 8H), 1.41 (s, 9H), 0.94 (s, 6H). LC/MS [M+H] 682.36 (calculated); LC/MS [M+H] 682.40 (observed).

Example 4: Synthesis of Bz-6

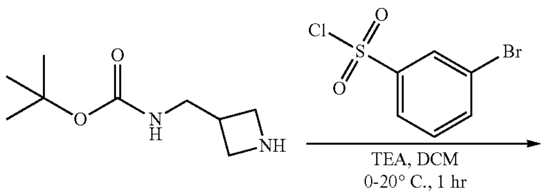

-continued

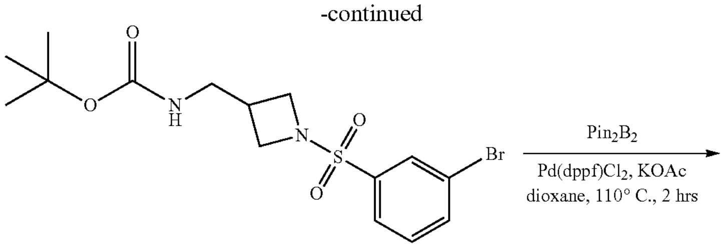

Bz-6a

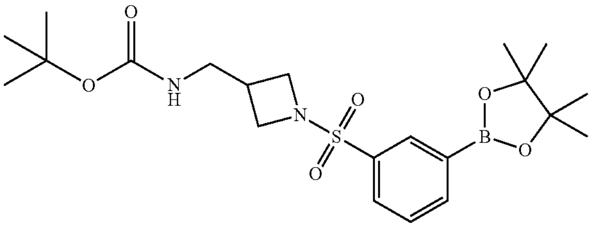

Bz-6b

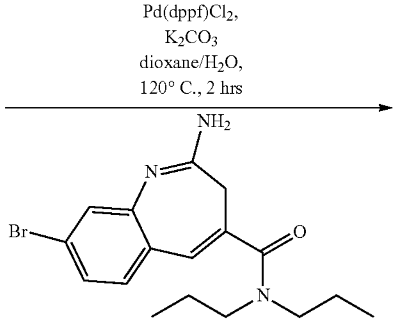

Bz-6c

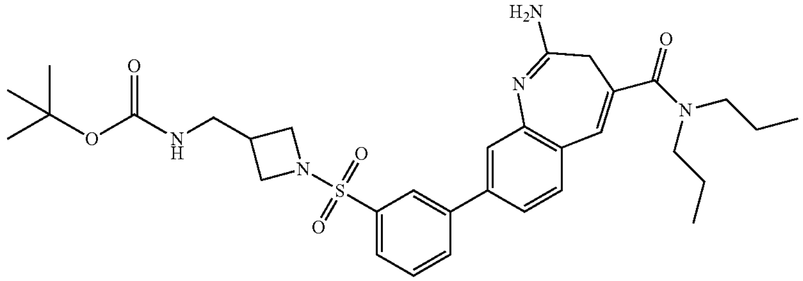

Bz-6

Synthesis of tert-butyl ((1-((3-bromophenyl)sulfonyl)azetidin-3-yl)methyl)carbamate, Bz-6a. To a mixture of tert-butyl N-(azetidin-3-ylmethyl)carbamate (1.6 g, 8.59 mmol, 1.2 eq) in DCM (5 mL) was added TEA (1.45 g, 14.32 mmol, 1.99 mL, 2 eq) and 3-bromobenzenesulfonyl chloride (1.83 g, 7.16 mmol, 1.03 mL, 1 eq) at 0° C. The mixture was stirred at 20° C. for 1 h. The mixture was diluted with water (50 mL) and extracted with DCM (25 ml×3). The organic layer was washed with brine (25 mL), dried over $Na_2SO_4$, filtered and concentrated. The residue was purified by flash silica gel chromatography (ISCO™; 4 g SEPAFLASH™ Silica Flash Column, eluent of 0~100% ethyl acetate/petroleum ether gradient at 35 mL/min). Compound tert-butyl N-[[1-(3-bromophenyl)sulfonylazetidin-3-yl]methyl]carbamate, Bz-6a (2.5 g, 6.17 mmol, 86.16% yield) was obtained as white solid. $^1H$ NMR ($CDCl_3$, 400 MHz) δ 7.99 (t, J=4.0 Hz, 1H), 7.74-7.81 (m, 2H), 7.47 (t, J 8.0 Hz, 1H), 4.61 (s, 1H), 3.86 (t, J=8.0 Hz, 2H), 3.50-3.58 (m, 2H), 3.19 (t, J=4.0 2H), 2.58-2.70 (m, 1H), 1.42 (s, 9H).

Preparation of tert-butyl N-[[1-[3-(4,4,5,5-tetramethyl-1,3,2-dioxaborolan-2-yl)phenyl]sulfonylazetidin-3-yl]methyl]carbamate, Bz-6b. To a mixture of tert-butyl-N-[[1-(3-bromophenyl)sulfonylazetidin-3-yl]methyl] carbamate, Bz-6a (1 g, 2.47 mmol, 1 eq) in dioxane (10 mL) was added $Pin_2B_2$ (939.80 mg, 3.70 mmol, 1.5 eq) and KOAc (484.29 mg, 4.93 mmol, 2 eq), $Pd(dppf)Cl_2$ (90.27 mg, 123.36 μmol, 0.05 eq) at 15° C. under $N_2$. The mixture was stirred at 110° C. for 2 h. The product tert-butyl N-[[1-[3-(4,4,5,5-tetramethyl-1,3,2-dioxaborolan-2-yl)phenyl] sulfonylazetidin-3-yl]methyl]carbamate, Bz-6b was not isolated and used into next step.

Synthesis of tert-butyl ((1-((3-(2-amino-4-(dipropylcarbamoyl)-3H-benzo[b]azepin-8-yl)phenyl)sulfonyl)azetidin-3-yl)methyl)carbamate, Bz-6. To a mixture of tert-butyl N-[[1-[3-(4,4,5,5-tetramethyl-1,3,2-dioxaborolan-2-yl) phenyl]sulfonylazetidin-3-yl]methyl]carbamate, Bz-6b (1.12 g, 2.48 mmol, 1 eq) and 2-amino-8-bromo-N,N-dipropyl-3H-1-benzazepine-4-carboxamide, Bz-6c (901.90 mg, 2.48 mmol, 1 eq) in dioxane (3 mL) was added $K_2CO_3$ (684.35 mg, 4.95 mmol, 2 eq) and $Pd(dppf)Cl_2$ (90.58 mg, 123.79 μmol, 0.05 eq) at 15° C. under $N_2$. The mixture was stirred at 120° C. for 2 h. The mixture was filtered and concentrated. The residue was purified by flash silica gel chromatography (ISCO™; 2 g SEPAFLASH™ Silica Flash Column, eluent of 0~100% ethyl acetate/petroleum ether gradient at 60 mL/min) to give Bz-6 (600 mg, 983.97 μmol, 39.74% yield, 100% purity) as yellow solid. $^1H$ NMR (MeOD-$d_4$, 400 MHz) δ 7.99-8.10 (m, 2H), 7.74-7.86 (m, 2H), 7.36-7.52 (m, 3H), 6.89 (s, 1H), 3.83 (t, J=8.0 Hz, 2H), 3.54 (t, J=8.0 Hz, 2H), 3.34-3.48 (m, 6H), 3.02 (d, J=8.0 Hz, 2H), 2.48-2.64 (m, 1H), 1.59-1.76 (m, 4H), 1.37 (s, 9H), 0.96-0.89 (m, 6H). LC/MS [M+H] 610.31 (calculated); LC/MS [M+H] 610.40 (observed).

Example 5: Synthesis of Bz-9

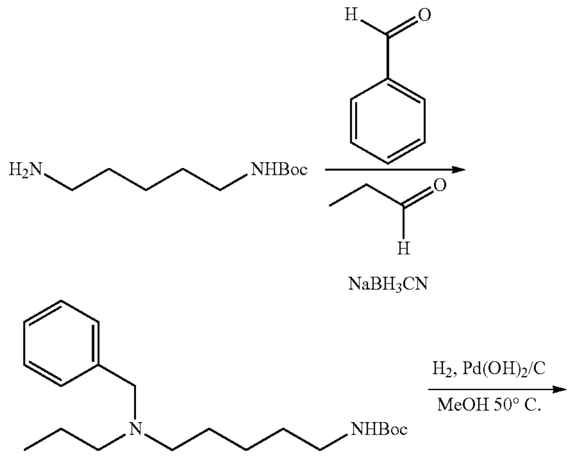

Bz-9a

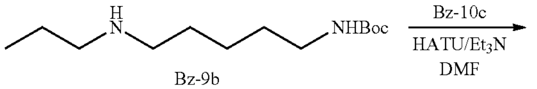

Bz-9b

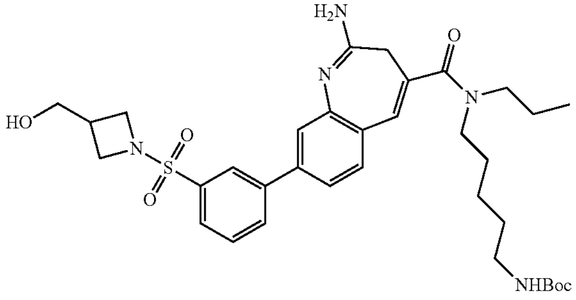

Bz-9

Synthesis of tert-butyl (5-(benzyl(propyl)amino)pentyl) carbamate, Bz-9a. To a mixture of tert-butyl N-(5-aminopentyl)carbamate (1 g, 4.94 mmol, 1.03 mL, 1 eq) and benzaldehyde (524.59 mg, 4.94 mmol, 499.61 μL, 1 eq) in DCE (10 mL) and stirred at 60° C. for 12 h. Then the mixture was cooled to 0° C. and MeOH (10 mL) was added to the mixture. $NaBH_3CN$ (931.94 mg, 14.83 mmol, 3 eq) was added to the mixture and stirred for 1 h at 0° C. Propanal (574.20 mg, 9.89 mmol, 719.55 μL, 2 eq) was added to the mixture and stirred for 1 h. LCMS showed the reaction was finished. The mixture was concentrated. The residue was further purification by prep-HPLC (column: Luna C18 100×30 mm, 5 μm particle size; mobile phase: [water (0.1% TFA)-ACN]; B %: 25%-40%, 10 min) to give tert-butyl-N-[5-[benzyl(propyl)amino] pentyl]carbamate Bz-9a (0.5 g, 1.49 mmol, 30.24% yield) as a yellow oil. $^1H$ NMR (400 MHz, METHANOL-$d_4$) δ=7.33-7.28 (m, 3H), 7.27-7.19 (m, 1H), 3.58 (s, 2H), 3.00 (t, J=7.2 Hz, 2H), 2.47-2.37 (m, 4H), 1.58-1.46 (m, 6H), 1.47 (s, 9H) 1.37-1.20 (m, 3H), 0.87 (t, J=7.6 Hz, 3H).

Synthesis of tert-butyl (5-(propylamino)pentyl)carbamate, Bz-9b. To a solution of tert-butyl N-[5-[benzyl(propyl) amino]pentyl]carbamate Bz-9a (0.5 g, 1.49 mmol, 1 eq) in MeOH (20 mL) was added $Pd(OH)_2/C$ (0.2 g, 5% purity) at 25° C. under $N_2$. The suspension was degassed under vacuum and purged with $H_2$ several times. The mixture was stirred under $H_2$ (50 psi) at 50° C. for 12 hours. LCMS showed the reaction was finished. The mixture was filtered and concentrated. To give the product tert-butyl N-[5-(propylamino)pentyl]carbamate Bz-9b (0.3 g, crude) as colorless oil. $^1H$ NMR (400 MHz, METHANOL-$d_4$) δ=3.03 (t, J=6.8 Hz, 2H), 2.55 (d, J=7.6, 13.6 Hz, 4H), 1.59-1.44 (m, 6H), 1.47 (s. 9H) 1.43-1.20 (m, 2H), 0.97-0.88 (m, 3H).

To a mixture of tert-butyl N-[5-(propylamino)pentyl]carbamate Bz-9b (57.17 mg, 233.93 μmol, 1 eq) and 2-amino-8-[3-[3-(hydroxymethyl)azetidin-1-yl]sulfonylphenyl]-3H-1-benzazepine-4-carboxylic acid Bz-10c (0.1 g, 233.93 μmol, 1 eq) in DMF (4 mL) was added HATU (133.42 mg, 350.90 μmol, 1.5 eq) and $Et_3N$ (71.02 mg, 701.80 μmol, 97.68 μL, 3 eq) in one portion at 25° C. The mixture was stirred at 25° C. for 0.5 h. LCMS showed the reaction was finished. The mixture was diluted with water and extracted with EA (30 ml×3). The organic layer was washed with brine, dried over $Na_2SO_4$, filtered and concentrated. The residue was further purification by pre-HPLC (column: Xtimate C18 150×25 mm, 5 μm particle size; mobile phase: [water (0.1% TFA)-ACN]; B %: 32%-62%, 10.5 min) to give tert-butyl N-[5-[[2-amino-8-[3-[3-(hydroxymethyl) azetidin-1-yl] sulfonylphenyl]-3H-1-benzazepine-4-carbonyl]-propyl-amino]pentyl]carbamate Bz-9 (0.128 g, 179.48 μmol, 76.72% yield, 91.68% purity) as yellow solid. $^1H$ NMR (400 MHz, METHANOL-$d_4$) δ=8.10 (s, 1H), 8.07 (d, J=7.6 Hz, 1H), 7.89 (d, J=7.8 Hz, 1H), 7.83-7.78 (m, 1H), 7.77-7.65 (m, 3H), 7.09 (s, 1H), 3.86 (t, J=8.2 Hz, 2H), 3.61 (J=5.6, 8.0 Hz, 2H), 3.56-3.35 (m, 8H), 3.31 (s, 2H), 3.10-2.99 (m, 2H), 2.64-2.53 (m, 1H), 1.80-1.59 (m, 4H), 1.57-1.47 (m, 2H), 1.40 (s, 9H), 1.03-0.86 (m, 3H). LC/MS [M+H] 654.33 (calculated); LC/MS [M+H] 654.50 (observed).

Example 6: Synthesis of Bz-10

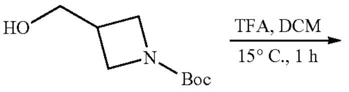

Bz-10d

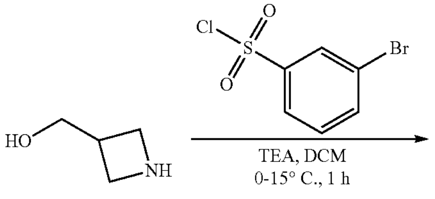

Bz-10e

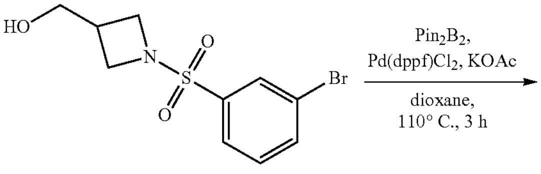

Bz-10f

-continued

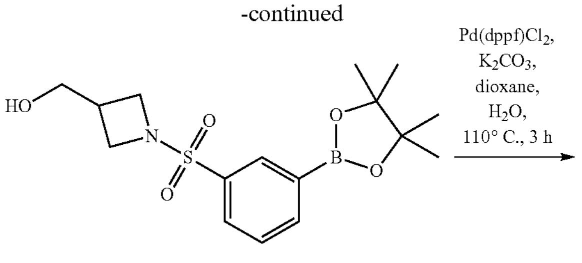

Bz-10g

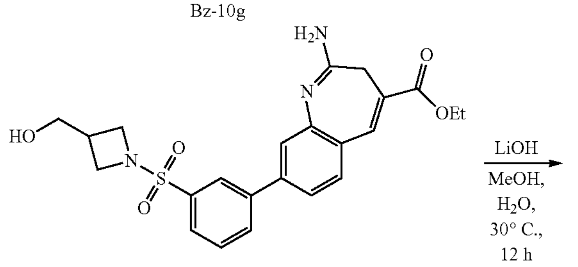

Bz-10h

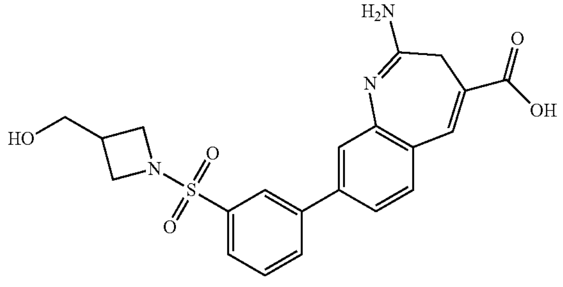

Bz-10c

Preparation of Bz-10c. To a mixture of tert-butyl 3-(hydroxymethyl)azetidine-1-carboxylate Bz-10d (15 g, 80.11 mmol) in DCM (100 mL) was added TFA (63.94 g, 560.79 mmol, 41.52 mL, 7 eq) at 15° C. The mixture was stirred at 15° C. for 1 h. The mixture was concentrated to give azetidin-3-ylmethanol Bz-10e (36 g, crude, TFA) as yellow oil. $^{1}$H NMR (DMSO-$d_6$, 400 MHz) δ 4.50-4.56 (m, 2H), 3.94-4.10 (m, 2H), 3.80-3.93 (m, 2H), 3.15-3.30 (m, 1H).

Preparation of [1-(3-bromophenyl)sulfonylazetidin-3-yl] methanol, Bz-10f. To a mixture of azetidin-3-ylmethanol (33.06 g, 164.37 mmol, 2 eq, TFA) and 3-bromobenzenesulfonyl chloride (21 g, 82.19 mmol, 11.86 mL, 1 eq) in DCM (200 mL) was added TEA (33.27 g, 328.75 mmol, 45.76 mL, 4 eq) at 0° C. The mixture was stirred at 15° C. for 1 h. The residue was poured into saturated sodium bicarbonate in aqueous solution (200 mL) and stirred 10 min. The aqueous phase was extracted with DCM (100 mL×3). The combined organic phase was washed with brine (100 mL), dried with anhydrous $Na_2SO_4$, filtered and concentrated in vacuum. The residue was purified by flash silica gel chromatography (ISCO™; 1 g SEPAFLASH™ Silica Flash Column, eluent of 0~100% ethyl acetate/petroleum ether gradient at 50 mL/min). Compound [1-(3-bromophenyl)sulfonylazetidin-3-yl] methanol Bz-10f (21 g, 68.59 mmol, 83.45% yield) was obtained as white solid. $^{1}$H NMR ($CDCl_3$, 400 MHz) δ 7.89-8.11 (m, 1H), 7.78 (dd, J=8.0, 2.0 Hz, 2H), 7.39-7.54 (m, 1H), 3.78-3.97 (m, 2H), 3.49-3.74 (m, 4H), 2.41-2.77 (m, 1H).

Preparation of [1-[3-(4,4,5,5-tetramethyl-1,3,2-dioxaborolan-2-yl)phenyl]sulfonylazetidin-3-yl]methanol, Bz-10g. To a mixture of [1-(3-bromophenyl)sulfonylazetidin-3-yl]methanol (8 g, 26.13 mmol, 1 eq) in dioxane (10 mL) was added $Pin_2B_2$ (9.95 g, 39.19 mmol, 1.5 eq), KOAc (5.13 g, 52.26 mmol, 2 eq) and Pd(dppf)$Cl_2$ (1.91 g, 2.61 mmol, 0.1 eq) at 15° C. The mixture was stirred at 110° C. for 3 h. LC-MS showed reactant 1 was consumed completely and one main peak with desired mass was detected. The mixture was filtered, washed by using ethyl acetate. Then the filtrate was concentrated in vacuum. The residue was purified by silica gel chromatography (column height: 250 mm, diameter: 100 mm, 100-200 mesh silica gel, petroleum ether/ethyl acetate=1/1, 0/1) to give 12 g crude product. The crude product was triturated with heptane/methyl tertiary butyl ether=5/1 (50 mL), filtered, the filter cake was dried in vacuum. Compound [1-[3-(4,4,5,5-tetramethyl-1,3,2-dioxaborolan-2-yl)phenyl] sulfonylazetidin-3-yl]methanol (8.2 g, 23.21 mmol, 88.84% yield) was obtained as pink solid. $^{1}$H NMR ($CDCl_3$, 400 MHz) δ 8.28 (s, 1H), 8.06 (d, J=8.0 Hz, 1H), 7.89-7.95 (m, 1H), 7.58 (t, J=8.0 Hz, 1H), 3.87 (t, J=8.0 Hz, 2H), 3.62-3.68 (m, 4H), 2.55-2.65 (m, 1H), 1.37 (s, 12H).

Preparation of ethyl 2-amino-8-[3-[3-(hydroxymethyl)azetidin-1-yl]sulfonylphenyl]-3H-1-benzazepine-4-carboxylate, Bz-10h. To a mixture of [1-[3-(4,4,5,5-tetramethyl-1,3,2-dioxaborolan-2-yl)phenyl] sulfonylazetidin-3-yl]methanol, Bz-10g (4.11 g, 11.64 mmol, 1.2 eq) and ethyl 2-amino-8-bromo-3H-1-benzazepine-4-carboxylate (3 g, 9.70 mmol, 1 eq) in dioxane (40 mL) and $H_2O$ (3 mL) was added $K_2CO_3$ (2.68 g, 19.41 mmol, 2 eq) and Pd(dppf)$Cl_2$ (355.02 mg, 485.19 μmol, 0.05 eq) at 15° C. under $N_2$. The mixture was stirred at 110° C. for 3 h. LC-MS showed reactant 1 was consumed completely and one main peak with desired mass was detected. The mixture was concentrated. The crude product was triturated with EtOAc/H2O=1:1 (200 mL) at 0° C. for 10 min and filtered, the filter cake was dried in vacuum. Compound ethyl 2-amino-8-[3-[3-(hydroxymethyl)azetidin-1-yl]sulfonylphenyl]-3H-1-benzazepine-4-carboxylate, Bz-10h (4 g, crude) was obtained as a white solid. $^{1}$H NMR (DMSO-$d_6$, 400 MHz) δ 8.06-8.15 (m, 1H), 7.96 (s, 1H), 7.71-7.85 (m, 3H), 7.57 (d, J=8.0 Hz, 1H), 7.29-7.38 (m, 2H), 6.94 (s, 2H), 4.17-4.30 (m, 2H), 3.77 (t, J=8.0 Hz, 2H), 3.49 (t, J=8.0 Hz, 2H), 3.2 (d, J=8.0 Hz, 2H), 2.93 (s, 2H), 2.43-2.49 (m, 1H), 1.31 (t, J=8.0 Hz, 3H).

Preparation of 2-Amino-8-[3-[3-(hydroxymethyl)azetidin-1-yl]sulfonylphenyl]-3H-1-benzazepine-4-carboxylic acid, Bz-10c. To a solution of ethyl 2-amino-8-[3-[3-(hydroxymethyl)azetidin-1-yl]sulfonylphenyl]-3H-1-benzazepine-4-carboxylate, Bz-10h (4 g, 8.78 mmol, 1 eq) in MeOH (50 mL) and $H_2O$ (10 mL) was added LiOH·$H_2O$ (1.84 g, 43.91 mmol, 5 eq). The mixture was stirred at 30° C. for 12 h. LC-MS showed reactant 1 was consumed completely and one main peak with desired mass was detected. The reaction mixture was concentrated under reduced pressure to remove MeOH. The mixture was filtered. The filtrate was adjusted pH to around 6 by progressively adding a solution of HCl (1 M) and then filtered to give crude product. The crude product was triturated with $CH_3CN$ (100 mL) at 0° C. for 10 min. The product was dried in vacuum. Compound 2-amino-8-[3-[3-(hydroxymethyl)azetidin-1-yl]sulfonylphenyl]-3H-1-benzazepine-4-carboxylic acid, Bz-10c (2.51 g, 5.72 mmol, 65.11% yield, 97.375% purity) was obtained as a gray solid. $^{1}$H NMR (DMSO-$d_6$, 400 MHz) δ 8.11-8.16 (m, 1H), 8.02 (s, 1H), 7.92 (s, 1H), 7.78-7.88 (m, 4H), 7.75 (s, 1H), 3.76 (t, J=8.0 Hz, 2H), 3.45-3.54 (m, 4H), 3.20 (d, J=4.0 Hz, 2H), 2.45-2.49 (m, 1H). LC/MS [M+H] 428.13 (calculated); LC/MS [M+H] 428.20 (observed).

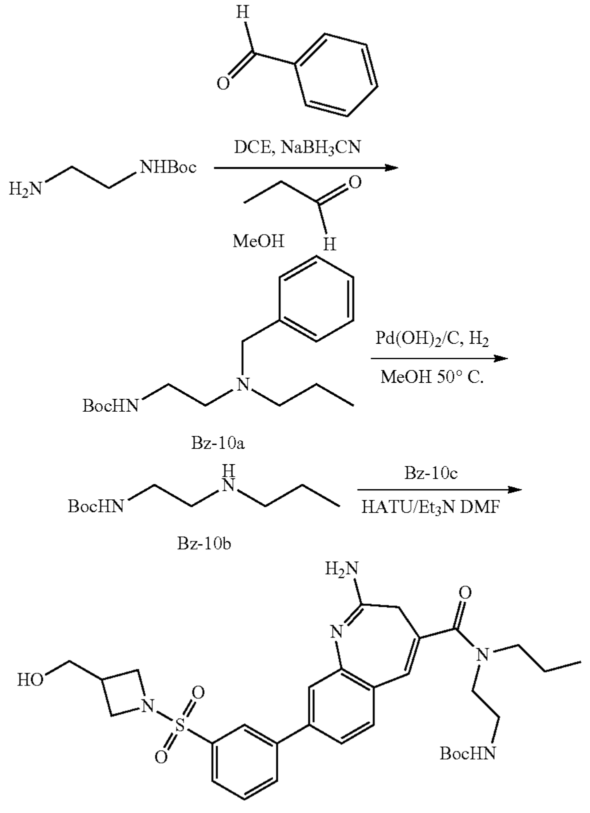

Bz-10a

Bz-10b

Bz-10

Synthesis of tert-butyl N-[2-[benzyl(propyl)amino]ethyl] carbamate, Bz-10a. To a mixture of benzaldehyde (2 g, 18.85 mmol, 1.90 mL, 1 eq) and tert-butyl N-(2-aminoethyl) carbamate (3.32 g, 20.73 mmol, 3.26 mL, 1.1 eq) in DCE (30 mL) was added $NaBH_3CN$ (2.37 g, 37.69 mmol, 2 eq) at 0° C. The mixture was stirred at 0° C. for 30 min, propanal (5.47 g, 94.23 mmol, 6.86 mL, 5 eq) was added to the mixture and stirred for 1 hour at 25° C. The mixture was poured into ice water (50 mL) and the aqueous phase was extracted with ethyl acetate (50 mL×3). The combined organic phase was washed with brine (50 mL), dried with anhydrous $Na_2SO_4$, filtered and concentrated in vacuum. The residue was purified by silica gel chromatography (column height: 250 mm, diameter: 100 mm, 100-200 mesh silica gel, petroleum ether/ethyl acetate=5/1, 1/1) to afford tert-butyl N-[2-[benzyl(propyl)amino]ethyl] carbamate Bz-10a (3 g, 10.26 mmol, 54.44% yield) as a colorless oil.

Synthesis of tert-butyl N-[2-(propylamino)ethyl]carbamate, Bz-10b. To a solution of tert-butyl N-[2-[benzyl(propyl) amino]ethyl]carbamate (2 g, 6.84 mmol, 1 eq) in MeOH (50 mL) was added $Pd(OH)_2/C$ (10%, 1 g) under $N_2$. The suspension was degassed under vacuum and purged with $H_2$ several times. The mixture was stirred under $H_2$ (50 psi) at 50° C. for 12 hours. TLC (petroleum ether/ethyl acetate=3: 1) showed the starting material was consumed completely. The reaction mixture was filtered, and the filtrate was concentrated to give the crude product tert-butyl N-[2-(propylamino)ethyl]carbamate (1.3 g, 6.43 mmol, 93.96% yield) as colorless oil which was used into the next step without further purification. $^1H$ NMR (MeOD, 400 MHz) δ 3.18 (t, J=6.0 Hz, 2H), 2.68 (t, J=6.0 Hz, 2H), 2.56 (t, J=8.0 Hz, 2H), 1.58-1.48 (m, 2H), 1.44 (s, 9H), 0.94 (t, J=8.0 Hz, 3H).

Synthesis of tert-butyl (2-(2-amino-8-(3-((3-(hydroxymethyl)azetidin-1-yl)sulfonyl)phenyl)-N-propyl-3H-benzo[b]azepine-4-carboxamido)ethyl)carbamate, Bz-10. To a mixture of 2-amino-8-[3-[3-(hydroxymethyl)azetidin-1-yl]sulfonylphenyl]-3H-1-benzazepine-4-carboxylic acid, Bz-10c (0.15 g, 350.90 μmol, 1 eq) and tert-butyl-N-[2-(propylamino)ethyl]carbamate (141.97 mg, 701.80 μmol, 2 eq) in DMF (4 mL) was added HATU (160.11 mg, 421.08 μmol, 1.2 eq), $Et_3N$ (106.52 mg, 1.05 mmol, 146.52 μL, 3 eq) in one portion at 25° C. The mixture was stirred at 25° C. for 12 h. LCMS showed the reaction was finished. The mixture was filtered and purified by prep-HPLC (column: Waters Xbridge 150×25 5μ; mobile phase: [water (10 mM $NH_4HCO_3$)-ACN]; B %: 25%-45%, 20 min) to give tert-butyl N-[2-[[2-amino-8-[3-[3-(hydroxymethyl)azetidin-1-yl]sulfonylphenyl]-3H-1-benzazepine-4-carbonyl]-propyl-amino]ethyl]carbamate (0.036 g, 55.05 μmol, 15.69% yield, 93.54% purity) as yellow solid. $^1H$ NMR (MeOD, 400 MHz) δ 8.07 (s, 1H), 8.03 (d, J=7.6 Hz, 1H), 7.86-7.81 (d, J=8.0 Hz, 1H), 7.78-7.73 (m, 1H), 7.47 (s, 2H), 7.41-7.36 (m, 1H), 6.95 (s, 1H), 3.86 (t, J=8.4 Hz, 2H), 3.62-3.53 (m, 4H), 3.49-3.44 (m, 2H), 3.41 (d, J=6.4 Hz, 2H), 3.32-3.29 (m, 3H), 2.63-2.51 (m, 1H), 1.68 (d, J=7.2 Hz, 2H), 1.43 (s, 9H), 0.98-0.83 (m, 3H). LC/MS [M+H] 612.29 (calculated); LC/MS [M+H] 612.40 (observed).

Example 7: Synthesis of Bz-11

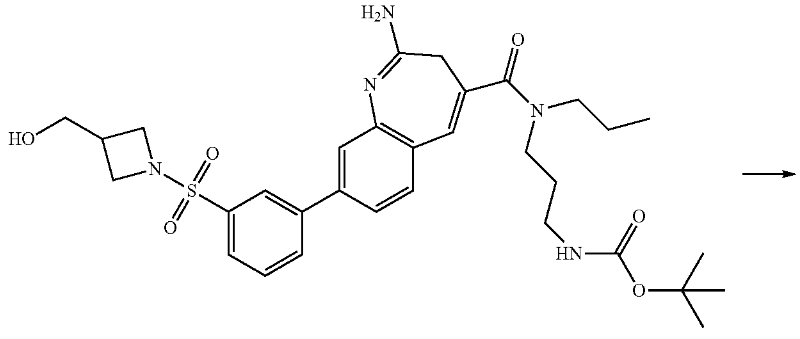

Bz-1

-continued

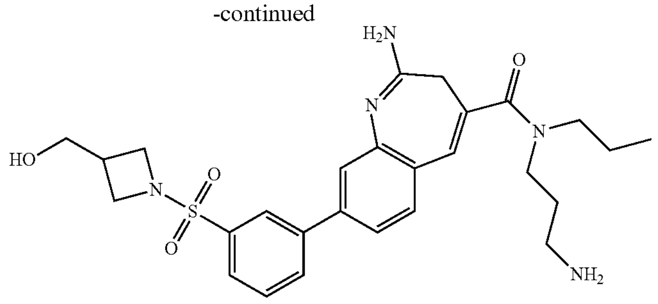

Bz-11a

Synthesis of 2-amino-N-(3-aminopropyl)-8-[3-[3-(hydroxymethyl)azetidin-1-yl]sulfonylphenyl]-N-propyl-3H-1-benzazepine-4-carboxamide, Bz-11a. To a mixture of tert-butyl N-[3-[[2-amino-8-[3-[3-(hydroxymethyl)azetidin-1-yl] sulfonylphenyl]-3H-1-benzazepine-4-carbonyl]-propyl-amino]propyl]carbamate, Bz-1 (0.5 g, 799.01 μmol, 1 eq) in DCM (20 mL) was added TFA (1.82 g, 15.98 mmol, 1.18 mL, 20 eq) in one portion at 15° C. The mixture was stirred at 15° C. for 3 hours. LCMS showed the reactant was consumed. The mixture was concentrated in vacuum, the residue was poured into ice water (30 mL) and adjusted pH=11 with $Na_2CO_3$.aq. The aqueous phase was extracted with DCM/i-PrOH=3/1 (20 mL×3). The combined organic phase was washed with brine (10 mL), dried with anhydrous $Na_2SO_4$, filtered and concentrated in vacuum. The crude product 2-amino-N-(3-aminopropyl)-8-[3-[3-(hydroxymethyl)azetidin-1-yl] sulfonylphenyl]-N-propyl-3H-1-benzazepine-4-carboxamide, Bz-11a (0.4 g, crude) as yellow oil which was used into the next step without further purification.

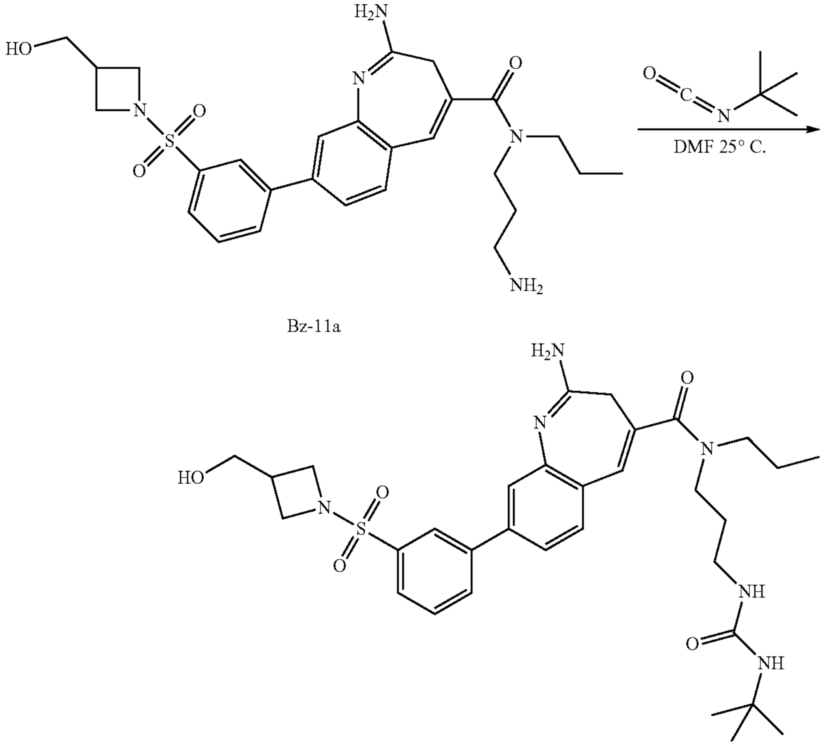

Bz-11a

Bz-11

Synthesis of 2-amino-N-[3-(tert-butylcarbamoylamino) propyl]-8-[3-[3-(hydroxymethyl)azetidin-1-yl]sulfonylphenyl]-N-propyl-3H-1-benzazepine-4-carboxamide, Bz-11. To a solution of 2-amino-N-(3-aminopropyl)-8-[3-[3-(hydroxymethyl)azetidin-1-yl]sulfonylphenyl]-N-propyl-3H-1-benzazepine-4-carboxamide, Bz-11a (0.1 g, 190.24 μmol, 1 eq) in DMF (2 mL) was added 2-isocyanato-2-methyl-propane (18.86 mg, 190.24 μmol, 22.45 μL, 1 eq) in one portion at 15° C. The mixture was stirred at 15° C. for 12 hours. LCMS showed the reaction was completed. The mixture was filtered and purified by prep-HPLC (column: Nano-micro KROMASIL™ (Nouryon) C18 100×30 mm, 5 μm particle size; mobile phase: [water (0.10% TFA)-ACN]; B %: 25%-45%, 10 min) to give crude product, then purified by prep-HPLC (column: Welch Xtimate C18 150×25 mm, 5

μm particle size; mobile phase: [water (10 mM $NH_4HCO_3$)-ACN]; B %: 25%-65%, 10.5 min) to give Bz-11 (0.007 g, 11.20 μmol, 5.89% yield) as light yellow solid. $^1H$ NMR (MeOD, 400 MHz) δ 8.09 (s, 1H), 8.05 (d, J=8.0 Hz, 1H), 7.87-7.85 (m, 1H), 7.80-7.76 (m, 1H), 7.51-7.49 (m, 2H), 7.43-7.41 (m, 1H), 6.94 (s, 1H), 3.88 (t, J=8.0 Hz, 2H), 3.63-3.60 (m, 2H), 3.54-3.50 (m, 2H), 3.44-3.43 (m, 4H), 3.15-2.91 (m, 4H), 2.67-2.58 (m, 1H), 1.84-1.79 (m, 2H), 1.73-1.66 (m, 2H), 1.40-1.14 (m, 9H), 1.00-0.90 (m, 3H).

Example 8: Synthesis of Bz-12

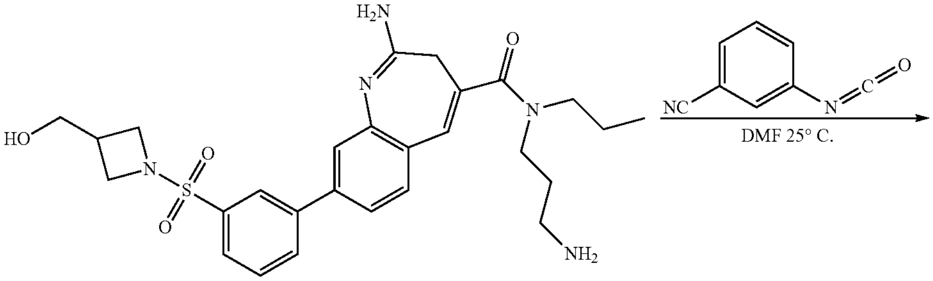

Bz-11a

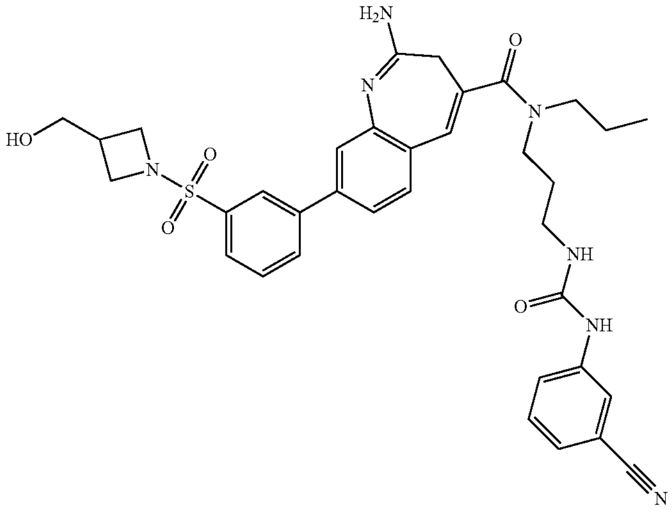

Bz-12

To a solution of 2-amino-N-(3-aminopropyl)-8-[3-[3-(hydroxymethyl)azetidin-1-yl] sulfonylphenyl]-N-propyl-3H-1-benzazepine-4-carboxamide, Bz-11a (0.1 g, 190.24 μmol, 1 eq) in DMF (0.3 mL) was added 3-isocyanatobenzonitrile (27.42 mg, 190.24 μmol, 1 eq) in one portion at 15° C. The mixture was stirred at 15° C. for 12 hours. LCMS showed the reaction was completed. The mixture was filtered and purified by prep-HPLC (column: Nano-micro KROMASIL™ (Nouryon) C18 100×30 mm, 5 μm particle size; mobile phase: [water (0.1% TFA)-ACN]; B %: 25%-45%, 10 min) to give 2-amino-N-[3-[(3-cyanophenyl)carbamoylamino]propyl]-8-[3-[3-(hydroxymethyl)azetidin-1-yl] sulfonylphenyl]-N-propyl-3H-1-benzazepine-4-carboxamide, Bz-12 (10 mg, 14.93 μmol, 7.85% yield) as yellow solid. $^1H$ NMR ($CD_3OD$, 400 MHz) δ 8.21-7.88 (m, 4H), 7.86-7.80 (m, 1H), 7.68 (s, 3H), 7.59-7.24 (m, 3H), 7.15 (s, 1H), 3.89 (t, J=8.0 Hz, 2H), 3.64 (m, 4H), 3.51 (s, 2H), 3.46 (d, J=6.0 Hz, 2H), 3.40 (s, 2H), 3.30-3.19 (m, 2H), 2.63-2.60 (m, 1H), 1.96-1.92 (m, 2H), 1.77-1.71 (m, 2H), 1.07-0.86 (m, 3H).

Example 9: Synthesis of Bz-13

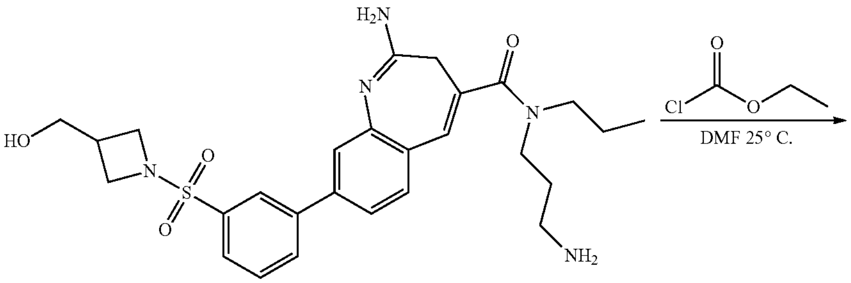

Bz-11a

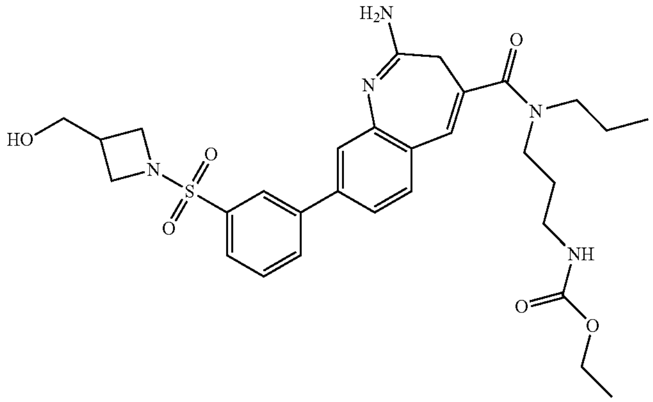

Bz-13

To a mixture of 2-amino-N-(3-aminopropyl)-8-[3-[3-(hydroxymethyl)azetidin-1-yl] sulfonylphenyl]-N-propyl-3H-1-benzazepine-4-carboxamide, Bz-11a (0.1 g, 190.24 μmol, 1 eq) in DMF (2 mL) was added ethyl carbonochloridate (ethylchloroformate) (61.94 mg, 570.72 μmol, 54.33 μL, 3 eq) in one portion at 15° C. The mixture was stirred at 15° C. for 1 hour. LCMS and HPLC showed the desired was detected. The mixture was filtered and purified by prep-HPLC (column: Waters Xbridge BEH C18 100×25 mm, 5 μm particle size; mobile phase: [water (0.1% TFA)-ACN]; B %: 25%-45%, 20 min) to give ethyl N-[3-[[2-amino-8-[3-[3-(hydroxymethyl)azetidin-1-yl] sulfonylphenyl]-3H-1-benzazepine-4-carbonyl]-propyl-amino]propyl]carbamate, Bz-13 (0.018 g, 30.11 μmol, 15.83% yield) as light yellow solid. $^1H$ NMR ($CD_3OD$, 400 MHz) δ 8.11 (s, 1H), 8.08 (d, J=8.0 Hz, 1H), 7.91 (d, J=8.0 Hz, 1H), 7.83 (d, J=8.0 Hz, 1H), 7.81-7.75 (m, 1H), 7.74-7.68 (m, 2H), 7.12 (s, 1H), 4.07 (brs, 2H), 3.87 (t, J=8.0 Hz, 2H), 3.61 (m, 2H), 3.55 (m, 2H), 3.48 (m, 2H), 3.42 (d, J=6.4 Hz, 2H), 3.37 (s, 2H), 3.14 (m, 2H), 2.67-2.51 (m, 1H), 1.93-1.80 (m, 2H), 1.77-1.64 (m, 2H), 1.33-1.06 (m, 3H), 0.95 (s, 3H).

Example 10: Synthesis of Bz-14

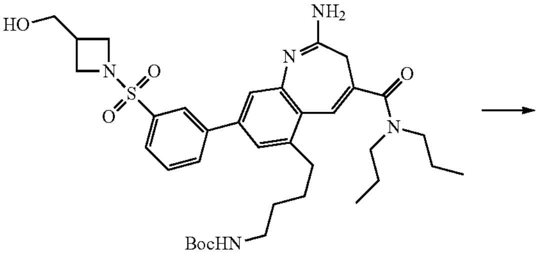

Bz-5

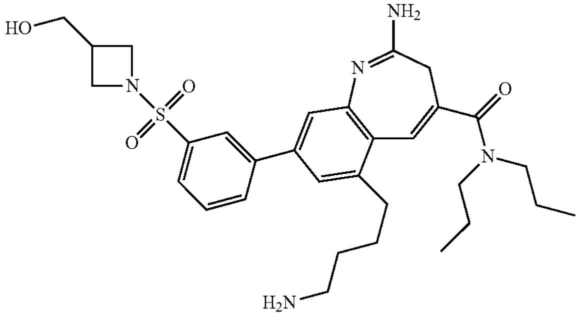

Bz-14

2-Amino-6-(4-aminobutyl)-8-(3-((3-(hydroxymethyl)azetidin-1-yl)sulfonyl)phenyl)-N,N-dipropyl-3H-benzo[b]azepine-4-carboxamide, Bz-14 was synthesized from Bz-5 according to the procedure described for Bz-11a. LC/MS [M+H]582.31 (calculated); LC/MS [M+H] 582.57 (observed).

Example 11: Synthesis of Bz-15

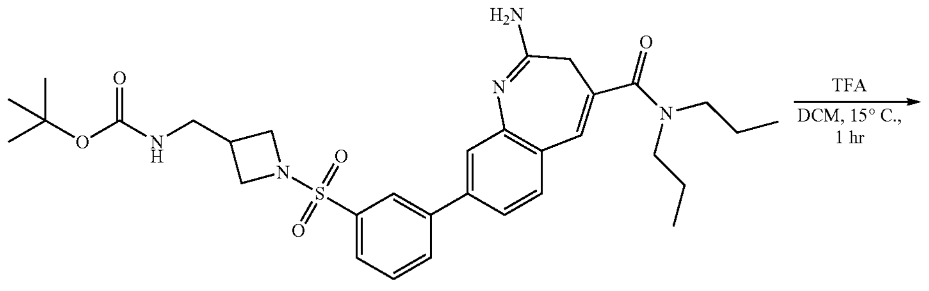

Bz-5

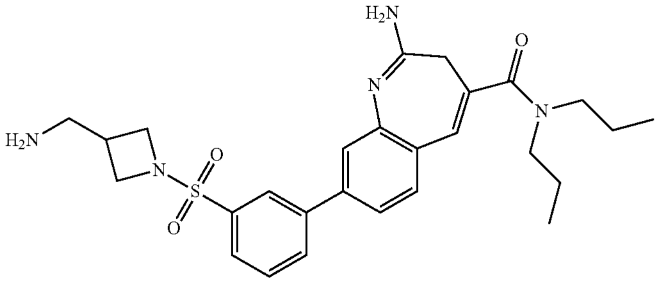

Bz-15

To a solution of tert-butyl N-[[1-[3-[2-amino-4-(dipropylcarbamoyl)-3H-1-benzazepin-8-yl]phenyl]sulfonylazetidin-3-yl]methyl]carbamate, Bz-6 (0.15 g, 245.99 μmol, 1 eq) in DCM (20 mL) was added TFA (56.10 mg, 491.98 μmol, 36.43 μL, 2 eq) at 25° C. and stirred for 1 hour. The mixture was concentrated in reduced pressure at 40° C. The residue was purified by prep-HPLC (column: Nano-micro KROMASIL™ (Nourvon) C18 100×30 mm, 5 μm particle size; mobile phase: [water (0.1% TFA)-ACN]; B %: 25%-50%, 10 min) to give-amino-8-[3-[3-(aminomethyl)azetidin-1-yl]sulfonylphenyl]-N,N-dipropyl-3H-1-benzazepine-4-carboxamide, Bz-15 (0.0546 g, 105.69 μmol, 42.97% yield, 98.66% purity) as a yellow solid. $^1$H NMR (MeOD-$d_4$, 400 MHz) δ 8.16-8.07 (m, 2H), 7.92 (d, J=8.0 Hz, 1H), 7.83 (t, J=7.6 Hz, 1H), 7.79-7.72 (m, 2H), 7.68 (d, J=8.4 Hz, 1H), 7.09 (s, 1H), 3.96 (t, J=8.4 Hz, 2H), 3.67-3.63 (m, 2H), 3.50-3.42 (m, 4H), 3.37 (s, 2H), 3.05 (d, J=7.4 Hz, 2H), 2.78-2.65 (m, 1H), 1.75-1.66 (m, 4H), 1.08-0.82 (m, 6H). LC/MS [M+H] 510.25 (calculated); LC/MS [M+H] 510.10 (observed).

Example 12: Synthesis of Bz-16

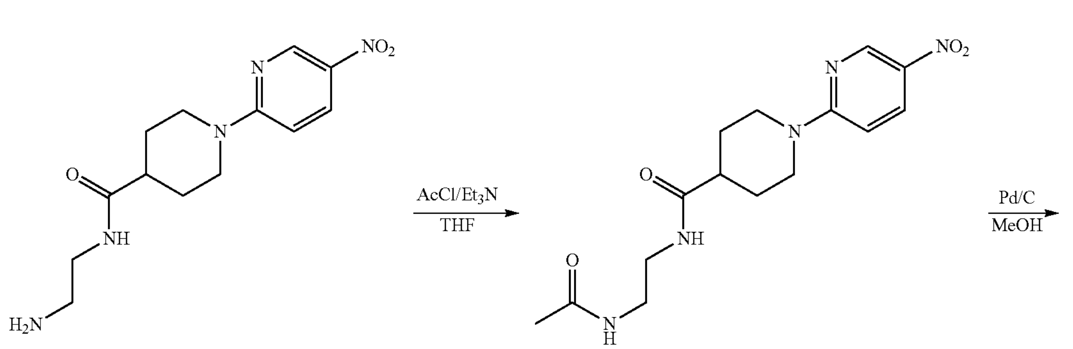

BzL-23b Bz-16a

-continued

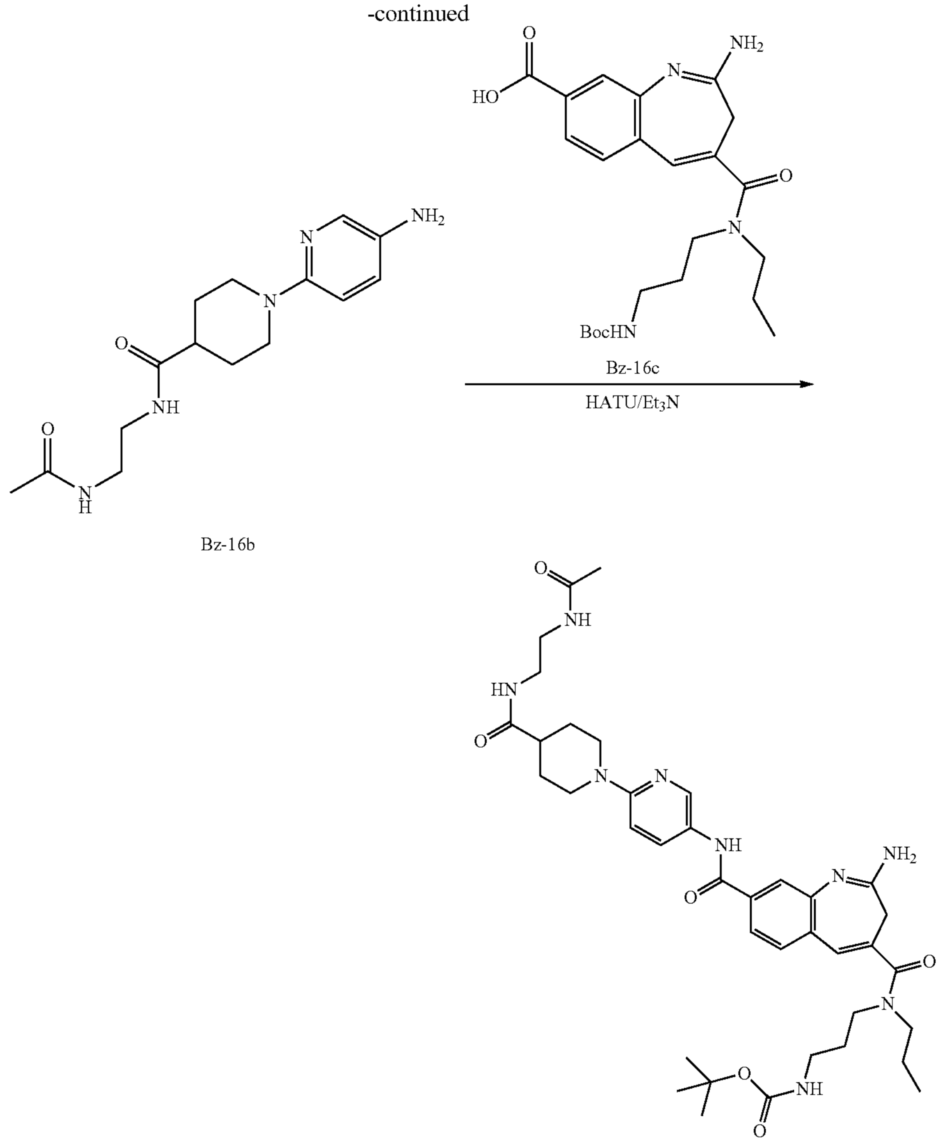

Bz-16b

Bz-16c

Bz-16

Synthesis of N-(2-acetamidoethyl)-1-(5-nitropyridin-2-yl) piperidine-4-carboxamide, Bz-16a. To a mixture of acetyl chloride (142.82 mg, 1.82 mmol, 129.83 μL, 3 eq) and N-(2-aminoethyl)-1-(5-nitro-2-pyridyl)piperidine-4-carboxamide, BzL-23b (0.2 g, 606.46 μmol, 1 eq, HCl) in THE (10 mL) was added $Et_3N$ (245.47 mg, 2.43 mmol, 337.65 μL, 4 eq) at 25° C. under $N_2$. The mixture was stirred at 25° C. for 1 hour. LCMS showed the reaction was completed. The mixture was poured into water (20 mL). The mixture was filtered to give Bz-16a (0.2 g, 596.38 μmol, 98.34% yield) as a yellow solid. $^1H$ NMR (DMSO-$d_6$, 400 MHz) δ 8.95 (d, J=2.4 Hz, 1H), 8.19 (dd, J=9.6, 2.4 Hz, 1H), 7.78-7.98 (m, 2H), 6.95 (d, J=9.6 Hz, 1H), 4.50 (d, J=9.6 Hz, 2H), 2.93-3.15 (m, 7H), 1.73-1.80 (m, 5H), 1.43-1.62 (m, 2H), 1.07-1.28 (m, 3H).

Synthesis of N-(2-acetamidoethyl)-1-(5-aminopyridin-2-yl) piperidine-4-carboxamide, Bz-16b. To a solution of N-(2-acetamidoethyl)-1-(5-nitro-2-pyridyl)piperidine-4-carboxamide, Bz-16a (0.2, 596.38 μmol, 1 eq) in MeOH (20 mL) was added Pd/C (0.2 g, 5% purity) under $N_2$. The suspension was degassed under vacuum and purged with $H_2$ several times. The mixture was stirred under $H_2$ (15 psi) at 25° C. for 4 hours. LCMS showed the reaction was completed. The mixture was filtered and concentrated to give Bz-16b (0.18 g, 589.44 μmol, 98.84% yield) as yellow solid.

Synthesis of tert-butyl (3-(8-((6-(4-((2-acetamidoethyl) carbamoyl)piperidin-1-yl)pyridin-3-yl)carbamoyl)-2-amino-N-propyl-3H-benzo[b]azepine-4-carboxamido)propyl)carbamate, Bz-16. To a mixture of 2-amino-4-[3-(tert-butoxycarbonylamino) propyl-propyl-carbamoyl]-3H-1-benzazepine-8-carboxylic acid, Bz-16c (0.22 g, 494.91 μmol, 1 eq) HATU (225.82 mg, 593.90 μmol, 1.2 eq) in DMF (5 mL) was added $Et_3N$ (150.24 mg, 1.48 mmol, 206.66 μL, 3 eq) at 25° C. The mixture was stirred at 25° C. for 5 min, then N-(2-acetamidoethyl)-1-(5-amino-2-pyridyl) piperidine-4-carboxamide, Bz-16b (151.13 mg, 494.91 μmol, 1 eq) was added to the mixture, stirred for 30 min. The mixture was poured into water (50 mL). The aqueous phase was extracted with ethyl acetate (50 mL). The combined organic phase was washed with brine (50 mL), dried with anhydrous $Na_2SO_4$, filtered and concentrated in vacuum. The residue was purified by prep-HPLC column: Welch Xtimate C18 150×25 mm, 5 μm particle size; mobile phase: [water (10 mM $NH_4HCO_3$)-ACN]; B %: 30%-50%, 10.5 min to afford Bz-16 (96 mg, 131.17 μmol, 26.50% yield) as an off-white solid. $^1$H NMR (MeOD, 400 MHz) δ 8.39 (d, J=2.6 Hz, 1H), 7.90 (dd, J=9.2, 2.6 Hz, 1H), 7.69 (d, J=1.2 Hz, 1H), 7.54-7.60 (m, 1H), 7.46 (br d, J=8.0 Hz, 1H), 6.85-6.95 (m, 2H), 4.30 (d, J=13.6 Hz, 2H), 3.39-3.53 (m, 4H), 3.28 (s, 2H), 3.08-3.12 (m, 2H), 2.83-2.93 (m, 2H), 2.37-2.47 (m, 1H), 1.94 (s, 3H), 1.60-1.90 (m, 8H), 1.24-1.50 (m, 9H). LC/MS [M+H] 732.42 (calculated); LC/MS [M+H] 732.40 (observed).

Example 13: Synthesis of Bz-17

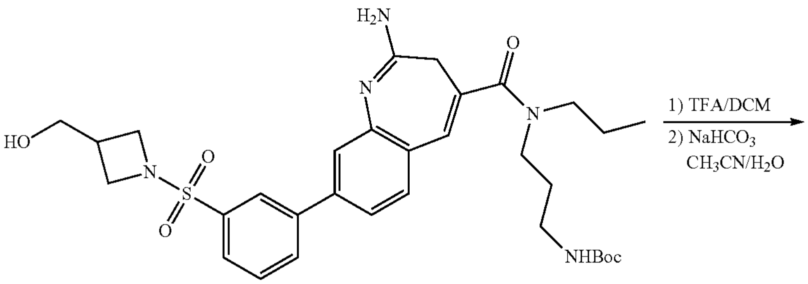

Bz-1

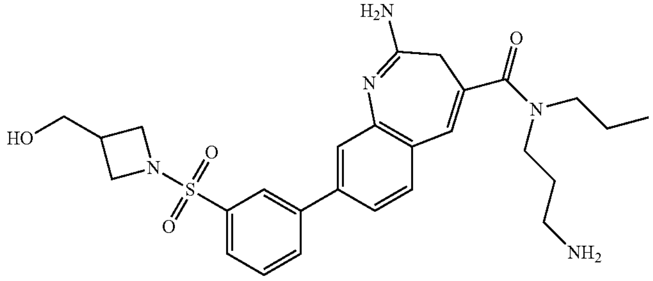

Bz-17

To a solution of tert-butyl N-[3-[[2-amino-8-[3-[3-(hydroxymethyl)azetidin-1-yl]sulfonylphenyl]-3H-1-benzazepine-4-carbonyl]-propyl-amino]propyl]carbamate, Bz-1 (1.5 g, 2.40 mmol, 1 eq) in DCM (20 mL) was added TFA (6.16 g, 54.03 mmol, 4 mL, 22.54 eq) at 25° C. under $N_2$ and then stirred at this temperature for 1 h. The reaction mixture was concentrated under reduced pressure. The residue was diluted with $CH_3CN$ (30 mL) and $H_2O$ (10 mL) and adjusted pH=8-9 with aq. $NaHCO_3$ at 0° C. The mixture was stirred for 30 min at 25° C. and then concentrated under reduced pressure to remove $CH_3CN$. The aqueous phase was extracted with DCM/i-PrOH=3/1 (20 mL×3), dried over $Na_2SO_4$, filtered and concentrated under reduced pressure. The residue was purified by prep-HPLC (TFA condition; column: lunaLUNA™ (Phenomenex) C18 250×80 mm, 10 μm particle size; mobile phase: [water (0.1% TFA)-ACN]; B %: 10%-40%, 20 min) to afford 2-amino-N-(3-aminopropyl)-8-[3-[3-(hydroxymethyl)azetidin-1-yl]sulfonylphenyl]-N-propyl-3H-1-benzazepine-4-carboxamide, Bz-17 (1.00 g, 1.57 mmol, 65.48% yield, TFA salt) as a white solid. $^1$H NMR (MeOD-$d_4$, 400 MHz) δ 8.14-8.05 (m, 2H), 7.91 (d, J=7.6 Hz, 1H), 7.86-7.81 (m, 1H), 7.80-7.72 (m, 2H), 7.71-7.67 (m, 1H), 7.15 (s, 1H), 3.87 (t, J=8.0 Hz, 2H), 3.65-3.57 (m, 4H), 3.55-3.52 (m, 2H), 3.45-3.36 (m, 4H), 3.04-3.01 (m, 2H), 2.63-2.53 (m, 1H), 2.04 (quin, J=7.2 Hz, 2H), 1.77-1.70 (m, 2H), 0.94 (br t, J=6.8 Hz, 3H). LC/MS [M+H]526.2 (calculated); LC/MS [M+H] 526.2 (observed).

Example 14: Synthesis of Bz-18

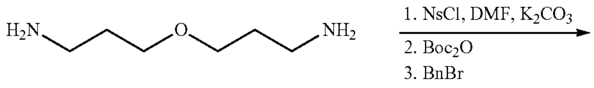

-continued

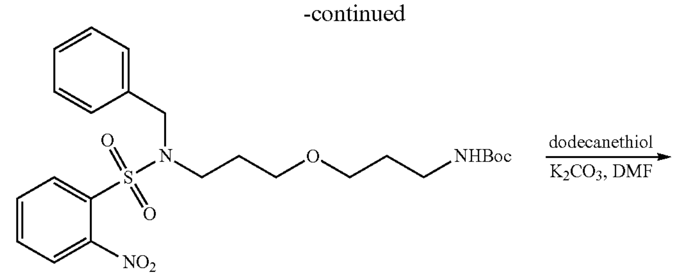

Bz-18a

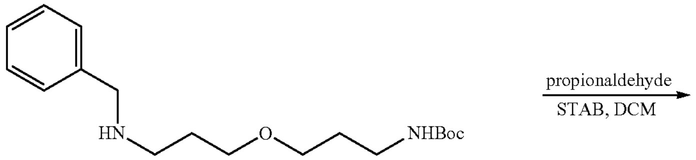

Bz-18b

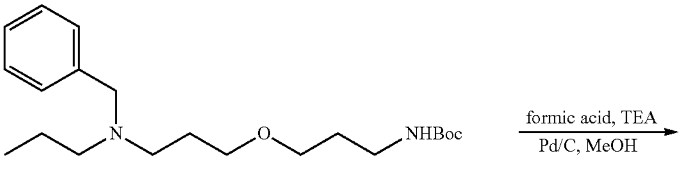

Bz-18c

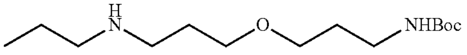

Bz-18d

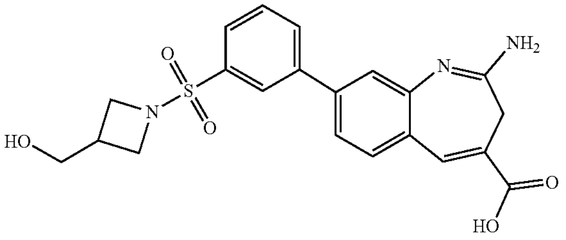

Bz-18e

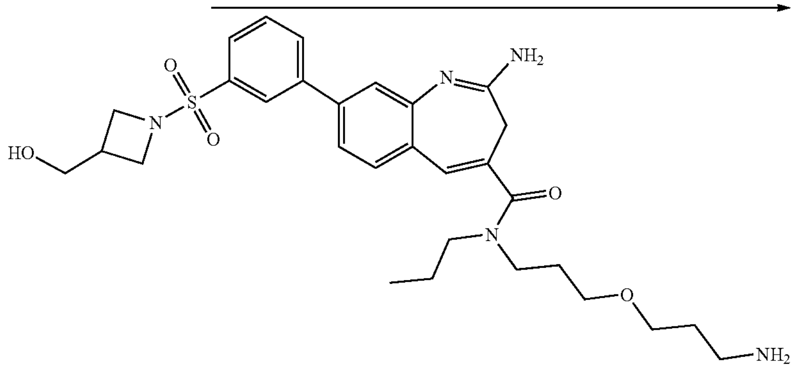

Bz-18

Preparation of tert-butyl (3-(3-((N-benzyl-2-nitrophenyl) sulfonamido)propoxy)propyl)carbamate, Bz-18a. 3,3'-Oxybis(propan-1-amine) (0.5 g, 3.8 mmol, 1 eq) and potassium carbonate (1.3 g, 9.5 mmol, 2.5 eq) were taken up in 10 ml DMF. 2-Nitrophenyl sulfonyl chloride (0.84 g, 3.8 mmol, 1 eq) was added and the reaction monitored by LCMS. Di-tert-butyl dicarbonate (0.87 ml, 3.8 mmol, 1 eq) was subsequently added. After approximately one additional hour, benzyl bromide (0.45 ml, 3.8 mmol, 1 eq) was added and the reaction heated to 75° C. Upon completion, the reaction was filtered, concentrated, and purified by flash chromatography to give Bz-18a (0.47 g, 0.93 mmol, 25%). LC/MS [M+H] 508.21 (calculated); LC/MS [M+H] 508.43 (observed).

Preparation of tert-butyl (3-(3-(benzylamino)propoxy) propyl)carbamate, Bz-18b. Bz-18a (0.47 g, 0.93 mmol, 1 eq) was dissolved in DMF. Potassium carbonate (0.19 g, 1.4 mmol, 1.5 eq) was added, followed by dodecanethiol (0.33 ml, 1.4 mmol, 1.5 eq). The reaction was stirred at 60° C. overnight, and then purified by column chromatography to give Bz-18b (0.18 g, 0.57 mmol, 61%). LC/MS [M+H] 323.23 (calculated); LC/MS [M+H]323.38 (observed).

Preparation of tert-butyl (3-(3-(benzyl(propyl)amino)propoxy)propyl)carbamate, Bz-18c. Bz-18b (0.183 g, 0.57 mmol, 1 eq) was dissolved in DCM. Propionaldehyde (0.1 ml, 1.4 mmol, 2.5 eq) and sodium triacetoxyborohydride (0.3 g, 1.4 mmol, 2.5 eq) were added. The reaction was stirred at room temperature, then concentrated and purified by HPLC to give Bz-18c (0.058 g, 0.159 mmol, 31%). LC/MS [M+H] 365.28 (calculated); LC/MS [M+H] 365.44 (observed).

Preparation of tert-butyl (3-(3-(propylamino)propoxy)propyl)carbamate, Bz-18d. Bz-18c (0.058 g, 0.159 mmol, 1 eq) was dissolved in 4 ml methanol. To the solution were added triethylamine (0.067 ml, 0.48 mmol, 3 eq), followed by formic acid (0.015 ml, 0.40 mmol, 2.5 eq) and then Pd/C (5 mg, 10 wt %). The mixture was heated to 60° C. Upon consumption of starting material, the reaction mixture was filtered and concentrated to give Bz-18d (0.007 g, 0.0092 mmol, 26%). LC/MS [M+H] 275.23 (calculated); LC/MS [M+H]275.27 (observed).

Preparation of Bz-18. 2-Amino-8-(3-((3-(hydroxymethyl)azetidin-1-yl)sulfonyl)phenyl)-3H-benzo[b]azepine-4-carboxylic acid, Bz-18e (0.025 g, 0.075 mmol, 1 eq), Bz-18d (0.02 g, 0.075 mmol, 1 eq), and diisopropylethylamine (0.065 ml, 0.38 mmol, 5 eq) were dissolved in DMF. HATU (0.043 g, 0.113 mmol, 1.5 eq) was added and the mixture stirred at room temperature. When complete, the reaction mixture was concentrated and purified by RP-HPLC. The isolated product was concentrated, dissolved in minimal TFA, and allowed to stand at room temperature for 15 minutes. The solution was then concentrated, purified by RP-HPLC, and lyophilized to give 2-amino-N-(3-(3-aminopropoxy)propyl)-8-(3-((3-(hydroxymethyl)azetidin-1-yl)sulfonyl)phenyl)-N-propyl-3H-benzo[b]azepine-4-carboxamide, Bz-18 as a white powder (1.2 mg, 0.002 mmol, 3%). LC/MS [M+H] 584.29 (calculated); LC/MS [M+H] 584.50 (observed).

Example 15: Synthesis of Bz-19

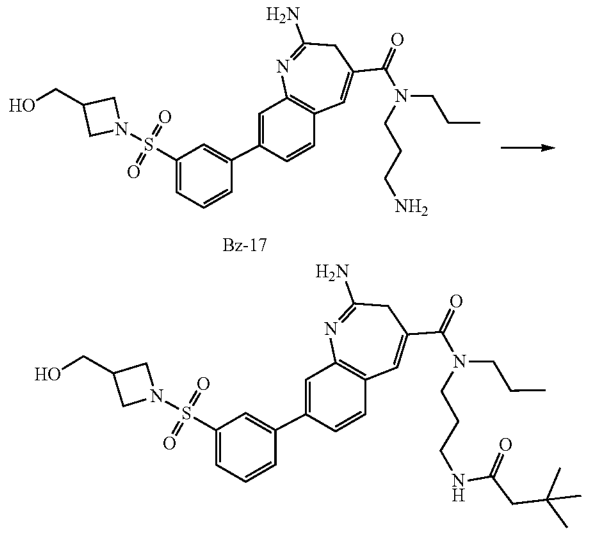

Bz-17

Bz-19

A vial was charged with Bz-17 (0.0275 mmol), diisopropylethylamine (15 μL, 0.0825 mmol), tert-butylacetyl chloride (0.0275 mmol), 250 μL DCM, and 250 μL DMF. The reaction was maintained for three hours and purified by normal phase chromatography using a 0-10% MeOH:DCM gradient affording 6.6 mg of 2-amino-N-(3-(3,3-dimethylbutanamido)propyl)-8-(3-((3-(hydroxymethyl)azetidin-1-yl)sulfonyl)phenyl)-N-propyl-3H-benzo[b]azepine-4-carboxamide, Bz-19 in 39% yield. LC/MS [M+H] 624.3 (calculated); LC/MS [M+H] 624.3 (observed).

Example 16: Synthesis of Bz-20

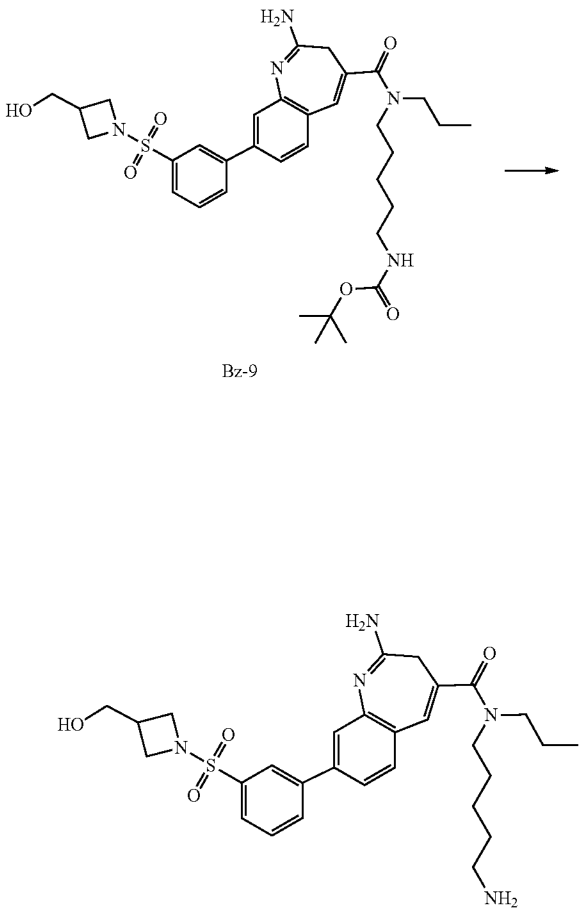

Bz-9

Bz-20

A vial was charged with Bz-9 (28 mg, 0.043 mmol), 300 μL DCM and 100 μL trifluoroacetic acid. The reaction was maintained for 1 h, upon which it was concentrated under reduced pressure. The resultant oil was azeotroped thrice with 1 mL toluene, after which was added 1 mL methanol and $K_2CO_3$ (38 mg, 0.28 mmol). After stirring for 16 h, the reaction was filtered and concentrated under reduced pressure and then purified by reverse phase preparative HPLC utilizing a 25-75% gradient of acetonitrile:water containing 0.1% trifluoroacetic acid. The purified fractions were combined and lyophilized to afford 5.8 mg of 2-amino-N-(5-aminopentyl)-8-(3-((3-(hydroxymethyl)azetidin-1-yl)sulfonyl)phenyl)-N-propyl-3H-benzo[b]azepine-4-carboxamide, Bz-20 in 24% yield. LC/MS [M+H] 554.28 (calculated); LC/MS [M+H] 554.47 (observed).

Example 17: Synthesis of Bz-21

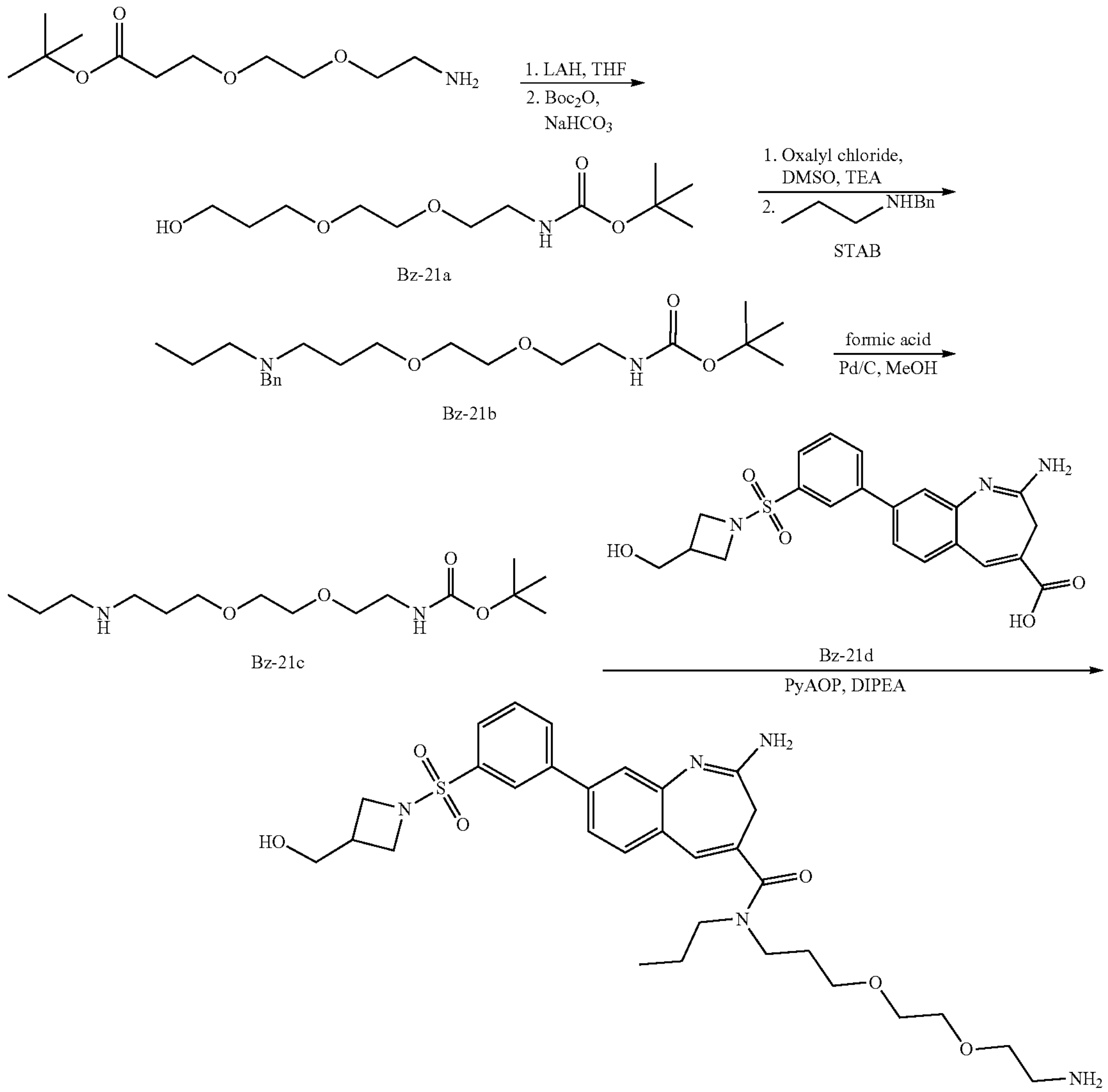

Preparation of tert-butyl (2-(2-(3-hydroxypropoxy) ethoxy)ethyl)carbamate, Bz-21a. tert-butyl 3-(2-(2-amino-ethoxy)ethoxy)propanoate (0.5 g, 2.1 mmol, 1 eq) was dissolved in THF. Lithium aluminum hydride (0.244 g, 6.4 mmol, 3 eq) was added, and the reaction heated to 60° C. Upon complete ester reduction, the reaction was cooled on ice and saturated aqueous sodium bicarbonate was added. The mixture was stirred for 10 minutes, and then Di-tert-butyl dicarbonate (0.49 ml, 2.1 mmol, 1 eq) added. The reaction was stirred at room temperature, and then concentrated to remove THE before HPLC purification to give Bz-21a (0.205 g, 0.78 mmol, 36%). LC/MS [M+H] 264.18 (calculated); LC/MS [M+H]264.27 (observed).

Preparation of tert-butyl (2-(2-(3-(benzyl(propyl)amino) propoxy)ethoxy)ethyl)carbamate, Bz-21b. Oxalyl chloride (0.205 ml, 2.4 mmol, 3 eq) was dissolved in 0.5 ml DCM at −78° C. DMSO (0.34 ml, 4.8 mmol, 6 eq) was added dropwise. The reaction was stirred at −78° C. for 15 minutes, then Bz-21a (0.21 g, 0.80 mmol, 1 eq) added dropwise as a solution in 0.5 ml DCM. The reaction was stirred 30 minutes at −78° C., and then triethylamine (1 ml, 7.2 mmol, 9 eq) was added dropwise. The reaction was stirred 30 more minutes at −78° C., then removed from cooling and allowed to warm to ambient temperature over 30 minutes. N-Benzylpropan-1-amine (0.119 g, 0.80 mmol, 1 eq) and sodium triacetoxyborohydride, STAB (0.845 g, 4.0 mmol, 5 eq) were suspended in 2 ml DCM. The crude aldehyde solution was added to the stirring amine solution. After 30 minutes, the reaction was added to a separatory funnel and washed with saturated $NaHCO_3$, water, and then brine. The organic fraction was dried over sodium sulfate, filtered, concentrated, and then purified by RP-HPLC to give Bz-21b (0.228 g, 0.58 mmol, 73%). LC/MS [M+H] 395.29 (calculated); LC/MS [M+H] 395.44 (observed).

Preparation of tert-butyl (2-(2-(3-(propylamino)propoxy) ethoxy)ethyl)carbamate, Bz-21c. Bz-21b (0.228 g, 0.58 mmol, 1 eq) was dissolved in methanol. Formic acid (0.033 mol, 0.87 mmol, 1.5 eq) was added, followed by 10 wt % Pd/C (0.02 g). The reaction was stirred at 60° C. and then filtered, concentrated, and purified by HPLC to give Bz-21c as a TFA salt (0.193 g, 0.46 mmol, 80%). LC/MS [M+H] 305.24 (calculated); LC/MS [M+H]305.38 (observed).

Preparation of Bz-21. 2-Amino-8-(3-((3-(hydroxymethyl) azetidin-1-yl)sulfonyl)phenyl)-3H-benzo[b]azepine-4-carboxylic acid, Bz-21d (0.042 g, 0.099 mmol, 1 eq), Bz-21c (0.03 g, 0.099 mmol, 1 eq), and diisopropylethylamine (0.1 ml, 0.57 mmol, 5.8 eq) were dissolved in DMF. 7-Azabenzotriazol-1-yloxy-tripyrrolidino-phosphonium hexafluorophosphate, PyAOP, CAS Reg. No. 156311-83-0 (0.077 g, 0.15 mmol, 1.5 eq) was added and the mixture stirred at room temperature. When complete, the reaction mixture was concentrated and purified by HPLC. The isolated product was concentrated, dissolved in minimal TFA, and allowed to stand at room temperature for 15 minutes. The solution was then concentrated and purified by HPLC to give an oil that was triturated with diethyl ether to give 2-amino-N-(3-(2-(2-aminoethoxy)ethoxy)propyl)-8-(3-((3-(hydroxymethyl) azetidin-1-yl)sulfonyl)phenyl)-N-propyl-3H-benzo[b] azepine-4-carboxamide, Bz-21 as a white solid (0.037 g, 0.060 mmol, 61%). LC/MS [M+H] 614.30 (calculated); LC/MS [M+H] 614.58 (observed).

Example 18: Synthesis of Bz-22

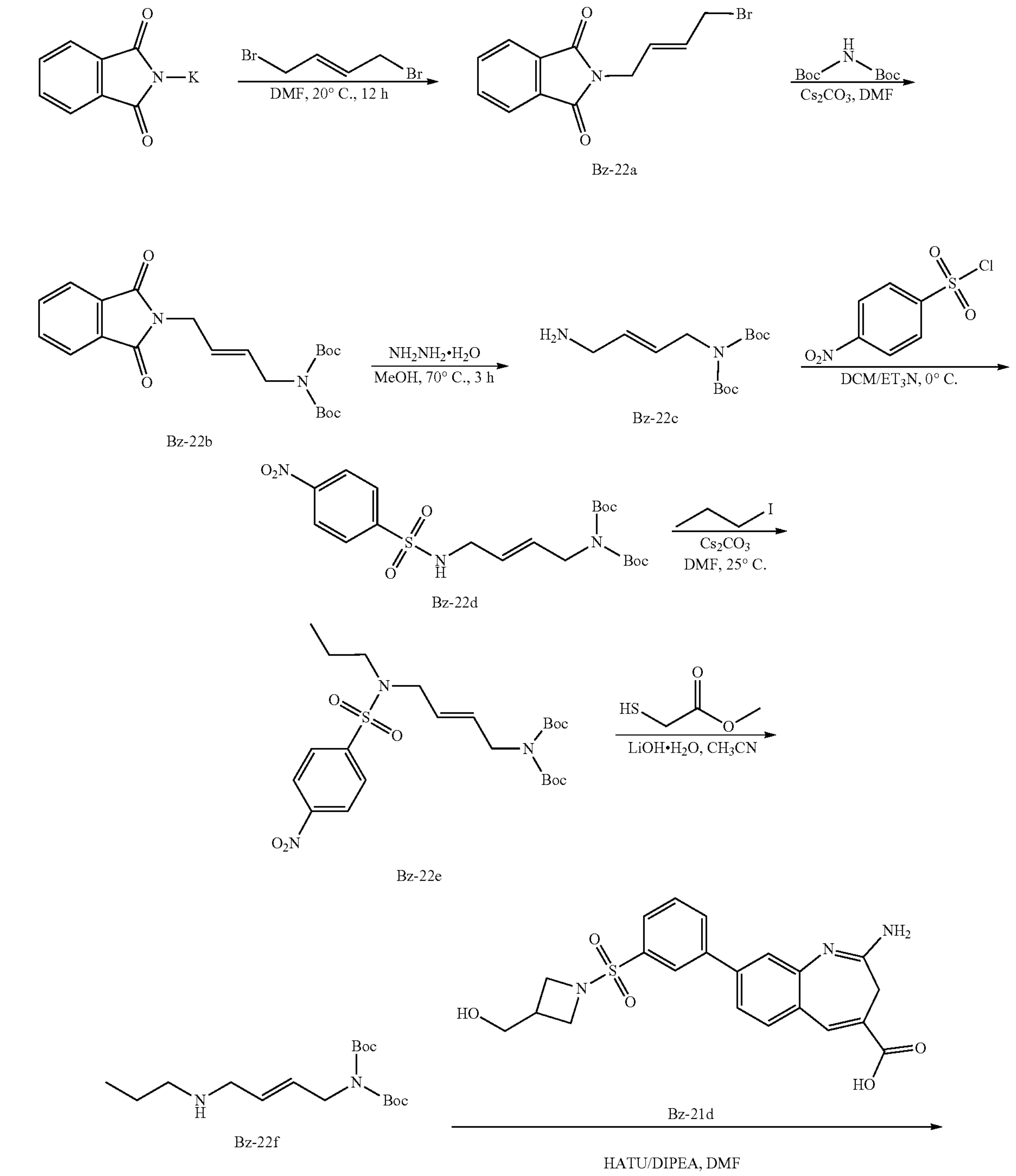

Bz-22a
Bz-22b
Bz-22c
Bz-22d
Bz-22e
Bz-22f
Bz-21d

-continued

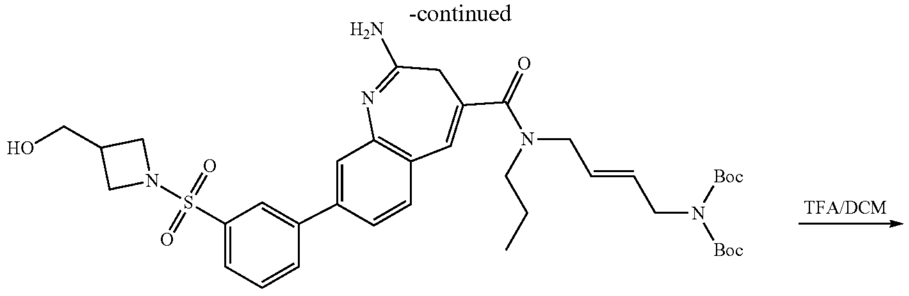

Bz-22g

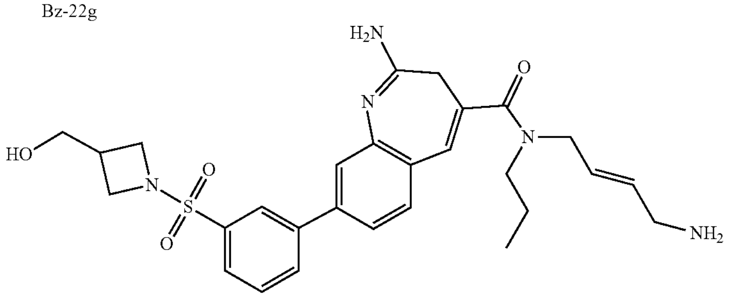

Bz-22

Preparation of (E)-2-(4-bromobut-2-en-1-yl)isoindoline-1,3-dione, Bz-22a. To a solution of (1,3-dioxoisoindolin-2-yl)potassium (7.5 g, 40.5 mmol, 1 eq) in DMF (100 mL) was added (E)-1,4-dibromobut-2-ene (17.3 g, 80.9 mmol, 2 eq). The mixture was stirred at 20° C. for 12 h and then diluted with water (200 mL) and extracted with EtOAc (80 mL×3). The organic layer was washed with brine (50 mL), dried over $Na_2SO_4$, filtered and concentrated. The residue was purified by flash silica gel chromatography (ISCO™; 12 g SEPAFLASH™ Silica Flash Column, eluent of 0-60% ethyl acetate/petroleum ether gradient at 60 mL/min) to give Bz-22a (8.6 g, 30.7 mmol, 75.82% yield) as white solid. $^1$H NMR ($CDCl_3$, 400 MHz) δ 7.90-7.83 (m, 2H), 7.78-7.70 (m, 2H), 6.01-5.90 (m, 1H), 5.89-5.79 (m, 1H), 4.32 (d, J=5.6 Hz, 2H), 3.92 (d, J=7.2 Hz, 2H).

Preparation of tert-butyl N-tert-butoxycarbonyl-N-[(E)-4-(1,3-dioxoisoindolin-2-yl)but-2-enyl]carbamate, Bz-22b. To a solution of Bz-22a (11 g, 39.3 mmol, 1 eq) in DMF (200 mL) was added $Cs_2CO_3$ (19.2 g, 58.9 mmol, 1.5 eq) and tert-butyl N-tert-butoxycarbonylcarbamate (11.1 g, 51.1 mmol, 1.3 eq). The mixture was stirred at 20° C. for 12 h and then diluted with water (400 mL) and extracted with EtOAc (100 mL×3). The organic layer was washed with brine (80 mL×3), dried over $Na_2SO_4$, filtered and concentrated. The residue was purified by flash silica gel chromatography (ISCO™; 5 g SEPAFLASH™ Silica Flash Column, eluent of 0~$_{70}$% ethyl acetate/petroleum ether gradient at 65 mL/min) to give Bz-22b (16 g, 38.4 mmol, 97.83% yield) as white solid. $^1$H NMR (DMSO-$d_6$, 400 MHz) δ 7.90-7.83 (m, 4H), 5.63-5.53 (m, 2H), 4.20-4.12 (m, 2H), 4.05-3.99 (m, 2H), 1.36 (s, 18H).

Preparation of tert-butyl N-[(E)-4-aminobut-2-enyl]-N-tert-butoxycarbonyl-carbamate, Bz-22c. To a solution of Bz-22b (18 g, 43.2 mmol, 1 eq) in MeOH (200 mL) was added hydrazine; hydrate (10.2 g, 173 mmol, 9.90 mL 85% purity, 4 eq) at 20° C. and then stirred at 70° C. for 3 h. The mixture was filtered, and the filtrate was concentrated. The crude product was triturated with $CH_3CN$ at 20° C. for 20 min and filtered, the filtrate was concentrated to give Bz-22c (10 g, 34.9 mmol, 80.80% yield) as light yellow oil. $^1$H NMR ($CDCl_3$, 400 MHz) δ 5.78-5.69 (m, 1H), 5.64-5.54 (m, 1H), 4.17-4.09 (m, 2H), 3.31-3.23 (m, 2H), 1.49 (s, 18H).

Preparation of tert-butyl N-tert-butoxycarbonyl-N-[(E)-4-[(4-nitrophenyl)sulfonylamino]but-2-enyl]carbamate, Bz-22d. To a solution of Bz-22c (1 g, 3.49 mmol, 1 eq) in DCM (10 mL) was added TEA (706.72 mg, 6.98 mmol, 972.10 μL (microliters), 2 eq) and 4-nitrobenzenesulfonyl chloride (851.29 mg, 3.84 mmol, 1.1 eq) at 0° C. under $N_2$. The mixture was stirred at 25° C. for 1 h and then quenched by addition of $H_2O$ (20 mL) at 0° C., and then extracted with EtOAc (10 mL×3). The combined organic layers were washed with brine (5 mL), dried over $Na_2SO_4$, filtered and concentrated under reduced pressure to give a residue which was purified by column chromatography ($SiO_2$, petroleum ether/ethyl acetate=1/0 to 1/1) to give Bz-22d (1.2 g, 2.54 mmol, 72.74% yield) as a light yellow oil. $^1$H NMR ($CDCl_3$, 400 MHz) δ 8.41-8.35 (m, 2H), 8.05 (d, J=9.2 Hz, 2H), 5.71-5.61 (m, 1H), 5.57-5.47 (m, 1H), 4.61 (t, J=5.6 Hz, 1H), 4.10 (d, J=5.6 Hz, 2H), 3.67 (t, J=6.0 Hz, 2H), 1.49 (s, 18H).

Preparation of tert-butyl N-tert-butoxycarbonyl-N-[(E)-4-[(4-nitrophenyl)sulfonyl-propyl-amino]but-2-enyl]carbamate, Bz-22e. To a solution of Bz-22d (1 g, 2.12 mmol, 1 eq) in DMF (10 mL) was added $Cs_2CO_3$ (1.38 g, 4.24 mmol, 2 eq) and 1-iodopropane (360.52 mg, 2.12 mmol, 207.19 μL, 1 eq) at 25° C. and then stirred at this temperature for 12 h. The reaction mixture was quenched by addition of $H_2O$ (50 mL) at 0° C., and then extracted with EtOAc (30 mL×3). The combined organic layers were washed with brine (10 mL×3), dried over $Na_2SO_4$, filtered and concentrated under reduced pressure. The residue was purified by column chromatography ($SiO_2$, petroleum ether/ethyl acetate=1/0 to 3/1) to give Bz-22e (0.89 g, 1.73 mmol, 81.71% yield) as a light yellow oil. $^1$H NMR ($CDCl_3$, 400 MHz) δ 8.36 (d, J=8.8 Hz, 2H), 7.99 (d, J=8.8 Hz, 2H), 5.74-5.60 (m, 1H), 5.51-5.37 (m, 1H), 4.11 (d, J=7.2 Hz, 2H), 3.86 (d, J=6.4 Hz, 2H), 3.16-3.07 (m, 2H), 1.55-1.46 (m, 20H), 0.86 (t, J=7.6 Hz, 3H).

Preparation of tert-butyl N-tert-butoxycarbonyl-N-[(E)-4-(propylamino)but-2-enyl] carbamate, Bz-22f. To a solution of Bz-22e (0.79 g, 1.54 mmol, 1 eq) in $CH_3CN$ (10 mL) was added $LiOH \cdot H_2O$ (387.25 mg, 9.23 mmol, 6 eq) and methyl 2-sulfanylacetate (490 mg, 4.61 mmol, 419 μL, 3 eq) at 0° C. The resulting mixture was stirred at 25° C. for 12 h and then filtered and concentrated under reduced pressure. The residue was diluted with $H_2O$ (20 mL) at 0° C., and then adjusted pH=2-3 with 1 M HCl and extracted with MTBE (10 mL×3). The pH of water phase was adjusted to ~10 with aq. $K_2CO_3$ and extracted with (10 mL×3). The combined organic layers were dried over $Na_2SO_4$, filtered and concentrated under reduced pressure to give Bz-22f (0.35 g, 1.07 mmol, 69.28% yield) as a colorless oil. $^1H$ NMR ($CDCl_3$, 400 MHz) δ 5.79-5.58 (m, 2H), 4.15 (d, J=5.2 Hz, 2H), 3.23 (d, J=5.6 Hz, 2H), 2.56 (t, J=6.8 Hz, 2H), 1.56-1.42 (m, 20H), 0.92 (t, J=7.6 Hz, 3H).

Preparation of tert-butyl N-[(E)-4-[[2-amino-8-[3-[3-(hydroxymethyl)azetidin-1-yl]sulfonylphenyl]-3H-1-benzazepine-4-carbonyl]-propyl-amino]but-2-enyl]-N-tert-butoxycarbonyl-carbamate, Bz-22g. To a mixture of 2-amino-8-(3-((3-(hydroxymethyl)azetidin-1-yl)sulfonyl)phenyl)-3H-benzo[b]azepine-4-carboxylic acid, Bz-21d (0.45 g, 1.05 mmol, 1 eq) in DMF (5 mL) was added HATU (440 mg, 1.16 mmol, 1.1 eq) and DIPEA (408 mg, 3.16 mmol, 550 μL, 3 eq) at 25° C. After 10 min, Bz-22f (345.75 mg, 1.05 mmol, 1 eq) was added to the mixture at 25° C. and then stirred at this temperature for 1 h. The reaction mixture was poured into ice water (30 mL) at 0° C., and extracted with DCM/i-PrOH=3/1 (20 mL×3). The combined organic layers were dried over $Na_2SO_4$, filtered and concentrated under reduced pressure to give Bz-22g (0.41 g, crude) as a brown solid.

Preparation of Bz-22. To a solution of tert-butyl N-[(E)-4-[[2-amino-8-[3-[3-(hydroxymethyl)azetidin-1-yl] sulfonylphenyl]-3H-1-benzazepine-4-carbonyl]-propyl-amino] but-2-enyl]-N-tert-butoxycarbonyl-carbamate (13 mg, 17.6 μmol (micromoles), 1 eq) in DCM (1 mL) was added TFA (154 mg, 1.35 mmol, 0.1 mL, 76.7 eq) at 25° C. and then stirred at this temperature for 1 h. The reaction mixture was concentrated under reduced pressure. The residue was dissolved with $CH_3CN$ (10 mL) and $H_2O$ (1 mL) and adjusted pH=9 with aq. LiOH at 0° C. The mixture was concentrated under reduced pressure. The residue was purified by prep-HPLC (TFA condition; column: Welch Xtimate C18 100×25 mm, 3 μm particle size; mobile phase: [water (0.1% TFA)-ACN]; B %: 5%-35%, 12 min) to give 2-amino-N-[(E)-4-aminobut-2-enyl]-8-[3-[3-(hydroxymethyl)azetidin-1-yl] sulfonylphenyl]-N-propyl-3H-1-benzazepine-4-carboxamide, Bz-22 (7 mg, 10.74 μmol, 60.97% yield, TFA) as a white solid. $^1H$ NMR (MeOD-$d_4$, 400 MHz) δ 8.15-8.04 (m, 2H), 7.91 (d, J=8.0 Hz, 1H), 7.86-7.72 (m, 3H), 7.68 (d, J=8.0 Hz, 1H), 7.13 (s, 1H), 6.07-5.94 (m, 1H), 5.89-5.77 (m, 1H), 4.21 (br s, 2H), 3.87 (t, J=8.4 Hz, 2H), 3.67-3.56 (m, 4H), 3.48 (br s, 2H), 3.45-3.37 (m, 4H), 2.68-2.50 (m, 1H), 1.77-1.61 (m, 2H), 0.95-0.93 (m, 3H). LC/MS [M+H] 538.2 (calculated); LC/MS [M+H] 538.3 (observed).

Example 19: Synthesis of Bz-23

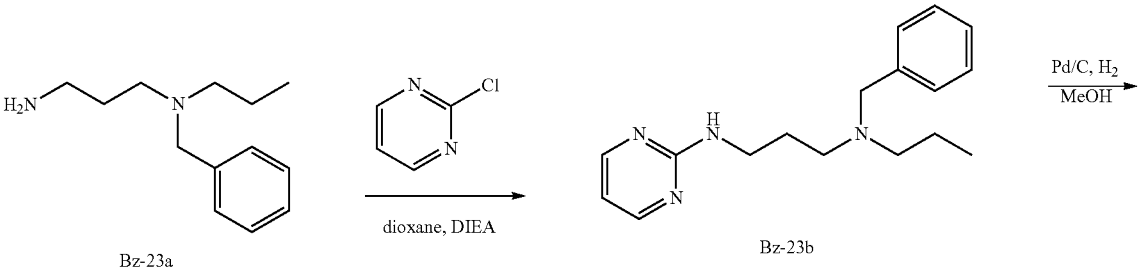

Bz-23a

Bz-23b

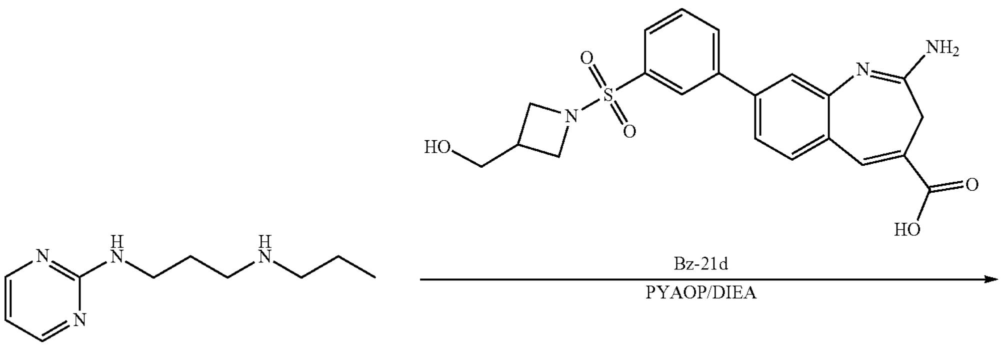

Bz-23c

-continued

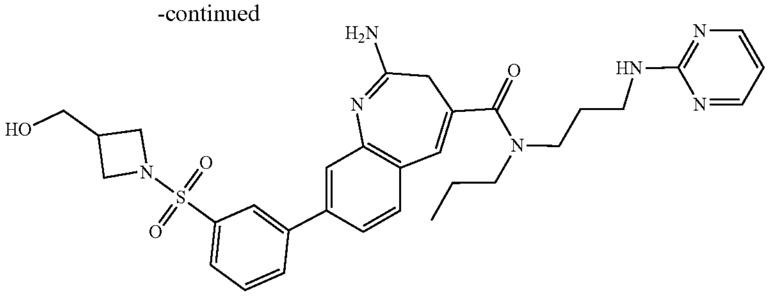

Bz-23

Preparation of N'-benzyl-N'-propyl-N-pyrimidin-2-yl-propane-1,3-diamine, Bz-23b. A mixture of N'-benzyl-N'-propyl-propane-1,3-diamine, Bz-23a (0.2 g, 823.77 μmol, 1 eq, HCl), DIEA (426 mg, 3.30 mmol, 574 μL, 4 eq) in dioxane (4 mL) was stirred at 25° C. for 10 min, and then 2-chloropyrimidine (188.70 mg, 1.65 mmol, 2 eq) was added, then mixture was stirred at 25° C. for 16 h. The reaction was quenched with $H_2O$ (15 mL) and extracted with ethyl acetate (15 mL×3). The combined organic phase was washed with brine (10 mL), dried with anhydrous $Na_2SO_4$, filtered and concentrated in vacuum. The residue was purified by prep-TLC ($SiO_2$, DCM:MeOH=7:1) to give Bz-23b (130 mg, 457 μmol, 55.49% yield) as yellow oil. $^1H$ NMR ($CDCl_3$, 400 MHz) δ 8.26 (d, J=4.8 Hz, 2H), 7.38-7.32 (m, 2H), 7.30 (t, J=7.2 Hz, 2H), 7.26-7.20 (m, 1H), 6.49 (t, J=5.2 Hz, 1H), 5.74 (br s, 1H), 3.58 (s, 2H), 3.47-3.39 (m, 2H), 2.54 (t, J=6.8 Hz, 2H), 2.44-2.38 (m, 2H), 1.77 (quin, J=6.4 Hz, 2H), 1.57-1.50 (m, 2H), 0.88 (t, J=7.2 Hz, 3H).

Preparation of N-propyl-N'-pyrimidin-2-yl-propane-1,3-diamine, Bz-23c. To a solution of Bz-23b (130 mg, 457 μmol, 1 eq) in MeOH (10 mL) was added Pd/C (0.1 g, 10% purity) under $N_2$ atmosphere. The suspension was degassed and purged thrice with hydrogen gas, $H_2$, the mixture was stirred at 25° C. for 16 h and then filtered and concentrated under reduced pressure. The residue was purified by prep-TLC ($SiO_2$, DCM:MeOH=5:1) to give Bz-23c (80 mg, 412 μmol, 90.09% yield) as a brown oil.

Preparation of Bz-23. To a solution of 2-amino-8-[3-[3-(hydroxymethyl)azetidin-1-yl]sulfonylphenyl]-3H-1-benzazepine-4-carboxylic acid, Bz-21d (264 mg, 618 μmol, 1 eq) in DMF (2 mL) was added DIEA (240 mg, 1.85 mmol, 323 μL, 3 eq), 7-Aza-benzotriazol-1-yloxy-tripyrrolidinophosphonium hexafluorophosphate, PYAOP (483 mg, 927 μmol, 1.5 eq) and Bz-23c (120 mg, 618 μmol, 1 eq). The mixture was stirred at 25° C. for 1 h, and then filtered and concentrated under reduced pressure. The residue was purified by prep-HPLC WelchXtimate C18 100×25 mm, 3 μm particle size; mobile phase: [water (0.1% TFA)-ACN]; B %: 15%-35%, 12 min) to give 2-amino-8-[3-[3-(hydroxymethyl)azetidin-1-yl]sulfonylphenyl]-N-propyl-N-[3-(pyrimidin-2-ylamino)propyl]-3H-1-benzazepine-4-carboxamide, Bz-23 (16 mg, 26.5 μmol, 4.29% yield) as a white solid. $^1H$ NMR (MeOD-$d_4$, 400 MHz) δ 8.38 (br s, 1H), 8.15 (s, 1H), 8.11 (s, 1H), 8.08 (d, J=8.4 Hz, 1H), 7.92 (d, J=8.4 Hz, 1H), 7.85-7.79 (m, 1H), 7.75 (br s, 1H), 7.71 (br s, 1H), 7.53 (s, 1H), 7.11 (br s, 1H), 6.74 (br s, 1H), 3.87 (t, J 8.0 Hz, 2H), 3.62 (dd, J=6.0, 8.0 Hz, 4H), 3.54-3.49 (m, 2H), 3.42 (d, J=6.8 Hz, 2H), 3.35 (br s, 2H), 2.64-2.51 (m, 1H), 2.08-1.95 (m, 2H), 1.77-1.66 (m, 2H), 0.99-0.94 (m, 3H). LC/MS [M+H] 604.3 (calculated); LC/MS [M+H] 604.3 (observed).

Example 20: Synthesis of Bz-24

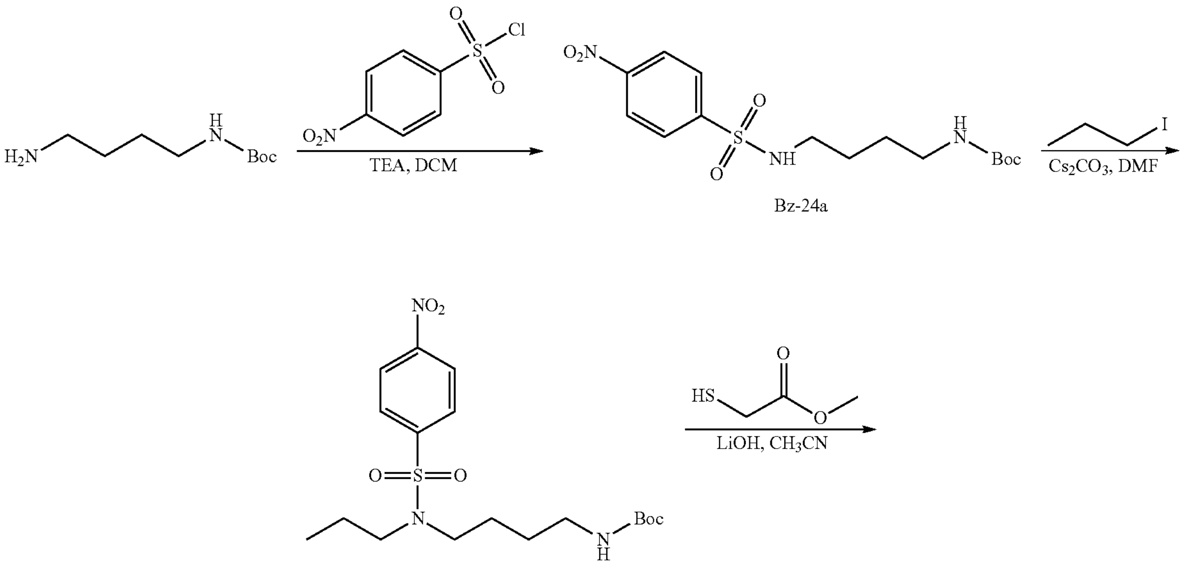

Bz-24a

Bz-24b

-continued

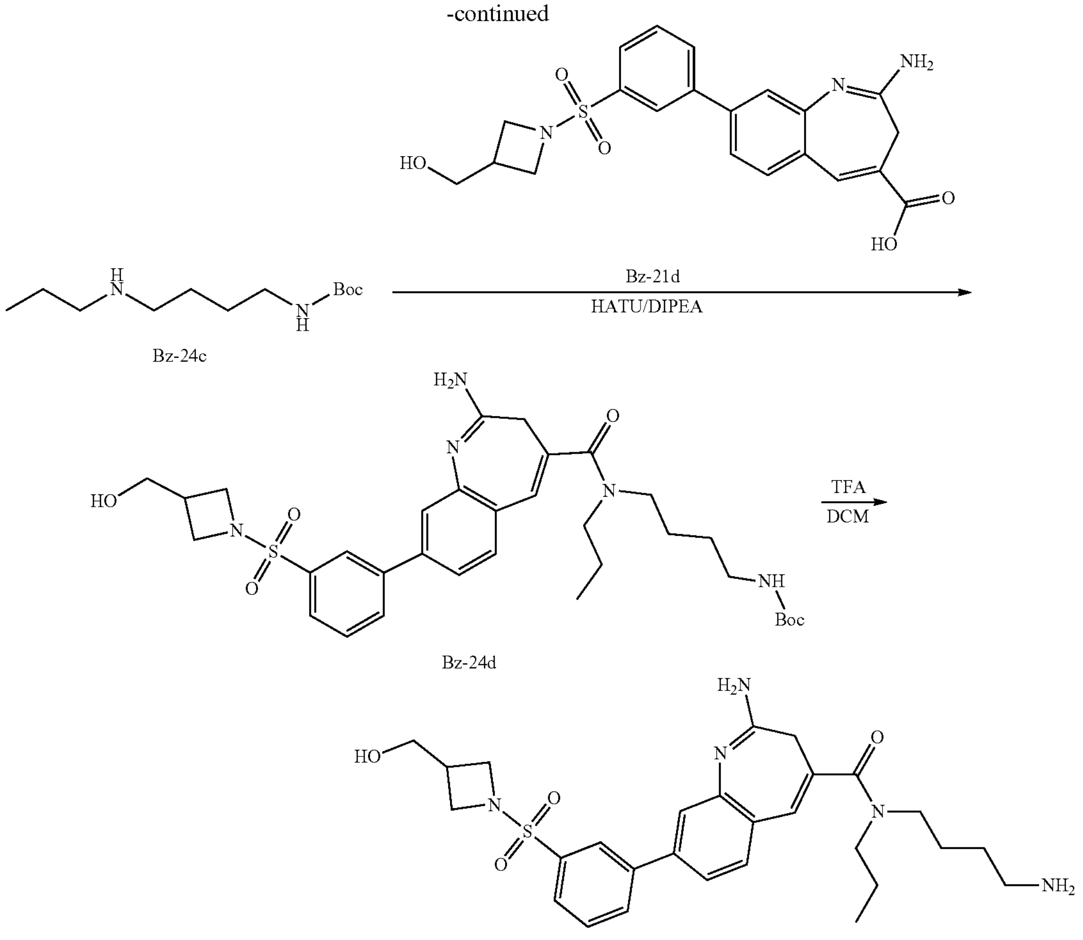

Bz-24c

Bz-24d

Bz-24

Preparation of tert-butyl N-[4-[(4-nitrophenyl)sulfonylamino]butyl]carbamate, Bz-24a. To a solution of tert-butyl N-(4-aminobutyl)carbamate (0.5 g, 2.66 mmol, 1 eq) and $Et_3N$ (537 mg, 5.31 mmol, 739 μL, 2 eq) in DCM (5 mL) was added 4-nitrobenzenesulfonyl chloride (647 mg, 2.92 mmol, 1.1 eq) at 0° C. After addition, the resulting mixture was stirred at 25° C. for 1 h and then quenched by addition of $H_2O$ (20 mL) at 0° C., and then extracted with DCM (10 mL×3). The combined organic layers were washed with brine (5 mL), dried over $Na_2SO_4$, filtered and concentrated under reduced pressure. The residue was triturated with PE/MTBE=10/1 (20 mL) and stirred for 30 min, filtered and the filter cake was dried under reduced pressure to give Bz-24a (0.99 g, 2.65 mmol, 99.82% yield) as a white solid. $^1$H NMR ($CDCl_3$, 400 MHz) δ 8.37 (d, J=8.8 Hz, 2H), 8.07 (d, J=8.4 Hz, 2H), 5.28 (br s, 1H), 4.59 (br s, 1H), 3.12-3.03 (m, 4H), 1.58-1.48 (m, 4H), 1.44 (s, 9H).

Preparation of tert-butyl N-[4-[(4-nitrophenyl)sulfonyl-propyl-amino]butyl]carbamate, Bz-24b. To a solution of Bz-24a (0.99 g, 2.65 mmol, 1 eq) in DMF (7 mL) was added $Cs_2CO_3$ (1.73 g, 5.30 mmol, 2 eq) and 1-iodopropane (451 mg, 2.65 mmol, 259 μL, 1 eq) at 0° C. The mixture was stirred at 25° C. for 12 h and then poured into ice water (30 mL) at 0° C., and then extracted with EtOAc (20 mL×3). The combined organic layers were washed with brine (10 mL×3), dried over $Na_2SO_4$, filtered and concentrated under reduced pressure. The residue was triturated with PE/MTBE=10/1 (20 mL) and stirred at 25° C. for 30 min, filtered and the filter cake was dried under reduced pressure to give Bz-24b (0.97 g, 2.33 mmol, 88.06% yield) as a light yellow solid. $^1$H NMR (DMSO-$d_6$, 400 MHz) δ 8.39 (d, J=8.8 Hz, 2H), 8.07 (d, J=8.8 Hz, 2H), 6.79 (br t, J=6.0 Hz, 1H), 3.13-3.05 (m, 4H), 2.88 (q, J=6.4 Hz, 2H), 1.54-1.40 (m, 4H), 1.39-1.27 (m, 11H), 0.81 (t, J=7.2 Hz, 3H).

Preparation of tert-butyl N-[4-(propylamino)butyl]carbamate, Bz-24c. To a solution of Bz-24b (0.97 g, 2.33 mmol, 1 eq) in $CH_3CN$ (10 mL) was added $LiOH{\cdot}H_2O$ (587.74 mg, 14.01 mmol, 6 eq) and methyl 2-sulfanylacetate (744 mg, 7.00 mmol, 635 μL, 3 eq) at 0° C. The resulting mixture was stirred at 25° C. for 12 h and then filtered and concentrated under reduced pressure. The residue was diluted with $H_2O$ (20 mL) at 0° C., and then adjusted pH=2-3 with 1 M HCl and extracted with MTBE (10 mL×3). The pH of water phase was adjusted to ~ 10 with aq. $K_2CO_3$ and extracted with EtOAc (10 mL×3). The combined organic layers were dried over $Na_2SO_4$, filtered and concentrated under reduced pressure to give Bz-24c (445 mg, 1.93 mmol, 82.75% yield) as a brown oil. $^1$H NMR (DMSO-$d_6$, 400 MHz) δ 6.81 (br s, 1H), 2.89 (q, J=6.4 Hz, 2H), 2.47-2.39 (m, 4H), 1.44-1.31 (m, 15H), 0.85 (t, J=7.6 Hz, 3H).

Preparation of tert-butyl N-[4-[[2-amino-8-[3-[3-(hydroxymethyl)azetidin-1-yl]sulfonylphenyl]-3H-1-benzazepine-4-carbonyl]-propyl-amino]butyl]carbamate, Bz-24d. To a solution of 2-amino-8-[3-[3-(hydroxymethyl) azetidin-1-yl]sulfonylphenyl]-3H-1-benzazepine-4-carboxylic acid, Bz-21d (100 mg, 234 μmol, 1 eq) and DIPEA (90.7 mg, 702 μmol, 122.24 μL, 3 eq) in DMF (1 mL) was added HATU (97.8 mg, 257 μmol, 1.1 eq) at 25° C. After 10 min, Bz-24c (64.66 mg, 280.72 μmol, 1.2 eq) was added at 25° C. and then stirred at this temperature for 1 h. The reaction mixture was filtered and concentrated under reduced pressure. The residue was purified by prep-HPLC (TFA condition; column: Welch Xtimate C18 100×25 mm, 3 μm particle size; mobile phase: [water (0.1% TFA)-ACN]; B %: 30%-45%, 12 min). Bz-24d (8 mg, 12.50 μmol, 5.35% yield) was obtained as a yellow solid.

$^1$H NMR (MeOD-$d_4$, 400 MHz) δ 8.14-8.04 (m, 2H), 7.92 (d, J=8.0 Hz, 1H), 7.85-7.81 (m, 1H), 7.81-7.76 (m, 1H), 7.73-7.68 (m, 2H), 7.11 (s, 1H), 3.87 (t, J=7.6 Hz, 2H), 3.61 (dd, J=6.0 Hz, 7.6 Hz, 2H), 3.58-3.45 (m, 4H), 3.44-3.35 (m, 4H), 3.12-3.04 (m, 2H), 2.65-2.52 (m, 1H), 1.78-1.63 (m, 4H), 1.55-1.40 (m, 11H), 0.95-0.93 (m, 3H). LC/MS [M+H] 640.3 (calculated); LC/MS [M+H] 640.3 (observed).

Preparation of Bz-24. To a solution of Bz-24d (0.1 g, 156 μmol, 1 eq) in DCM (2 mL) was added TFA (308 mg, 2.70 mmol, 0.2 mL, 17.28 eq) at 25° C. and then stirred at this temperature for 1 h. The reaction mixture was concentrated under reduced pressure. The residue was dissolved with $CH_3CN$ (10 mL) and $H_2O$ (1 mL) and adjusted pH=9 with aq. LiOH at 0° C. The mixture was stirred for 1 h at 25° C. and then filtered and concentrated under reduced pressure. The residue was purified by prep-HPLC (TFA condition; column: Welch Xtimate C18 100×25 mm, 3 μm particle size; mobile phase: [water (0.1% TFA)-ACN]; B %: 5%-30%, 12 min) to give 2-amino-N-(4-aminobutyl)-8-[3-[3-(hydroxymethyl)azetidin-1-yl]sulfonylphenyl]-N-propyl-3H-1-benzazepine-4-carboxamide, Bz-24 (34 mg, 52.01 μmol, 33.28% yield, TFA) as a white solid. $^1$H NMR (MeOD-$d_4$, 400 MHz) δ 8.13-8.05 (m, 2H), 7.90 (d, J=8.0 Hz, 1H), 7.85-7.78 (m, 1H), 7.77-7.72 (m, 2H), 7.71-7.65 (m, 1H), 7.10 (s, 1H), 3.86 (t, J=8.4 Hz, 2H), 3.61 (dd, J=5.6 Hz, 7.6 Hz, 2H), 3.58-3.46 (m, 4H), 3.44-3.36 (m, 4H), 3.05-2.94 (m, 2H), 2.64-2.52 (m, 1H), 1.84-1.62 (m, 6H), 1.03-0.85 (m, 3H). LC/MS [M+H] 540.3 (calculated); LC/MS [M+H] 540.3 (observed).

Example 21: Synthesis of B7-25

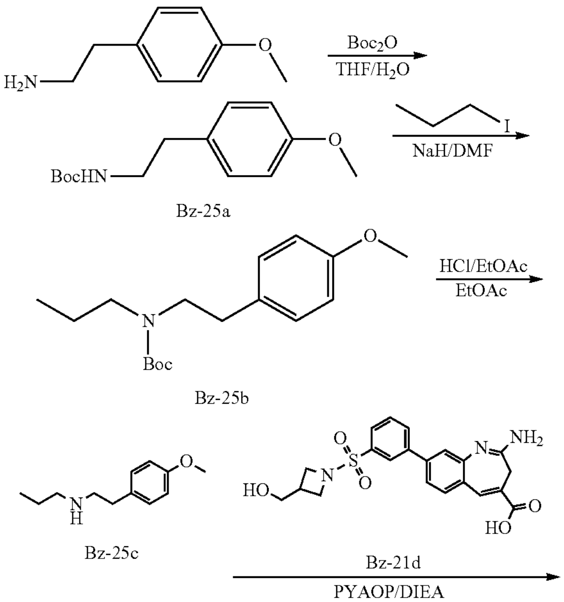

Bz-25a

Bz-25b

Bz-25c

Bz-21d

-continued

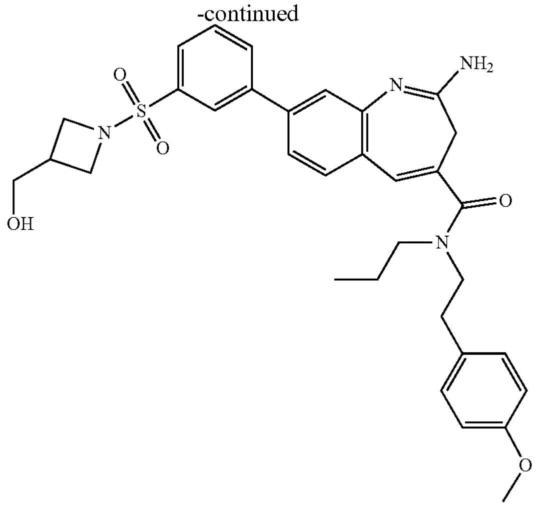

Bz-25

Preparation of tert-butyl N-[2-(4-methoxyphenyl)ethyl]carbamate, Bz-25a. To a mixture of 2-(4-methoxyphenyl)ethanamine (1 g, 6.61 mmol, 970.87 μL, 1 eq) in THE and $H_2O$ (10 mL) was added $Boc_2O$ (2.17 g, 9.92 mmol, 2.28 mL, 1.5 eq) and then stirred at 25° C. for 30 min under $N_2$ atmosphere. The mixture was diluted with water and extracted with EtOAc (50 ml×3). The organic layer was washed with brine, dried over $Na_2SO_4$, filtered and concentrated. The residue was purified by silica gel chromatography (column height: 250 mm, diameter: 100 mm, 100-200 mesh silica gel, petroleum ether/ethyl acetate=5/1-1/1) to give Bz-25a (1.60 g, 6.37 mmol, 96.26% yield) as a white solid. $^1$H NMR ($CDCl_3$, 400 MHz) δ7.12 (d, J=8.4 Hz, 2H), 6.85 (d, J=8.4 Hz, 2H), 4.53 (br s, 1H), 3.80 (s, 3H), 3.37-3.33 (m, 2H), 2.74 (br t, J=6.4 Hz, 2H), 1.44 (s, 9H).

Preparation of tert-butyl 4-methoxyphenethyl(propyl)carbamate, Bz-25b. To a mixture of Bz-25a (0.8 g, 3.18 mmol, 1 eq) and 1-iodopropane (1.08 g, 6.37 mmol, 621 μL, 2 eq) in DMF (8 mL) was added NaH (191 mg, 4.77 mmol, 60% purity, 1.5 eq) at 0° C., and then stirred at 25° C. for 2 h. The mixture was poured into water (20 mL). The aqueous phase was extracted with ethyl acetate (15 mL×3). The combined organic phase was washed with brine (10 mL), dried with anhydrous $Na_2SO_4$, filtered and concentrated under reduced pressure to give a residue. The residue was purified by silica gel chromatography (column height: 250 mm, diameter: 100 mm, 100-200 mesh silica gel, petroleum ether/ethyl acetate=5/1,1/1) to afford Bz-25b (365 mg, 1.24 mmol, 39.08% yield) as white solid. $^1$H NMR ($CDCl_3$, 400 MHz) δ 7.11 (d, J=8.4 Hz, 2H), 6.84 (d, J=8.4 Hz, 2H), 3.79 (s, 3H), 3.36-3.30 (m, 2H), 3.15-3.09 (m, 2H), 2.79-2.71 (m, 2H), 1.57-1.50 (m, 2H), 1.46 (s, 9H), 0.87 (t, J=7.6 Hz, 3H).

Preparation of N-[2-(4-methoxyphenyl)ethyl]propan-1-amine, Bz-25c. To a solution of Bz-25b (365 mg, 1.24 mmol, 1 eq) in EtOAc (5 mL) was added HCl/EtOAc (5 mL). The mixture was stirred at 25° C. for 3 h and then concentrated in vacuum to give Bz-25c.

Preparation of Bz-25. To a solution of 2-amino-8-[3-[3-(hydroxymethyl)azetidin-1-yl]sulfonylphenyl]-3H-1-benzazepine-4-carboxylic acid, Bz-21d (186 mg, 435 μmol, 1 eq) in DMF (1.00 mL) was added PYAOP (340 mg, 653 μmol, 1.5 eq) and DIEA (393 mg, 3.05 mmol, 531 μL, 7 eq), and then Bz-25c (100 mg, 435 μmol, 1 eq, HCl) was added. The mixture was stirred at 25° C. for 3 h, and then filtered and concentrated. The residue was purified by pre-HPLC (column: Nano-micro KROMASIL™ C18 100×30 mm, 8 m particle size; mobile phase: [water (0.1% TFA)-ACN]; B %: 25%-55%, 10 min]) to give 2-amino-8-[3-[3-(hydroxymethyl)azetidin-1-yl]sulfonylphenyl]-N-[2-(4-methoxyphenyl)ethyl]-N-propyl-3H-1-benzazepine-4-carboxamide, Bz-25 (14 mg, 23.23 μmol, 5.34% yield) as a light yellow solid. $^1$H NMR (MeOD-$d_4$, 400 MHz) δ 8.13-8.03 (m, 2H), 7.93-7.87 (m, 1H), 7.84-7.80 (m, 1H), 7.79-7.74 (m, 1H), 7.69 (br s, 1H), 7.60 (br d, J=8.0 Hz, 1H), 7.08-6.51 (m, 5H), 3.86 (t, J=8.4 Hz, 2H), 3.75 (s, 4H), 3.61 (dd, J=5.8, 8.1 Hz, 2H), 3.56-3.45 (m, 1H), 3.54-3.49 (m, 1H), 3.42 (d, J=6.2 Hz, 2H), 2.93-2.87 (m, 2H), 2.65-2.47 (m, 1H), 1.75-1.68 (m, 2H), 1.03-0.94 (m, 3H). LC/MS [M+H] 603.3 (calculated); LC/MS [M+H] 603.3 (observed).

Example 22: Synthesis of Bz-26

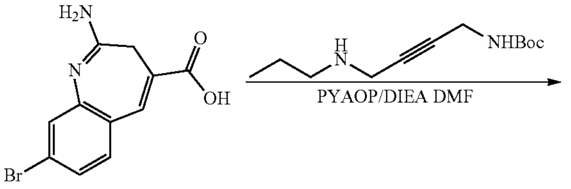

Bz-26a

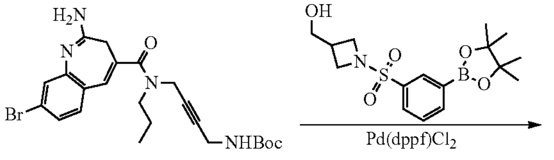

Bz-26b

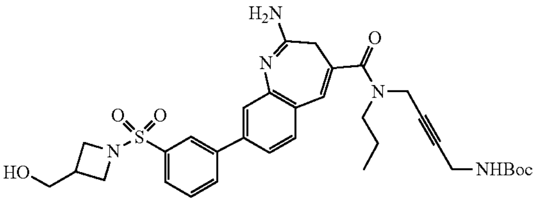

Bz-26

Preparation of Bz-26b. To a mixture of 2-amino-8-bromo-3H-1-benzazepine-4-carboxylic acid, Bz-26a (0.5 g, 1.78 mmol, 1.0 eq), PYAOP (1.02 g, 1.96 mmol, 1.1 eq) and DIEA (920 mg, 7.11 mmol, 1.24 mL, 4.0 eq) in DMF (8 mL) was added tert-butyl N-[4-(propylamino)but-2-ynyl]carbamate (400 mg, 1.78 mmol, 1.0 eq) at 25° C. and then stirred for 0.5 hours at this temperature. The mixture was poured into water (40 mL). The aqueous phase was extracted with ethyl acetate (30 mL×3). The combined organic phase was washed with brine (30 mL), dried with anhydrous $Na_2SO_4$, filtered and concentrated in vacuum. The residue was purified by silica gel chromatography (column height: 250 mm, diameter: 100 mm, 100-200 mesh silica gel, petroleum ether/ethyl acetate=1/1, 0/1) to give tert-butyl N-[4-[(2-amino-8-bromo-3H-1-benzazepine-4-carbonyl)-propyl-amino]but-2-ynyl]carbamate, Bz-26b (0.5 g, 1.02 mmol, 57.4% yield) as light yellow solid. $^1$H NMR ($CDCl_3$, 400 MHz) δ 7.52 (s, 1H), 7.39 (s, 2H), 7.07 (br s, 1H), 4.37 (s, 2H), 4.06 (d, J=5.2 Hz, 2H), 3.65 (s, 2H), 2.91 (s, 2H), 1.88-1.74 (m, 2H), 1.57 (s, 9H), 1.06 (t, J=7.2 Hz, 3H).

Preparation of Bz-26. To a mixture of [1-[3-(4,4,5,5-tetramethyl-1,3,2-dioxaborolan-2-yl)phenyl] sulfonylazetidin-3-yl]methanol (1.73 g, 4.90 mmol, 1.2 eq), Bz-26b (2.0 g, 4.09 mmol, 1.0 eq) and Pd(dppf)$Cl_2$ (150 mg, 204 μmol, 0.05 eq) in dioxane (40 mL) was added $K_2CO_3$ (1.13 g, 8.17 mmol, 2 eq) in $H_2O$ (5 mL) at 25° C. under $N_2$ and then stirred at 100° C. for 1 hour. The mixture was filtered and concentrated in vacuum. The residue was purified by silica gel chromatography (column height: 250 mm, diameter: 100 mm, 100-200 mesh silica gel, petroleum ether/ethyl acetate=1/1, 0/1) to afford tert-butyl N-[4-[[2-amino-8-[3-[3-(hydroxymethyl)azetidin-1-yl]sulfonylphenyl]-3H-1-benzazepine-4-carbonyl]-propyl-amino]but-2-ynyl]carbamate, Bz-26 (2.0 g, 3.15 mmol, 76.9% yield) as light yellow solid. $^1$H NMR (MeOD, 400 MHz) δ 8.07 (s, 1H), 8.04 (br d, J=7.6 Hz, 1H), 7.88-7.82 (m, 1H), 7.79-7.73 (m, 1H), 7.53-7.46 (m, 2H), 7.43-7.37 (m, 1H), 7.12 (s, 1H), 4.29 (s, 2H), 3.93-3.82 (m, 4H), 3.62-3.50 (m, 4H), 3.42 (d, J=6.4 Hz, 2H), 3.31 (s, 2H), 2.64-2.52 (m, 1H), 1.76-1.70 (m, 2H), 1.43 (s, 9H), 0.99-0.91 (m, 3H). LC/MS [M+H] 636.3 (calculated); LC/MS [M+H] 636.3 (observed). LCMS (ESI): mass calcd. for $C_{33}H_{41}N_5O_6S$ 635.28. m/z found 636.3[M+H]$^+$.

Example 23: Synthesis of Bz-27

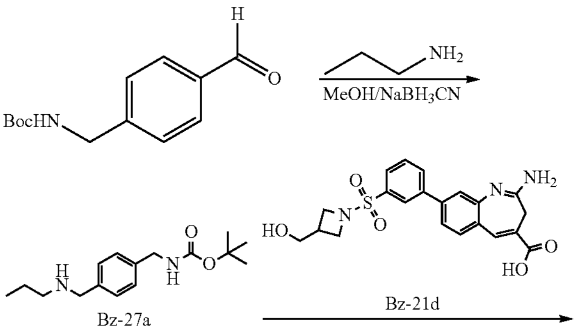

Bz-27a

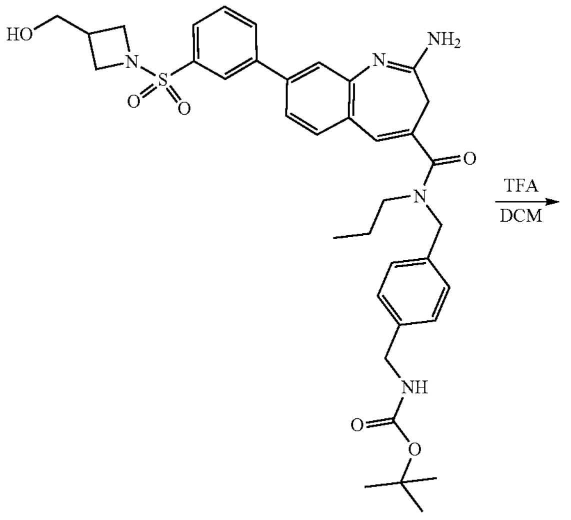

Bz-27b

-continued

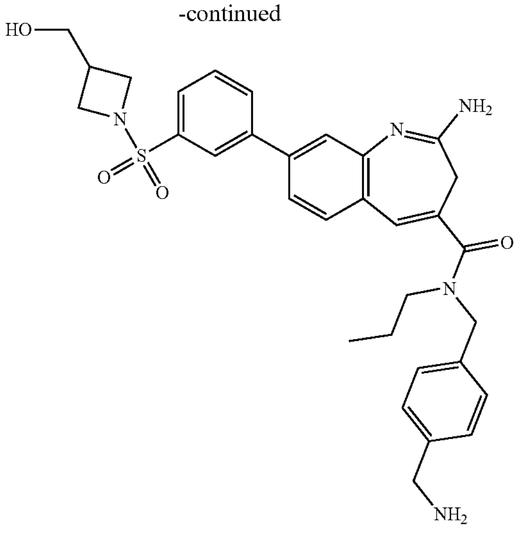

Bz-27

Preparation of Bz-27a. To a solution of tert-butyl N-[(4-formylphenyl)methyl]carbamate (400 mg, 1.70 mmol, 1 eq), propan-1-amine (1.00 g, 17.0 mmol, 1.40 mL, 10 eq) and AcOH (10 mg, 170 μmol, 9.72 μL, 0.1 eq) in MeOH (1 mL) was added $NaBH_3CN$ (213 mg, 3.40 mmol, 2 eq), the mixture was stirred at 25° C. for 3 h. The reaction mixture was poured into water (10 mL), and then extracted with EtOAc (5 mL×3). The combined organic layers were washed with brine (5 mL×1), dried over, filtered and concentrated under reduced pressure to give a residue. The residue was purified by prep-TLC ($SiO_2$, EtOAC:MeOH=5:1) to give tert-butyl-N-[[4-(propylaminomethyl)phenyl]methyl]carbamate, Bz-27a (200 mg, 718 μmol, 42.26% yield) as colorless oil. $^1$H NMR (MeOD-$d_4$, 400 MHz) δ 7.43 (d, J=8.0 Hz, 2H), 7.37 (d, J=8.0 Hz, 2H), 4.24 (s, 2H), 4.17 (s, 2H), 3.00-2.96 (m, 2H), 1.77-1.67 (m, 2H), 1.44 (s, 9H), 1.01 (t, J=7.6 Hz, 3H).

Preparation of Bz-27b. To a solution of 2-amino-8-[3-[3-(hydroxymethyl)azetidin-1-yl]sulfonylphenyl]-3H-1-benzazepine-4-carboxylic acid, Bz-21d (122 mg, 287 μmol, 1 eq) in DMF (0.80 mL) was added PYAOP (224 mg, 431.05 μmol, 1.5 eq) and DIEA (111 mg, 862.10 μmol, 150.16 μL, 3 eq). And then the tert-butyl N-[[4-(propylaminomethyl)phenyl]methyl]carbamate (80 mg, 287 μmol, 1 eq) was added. The mixture was stirred at 25° C. for 3 h, which was filtered and concentrated. The residue was purified by prep-HPLC (column: Welch Xtimate C18 100×25 mm, 3 μm particle size; mobile phase: [water (0.1% TFA)-ACN]; B %: 30%-50%, 12 min]). Compound tert-butylN-[[4-[[[2-amino-8-[3-[3-(hydroxymethyl)azetidin-1-yl]sulfonylphenyl]-3H-1-benzazepine-4-carbonyl]-propyl-amino]methyl]phenyl]methyl]carbamate (27 mg, 39.3 μmol, 13.66% yield) was obtained as a light yellow solid. $^1$H NMR (MeOD-$d_4$, 400 MHz) δ 8.08 (t, J=9.6 Hz, 2H), 7.92-7.90 (m, 1H), 7.82 (t, J=8.4 Hz, 1H), 7.81-7.79 (m, 1H), 7.69-7.64 (m, 4H), 7.57 (s, 1H), 7.30-7.29 (m, 4H), 7.13 (s, 1H), 4.23 (s, 2H), 3.87 (t, J=8.4 Hz, 2H), 3.61 (t, J=6.0 Hz, 2H), 3.42-3.41 (m, 2H), 3.31 (t, J=1.6 Hz, 2H), 2.60-2.55 (m, 1H), 1.71-1.70 (m, 2H), 1.44 (s, 9H), 0.99-0.90 (m, 3H). LC/MS [M+H] 688.3 (calculated); LC/MS [M+H] 688.3 (observed).

Preparation of Bz-27. To a solution of Bz-27b (50 mg, 72.7 μmol, 1 eq) in DCM (1 mL) was added TFA (165 mg, 1.45 mmol, 108 μL, 20 eq), and then stirred at 25° C. for 2 h. The mixture was filtered and concentrated. The residue was purified by prep-HPLC (column: Nano-micro KROMASIL™ C18 100×30 mm, 8 m particle size; mobile phase: [water (0.1% TFA)-CAN]; B %: 5%-30%, 10 min]) to give 2-amino-N-[[4-(aminomethyl)phenyl]methyl]-8-[3-[3-(hydroxymethyl)azetidin-1-yl]sulfonylphenyl]-N-propyl-3H-1-benzazepine-4-carboxamide, Bz-27 (4 mg, 6.81 μmol, 9.36% yield) as a white solid. $^1$H NMR (MeOH-$d_4$, 400 MHz) δ 8.13-8.03 (m, 2H), 7.91 (d, J=8.0 Hz, 1H), 7.85-7.78 (m, 1H), 7.75-7.70 (m, 2H), 7.59-7.33 (m, 5H), 7.15 (s, 1H), 4.13 (s, 2H), 3.86 (t, J=8.4 Hz, 2H), 3.61 (dd, J=6.1, 7.8 Hz, 2H), 3.48 (br d, J=7.6 Hz, 2H), 3.42 (d, J=6.2 Hz, 4H), 3.32 (br s, 1H), 3.31-3.31 (m, 1H), 3.31-3.30 (m, 2H), 2.63-2.52 (m, 1H), 1.76-1.61 (m, 2H), 0.91 (br s, 3H). LC/MS [M+H] 588.3 (calculated); LC/MS [M+H] 588.3 (observed).

Example 24: Synthesis of Bz-28

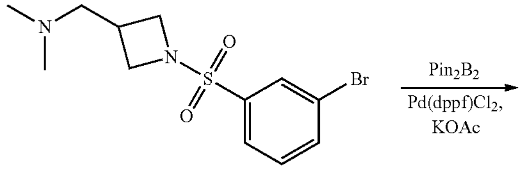

Bz-28a

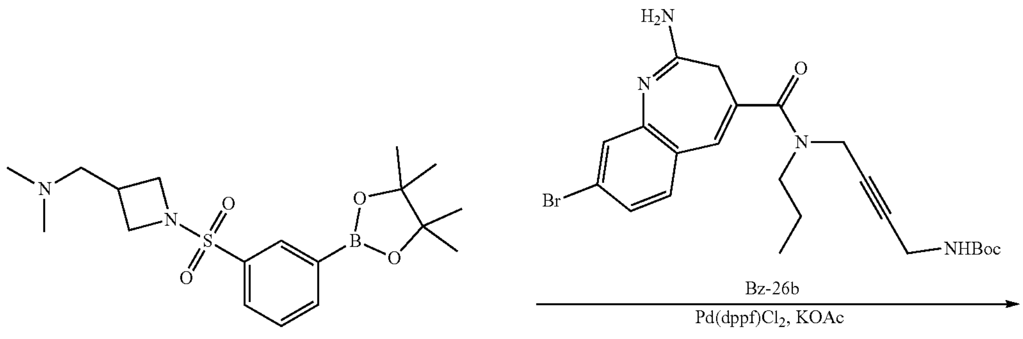

Bz-28b

Bz-26b

-continued

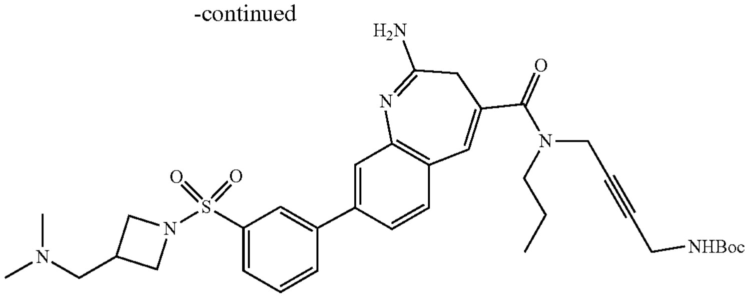

Bz-28

Preparation of Bz-28b. A mixture of 1-[1-(3-bromophenyl)sulfonylazetidin-3-yl]-N,N-dimethyl-methanamine, Bz-28a (0.3 g, 900.24 μmol, 1 eq), $Pin_2B_2$ (342.91 mg, 1.35 mmol, 1.5 eq), $Pd(dppf)Cl_2$ (32.94 mg, 45.01 μmol, 0.05 eq) and KOAc (176.70 mg, 1.80 mmol, 2 eq) in dioxane (6 mL) was degassed and purged with $N_2$ for 3 times, and then stirred at 90° C. for 2 h under $N_2$ atmosphere. The reaction mixture was cooled to 25° C., added with de-Pd silica gel (1 g), and then stirred at 25° C. for 30 min. The mixture was filtered and washed with EtOAc (10 mL×5) and concentrated under reduced pressure to give N,N-dimethyl-1-[1-[3-(4,4,5,5-tetramethyl-1,3,2-dioxaborolan-2-yl)phenyl]sulfonylazetidin-3-yl]methanamine, Bz-28b (0.6 g, crude) as a yellow oil.

Preparation of Bz-28. A mixture of Bz-28b (699 mg, 920 μmol, 1.5 eq), tert-butyl N-[4-[(2-amino-8-bromo-3H-1-benzazepine-4-carbonyl)-propyl-amino]but-2-ynyl]carbamate, Bz-26b (300 mg, 613 μmol, 1 eq), $Pd(dppf)Cl_2$ (22.4 mg, 30.6 μmol, 0.05 eq) and $K_2CO_3$ (169 mg, 1.23 mmol, 2 eq) in dioxane (20 mL) and $H_2O$ (2 mL) was degassed and purged with $N_2$ for 3 times, and then stirred at 90° C. for 2 h under $N_2$ atmosphere. The reaction mixture was quenched by addition of $H_2O$ (60 mL) at 0° C., and then extracted with EtOAc (30 mL×3). The combined organic layers were washed with brine (10 mL×3), dried over $Na_2SO_4$, filtered and concentrated under reduced pressure. The residue was purified by column chromatography ($SiO_2$, petroleum ether: ethyl acetate=1:0 to 0:1) and then ($SiO_2$, EtOAc:MeOH=1:0 to 1:1) to give tert-butyl N-[4-[[2-amino-8-[3-[3-[(dimethylamino)methyl]azetidin-1-yl]sulfonylphenyl]-3H-1-benzazepine-4-carbonyl]-propyl-amino]but-2-ynyl]carbamate, Bz-28 (230 mg crude product, 347 μmol, 56.61% yield) as a brown solid. $^1H$ NMR (MeOD-$d_4$, 400 MHz) δ 8.16-8.06 (m, 2H), 7.97-7.90 (m, 1H), 7.89-7.65 (m, 4H), 7.34 (br s, 1H), 4.34 (s, 2H), 4.01 (t, J=8.4 Hz, 2H), 3.87 (s, 2H), 3.69 (dd, J=5.6, 8.4 Hz, 2H), 3.56 (br s, 2H), 3.39 (s, 2H), 3.33 (s, 2H), 3.03-2.89 (m, 1H), 2.82 (s, 6H), 1.81-1.67 (m, 2H), 1.43 (s, 9H), 0.97 (br t, J=6.8 Hz, 3H). LC/MS [M+H] 663.3 (calculated); LC/MS [M+H] 663.3 (observed).

Example 25: Synthesis of Bz-29

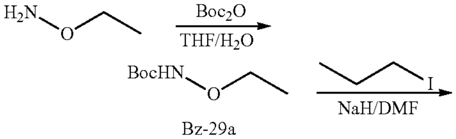

Bz-29a

-continued

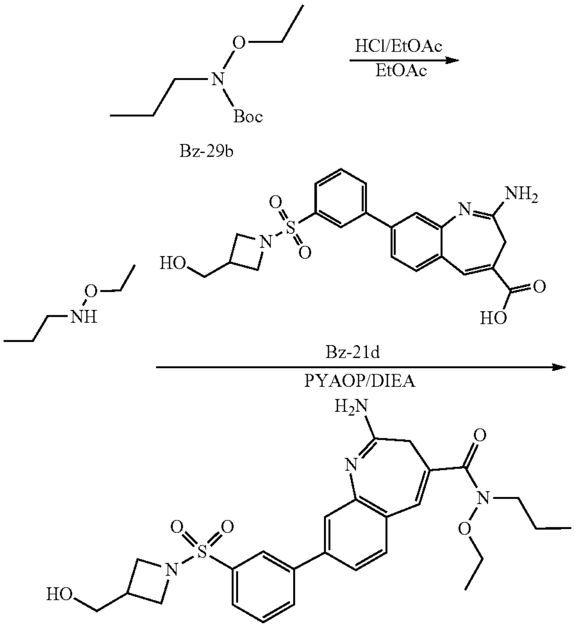

Bz-29b

Bz-21d

Bz-29

Preparation of Bz-29a. To a mixture of O-ethylhydroxylamine (3 g, 30.8 mmol, 1 eq, HCl) and $Na_2CO_3$ (32.6 g, 307.55 mmol, 10 eq) in DCM (30 mL) and Water (30 mL) was added tert-butoxycarbonyl tert-butyl carbonate (8.05 g, 36.9 mmol, 8.48 mL, 1.2 eq) at 25° C. and then stirred for 3 hr. The mixture was separated, and the organic layer was dried over $Na_2SO_4$, concentrated to residue. The crude was purified by column chromatography ($SiO_2$, petroleum ether/ethyl acetate=1:0-5:1) to give tert-butyl N-ethoxycarbamate, Bz-29a (4 g, 24.81 mmol, 80.68% yield) as colorless oil. $^1H$ NMR (400 MHz, CHLOROFORM-d) δ 3.87 (q, J=7.2 Hz, 2H), 1.45 (s, 9H), 1.20 (t, J=7.2 Hz, 3H).

Preparation of Bz-29b. To a mixture of Bz-29a (1 g, 6.20 mmol, 1 eq) in DMF (10 mL) was added NaH (298 mg, 7.44 mmol, 60% purity, 1.2 eq) at 0° C., and then stirred at 0° C. for 0.5 h, 1-iodopropane (1.16 g, 6.82 mmol, 666.67 μL, 1.1 eq) was added to the mixture at 0° C. and it was stirred at 25° C. for 10 h. The mixture was quenched with saturated solution of $NH_4Cl$ (10 mL), and then extracted with EtOAc (3×10 mL). The organic layer was dried over $Na_2SO_4$, concentrated to give a residue. The residue was purified by column chromatography ($SiO_2$, petroleum ether/ethyl acetate=1:0-5:1) to give tert-butyl N-ethoxy-N-propyl-carbamate, Bz-29b (0.84 g, 4.13 mmol, 66.61% yield) as colorless oil. $^1$H NMR (400 MHz, CHLOROFORM-d) δ3.89 (q, J=7.2 Hz, 2H), 3.47-3.25 (m, 2H), 1.69-1.59 (m, 2H), 1.49 (s, 9H), 1.23 (t, J=7.2 Hz, 3H), 0.91 (t, J=7.2 Hz, 3H).

Preparation of Bz-29c. To a mixture of Bz-29b (0.84 g, 4.13 mmol, 1 eq) in EtOAc (10 mL) was added HCl/EtOAc (4 M, 5 mL, 4.84 eq). The mixture was stirred at 25° C. for 2 h. The mixture was concentrated to give N-ethoxypropan-1-amine, Bz-29c (0.4 g, 2.86 mmol, 69.33% yield, HCl) as white solid. $^1$H NMR (400 MHz, METHANOL-$d_4$) δ 4.16 (dq, J=2.0, 7.2 Hz, 2H), 3.29-3.23 (m, 2H), 1.76 (sxt, J=7.6 Hz, 2H), 1.32 (t, J=7.2 Hz, 3H), 1.05 (t, J=7.2 Hz, 3H).

Preparation of Bz-29. To a mixture of 2-amino-8-[3-[3-(hydroxymethyl)azetidin-1-yl]sulfonylphenyl]-3H-1-benzazepine-4-carboxylic acid (200 mg, 468 μmol, 1 eq) in DMF (2 mL) was added PYAOP (293 mg, 561 μmol, 1.2 eq) and DIEA (181 mg, 1.40 mmol, 245 μL, 3 eq), after 3 min, N-ethoxypropan-1-amine (71.86 mg, 514.65 μmol, 1.1 eq, HCl) was added. The mixture was stirred at 25° C. for 1 h, and then concentrated to get a residue. The residue was purified by Prep-HPLC (column: Phenomenex Gemini-NX C18 75×30 mm, 3 μm particle size; mobile phase: [water (10 mM $NH_4HCO_3$)-ACN]; B %: 30%-60%, 10.5 min) to give 2-amino-N-ethoxy-8-[3-[3-(hydroxyl methyl)azetidin-1-yl]sulfonylphenyl]-N-propyl-3H-1-benzazepine-4-carboxamide, Bz-29 (3.5 mg, 6.36 μmol, 1.36% yield, 93.17% purity) as white solid. $^1$H NMR (400 MHz, METHANOL-$d_4$) δ 8.10-8.02 (m, 2H), 7.89-7.73 (m, 2H), 7.53-7.48 (m, 2H), 7.46-7.40 (m, 1H), 7.31 (s, 1H), 3.95 (q, J=7.2 Hz, 2H), 3.86 (t, J=8.4 Hz, 2H), 3.74 (t, J=7.2 Hz, 2H), 3.60 (dd, J=6.4, 8.2 Hz, 2H), 3.41 (d, J=6.4 Hz, 2H), 3.34-3.31 (m, 2H), 2.67-2.43 (m, 1H), 1.77 (sxt, J=7.2 Hz, 2H), 1.18 (t, J=7.2 Hz, 3H), 0.99 (t, J=7.6 Hz, 3H). LC/MS [M+H] 513.2 (calculated); LC/MS [M+H] 513.4 (observed).

Example 26: Synthesis of Bz-30

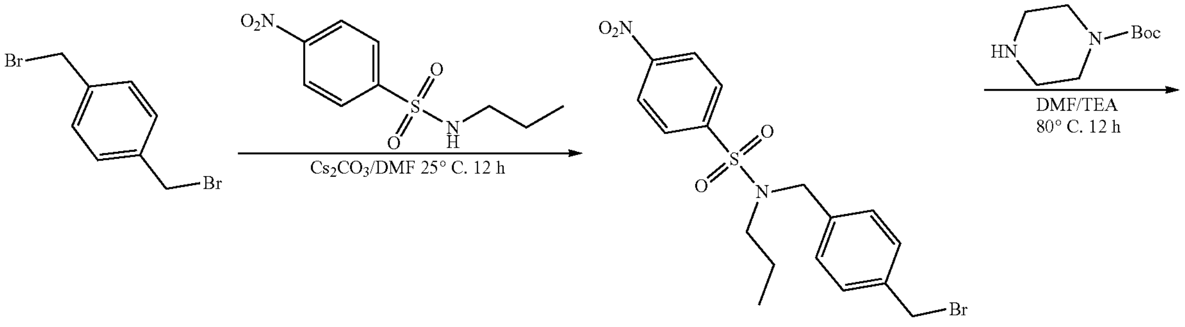

Bz-30a

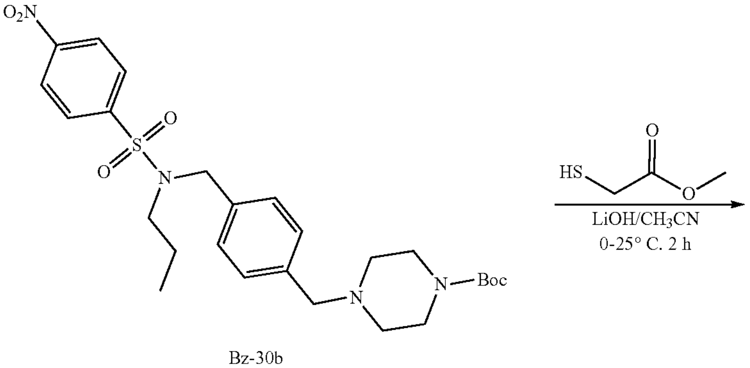

Bz-30b

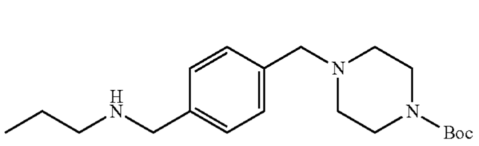

Bz-30c

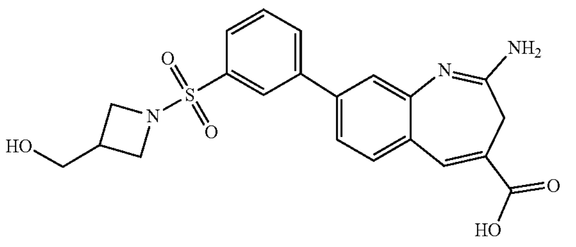

Bz-21d

PYAOP/DIEA
DMF 25° C. 1 h

-continued

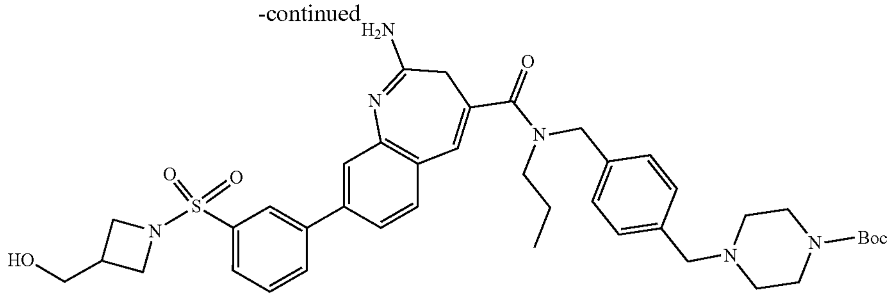

Bz-30

Preparation of Bz-30a. To a mixture of 1,4-bis(bromomethyl)benzene (6.48 g, 24.6 mmol, 2.0 eq) and 4-nitro-N-propyl-benzenesulfonamide (3.0 g, 12.3 mmol, 1.0 eq) in DMF (40 mL) was added $Cs_2CO_3$ (4.80 g, 14.7 mmol, 1.2 eq) in one portion at 25° C. and then stirred for 12 h. The reaction was diluted with water (100 mL) and extracted with EtOAc (50 mL×3). The organic layer was washed with brine, dried over $Na_2SO_4$ filtered and concentrated. The residue was purified by silica gel chromatography (petroleum ether/ethyl acetate=1/0, 3/1) to afford N-[[4-(bromomethyl)phenyl]methyl]-4-nitro-N-propyl-benzenesulfonamide, Bz-30a (1.5 g, 3.51 mmol, 28.6% yield) as white solid. $^1H$ NMR ($CDCl_3$, 400 MHz) δ 8.35 (d, J=8.8 Hz, 2H), 7.98 (d, J=8.8 Hz, 2H), 7.35 (d, J=8.0 Hz, 2H), 7.24 (d, J=8.0 Hz, 2H), 4.48 (s, 2H), 4.40 (s, 2H), 3.19-3.11 (m, 2H), 1.42 (m, 2H), 0.76 (t, J=7.6 Hz, 3H).

Preparation of Bz-30b. To a mixture of Bz-30a (1.3 g, 3.04 mmol, 1.0 eq) and tert-butyl piperazine-1-carboxylate (2.27 g, 12.2 mmol, 4.0 eq) in DMF (15 mL) was added $Et_3N$ (1.23 g, 12.2 mmol, 1.69 mL, 4.0 eq) at 25° C. and then stirred at 80° C. for 12 h. The mixture was diluted with water (50 mL) and extracted with EtOAc (50 mL×3). The organic layer was washed with brine, dried over $Na_2SO_4$, filtered and concentrated. The residue was purified by silica gel chromatography (petroleum ether/ethyl acetate=1/0, 3/1) to afford tert-butyl 4-[[4-[[(4-nitrophenyl)sulfonyl-propyl-amino] methyl]phenyl]methyl]piperazine-1-carboxylate, Bz-30b (1.7 g, crude) as yellow solid. $^1H$ NMR (DMSO, 400 MHz) δ 8.39 (d, J=8.8 Hz, 2H), 8.11 (d, J=8.8 Hz, 2H), 7.21 (s, 4H), 4.36 (s, 2H), 3.45 (s, 2H), 3.31-2.27 (m, 4H), 3.12-3.05 (m, 2H), 2.28-2.26 (m, 4H), 1.38 (s, 9H), 1.33-1.25 (m, 2H), 0.65 (t, J=7.6 Hz, 3H).

Preparation of Bz-30c. To a solution of Bz-30b (1.0 g, 1.88 mmol, 1.0 eq) in $CH_3CN$ (6 mL) was added $LiOH{\cdot}H_2O$ (473 mg, 11.3 mmol, 6.0 eq) in one portion at 0° C. Then methyl 2-sulfanylacetate (598 mg, 5.63 mmol, 511 μL, 3.0 eq) was added and it was stirred at 25° C. for 2 h. The mixture was filtered and concentrated. The residue was diluted with MTBE (5 ml) and then adjusted the pH of the mixture to about 2 with aq. HCl (1 M), extracted with MTBE (20 mL) (discarded). The aqueous phase was adjusted pH=9 with aq.$NaHCO_3$ and then extracted with EtOAc (30 mL×3). The organic layer was washed with brine, dried over $Na_2SO_4$, filtered and concentrated to obtain tert-butyl 4-[[4-(propylaminomethyl)phenyl] methyl]piperazine-1-carboxylate, Bz-30c (0.5 g, crude) as yellow oil. $^1H$ NMR (MeOD, 400 MHz) δ 7.32-7.30 (m, 4H), 3.73 (s, 2H), 3.53 (s, 2H), 3.43-3.40 (m, 4H), 2.57-2.50 (m, 2H), 2.41-2.48 (m, 4H), 1.58-1.51 (m, 2H), 1.45 (s, 9H), 0.92 (t, J=7.6 Hz, 3H).

Preparation of Bz-30. To a mixture of 2-amino-8-[3-[3-(hydroxymethyl)azetidin-1-yl]sulfonylphenyl]-3H-1-benzazepine-4-carboxylic acid, Bz-21d (400 mg, 936 μmol, 1.0 eq) in DMF (8 mL) was added PYAOP (585 mg, 1.12 mmol, 1.2 eq), DIEA (363 mg, 2.81 mmol, 489 μL, 3.0 eq) and Bz-30c (358 mg, 1.03 mmol, 1.1 eq) in one portion at 25° C. and then stirred for 1 h. The mixture was filtered and concentrated. The residue was purified by prep-HPLC (column: Phenomenex Luna C18 100×30 mm, 5 μm particle size; mobile phase: [water (0.1% TFA)-ACN]; B %: 15%-45%, 10 min) to give tert-butyl 4-[[4-[[[2-amino-8-[3-[3-(hydroxymethyl)azetidin-1-yl]sulfonylphenyl]-3H-1-benzazepine-4-carbonyl]-propyl-amino]methyl]phenyl]methyl] piperazine-1-carboxylate, Bz-30 (0.35 g, 462 μmol, 49.4% yield) as white solid. $^1H$ NMR (MeOD, 400 MHz) δ 8.14-8.05 (m, 2H), 7.92 (d, J=7.6 Hz, 1H), 7.82 (t, J=7.6 Hz, 1H), 7.78-7.69 (m, 2H), 7.63-7.42 (m, 5H), 7.17 (s, 1H), 4.37 (s, 2H), 3.86 (t, J=8.0 Hz, 2H), 3.61 (dd, J=6.0, 8.0 Hz, 2H), 3.53-3.49 (m, 2H), 3.43-3.41 (m, 6H), 3.31-3.29 (m, 8H), 2.63-2.54 (m, 1H), 1.76-1.65 (m, 2H), 1.47 (s, 9H), 0.95-0.89 (m, 3H). LC/MS [M+H] 757.4 (calculated); LC/MS [M+H] 757.4 (observed).

Example 27: Synthesis of Bz-31

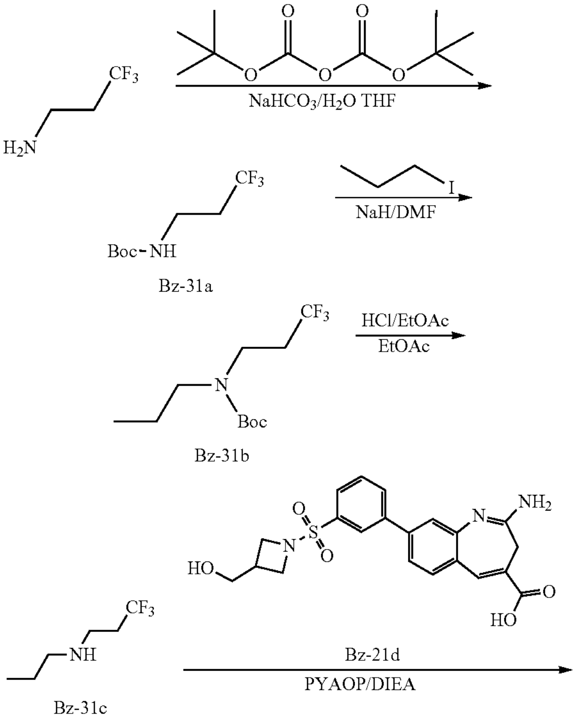

Bz-31a

Bz-31b

Bz-31c

-continued

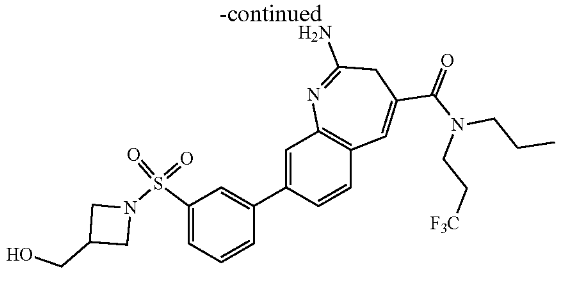

Bz-31

Preparation of Bz-31a. To a mixture of 3,3,3-trifluoropropan-1-amine (0.5 g, 3.34 mmol, 1 eq, HCl) and $NaHCO_3$ (842.64 mg, 10.03 mmol, 390.11 μL, 3 eq) in THE (3 mL) and $H_2O$ (3 mL) was added tert-butoxycarbonyl tert-butyl carbonate (730 mg, 3.34 mmol, 768 μL, 1 eq), and then stirred at 25° C. for 1 h under $N_2$ atmosphere. The mixture was poured into $H_2O$ (15 mL), extracted with ethyl acetate (15 mL×3). The combined organic phase was washed with brine (15 mL), dried with anhydrous $Na_2SO_4$, filtered and concentrated in vacuum. The crude product was purified by silica gel chromatography eluted with (petroleum ether:ethyl acetate=5:0 to 1:1) to give tert-butyl N-(3,3,3-trifluoropropyl)carbamate, Bz-31a (500 mg, 2.35 mmol, 70.14% yield) as a colorless oil. $^1$H NMR ($CDCl_3$, 400 MHz) δ 4.75 (br s, 1H), 3.40 (q, J=6.4 Hz, 2H), 2.40-2.27 (m, 2H), 1.45 (s, 9H).

Preparation of Bz-31b. To a solution of Bz-31a (400 mg, 1.88 mmol, 1 eq) in DMF (5 mL) was added NaH (113 mg, 2.81 mmol, 60% purity, 1.5 eq) at 0° C. After 30 min, 1-iodopropane (637.88 mg, 3.75 mmol, 366 μL, 2 eq) was added to the mixture and then stirred at 20° C. for 2 h. The reaction mixture was quenched at 0° C. by the addition of saturated $NH_4Cl$ (10 mL), then extracted with EtOAc (10 mL×3). The organic phase was dried with anhydrous $Na_2SO_4$, filtered and concentrated in vacuum. The reaction mixture was purified by silica gel column chromatography (petroleum ether:ethyl acetate=5:1 to 1:1). Compound tert-butyl N-propyl-N-(3,3,3-trifluoropropyl)carbamate, Bz-31b (400 mg, 1.57 mmol, 83.52% yield) was obtained as a colorless oil. $^1$H NMR ($CDCl_3$, 400 MHz) δ 3.41 (t, J=7.2 Hz, 2H), 3.19-3.12 (m, 1H), 2.40-2.32 (m, 2H), 1.58-1.50 (m, 2H), 1.47 (s, 9H), 0.89 (t, J=7.6 Hz, 3H).

Preparation of Bz-31c. To a solution of tert-butyl N-propyl-N-(3,3,3-trifluoropropyl)carbamate (400 mg, 1.57 mmol, 1 eq) in EtOAc (3 mL) was added HCl/EtOAc (4 M, 5.88 mL, 15 eq) and then stirred at 20° C. for 2 h. The mixture was filtered and concentrated in vacuum to give 3,3,3-trifluoro-N-propyl-propan-1-amine, Bz-31c (240 mg, crude, HCl) as a white solid. $^1$H NMR (MeOD-$d_4$, 400 MHz) δ 3.34-3.31 (m, 2H), 3.06-3.00 (m, 2H), 2.78-2.64 (m, 2H), 1.80-1.68 (m, 2H), 1.04 (t, J=7.6 Hz, 3H).

Preparation of Bz-31. To a solution of 2-amino-8-[3-[3-(hydroxymethyl)azetidin-1-yl]sulfonylphenyl]-3H-1-benzazepine-4-carboxylic acid, Bz-21d (100 mg, 233 μmol, 1 eq), DIEA (90.7 mg, 702 μmol, 122 μL, 3 eq) and PYAOP (183 mg, 351 μmol, 1.5 eq) in DMF (1 mL) was added Bz-31c (44.8 mg, 234 μmol, 1 eq, HCl), and then stirred at 20° C. for 1 h. The mixture was filtered and concentrated in vacuum. The residue was purified by prep-HPLC (column: Waters Xbridge BEH C18 100×30 mm, 10 μm particle size; mobile phase: [water (10 mM $NH_4HCO_3$)-ACN]; B %: 30%-60%, 8 min) to afford 2-amino-8-[3-[3-(hydroxymethyl)azetidin-1-yl]sulfonylphenyl]-N-propyl-N-(3,3,3-trifluoropropyl)-3H-1-benzazepine-4-carboxamide, Bz-31 (7 mg, 12.40 μmol, 5.30% yield) as a white solid. $^1$H NMR (MeOD-$d_4$, 400 MHz) δ 8.07 (s, 1H), 8.04 (br d, J=7.6 Hz, 1H), 7.86-7.81 (m, 1H), 7.80-7.73 (m, 1H), 7.49-7.44 (m, 2H), 7.42-7.37 (m, 1H), 6.94 (s, 1H), 3.86 (t, J=8.4 Hz, 2H), 3.73 (br s, 2H), 3.60 (dd, J=6.0, 8.0 Hz, 2H), 3.52-3.45 (m, 2H), 3.42 (d, J=6.4 Hz, 2H), 3.33-3.32 (m, 2H), 2.68-2.53 (m, 3H), 1.74-1.64 (m, 2H), 0.91 (br s, 3H). LC/MS [M+H] 565.2 (calculated); LC/MS [M+H] 565.3 (observed).

Example 28. Synthesis of Bz-32

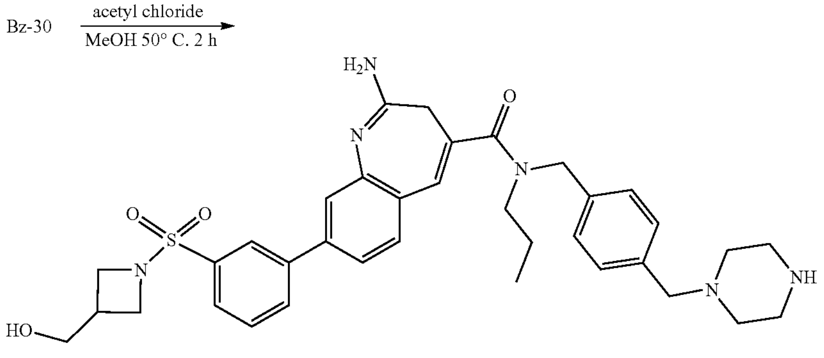

Bz-32

Preparation of Bz-32. To a solution of tert-butyl 4-[[4-[[[2-amino-8-[3-[3-(hydroxymethyl)azetidin-1-yl] sulfonylphenyl]-3H-1-benzazepine-4-carbonyl]-propyl-amino] methyl]phenyl]methyl]piperazine-1-carboxylate, Bz-30 (0.16 g, 211 μmol, 1.0 eq) in MeOH (10 mL) was added acetyl chloride (49.8 mg, 634 μmol, 45.3 μL, 3.0 eq) at 25° C. and it was stirred at 50° C. for 2 h. The mixture was concentrated in vacuum, and the residue was purification by prep-HPLC (column: Waters Xbridge BEH C18 100×25 mm, 5 μm particle size; mobile phase: [water (10 mM $NH_4HCO_3$)-ACN]; B %: 25%-55%, 10 min) to give 2-amino-8-[3-[3-(hydroxymethyl)azetidin-1-yl]sulfonylphenyl]-N-[[4-(piperazin-1-ylmethyl)phenyl]methyl]-N-propyl-3H-1-benzazepine-4-carboxamide, Bz-32 (36 mg, 54.8 μmol, 25.9% yield) as white solid. $^1$H NMR (MeOD, 400 MHz) δ 8.06 (s, 1H), 8.02 (d, J=7.6 Hz, 1H), 7.83 (d, J=8.0 Hz, 1H), 7.79-7.72 (m, 1H), 7.46 (s, 2H), 7.40-7.22 (m, 5H), 6.93 (s, 1H), 4.74 (s, 2H), 3.85 (t, J=8.4 Hz, 2H), 3.62-3.56 (m, 2H), 3.52 (s, 2H), 3.45-3.34 (m, 4H), 2.85 (t, J=4.4 Hz, 4H), 2.66-2.52 (m, 2H), 2.48-2.44 (m, 4H), 1.72-1.60 (m, 2H), 0.90-0.88 (m, 3H). LC/MS [M+H] 657.3 (calculated); LC/MS [M+H] 657.5 (observed).

Example 29: Synthesis of Bz-33

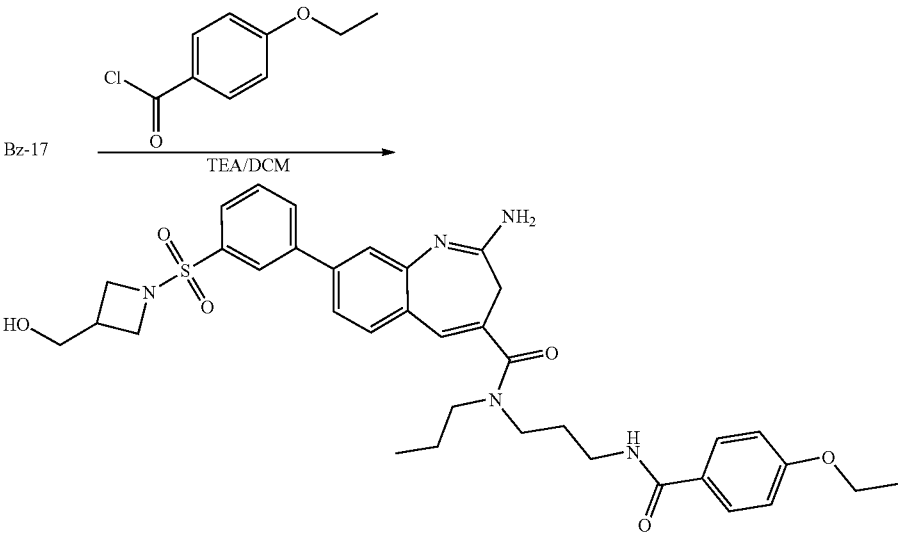

Bz-33

2-Amino-N-(3-aminopropyl)-8-(3-((3-(hydroxymethyl)azetidin-1-yl)sulfonyl)phenyl)-N-propyl-3H-benzo[b]azepine-4-carboxamide, Bz-17 (0.01 g, 0.019 mmol, 1 eq) was dissolved in DCM. Triethylamine (4 μl, 0.029 mmol, 1.5 eq) was added, followed by 4-ethoxybenzoyl chloride (0.004 g, 0.019 mmol, 1 eq). The reaction was stirred at room temperature, then concentrated and purified by HPLC to give 2-amino-N-(3-(4-ethoxybenzamido)propyl)-8-(3-((3-(hydroxymethyl)azetidin-1-yl)sulfonyl)phenyl)-N-propyl-3H-benzo[b]azepine-4-carboxamide, Bz-33 (0.0028 g, 0.0042 mmol, 22%). LC/MS [M+H]674.30 (calculated); LC/MS [M+H] 674.74 (observed).

Example 30: Synthesis of Bz-34

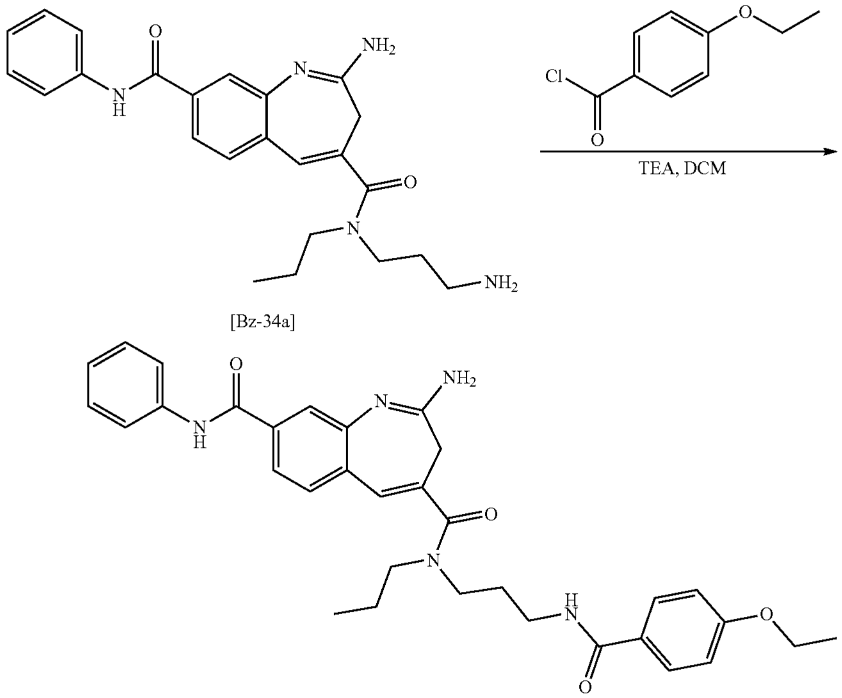

Bz-34

2-Amino-$N^4$-(3-aminopropyl)-$N^8$-phenyl-$N^4$-propyl-3H-benzo[b]azepine-4,8-dicarboxamide, Bz-34a (0.01 g, 0.024 mmol, 1 eq) was dissolved in DCM. Triethylamine (5 μl, 0.036 mmol, 1.5 eq) was added, followed by 4-ethoxybenzoyl chloride (0.004 g, 0.024 mmol, 1 eq). The reaction was stirred at room temperature, then concentrated and purified by HPLC to give 2-amino-$N^4$-(3-(4-ethoxybenzamido)propyl)-$N^8$-phenyl-$N^4$-propyl-3H-benzo[b]azepine-4,8-dicarboxamide, Bz-34 (0.005 g, 0.009 mmol, 38%). LC/MS [M+H]568.29 (calculated); LC/MS [M+H] 568.50 (observed).

Preparation of Aminobenzazepine-Linker Formula II Compounds (BzL) and Intermediates Example 31: Synthesis of BzL-1

Following the procedures described herein, ethyl 2-amino-8-(3-((2-(2-(3-oxo-3-(2,3,5,6-tetrafluorophenoxy)propoxy)ethoxy)ethyl)carbamoyl)phenyl)-3H-benzo[b]azepine-4-carboxylate, BzL-1 was prepared and characterized.

Example 32: Synthesis of BzL-2

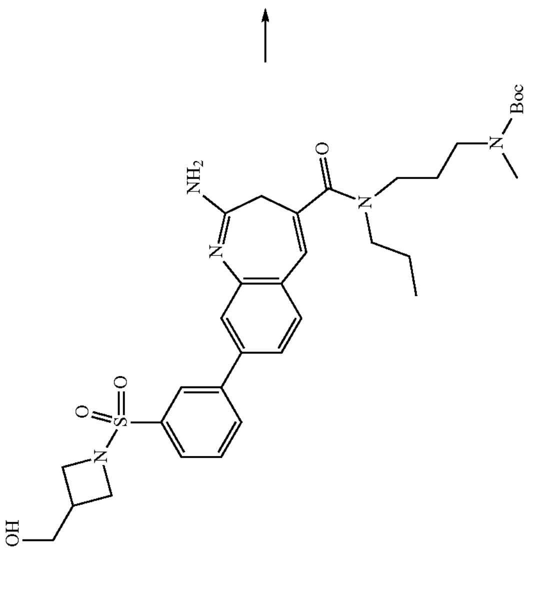
Bz-3
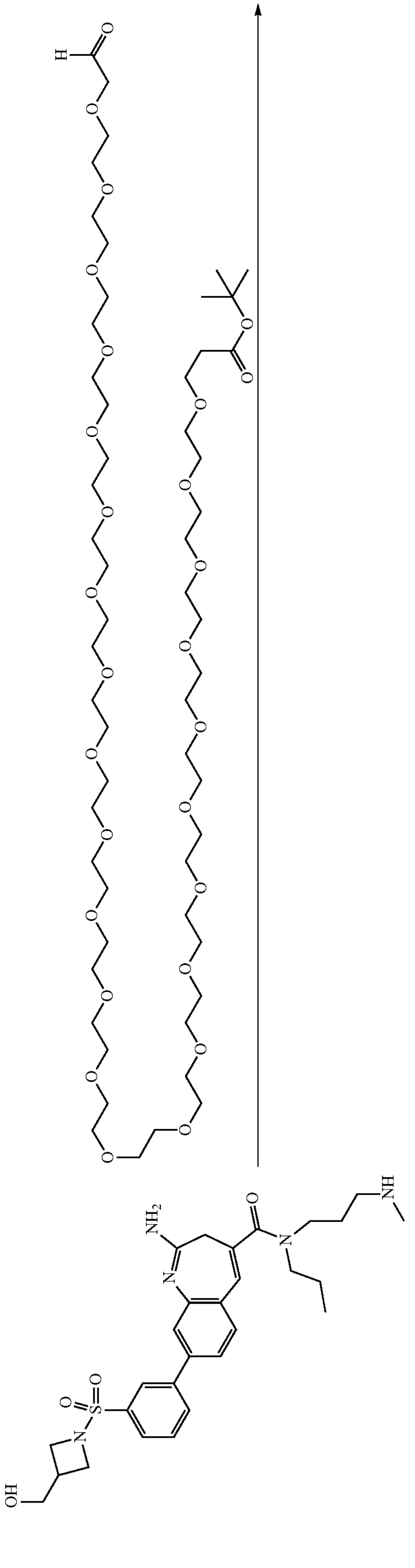
BzL-2a

-continued
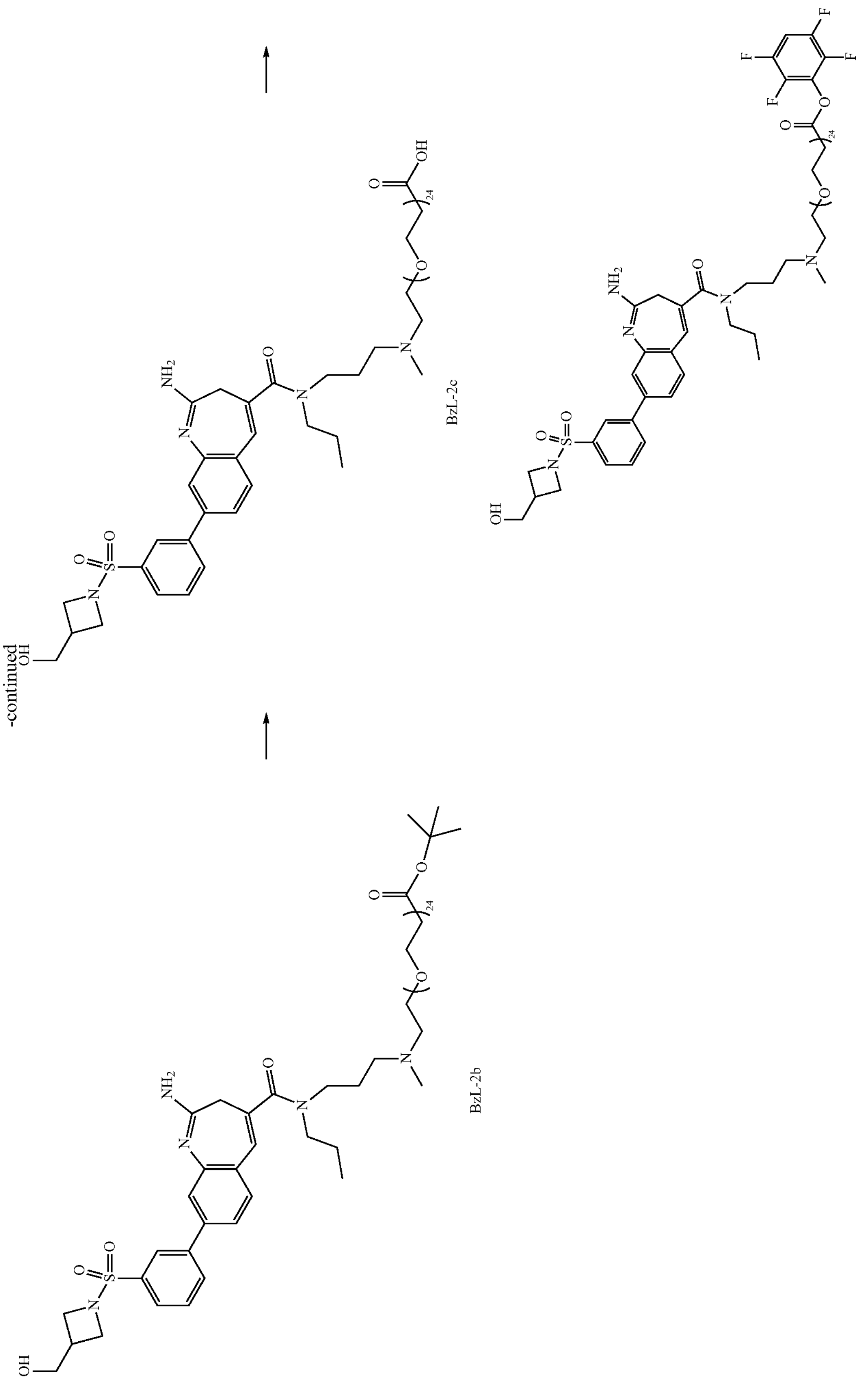
BzL-2b
BzL-2c
BzL-2

Synthesis of 2-amino-8-(3-((3-(hydroxymethyl)azetidin-1-yl)sulfonyl)phenyl)-N-(3-(methylamino)propyl)-N-propyl-3H-benzo[b]azepine-4-carboxamide, BzL-2a. BzL-2a was synthesized from Bz-3 according to the procedure described for Bz-11a. LC/MS [M+H]540.26 (calculated); LC/MS [M+H] 540.53 (observed).

Synthesis of tert-butyl 80-(2-amino-8-(3-((3-(hydroxymethyl)azetidin-1-yl)sulfonyl)phenyl)-3H-benzo[b]azepine-4-carbonyl)-76-methyl-4,7,10,13,16,19,22,25,28,31,34,37,40,43,46,49,52,55,58,61,64,67,70,73-tetracosaoxa-76,80-diazatrioctacontanoate, BzL-2b. A vial was charged with BzL-2a (15.1 mg, 0.028 mmol), tert-butyl 1-oxo-3,6,9,12,15,18,21,24,27,30,33,36,39,42,45,48,51,54,57,60,63,66,69,72-tetracosaoxapentaheptacontan-75-oate (0.042 mmol), sodium triacetoxyborohydride (30 mg, 0.14 mmol) in 100 µL DMF. The reaction was stirred for 5 h, upon which 100 µL of 10% sodium carbonate was added and stirred for 1 h. The mixture was filtered and purified by reverse phase preparative HPLC utilizing a 25-75% gradient of acetonitrile:water containing 0.1% trifluoroacetic acid. The purified fractions were combined and lyophilized to afford 40.7 mg of BzL-2b in 84% yield. LC/MS [M+H] 1724.98 (calculated); LC/MS [M+H]1726.52 (observed).

Synthesis of 80-(2-amino-8-(3-((3-(hydroxymethyl)azetidin-1-yl)sulfonyl)phenyl)-3H-benzo[b]azepine-4-carbonyl)-76-methyl-4,7,10,13,16,19,22,25,28,31,34,37,40,43,46,49,52,55,58,61,64,67,70,73-tetracosaoxa-76,80-diazatrioctacontanoic acid, BzL-2c. A vial was charged with BzL-2b (18 mg, 0.010 mmol), 300 µL DCM, and 100 µL trifluoroacetic acid. The reaction was maintained for 45 min, concentrated under vacuum, and azeotroped thrice with 1 mL toluene. The reaction was taken forward without any further purification.

2,3,5,6-Tetrafluorophenyl 80-(2-amino-8-(3-((3-(hydroxymethyl)azetidin-1-yl)sulfonyl)phenyl)-3H-benzo[b]azepine-4-carbonyl)-76-methyl-4,7,10,13,16,19,22,25,28,31,34,37,40,43,46,49,52,55,58,61,64,67,70,73-tetracosaoxa-76,80-diazatrioctacontanoate, BzL-2 was synthesized according to the procedure described for BzL-22. LC/MS [M+H] 1816.91 (calculated); LC/MS [M+H] 1818.51 (observed).

Example 33: Synthesis of BzL-3

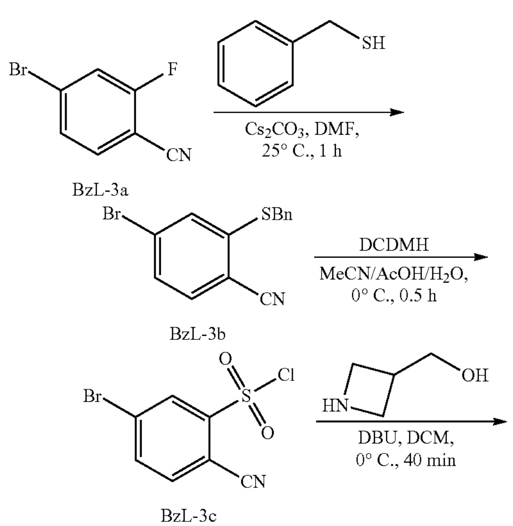

BzL-3a
BzL-3b
BzL-3c

-continued

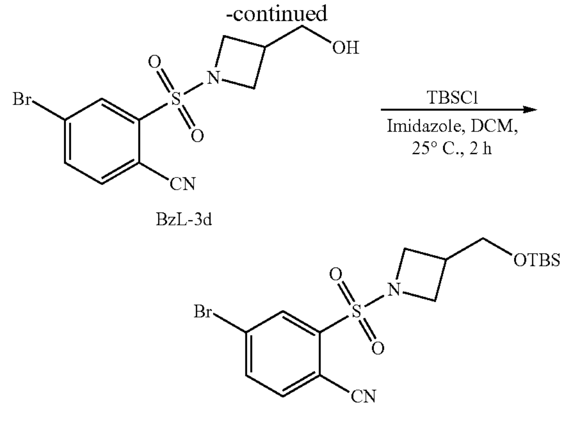

BzL-3d
BzL-3e

Synthesis of 2-benzylsulfanyl-4-bromo-benzonitrile, BzL-3b. To a mixture of phenylmethanethiol (3.10 g, 25.00 mmol, 2.93 mL, 1 eq) and 4-bromo-2-fluoro-benzonitrile, BzL-3a (5 g, 25.00 mmol, 1 eq) in DMF (10 mL) was added $Cs_2CO_3$ (12.22 g, 37.50 mmol, 1.5 eq) at 25° C. The mixture was stirred at 25° C. for 1 hour. TLC and LCMS showed the reaction was completed. The mixture was poured into ice water (100 mL), stirred for 5 min and filtered to give BzL-3b (4 g, 13.15 mmol, 52.60% yield) as a white solid which was used into next step without further purification. $^1H$ NMR ($CDCl_3$, 400 MHz) δ 7.50 (d, J=2.0 Hz, 1H), 7.47-7.43 (m, 1H), 7.41-7.38 (m, 1H), 7.35-7.28 (m, 5H), 4.23 (s, 2H).

Synthesis of 5-bromo-2-cyano-benzenesulfonyl chloride, BzL-3c. To a mixture of 2-benzylsulfanyl-4-bromo-benzonitrile (1 g, 3.29 mmol, 1 eq) in $CH_3CN$ (20 mL), AcOH (0.7 mL) and $H_2O$ (0.5 mL) was added 1,3-dichloro-5,5-methyl-imidazolidine-2,4-dione (1.30 g, 6.57 mmol, 2 eq) in portions at 0° C. The mixture was stirred at 0° C. for 30 min. TLC and LCMS showed the reaction was completed. The mixture was poured into ice water (50 mL) and stirred for 2 min. The aqueous phase was extracted with DCM (20 mL×2). The combined organic phase was washed with brine (30 mL), dried with anhydrous $Na_2SO_4$, filtered and concentrated in vacuum. The residue was purified by silica gel chromatography (petroleum ether/ethyl acetate=20/1, 10/1) to afford BzL-3c (0.8 g, 2.85 mmol, 86.75% yield) as a white solid. $^1H$ NMR ($CDCl_3$, 400 MHz) δ 8.34 (d, J=2.0 Hz, 1H), 7.99 (dd, J=8.4, 2.0 Hz, 1H), 7.83 (d, J=8.4 Hz, 1H).

Synthesis of 4-bromo-2-[3-(hydroxymethyl)azetidin-1-yl]sulfonyl-benzonitrile, BzL-3d. To a mixture of azetidin-3-ylmethanol (1.54 g, 12.48 mmol, 1 eq, HCl) in DCM (100 mL) was added DBU (3.80 g, 24.95 mmol, 3.76 mL, 2 eq) dropwise at 0° C. and stirred for 10 min. The mixture was added 5-bromo-2-cyano-benzenesulfonyl chloride, BzL-3c (3.5 g, 12.48 mmol, 1 eq) and stirred at 0° C. for 30 min. TLC showed the reaction was completed. The mixture was poured into ice water (100 mL) and stirred for 2 min. The aqueous phase was extracted with DCM (50 mL×3). The combined organic phase was washed with brine (20 mL), dried with anhydrous $Na_2SO_4$, filtered and concentrated to obtain BzL-3d (3.5 g, crude) as colorless oil which was used into the next step without further purification.

Synthesis of 4-bromo-2-[3-[[tert-butyl(dimethyl)silyl]oxymethyl]azetidin-1-yl]sulfonyl-benzonitrile, BzL-3e. To a mixture of 4-bromo-2-[3-(hydroxymethyl)azetidin-1-yl]sulfonyl-benzonitrile, BzL-3d (3.5 g, 10.57 mmol, 1 eq) and tert-butyldimethylsilyl chloride, TBSCl (1.91 g, 12.68 mmol, 1.55 mL, 1.2 eq) in DCM (30 mL) was added imidazole (1.08 g, 15.85 mmol, 1.5 eq) in one portion at 25° C. The mixture was stirred at 25° C. for 2 hours. LCMS showed the reaction was completed. The mixture was poured into ice water (200 mL) and stirred for 2 min. The aqueous phase was extracted with DCM (100 mL×3). The combined organic phase was washed with brine (50 mL), dried with anhydrous $Na_2SO_4$, filtered and concentrated in vacuum. The residue was purified by silica gel chromatography (petroleum ether/ethyl acetate=20/1, 10/1) to afford BzL-3e (3.8 g, 8.53 mmol, 80.72% yield) as colorless oil. $^1H$ NMR ($CDCl_3$, 400 MHz) δ 8.20 (d, J=2.0 Hz, 1H), 7.82 (dd, J=8.4, 2.0 Hz, 1H), 7.72 (d, J=8.4 Hz, 1H), 4.10-4.06 (m, 2H), 3.96-3.93 (m, 2H), 3.68 (d, J=5.2 Hz, 2H), 2.82-2.76 (m, 1H), 0.86 (s, 9H), 0.00 (s, 6H).

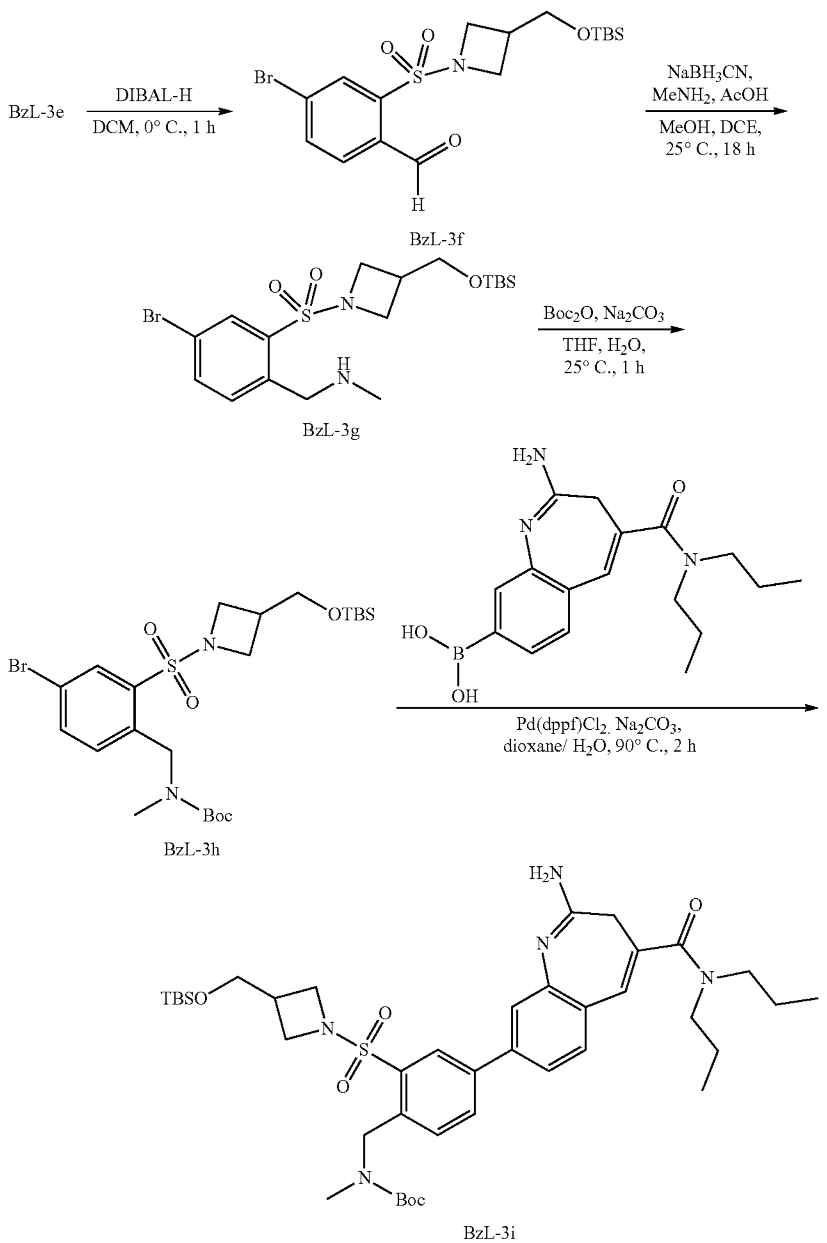

BzL-3f

BzL-3g

BzL-3h

BzL-3i

Synthesis of 4-bromo-2-[3-[[tert-butyl(dimethyl)silyl]oxymethyl]azetidin-1-yl]sulfonyl-benzaldehyde, BzL-3f. To a solution of 4-bromo-2-[3-[[tert-butyl(dimethyl)silyl]oxymethyl]azetidin-1-yl] sulfonyl-benzonitrile, BzL-3e (3.8 g, 8.53 mmol, 1 eq) in DCM (100 mL) was added diisobutylaluminum hydride, DIBAL-H (1 M, 9.38 mL, 1.1 eq) dropwise at 0° C. under $N_2$. The mixture was stirred at 0° C. for 1 hour. LCMS showed the reaction was completed. The mixture was added saturated aqueous $NH_4Cl$ (3 mL), dried with anhydrous $Na_2SO_4$, filtered and concentrated in vacuum. The residue was purified by silica gel chromatography (column height: 250 mm, diameter: 100 mm, 100-200 mesh silica gel, petroleum ether/ethyl acetate=20/1, 5/1) to give BzL-3f (3.5 g, 7.80 mmol, 91.49% yield) as a light yellow oil. $^1H$ NMR ($CDCl_3$, 400 MHz) δ 10.69 (s, 1H), 8.16 (d, J=1.6 Hz, 1H), 7.97 (d, J=8.4 Hz, 1H), 7.86 (dd, J=1.6, 8.4 Hz, 1H), 3.95-3.88 (m, 2H), 3.81-3.76 (m, 2H), 3.65-3.64 (m, 2H), 2.85-2.71 (m, 1H), 0.85 (s, 8H), 0.03 (s, 6H).

Synthesis of 1-[4-bromo-2-[3-[[tert-butyl(dimethyl)silyl] oxymethyl] azetidin-1-yl]sulfonyl-phenyl]-N-methyl-methanamine, BzL-3g. To a solution of methanamine (4.16 g, 40.14 mmol, 5 eq) (30% in MeOH) and 4-bromo-2-[3-[[tert-butyl(dimethyl)silyl]oxymethyl]azetidin-1-yl]sulfonyl-benzaldehyde, BzL-3f (3.6 g, 8.03 mmol, 1 eq) in MeOH (15 mL) and DCE (15 mL) was added AcOH (482.08 mg, 8.03 mmol, 459.12 μL, 1 eq) and $NaBH_3CN$ (1.26 g, 20.07 mmol, 2.5 eq). The mixture was stirred at 25° C. for 18 h. The mixture was added a few drops of water and concentrated. The residue was purified by column chromatography ($SiO_2$, petroleum ether/ethyl acetate=1:1) to obtain BzL-3g (2 g, 4.31 mmol, 53.75% yield) as colorless oil. $^1H$ NMR (DMSO-$d_6$, 400 MHz) δ 8.09-8.06 (m, 1H), 8.01-7.99 (m, 1H), 7.71 (d, J=8.4 Hz, 1H), 4.27 (s, 2H), 3.85-3.80 (m, 2H), 3.62-3.58 (m, 2H), 3.55 (d, J=5.2 Hz, 2H), 2.69-2.75 (m, 1H), 2.56 (s, 3H), 0.82 (s, 9H), 0.00 (s, 6H).

Synthesis of tert-butyl N-[[4-bromo-2-[3-[[tert-butyl(dimethyl)silyl]oxymethyl]azetidin-1-yl]sulfonyl-phenyl] methyl]-N-methyl-carbamate, BzL-3h. To a mixture of 1-[4-bromo-2-[3-[[tert-butyl(dimethyl)silyl]oxymethyl]azetidin-1-yl]sulfonyl-phenyl]-N-methyl-methanamine, BzL-3g (2 g, 4.31 mmol, 1 eq) in THE (15 mL) and $H_2O$ (3 mL) was added $Na_2CO_3$ (914.68 mg, 8.63 mmol, 2 eq) and $Boc_2O$ (1.41 g, 6.47 mmol, 1.49 mL, 1.5 eq) in one portion at 25° C. The mixture was stirred at 25° C. for 1 h. The mixture was poured into ice water (10 mL) and stirred for 1 min. The aqueous phase was extracted with ethyl acetate (10 mL×3). The combined organic phase was washed with brine (20 mL), dried with anhydrous $Na_2SO_4$, filtered and concentrated in vacuum. The residue was purified by flash silica gel chromatography (ISCO™; 2 g SEPAFLASH™ Silica Flash Column, eluent of 0-50% ethyl acetate/petroleum ether gradient at 45 mL/min) to give BzL-3h (1.4 g, 2.48 mmol, 57.57% yield) was obtained as colorless oil. $^1H$ NMR (DMSO-$d_6$, 400 MHz) δ 8.00-7.99 (m, 2H), 7.23 (d, J=8.4 Hz, 1H), 4.66 (s, 2H), 3.85-3.79 (m, 2H), 3.61-3.57 (m, 4H), 2.85 (s, 3H), 2.51-2.49 (m, 1H), 1.47-1.31 (m, 9H), 0.81 (s, 9H), −0.01 (s, 6H).

Synthesis of tert-butyl N-[[4-[2-amino-4-(dipropylcarbamoyl)-3H-1-benzazepin-8-yl]-2-[3-[[tert-butyl(dimethyl) silyl]oxymethyl]azetidin-1-yl]sulfonyl-phenyl]methyl]-N-methyl-carbamate, BzL-3i. To a mixture of [2-amino-4-(dipropylcarbamoyl)-3H-1-benzazepin-8-yl]boronic acid (360 mg, 1.09 mmol, 1 eq) and tert-butyl N-[[4-bromo-2-[3-[[tert-butyl(dimethyl)silyl] oxymethyl]azetidin-1-yl] sulfonyl-phenyl]methyl]-N-methyl-carbamate, BzL-3h (616.35 mg, 1.09 mmol, 1 eq) in dioxane (3 mL) and $H_2O$ (0.5 mL) was added $Pd(dppf)Cl_2$ (80.02 mg, 109.36 μmol, 0.1 eq) and $Na_2CO_3$ (231.81 mg, 2.19 mmol, 2 eq) in one portion at 25° C. under $N_2$. The mixture was stirred at 90° C. for 2 h. The mixture was filtered and concentrated. The residue was poured into $H_2O$ (20 mL) and extracted with ethyl acetate (20 mL×2). The combined organic phase was washed with brine (20 mL), dried with anhydrous $Na_2SO_4$, filtered and concentrated in vacuum. The residue was purified by flash silica gel chromatography (ISCO™; 1 g SEPAFLASH™ Silica Flash Column, eluent of 0-100% ethyl acetate/petroleum ether gradient at 75 mL/min) to obtain BzL-3i (360 mg, 468.69 μmol, 42.86% yield) was obtained as yellow solid.

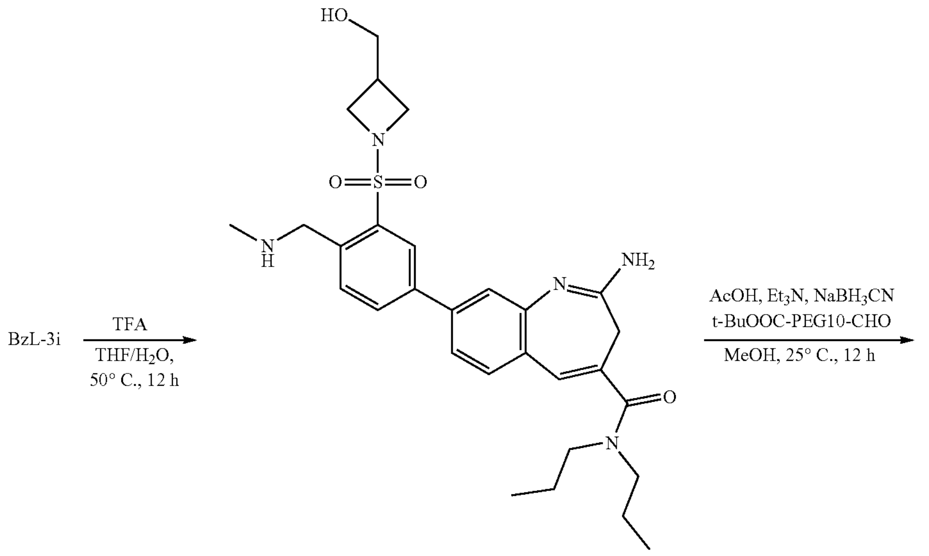

BzL-3j

-continued
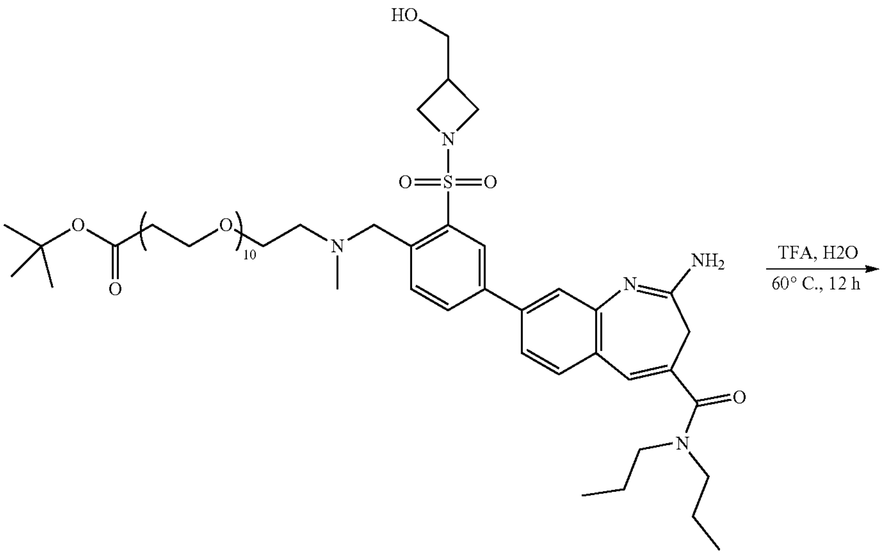
BzK-3k
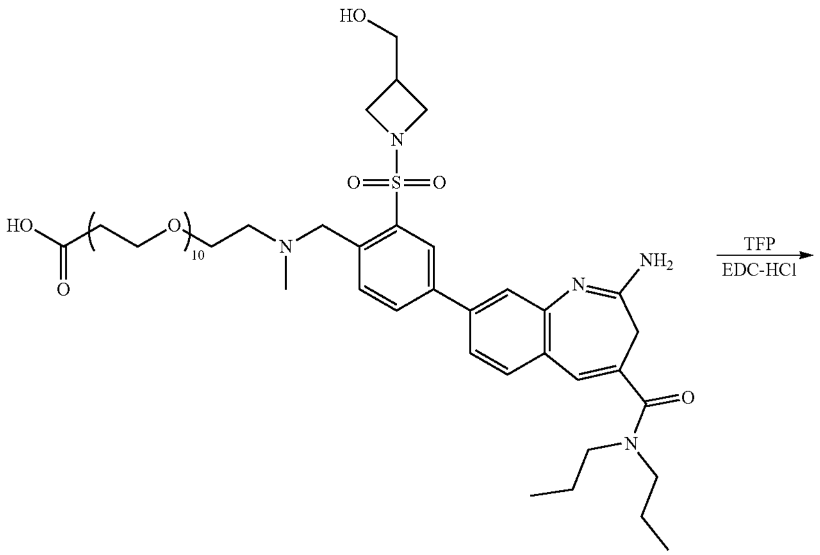
BzL-31

-continued

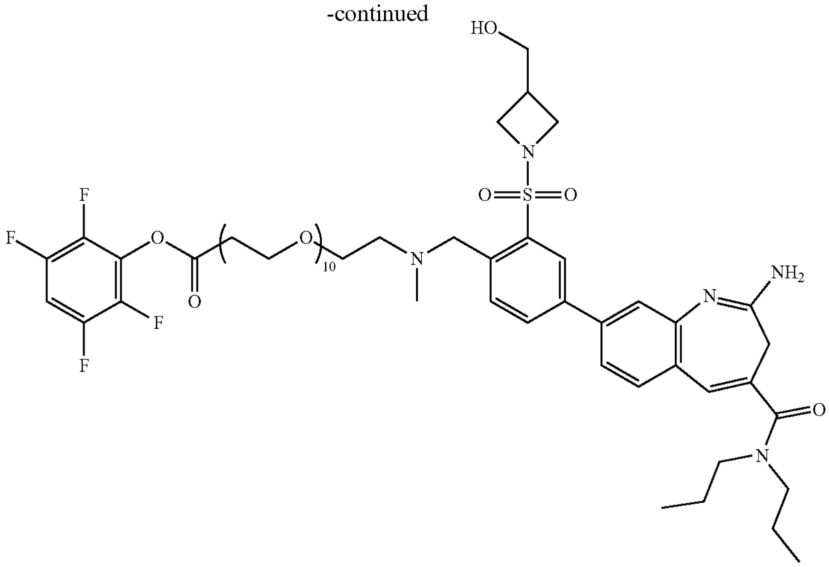

BzL-3

Synthesis of 2-amino-8-[3-[3-(hydroxymethyl)azetidin-1-yl]sulfonyl-4-(methylaminomethyl)phenyl]-N,N-dipropyl-3H-1-benzazepine-4-carboxamide, BzL-3j. A mixture of tert-butyl N-[[4-[2-amino-4-(dipropylcarbamoyl)-3H-1-benzazepin-8-yl]-2-[3-[[tert-butyl(dimethyl)silyl]oxymethyl]azetidin-1-yl]sulfonyl-phenyl]methyl]-N-methyl-carbamate, BzL-3i (170 mg, 221.33 μmol, 1 eq) in THE (5 mL) and $H_2O$ (1 mL) was added TFA (504.72 mg, 4.43 mmol, 327.74 μL, 20 eq) the mixture was stirred at 50° C. for 12 h. LC-MS showed reactant 1 was consumed completely and one main peak with desired mass was detected. The reaction mixture was filtered, and the filtrate was concentrated under reduced. The residue was purified by prep-HPLC (column: Nano-micro KROMASIL™ (Nouryon) C18 100×30 mm, 5 μm particle size; mobile phase: [water (0.1% TFA)-ACN]; B %: 20%-45%, 10 min) to give BzL-3j (95 mg crude) product as a yellow solid. $^1$H NMR (DMSO-$d_6$, 400 MHz) δ 12.49 (s, 1H), 9.88 (s, 1H), 9.50 (s, 1H), 8.87 (s, 2H), 8.24-8.22 (m, 1H), 8.17-8.16 (m, 1H), 7.92-7.90 (m, 1H), 7.74-7.71 (m, 1H), 7.67-7.70 (m, 2H), 7.06 (s, 1H), 4.79 (s, 1H), 4.46 (s, 2H), 3.85 (t, J=8.0 Hz, 2H), 3.61 (t, J=4.0 Hz, 2H), 3.35 (s, 4H), 2.67 (s, 3H), 2.64-2.55 (m, 2H), 1.74-1.39 (m, 4H), 0.86-0.80 (m, 6H). LC/MS [M+H]554.28 (calculated); LC/MS [M+H] 554.40 (observed).

Synthesis of tert-butyl 3-[2-[2-[2-[2-[2-[2-[2-[2-[2-[2-[[4-[2-amino-4-(dipropylcarbamoyl)-3H-1-benzazepin-8-yl]-2-[3-(hydroxymethyl)azetidin-1-yl]sulfonyl-phenyl]methyl-methyl-amino]ethoxy]ethoxy]ethoxy]ethoxy]ethoxy]ethoxy]ethoxy]ethoxy]ethoxy]ethoxy]propanoate, BzL-3k. To a mixture of 2-amino-8-[3-[3-(hydroxymethyl)azetidin-1-yl]sulfonyl-4-(methylaminomethyl)phenyl]-N,N-dipropyl-3H-1-benzazepine-4-carboxamide, BzL-3j (0.05 g, 90.30 μmol, 1 eq) and tert-butyl 3-[2-[2-[2-[2-[2-[2-[2-[2-[2-(2-oxoethoxy)ethoxy]ethoxy]ethoxy]ethoxy]ethoxy]ethoxy]ethoxy]ethoxy]ethoxy]propanoate, t-BuOOC-PEG10-CHO (52.80 mg, 90.30 μmol, 1 eq) in MeOH (2 mL) was added $Et_3N$ (27.41 mg, 270.90 μmol, 37.71 μL, 3 eq) and AcOH (5.42 mg, 90.30 μmol, 5.16 μL, 1 eq) and $NaBH_3CN$ (14.19 mg, 225.75 μmol, 2.5 eq) at 25° C. The mixture was stirred for 12 h. The mixture was concentrated in vacuum to afford BzL-3k (100 mg crude) as yellow oil.

Synthesis of 3-[2-[2-[2-[2-[2-[2-[2-[2-[2-[2-[[4-[2-amino-4-(dipropylcarbamoyl)-3H-1-benzazepin-8-yl]-2-[3-(hydroxymethyl)azetidin-1-yl]sulfonyl-phenyl]methyl-methyl-amino]ethoxy]ethoxy]ethoxy]ethoxy]ethoxy]ethoxy]ethoxy]ethoxy]ethoxy]ethoxy]propanoic acid, BzL-31. To a solution of BzL-3k (100 mg, 89.09 μmol, 1 eq) in $H_2O$ (1 mL) was added TFA (203.18 mg, 1.78 mmol, 131.93 μL, 20 eq). The mixture was stirred at 60° C. for 12 h. The reaction mixture was filtered, and the filtrate was concentrated under reduced pressure to give a residue. The residue was purified by prep-HPLC (column: Luna C18 100×30 mm, 5 μm particle size; liquid phase: [A—TFA/$H_2O$=0.075% v/v; B—ACN], B %: 20%-45%, 10 min]) to obtain BzL-31 (20 mg, 18.38 μmol, 20.63% yield, 97.989% purity) as colorless oil. $^1$H NMR (MeOD, 400 MHz) δ 8.39-8.38 (m, 1H), 8.23-8.20 (m, 1H), 7.98-7.96 (m, 1H), 7.83-7.81 (m, 2H), 7.73-7.71 (m, 1H), 7.11 (s, 1H), 4.02-4.00 (m, 2H), 3.94-3.88 (m, 2H), 3.79-3.74 (m, 2H), 3.74-3.40 (m, 45H), 3.40-3.35 (m, 2H), 2.98-2.94 (m, 3H), 2.79-2.71 (m, 2H), 2.56-2.51 (m, 2H), 1.80-1.66 (m, 5H), 0.95 (s, 6H). LC/MS [M+2H/2] 533.78 (calculated); LC/MS [M+2H/2] 534.20 (observed).

2,3,5,6-Tetrafluorophenyl 1-(4-(2-amino-4-(dipropylcarbamoyl)-3H-benzo[b]azepin-8-yl)-2-((3-(hydroxymethyl)azetidin-1-yl)sulfonyl)phenyl)-2-methyl-5,8,11,14,17,20,23,26,29,32-decaoxa-2-azapentatriacontan-35-oate, BzL-3 was synthesized according to the procedure described for BzL-22. LC/MS [M+H] 1214.56 (calculated); LC/MS [M+H] 1214.97 (observed).

Example 34: Synthesis of BzL-4
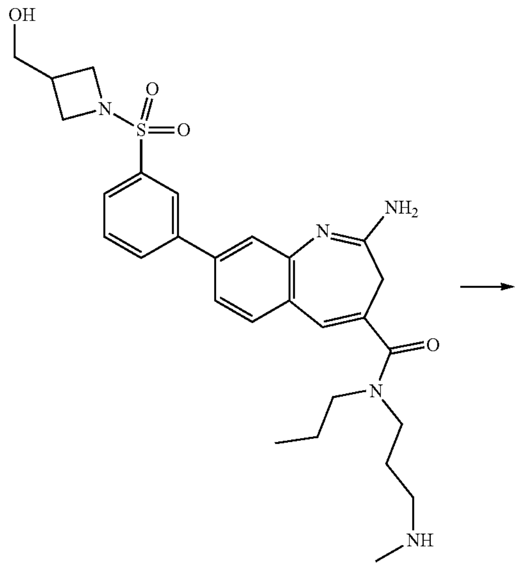
BzL-2a
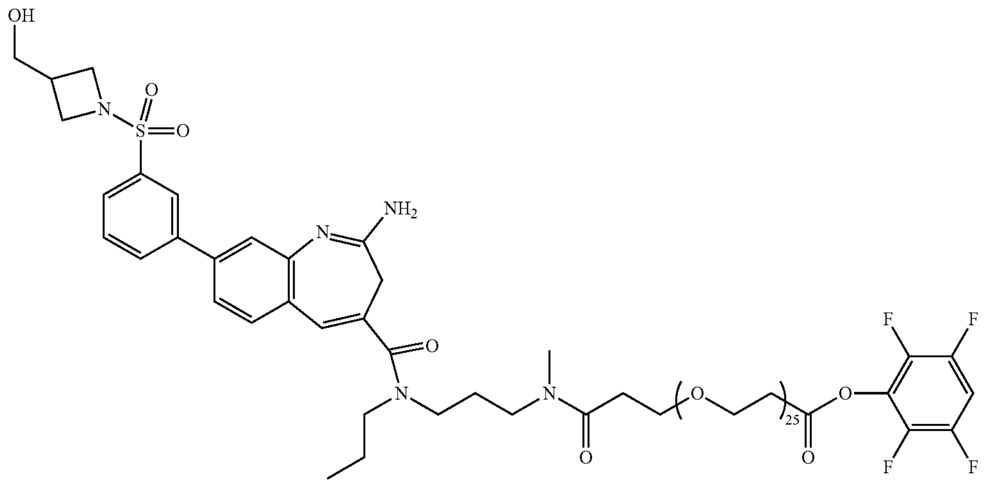
BzL-4
2,3,5,6-Tetrafluorophenyl 84-(2-amino-8-(3-((3-(hydroxymethyl)azetidin-1-yl)sulfonyl)phenyl)-3H-benzo[b]azepine-4-carbonyl)-80-methyl-79-oxo-4,7,10,13,16,19,22,25,28,31,34,37,40,43,46,49,52,55,58,61,64,67,70,73,76-pentacosaoxa-80,84-diazaheptaoctacontanoate, BzL-4 was synthesized according to the procedure described for BzL-15. LC/MS [M+H] 1888.93 (calculated); LC/MS [M+H] 1889.53 (observed).

Example 35: Synthesis of BzL-5
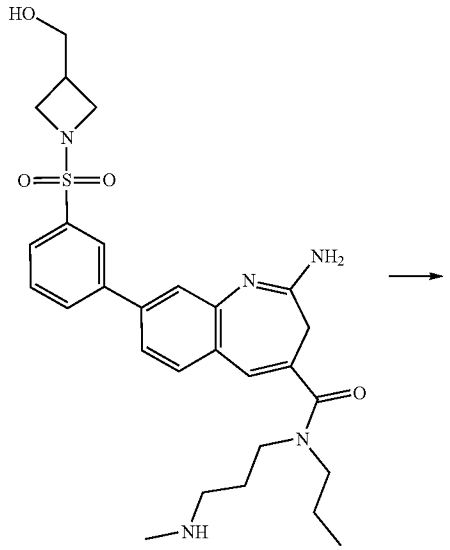
BzL-2a
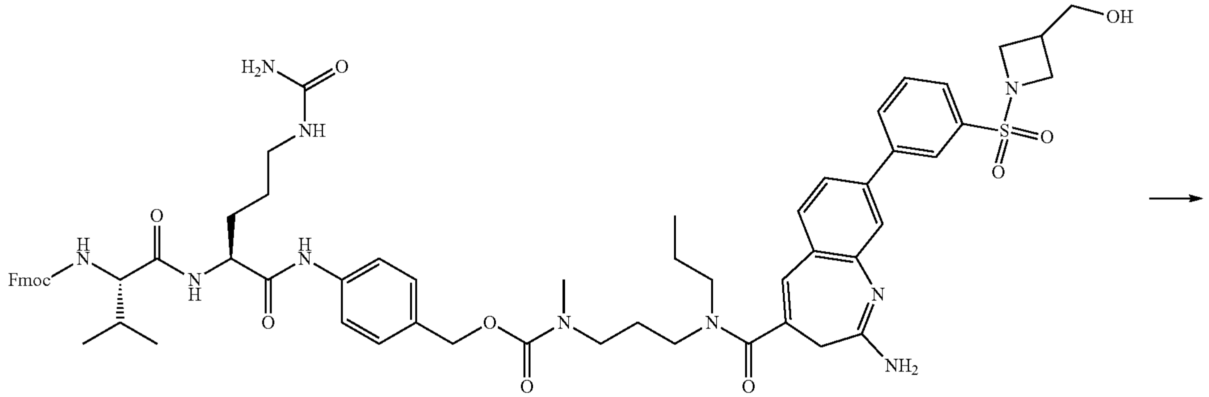
BzL-5a
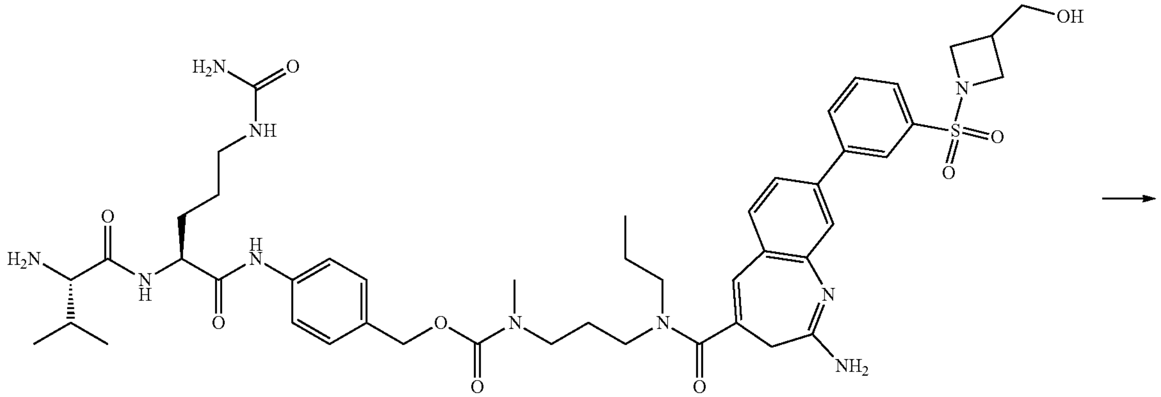
BzL-5b -continued

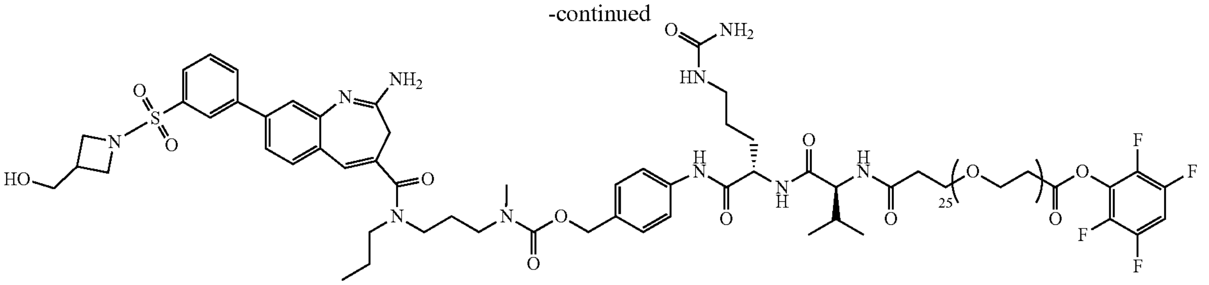

BzL-5

4-((S)-2-((S)-2-((((9H-Fluoren-9-yl)methoxy)carbonyl)amino)-3-methylbutanamido)-5-ureidopentanamido)benzyl (3-(2-amino-8-(3-((3-(hydroxymethyl)azetidin-1-yl)sulfonyl)phenyl)-N-propyl-3H-benzo[b]azepine-4-carboxamido)propyl)(methyl)carbamate, BzL-5a was synthesized according to the procedure described for BzL-26a.

4-((S)-2-((S)-2-Amino-3-methylbutanamido)-5-ureidopentanamido)benzyl (3-(2-amino-8-(3-((3-(hydroxymethyl)azetidin-1-yl)sulfonyl)phenyl)-N-propyl-3H-benzo[b]azepine-4-carboxamido)propyl)(methyl)carbamate, BzL-5b was synthesized according to the procedure described for BzL-26. LC/MS [M+H] 945.47 (calculated); LC/MS [M+H] 945.82 (observed).

2,3,5,6-Tetrafluorophenyl (6S,9S)-1-amino-6-((4-((((3-(2-amino-8-(3-((3-(hydroxymethyl)azetidin-1-yl)sulfonyl)phenyl)-N-propyl-3H-benzo[b]azepine-4-carboxamido)propyl)(methyl)carbamoyl)oxy)methyl)phenyl)carbamoyl)-9-isopropyl-1,8,11-trioxo-14,17,20,23,26,29,32,35,38,41,44,47,50,53,56,59,62,65,68,71,74,77,80,83,86-pentacosaoxa-2,7,10-triazanonaoctacontan-89-oate, BzL-5 was synthesized according to the procedure described for BzL-15. LC/MS [M+2H/2] 1147.57 (calculated); LC/MS [M+H] 1148.37 (observed).

Example 36: Synthesis of BzL-13

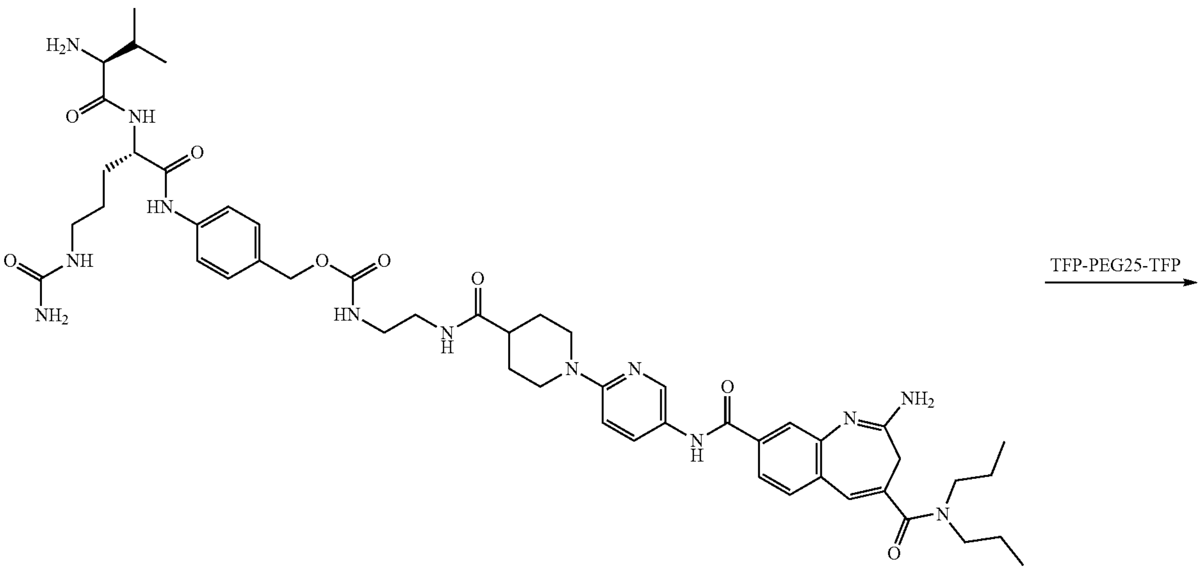

BzL-13a

-continued

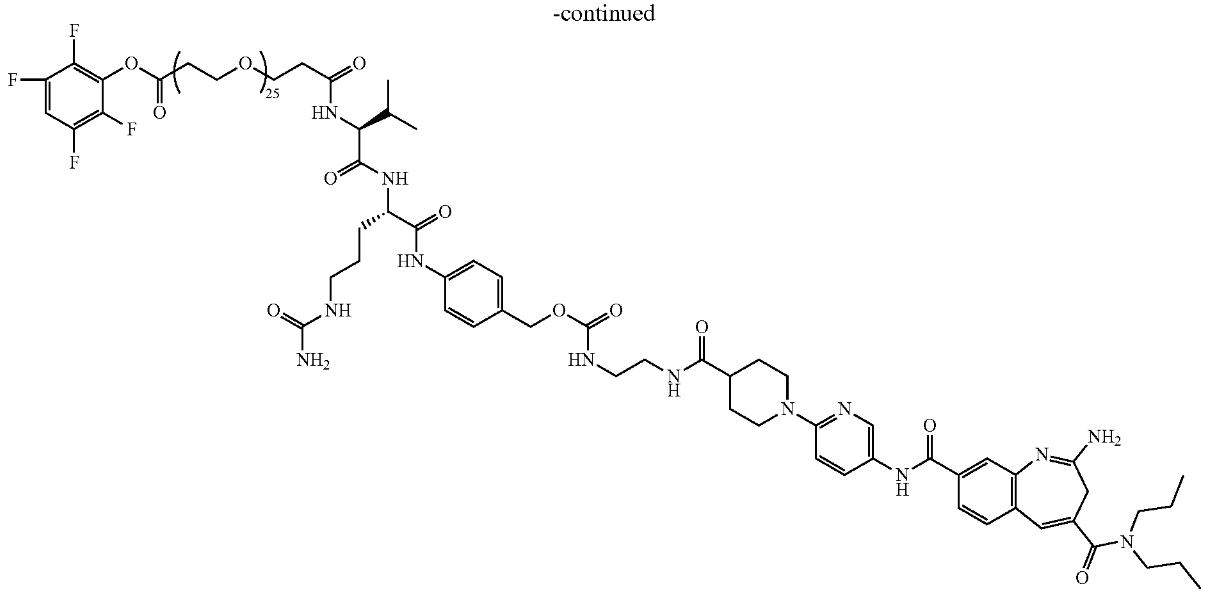

BzL-13

2,3,5,6-Tetrafluorophenyl (6S,9S)-1-amino-6-((4-((((2-(1-(5-(2-amino-4-(dipropylcarbamoyl)-3H-benzo[b]azepine-8-carboxamido)pyridin-2-yl)piperidine-4-carboxamido)ethyl)carbamoyl)oxy)methyl)phenyl)carbamoyl)-9-isopropyl-1,8,11-trioxo-14,17,20,23,26,29,32,35,38,41,44,47,50,53,56,59,62,65,68,71,74,77,80,83,86-pentacosaoxa-2,7,10-triazanonaoctacontan-89-oate, BzL-13 was synthesized from BzL-13a and TFP-PEG25-TFP according to the procedure described for BzL-15. LC/MS [M+2H/2] 1165.10 (calculated); LC/MS [M+H] 1165.91 (observed).

Example 37: Synthesis of BzL-14

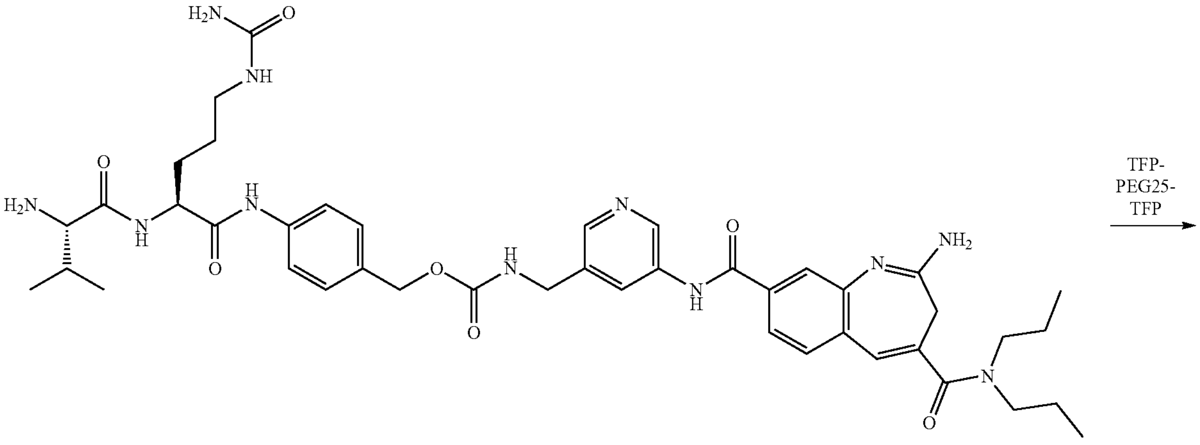

BzL-11

-continued

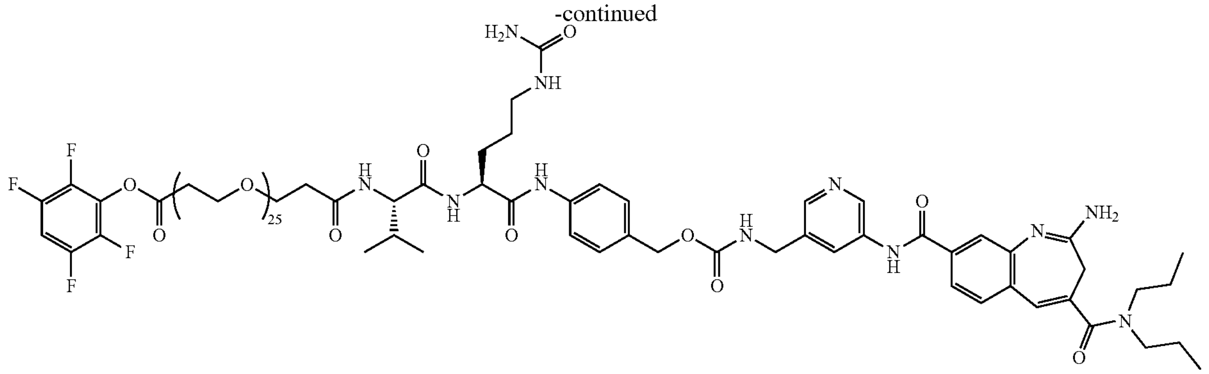

BzL-14

2,3,5,6-Tetrafluorophenyl (6S,9S)-1-amino-6-((4-(((((6-(2-amino-4-(dipropylcarbamoyl)-3H-benzo[b]azepine-8-carboxamido)pyridin-3-yl)methyl)carbamoyl)oxy)methyl)phenyl)carbamoyl)-9-isopropyl-1,8,11-trioxo-14,17,20,23,26,29,32,35,38,41,44,47,50,53,56,59,62,65,68,71,74,77,80,83,86-pentacosaoxa-2,7,10-triazanonaoctacontan-89-oate, BzL-14 was synthesized from BzL-11 and TFP-PEG25-TFP according to the procedure described for BzL-15. LC/MS [M+2H/2] 1095.06 (calculated); LC/MS [M+H] 1095.87 (observed).

Example 38: Synthesis of BzL-15

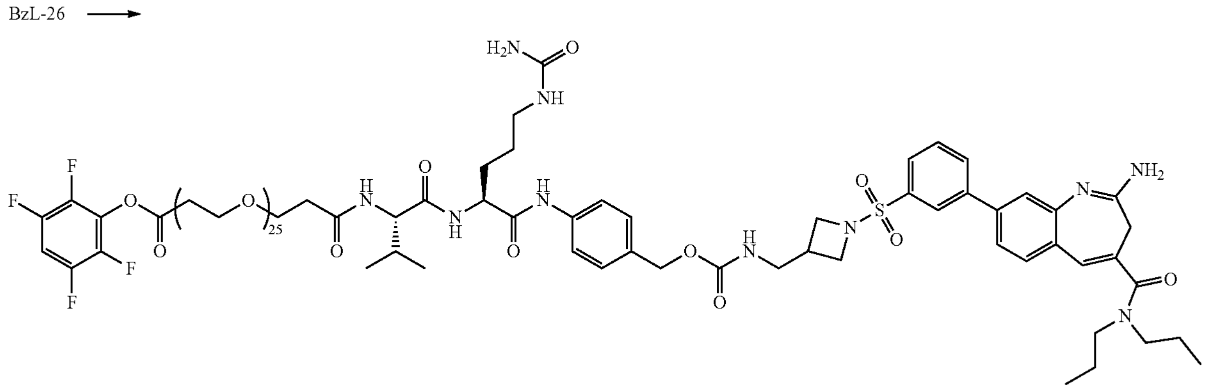

BzL-15

Synthesis of 2,3,5,6-tetrafluorophenyl (6S,9S)-1-amino-6-((4-(((((1-((3-(2-amino-4-(dipropylcarbamoyl)-3H-benzo[b]azepin-8-yl)phenyl)sulfonyl)azetidin-3-yl)methyl)carbamoyl)oxy)methyl)phenyl)carbamoyl)-9-isopropyl-1,8,11-trioxo-14,17,20,23,26,29,32,35,38,41,44,47,50,53,56,59,62,65,68,71,74,77,80,83,86-pentacosaoxa-2,7,10-triazanonaoctacontan-89-oate, BzL-15).

Synthesis of bis(2,3,5,6-tetrafluorophenyl) 4,7,10,13,16,19,22,25,28,31,34,37,40,43,46,49,52,55,58,61,64,67,70,73,76-pentacosaoxanonaheptacontanedioate, TFP-PEG25-TFP.

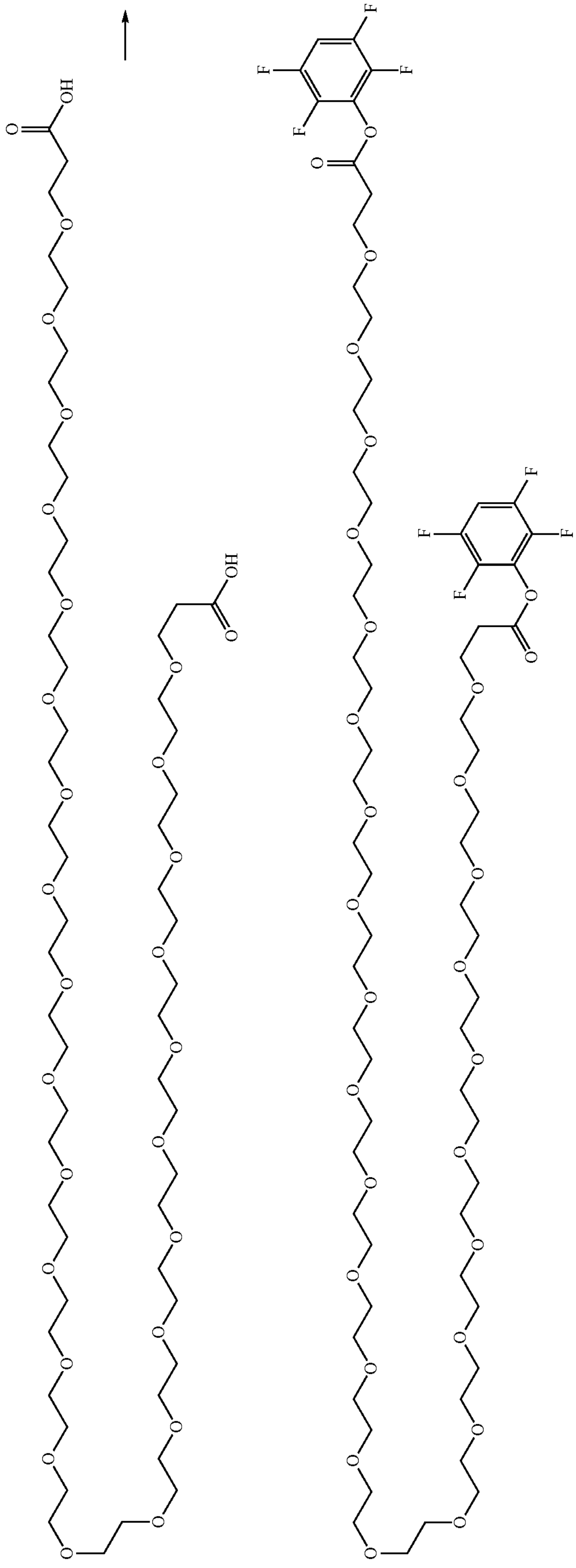
TFP-PEG25-TFP

A vial was charged with 4,7,10,13,16,19,22,25,28,31,34,37,40,43,46,49,52,55,58,61,64,67,70,73,76-pentacosaoxanonaheptacontanedioic acid (269 mg, 0.221 mmol), 2,3,5,6-tetrafluorophenol (110 mg, 0.662 mmol), collidine (176 μL, 1.33 mmol), 1-ethyl-3-(3-dimethylaminopropyl) carbodiimide (127 mg, 0.221 mmol) and 3 mL DMF. The reaction was stirred for 16 h, then purified by reverse phase preparative HPLC utilizing a 25-75% gradient of acetonitrile:water containing 0.1% trifluoroacetic acid. The purified fractions were combined and lyophilized to afford 266 mg of TFP-PEG25-TFP in 79% yield. LC/MS [M+H] 1515.68 (calculated); LC/MS [M+H] 1516.00 (observed).

A vial was charged with BzL-26 (11.9 mg, 0.013 mmol), TFP-PEG25-TFP (19.7 mg, 0.013 mmol), collidine (5.6 μL, 0.042 mmol) in 300 μL DMF. The reaction was maintained for 5 h and then purified by reverse phase preparative HPLC utilizing a 25-75% gradient of acetonitrile:water containing 0.1% trifluoroacetic acid. The purified fractions were combined and lyophilized to afford 7.7 mg of BzL-15 in 26% yield. LC/MS [M+2H/2]1132.56 (calculated); LC/MS [M+2H/2] 1133.30 (observed).

Example 39: Synthesis of BzL-16

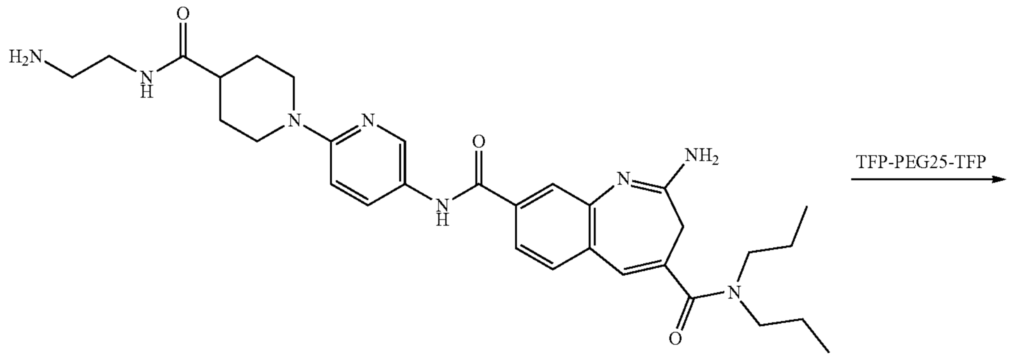

BzL-10

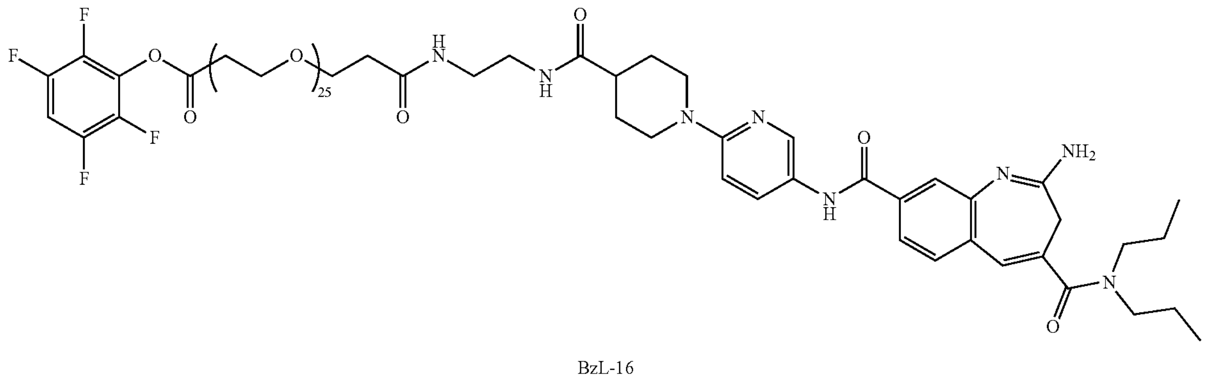

BzL-16

Synthesis of 2,3,5,6-tetrafluorophenyl 1-(1-(5-(2-amino-4-(dipropylcarbamoyl)-3H-benzo[b]azepine-8-carboxamido)pyridin-2-yl)piperidin-4-yl)-1,6-dioxo-9,12,15,18,21,24,27,30,33,36,39,42,45,48,51,54,57,60,63,66,69,72,75,78,81-pentacosaoxa-2,5-diazatetraoctacontan-84-oate, BzL-16 was synthesized from BzL-10 and TFP-PEG25-TFP according to the procedure described for Bz-31. LC/MS [M+H] 1924.01 (calculated); LC/MS [M+H] 1925.23 (observed).
Example 40: Synthesis of BzL-17
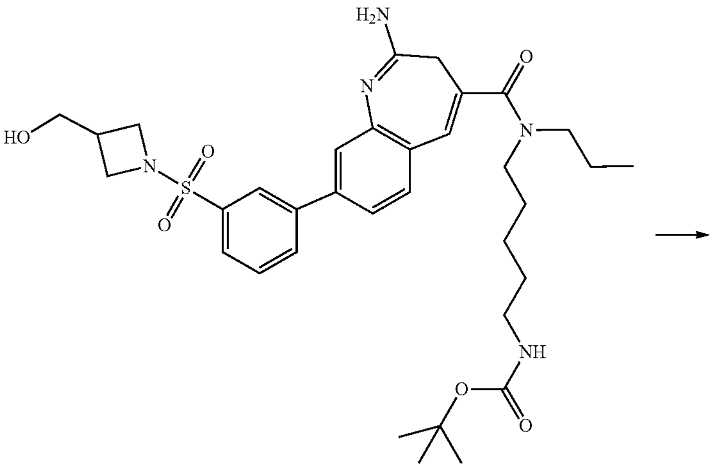
Bz-9
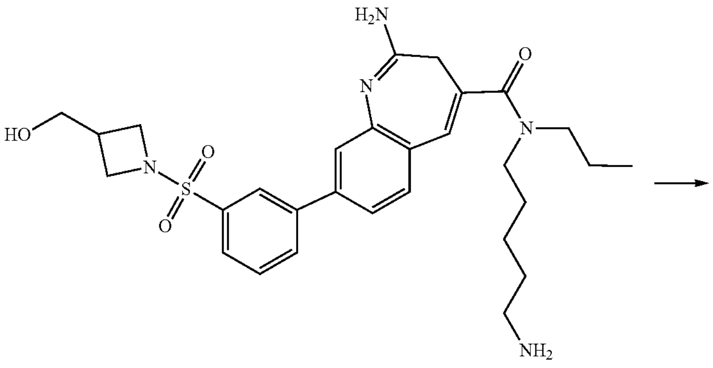
BzL-17a
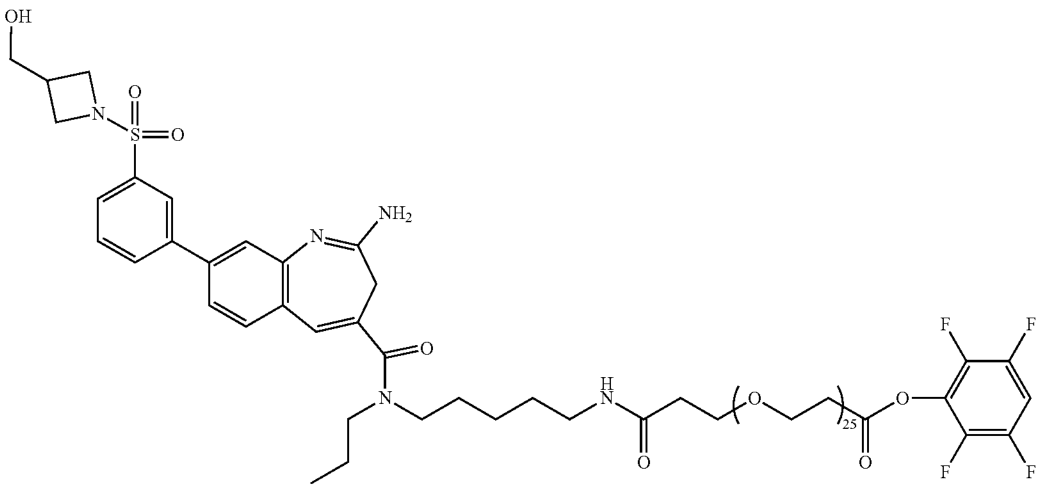
BzL-17

Synthesis of 2-amino-N-(5-aminopentyl)-8-(3-((3-(hydroxymethyl)azetidin-1-yl)sulfonyl)phenyl)-N-propyl-3H-benzo[b]azepine-4-carboxamide, BzL-17a. A vial was charged with Bz-9 (28 mg, 0.043 mmol), 300 μL DCM and 100 μL trifluoroacetic acid. The reaction was maintained for 1 h, upon which it was concentrated under reduced pressure. The resultant oil was azeotroped thrice with 1 mL toluene, after which was added 1 mL methanol and $K_2CO_3$ (38 mg, 0.28 mmol). After stirring for 16 h, the reaction was filtered and concentrated under reduced pressure and then purified by reverse phase preparative HPLC utilizing a 25-75% gradient of acetonitrile:water containing 0.1% trifluoracetic acid. The purified fractions were combined and lyophilized to afford 5.8 mg of BzL-17a in 24% yield. LC/MS [M+H] 554.28 (calculated); LC/MS [M+H] 554.47 (observed).

Synthesis of 2,3,5,6-tetrafluorophenyl 86-(2-amino-8-(3-((3-(hydroxymethyl)azetidin-1-yl)sulfonyl)phenyl)-3H-benzo[b]azepine-4-carbonyl)-79-oxo-4,7,10,13,16,19,22,25,28,31,34,37,40,43,46,49,52,55,58,61,64,67,70,73,76-pentacosaoxa-80,86-diazanonaoctacontanoate, BzL-17. A vial was charged with BzL-17a (5.8 mg, 0.011 mmol), TFP-PEG25-TFP (23.8 mg, 0.016 mmol), collidine (5.6 μL, 0.042 mmol) in 300 μL DMF. The reaction was maintained for 5 h and then purified by reverse phase preparative HPLC utilizing a 25-75% gradient of acetonitrile:water (ACN:H2O) containing 0.1% trifluoroacetic acid (TFA). The purified fractions were combined and lyophilized to afford 5.0 mg of BzL-17 in 25% yield. LC/MS [M+H] 1902.95 (calculated); LC/MS [M+H]1903.37 (observed).

Example 41: Synthesis of BzL-18

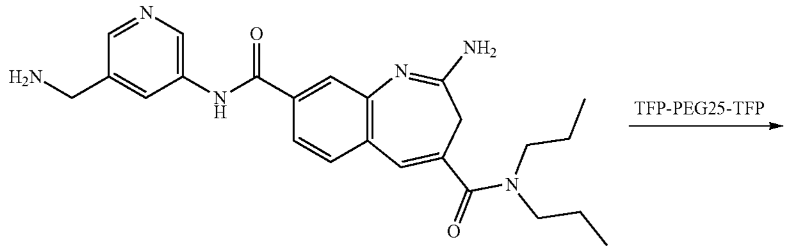

BzL-18a

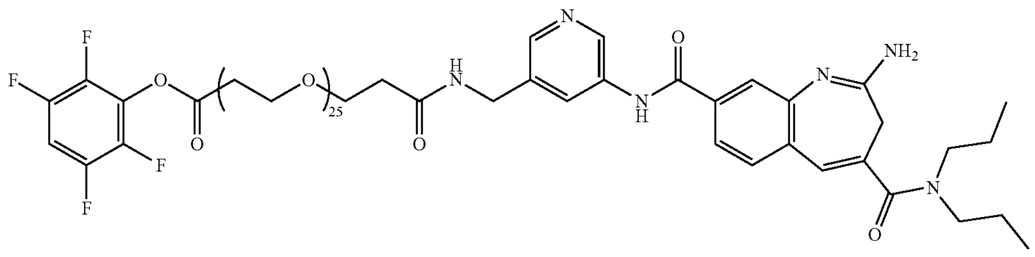

BzL-18

2,3,5,6-Tetrafluorophenyl 1-(6-(2-amino-4-(dipropylcarbamoyl)-3H-benzo[b]azepine-8-carboxamido)pyridin-3-yl)-3-oxo-6,9,12,15,18,21,24,27,30,33,36,39,42,45,48,51,54,57,60,63,66,69,72,75,78-pentacosaoxa-2-azahenoctacontan-81-oate, BzL-18 was synthesized from BzL-18a and TFP-PEG25-TFP according to the procedure described for BzL-15. LC/MS [M+H] 1783.92 (calculated); LC/MS [M+H] 1784.19 (observed).

Example 42: Synthesis of BzL-19

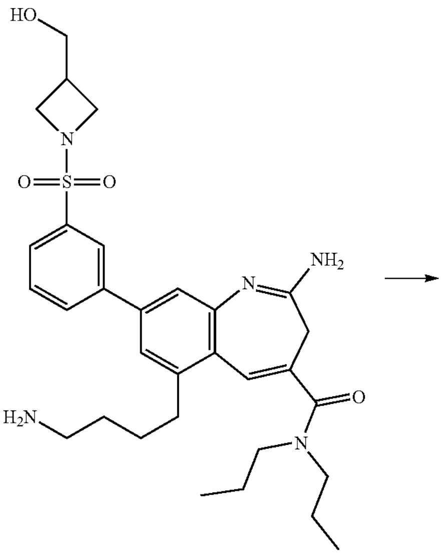

BzL-14

-continued

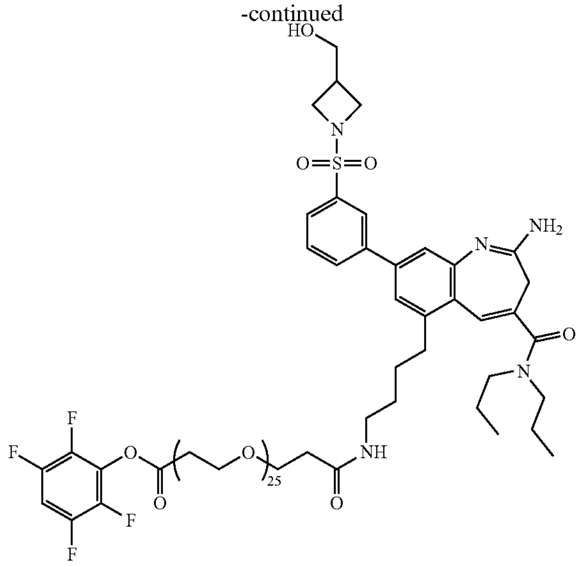

BzL-19

2,3,5,6-Tetrafluorophenyl 84-(2-amino-4-(dipropylcarbamoyl)-8-(3-((3-(hydroxymethyl)azetidin-1-yl)sulfonyl)phenyl)-3H-benzo[b]azepin-6-yl)-79-oxo-4,7,10,13,16,19,22,25,28,31,34,37,40,43,46,49,52,55,58,61,64,67,70,73,76-pentacosaoxa-80-azatetraoctacontanoate, BzL-19 was synthesized from Bz-14 and TFP-PEG25-TFP according to the procedure described for BzL-15. LC/MS [M+H] 1930.98 (calculated); LC/MS [M+H]1931.24 (observed).

Example 43: Synthesis of BzL-20

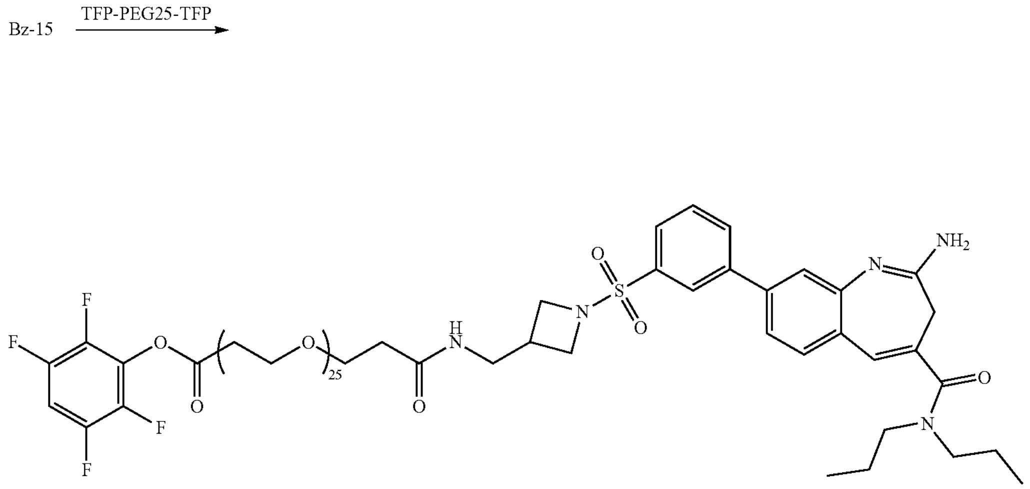

BzL-20

2,3,5,6-Tetrafluorophenyl 1-(1-((3-(2-amino-4-(dipropylcarbamoyl)-3H-benzo[b]azepin-8-yl)phenyl)sulfonyl)azetidin-3-yl)-3-oxo-6,9,12,15,18,21,24,27,30,33,36,39,42,45,48,51,54,57,60,63,66,69,72,75,78-pentacosaoxa-2-azahenoctacontan-81-oate, BzL-20 was synthesized from reaction of TFP-PEG25-TFP and Bz-15 according to the procedure described for BzL-15. LC/MS [M+H] 1858.92 (calculated); LC/MS [M+H] 1859.59 (observed).

Example 44: Synthesis of BzL-21
Bz-11a
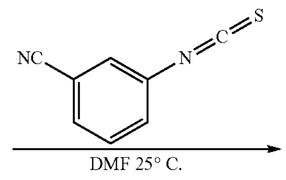
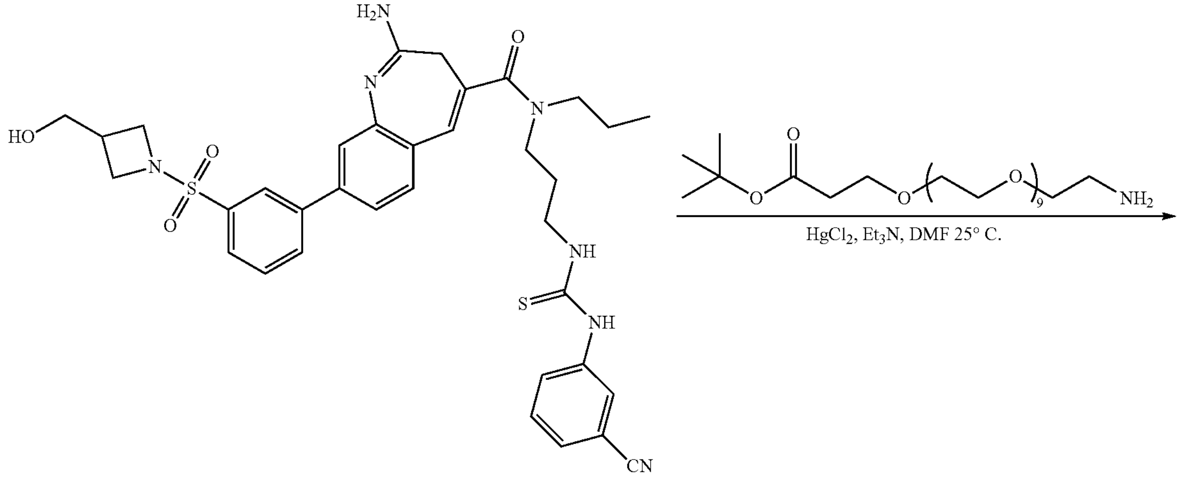
BzL-21a
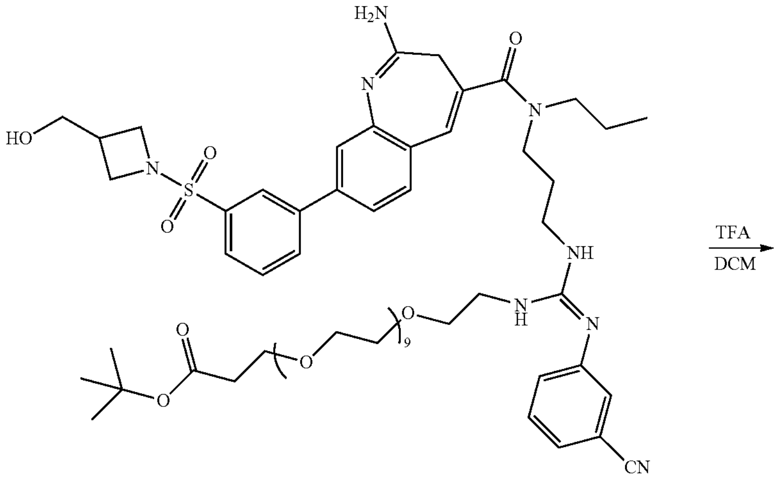
BzL-21b -continued

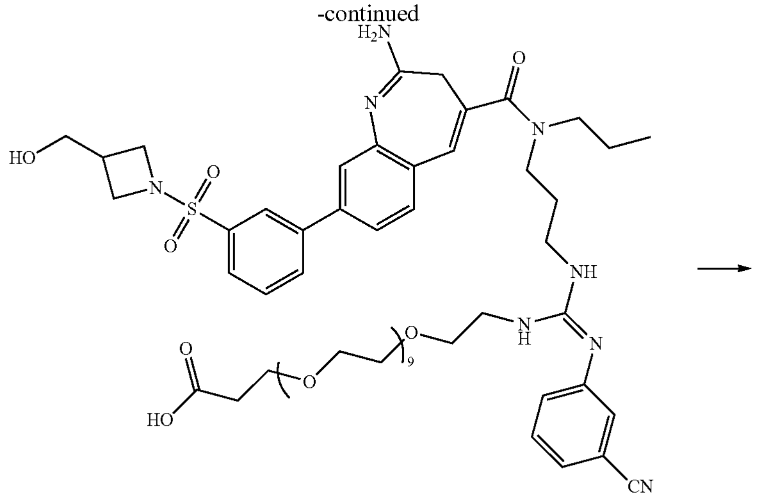

BzL-21c

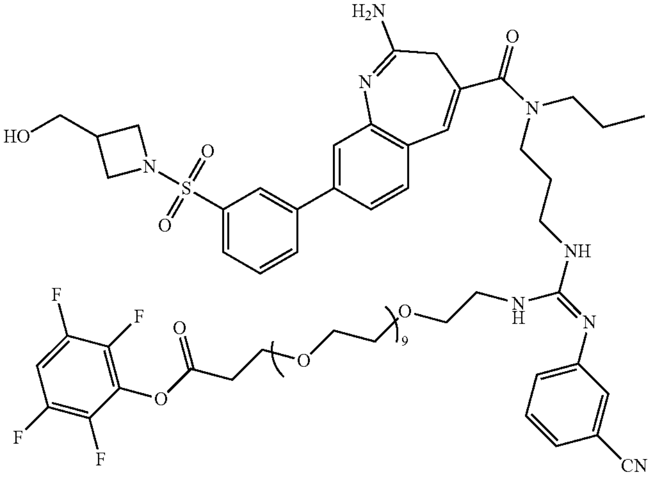

BzL-21

Synthesis of 2-amino-N-[3-[(3-cyanophenyl)carbamothioylamino]propyl]-8-[3-[3-(hydroxymethyl)azetidin-1-yl] sulfonylphenyl]-N-propyl-3H-1-benzazepine-4-carboxamide, BzL-21a. To a mixture of 2-amino-N-(3-aminopropyl)-8-[3-[3-(hydroxymethyl)azetidin-1-yl] sulfonylphenyl]-N-propyl-3H-1-benzazepine-4-carboxamide, Bz-11a (0.1 g, 190.24 μmol, 1 eq) in DMF (2 mL) was added 3-isothiocyanatobenzonitrile (30.48 mg, 190.24 μmol, 1 eq) in one portion at 15° C. The mixture was stirred at 15° C. for 3 hours. LCMS showed the desired was detected. The mixture was filtered and purified by prep-HPLC (column: Nano-micro KROMASIL™ (Nouryon) C18 100×30 mm, 5 μm particle size; mobile phase: [water (0.1% TFA)-ACN]; B %: 20%-60%, 10 min) to give 2-amino-N-[3-[(3-cyanophenyl) carbamothioylamino]propyl]-8-[3-[3-(hydroxymethyl)azetidin-1-yl]sulfonylphenyl]-N-propyl-3H-1-benzazepine-4-carboxamide, BzL-21a (0.06 g, 87.48 μmol, 45.99% yield) was obtained as light yellow solid.

Synthesis of tert-butyl 3-[2-[2-[2-[2-[2-[2-[2-[2-[2-[2-[(Z)-[[3-[[2-amino-8-[3-[3-(hydroxymethyl)azetidin-1-yl] sulfonylphenyl]-3H-1-benzazepine-4-carbonyl]-propyl-amino]propylamino]-(3-cyanoanilino)methylene]amino] ethoxy]ethoxy]ethoxy]ethoxy]ethoxy]ethoxy]ethoxy] ethoxy]ethoxy]ethoxy]propanoate, BzL-21b. To a mixture of BzL-21a (0.06 g, 87.48 μmol, 1 eq) and tert-butyl 3-[2-[2-[2-[2-[2-[2-[2-[2-[2-(2-aminoethoxy)ethoxy] ethoxy]ethoxy]ethoxy]ethoxy]ethoxy]ethoxy]ethoxy] ethoxy]propanoate (61.49 mg, 104.98 μmol, 1.2 eq) in DMF (2 mL) was added $Et_3N$ (17.70 mg, 174.96 μmol, 24.35 μL, 2 eq) and $HgCl_2$ (28.50 mg, 104.98 μmol, 5.24 μL, 1.2 eq). The mixture was stirred at 15° C. for 18 hours. LCMS showed the reactant was consumed. The mixture was filtered and poured into water (10 mL). The aqueous phase was extracted with ethyl acetate (10 mL×3). The combined organic phase was concentrated to give BzL-21b (0.1 g, crude) as light yellow oil which was used into the next step without further purification.

Synthesis of 3-[2-[2-[2-[2-[2-[2-[2-[2-[2-[2-[(Z)-[[3-[[2-amino-8-[3-[3-(hydroxymethyl)azetidin-1-yl]sulfonylphenyl]-3H-1-benzazepine-4-carbonyl]-propyl-amino]propylamino]-(3-cyanoanilino)methylene]amino]ethoxy]ethoxy] ethoxy]ethoxy]ethoxy]ethoxy]ethoxy]ethoxy]ethoxy] ethoxy]propanoic acid, BzL-21c. To a mixture of BzL-21b (86.04 mg, 69.52 μmol, 1 eq) in $H_2O$ (10 mL) was added TFA (396.36 mg, 3.48 mmol, 257.38 μL, 50 eq) in one portion at 15° C. The mixture was stirred at 85° C. for 10 min. LCMS showed the reactant was consumed. The mixture was concentrated. The residue was purified by prep- HPLC (column: Nano-micro KROMASIL™ (Nouryon) C18 100×30 mm, 5 μm particle size; mobile phase: [water (0.10% TFA)-ACN]; B %: 10%-40%, 10 min) to give BzL-21c (18 mg, 13.71 μmol, 19.72% yield, 90% purity) was obtained as a white solid. $^{1}H$ NMR (MeOD, 400 MHz) δ 8.12-8.08 (m, 2H), 7.92 (d, J=8.0 Hz, 1H), 7.84-7.81 (m, 4H), 7.64 (s, 3H), 7.12 (s, 1H), 3.87 (t, J=8.4 Hz, 2H), 3.72-3.70 (m, 9H), 3.63-3.58 (m, 38H), 3.43-3.41 (m, 6H), 2.62-2.57 (m, 1H), 2.52 (t, J=6.0 Hz, 2H), 2.04 (s, 2H), 1.75-1.70 (m, 3H), 0.96-0.92 (m, 3H).

2,3,5,6-Tetrafluorophenyl (Z)-40-(2-amino-8-(3-((3-(hydroxymethyl)azetidin-1-yl)sulfonyl)phenyl)-3H-benzo[b]azepine-4-carbonyl)-35-((3-cyanophenyl)imino)-4,7,10,13,16,19,22,25,28,31-decaoxa-34,36,40-triazatritetracont-anoate, BzL-21 was synthesized according to the procedure described for BzL-22. LC/MS [M+H] 1329.57 (calculated); LC/MS [M+H] 1329.77 (observed).

Example 45: Synthesis of BzL-22

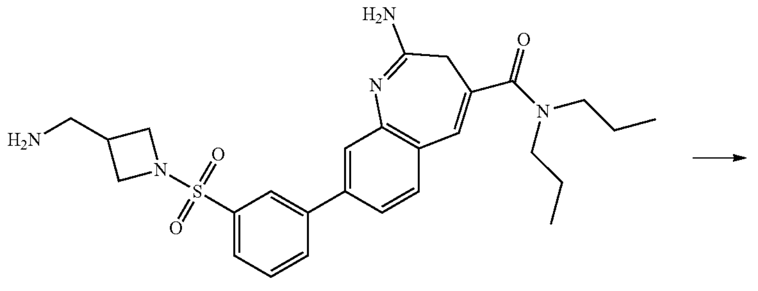

Bz-15

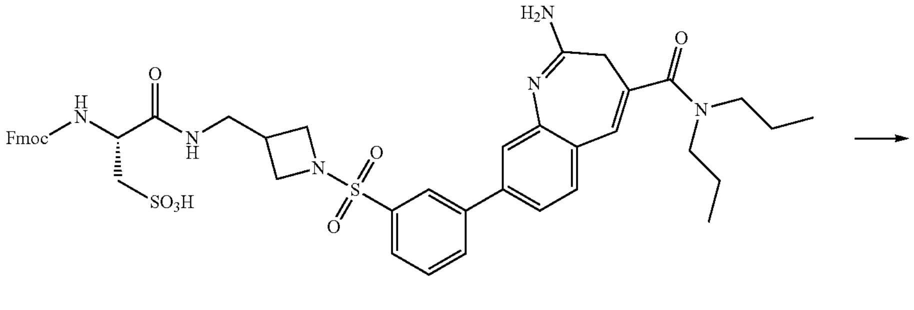

BzL-22a

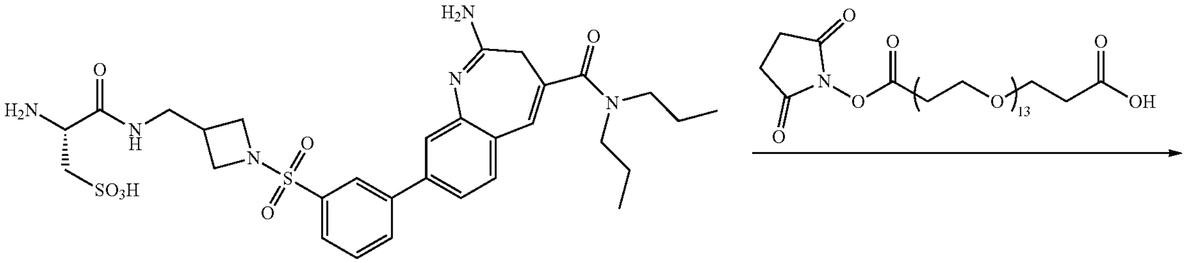

BzL-22b

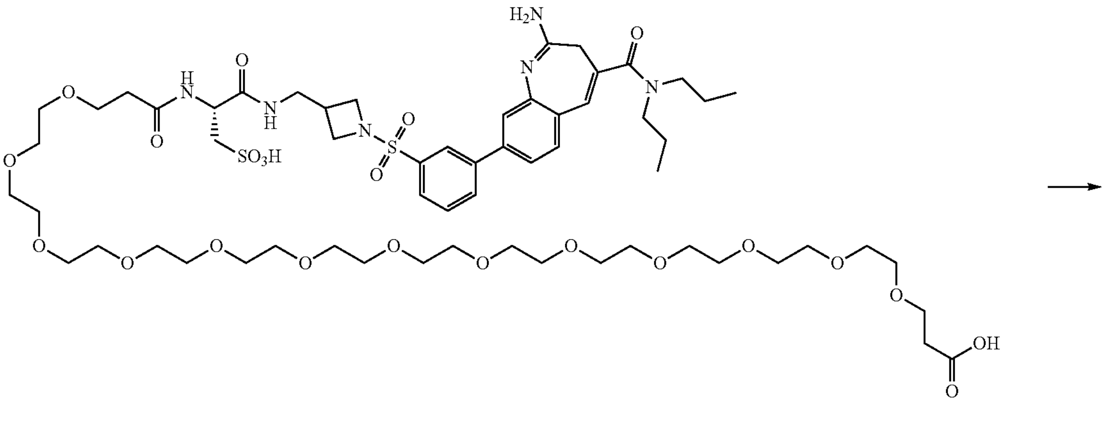

BzL-22c

-continued

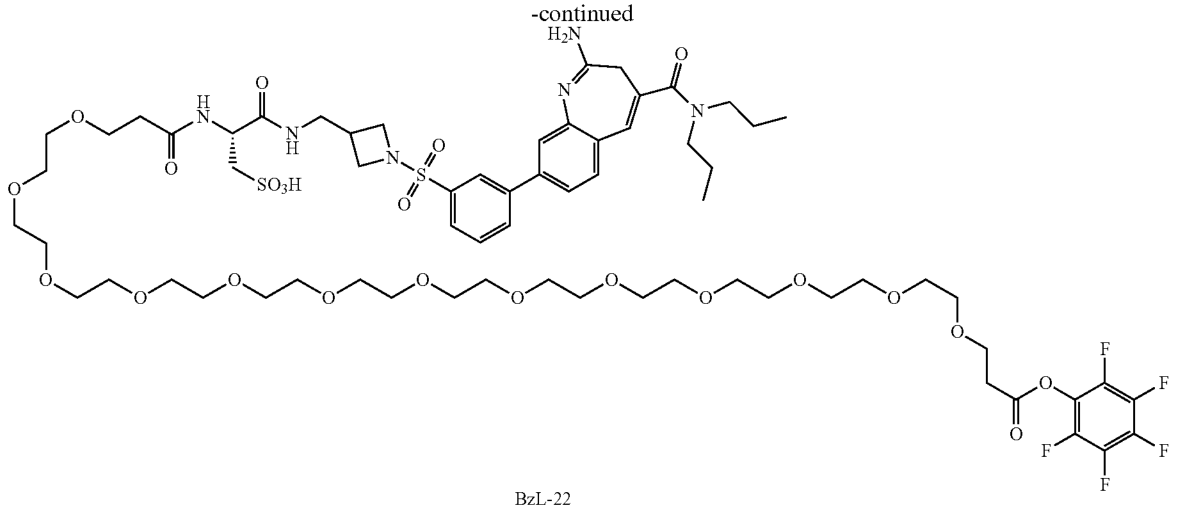

BzL-22

Synthesis of (R)-2-((((9H-fluoren-9-yl)methoxy)carbonyl)amino)-3-(((1-((3-(2-amino-4-(dipropylcarbamoyl)-3H-benzo[b]azepin-8-yl)phenyl)sulfonyl)azetidin-3-yl)methyl)amino)-3-oxopropane-1-sulfonic acid, BzL-22a. A vial was charged with Bz-15 (14.7 mg, 0.024 mmol), Fmoc-L-Cysteic Acid (11.2 mg, 0.024 mmol), collidine (12 μL, 0.090 mmol), HATU (12 mg, 0.032 mmol) and 500 μL DMF. The reaction was stirred until Bz-15 was consumed by LCMS. The crude mixture was purified by reverse phase preparative HPLC utilizing a 25-75% gradient of acetonitrile:water containing 0.1% trifluoroacetic acid. The purified fractions were combined and lyophilized to afford 8.6 mg of BzL-22a in 41% yield. LC/MS [M+H] 883.32 (calculated); LC/MS [M+H] 883.49 (observed).

Synthesis of (R)-2-amino-3-(((1-((3-(2-amino-4-(dipropylcarbamoyl)-3H-benzo[b]azepin-8-yl)phenyl)sulfonyl)azetidin-3-yl)methyl)amino)-3-oxopropane-1-sulfonic acid, BzL-22b. A vial was charged with BzL-22a (8.6 mg, 0.01 mmol), diethylamine (10 μL, 0.10 mmol), 100 μL acetonitrile and 50 μL DMF. The reaction was stirred for 3 h, then concentrated under reduced pressure. The crude reaction was azeotroped thrice with 2 mL toluene and take on to the subsequent step.

Synthesis of (R)-1-(1-((3-(2-amino-4-(dipropylcarbamoyl)-3H-benzo[b]azepin-8-yl)phenyl)sulfonyl)azetidin-3-yl)-3,6-dioxo-4-(sulfomethyl)-9,12,15,18,21,24,27,30,33,36,39,42,45-tridecaoxa-2,5-diazaoctatetracontan-48-oic acid, BzL-22c. A vial was charged with crude BzL-22b (0.01 mmol), 43-((2,5-dioxopyrrolidin-1-yl)oxy)-43-oxo-4,7,10,13,16,19,22,25,28,31,34,37,40-tridecaoxatritetracontanoic acid (7.7 mg, 0.01 mmol), diisopropylethylamine (5.3 μL, 0.03 mmol), 1-hydroxy-7-azabenzotriazole, HOAt, CAS Reg. No. 39968-33-7 (4 mg, 0.03 mmol) and 140 μL DMF. The reaction was stirred for 8 h, then purified by reverse phase preparative HPLC utilizing a 25-75% gradient of acetonitrile:water containing 0.1% trifluoroacetic acid. The purified fractions were combined and lyophilized to afford 8.4 mg of BzL-22c in 64% yield. LC/MS [M+H]1333.60 (calculated); LC/MS [M+H] 1333.69 (observed).

Synthesis of (R)-2-(((1-((3-(2-amino-4-(dipropylcarbamoyl)-3H-benzo[b]azepin-8-yl)phenyl)sulfonyl)azetidin-3-yl)methyl)carbamoyl)-4,46-dioxo-46-(2,3,5,6-tetrafluorophenoxy)-7,10,13,16,19,22,25,28,31,34,37,40,43-tridecaoxa-3-azahexatetracontane-1-sulfonic acid, BzL-22. A vial was charged with BzL-22c (7.2 mg, 0.005 mmol), 2,3,5,6-tetrafluorophenol (1.8 mg, 0.011 mmol), collidine (2.2 μL, 0.016 mmol), 1-ethyl-3-(3-dimethylaminopropyl) carbodiimide (1 mg, 0.005 mmol) and 100 μL DMF. The reaction was stirred for 16 h, then purified by reverse phase preparative HPLC utilizing a 25-75% gradient of acetonitrile:water containing 0.1% trifluoroacetic acid. The purified fractions were combined and lyophilized to afford 5.3 mg of BzL-22 in 66% yield. LC/MS [M+H] 1481.60 (calculated); LC/MS [M+H] 1481.82 (observed).

Example 46: Synthesis of BzL-23

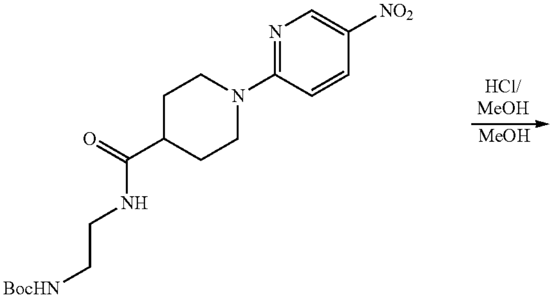

BzL-23a

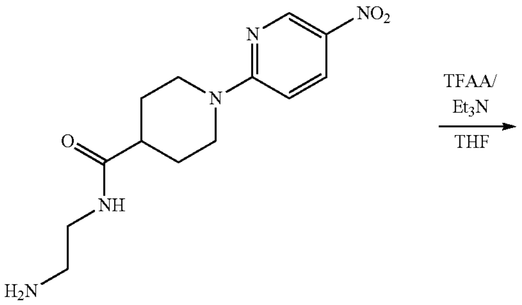

BzL-23b

-continued

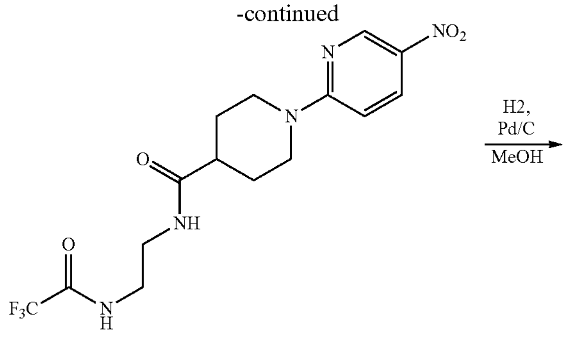

BzL-23c

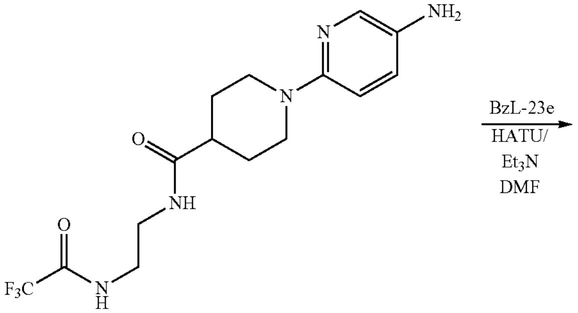

BzL-23d

Synthesis of N-(2-aminoethyl)-1-(5-nitropyridin-2-yl)piperidine-4-carboxamide, BzL-23b. To a mixture of tert-butyl N-[2-[[1-(5-nitro-2-pyridyl)piperidine-4-carbonyl]amino] ethyl]carbamate, BzL-23a (0.5 g, 1.27 mmol, 1 eq) in EtOAc (10 mL) was added HCl/EtOAc (4 M, 3.18 mL, 10 eq) at 25° C. The mixture was stirred at 25° C. for 2 hours. LCMS showed the reaction was completed. The reaction was concentrated in vacuum to give BzL-23b (0.4 g, 1.21 mmol, 95.44% yield, HCl) as a yellow solid.

Synthesis of 1-(5-nitropyridin-2-yl)-N-(2-(2,2,2-trifluoroacetamido) ethyl)piperidine-4-carboxamide, BzL-23c. To a mixture of N-(2-aminoethyl)-1-(5-nitro-2-pyridyl)piperidine-4-carboxamide, BzL-23b (0.4 g, 1.21 mmol, 1 eq, HCl) in THE (10 mL) was added $Et_3N$ (368.21 mg, 3.64 mmol, 506.47 μL, 3 eq) and (2,2,2-trifluoroacetyl) 2,2,2-trifluoroacetate (382.13 mg, 1.82 mmol, 253.06 μL, 1.5 eq) at 25° C. The mixture was stirred at 25° C. for 1 hours. LCMS showed major as desired. The mixture was poured into water (50 mL). The aqueous phase was extracted with ethyl acetate (30 mL×3). The combined organic phase was washed with brine (30 mL), dried with anhydrous $Na_2SO_4$, filtered and concentrated in vacuum. The residue was used to next step directly, containing BzL-23c (0.4 g, 1.03 mmol, 84.71% yield) as a yellow solid. $^1$H NMR (DMSO-$d_6$, 400 MHz) δ 9.37-9.45 (m, 1H), 8.95 (d, J=2.8 Hz, 1H), 8.19 (dd, J=9.6, 2.8 Hz, 1H), 8.03 (br t, J=5.2 Hz, 1H), 6.96 (d, J=9.6 Hz, 1H), 4.47-4.53 (m, 2H), 2.99-3.25 (m, 6H), 2.38-2.47 (m, 3H), 1.73-1.80 (m, 2H), 1.41-1.58 (m, 2H).

Synthesis of 1-(5-aminopyridin-2-yl)-N-(2-(2,2,2-trifluoroacetamido) ethyl)piperidine-4-carboxamide, BzL-23d. To a solution of 1-(5-nitro-2-pyridyl)-N-[2-[(2,2,2-trifluoroacetyl)amino]ethyl] piperidine-4-carboxamide, BzL-23c (0.4 g, 1.03 mmol, 1 eq) in MeOH (30 mL) was added Pd/C (0.5 g, 5% purity) under $N_2$. The suspension was degassed under vacuum and purged with $H_2$ several times. The mixture was stirred under $H_2$ (50 psi) at 25° C. for 2 hours. TLC showed the reaction was completed. The mixture was filtered and concentrated in vacuum to give BzL-23d (0.3 g, 834.85 μmol, 81.26% yield) as a gray solid. $^1$H NMR (DMSO-$d_6$, 400 MHz) δ 9.39-9.46 (m, 1H), 7.97 (t, J=5.2 Hz, 1H), 7.59 (d, J=2.8 Hz, 1H), 6.90 (dd, J=8.8, 2.8 Hz, 1H), 6.64 (d, J=8.8 Hz, 1H), 3.99 (d, J=12.8 Hz, 2H), 3.15-3.26 (m, 6H), 2.54-2.63 (m, 2H), 2.16-2.26 (m, 1H), 1.65-1.71 (m, 2H), 1.48-1.60 (m, 2H).

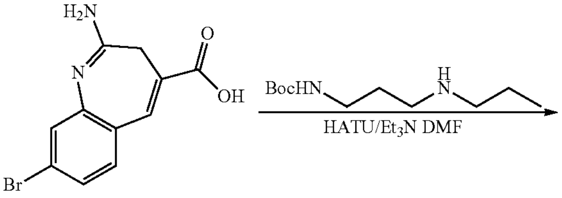

BzL-23f

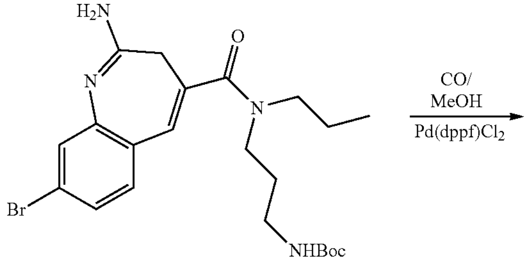

BzL-23g

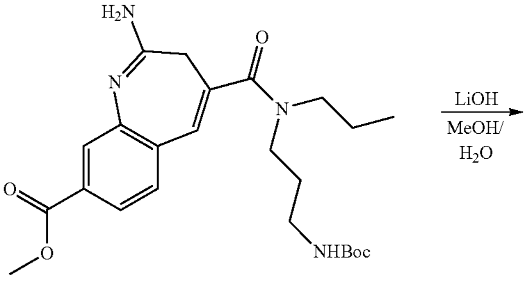

BzL-23h

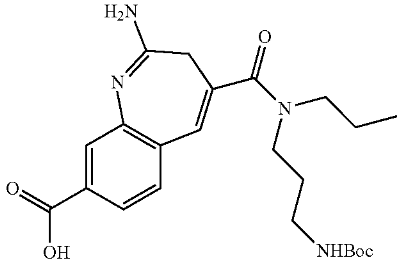

BzL-23e

Synthesis of tert-butyl (3-(2-amino-8-bromo-N-propyl-3H-benzo[b]azepine-4-carboxamido)propyl)carbamate, BzL-23g. To a mixture of 2-amino-8-bromo-3H-1-benzazepine-4-carboxylic acid, BzL-23f (4.09 g, 14.56 mmol, 1 eq) and tert-butyl N-[3-(propylamino)propyl]carbamate (3.78 g, 17.47 mmol, 1.2 eq) in DMF (10 mL) was added HATU (6.64 g, 17.47 mmol, 1.2 eq) and $Et_3N$ (2.95 g, 29.12 mmol, 4.05 mL, 2 eq) in one portion at 25 C. The mixture was stirred at 25° C. for 1 h. LCMS showed the reaction was finished. The mixture was diluted with water and extracted with EtOAc (50 mL×3). The organic layer was washed with brine, dried over $Na_2SO_4$, filtered and concentrated. The residue was purified by silica gel chromatography (column height: 250 mm, diameter: 100 mm, 100-200 mesh silica gel, petroleum ether/ethyl acetate=1/0, 0/1) to afford BzL-23g (6 g, 12.52 mmol, 85.95% yield) as a yellow oil.

Synthesis of methyl 2-amino-4-[3-(tert-butoxycarbonylamino)propyl-propyl-carbamoyl]-3H-1-benzazepine-8-carboxylate, BzL-23h. To a solution of tert-butyl N-[3-[(2-amino-8-bromo-3H-1-benzazepine-4-carbonyl)-propyl-amino]propyl] carbamate, BzL-23g (5 g, 10.43 mmol, 1 eq) in MeOH (50 mL) was added $Et_3N$ (3.17 g, 31.29 mmol, 4.35 mL, 3 eq) and $Pd(dppf)Cl_2$ (763.13 mg, 1.04 mmol, 0.1 eq) under $N_2$. The suspension was degassed under vacuum and purged with CO (10.43 mmol, 1 eq) several times. The mixture was stirred under CO (50 psi) at 80° C. for 12 hours. LCMS showed the reaction was finished. The mixture was filtered and concentrated to give BzL-23h (7 g, crude) as yellow oil.

Synthesis of 2-amino-4-((3-((tert-butoxycarbonyl)amino)propyl)(propyl)carbamoyl)-3H-benzo[b]azepine-8-carboxylic acid, BzL-23e. To a mixture of methyl 2-amino-4-[3-(tert-butoxycarbonylamino)propyl-propyl-carbamoyl]-3H-1-benzazepine-8-carboxylate, BzL-23h (6 g, 13.08 mmol, 1 eq) in MeOH (80 mL) was added LiOH (1.25 g, 52.34 mmol, 4 eq) in one portion at 30° C. The mixture was stirred at 30° C. for 12 h. LCMS showed the reaction was finished. The mixture was adjusted pH 6 with aq. HCl (1 M) at 25° C. The mixture was concentrated. The mixture was further purification by pre-HPLC (column: Phenomenex luna C18 250×50 mm, 10 μm (micron); mobile phase: [water (0.1% TFA)-ACN]; B %: 10%-40%, 20 min) to give BzL-23e (1.4 g, 3.09 mmol, 23.64% yield, 98.23% purity) as yellow oil. $^1H$ NMR (MeOD, 400 MHz) δ 8.06 (d, J=1.2 Hz, 1H), 8.02 (dd, J=1.6, 8.0 Hz, 1H), 7.68 (s, 1H), 7.14 (s, 1H), 3.58-3.44 (m, 4H), 3.37 (s, 2H), 3.10 (m, 2H), 1.85 (m, 2H), 1.71 (m, 2H), 1.51-1.33 (m, 9H), 0.92-0.98 (m, 3H). LC/MS [M+H] 445.25 (calculated); LC/MS [M+H] 445.10 (observed).

BzL-23e

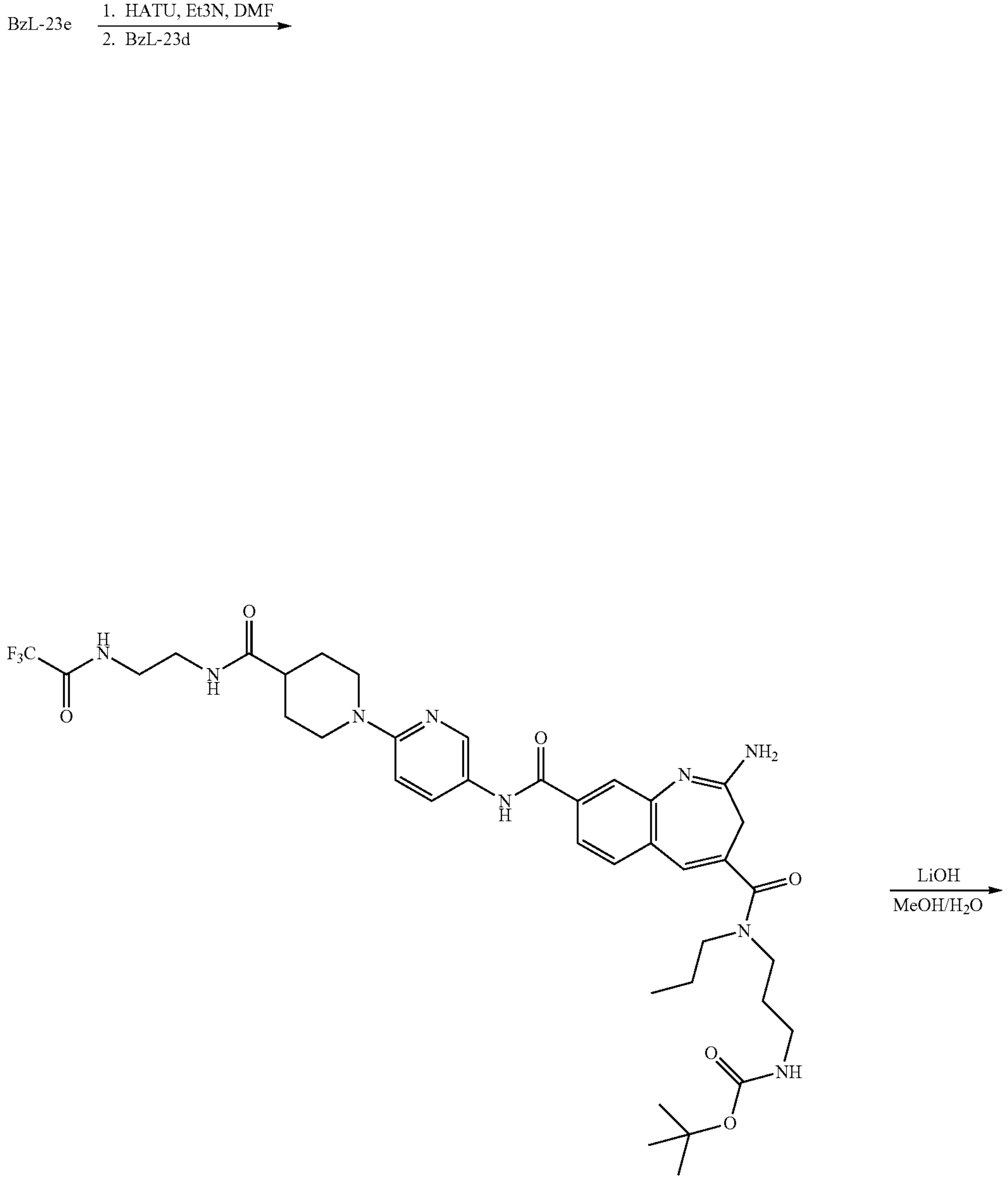

BzL-23i

-continued

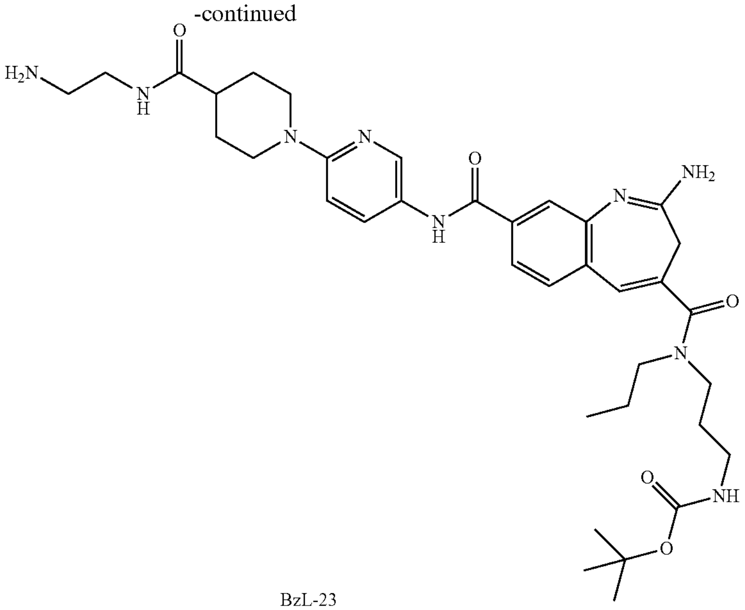

BzL-23

Synthesis of tert-butyl (3-(2-amino-N-propyl-8-((6-(4-((2-(2,2,2-trifluoroacetamido)ethyl)carbamoyl)piperidin-1-yl)pyridin-3-yl)carbamoyl)-3H-benzo[b]azepine-4-carboxamido)propyl)carbamate, BzL-23i. To a mixture of 2-amino-4-[3-(tert-butoxycarbonylamino)propyl-propyl-carbamoyl]-3H-1-benzazepine-8-carboxylic acid, BzL-23e (200 mg, 449.92 μmol, 1 eq) HATU (205.29 mg, 539.90 μmol, 1.2 eq) in DMF (3 mL) was added $Et_3N$ (136.58 mg, 1.35 mmol, 187.87 μL, 3 eq) at 25° C. The mixture was stirred at 25° C. for 5 min, then 1-(5-amino-2-pyridyl)-N-[2-[(2,2,2-trifluoroacetyl)amino]ethyl]piperidine-4-carboxamide, BzL-23d (161.68 mg, 449.92 μmol, 1 eq) was added to the mixture, stirred for 30 min. LCMS showed major as desired. The mixture was poured into water (50 mL). The aqueous phase was extracted with ethyl acetate (50 mL). The combined organic phase was washed with brine (50 mL), dried with anhydrous $Na_2SO_4$, filtered and concentrated in vacuum to give BzL-23i (0.3 g, 381.75 μmol, 84.85% yield) as yellow oil.

Synthesis of tert-butyl (3-(2-amino-8-((6-(4-((2-aminoethyl)carbamoyl)piperidin-1-yl)pyridin-3-yl)carbamoyl)-N-propyl-3H-benzo[b]azepine-4-carboxamido)propyl)carbamate, BzL-23. To a mixture of tert-butyl N-[3-[[2-amino-8-[[6-[4-[2-[(2,2,2-trifluoroacetyl) amino]ethylcarbamoyl]-1-piperidyl]-3-pyridyl]carbamoyl]-3H-1-benzazepine-4-carbonyl]-propyl-amino]propyl]carbamate, BzL-23i (0.25 g, 318.13 μmol, 1 eq) in MeOH (10 mL) was added $LiOH{\cdot}H_2O$ (40.05 mg, 954.38 μmol, 3 eq) in $H_2O$ (1 mL) at 25° C. The mixture was stirred at 40° C. for 12 hours. LCMS showed major as desired. The mixture was concentrated in vacuum. The residue was purified by prep-HPLC column: Nano-micro KROMASIL™ (Nouryon) C18 100×30 mm, 5 μm particle size; mobile phase: [water (0.1% TFA)-ACN]; B %: 15%-45%, 10 min to give BzL-23 (45 mg, 65.23 μmol, 20.51% yield) as a white solid. $^1$H NMR (MeOD, 400 MHz) δ 8.73 (d, J=2.4 Hz, 1H), 8.24 (dd, J=9.8, 2.4 Hz, 1H), 7.75 (br s, 1H), 7.45 (d, J=9.8 Hz, 1H), 7.15 (br s, 1H), 4.24 (br d, J=13.6 Hz, 2H), 3.35-3.62 (m, 9H), 3.05-3.12 (m, 4H), 2.59-2.72 (m, 1H), 1.99-2.09 (m, 2H), 1.65-1.94 (m, 6H), 1.45 (s, 9H), 0.90-0.98 (m, 3H). LC/MS [M+H] 690.41 (calculated); LC/MS [M+H] 690.40 (observed).

Example 47: Synthesis of BzL-24
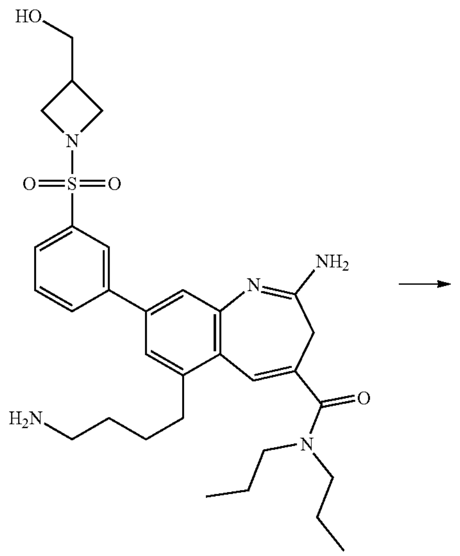
Bz-14
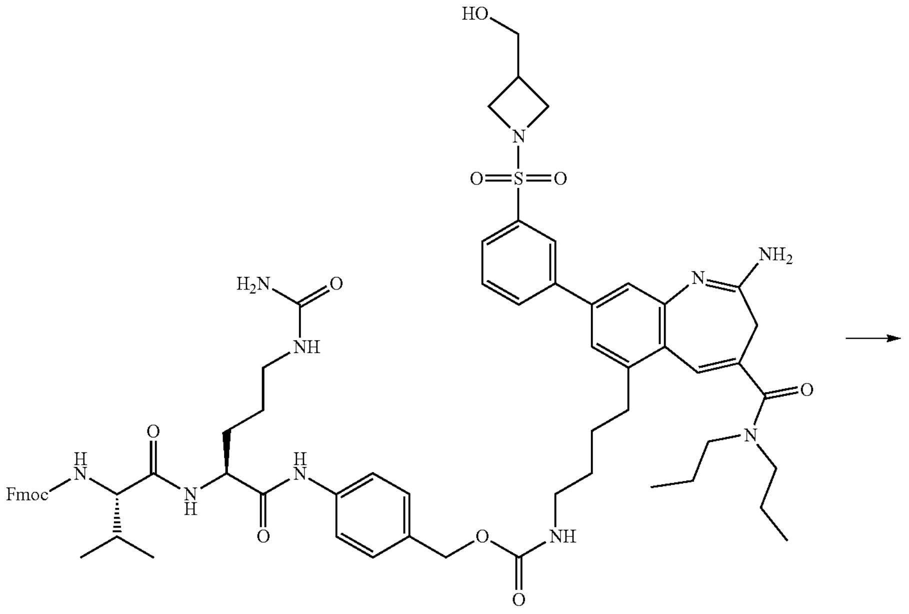
BzL-24a

-continued

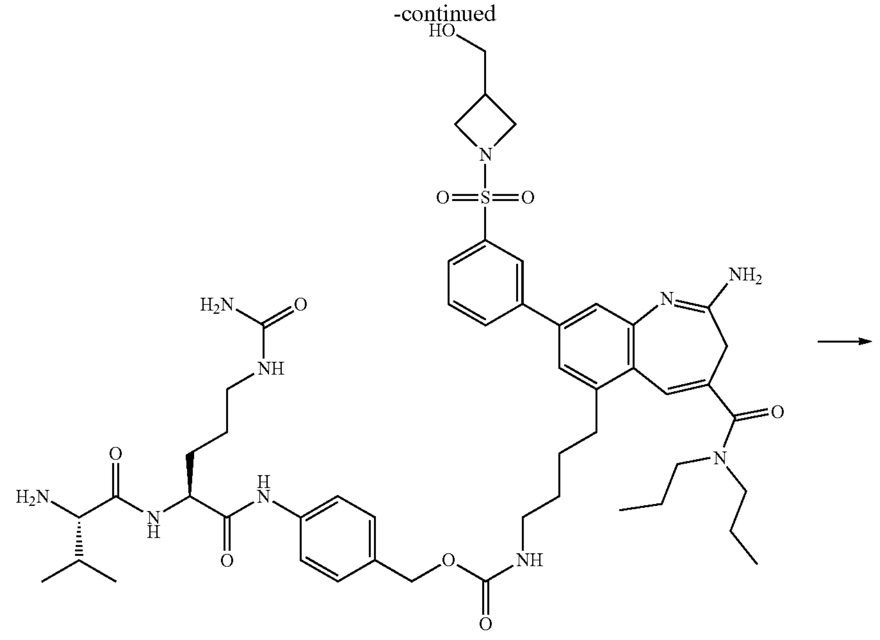

BzL-24b

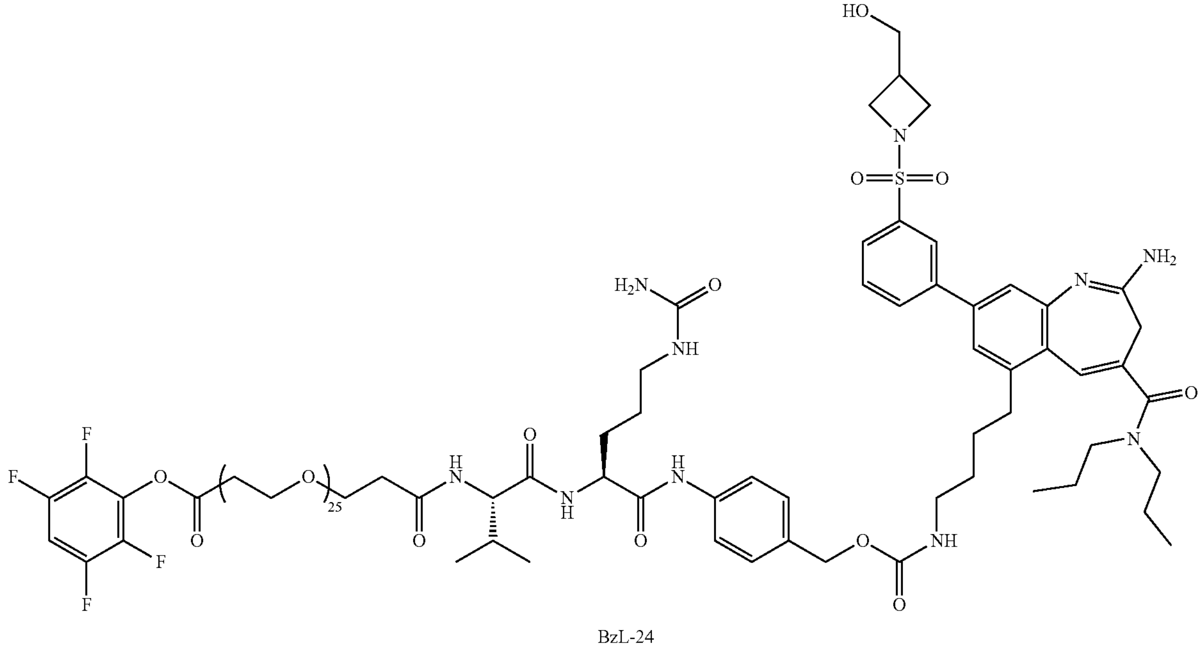

BzL-24

4-((S)-2-((S)-2-((((9H-Fluoren-9-yl)methoxy)carbonyl)amino)-3-methylbutanamido)-5-ureidopentanamido)benzyl (4-(2-amino-4-(dipropylcarbamoyl)-8-(3-((3-(hydroxymethyl)azetidin-1-yl)sulfonyl)phenyl)-3H-benzo[b]azepin-6-yl)butyl)carbamate, BzL-24a was synthesized from Bz-14 according to the procedure described for BzL-26a. LC/MS [M+H] 1209.58 (calculated); LC/MS [M+H] 1209.85 (observed).

4-((S)-2-((S)-2-Amino-3-methylbutanamido)-5-ureidopentanamido)benzyl (4-(2-amino-4-(dipropylcarbamoyl)-8-(3-((3-(hydroxymethyl)azetidin-1-yl)sulfonyl)phenyl)-3H-benzo[b]azepin-6-yl)butyl)carbamate, BzL-24b was synthesized according to the procedure described for BzL-26. LC/MS [M+H] 987.51 (calculated); LC/MS [M+H] 987.75 (observed).

2,3,5,6-Tetrafluorophenyl (6S,9S)-1-amino-6-((4-((((4-(2-amino-4-(dipropylcarbamoyl)-8-(3-((3-(hydroxymethyl)azetidin-1-yl)sulfonyl)phenyl)-3H-benzo[b]azepin-6-yl)butyl)carbamoyl)oxy)methyl)phenyl)carbamoyl)-9-isopropyl-1,8,11-trioxo-14,17,20,23,26,29,32,35,38,41,44,47,50,53,56,59,62,65,68,71,74,77,80,83,86-pentacosaoxa-2,7,10-triazanonaoctacontan-89-oate, BzL-24 was synthesized according to the procedure described for BzL-15. LC/MS [M+2H/2] 1168.59 (calculated); LC/MS [M+2H/2]1169.36 (observed).

Example 48: Synthesis of BzL-26

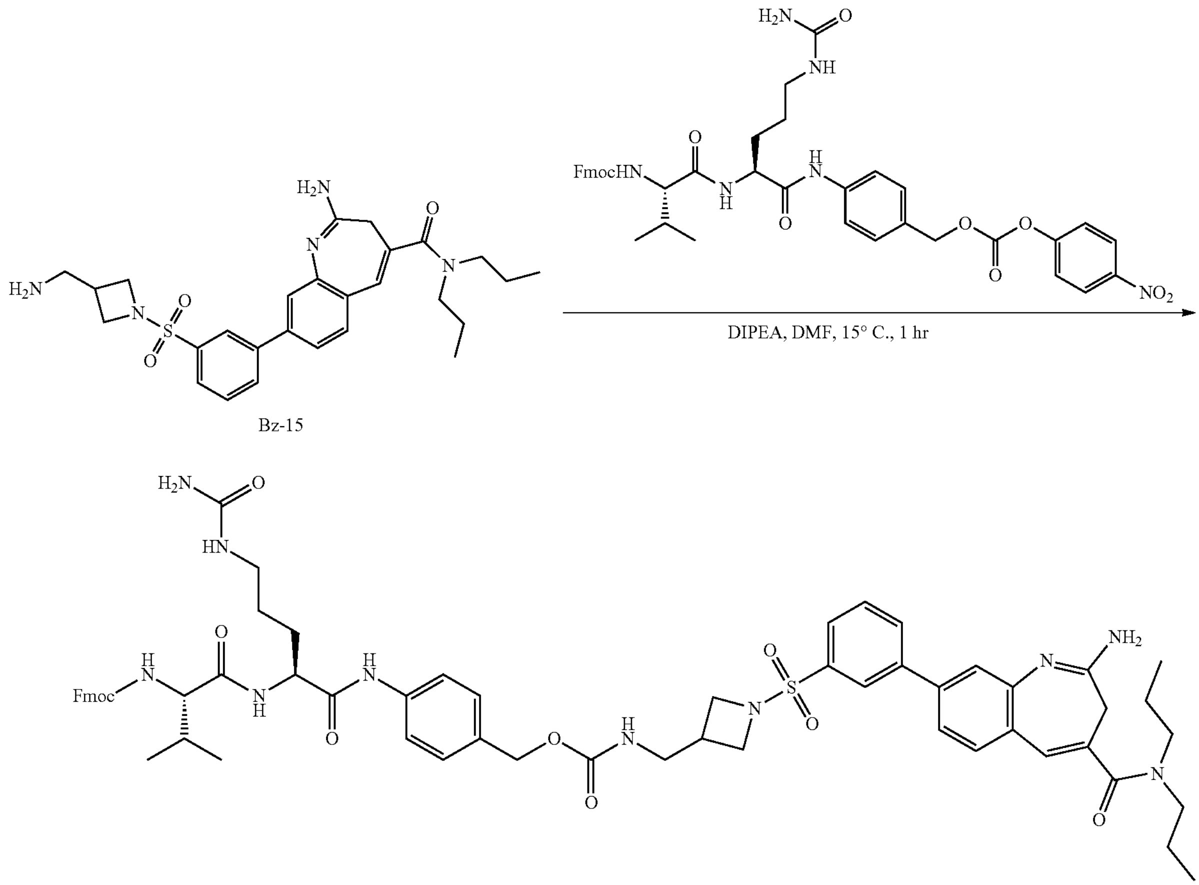

Bz-15

BzL-26a

Synthesis of (9H-fluoren-9-yl)methyl ((S)-1-(((S)-1-((4-(((((1-((3-(2-amino-4-(dipropylcarbamoyl)-3H-benzo[b]azepin-8-yl)phenyl)sulfonyl)azetidin-3-yl)methyl)carbamoyl)oxy)methyl)phenyl)amino)-1-oxo-5-ureidopentan-2-yl)amino)-3-methyl-1-oxobutan-2-yl)carbamate, BzL-26a. To a solution of [4-[[(2S)-2-[[(2S)-2-(9H-fluoren-9-ylmethoxycarbonylamino)-3-methyl-butanoyl]amino]-5-ureido-pentanoyl]amino]phenyl]methyl (4-nitrophenyl) carbonate (200 mg, 260.83 μmol, 1 eq) in DMF (1 mL) was added a solution of 2-amino-8-[3-[3-(aminomethyl)azetidin-1-yl]sulfonylphenyl]-N,N-dipropyl-3H-1-benzazepine-4-carboxamide, Bz-15 (325.35 mg, 521.65 μmol, 2 eq, TFA) and DIPEA (67.42 mg, 521.65 μmol, 90.86 μL, 2 eq) in DMF (1 mL) at 15° C. under $N_2$. The mixture was stirred at 15° C. for 1 h. The mixture was filtered. The residue was purified by prep-HPLC (column: Nano-micro KROMASIL™ (Nouryon) C18 100×30 mm, 5 μm particle size; liquid phase: [A—TFA/$H_2O$=0.1% v/v; B—ACN] B %: 30%-60%, 12 min]) to give [4-[[(2S)-2-[[(2S)-2-(9H-fluoren-9-ylmethoxycarbonylamino)-3-methyl-butanoyl]amino]-5-ureido-pentanoyl]amino]phenyl]methyl N-[[1-[3-[2-amino-4-(dipropylcarbamoyl)-3H-1-benzazepin-8-yl]phenyl]sulfonylazetidin-3-yl]methyl]carbamate, BzL-26a (73 mg, 63.07 μmol, 24.18% yield, 98.259% purity) as white solid. $^1H$ NMR (MeOD-$d_4$, 400 MHz) δ 8.05-8.09 (m, 1H), 7.92-7.98 (m, 1H), 7.84-7.90 (m, 1H), 7.58-7.83 (m, 8H), 7.46-7.57 (m, 2H), 7.33-7.42 (m, 2H), 7.25-7.33 (m, 2H), 7.11-7.23 (m, 2H), 7.04-7.09 (m, 1H), 4.87-4.94 (m, 2H), 4.46-4.56 (m, 1H), 4.31-4.45 (m, 2H), 4.16-4.26 (m, 1H), 3.95 (br d, J=7.0 Hz, 1H), 3.85 (br t, J=8.0 Hz, 2H), 3.52-3.63 (m, 2H), 3.46 (br d, J=2.0 Hz, 4H), 3.35 (s, 3H), 3.15-3.23 (m, 1H), 3.01-3.13 (m, 3H), 2.58-2.71 (m, 1H), 2.00-2.16 (m, 1H), 1.84-1.96 (m, 1H), 1.64-1.77 (m, 4H), 1.49-1.62 (m, 2H), 0.75-1.09 (m, 12H) LC/MS [M+H] 1137.52 (calculated); LC/MS [M+H] 1137.10 (observed).

Synthesis of 4-((S)-2-((S)-2-amino-3-methylbutanamido)-5-ureidopentanamido)benzyl ((1-((3-(2-amino-4-(dipropylcarbamoyl)-3H-benzo[b]azepin-8-yl)phenyl)sulfonyl)azetidin-3-yl)methyl)carbamate, BzL-26.

BzL-26a

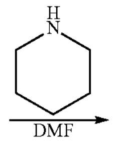

-continued

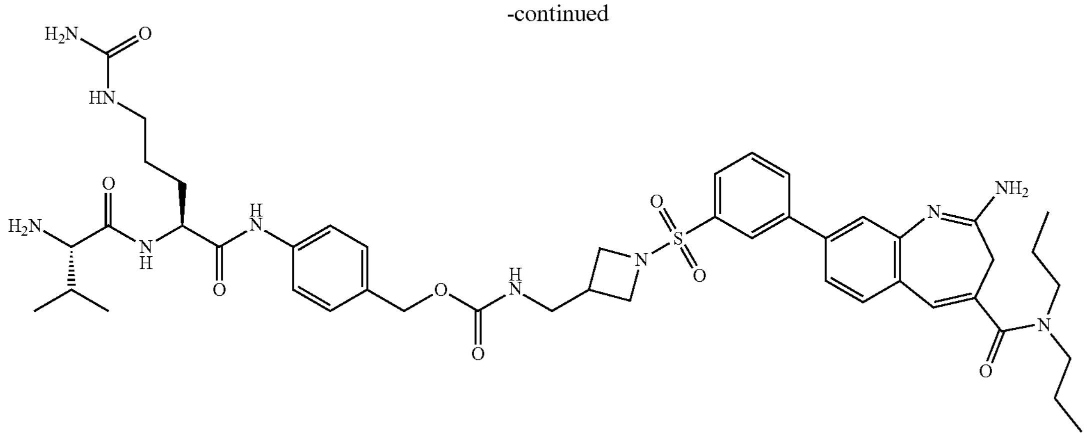

BzL-26

To a solution of [4-[[(2S)-2-[[(2S)-2-(9H-fluoren-9-yl-methoxycarbonylamino)-3-methyl-butanoyl]amino]-5-ureido-pentanoyl]amino]phenyl]methyl N-[[1-[3-[2-amino-4-(dipropylcarbamoyl)-3H-1-benzazepin-8-yl]phenyl]sulfonylazetidin-3-yl]methyl]carbamate, BzL-26a (0.12 g, 105.51 μmol, 1 eq) in DMF (2 mL) was added piperidine (44.92 mg, 527.54 μmol, 52.10 μL, 5 eq) at 25° C. and stirred for 1 hour. The reaction mixture was filtered, and the filter was concentrated. The residue was purified by prep-HPLC (column: Welch Xtimate C18 100×25 mm, 3 μm particle size; mobile phase: [water (10 mM $NH_4HCO_3$)-ACN]; B %: 25%-65%, 12 min). Compound [4-[[(2S)-2-[[(2S)-2-amino-3-methyl-butanoyl]amino]-5-ureido-pentanoyl]amino]phenyl]methyl N-[[1-[3-[2-amino-4-(dipropylcarbamoyl)-3H-1-benzazepin-8-yl]phenyl]sulfonylazetidin-3-yl]methyl] carbamate, BzL-26 (0.037 g, 38.51 μmol, 36.50% yield, 95.25% purity) was obtained as a yellow solid. $^1H$ NMR (MeOD, 400 MHz) δ 8.06 (s, 1H), 7.98 (d, J=7.4 Hz, 1H), 7.82 (d, J=7.4 Hz, 1H), 7.74 (t, J=7.4 Hz, 1H), 7.54 (d, J=8.4 Hz, 2H), 7.50-7.43 (m, 2H), 7.38 (d, J=8.0 Hz, 1H), 7.23 (d, J=8.8 Hz, 2H), 6.90 (s, 1H), 4.95-4.90 (m, 2H), 4.62-4.54 (m, 2H), 3.84 (t, J=8.2 Hz, 2H), 3.56 (t, J=4.2 Hz, 2H), 3.44 (t, J=4.0 Hz, 4H), 3.23 (d, J=5.2 Hz, 2H), 3.14-3.03 (m, 2H), 2.68-2.62 (m, 1H), 2.04-1.99 (m, 2H), 1.92-1.84 (m, 2H), 1.79-1.47 (m, 8H), 1.08-0.75 (m, 12H). LC/MS [M+H] 915.46 (calculated); LC/MS [M+H] 915.10 (observed).

Example 49: Synthesis of BzL-27

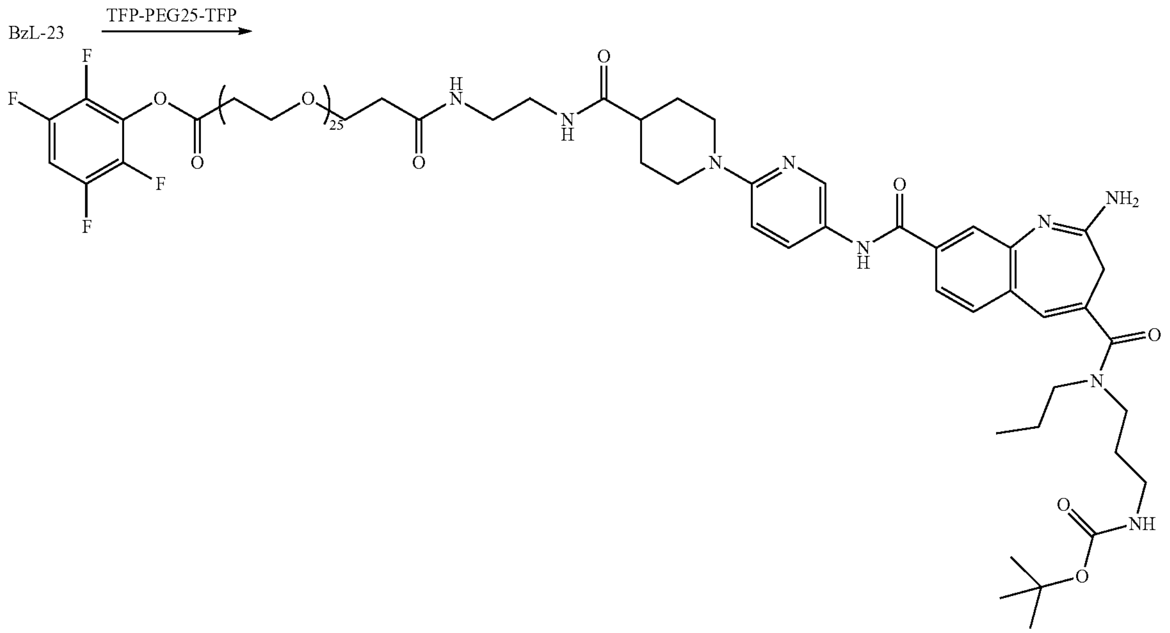

BzL-27

2,3,5,6-Tetrafluorophenyl 1-(1-(5-(2-amino-4-((3-((tert-butoxycarbonyl)amino)propyl)(propyl)carbamoyl)-3H-benzo[b]azepine-8-carboxamido)pyridin-2-yl)piperidin-4-yl)-1,6-dioxo-9,12,15,18,21,24,27,30,33,36,39,42,45,48,51,54,57,60,63,66,69,72,75,78,81-pentacosaoxa-2,5-diazatetraoctacontan-84-oate, BzL-27 was synthesized from BzL-23 and TFP-PEG25-TFP according to the procedure described for Bz-31. LC/MS [M+H] 2039.07 (calculated); LC/MS [M+H] 2039.40 (observed).
Example 50: Synthesis of BzL-28
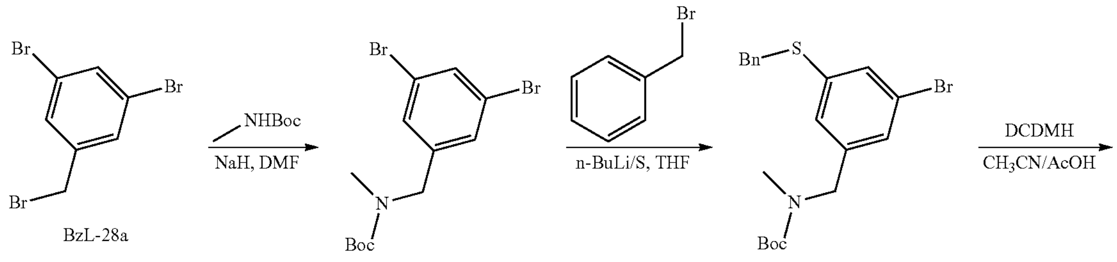
BzL-28a
BzL-28b
BzL-28c
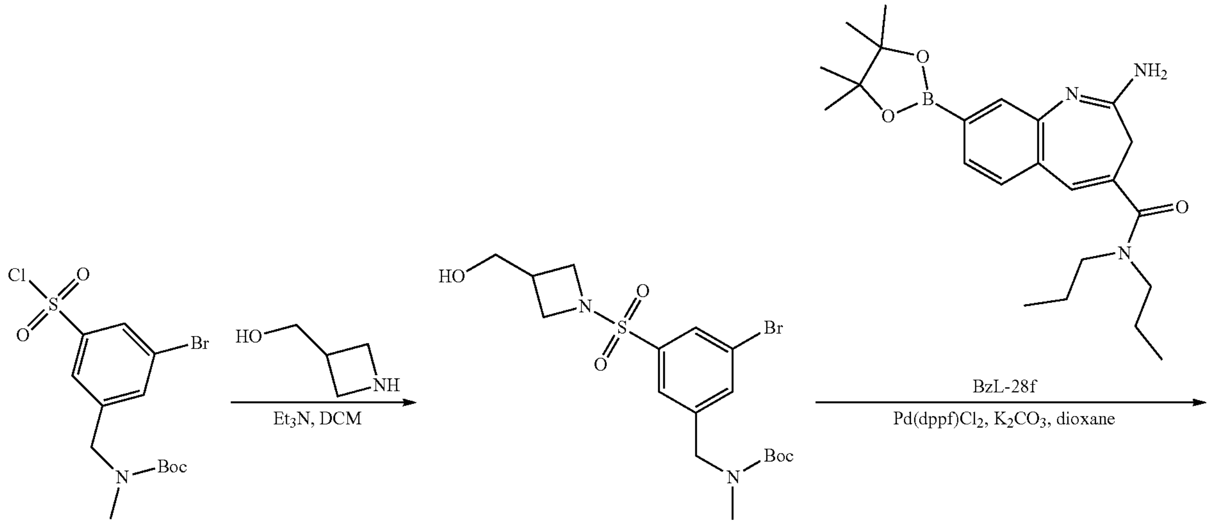
BzL-28d
BzL-28e
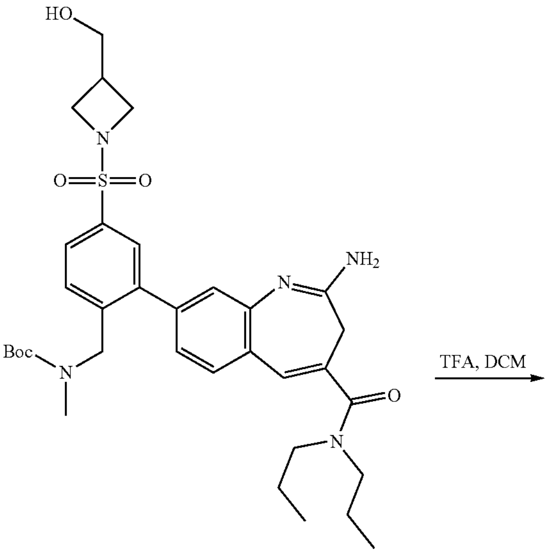
BzL-28g -continued
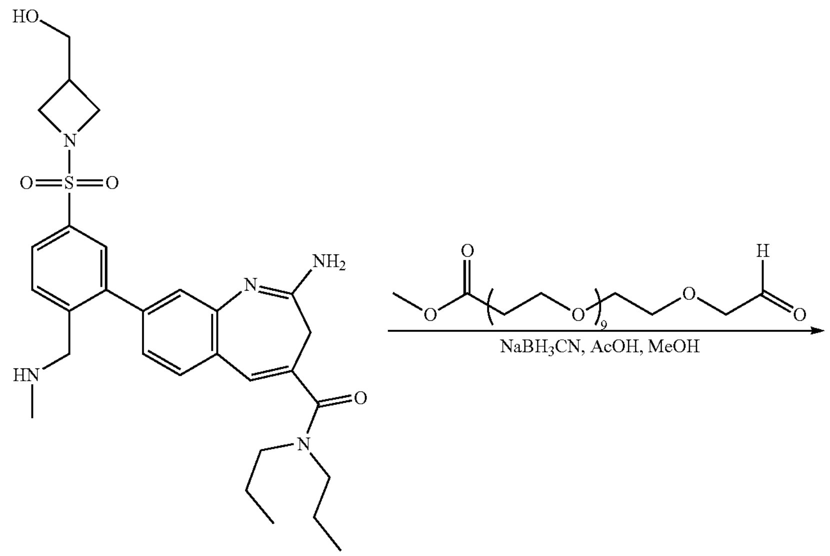
BzL-28h
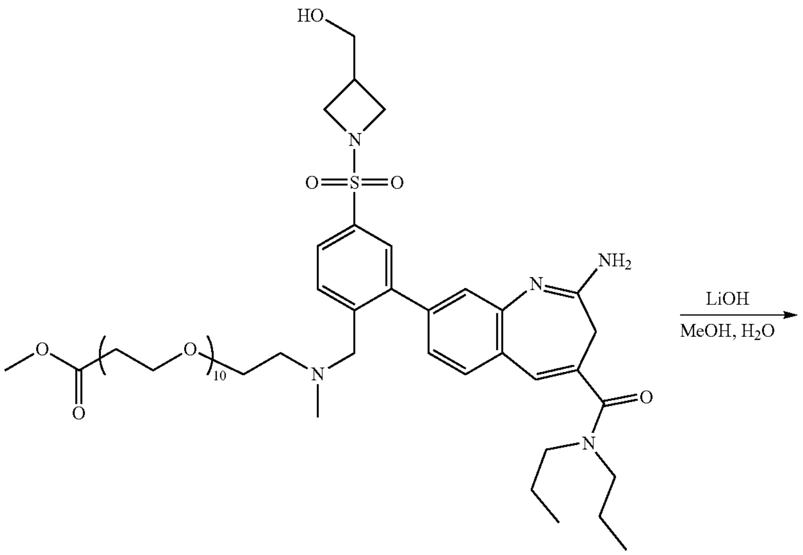
BzL-28i -continued

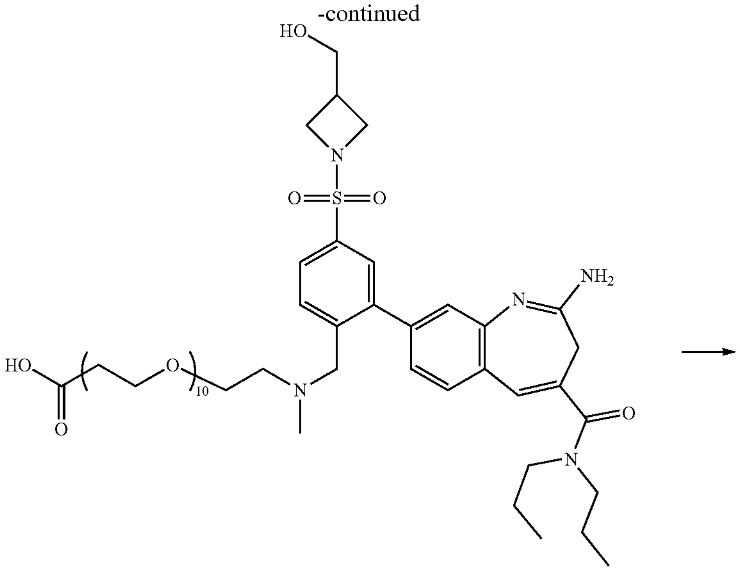

BzL-28j

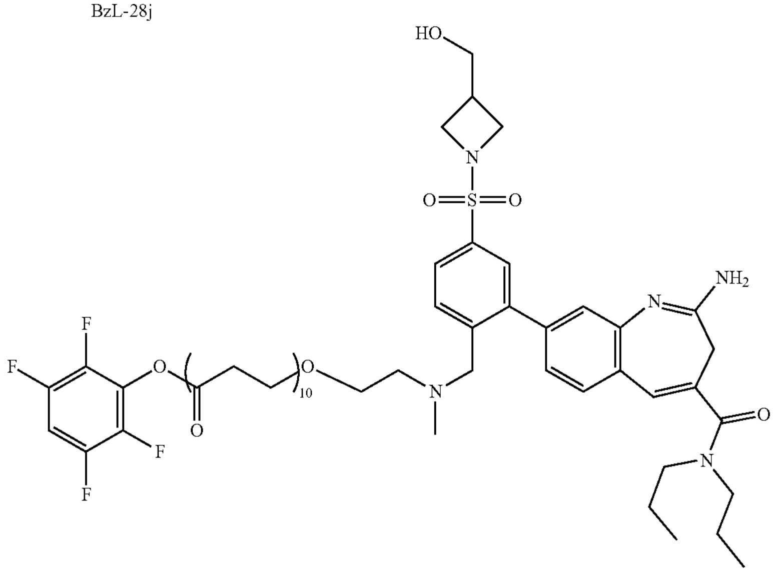

BzL-28

Synthesis of tert-butyl 3,5-dibromobenzyl(methyl)carbamate, BzL-28b. To a solution of tert-butyl N-methylcarbamate (2.5 g, 19.06 mmol, 1 eq) in DMF (80 mL) was added NaH (914.82 mg, 22.87 mmol, 60% purity, 1.2 eq) slowly at 0° C. After addition, the mixture was stirred at 15° C. for 30 min, and then 1,3-dibromo-5-(bromomethyl)benzene, BzL-28a (8.77 g, 26.68 mmol, 1.4 eq) was added at 0° C. The resulting mixture was stirred at 15° C. for 2 h. TLC indicated the reactant was consumed completely. The reaction mixture was quenched by addition of aq. $NH_4Cl$ (250 mL) at 0° C., and then extracted with EtOAc (100 mL×3). The combined organic layers were washed with brine (30 mL×3), dried over $Na_2SO_4$, filtered and concentrated under reduced pressure to give a residue. The residue was purified by column chromatography ($SiO_2$, petroleum ether:ethyl acetate=1:0 to 5:1) to give BzL-28b (6.6 g, 17.41 mmol, 91.35% yield) as a white solid. $^1H$ NMR ($CDCl_3$, 400 MHz) δ 7.59-7.56 (m, 1H), 7.31 (s, 2H), 4.36 (s, 2H), 2.87 (s, 3H), 1.49 (s, 9H).

Synthesis of tert-butyl 3-(benzylthio)-5-bromobenzyl (methyl)carbamate, BzL-28c. To a solution of tert-butyl 3,5-dibromobenzyl(methyl)carbamate, BzL-28b (3.6 g, 9.50 mmol, 1 eq) in THE (70 mL) was added dropwise n-BuLi (2.5 M, 3.80 mL, 1 eq) at −78° C. under $N_2$. After addition, the mixture was stirred at −78° C. for 15 min, and then sulfur, S (304.55 mg, 9.50 mmol, 1 eq) was added at −78° C. After addition, the mixture was stirred at −78° C. for 45 min, and then bromomethylbenzene (1.62 g, 9.50 mmol, 1.13 mL, 1 eq) was added at −78° C. The resulting mixture was warmed to 15° C. and stirred at 15° C. for 30 min. TLC indicated BzL-28b was consumed completely. The reaction mixture was quenched by addition of aq. $NH_4Cl$ (70 mL) at 0° C., and then extracted with EtOAc (50 mL×3). The combined organic layers were washed with brine (20 mL), dried over $Na_2SO_4$, filtered and concentrated under reduced pressure to give a residue. The residue was purified by column chromatography ($SiO_2$, petroleum ether:ethyl acetate=1:0 to 5:1) to give BzL-28c (0.97 g, 2.30 mmol, 24.18% yield) as a yellow oil. $^{1}H$ NMR ($CDCl_3$, 400 MHz) δ 7.35-7.26 (m, 5H), 7.26-7.21 (m, 1H), 7.17 (s, 1H), 7.04 (s, 1H), 4.34 (s, 2H), 4.12 (s, 2H), 2.79 (s, 3H), 1.48 (s, 9H).

Synthesis of tert-butyl 3-bromo-5-(chlorosulfonyl)benzyl (methyl)carbamate, BzL-28d. To a solution of tert-butyl 3-(benzylthio)-5-bromobenzyl(methyl)carbamate, BzL-28c (1.22 g, 2.89 mmol, 1 eq) in $CH_3CN$ (25 mL) and $H_2O$ (1 mL) and acetic acid, AcOH (520.35 mg, 8.67 mmol, 495.57 μL, 3 eq) was added 1,3-dichloro-5,5-dimethyl-imidazolidine-2,4-dione, DCDMH (1.14 g, 5.78 mmol, 2 eq) at 0° C. The mixture was stirred at 0° C. for 1 h. TLC indicated BzL-28c was consumed completely. The reaction mixture was concentrated under reduced pressure to give a residue. The residue was diluted with $H_2O$ (20 mL) and extracted with EtOAc (20 mL×3). The combined organic layers were washed with brine (10 mL), dried over $Na_2SO_4$, filtered and concentrated under reduced pressure to give a residue. The residue was purified by column chromatography ($SiO_2$, petroleum ether:ethyl acetate=1:0 to 5:1) to give BzL-28d (0.51 g, 1.28 mmol, 44.29% yield) as a light yellow oil. $^{1}H$ NMR ($CDCl_3$, 400 MHz) δ 8.08 (s, 1H), 7.83 (s, 1H), 7.74 (s, 1H), 4.50 (s, 2H), 2.91 (s, 3H), 1.49 (s, 9H).

Synthesis of tert-butyl 3-bromo-5-((3-(hydroxymethyl) azetidin-1-yl)sulfonyl)benzyl(methyl)carbamate, BzL-28e. To a solution of tert-butyl 3-bromo-5-(chlorosulfonyl)benzyl(methyl)carbamate, BzL-28d (0.74 g, 1.86 mmol, 1 eq) and azetidin-3-ylmethanol (746.66 mg, 3.71 mmol, 2 eq, TFA) in DCM (15 mL) was added TEA (751.25 mg, 7.42 mmol, 1.03 mL, 4 eq) at 0° C. The mixture was stirred at 15° C. for 1 h. TLC indicated Reactant 1 was consumed completely. The reaction mixture was quenched by addition of $H_2O$ (15 mL) at 0° C., and then extracted with EtOAc (15 mL×3). The combined organic layers were washed with brine (10 mL), dried over $Na_2SO_4$, filtered and concentrated under reduced pressure to give a residue purified by column chromatography ($SiO_2$, petroleum ether:ethyl acetate=10:1 to 0:1) to give BzL-28e (640 mg, 1.42 mmol, 76.74% yield) as a light yellow oil. $^{1}H$ NMR ($CDCl_3$, 400 MHz) δ 7.90 (s, 1H), 7.69-7.53 (m, 2H), 4.48 (s, 2H), 3.89 (t, J=8.0 Hz, 2H), 3.64 (d, J=6.0 Hz, 3H), 3.42 (s, 1H), 2.95 (s, 3H), 2.65 (s, 1H), 1.49 (s, 9H).

Synthesis of tert-butyl 3-(2-amino-4-(dipropylcarbamoyl)-3H-benzo[b]azepin-8-yl)-5-((3-(hydroxymethyl)azetidin-1-yl)sulfonyl)benzyl(methyl)carbamate, BzL-28g. A mixture of tert-butyl 3-bromo-5-((3-(hydroxymethyl)azetidin-1-yl)sulfonyl)benzyl(methyl)carbamate, BzL-28e (590 mg, 1.31 mmol, 1 eq), 2-amino-N,N-dipropyl-8-(4,4,5,5-tetramethyl-1,3,2-dioxaborolan-2-yl)-3H-benzo[b]azepine-4-carboxamide, BzL-28f (702.11 mg, 1.71 mmol, 1.3 eq), $Pd(dppf)Cl_2$ (48.0 mg, 65.7 μmol, 0.05 eq), $K_2CO_3$ (362.9 mg, 2.63 mmol, 2 eq) in dioxane (10 mL) and $H_2O$ (1 mL) was degassed and purged with $N_2$ for 3 times, and then the mixture was stirred at 90° C. for 3 h under $N_2$ atmosphere. The reaction mixture was filtered and concentrated under reduced pressure to give a residue. The residue was purified by prep-HPLC (TFA condition: column: Nano-micro KROMASIL™ (Nouryon) C18 100×30 mm, 5 μm particle size; mobile phase: [water (0.1% TFA)-ACN]; B %: 40%-60%, 10 min) to give BzL-28g (180 mg, 275.30 μmol, 20.97% yield) as a yellow solid.

Synthesis of 2-amino-8-(3-((3-(hydroxymethyl)azetidin-1-yl)sulfonyl)-5-((methylamino)methyl)phenyl)-N,N-dipropyl-3H-benzo[b]azepine-4-carboxamide, BzL-28h. To a solution of tert-butyl 3-(2-amino-4-(dipropylcarbamoyl)-3H-benzo[b]azepin-8-yl)-5-((3-(hydroxymethyl)azetidin-1-yl)sulfonyl)benzyl(methyl)carbamate, BzL-28g (180 mg, 275.30 μmol, 1 eq) in DCM (2 mL) was added TFA (627.80 mg, 5.51 mmol, 407.66 μL, 20 eq) at 15° C. The mixture was stirred at 15° C. for 1 h. LC-MS showed Reactant 1 was consumed. The reaction mixture was concentrated under reduced pressure to give a residue. The residue was added with THE (5 mL) and aq. $NaHCO_3$ (5 mL) to pH 8-9 at 0° C., and then stirred at 15° C. for 30 min. The reaction mixture was concentrated under reduced pressure to give a residue and extracted with EtOAc (10 mL×3). The combined organic layers were washed with brine (5 mL), dried over $Na_2SO_4$, filtered and concentrated under reduced pressure to give BzL-28h (110 mg, 198.66 μmol, 72.16% yield) as a yellow oil. LC/MS [M+H] 554.28 (calculated); LC/MS [M+H] 554.30 (observed).

Synthesis of methyl 1-(3-(2-amino-4-(dipropylcarbamoyl)-3H-benzo[b]azepin-8-yl)-5-((3-(hydroxymethyl)azetidin-1-yl)sulfonyl)phenyl)-2-methyl-5,8,11,14,17,20,23,26,29,32-decaoxa-2-azapentatriacontan-35-oate, BzL-28i. To a solution of 2-amino-8-(3-((3-(hydroxymethyl)azetidin-1-yl) sulfonyl)-5-((methylamino)methyl)phenyl)-N,N-dipropyl-3H-benzo[b]azepine-4-carboxamide, BzL-28h (110 mg, 198.66 μmol, 1 eq) and methyl 1-oxo-3,6,9,12,15,18,21,24,27,30-decaoxatritriacontan-33-oate (140.13 mg, 258.26 μmol, 1.3 eq) in MeOH (2 mL) was added AcOH (11.93 mg, 198.66 μmol, 11.36 μL, 1 eq) at 15° C. After addition, the mixture was stirred at 15° C. for 15 min, and then $NaBH_3CN$ (24.97 mg, 397.32 μmol, 2 eq) was added at 15° C. The resulting mixture was stirred at 15° C. for 12 h. The reaction mixture was used for next step directly, containing BzL-28i (0.22 g, crude) (in MeOH) as a light yellow liquid. LC/MS [M+2H/2] 540.79 (calculated); LC/MS [M+H] 541.1 (observed).

Synthesis of 1-(3-(2-amino-4-(dipropylcarbamoyl)-3H-benzo[b]azepin-8-yl)-5-((3-(hydroxymethyl)azetidin-1-yl) sulfonyl)phenyl)-2-methyl-5,8,11,14,17,20,23,26,29,32-decaoxa-2-azapentatriacontan-35-oic acid, BzL-28j. To a solution of methyl 1-(3-(2-amino-4-(dipropylcarbamoyl)-3H-benzo[b]azepin-8-yl)-5-((3-(hydroxymethyl)azetidin-1-yl)sulfonyl)phenyl)-2-methyl-5,8,11,14,17,20,23,26,29,32-decaoxa-2-azapentatriacontan-35-oate, BzL-28i (0.22 g, 203.64 μmol, 1 eq) in MeOH (2 mL) and $H_2O$ (1 mL) was added $LiOH·H_2O$ (68.36 mg, 1.63 mmol, 8 eq) at 15° C. The mixture was stirred at 15° C. for 5 h. LC-MS showed BzL-28i was consumed. The reaction mixture was adjusted to pH 6-7 with 1 N HCl at 0° C., and then concentrated under reduced pressure. The residue was purified by prep-HPLC (TFA condition: column: Welch Xtimate C18 100×25 mm, 3 μm; mobile phase: [water (0.1% TFA)-ACN]; B %: 20%-40%, 12 min) twice to give BzL-28j (104 mg, 94.31 μmol, 46.31% yield, HCl) as a light yellow oil. $^{1}H$ NMR (MeOD-$d_4$, 400 MHz) δ 8.33 (s, 1H), 8.24 (s, 1H), 8.12 (s, 1H), 7.90-7.84 (m, 2H), 7.74 (d, J=8.8 Hz, 1H), 7.12 (s, 1H), 3.96-3.88 (m, 4H), 3.76-3.67 (m, 8H), 3.66-3.52 (m, 33H), 3.51-3.37 (m, 9H), 3.02 (s, 3H), 2.71-2.59 (m, 1H), 2.53 (t, J=6.0 Hz, 2H), 1.77-1.63 (m, 4H), 0.95 (br s, 6H). LC/MS [M+H] 1066.56 (calculated); LC/MS [M+H] 1066.10 (observed).

2,3,5,6-Tetrafluorophenyl 1-(3-(2-amino-4-(dipropylcarbamoyl)-3H-benzo[b]azepin-8-yl)-5-((3-(hydroxymethyl) azetidin-1-yl)sulfonyl)phenyl)-2-methyl-5,8,11,14,17,20,23,26,29,32-decaoxa-2-azapentatriacontan-35-oate, BzL-28 was synthesized by reaction with 2,3,5,6-tetrafluorophenol according to the procedure described for BzL-22. LC/MS [M+H] 1214.56 (calculated); LC/MS [M+H] 1214.83 (observed).

Example 51: Synthesis of BzL-29
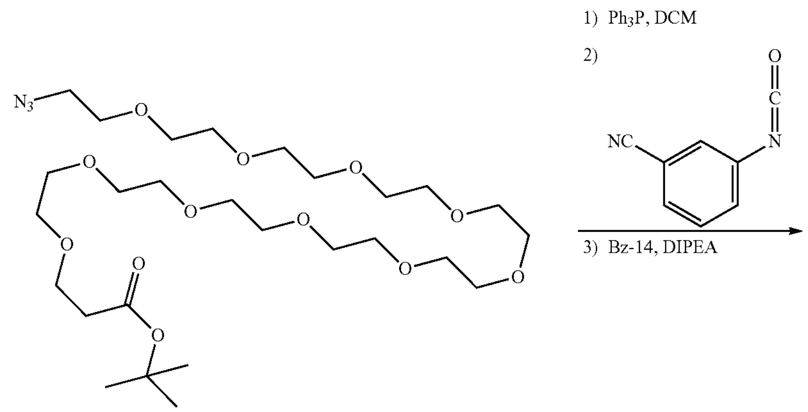
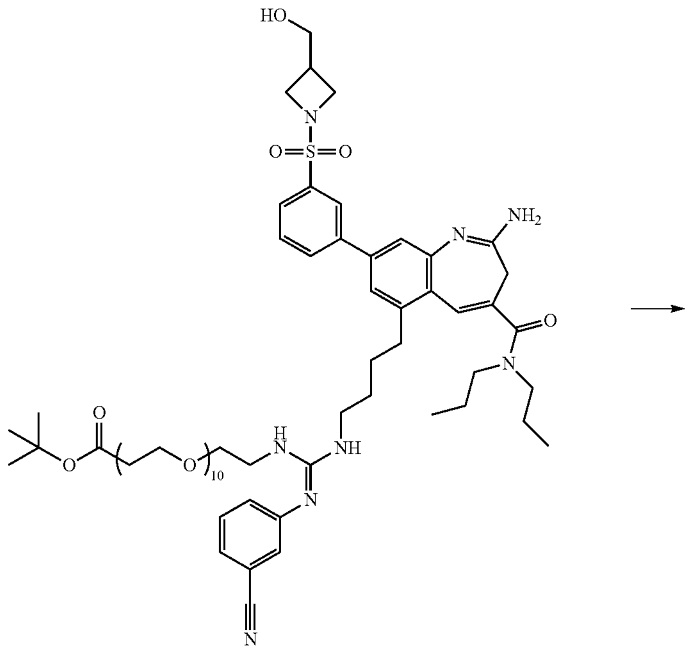
BzL-29a

-continued

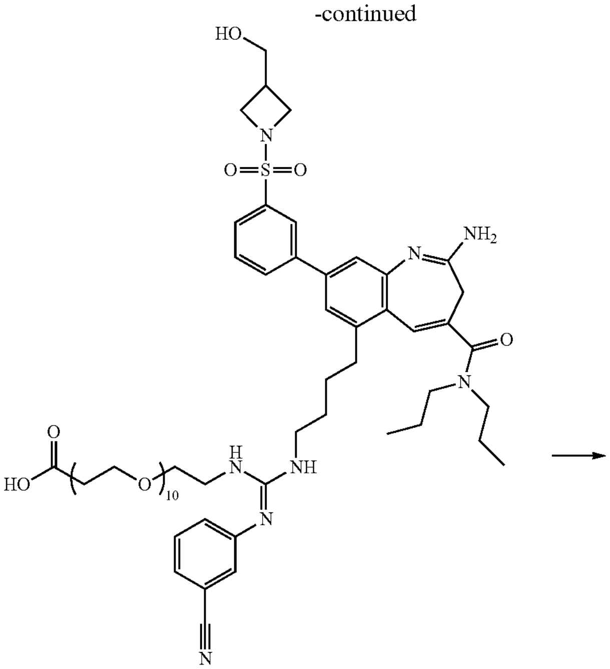

BzL-29b

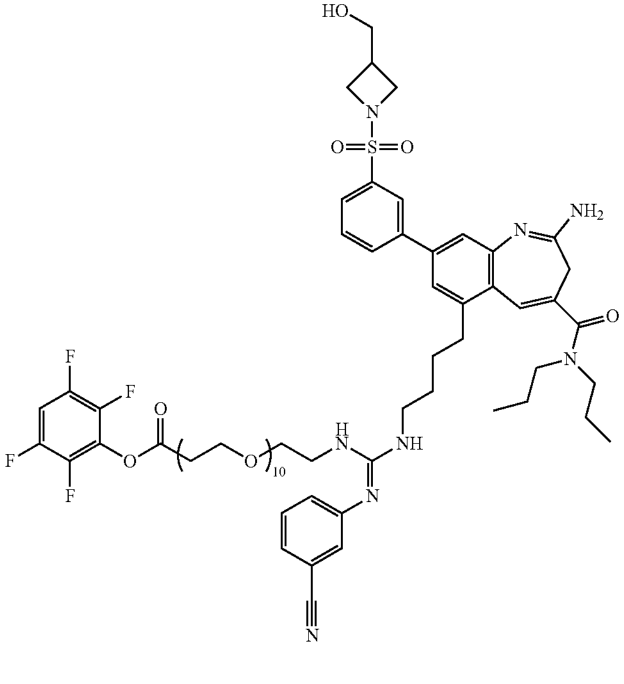

BzL-29

Synthesis of tert-butyl (Z)-40-(2-amino-4-(dipropylcarbamoyl)-8-(3-((3-(hydroxymethyl)azetidin-1-yl)sulfonyl)phenyl)-3H-benzo[b]azepin-6-yl)-35-((3-cyanophenyl)imino)-4,7,10,13,16,19,22,25,28,31-decaoxa-34,36-diazatetracontanoate, BzL-29a. A 4 mL vial was charged with tert-butyl 1-azido-3,6,9,12,15,18,21,24,27,30-decaoxatritriacontan-33-oate (0.011 mmol, 6.9 mg), triphenylphosphine (0.011 mmol, 3 mg) and 200 μL of anhydrous dichloromethane. The reaction was maintained at 30° C. for 90 min, at which point 3-cyanophenyl isocyanate (0.011 mmol, 1.6 mg) was added. After 45 min a solution containing Bz-14 (0.011 mmol) and diisopropylethylamine, Hunigs base (0.034 mmol) in 200 μL DMF was added. This reaction was maintained for 2 h then concentrated under reduced pressure. The crude reaction was purified using reverse phase preparative HPLC utilizing a 25-75% gradient of acetonitrile:water containing 0.1% trifluoroacetic acid. The purified fractions were combined and lyophilized to afford 4.1 mg of BzL-29a in 63% yield. LC/MS [M+H] 1293.71 (calculated); LC/MS [M+H] 1294.04 (observed).

Synthesis of (Z)-40-(2-amino-4-(dipropylcarbamoyl)-8-(3-((3-(hydroxymethyl)azetidin-1-yl)sulfonyl)phenyl)-3H- benzo[b]azepin-6-yl)-35-((3-cyanophenyl)imino)-4,7,10,13,16,19,22,25,28,31-decaoxa-34,36-diazatetracontanoic acid, BzL-29b. A vial was charged with BzL-29a (4.1 mg, 0.003 mmol), 500 μL DCM, and 100 μL trifluoroacetic acid. The reaction was maintained for 1 h, concentrated under reduced pressure, and azeotroped thrice with 1 mL toluene. The crude product BzL-29b was taken onto the subsequent step.

2,3,5,6-Tetrafluorophenyl (Z)-40-(2-amino-4-(dipropylcarbamoyl)-8-(3-((3-(hydroxymethyl)azetidin-1-yl)sulfonyl)phenyl)-3H-benzo[b]azepin-6-yl)-35-((3-cyanophenyl)imino)-4,7,10,13,16,19,22,25,28,31-decaoxa-34,36-diazatetracontanoate, BzL-29 was synthesized by reaction of BzL-29b with 2,3,5,6-tetrafluorophenol according to the procedure described for Bz-22. LC/MS [M+H] 1385.64 (calculated); LC/MS [M+H]1385.84 (observed).

Example 52: Synthesis of BzL-31

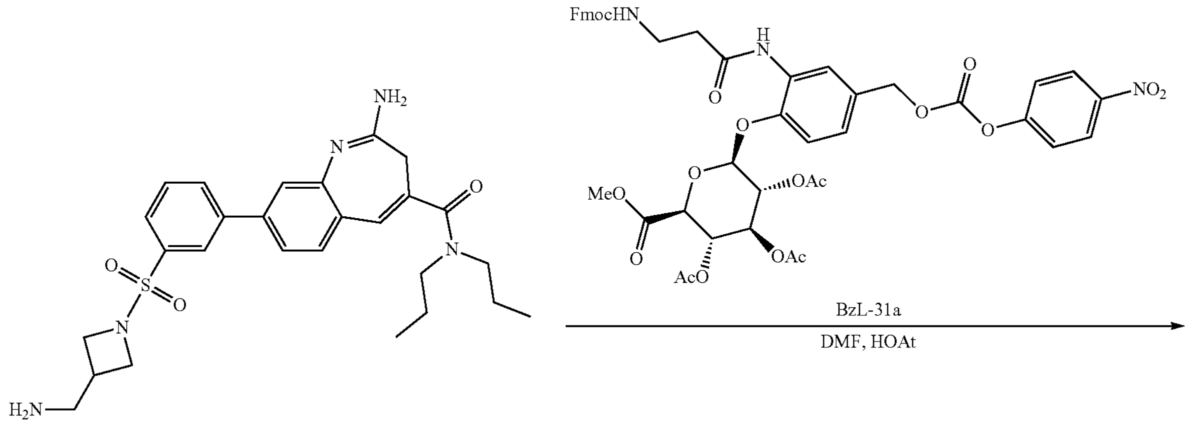

Bz-15

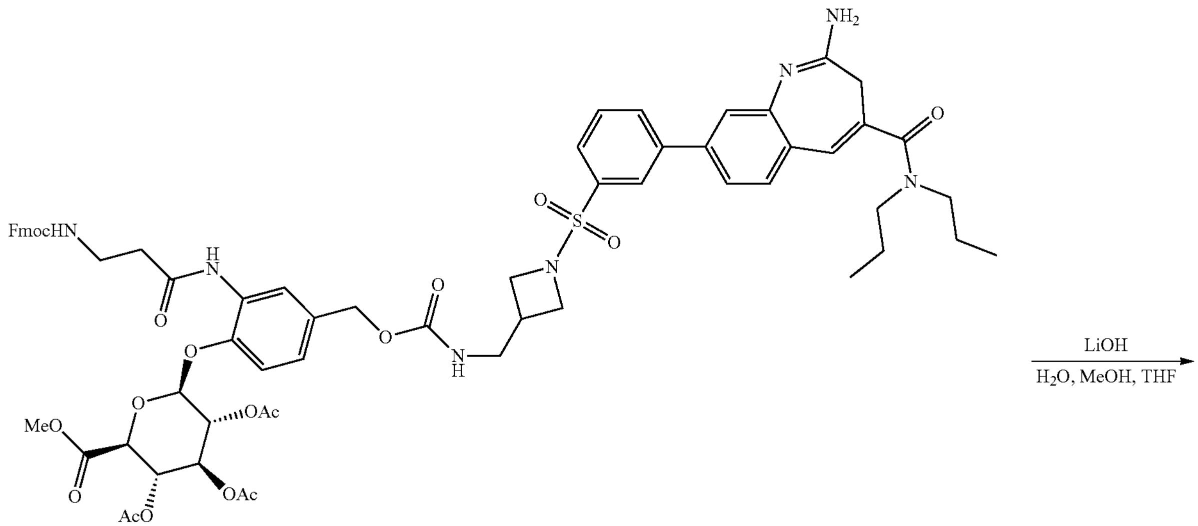

BzL-31b

-continued

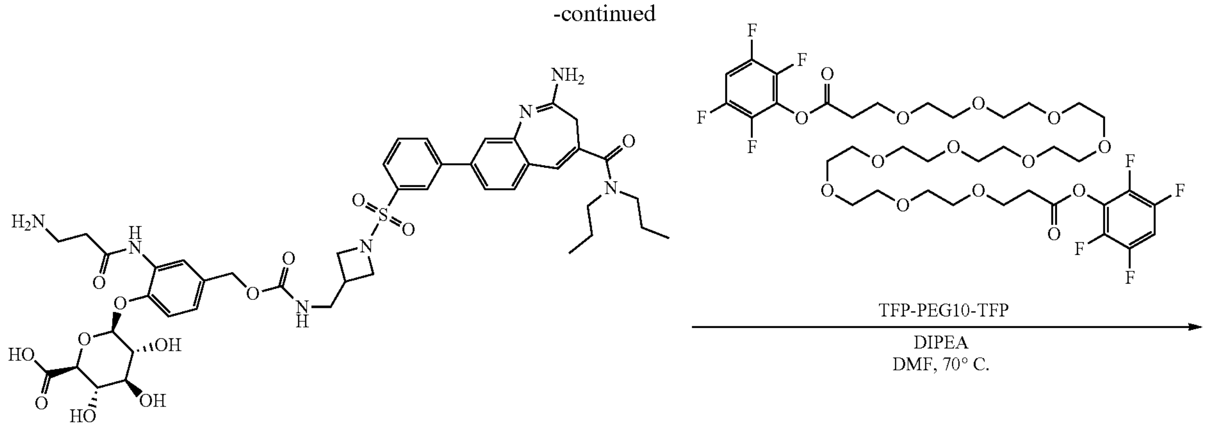

BzL-31c

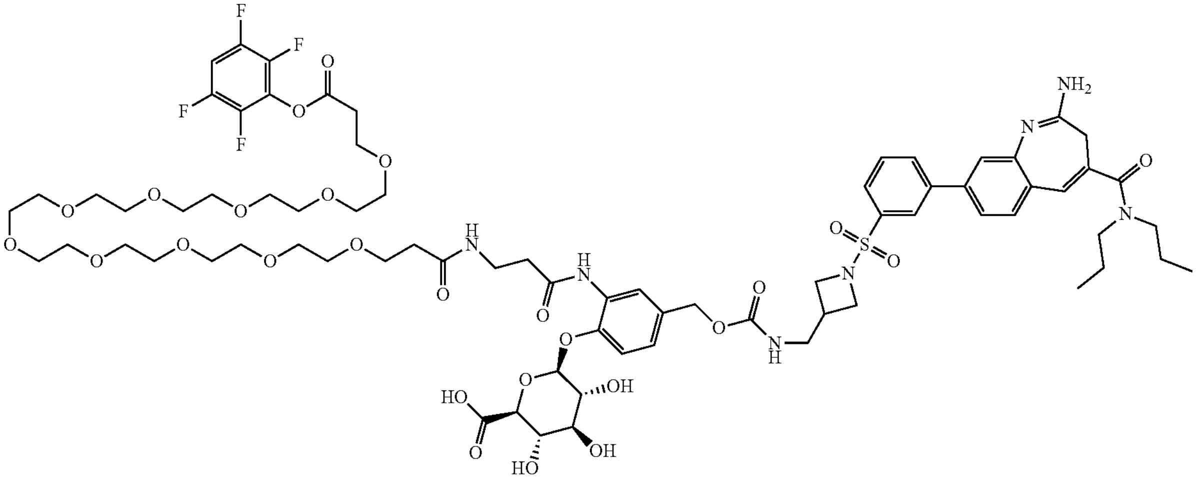

BzL-31

Synthesis of rac-(2R,3S,4R,5R,6R)-2-(2-(3-((((9H-fluoren-9-yl)methoxy)carbonyl)amino)propanamido)-4-(((((1-((3-(2-amino-4-(dipropylcarbamoyl)-3H-benzo[b]azepin-8-yl)phenyl)sulfonyl)azetidin-3-yl)methyl)carbamoyl)oxy)methyl)phenoxy)-6-(methoxycarbonyl)tetrahydro-2H-pyran-3,4,5-triyl triacetate, BzL-31b. To a solution of Bz-15 (50 mg, 0.098 mmol, 1 eq) and rac-(2R,3S,4R,5R,6R)-2-(2-(3-((((9H-fluoren-9-yl)methoxy)carbonyl)amino)propanamido)-4-((((4-nitrophenoxy)carbonyl)oxy)methyl)phenoxy)-6-(methoxycarbonyl)tetrahydro-2H-pyran-3,4,5-triyl triacetate, BzL-31a (90 mg, 0.098 mmol, 1 eq) in DMF (0.2 ml) was added HOAt (13.3 mg, 0.098 mmol, 1 eq). The reaction was stirred at ambient temperature and monitored by LCMS. The reaction mixture was diluted with 1:1 water:acetonitrile and purified by HPLC to give BzL-31b (67 mg, 0.052 mmol, 53%). LC/MS [M+H] 1284.48 (calculated); LC/MS [M+H] 1284.81 (observed).

Synthesis of rac-(2R,3R,4R,5S,6R)-6-(4-(((((1-((3-(2-amino-4-(dipropylcarbamoyl)-3H-benzo[b]azepin-8-yl)phenyl)sulfonyl)azetidin-3-yl)methyl)carbamoyl)oxy)methyl)-2-(3-aminopropanamido)phenoxy)-3,4,5-trihydroxytetrahydro-2H-pyran-2-carboxylic acid, BzL-31c. BzL-31b (67 mg, 0.052 mmol, 1 eq) was dissolved in a 20 mM solution of LiOH in 5:2:1 THF:MeOH:$H_2O$ (2.6 ml). The reaction was stirred for 1 hour at ambient temperature, then concentrated and purified by HPLC to give BzL-31c as a white solid (25 mg, 0.027 mmol, 52%). LC/MS [M+H] 922.37 (calculated); LC/MS [M+H] 922.56 (observed).

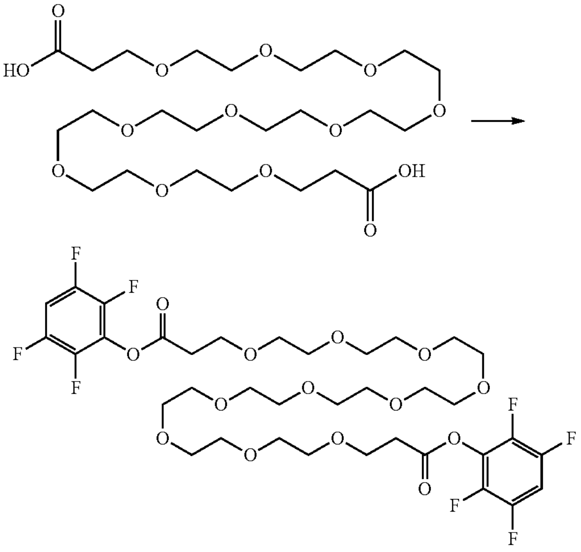

TFP-PEG-10-TFP

Bis(2,3,5,6-tetrafluorophenyl) 4,7,10,13,16,19,22,25,28,31-decaoxatetratriacontanedioate, TFP-PEG10-TFP was synthesized from 4,7,10,13,16,19,22,25,28,31-decaoxatetratriacontanedioic acid according to the procedure described for TFP-PEG25-TFP. LC/MS [M+H] 855.28 (calculated); LC/MS [M+H] 855.53 (observed).

Synthesis of rac-(2R,3R,4R,5S,6R)-6-(4-(((((1-((3-(2-amino-4-(dipropylcarbamoyl)-3H-benzo[b]azepin-8-yl) phenyl)sulfonyl)azetidin-3-yl)methyl)carbamoyl)oxy) methyl)-2-(1,34-dioxo-1-(2,3,5,6-tetrafluorophenoxy)-4,7,10,13,16,19,22,25,28,31-decaoxa-35-azaoctatriacontan-38-amido)phenoxy)-3,4,5-trihydroxytetrahydro-2H-pyran-2-carboxylic acid, BzL-31. BzL-31c (25 mg, 0.027 mmol, 1 eq) and TFP-PEG10-TFP bis(2,3,5,6-tetrafluorophenyl) 4,7,10,13,16,19,22,25,28,31-decaoxatetratriacontanedioate (35 mg, 0.040 mmol, 1.5 eq) were dissolved in DMF (5 ml). The reaction was neutralized to approximately pH 7 with DIPEA and heated to 70° C. After 1 hour, another portion of bis(2,3,5,6-tetrafluorophenyl) 4,7,10,13,16,19,22,25,28,31-decaoxatetratriacontanedioate (35 mg, 0.040 mmol, 1.5 eq) was added to the reaction mixture. Upon consumption of BzL-31c, the reaction was concentrated to a yellow film, then triturated with 6×3 ml diethyl ether to give a yellow solid that was purified by HPLC to give BzL-31 (14.3 mg, 0.0089 mmol, 33%). LC/MS [M+H] 1610.64 (calculated); LC/MS [M+H]1610.99 (observed).

Example 53: Synthesis of BzL-33

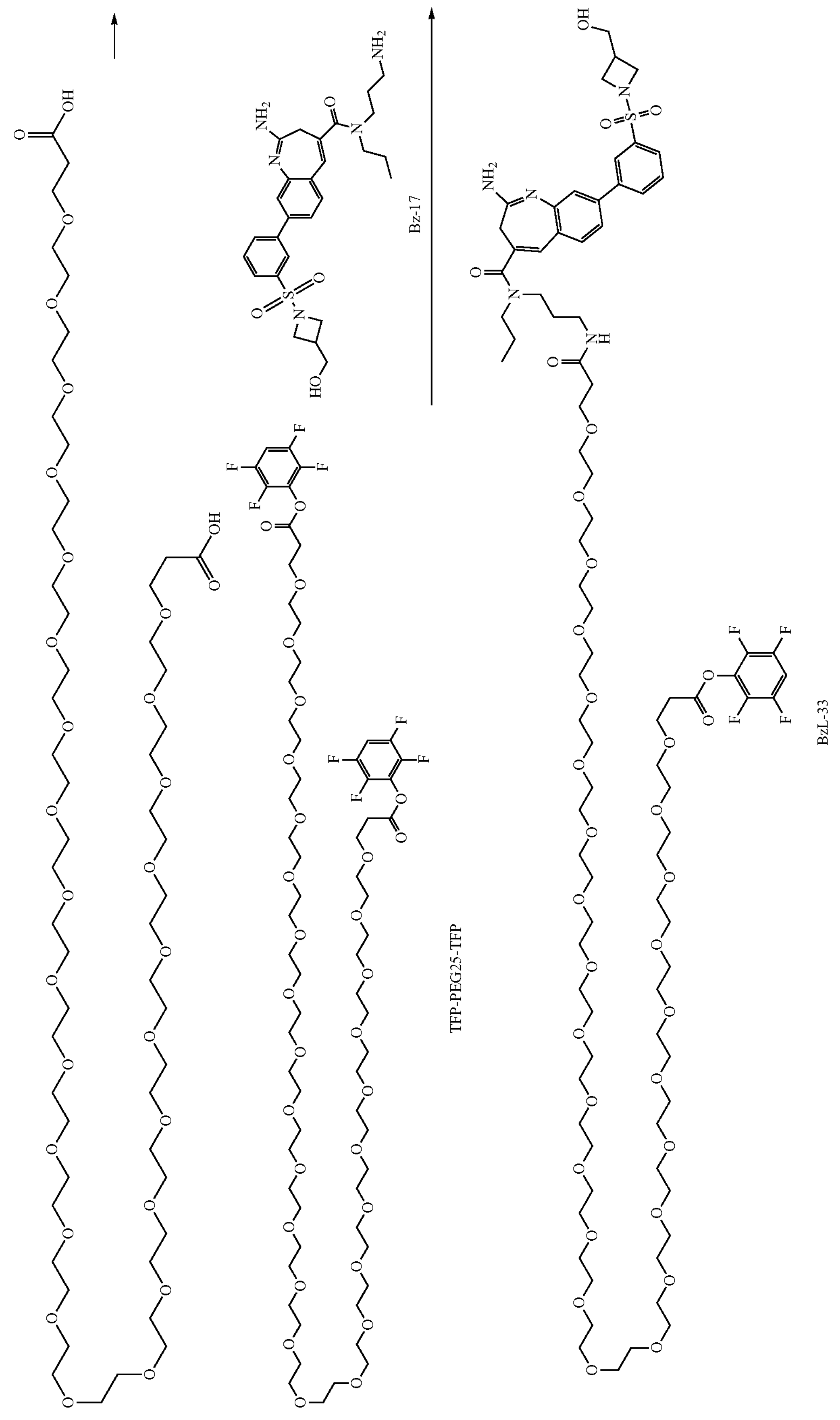
Bz-17
TFP-PEG25-TFP
BzL-33

A vial was charged with 4,7,10,13,16,19,22,25,28,31,34,37,40,43,46,49,52,55,58,61,64,67,70,73,76-pentacosaoxanonaheptacontanedioic acid (269 mg, 0.221 mmol), 2,3,5,6-tetrafluorophenol (110 mg, 0.662 mmol), collidine (176 μL, 1.33 mmol), 1-ethyl-3-(3-dimethylaminopropyl) carbodiimide (127 mg, 0.221 mmol) and 3 mL DMF. The reaction was stirred for 16 h, then purified by reverse phase preparative HPLC utilizing a 25-75% gradient of acetonitrile:water containing 0.1% trifluoroacetic acid. The purified fractions were combined and lyophilized to afford 266 mg of bis(2,3,5,6-tetrafluorophenyl) 4,7,10,13,16,19,22,25,28,31,34,37,40,43,46,49,52,55,58,61,64,67,70,73,76-pentacosaoxanonaheptacontanedioate, TFP-PEG25-TFP in 79% yield. LC/MS [M+H]1515.68 (calculated); LC/MS [M+H] 1516.00 (observed).

A vial was charged with 2-amino-N-(3-aminopropyl)-8-[3-[3-(hydroxymethyl)azetidin-1-yl]sulfonylphenyl]-N-propyl-3H-1-benzazepine-4-carboxamide, Bz-17 (0.0275 mmol), TFP-PEG25-TFP (0.0275 mmol), collidine (0.0825 mmol) in 300 μL DMF. The reaction was maintained for 5 h and then purified by reverse phase preparative HPLC utilizing a 25-75% gradient of acetonitrile:water containing 0.1% trifluoroacetic acid. The purified fractions were combined and lyophilized to afford 8.2 mg of 2,3,5,6-tetrafluorophenyl 84-(2-amino-8-(3-((3-(hydroxymethyl)azetidin-1-yl)sulfonyl)phenyl)-3H-benzo[b]azepine-4-carbonyl)-79-oxo-4,7,10,13,16,19,22,25,28,31,34,37,40,43,46,49,52,55,58,61,64,67,70,73,76-pentacosaoxa-80,84-diazaheptaoctacontanoate, BzL-33 in 25% yield. LC/MS [M+H] 1874.9 (calculated); LC/MS [M+H] 1874.9 (observed).

Example 54: Synthesis of BzL-34

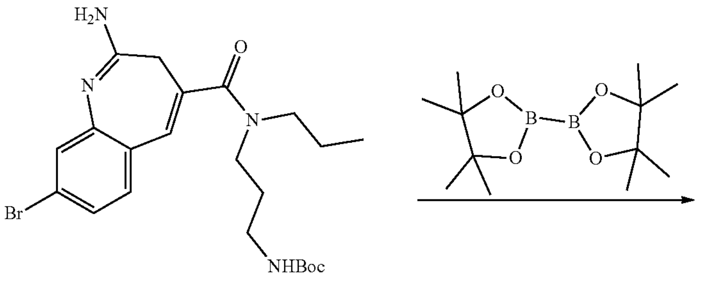

BzL-34a

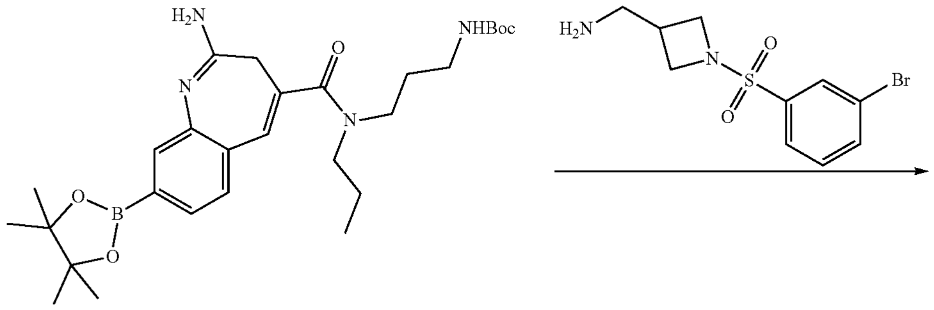

BzL-34b

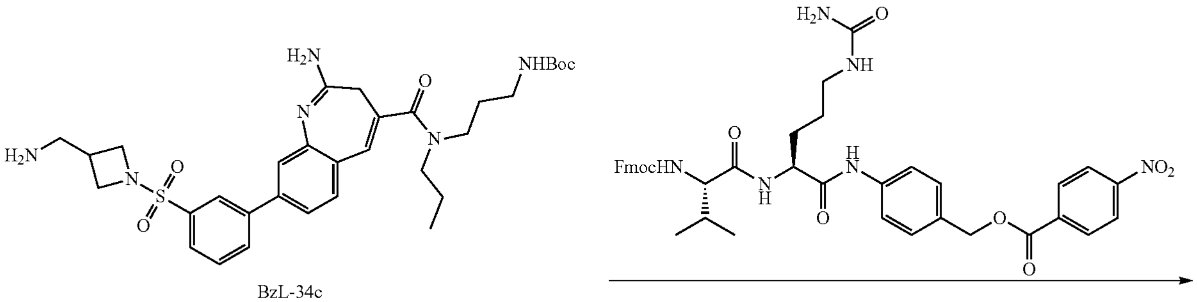

BzL-34c

-continued
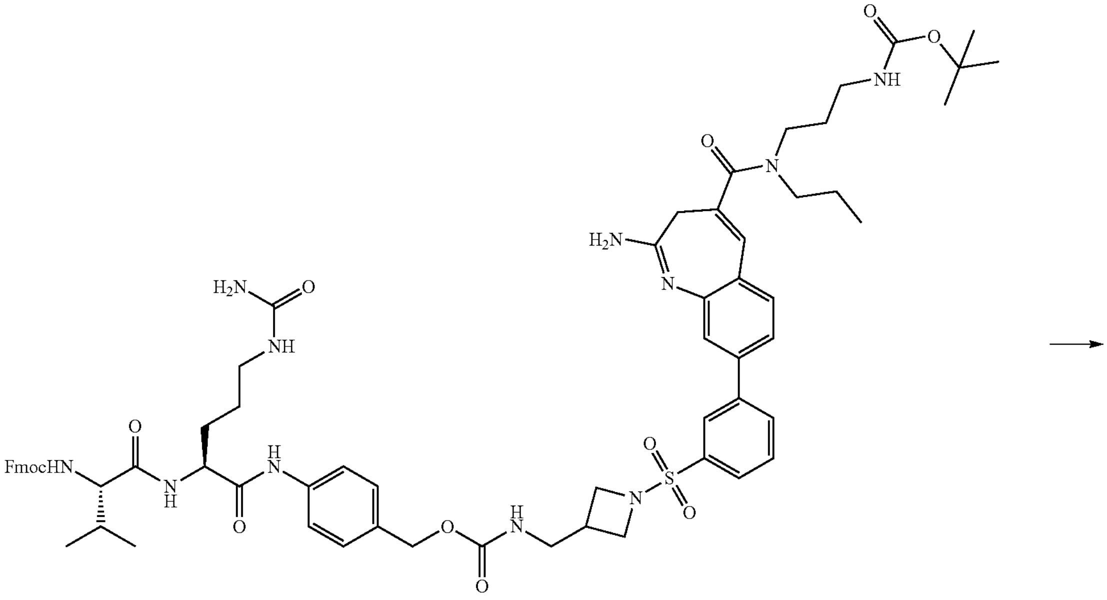
BzL-34d
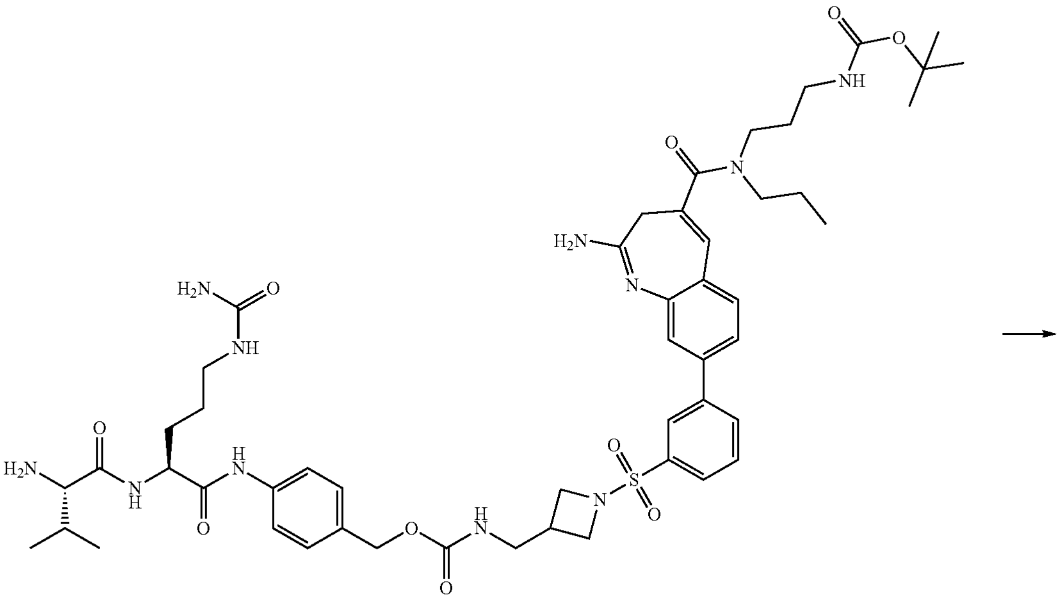
BzL-34e

-continued

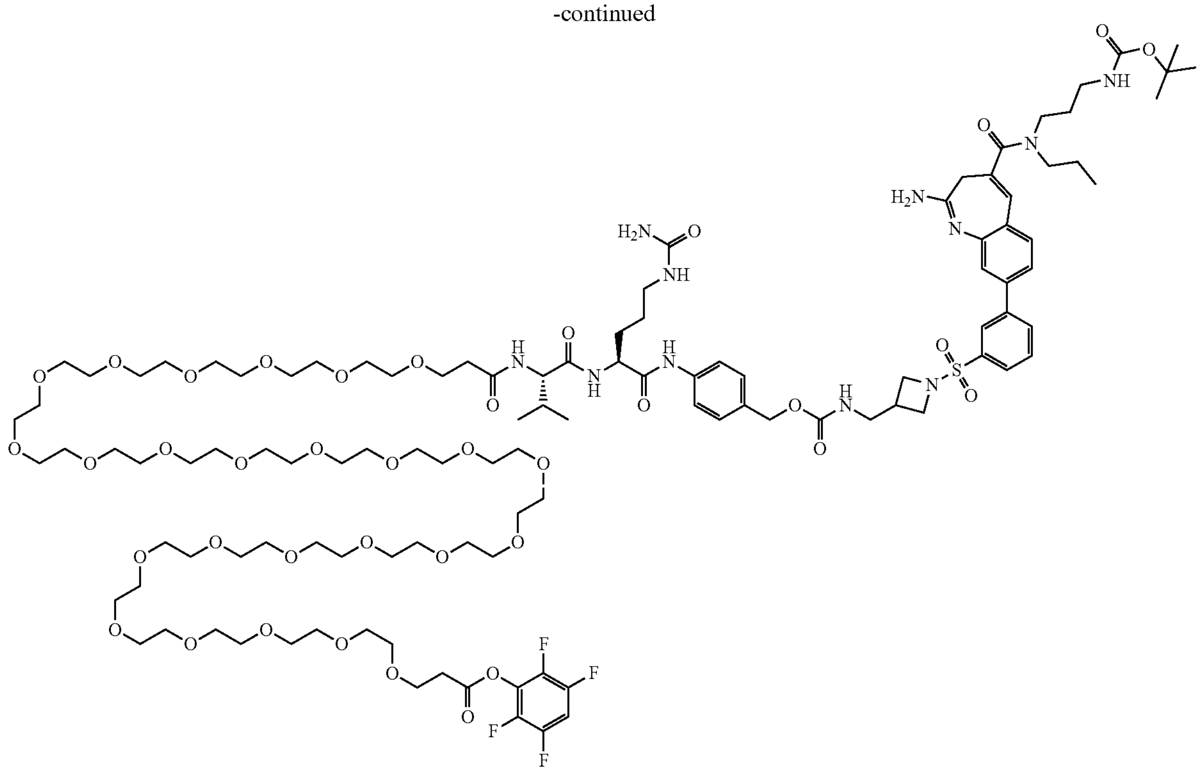

BzL34

Preparation of BzL-34b. To a mixture of tert-butyl N-[3-[(2-amino-8-bromo-3H-1-benzazepine-4-carbonyl)-propyl-amino]propyl]carbamate, BzL-34a (0.80 g, 1.67 mmol, 1.0 eq) in dioxane (10 mL) was added 4,4,4',4',5,5,5',5'-octamethyl-2,2'-bi(1,3,2-dioxaborolane), $Pin_2B_2$ (509 mg, 2.00 mmol, 1.2 eq), KOAc (246 mg, 2.50 mmol, 1.5 eq) and $Pd(dppf)Cl_2$ (122 mg, 167 μmol, 0.1 eq) in one portion at 15° C. under $N_2$ and then stirred at 90° C. for 12 h. The mixture was filtered and concentrated to give tert-butyl N-[3-[[2-amino-8-(4,4,5,5-tetramethyl-1,3,2-dioxaborolan-2-yl)-3H-1-benzazepine-4-carbonyl]-propyl-amino]propyl]carbamate, BzL-34b (0.90 g, crude) as black solid.

Preparation of BzL-34c. To a mixture of [1-(3-bromophenyl)sulfonylazetidin-3-yl]methanamine (0.40 g, 1.17 mmol, 1 eq, HCl) and BzL-34b (493 mg, 937 μmol, 0.8 eq) in dioxane (4 mL) was added a solution of $K_2CO_3$ (728 mg, 5.27 mmol, 4.5 eq) in $H_2O$ (0.4 mL) and $Pd(dppf)Cl_2$ (85.7 mg, 117 μmol, 0.1 eq) at 15° C. under $N_2$ and then stirred at 90° C. for 2 h. The mixture was filtered and concentrated. The residue was purified by prep-HPLC (column: Welch Xtimate C18 100×25 mm, 3 μm particle size; mobile phase: [water (0.1% TFA)-ACN]; B %: 20%-45%, 10.5 min) to give tert-butyl N-[3-[[2-amino-8-[3-[3-(aminomethyl)azetidin-1-yl] sulfonylphenyl]-3H-1-benzazepine-4-carbonyl]-propyl-amino]propyl]carbamate, BzL-34c (0.223 g, 357 μmol, 30.5% yield) as white solid. $^1H$ NMR (MeOD, 400 MHz) δ 8.14-8.07 (m, 2H), 7.92 (d, J=8.0 Hz, 1H), 7.86-7.81 (m, 1H), 7.79-7.70 (m, 3H), 7.12 (s, 1H), 3.96 (t, J=8.4 Hz, 2H), 3.65 (dd, J=5.2, 8.4 Hz, 2H), 3.58-3.42 (m, 4H), 3.37 (s, 2H), 3.06 (d, J=7.2 Hz, 4H), 1.90-1.78 (m, 2H), 1.74-1.64 (m, 2H), 1.44 (s, 9H), 0.96-0.90 (m, 3H). LC/MS [M+H] 625.3 (calculated); LC/MS [M+H] 625.0 (observed).

Preparation of BzL-34d. To a mixture of BzL-34c (0.18 g, 288 μmol, 1.0 eq) and [4-[[(2S)-2-[[(2S)-2-(9H-fluoren-9-ylmethoxycarbonylamino)-3-methyl-butanoyl]amino]-5-ureido-pentanoyl]amino]phenyl]methyl (4-nitrophenyl) carbonate (176.7 mg, 230 μmol, 0.8 eq) in DMF (2 mL) was added DIEA (74.5 mg, 576 μmol, 100 μL, 2.0 eq) in one portion at 15° C. The mixture was stirred at the same temperature for 0.5 h. Then it was filtered and purified by prep-HPLC (column: Welch Xtimate C18 150×25 mm, 5 μm particle size; mobile phase: [water (10 mM $NH_4HCO_3$)-ACN]; B %: 55%-75%, 10.5 min) to give [4-[[(2S)-2-[[(2S)-2-(9H-fluoren-9-ylmethoxycarbonylamino)-3-methyl-butanoyl]amino]-5-ureido-pentanoyl]amino]phenyl] methyl N-[[1-[3-[2-amino-4-[3-(tert-butoxycarbonylamino)propyl-propyl-carbamoyl]-3H-1-benzazepin-8-yl]phenyl]sulfonylazetidin-3-yl]methyl]carbamate, BzL-34d (0.024 g, 19.16 μmol, 6.65% yield) as yellow solid. $^1H$ NMR (MeOH, 400 MHz) δ 8.04 (s, 1H), 7.95 (d, J=6.4 Hz, 1H), 7.81-7.79 (m, 3H), 7.73 (d, J=7.6 Hz, 1H), 7.65 (t, J=6.8 Hz, 2H), 7.54 (d, J=8.0 Hz, 2H), 7.48-7.43 (m, 2H), 7.41-7.33 (m, 3H), 7.32-7.27 (m, 2H), 7.20 (d, J=8.0 Hz, 2H), 6.91 (s, 1H), 4.59 (s, 2H), 4.52 (s, 1H), 4.42-4.32 (m, 2H), 4.24-4.17 (m, 1H), 3.95 (d, J=7.2 Hz, 1H), 3.86-3.77 (m, 2H), 3.58-3.47 (m, 4H), 3.46-3.39 (m, 2H), 3.19-3.02 (m, 6H), 2.62 (d, J=7.6 Hz, 1H), 2.13-2.01 (m, 1H), 1.97-1.80 (m, 3H), 1.66 (s, 3H), 1.57 (s, 2H), 1.49-1.28 (m, 8H), 1.00-0.95 (m, 10H). LC/MS [M+H] 1252.6 (calculated); LC/MS [M+H] 1252.2 (observed).

Preparation of BzL-34e. A vial was charged with Bz-34d (20 mg, 0.016 mmol), diethylamine (0.08 mmol) and 150 μL DMF. The reaction was maintained for 6 h, then concentrated under reduced pressure to give 4-((S)-2-((S)-2-amino-3-methylbutanamido)-5-ureidopentanamido)benzyl ((1-((3-(2-amino-4-((3-((tert-butoxycarbonyl)amino)propyl)(propyl)carbamoyl)-3H-benzo[b]azepin-8-yl)phenyl)

sulfonyl)azetidin-3-yl)methyl)carbamate, BzL-34e which was used in the subsequent step without further purification.

Preparation of BzL-34. Using the procedures described for BzL-33, 2,3,5,6-tetrafluorophenyl (6S,9S)-1-amino-6-((4-(((((1-((3-(2-amino-4-((3-((tert-butoxycarbonyl)amino)propyl)(propyl)carbamoyl)-3H-benzo[b]azepin-8-yl)phenyl)sulfonyl)azetidin-3-yl)methyl)carbamoyl)oxy)methyl)phenyl)carbamoyl)-9-isopropyl-1,8,11-trioxo-14,17,20,23,26,29,32,35,38,41,44,47,50,53,56,59,62,65,68,71,74,77,80,83,86-pentacosaoxa-2,7,10-triazanonaoctacontan-89-oate, BzL-34 was obtained. LC/MS [M+H] 2379.2 (calculated); LC/MS [M+2H/2] 1190.1 (observed).

Example 55: Synthesis of BzL-35

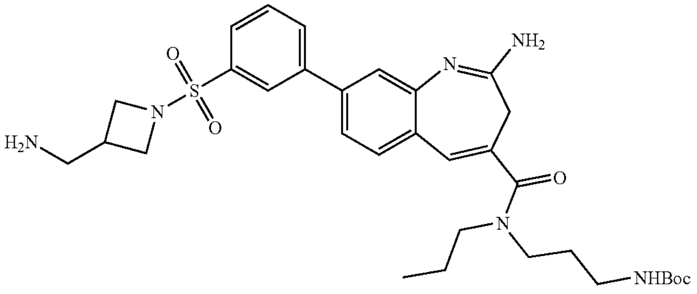

BzL-34c

+

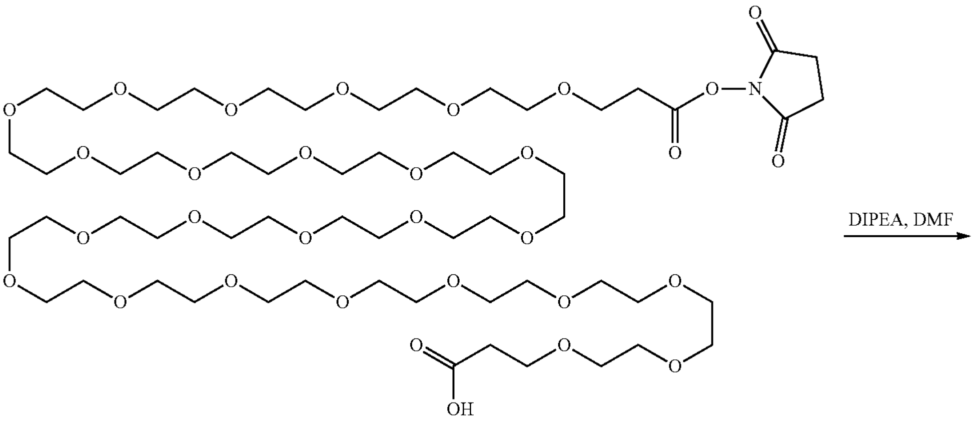

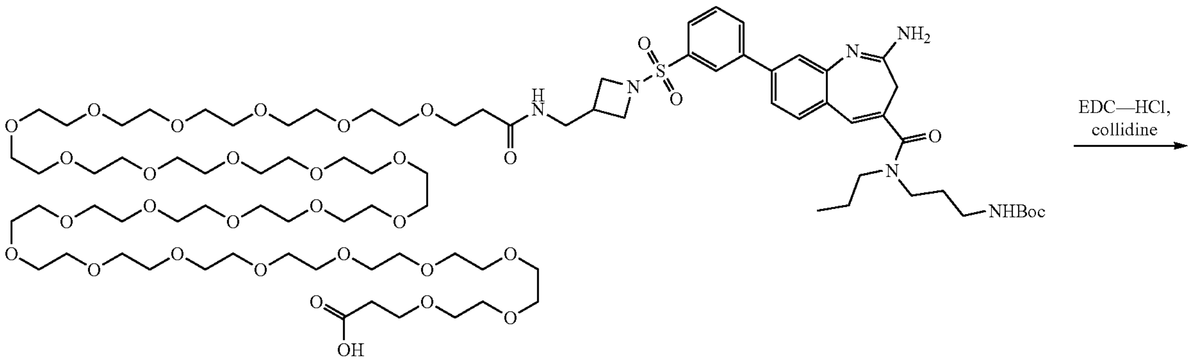

BzL-35a

-continued

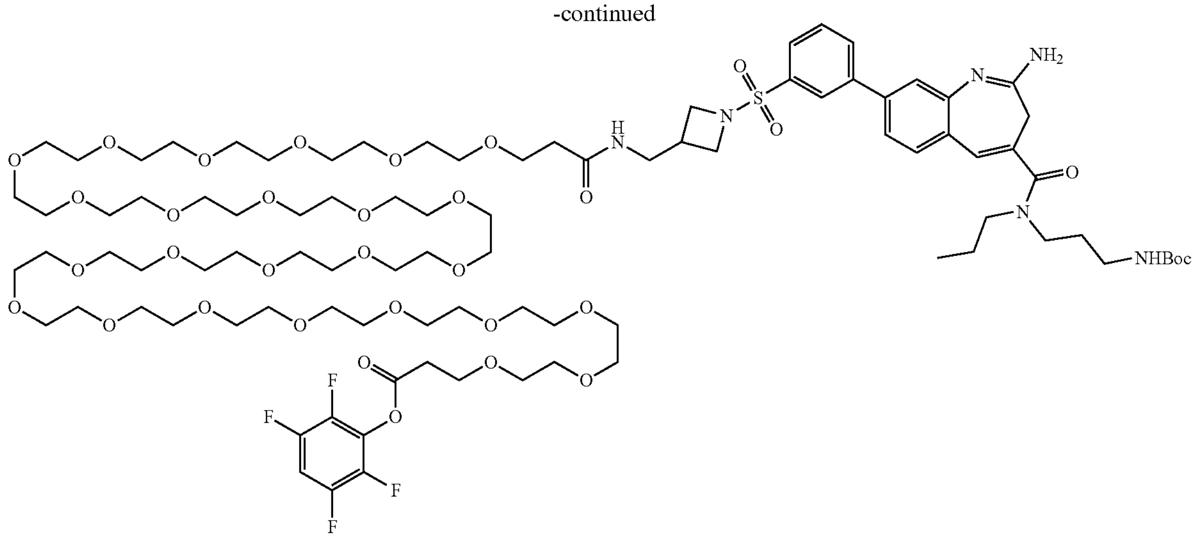

BzL-35

Preparation of BzL-35a. tert-Butyl (3-(2-amino-8-(3-((3-(aminomethyl)azetidin-1-yl)sulfonyl)phenyl)-N-propyl-3H-benzo[b]azepine-4-carboxamido)propyl)carbamate, BzL-34c (0.04 g, 0.064 mmol, 1 eq) and 79-((2,5-dioxopyrrolidin-1-yl)oxy)-79-oxo-4,7,10,13,16,19,22,25,28,31,34,37,40,43,46,49,52,55,58,61,64,67,70,73,76-pentacosaoxanonaheptacontanoic acid (0.084 mg, 0.064 mmol, 1 eq) were dissolved in DMF with diisopropylethylamine (0.033 ml, 0.192 mmol, 3 eq). The reaction was monitored by LCMS and purified by HPLC to give 1-(1-((3-(2-amino-4-((3-((tert-butoxycarbonyl)amino)propyl)(propyl)carbamoyl)-3H-benzo[b]azepin-8-yl)phenyl)sulfonyl)azetidin-3-yl)-3-oxo-6,9,12,15,18,21,24,27,30,33,36,39,42,45,48,51,54,57,60,63,66,69,72,75,78-pentacosaoxa-2-azahenoctacontan-81-oic acid, BzL-35a (0.056, 0.031 mmol, 48%). LC/MS [M+H] 1825.99 (calculated); LC/MS [M+H] 1826.24 (observed).

Preparation of BzL-35. BzL-35a (0.060 g, 0.033 mmol, 1 eq) and 2,3,5,6-tetrafluorophenol, TFP (0.011 g, 0.065 mmol, 2 eq) were dissolved in 1 ml DMF. Collidine, 2,4,6-trimethylpyridine (0.022 ml, 0.16 mmol, 5 eq) was added, followed by N-(3-dimethylaminopropyl)-N-ethylcarbodiimide hydrochloride, EDC-HCl, CAS Reg. No. 25952-53-8 (0.019 g, 0.098 mmol, 3 eq). The reaction was stirred at room temperature and monitored by LCMS, then concentrated and purified by HPLC to give 2,3,5,6-tetrafluorophenyl 1-(1-((3-(2-amino-4-((3-((tert-butoxycarbonyl)amino)propyl)(propyl)carbamoyl)-3H-benzo[b]azepin-8-yl)phenyl)sulfonyl)azetidin-3-yl)-3-oxo-6,9,12,15,18,21,24,27,30,33,36,39,42,45,48,51,54,57,60,63,66,69,72,75,78-pentacosaoxa-2-azahenoctacontan-81-oate, BzL-35 (0.027 g, 0.014 mmol, 42%). LC/MS [M+H] 1973.98 (calculated); LC/MS [M+H] 1974.62 (observed).

Example 56: Synthesis of BzL-36

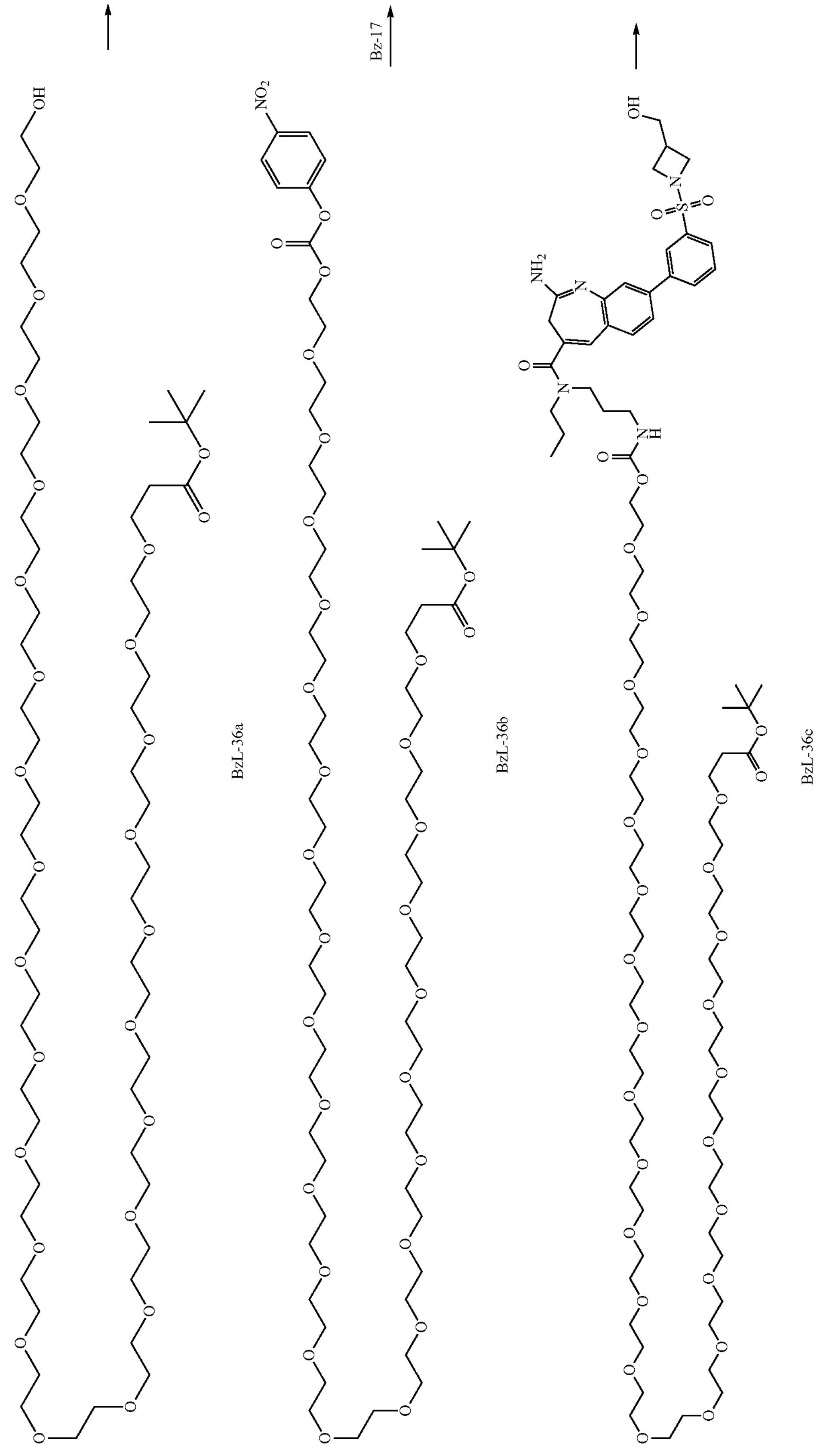
BzL-36a
BzL-36b
BzL-36c

-continued
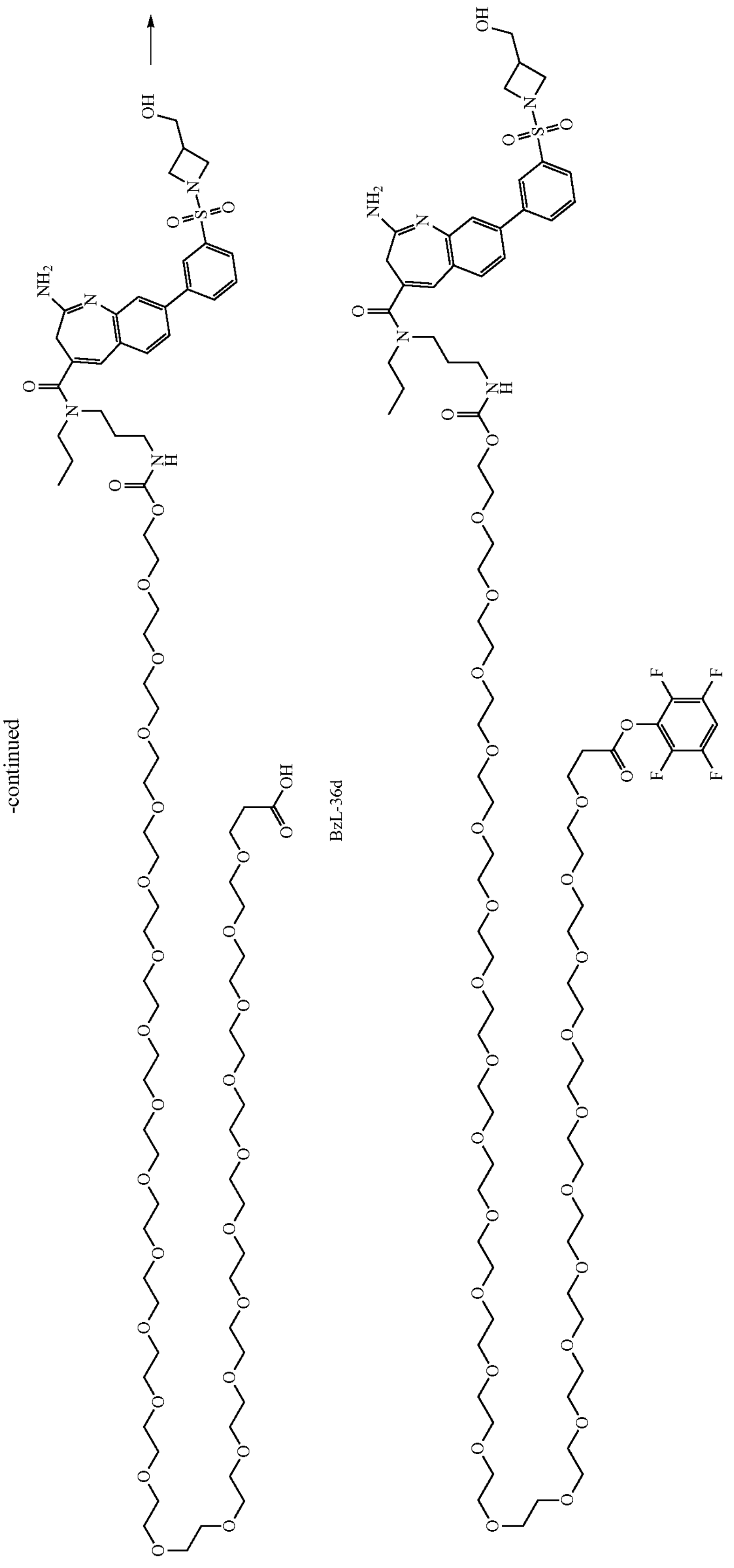
BzL-36d
BzL-36

Preparation of BzL-36b. A vial was charged with tert-butyl 1-hydroxy-3,6,9,12,15,18,21,24,27,30,33,36,39,42,45,48,51,54,57,60,63,66,69,72-tetracosaoxapentaheptacontan-75-oate, BzL-36a (148 mg, 0.123 mmol), diisopropylethylamine (0.369 mmol) and 0.6 mL anhydrous DMF. The vial was cooled to 0° C., then 4-nitrophenylchloroformate (0.123 mmol) was added portion-wise. The reaction was warmed to room temperature and maintained for 3 h, then purified by reverse phase preparative HPLC utilizing a 25-75% gradient of acetonitrile:water containing 0.1% trifluoroacetic acid. The purified fractions were combined and lyophilized to afford 42.5 mg of tert-butyl 1-(4-nitrophenoxy)-1-oxo-2,5,8,11,14,17,20,23,26,29,32,35,38,41,44,47,50,53,56,59,62,65,68,71,74-pentacosaoxaheptaheptacontan-77-oate, BzL-36b. LC/MS [M+H] 1368.7 (calculated); LC/MS [M+H] 1368.7 (observed).

Preparation of BzL-36c. A vial was charged with Bz-17 (0.0275 mmol), BzL-36b (0.0275 mmol), HOAT (0.02 mmol), diisopropylethylamine (0.0825 mmol), 250 μL DCM, and 250 μL DMF. The reaction was maintained until all starting material was consumed by LCMS. The crude reaction was purified by reverse phase preparative HPLC utilizing a 25-75% gradient of acetonitrile:water containing 0.1% trifluoroacetic acid. The purified fractions were combined and lyophilized to afford 22.5 mg of tert-butyl 82-(2-amino-8-(3-((3-(hydroxymethyl)azetidin-1-yl)sulfonyl)phenyl)-3H-benzo[b]azepine-4-carbonyl)-77-oxo-4,7,10,13,16,19,22,25,28,31,34,37,40,43,46,49,52,55,58,61,64,67,70,73,76-pentacosaoxa-78,82-diazapentaoctacontanoate, BzL-36c. LC/MS [M+H] 1754.9 (calculated); LC/MS [M+H] 1754.9 (observed).

Preparation of BzL-36d. A vial was charged with BzL-36c (0.0128 mmol), 1 mL DCM, and 0.2 mL trifluoroacetic acid. The reaction was maintained for 3 h, then concentrated under reduced pressure. The resultant residue was azeotroped thrice with toluene to give 82-(2-amino-8-(3-((3-(hydroxymethyl)azetidin-1-yl)sulfonyl)phenyl)-3H-benzo[b]azepine-4-carbonyl)-77-oxo-4,7,10,13,16,19,22,25,28,31,34,37,40,43,46,49,52,55,58,61,64,67,70,73,76-pentacosaoxa-78,82-diazapentaoctacontanoic acid, BzL-36d which was used immediately in the subsequent step.

Preparation of BzL-36. A vial was charged with BzL-36d (8.9 mg, 0.005 mmol), 2,3,5,6-tetrafluorophenol (1.8 mg, 0.011 mmol), collidine (2.2 μL, 0.016 mmol), 1-ethyl-3-(3-dimethylaminopropyl)carbodiimide (1 mg, 0.005 mmol) and 100 μL DMF. The reaction was stirred for 6 h, then purified by reverse phase preparative HPLC utilizing a 25-75% gradient of acetonitrile:water containing 0.1% trifluoroacetic acid. The purified fractions were combined and lyophilized to afford 6.3 mg of 2,3,5,6-tetrafluorophenyl 82-(2-amino-8-(3-((3-(hydroxymethyl)azetidin-1-yl)sulfonyl)phenyl)-3H-benzo[b]azepine-4-carbonyl)-77-oxo-4,7,10,13,16,19,22,25,28,31,34,37,40,43,46,49,52,55,58,61,64,67,70,73,76-pentacosaoxa-78,82-diazapentaoctacontanoate, BzL-36. LC/MS [M+H] 1846.9 (calculated); LC/MS [M+H] 1846.9 (observed).

Example 57: Synthesis of BzL-37

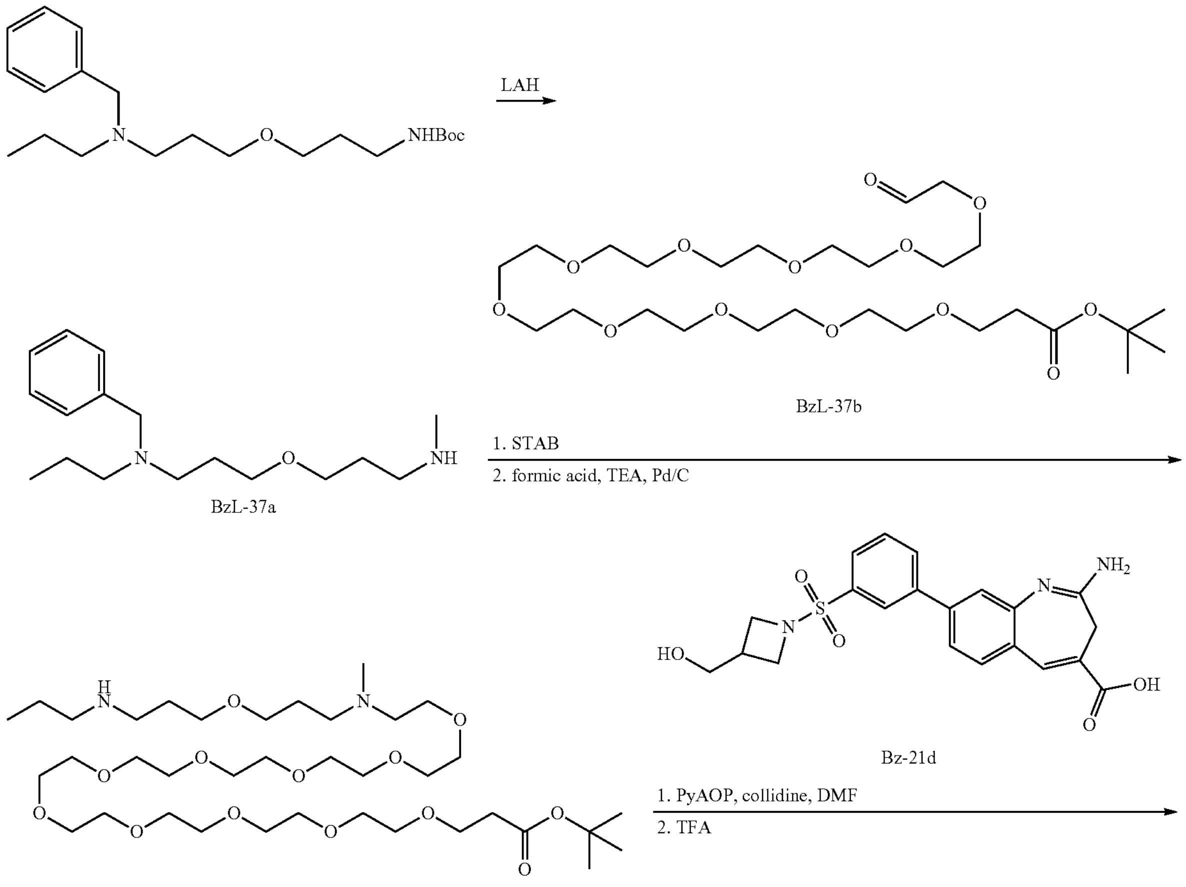

BzL-37b
BzL-37a
Bz-21d

BzL-37c

-continued

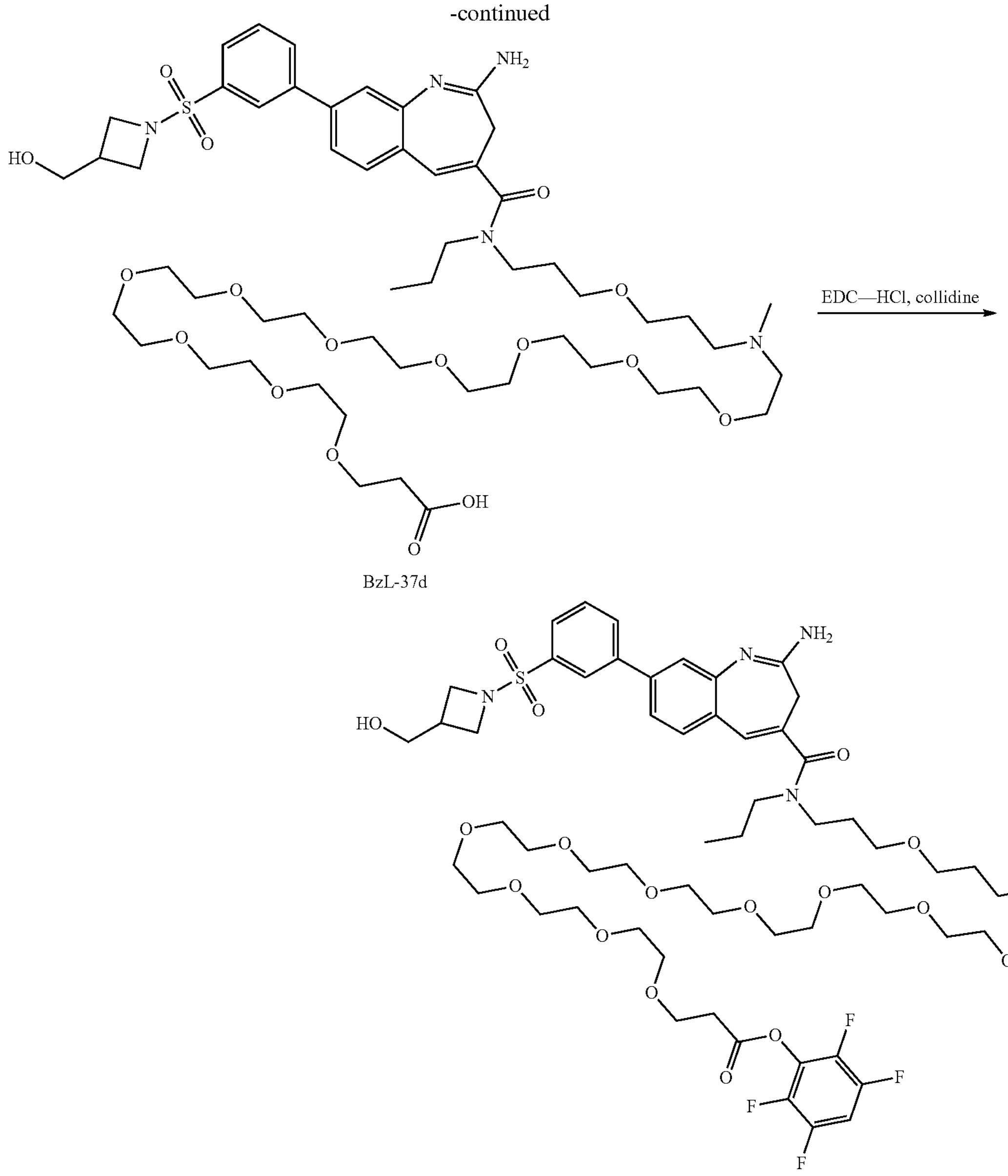

BzL-37d

BzL-37

Preparation of BzL-37a. tert-Butyl (3-(3-(benzyl(propyl) amino)propoxy)propyl)carbamate (0.032 g, 0.088 mmol, 1 eq) was dissolved in THF. Lithium aluminum hydride (0.01 g, 0.26 mmol, 3 eq) was added and the reaction heated to 60° C. The reaction was concentrated and purified by HPLC to give N-benzyl-3-(3-(methylamino)propoxy)-N-propylpropan-1-amine, BzL-37a (0.01 g, 0.036 mmol, 41%). LC/MS [M+H] 279.24 (calculated); LC/MS [M+H] 279.33 (observed).

Preparation of BzL-37c. BzL-37a (0.01 g, 0.036 mmol, 1 eq) and tert-butyl 1-oxo-3,6,9,12,15,18,21,24,27,30-decaoxatritriacontan-33-oate, BzL-37b (0.02 g, 0.036 mmol, 1 eq) were dissolved in DCM. Sodium triacetoxyborohydride, STAB (0.022 g, 0.11 mmol, 3 eq) was added and the reaction stirred at room temperature. The solution was concentrated and purified by HPLC. The purified product was taken up in methanol with triethylamine. Formic acid was added, followed by 10 wt % Pd/C, and the reaction heated to 60° C. Upon consumption of starting material, the reaction mixture was filtered and concentrated to give tert-butyl 34-methyl-4,7,10,13,16,19,22,25,28,31,38-undecaoxa-34,42-diazapentatetracontanoate, BzL-37c (0.007 g, 0.0092 mmol, 26%). LC/MS [M+H] 757.74 (calculated); LC/MS [M+H] 757.85 (observed).

Preparation of BzL-37d. 2-Amino-8-(3-((3-(hydroxymethyl)azetidin-1-yl)sulfonyl)phenyl)-3H-benzo[b]azepine-4-carboxylic acid, Bz-21d (0.0040 g, 0.0092 mmol, 1 eq), BzL-37c (0.007 g, 0.0092 mmol, 1 eq), and collidine (0.004 ml, 0.028 mmol, 3 eq) were dissolved in DMF. PyAOP (0.0072 g, 0.014 mmol, 1.5 eq) was added and the mixture stirred at room temperature. When complete, the reaction mixture was concentrated and purified by RP-HPLC. The isolated product was concentrated, dissolved in minimal TFA, and allowed to stand at room temperature for 15 minutes. The solution was then concentrated and purified by RP-HPLC to give 42-(2-amino-8-(3-((3-(hydroxymethyl)

azetidin-1-yl)sulfonyl)phenyl)-3H-benzo[b]azepine-4-carbonyl)-34-methyl-4,7,10,13,16,19,22,25,28,31,38-undecaoxa-34,42-diazapentatetracontanoic acid, BzL-37d (0.004 g, 0.0036 mmol, 39%). LC/MS [M+H] 1110.59 (calculated); LC/MS [M+H] 1110.93 (observed).

Preparation of BzL-37. BzL-37d (0.004 g, 0.0036 mmol, 1 eq) and TFP (0.0033 g, 0.018 mmol, 5 eq) were dissolved in 1 ml DMF. Collidine (0.005 ml, 0.036 mmol, 10 eq) was added, followed by EDC-HCl (0.0035 g, 0.018 mmol, 5 eq). The reaction was stirred at room temperature and monitored by LCMS, then concentrated and purified by HPLC to give 2,3,5,6-tetrafluorophenyl 42-(2-amino-8-(3-((3-(hydroxymethyl)azetidin-1-yl)sulfonyl)phenyl)-3H-benzo[b]azepine-4-carbonyl)-34-methyl-4,7,10,13,16,19,22,25,28,31,38-undecaoxa-34,42-diazapentatetracontanoate, BzL-37 (0.0016 g, 0.0013 mmol, 35%). LC/MS [M+H] 1258.58 (calculated); LC/MS [M+H] 1258.96 (observed).

Example 58: Synthesis of BzL-38

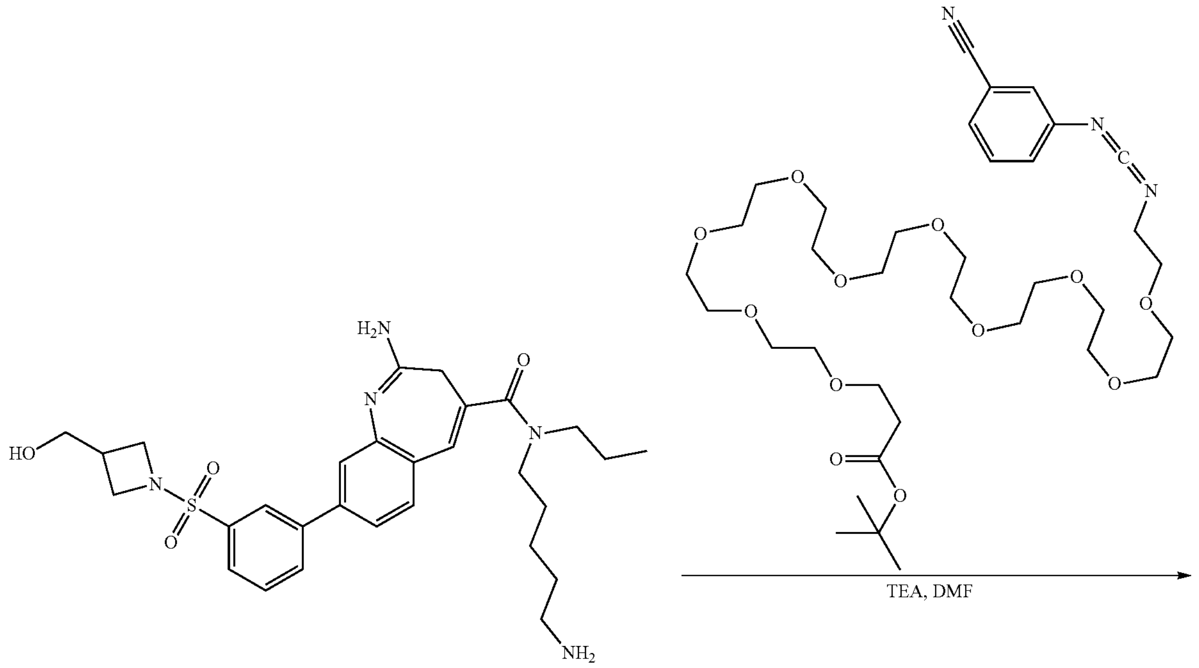

Bz-20

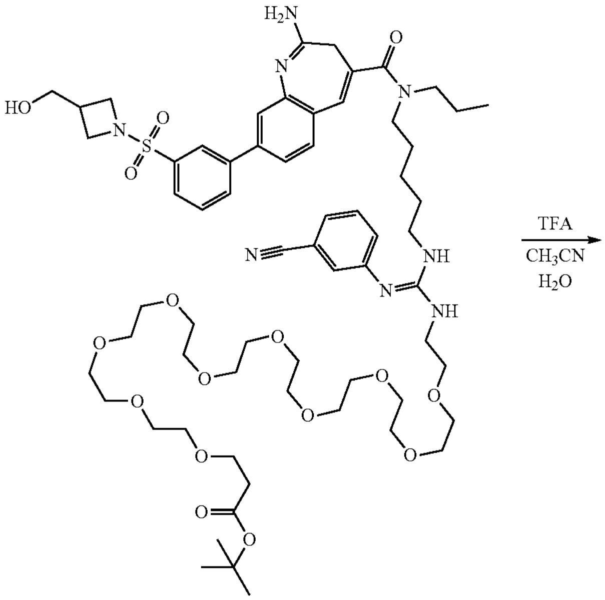

BzL-38a

-continued

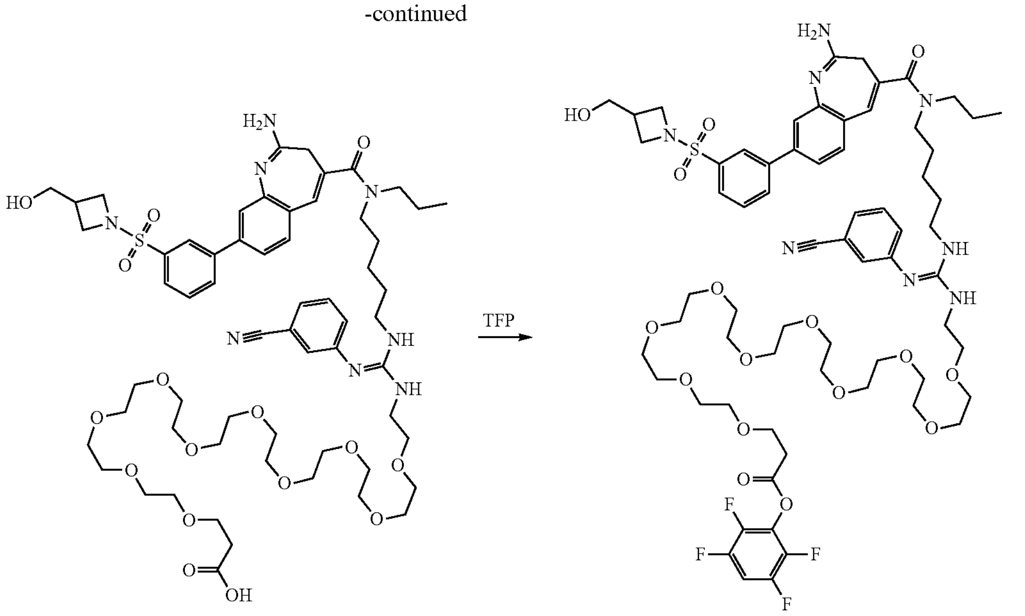

BzL-38b

BzL-38

Preparation of BzL-38a. This was prepared using the same methods as described in the synthesis of BzL-42. LC/MS [M+H] 1265.7 (calculated); LC/MS [M+H] 1265.7 (observed).

Preparation of BzL-38b. This was prepared using the same method as described in the synthesis of BzL-42. LC/MS [M+H] 1209.6 (calculated); LC/MS [M+H] 1209.6 (observed).

Preparation of BzL-38. This was prepared using the same method as described in the synthesis of BzL-42. LC/MS [M+H] 1357.6 (calculated); LC/MS [M+H] 1357.6 (observed).

Example 59: Synthesis of BzL-39

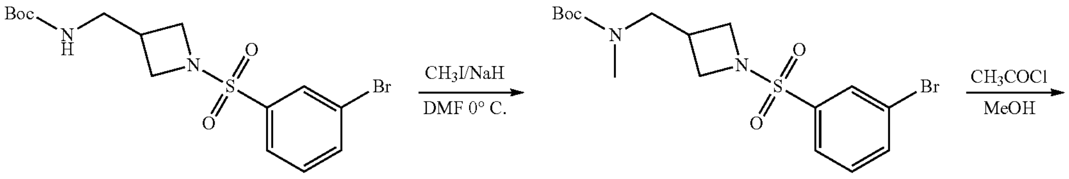

BzL-39a

BzL-39b

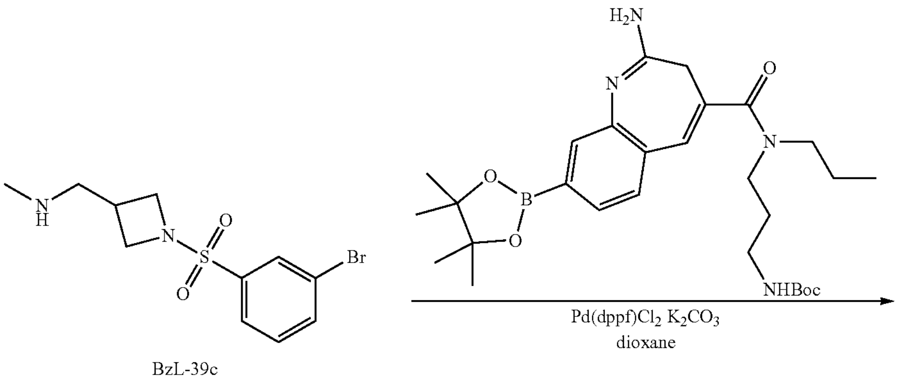

BzL-39c

-continued

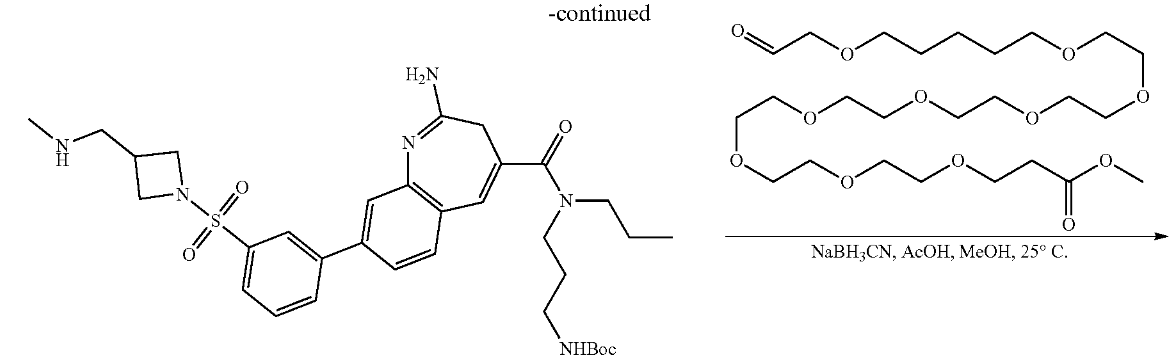

BzL-39d

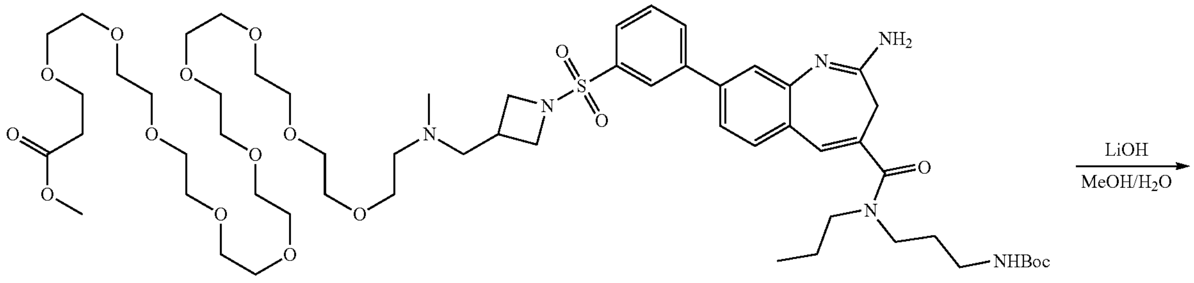

BzL-39e

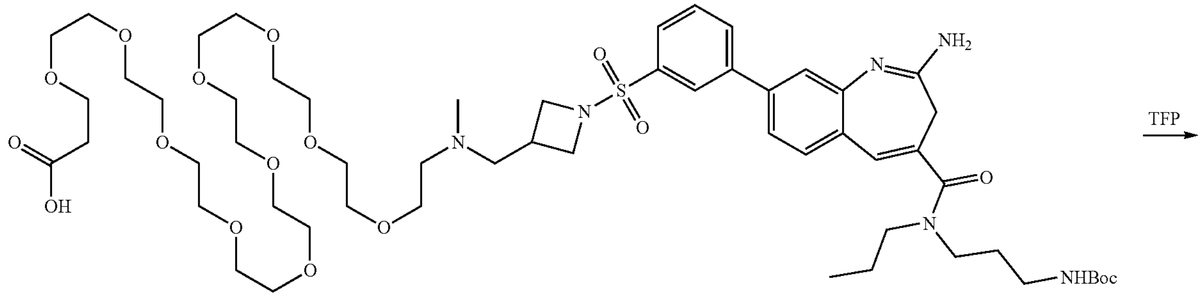

BzL-39f

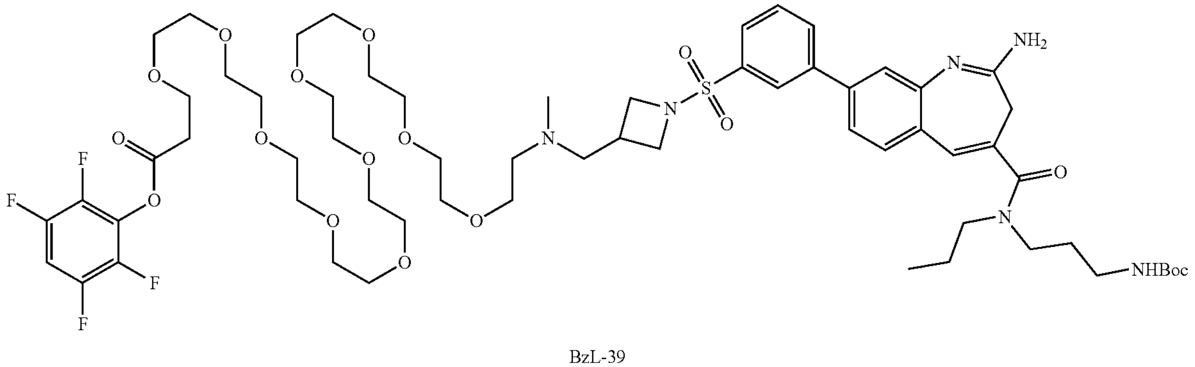 [SMILES: CCCN(CCCNC(=O)OC(C)(C)C)C(=O)C1=Cc2ccc(-c3cccc(S(=O)(=O)N4CC(CN(C)CCOCCOCCOCCOCCOCCOCCOCCOCCOCCOCCC(=O)Oc5c(F)c(F)cc(F)c5F)C4)c3)cc2N=C(N)C1]

BzL-39

Preparation of BzL-39b. To a solution of tert-butyl N-[[1-(3-bromophenyl)sulfonylazetidin-3-yl]methyl]carbamate, BzL-39a (1.0 g, 2.47 mmol, 1.0 eq) in DMF (10 mL) was added sodium hydride, NaH (148 mg, 3.70 mmol, 60% purity, 1.5 eq) in portions and it was stirred at 0° C. for 0.5 h. Then methyl iodide, $CH_3I$ (1.05 g, 7.40 mmol, 461 μL, 3.0 eq) was added and then stirred at 25° C. for 1 h. The reaction was quenched with water and extracted with EtOAc (30 mL×3). The organic layer was washed with brine, dried over $Na_2SO_4$, filtered and concentrated to give tert-butyl N-[[1-(3-bromophenyl) sulfonylazetidin-3-yl]methyl]-N-methyl-carbamate, BzL-39b (1.3 g, crude) as yellow oil. 1H NMR ($CDCl_3$, 400 MHz) δ 7.99 (t, J=2.0 Hz, 1H), 7.80-7.75 (m, 2H), 7.47 (t, J=8.0 Hz, 1H), 3.85 (t, J=7.6 Hz, 2H), 3.57 (t, J=7.2 Hz, 2H), 3.29 (d, J=7.2 Hz, 2H), 2.75 (s, 3H), 2.74-2.70 (m, 1H), 1.43 (s, 9H), 1.26 (t, J=7.2 Hz, 3H).

Preparation of BzL-39c. To a solution of BzL-39b (1.3 g, 3.10 mmol, 1.0 eq) in MeOH (20 mL) was added acetyl chloride (1.22 g, 15.5 mmol, 1.11 mL, 5.0 eq) at 25° C. and it was stirred at 50° C. for 1 h. Then the mixture was concentrated to give 1-[1-(3-bromophenyl)sulfonylazetidin-3-yl]-N-methyl-methanamine, BzL-39c (1 g, crude) as white solid. $^1H$ NMR (MeOD, 400 MHz) δ 8.00-7.98 (m, 1H), 7.93 (d, J=8.0 Hz, 1H), 7.84 (d, J=8.0 Hz, 1H), 7.64-7.59 (m, 1H), 3.94 (t, J=8.4 Hz, 2H), 3.64 (dd, J=5.6, 8.4 Hz, 2H), 3.14 (d, J=7.6 Hz, 2H), 2.84-2.77 (m, 1H), 2.66 (s, 3H).

Preparation of BzL-39d. To a mixture of tert-butyl N-[3-[[2-amino-8-(4,4,5,5-tetramethyl-1,3,2-dioxaborolan-2-yl)-3H-1-benzazepine-4-carbonyl]-propyl-amino]propyl]carbamate (0.44 g, 835 μmol, 1.0 eq) and Bzl-39c (357 mg, 1.00 mmol, 1.2 eq, HCl) in dioxane (4 mL) and $H_2O$ (0.5 mL) was added $Pd(dppf)Cl_2$ (30.6 mg, 41.79 μmol, 0.05 eq) and $K_2CO_3$ (231.0 mg, 1.67 mmol, 2.0 eq) at 15° C. under $N_2$. The mixture was stirred at 90° C. for 3 hours. The reaction was cooled to 15° C. and then filtered. The filtrate was poured into ice water (30 mL) and stirred for 5 min. The aqueous phase was extracted with ethyl acetate (20 mL×3) and combined organic phase was washed with brine (20 mL), dried with anhydrous $Na_2SO_4$, filtered and concentrated in vacuum. The residue was purified by flash silica gel chromatography (ISCO™; 40 g SEPAFLASH™ Silica Flash Column, eluent of 0-100% ethyl acetate/petroleum ether to EtOAc/MeOH=3/1 gradient at 60 mL/min) to afford tert-butyl N-[3-[[2-amino-8-[3-[3-(methylaminomethyl)azetidin-1-yl]sulfonylphenyl]-3H-1-benzazepine-4-carbonyl]-propyl-amino]propyl]carbamate, BzL-39d (0.32 g, 500.92 μmol, 59.94% yield) as yellow solid.

Preparation of BzL-39e. To a mixture of BzL-39d (0.2 g, 313 μmol, 1.0 eq) and methyl 3-[2-[2-[2-[2-[2-[2-[2-[2-[2-(2-oxoethoxy)ethoxy]ethoxy]ethoxy]ethoxy]ethoxy]ethoxy]ethoxy]ethoxy]ethoxy]propanoate (170 mg, 313 μmol, 1.0 eq) in MeOH (20 mL) was added acetic acid, AcOH (94.0 mg, 1.57 mmol, 5.0 eq) at 25° C. The mixture was stirred at this temperature for 10 min, then sodium cyanoborohydride, $NaBH_3CN$ (39.3 mg, 626. μmol, 2.0 eq) was added and the mixture was stirred at 25° C. for 18 hours. The reaction mixture was concentrated to give the crude product methyl 3-[2-[2-[2-[2-[2-[2-[2-[2-[2-[2-[[1-[3-[2-amino-4-[3-(tert-butoxycarbonylamino)propyl-propyl-carbamoyl]-3H-1-benzazepin-8-yl]phenyl]sulfonylazetidin-3-yl]methyl-methyl-amino]ethoxy]ethoxy]ethoxy]ethoxy]ethoxy]ethoxy]ethoxy]ethoxy]ethoxy]ethoxy]propanoate, BzL-39e (0.36 g, crude).

Preparation of BzL-39f. To a mixture of BzL-39e (0.36 g, 308 μmol, 1.0 eq) in MeOH (20 mL) was added a solution of lithium hydroxide hydrate, $LiOH{\cdot}H_2O$ (130 mg, 3.09 mmol, 10.0 eq) in $H_2O$ (2 mL) at 25° C. and then stirred at 25° C. for 18 hours. The reaction mixture was quenched with aq. HCl (4 M) until pH=7 and concentrated at 40° C. The residue was purified by prep-HPLC (column: Welch Xtimate C18 100×25 mm, 3 μm particle size; mobile phase: [water (0.1% TFA)-ACN]; B %: 20%-40%, 12 min) to give 3-[2-[2-[2-[2-[2-[2-[2-[2-[2-[2-[[1-[3-[2-amino-4-[3-(tert-butoxycarbonylamino)propyl-propyl-carbamoyl]-3H-1-benzazepin-8-yl]phenyl]sulfonylazetidin-3-yl]methyl-methyl-amino]ethoxy]ethoxy]ethoxy]ethoxy]ethoxy]ethoxy]ethoxy]ethoxy]ethoxy]ethoxy]propanoic acid, BzL-39f (56 mg, 48.64 μmol, 16% yield) as light yellow oil. $^1H$ NMR (MeOD, 400 MHz) δ 8.19-8.03 (m, 2H), 7.97-7.88 (m, 1H), 7.88-7.82 (m, 1H), 7.82-7.76 (m, 2H), 7.73-7.71 (m, 1H), 7.13 (s, 1H), 4.02 (t, J=8.0 Hz, 2H), 3.79 (t, J=4.8 Hz, 2H), 3.75-3.68 (m, 4H), 3.64-3.45 (m, 42H), 3.38 (s, 2H), 3.17-2.94 (m, 4H), 2.86 (s, 3H), 2.53 (t, J=6.4 Hz, 2H), 1.89-1.80 (m, 2H), 1.75-1.63 (m, 2H), 1.47-1.42 (m, 9H), 1.02-0.86 (m, 3H). LC/MS [M+H] 1151.61 (calculated); LC/MS [M+2H/2] 576.5 (observed).

Preparation of BzL-39. BzL-39f (0.056 g, 0.049 mmol, 1 eq) and TFP (0.040 g, 0.24 mmol, 5 eq) were dissolved in 2 ml DMF. Collidine (0.064 ml, 0.49 mmol, 10 eq) was added, followed by EDC-HCl (0.047 g, 0.24 mmol, 5 eq). The reaction was stirred at room temperature and monitored by LCMS, then concentrated and purified by HPLC to give 2,3,5,6-tetrafluorophenyl 1-(1-((3-(2-amino-4-((3-((tert-butoxycarbonyl)amino)propyl)(propyl)carbamoyl)-3H-benzo[b]azepin-8-yl)phenyl)sulfonyl)azetidin-3-yl)-2-methyl-5,8,11,14,17,20,23,26,29,32-decaoxa-2-azapentatriacontan-35-oate, BzL-39 (0.027 g, 0.021 mmol, 42%). LC/MS [M+H] 1299.61 (calculated); LC/MS [M+H] 1300.00 (observed).

Example 60. Synthesis of BzL-40

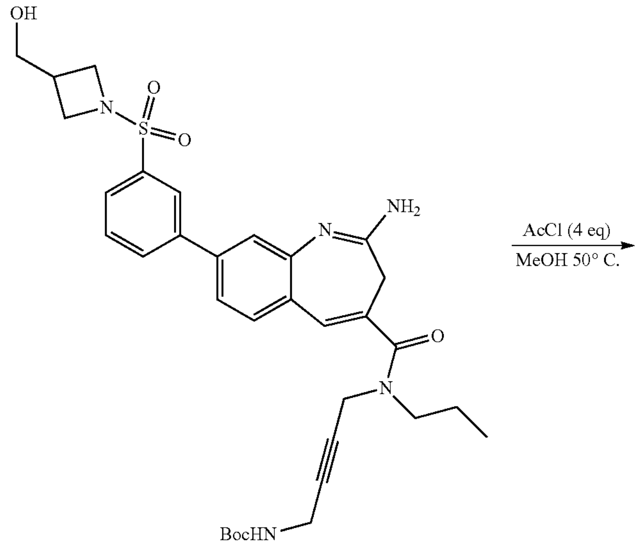

Bz-26

-continued
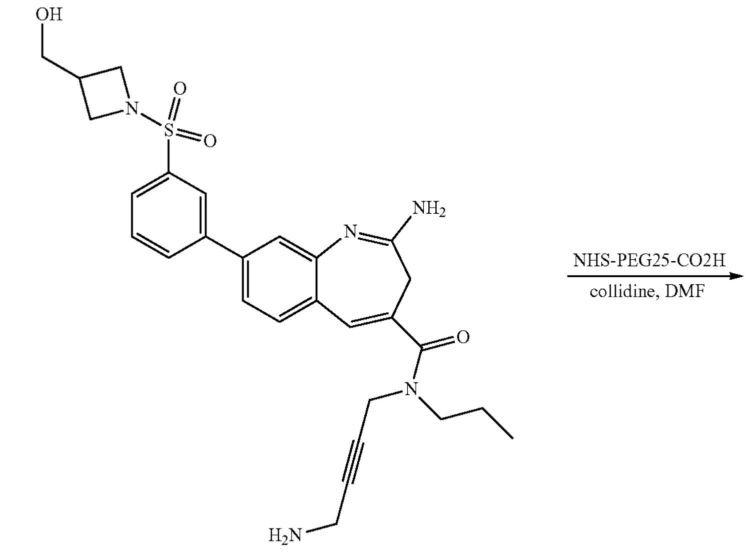
BzL-40a
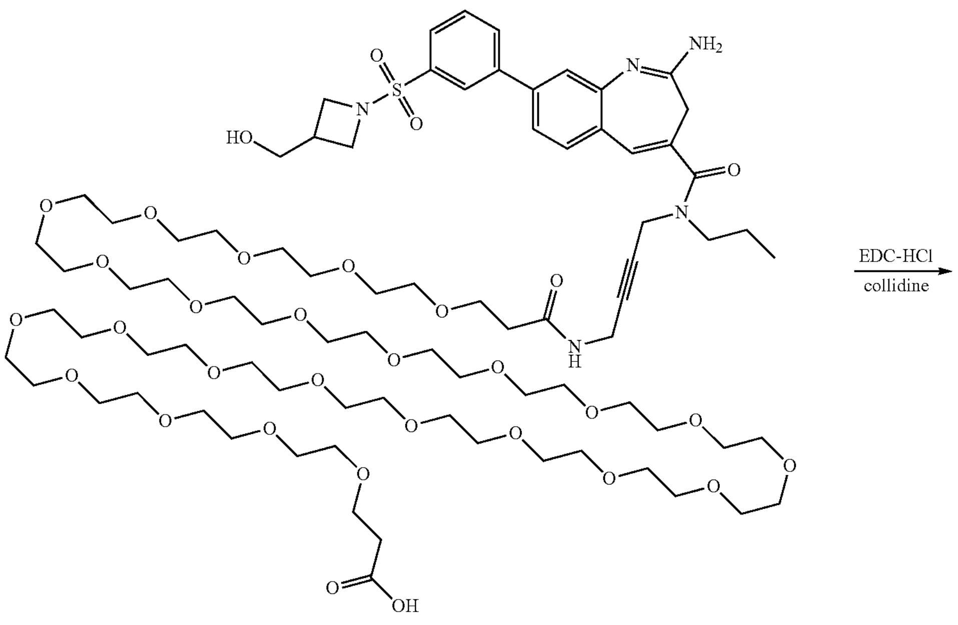
BzL-40b

-continued

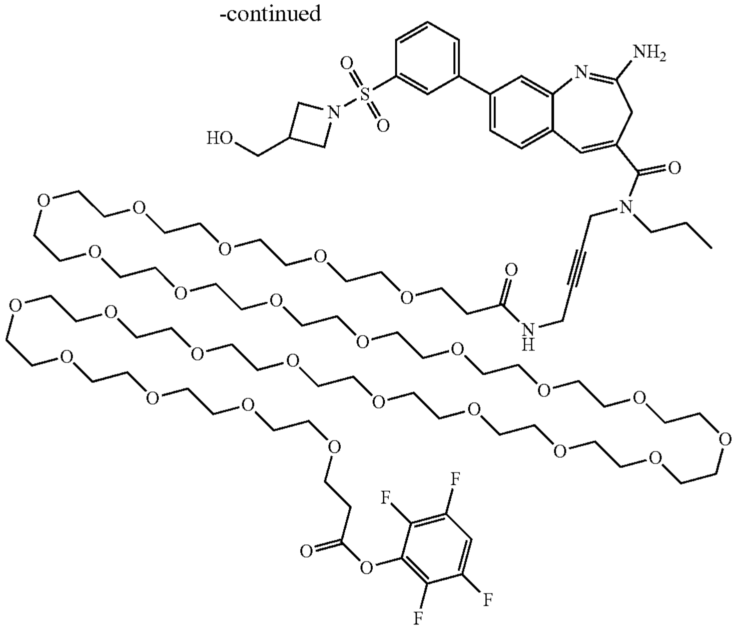

BzL-40b

Preparation of BzL-40a. To a mixture of tert-butyl N-[4-[[2-amino-8-[3-[3-(hydroxymethyl)azetidin-1-yl] sulfonylphenyl]-3H-1-benzazepine-4-carbonyl]-propyl-amino] but-2-ynyl]carbamate, Bz-26 (800 mg, 1.26 mmol, 1.0 eq) in MeOH (20 mL) was added acetyl chloride (395 mg, 5.03 mmol, 360 μL, 4.0 eq) at 25° C. under $N_2$ and then stirred at 50° C. for 1 hour. The mixture was quenched with solid $NaHCO_3$ until pH to ~8, then filtered and concentrated in vacuum. The residue was purified by prep-HPLC (column: Phenomenex Luna C18 200×40 mm, 10 μm particle size; mobile phase: [water (10 mM $NH_4HCO_3$)-ACN]; B %: 10%-40%, 10 min) to afford 2-amino-N-(4-aminobut-2-ynyl)-8-[3-[3-(hydroxymethyl)azetidin-1-yl]sulfonylphenyl]-N-propyl-3H-1-benzazepine-4-carboxamide, BzL-40a (220 mg, 411 μmol, 32.6% yield) as white solid. $^1$H NMR (MeOD, 400 MHz) δ 8.12-8.01 (m, 2H), 7.90-7.82 (m, 1H), 7.80-7.72 (m, 1H), 7.56-7.47 (m, 2H), 7.44-7.38 (m, 1H), 7.15 (s, 1H), 4.32 (s, 2H), 3.86 (t, J=8.0 Hz, 2H), 3.69-3.47 (m, 6H), 3.41 (d, J=6.4 Hz, 2H), 2.64-2.51 (m, 1H), 1.84-1.63 (m, 2H), 0.99-0.91 (m, 3H). LC/MS [M+H] 536.2 (calculated); LC/MS [M+H] 536.3 (observed).

Preparation of BzL-40b. BzL-40a (0.045 g, 0.084 mmol, 1 eq) and 79-((2,5-dioxopyrrolidin-1-yl)oxy)-79-oxo-4,7,10,13,16,19,22,25,28,31,34,37,40,43,46,49,52,55,58,61,64,67,70,73,76-pentacosaoxanonaheptacontanoic acid, NHS-PEG25-$CO_2$H (0.11 g, 0.084 mmol, 1 eq) were dissolved in DMF, followed by collidine (0.054 ml, 0.42 mmol, 5 eq). The reaction was purified by HPLC to give 85-(2-amino-8-(3-((3-(hydroxymethyl)azetidin-1-yl)sulfonyl)phenyl)-3H-benzo[b]azepine-4-carbonyl)-79-oxo-4,7,10,13,16,19,22,25,28,31,34,37,40,43,46,49,52,55,58,61,64,67,70,73,76-pentacosaoxa-80,85-diazaoctaoctacont-82-ynoic acid, BzL-40b (0.1 g, 0.0058 mmol, 69%). LC/MS [M+H]1736.90 (calculated); LC/MS [M+H] 1737.32 (observed).

Preparation of BzL-40. BzL-40b (0.1 g, 0.0058 mmol, 1 eq) and TFP (0.014 g, 0.086 mmol, 1.5 eq) were dissolved in DMF. Collidine (0.038 ml, 0.29 mmol, 5 eq) was added, followed by EDC-HCl (0.022 g, 0.115 mmol, 2 eq). The reaction was stirred at room temperature and monitored by LCMS, then concentrated and purified by HPLC to give 2,3,5,6-tetrafluorophenyl 85-(2-amino-8-(3-((3-(hydroxymethyl)azetidin-1-yl)sulfonyl)phenyl)-3H-benzo[b]azepine-4-carbonyl)-79-oxo-4,7,10,13,16,19,22,25,28,31,34,37,40,43,46,49,52,55,58,61,64,67,70,73,76-pentacosaoxa-80,85-diazaoctaoctacont-82-ynoate, BzL-40 (0.014 g, 0.0076 mmol, 13%). LC/MS [M+H]1884.90 (calculated); LC/MS [M+H] 1885.44 (observed).

Example 61: Synthesis of BzL-41
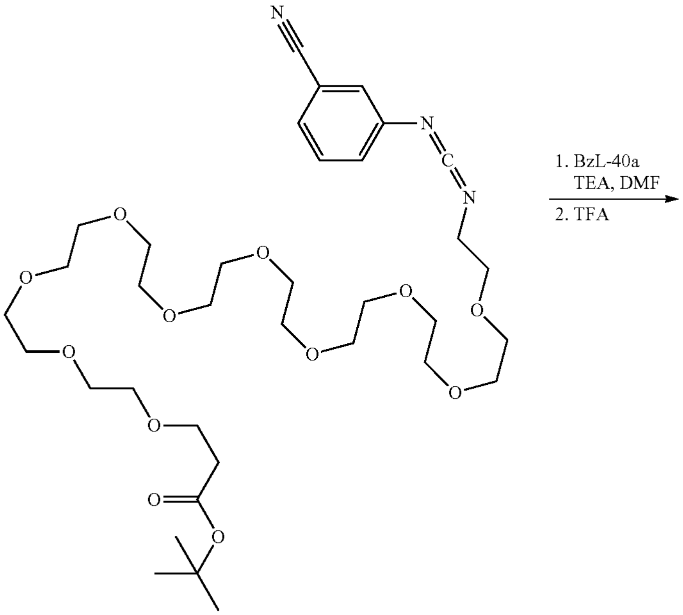
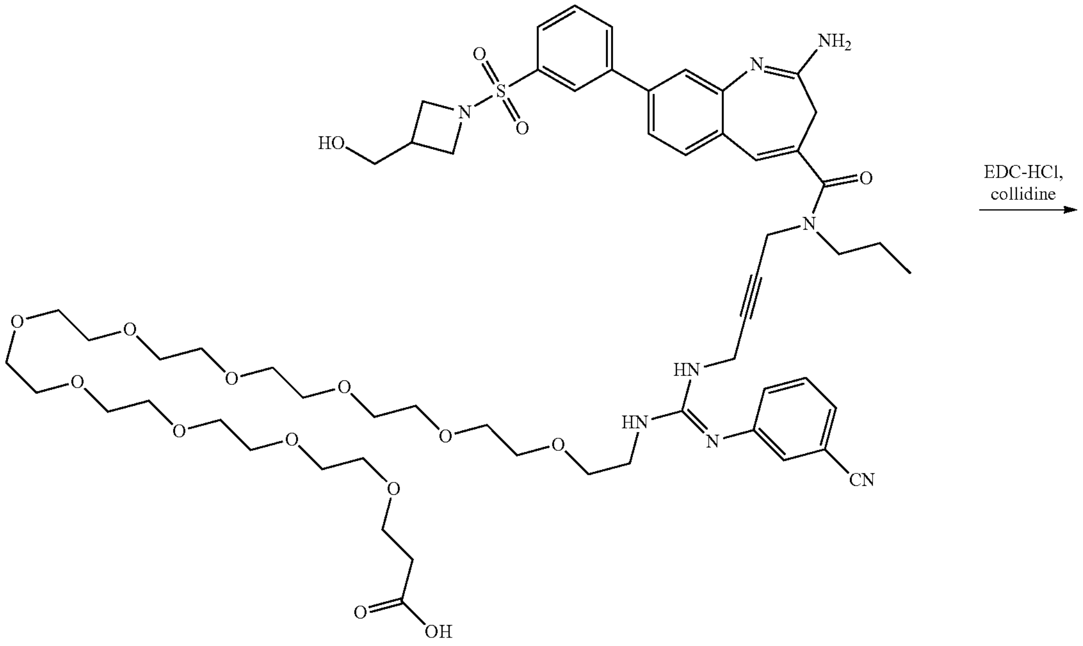
BzL-41a

-continued

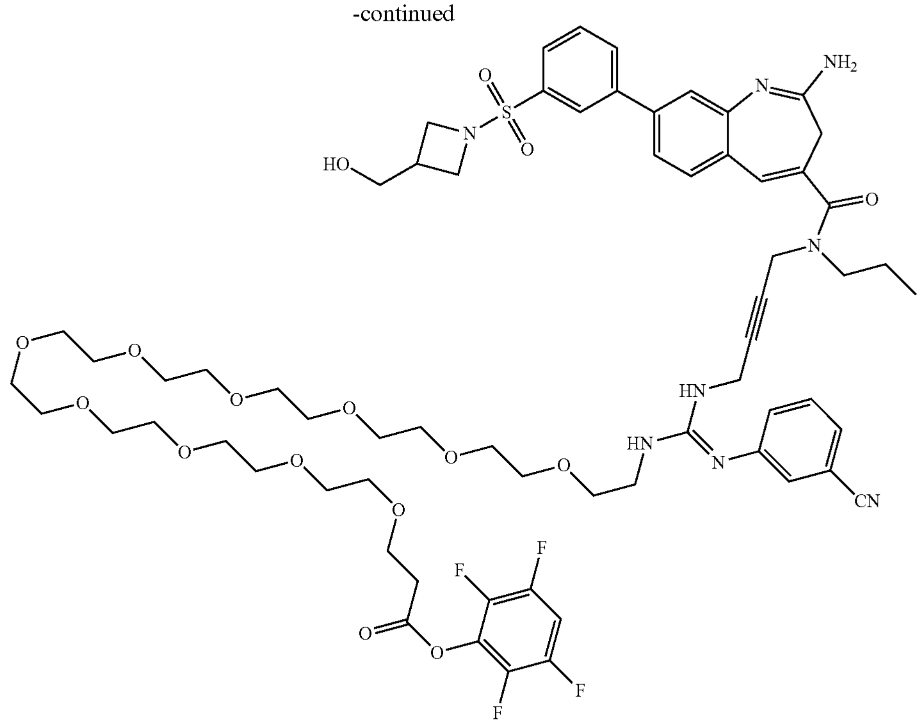

BzL-41

Preparation of BzL-41a. 2-Amino-N-(4-aminobut-2-yn-1-yl)-8-(3-((3-(hydroxymethyl)azetidin-1-yl)sulfonyl)phenyl)-N-propyl-3H-benzo[b]azepine-4-carboxamide, BzL-40a (0.05 g, 0.093 mmol, 1 eq) and tert-butyl 1-((3-cyanophenyl)imino)-5,8,11,14,17,20,23,26,29,32-decaoxa-2-azapentatriacont-1-en-35-oate (0.066 g, 0.093 mmol, 1 eq) were dissolved in DMF. Triethylamine (0.05 ml, 0.36 mmol, 3.8 eq) was added, and the reaction was stirred at ambient temperature. Upon consumption of amine starting material, the reaction was concentrated and purified by HPLC. The isolated t-butyl ester product was taken up in minimal TFA for 10 minutes, then concentrated to give 41-(2-amino-8-(3-((3-(hydroxymethyl)azetidin-1-yl)sulfonyl)phenyl)-3H-benzo[b]azepine-4-carbonyl)-35-((3-cyanophenyl)imino)-4, 7,10,13,16,19,22,25,28,31-decaoxa-34,36,41-triazatetratetracont-38-ynoic acid, BzL-41a (0.05 g, 0.042 mmol, 45%). LC/MS [M+H] 1191.56 (calculated); LC/MS [M+H] 1192.00 (observed).

Preparation of BzL-41. BzL-41a (0.05 g, 0.042 mmol, 1 eq) and TFP (0.01 g, 0.063 mmol, 1.5 eq) were dissolved in DMF. Collidine (0.028 ml, 0.21 mmol, 5 eq) was added, followed by EDC-HCl (0.016 g, 0.084 mmol, 2 eq). The reaction was stirred at room temperature and monitored by LCMS, then concentrated and purified by HPLC to give 2,3,5,6-tetrafluorophenyl 41-(2-amino-8-(3-((3-(hydroxymethyl)azetidin-1-yl)sulfonyl)phenyl)-3I-benzo[I]azepine-4-carbonyl)-35-((3-cyanophenyl)imino)-4,7,10,13,16,19,22, 25,28,31-decaoxa-34,36,41-triazatetratetracont-38-ynoate, BzL-41 (0.019 g, 0.014 mmol, 35%). LC/MS [M+H] 1339.56 (calculated); LC/MS [M+H] 1340.04 (observed).

Example 62: Synthesis of BzL-42

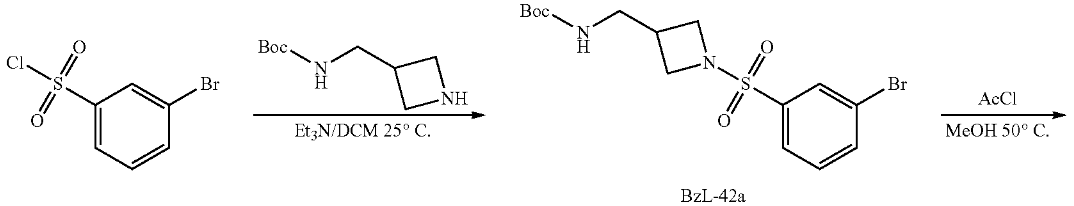

BzL-42a

-continued
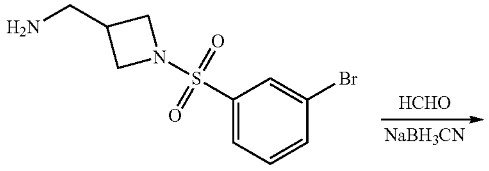
BzL-42b
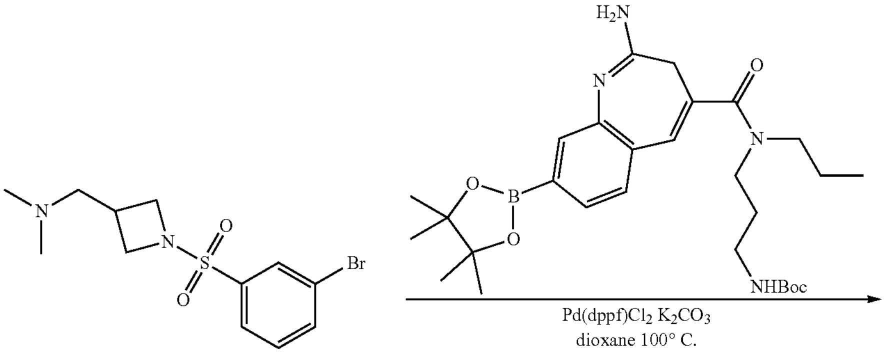
BzL-42c
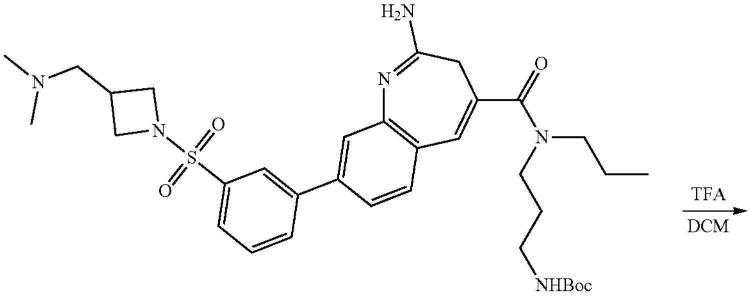
BzL-42d
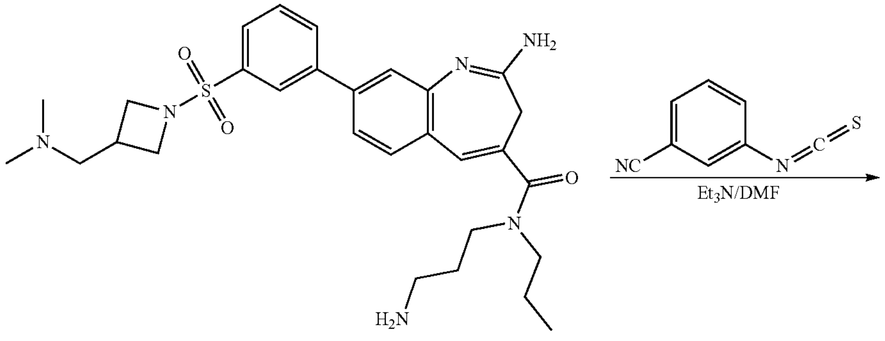
BzL-42e -continued
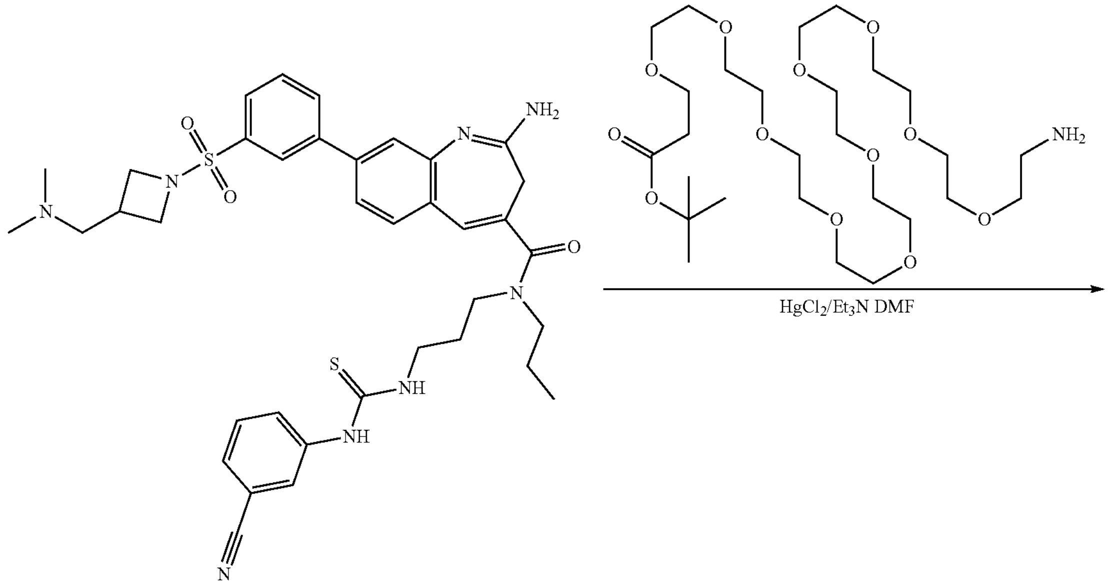
BzL-42f
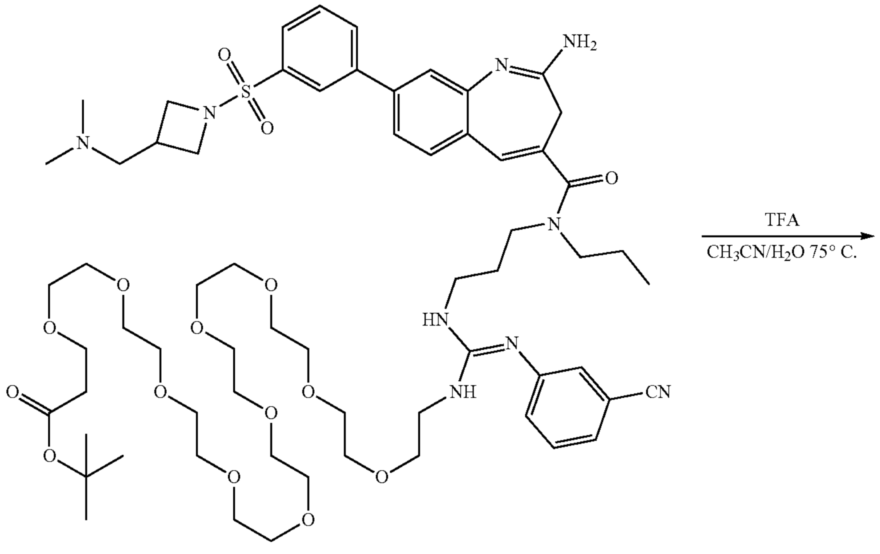
BzL-42g -continued

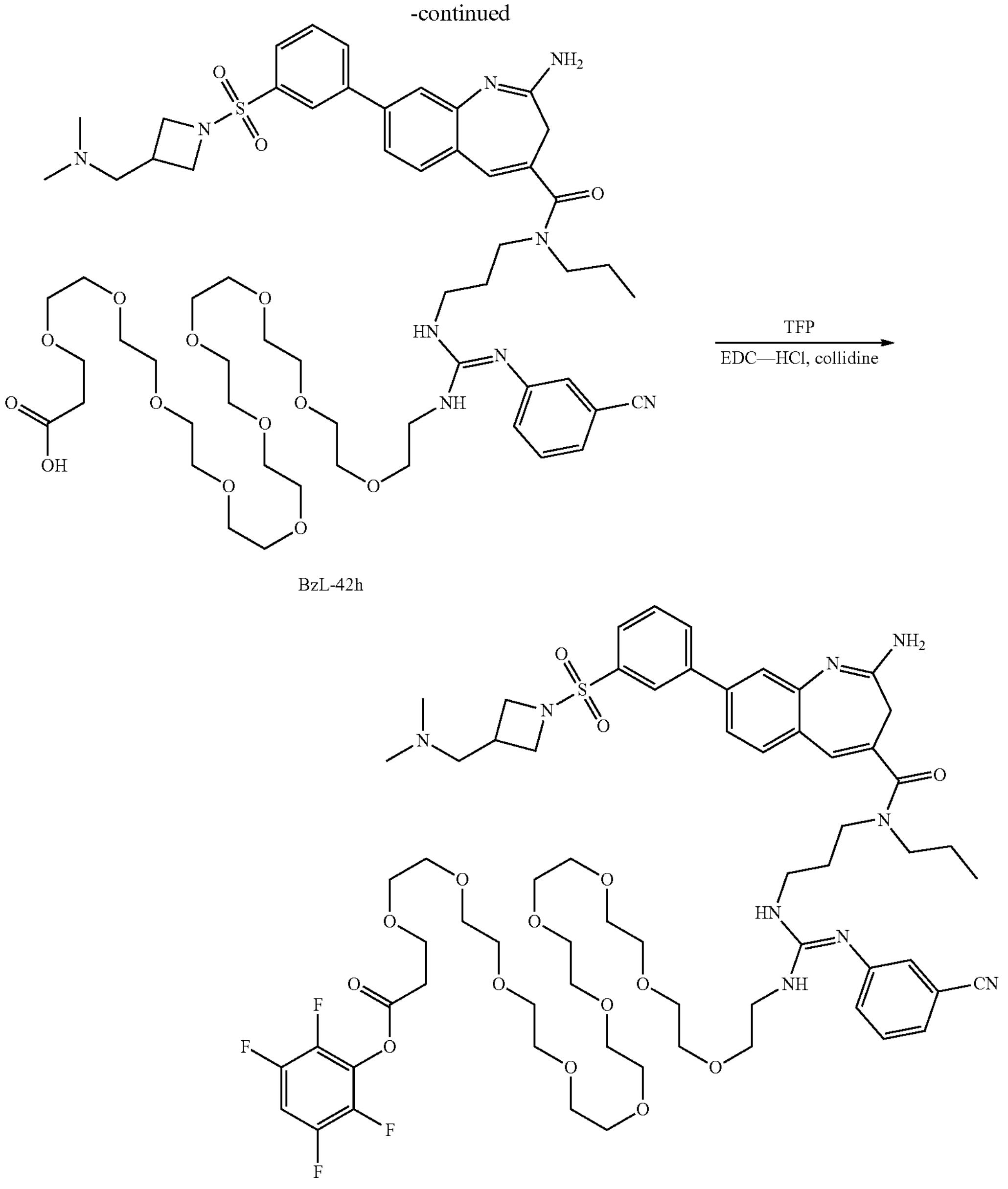

BzL-42h

BzL-42

Preparation of BzL-42a. To a mixture of 3-bromobenzenesulfonyl chloride (8.23 g, 32.2 mmol, 4.65 mL, 1.0 eq) and tert-butyl N-(azetidin-3-ylmethyl)carbamate (6.0 g, 32.2 mmol, 1.0 eq) in DCM (100 mL) was added $Et_3N$ (6.52 g, 64.4 mmol, 8.97 mL, 2.0 eq) at 0° C. and then stirred at this temperature for 1 h. The reaction was diluted with water and extracted with EtOAc (50 mL×3). The organic layer was washed with brine, dried over $Na_2SO_4$, filtered and concentrated to afford tert-butyl N-[[1-(3-bromophenyl)sulfonylazetidin-3-yl] methyl]carbamate, BzL-42a (12 g, crude) as white solid. $^1H$ NMR ($CDCl_3$, 400 MHz) δ7.99 (t, J=1.6 Hz, 1H), 7.78 (m, 2H), 7.47 (t, J=8.0 Hz, 1H), 4.63 (s, 1H), 3.85 (t, J=8.0 Hz, 2H), 3.54 (dd, J=5.6, 8.0 Hz, 2H), 3.21-3.16 (m, 2H), 2.67-2.62 (m, 1H), 1.42 (s, 9H). LC/MS [M+Na] 427.0 (calculated); LC/MS [M+Na] 427.0 (observed).

Preparation of BzL-42b. To a mixture of BzL-42a (2 g, 4.93 mmol, 1.0 eq) in MeOH (30 mL) was added acetyl chloride (1.94 g, 24.67 mmol, 1.76 mL, 5.0 eq) at 25° C. and then stirred at this temperature for 2 h. The mixture was concentrated to give [1-(3-bromophenyl)sulfonylazetidin-3-yl]methanamine, BzL-42b (1.5 g, crude) as white solid. $^1H$ NMR (MeOD, 400 MHz) δ 7.99 (t, J=1.6 Hz, 1H), 7.93 (d, J=8.0 Hz, 1H), 7.84 (d, J=7.2 Hz, 1H), 7.62 (t, J=8.0 Hz, 1H), 3.93 (t, J=8.4 Hz, 2H), 3.61 (m, 2H), 3.06-3.03 (m, 2H), 2.78-2.66 (m, 1H).

Preparation of BzL-42c. To a mixture of BzL-42b (4.0 g, 13.1 mmol, 1.0 eq) in MeOH (40 mL) was added $Et_3N$ (1.99 g, 19.7 mmol, 2.74 mL, 1.5 eq), formaldehyde (4.25 g, 52.4 mmol, 3.90 mL, 37% purity, 4.0 eq) and $NaBH_3CN$ (1.65 g, 26.2 mmol, 2.0 eq) at 25° C. and it was stirred at 25° C. for 2 h. The mixture was diluted with water and extracted with EtOAc (30 mL×3). The organic layer was washed with brine, dried over $Na_2SO_4$, filtered and concentrated. The residue was purified by silica gel chromatography (column height: 250 mm, diameter: 100 mm, 100-200 mesh silica gel, EtOAc (1.5% $NH_3 \cdot H_2O$):MeOH=1/0, 1/1) to afford 1-[1-(3-bromophenyl) sulfonylazetidin-3-yl]-N,N-dimethyl-methanamine, BzL-42c (1.6 g, 4.80 mmol, 36.6% yield) as yellow oil. $^1H$ NMR (MeOD, 400 MHz) δ 8.01 (t, J=1.6 Hz, 1H), 7.96-7.91 (m, 1H), 7.86 (d, J=8.0 Hz, 1H), 7.66-7.60 (m, 1H), 3.98-3.90 (m, 2H), 3.47 (dd, J=6.0, 8.4 Hz, 2H), 2.74-2.60 (m, 1H), 2.28 (d, J=7.6 Hz, 2H), 2.15 (s, 6H). LC/MS [M+H] 333.0 (calculated); LC/MS [M+H] 333.0 (observed).

Preparation of BzL-42d. To a mixture of BzL-42c (299 mg, 898 μmol, 1.1 eq) and tert-butyl N-[3-[[2-amino-8-(4,4,5,5-tetramethyl-1,3,2-dioxaborolan-2-yl)-3H-1-benzazepine-4-carbonyl]-propyl-amino]propyl]carbamate (0.43 g, 817 μmol, 1.0 eq) in dioxane (10 mL), $H_2O$ (1 mL) was added $K_2CO_3$ (395 mg, 2.86 mmol, 3.5 eq), Pd(dppf)$Cl_2$ (29.9 mg, 40.8 μmol, 0.05 eq) at 25° C. under $N_2$ and then stirred at 100° C. for 2 h. The mixture was filtered, diluted with water and extracted with EtOAc (30 mL×3). The organic layer was washed with brine, dried over $Na_2SO_4$, filtered and concentrated. The residue was purified by silica gel chromatography (column height: 250 mm, diameter: 100 mm, 100-200 mesh silica gel, petroleum ether/ethyl acetate=1/0, 0/1) to afford tert-butylN-[3-[[2-amino-8-[3-[3-[(dimethylamino)methyl]azetidin-1-yl]sulfonylphenyl]-3H-1-benzazepine-4-carbonyl]-propyl-amino]propyl]carbamate, BzL-42d (0.3 g, 459 μmol, 56.3% yield) as yellow solid.

Preparation of BzL-42e. To a mixture of BzL-42d (0.25 g, 383 μmol, 1.0 eq) in DCM (2 mL) was added TFA (1.31 g, 11.5 mmol, 851 μL, 30.0 eq) in one portion at 25° C. and then stirred for 1 h. The mixture was concentrated to afford 2-amino-N-(3-aminopropyl)-8-[3-[3-[(dimethylamino)methyl]azetidin-1-yl]sulfonylphenyl]-N-propyl-3H-1-benzazepine-4-carboxamide, BzL-42e (0.2 g, crude) as a yellow oil.

Preparation of BzL-42f. To a mixture of BzL-42e (0.2 g, 362 μmol, 1.0 eq) in DMF (0.5 mL) was added $Et_3N$ (256 mg, 2.53 mmol, 353 μL, 7.0 eq) and 3-isothiocyanatobenzonitrile (52.2 mg, 326 μmol, 0.9 eq) at 25° C. and then stirred at this temperature for 1 h. The mixture was filtered and the filtrate was purified by prep-HPLC (column: Welch Xtimate C18 100×25 mm, 3 μm particle size; mobile phase: [water (0.1% TFA)-ACN]; B %: 10%-40%, 12 min) to give 2-amino-N-[3-[(3-cyanophenyl) carbamothioylamino]propyl]-8-[3-[3-[(dimethylamino)methyl]azetidin-1-yl]sulfonylphenyl]-N-propyl-3H-1-benzazepine-4-carboxamide, BzL-42f (0.18 g, 252 μmol, 69.8% yield) as yellow solid. $^1H$ NMR (MeOD, 400 MHz) δ 8.12-8.06 (m, 2H), 7.92-7.02 (m, 10H), 4.01 (t, J=8.4 Hz, 2H), 3.76-3.40 (m, 8H), 3.40-3.36 (m, 2H), 3.34-3.32 (m, 2H), 3.03-2.91 (m, 1H), 2.82 (s, 6H), 2.04 (s, 2H), 1.77-1.67 (m, 2H), 0.97 (s, 3H).

Preparation of BzL-42g. To a mixture of BzL-42f (0.14 g, 196 μmol, 1.0 eq) and tert-butyl3-[2-[2-[2-[2-[2-[2-[2-[2-[2-(2-aminoethoxy) ethoxy]ethoxy]ethoxy]ethoxy]ethoxy]ethoxy]ethoxy]ethoxy]ethoxy]propanoate (138 mg, 236 μmol, 1.2 eq) in DMF (0.5 mL) was added $Et_3N$ (40.0 mg, 393 μmol, 2.0 eq) and $HgCl_2$ (64.0 mg, 236 μmol, 1.2 eq) at 25° C. and then stirred for 18 h at this temperature. The mixture was filtered and the filtrate was purified by prep-HPLC (column: Nano-micro KROMASIL™ C18 100×30 mm, 8 μm particle size; mobile phase: [water (0.1% TFA)-ACN]; B %: 15%-45%, 10 min) to give tert-butyl3-[2-[2-[2-[2-[2-[2-[2-[2-[2-[2-[[(Z)-N-[3-[[2-amino-8-[3-[3-[(dimethylamino)methyl]azetidin-1-yl]sulfonylphenyl]-3H-1-benzazepine-4-carbonyl]-propyl-amino]propyl]-N'-(3-cyanophenyl)carbamimidoyl]amino]ethoxy]ethoxy]ethoxy]ethoxy]ethoxy]ethoxy]ethoxy]ethoxy]ethoxy]ethoxy]propanoate, BzL-42g (0.14 g, 111 μmol, 56.4% yield) as yellow oil.

Preparation of BzL-42h. To a solution of BzL-42g (0.12 g, 94.9 μmol, 1.0 eq) in $H_2O$ (2 mL) and $CH_3CN$ (0.5 mL) was added TFA (325 mg, 2.85 mmol, 211 μL, 30.0 eq) at 25° C. and then stirred at 80° C. for 1 h. The mixture was concentrated in vacuum to give a residue, the residue was purified by prep-HPLC (column: Xtimate C18 100×30 mm, 3 μm particle size; mobile phase: [water (0.1% TFA)-ACN]; B %: 5%-35%, 10 min) to give 3-[2-[2-[2-[2-[2-[2-[2-[2-[2-[2-[[(Z)-N-[3-[[2-amino-8-[3-[3-[(dimethylamino)methyl]azetidin-1-yl]sulfonylphenyl]-3H-1-benzazepine-4-carbonyl]-propyl-amino]propyl]-N'-(3-cyanophenyl)carbamimidoyl]amino]ethoxy]ethoxy]ethoxy]ethoxy]ethoxy]ethoxy]ethoxy]ethoxy]ethoxy]ethoxy]propanoic acid, BzL-42h (32 mg, 26.5 μmol, 27.9% yield) as yellow oil. $^1H$ NMR (MeOD, 400 MHz) δ 8.16-8.09 (m, 2H), 7.93 (d, J=8.0 Hz, 1H), 7.87-7.81 (m, 1H), 7.81-7.74 (m, 3H), 7.66-7.62 (m, 4H), 7.12 (s, 1H), 4.01 (t, J=8.4 Hz, 2H), 3.80-3.66 (m, 10H), 3.66-3.45 (m, 40H), 3.40 (s, 3H), 2.82 (s, 6H), 2.53 (t, J=6.4 Hz, 2H), 2.07-2.01 (m, 1H), 1.77-1.67 (m, 2H), 0.98-0.90 (m, 3H). LC/MS [M+H] 1208.6 (calculated); LC/MS [M+H] 1208.6 (observed).

Preparation of BzL-42. BzL-42h (0.032 g, 0.026 mmol, 1 eq) and TFP (0.009 g, 0.05 mmol, 2 eq) were dissolved in DMF. Collidine (0.017 ml, 0.13 mmol, 5 eq) was added, followed by EDC-HCl (0.015 g, 0.079 mmol, 3 eq). The reaction was stirred at room temperature and monitored by LCMS, then concentrated and purified by HPLC to give 2,3,5,6-tetrafluorophenyl 40-(2-amino-8-(3-((3-((dimethylamino)methyl)azetidin-1-yl)sulfonyl)phenyl)-3H-benzo[b]azepine-4-carbonyl)-35-((3-cyanophenyl)imino)-4,7,10,13,16,19,22,25,28,31-decaoxa-34,36,40-triazatritetracontanoate (0.018 g, 0.013 mmol, 49%). LC/MS [M+H] 1356.62 (calculated); LC/MS [M+H] 1357.10 (observed).

Example 63: Synthesis of BzL-43

BzL-40a
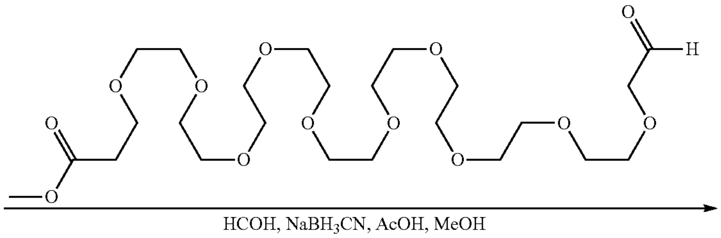

-continued
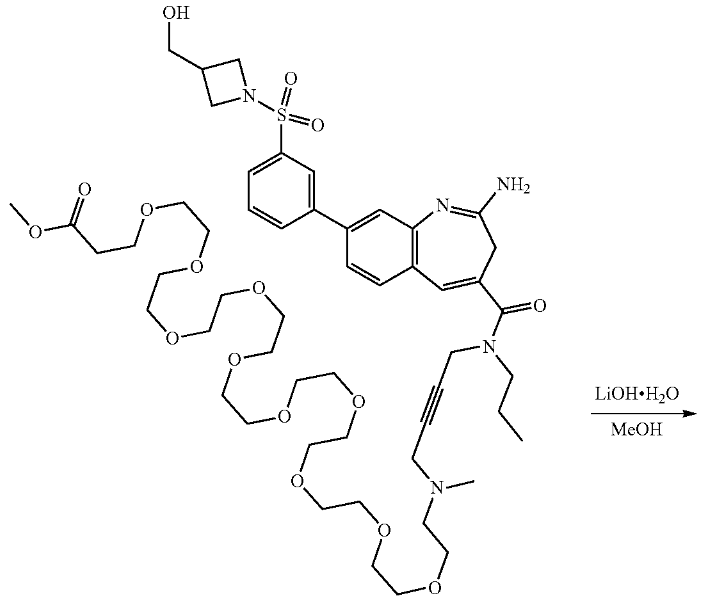
BzL-43a
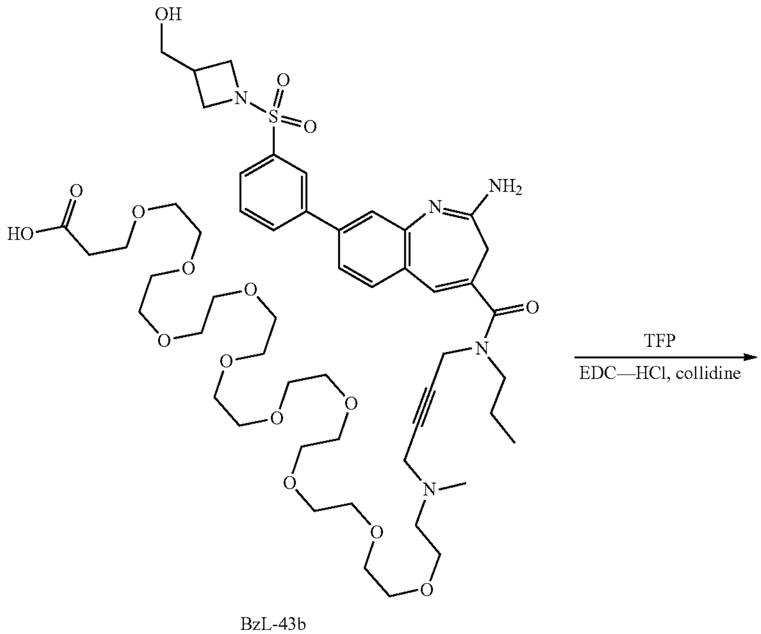
BzL-43b

-continued

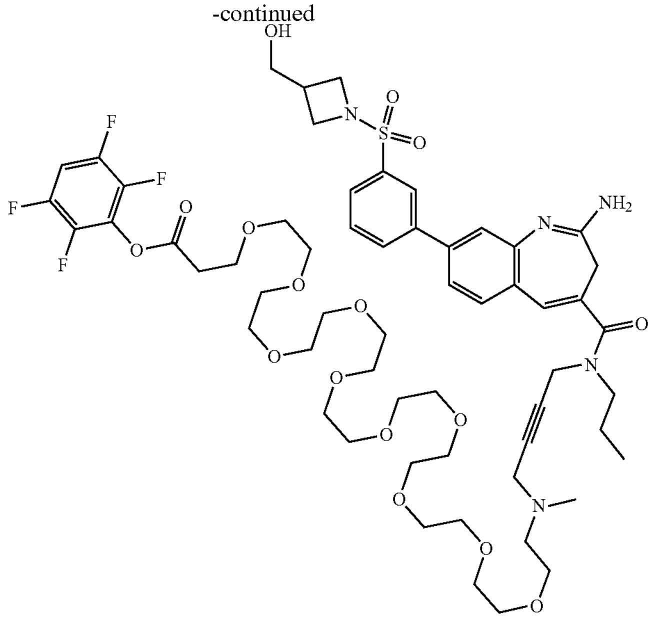

BzL-43

Preparation of BzL-43a. To a mixture of 2-amino-N-(4-aminobut-2-ynyl)-8-[3-[3-(hydroxymethyl)azetidin-1-yl]sulfonylphenyl]-N-propyl-3H-1-benzazepine-4-carboxamide, BzL-40a (0.1 g, 187 μmol, 1.0 eq) and methyl 3-[2-[2-[2-[2-[2-[2-[2-[2-[2-(2-oxoethoxy)ethoxy]ethoxy]ethoxy]ethoxy]ethoxy] ethoxy]ethoxy]ethoxy]ethoxy]propanoate (101.3 mg, 187 μmol, 1.0 eq) in MeOH (10 mL) was added AcOH (11.2 mg, 187 μmol, 11 μL, 1.0 eq) and $NaBH_3CN$ (35.2 mg, 560 μmol, 3.0 eq) in one portion at 25° C. and then stirred for 2 hours. Then formaldehyde (29.5 mg, 373 μmol, 27 μL, 2.0 eq) was added and it was stirred for 1 hour at the same temperature. The mixture was added a few drops water and concentrated. The residue was purified by prep-HPLC (column: Xtimate C18 100×30 mm, 3 μm particle size; mobile phase: [water (0.1% TFA)-ACN]; B %: 10%-35%, 10 min) to give methyl 3-[2-[2-[2-[2-[2-[2-[2-[2-[2-[2-[4-[[2-amino-8-[3-[3-(hydroxymethyl)azetidin-1-yl]sulfonylphenyl]-3H-1-benzazepine-4-carbonyl]-propyl-amino]but-2-ynyl-methyl-amino]ethoxy]ethoxy]ethoxy]ethoxy]ethoxy]ethoxy]ethoxy]ethoxy]ethoxy]ethoxy]propanoate, BzL-43a (0.05 g, 46.46 μmol, 24.88% yield) as colorless oil.

Preparation of BzL-43b. To a solution of BzL-43a (50 mg, 46.5 μmol, 1.0 eq) in MeOH (3.0 mL) and $H_2O$ (0.3 mL) was added $LiOH{\cdot}H_2O$ (19.5 mg, 465 μmol, 10.0 eq) in one portion at 25° C. and it was stirred at the same temperature for 16 hours. The mixture was cooled to 0° C., adjusted pH=7 with aq. HCl (1 M) and concentrated in reduced pressure at 40° C. The residue was purified by prep-HPLC (column: Nano-micro KROMASIL™ C18 100×30 mm, 8 μm particle size; mobile phase: [water (0.1% TFA)-ACN]; B %: 10%-40%, 10 min) to afford 3-[2-[2-[2-[2-[2-[2-[2-[2-[2-[2-[4-[[2-amino-8-[3-[3-(hydroxymethyl)azetidin-1-yl]sulfonylphenyl]-3H-1-benzazepine-4-carbonyl]-propyl-amino]but-2-ynyl-methyl-amino]ethoxy]ethoxy]ethoxy]ethoxy]ethoxy]ethoxy]ethoxy]ethoxy]ethoxy]ethoxy]propanoic acid, BzL-43b (30 mg, 28.24 μmol, 60.79% yield) as light yellow oil. $^1H$ NMR (MeOD, 400 MHz) δ 8.15-8.07 (m, 2H), 7.93 (d, J=8.0 Hz, 1H), 7.86-7.76 (m, 3H), 7.74-7.69 (m, 1H), 7.24 (s, 1H), 4.29 (s, 2H), 3.91-3.84 (m, 4H), 3.74-3.55 (m, 43H), 3.52-3.38 (m, 7H), 3.34-3.32 (m, 2H), 3.02 (s, 3H), 2.64-2.56 (m, 1H), 2.53 (t, J=6.4 Hz, 2H), 1.85-1.72 (m, 2H), 0.98 (t, J=7.2 Hz, 3H). LC/MS [M+H] 1062.5 (calculated); LC/MS [M+H] 1062.6 (observed).

Preparation of BzL-43. Bz-43b (0.03 g, 0.028 mmol, 1 eq) and TFP (0.009 g, 0.06 mmol, 2 eq) were dissolved in DMF. Collidine (0.019 ml, 0.14 mmol, 5 eq) was added, followed by EDC-HCl (0.016 g, 0.085 mmol, 3 eq). The reaction was stirred at room temperature and monitored by LCMS, then concentrated and purified by HPLC to give 2,3,5,6-tetrafluorophenyl 38-(2-amino-8-(3-((3-((dimethylamino)methyl)azetidin-1-yl)sulfonyl)phenyl)-3H-benzo[b]azepine-4-carbonyl)-33-methyl-3,6,9,12,15,18,21,24,27,30-decaoxa-33,38-diazahentetracont-35-ynoate, BzL-43 (0.016 g, 0.013 mmol, 46%). LC/MS [M+H] 1210.53 (calculated); LC/MS [M+H] 1210.95 (observed).

Example 64: Synthesis of BzL-44

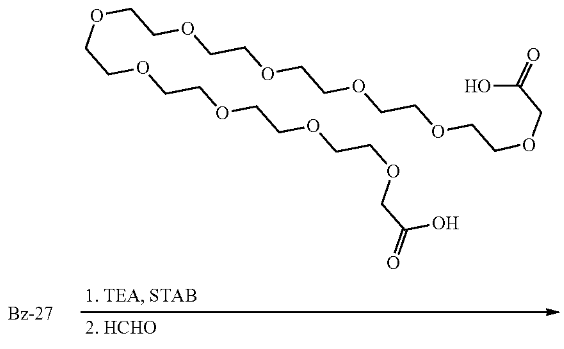

-continued

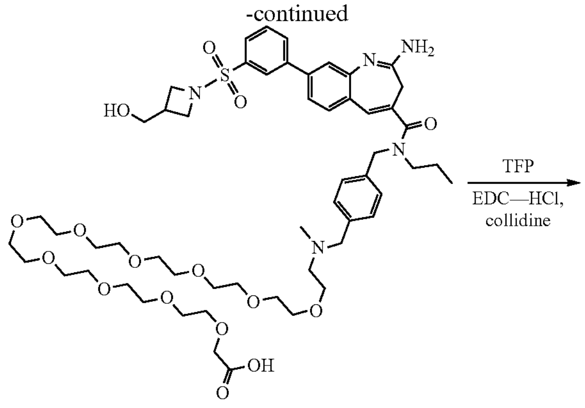

BzL-44a

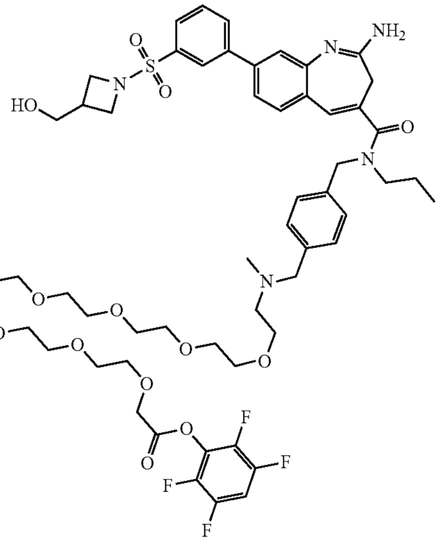

BzL-44

Preparation of BzL44a. 2-Amino-N-(4-(aminomethyl) benzyl)-8-(3-((3-(hydroxymethyl)azetidin-1-yl)sulfonyl) phenyl)-N-propyl-3H-benzo[b]azepine-4-carboxamide, Bz-27 (0.119 g, 0.203 mmol, 1 eq) and 32-oxo-3,6,9,12,15,18,21,24,27,30-decaoxadotriacontanoic acid (0.107 g, 0.203 mmol, 1 eq) were dissolved in 1:1 ACN:DCM. Triethylamine (0.17 ml, 1.2 mmol, 6 eq) was added, followed by sodium triacetoxyborohydride (0.13 g, 0.61 mmol, 3 eq). The reaction was stirred at room temperature for 40 minutes, and then formaldehyde was added (0.02 ml, 0.27 mmol, 1.3 eq, 37 wt. % in $H_2O$). After 10 minutes, the reaction was concentrated and purified by HPLC to give 1-(4-((2-amino-8-(3-((3-(hydroxymethyl)azetidin-1-yl)sulfonyl)phenyl)-N-propyl-3H-benzo[b]azepine-4-carboxamido)methyl)phenyl)-2-methyl-5,8,11,14,17,20,23,26,29,32-decaoxa-2-azatetratriacontan-34-oic acid, BzL44a (0.067 g, 0.060 mmol, 30%). LC/MS [M+H] 1114.56 (calculated); LC/MS [M+H] 1114.89 (observed).

Preparation of BzL-44. BzL-44a (0.067 g, 0.06 mmol, 1 eq) and TFP (0.020 g, 0.12 mmol, 2 eq) were dissolved in DMF. Collidine (0.040 ml, 0.30 mmol, 5 eq) was added, followed by EDC-HCl (0.035 g, 0.18 mmol, 3 eq). The reaction was stirred at room temperature and monitored by LCMS, then concentrated and purified by HPLC to give 2,3,5,6-tetrafluorophenyl 1-(4-((2-amino-8-(3-((3-(hydroxymethyl)azetidin-1-yl)sulfonyl)phenyl)-N-propyl-3H-benzo[b]azepine-4-carboxamido)methyl)phenyl)-2-methyl-5,8,11,14,17,20,23,26,29,32-decaoxa-2-azatetratriacontan-34-oate, BzL-44 (0.026 g, 0.021 mmol, 34%). LC/MS [M+H] 1262.56 (calculated); LC/MS [M+H] 1262.86 (observed).

Example 65: Synthesis of BzL-45

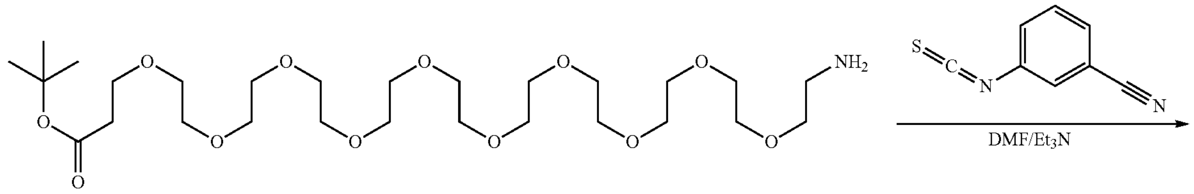

BzL-45a

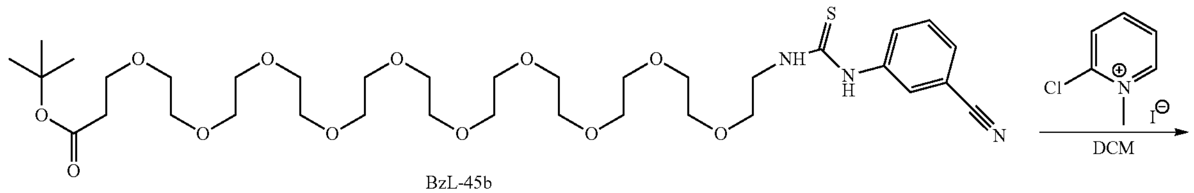

BzL-45b

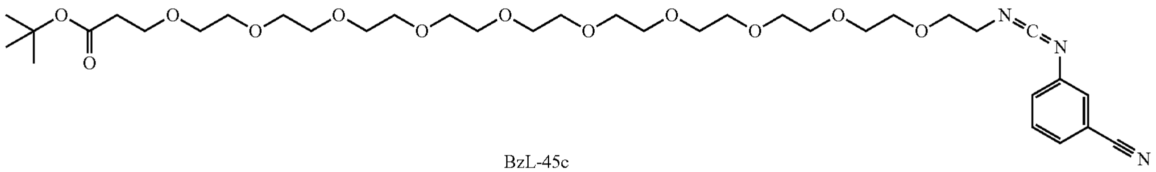

BzL-45c

Preparation of BzL-45b. To a mixture of tert-butyl 3-[2-[2-[2-[2-[2-[2-[2-[2-[2-(2-aminoethoxy)ethoxy]ethoxy]ethoxy]ethoxy]ethoxy]ethoxy]ethoxy]ethoxy]ethoxy]propanoate, BzL-45a (2.7 g, 4.61 mmol, 1.0 eq) in THF (20 mL) was added $Et_3N$ (700 mg, 6.91 mmol, 960 μL, 1.5 eq) and 3-isothiocyanatobenzonitrile (1.48 g, 9.22 mmol, 2.0 eq) at 25° C. and it was stirred for 1 hour at this temperature. Then the mixture was diluted with water (30 mL) and extracted with EtOAc (50 mL×3). The organic layer was washed with brine, dried over $Na_2SO_4$, filtered and concentrated. The residue was purified by silica gel chromatography (MeOH/ethyl acetate=0/1, 1/10) to afford tert-butyl 3-[2-[2-[2-[2-[2-[2-[2-[2-[2-[2-[(3-cyanophenyl)carbamothioylamino]ethoxy]ethoxy]ethoxy]ethoxy]ethoxy]ethoxy]ethoxy]ethoxy]ethoxy]ethoxy]propanoate, BzL-45b (0.5 g, 670 μmol, 14.54% yield) as yellow oil. 1H NMR ($CDCl_3$, 400 MHz) δ 7.99 (s, 1H), 7.89 (d, J=8.0 Hz, 1H), 7.44-7.39 (m, 2H), 3.76-3.58 (m, 42H), 2.55-2.46 (m, 2H), 1.45 (s, 9H).

Preparation of BzL-45c. To a mixture of BzL-45b (0.4 g, 536 μmol, 1.0 eq) and $Et_3N$ (163 mg, 1.61 mmol, 223 μL, 3.0 eq) in DCM (10 mL) and DMF (0.4 mL) was added 2-chloro-1-methylpyridin-1-ium iodide (164 mg, 643 μmol, 1.2 eq) at 25° C. under $N_2$. The mixture was stirred at 25° C. for 1 hour and then concentrated under reduce pressure. The residue was purified by silica gel chromatography ($CH_3CN$/ethyl acetate=0/1 to 1/1) to afford tert-butyl 3-[2-[2-[2-[2-[2-[2-[2-[2-[2-[2-[(3-cyanophenyl)iminomethyleneamino]ethoxy]ethoxy]ethoxy]ethoxy]ethoxy]ethoxy]ethoxy]ethoxy]ethoxy]ethoxy]propanoate, BzL-45c (0.29 g, 407 μmol, 75.9% yield) as yellow oil. 1H NMR ($CDCl_3$, 400 MHz) δ 7.43-7.33 (m, 4H), 3.70-3.62 (m, 42H), 2.51 (t, J=6.4 Hz, 2H), 1.45 (s, 9H).

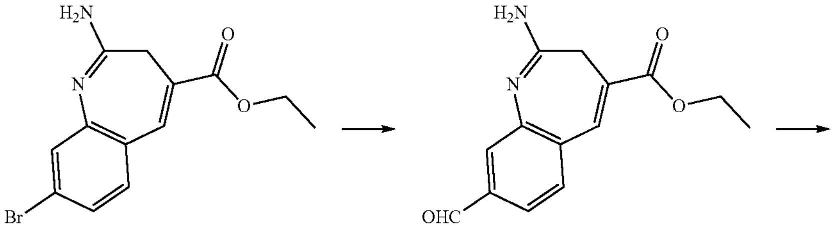

BzL-45d BzL-45e

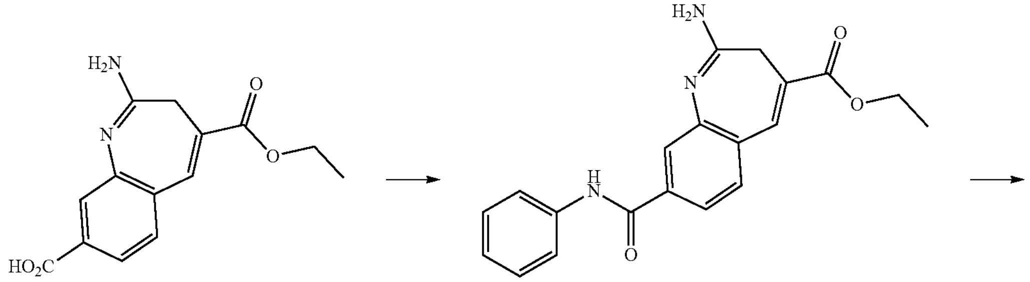

BzL-45f BzL-45g

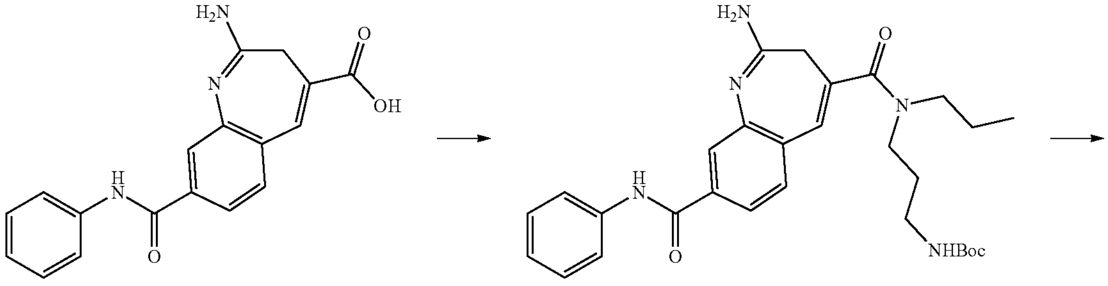

BzL-45h BzL-45i

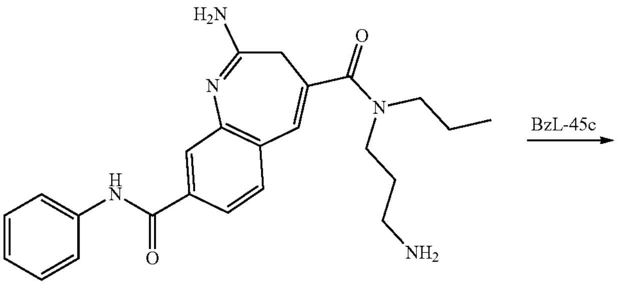

BzL-45j

-continued
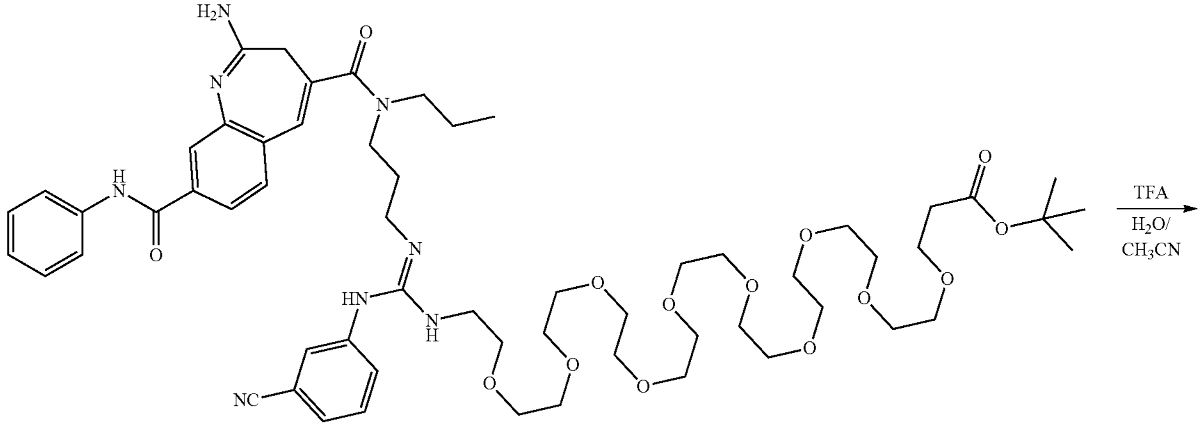
BzL-45k
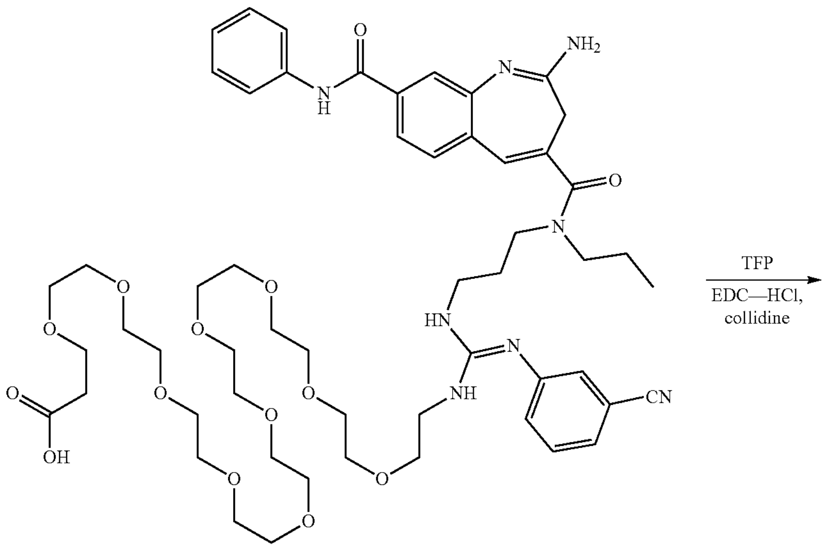
BzL-45l
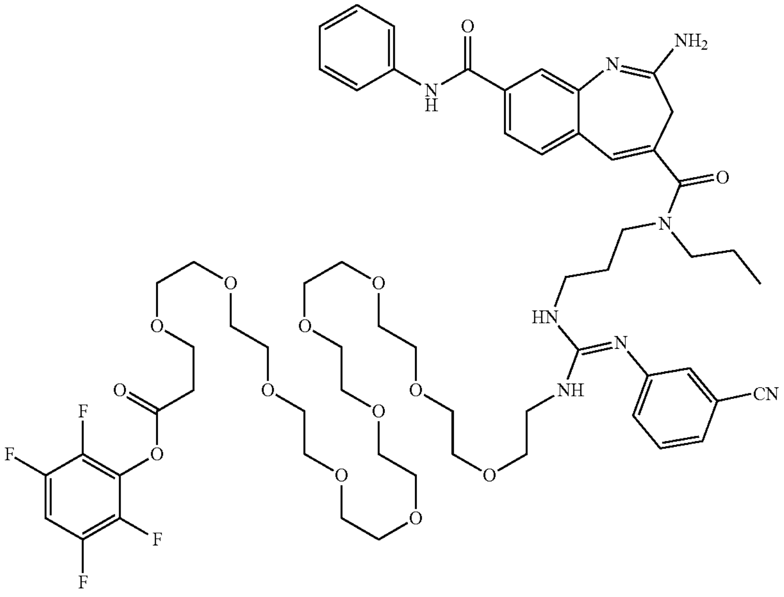
BzL-45

Preparation of BzL-45e. To a solution of ethyl 2-amino-8-bromo-3H-1-benzazepine-4-carboxylate, BzL-45d (10 g, 32.4 mmol, 1.0 eq) in DMF (100 mL) was added $Et_3SiH$ (72.8 g, 626.09 mmol, 100 mL, 19.36 eq), $Et_3N$ (6.5 g, 64.69 mmol, 9.00 mL, 2.0 eq) and $Pd(dppf)Cl_2$ (1.18 g, 1.62 mmol, 0.05 eq) under $N_2$. The suspension was degassed under vacuum and purged with CO several times and it was stirred under CO (50 psi) at 80° C. for 12 h. The mixture was diluted with water (300 mL) and extracted with EtOAc (80 mL×3). The organic layer was washed with brine (50 mL), dried over $Na_2SO_4$, filtered and concentrated, and the residue was purified by flash silica gel chromatography (ISCO™; 15 g SEPAFLASH™ Silica Flash Column, eluent of 0~100% ethyl acetate/petroleum ether gradient at 65 mL/min) to give ethyl 2-amino-8-formyl-3H-1-benzazepine-4-carboxylate, BzL-45e (3 g, 11.6 mmol, 35.9% yield) as yellow solid. $^1H$ NMR (DMSO-$d_6$, 400 MHz) δ 10.00 (s, 1H) 7.79 (s, 1H) 7.61 (d, J=8.4 Hz, 1H) 7.55 (d, J=1.2 Hz, 1H) 7.40 (dd, J=8.0, 1.2 Hz, 1H) 7.07 (s, 2H) 4.25 (q, J=6.8 Hz, 2H) 2.91 (s, 2H) 1.31 (t, J=6.8 Hz, 3H).

Preparation of BzL-45f. To a solution of BzL-45e (2.6 g, 10.1 mmol, 1.0 eq) in $CH_3CN$ (15 mL) was added $NaH_2PO_4$ (362 mg, 3.02 mmol, 0.3 eq), $H_2O_2$ (5.71 g, 50.33 mmol, 4.84 mL, 30% purity, 5.0 eq) and $NaClO_2$ (1.46 g, 16.1 mmol, 1.6 eq) at 0° C. and it was stirred at 25° C. for 5 h. The reaction mixture was quenched with $Na_2SO_3$ (aq.) and diluted with $H_2O$ (30 mL) and EtOAc (30 ml), the pH of the mixture was adjusted to 4 with aq. HCl (1 M), then filtered to give desired solid The solid was dried under vacuum to give 2-amino-4-ethoxycarbonyl-3H-1-benzazepine-8-carboxylic acid, BzL-45f (2.1 g, 7.66 mmol, 76.1% yield) as white solid. $^1H$ NMR (DMSO-$d_6$, 400 MHz) δ 7.87 (s, 1H), 7.81 (s, 1H), 7.72-7.67 (m, 2H), 4.27 (q, J=7.2 Hz, 2H), 3.28 (s, 2H), 1.31 (t, J=7.2 Hz, 3H).

Preparation of BzL-45g. To a mixture of BzL-45f (1.0 g, 3.65 mmol, 1.0 eq) in DMF (20 mL) was added PYAOP (2.28 g, 4.38 mmol, 1.2 eq) and DIEA (2.36 g, 18.2 mmol, 3.18 mL, 5.0 eq) at 25° C. and it was stirred for 10 min, then aniline (373 mg, 4.01 mmol, 366 μL, 1.1 eq) was added and stirred for 1 hour at 25° C. The mixture was poured into ice water (50 mL) and stirred for 2 min. The aqueous phase was extracted with ethyl acetate (20 mL×3). The combined organic phase was washed with brine (20 mL), dried with anhydrous $Na_2SO_4$, filtered and concentrated in vacuum and the residue was purified by silica gel chromatography (EtOAc/MeOH=1:0~2:1) to afford ethyl 2-amino-8-(phenylcarbamoyl)-3H-1-benzazepine-4-carboxylate, BzL-45g (0.5 g, 1.43 mmol, 39.25% yield) as yellow solid. $^1H$ NMR (MeOD, 400 MHz) δ 7.89 (s, 1H), 7.76-7.65 (m, 3H), 7.62-7.56 (m, 1H), 7.37 (t, J=8.0 Hz, 2H), 7.16 (t, J=8.0 Hz, 1H), 4.35 (q, J=7.2 Hz, 2H), 3.32 (s, 2H), 1.38 (t, J=7.2 Hz, 3H).

Preparation of BzL-45h. To a mixture of BzL-45g (0.36 g, 1.03 mmol, 1.0 eq) in EtOH (10 mL) was added a solution of $LiOH{\cdot}H_2O$ (216 mg, 5.15 mmol, 5.0 eq) in $H_2O$ (1 mL) at 25° C. and it was stirred for 16 hours at this temperature. The mixture was quenched with HCl (4 M) until pH to 5 and concentrated under reduced pressure at 40° C. to remove EtOH. Water (10 mL) was added and then filtered to give 2-amino-8-(phenylcarbamoyl)-3H-1-benzazepine-4-carboxylic acid, BzL-45h (0.2 g, 622 μmol, 60.41% yield) as yellow solid which was used in the next step without further purification. $^1H$ NMR (DMSO-$d_6$, 400 MHz) δ 7.84-7.74 (m, 3H), 7.66 (s, 1H), 7.56-7.47 (m, 2H), 7.34 (t, J=8.0 Hz, 2H), 7.09 (t, J=7.2 Hz, 2H), 2.92 (s, 2H).

Preparation of BzL-45i. To a solution of BzL-45h (0.2 g, 622 μmol, 1.0 eq) in DMF (5 mL) was added HATU (284 mg, 746 μmol, 1.2 eq) and DIEA (241 mg, 1.87 mmol, 325 μL, 3.0 eq) at 25° C. and it was stirred for 10 min at this temperature, then tert-butyl N-[3-(propylamino)propyl]carbamate, Bz-1b (161 mg, 746 μmol, 1.2 eq) was added to the mixture and stirred at 25° C. for 3 hours. The reaction was poured into ice water (30 mL) and stirred for 10 min. The aqueous phase was extracted with EtOAc (10 mL×3), and the combined organic phase was washed with $H_2O$ (10 mL×2) and brine (10 mL), dried by $Na_2SO_4$ and concentrated to give tert-butyl N-[3-[[2-amino-8-(phenylcarbamoyl)-3H-1-benzazepine-4-carbonyl]-propyl-amino]propyl] carbamate, BzL-45i (0.3 g, 577 μmol, 92.76% yield) as yellow oil.

Preparation of BzL-45j. To a solution of BzL-45i (0.4 g, 769 μmol, 1.0 eq) in MeOH (10 mL) was added HCl/MeOH (4 M, 9.62 mL, 50 eq) at 25° C. The mixture was stirred at 25° C. for 1 hour, and then concentrated under reduced pressure at 40° C. The residue was purified by prep-HPLC (column: Nano-micro KROMASIL™ C18 100×30 mm, 8 μm particle size; mobile phase: [water (0.1% TFA)-ACN]; B %: 5%-30%, 10 min) to afford 2-amino-N4-(3-aminopropyl)-N8-phenyl-N4-propyl-3H-1-benzazepine-4,8-dicarboxamide, BzL-45j (0.23 g, 431 μmol, 56.0% yield, TFA salt) as yellow solid. $^1H$ NMR (MeOD, 400 MHz) δ 8.01-7.94 (m, 2H), 7.76-7.70 (m, 3H), 7.41 (t, J=8.0 Hz, 2H), 7.21 (t, J=7.6 Hz, 2H), 3.63 (t, J=7.2 Hz, 2H), 3.58-3.49 (m, 2H), 3.41 (s, 2H), 3.10-2.95 (m, 2H), 2.12-1.99 (m, 2H), 1.82-1.68 (m, 2H), 0.95 (t, J=7.2 Hz, 3H). LC/MS [M+H] 420.2 (calculated); LC/MS [M+H] 420.2 (observed).

Preparation of BzL-45k. To a mixture of Bz-45j (0.06 g, 112 μmol, 1.0 eq, TFA salt) in DMF (1 mL) was added $Et_3N$ (28 mg, 281 μmol, 2.5 eq) and BzL-45c (88 mg, 123 μmol, 1.1 eq) at 25° C. The mixture was stirred at 25° C. for 1 hour and then filtered and purified by prep-HPLC (column: Nano-micro KROMASIL™ C18 100×30 mm, 8 m particle size; mobile phase: [water (0.1% TFA)-ACN]; B %: 20%-50%, 10 min) to afford tert-butyl 3-[2-[2-[2-[2-[2-[2-[2-[2-[2-[2-[[(Z)-N'-[3-[[2-amino-8-(phenylcarbamoyl)-3H-1-benzazepine-4-carbonyl]-propyl-amino]propyl]-N-(3-cyanophenyl)carbamimidoyl]amino]ethoxy]ethoxy]ethoxy]ethoxy]ethoxy]ethoxy]ethoxy]ethoxy]ethoxy]ethoxy]propanoate, BzL-45k (0.08 g, 70.7 μmol, 62.9% yield) as colorless oil.

Preparation of BzL-451. To a solution of BzL-45k (0.07 g, 61 μmol, 1.0 eq) in $H_2O$ (5 mL) and $CH_3CN$ (1 mL) was added TFA (211 mg, 1.86 mmol, 30 eq) at 25° C. The mixture was stirred at 80° C. for 2 hours and then concentrated under reduced pressure. The residue was freeze-dried to give 3-[2-[2-[2-[2-[2-[2-[2-[2-[2-[2-[[(Z)-N'-[3-[[2-amino-8-(phenylcarbamoyl)-3H-1-benzazepine-4-carbonyl]-propyl-amino]propyl]-N-(3-cyanophenyl)carbamimidoyl]amino]ethoxy]ethoxy]ethoxy]ethoxy]ethoxy]ethoxy]ethoxy]ethoxy]ethoxy]ethoxy]propanoic acid, BzL-451 (51 mg, 42.9 μmol, 69.3% yield, TFA salt) as light yellow oil. $^1H$ NMR (MeOD, 400 MHz) δ 8.01-7.94 (m, 2H), 7.79-7.75 (m, 1H), 7.72 (d, J=8.0 Hz, 2H), 7.66-7.64 (m, 4H), 7.39 (t, J=7.6 Hz, 2H), 7.19 (t, J=7.6 Hz, 1H), 7.13 (s, 1H), 3.76-3.52 (m, 46H), 3.42-3.40 (m, 4H), 2.53 (t, J=6.4 Hz, 2H), 2.04 (m, 2H), 1.79-1.65 (m, 2H), 0.93 (t, J=7.2 Hz, 3H). LC/MS [M+H] 1075.6 (calculated); LC/MS [M+H] 1075.6 (observed).

Preparation of BzL-45. BzL-451 (0.051 g, 0.047 mmol, 1 eq) and TFP (0.016 g, 0.095 mmol, 2 eq) were dissolved in DMF. Collidine (0.031 ml, 0.24 mmol, 5 eq) was added, followed by EDC-HCl (0.027 g, 0.14 mmol, 3 eq). The reaction was stirred at room temperature and monitored by LCMS, then concentrated and purified by HPLC to give 2,3,5,6-tetrafluorophenyl 40-(2-amino-8-(phenylcarbamoyl)-3H-benzo[b]azepine-4-carbonyl)-35-((3-cyanophenyl)imino)-4,7,10,13,16,19,22,25,28,31-decaoxa-34,36,40-triazatritetracontanoate, BzL-45 (0.043 g, 0.035 mmol, 74%).
LC/MS [M+H] 1223.56 (calculated); LC/MS [M+H] 1223.87 (observed).
Example 66: Synthesis of BzL-46
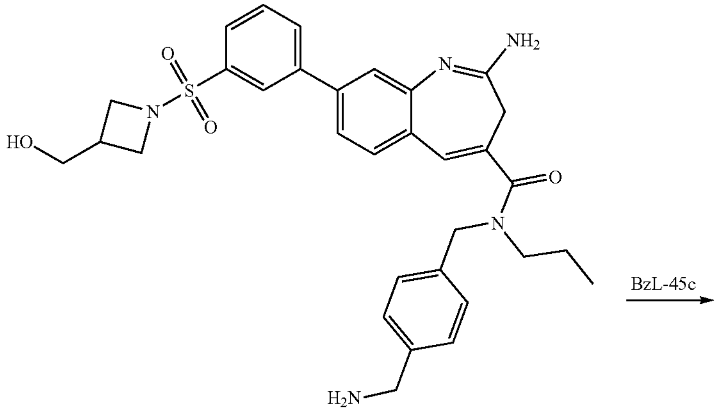
Bz-27
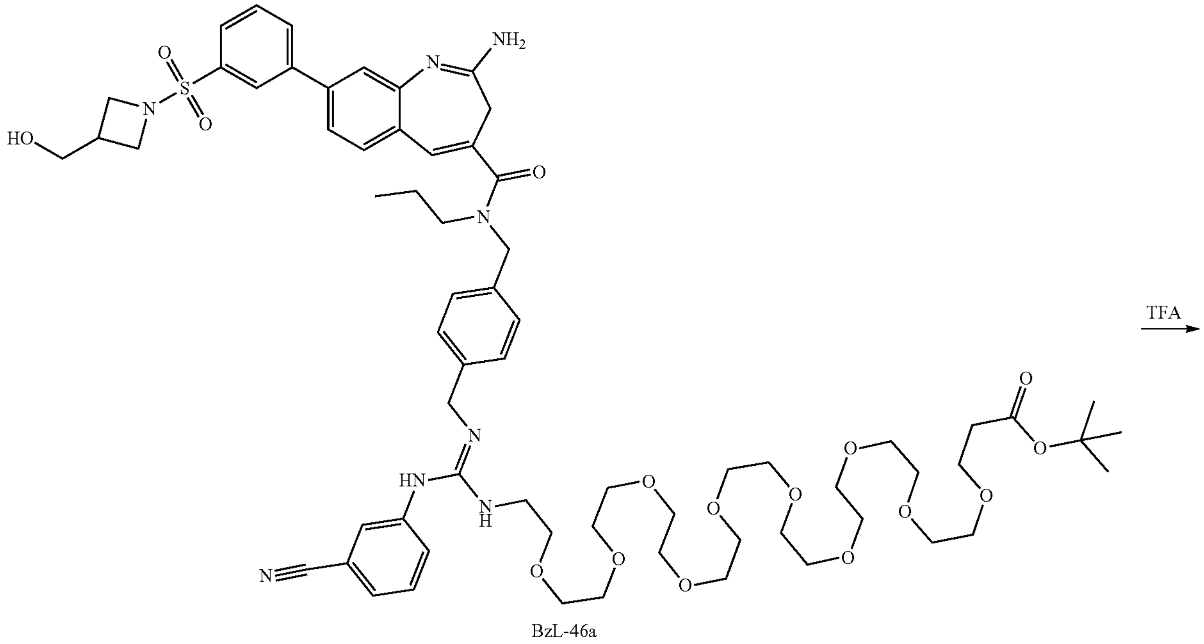
BzL-46a -continued

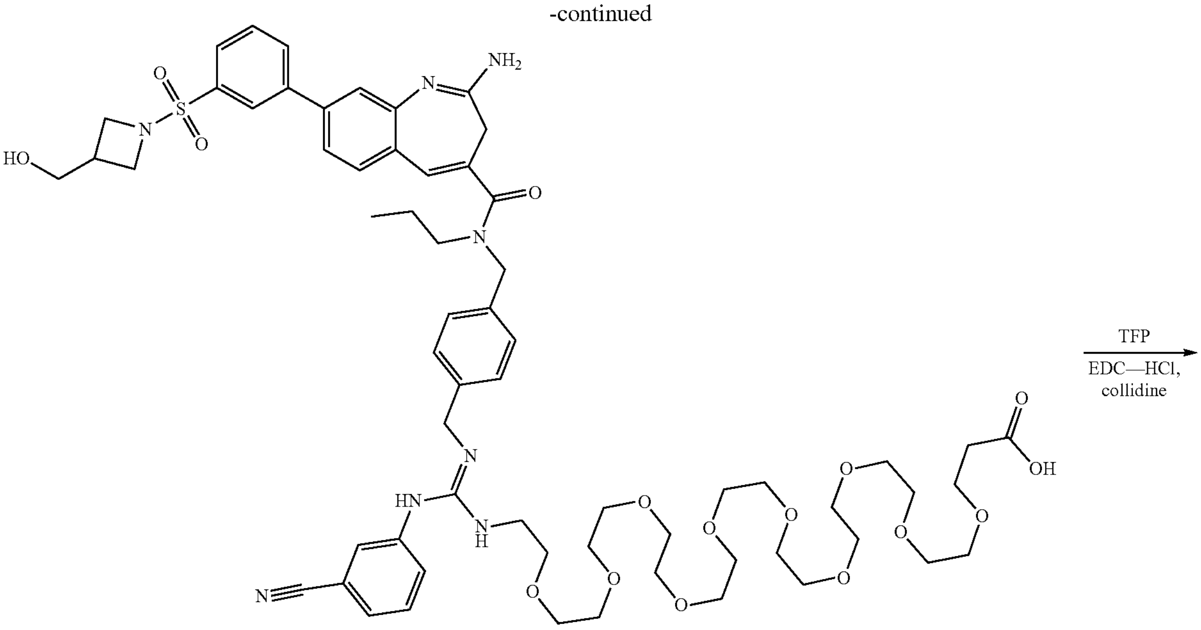

BzL-46b

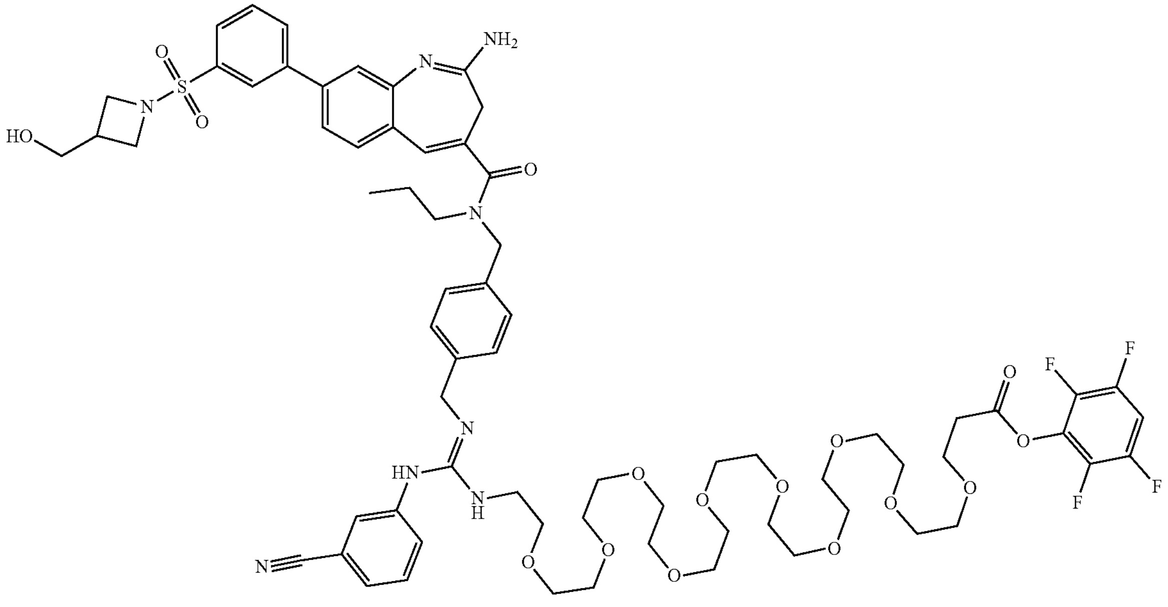

BzL-46

Preparation of BzL-46a. Reaction of Bz-27 and BzL-45c gave tert-butyl (Z)-1-(4-((2-amino-8-(3-((3-(hydroxymethyl)azetidin-1-yl)sulfonyl)phenyl)-N-propyl-3H-benzo[b]azepine-4-carboxamido)methyl)phenyl)-3-((3-cyanophenyl)amino)-7,10,13,16,19,22,25,28,31,34-decaoxa-2,4-diazaheptatriacont-2-en-37-oate, BzL-46a by the procedures described for BzL-42. LC/MS [M+H] 1299.7 (calculated); LC/MS [M+H] 1299.7 (observed).

Preparation of BzL-46b. Reaction of BzL-46a with trifluoroacetic acid, TFA by the procedures described in the synthesis of BzL-42 gave (Z)-1-(4-((2-amino-8-(3-((3-(hydroxymethyl)azetidin-1-yl)sulfonyl)phenyl)-N-propyl-3H-benzo[b]azepine-4-carboxamido)methyl)phenyl)-3-((3-cyanophenyl)amino)-7,10,13,16,19,22,25,28,31,34-decaoxa-2,4-diazaheptatriacont-2-en-37-oic acid, BzL-46b. LC/MS [M+H] 1243.6 (calculated); LC/MS [M+H] 1243.6 (observed).

Preparation of BzL-46. Reaction of BzL-46b with 2,3,5,6-tetrafluorophenol, TFP and EDC-HCl, as described in the procedures for the synthesis of BzL-42 gave 2,3,5,6-tetrafluorophenyl (Z)-1-(4-((2-amino-8-(3-((3-(hydroxymethyl)azetidin-1-yl)sulfonyl)phenyl)-N-propyl-3H-benzo[b]azepine-4-carboxamido)methyl)phenyl)-3-((3-cyanophenyl)amino)-7,10,13,16,19,22,25,28,31,34-decaoxa-2,4-diazaheptatriacont-2-en-37-oate, BzL-46. LC/MS [M+H] 1391.6 (calculated); LC/MS [M+H] 1391.6 (observed).

Example 67: HEK Reporter Assay

HEK293 reporter cells expressing human TLR7 or human TLR8 were purchased from Invivogen and vendor protocols were followed for cellular propagation and experimentation. Briefly, cells were grown to 80-85% confluence at 5% $CO_2$ in DMEM supplemented with 10% FBS, Zeocin, and Blasticidin. Cells were then seeded in 96-well flat plates at $4\times10^4$ cells/well with substrate containing HEK detection medium and immunostimulatory molecules. Activity was measured using a plate reader at 620-655 nm wavelength.

Example 68: Preparation of Macromolecule-Supported Compounds

Bovine Serum Albumin (BSA; ThermoFisher, Product #AM2618) was buffer exchanged into a conjugation buffer containing 100 mM boric acid, 50 mM sodium chloride, 1 mM ethylenediaminetetraacetic acid at pH 8.3, using a G-25 SEPHADEX™ desalting column (Sigma-Aldrich, St. Louis, MO) or a ZEBA™ desalting column (ThermoFisher, Waltham, MA). The eluates were then each adjusted to 6 mg/ml using the buffer and then sterile filtered. The BSA at 6 mg/ml was pre-warned to 30° C. and rapidly mixed with 2-20 (e.g., 7-10) molar equivalents of aminobenzazepine-linker compounds of formula BzL-39, BzL-40, BzL-79, or BzL-21. The reaction was allowed to proceed for about 16 hours at 30° C. and the resulting conjugates were separated from reactants by running over two successive G-25 desalting columns or ZEBA™ desalting columns equilibrated in phosphate buffered saline (PBS) at pH 7.2 to provide the BSA conjugates listed in Table 3. In some instances, the BSA conjugates were further purified by size exclusion chromatography (SEC) using a SUPERDEX™ SEC column (Sigma-Aldrich, St. Louis, MO). Adjuvant-BSA ratio (DAR) was determined by liquid chromatography mass spectrometry analysis using a C4 reverse phase column on an ACQUITY™ UPLC H-class (Waters Corporation, Milford, Massachusetts) connected to a XEVOT™ G2-XS TOF mass spectrometer (Waters Corporation).

TABLE 3

Macromolecule-Supported Compounds

| BSA Conjugate | Expected Molecular Weight for DAR 1 (Each L-Bza Add) | Observed Molecular Weight for DAR 1 (Each L-Bza Add) | DAR |
|---|---|---|---|
| BzL-39 (BSA) | 67,578 (1,148) Da | 67,576 (1,146) Da | 2.53 |
| BzL-40 (BSA) | 67,510 (1080.6) Da | 67,510 (1083) Da | 2.85 |
| BzL-79 (BSA) | 67,505.6 (1075.6) Da | 67.506 (1076) Da | 2.87 |
| BzL-21 (BSA) | 67,594 (1,164) Da | 67,594 (1,164) Da | 1.01 |

The same experimental procedure can be utilized for conjugation of aminobenzazepine-linker compounds to, for example, Keyhole Limpet Hemocyanin carrier protein (KLH; ThermoFisher, Product #77600) or Biotinylated Bovine Serum Albumin (BSA-Biotin; ThermoFisher, Product #29130).

For conjugation, KLH or (biotinylated)BSA may dissolved in a physiological buffer system known in the art that will not adversely impact the stability of the KLH or (biotinylated)BSA. Phosphate buffered saline may be used. The aminobenzazepine-linker intermediate compound is dissolved in a solvent system comprising at least one polar aprotic solvent as described elsewhere herein. In some such aspects, aminobenzazepine-linker intermediate is dissolved to a concentration of about 5 mM, 10 mM, about 20 mM, about 30 mM, about 40 mM or about 50 mM, and ranges thereof such as from about 50 mM to about 50 mM or from about 10 mM to about 30 mM in pH 8 Tris buffer (e.g., 50 mM Tris). In some aspects, the aminobenzazepine-linker intermediate is dissolved in DMSO or acetonitrile, or in DMSO. In the conjugation reaction, an equivalent excess of aminobenzazepine-linker intermediate solution is diluted and combined with chilled KLH or (biotinylated)BSA solution (e.g. from about 1° C. to about 10° C.). The aminobenzazepine-linker intermediate solution may suitably be diluted with at least one polar aprotic solvent and at least one polar protic solvent, examples of which include water, methanol, ethanol, n-propanol, and acetic acid. In some particular aspects, the aminobenzazepine-linker intermediate is dissolved in DMSO and diluted with acetonitrile and water prior to admixture with the KLH or (biotinylated)BSA solution. The molar equivalents of aminobenzazepine-linker intermediate to KLH or (biotinylated)BSA may be about 1.5:1, about 3:1, about 5:1, about 10:1 about 15:1 or about 20:1, and ranges thereof, such as from about 1.5:1 to about 20:1 from about 1.5:1 to about 15:1, from about 1.5:1 to about 10:1, from about 3:1 to about 15:1, from about 3:1 to about 10:1, from about 5:1 to about 15:1 or from about 5:1 to about 10:1. The reaction may suitably be monitored for completion by methods known in the art, such as LC-MS, and the reaction is typically complete in from about 1 hour to about 24 hours. After the reaction is complete, a reagent may be added to the reaction mixture to quench the reaction and/or cap unreacted KLH or (biotinylated)BSA thiol groups. An example of a suitable capping reagent is ethylmaleimide.

Following conjugation, the conjugates may be purified and separated from unconjugated reactants and/or conjugate aggregates by purification methods known in the art such as, for example and not limited to, size exclusion chromatography, hydrophobic interaction chromatography, ion exchange chromatography, chromatofocusing, ultrafiltration, centrifugal ultrafiltration, and combinations thereof. For instance, purification may be preceded by diluting the immunoconjugate, such in 20 mM sodium succinate, pH 5. The diluted solution is applied to a cation exchange column followed by washing with, e.g., at least 10 column volumes of 20 mM sodium succinate, pH 5. The conjugate may be suitably eluted with a buffer such as PBS.

The resulting KLH and (biotinylated)BSA conjugates can be used in any suitable application such as, for example, ELISA assays for pharmacokinetic detection or immunizations for antibody generation.

All references, including publications, patent applications, and patents, cited herein are hereby incorporated by reference to the same extent as if each reference were individually and specifically indicated to be incorporated by reference and were set forth in its entirety herein.

The use of the terms “a” and “an” and “the” and “at least one” and similar referents in the context of describing the invention (especially in the context of the following claims) are to be construed to cover both the singular and the plural, unless otherwise indicated herein or clearly contradicted by context. The use of the term “at least one” followed by a list of one or more items (for example, “at least one of A and B”) is to be construed to mean one item selected from the listed items (A or B) or any combination of two or more of the listed items (A and B), unless otherwise indicated herein or clearly contradicted by context. The terms “comprising,” “having,” “including,” and “containing” are to be construed as open-ended terms (i.e., meaning “including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A macromolecule-supported compound comprising a macromolecular support covalently attached to one or more aminobenzazepine moieties by a linker, and having Formula I:

$$Ms\text{-}[L\text{-}Bza]_p \qquad I$$

or a pharmaceutically acceptable salt thereof, wherein:

"$M_S$" is the macromolecular support, wherein the macromolecular support is a peptide, protein, or antibody construct;

p is an integer from 1 to 50;

Bza is the aminobenzazepine moiety having the formula:

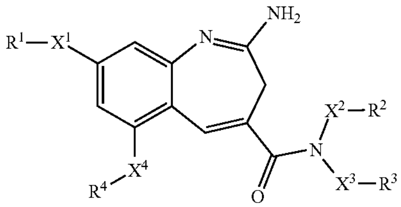

$R^1$ is $C_1$-$C_{20}$ heteroaryl, and $X^1$ is a bond;

$R^2$ is $C_1$-$C_{12}$ alkyl, and $X^2$ is a bond;

$R^3$ is $C_1$-$C_{12}$ alkyl, and $X^3$ is O;

$R^4$ is H, and $X^4$ is a bond;

wherein $R^1$ or $R^3$ is attached to a linker L;

L is the linker selected from the group consisting of:

—C(═O)—(PEG)-;

—C(═O)—(PEG)-C(═O)—;

—C(═O)—(PEG)-O—;

—C(═O)—(PEG)-C(═O)N($R^5$)—($C_1$-$C_{12}$ alkyldiyl)-;

—C(═O)—(PEG)-C(═O)N($R^5$)—($C_1$-$C_{12}$ alkyldiyl)-N($R^5$) C(═O)-($C_2$-$C_5$ monoheterocyclyldiyl)-; and

—C(═O)—(PEG)-N($R^5$)—;

$R^5$ is selected from the group consisting of H, $C_6$-$C_{20}$ aryl, $C_6$-$C_{20}$ aryldiyl, $C_1$-$C_{12}$ alkyl, and $C_1$-$C_{12}$ alkyldiyl, or two $R^5$ groups together form a 5- or 6-membered heterocyclyl ring;

PEG has the formula: $-(CH_2CH_2O)_n-(CH_2)_m-$; m is an integer from 1 to 5, and n is an integer from 5 to 20; and alkyl, alkyldiyl, aryl, aryldiyl, heterocyclyl, heterocyclyldiyl, and heteroaryl are substituted with one or more groups independently selected from H, F, —CN, $-CH_2NH_2$, $-CO_2C(CH_3)_3$, $-OCH_3$, $-OCH_2CH_3$.

2. The macromolecule-supported compound of claim 1, wherein subscript p is an integer from 1 to 25.

3. The macromolecule-supported compound of claim 2, wherein subscript p is an integer from 1 to 6.

4. The macromolecule-supported compound of claim 1 wherein $R^1$ is pyrimidinyl.

5. The macromolecule-supported compound of claim 4 wherein $R^1$ is attached to L, wherein L is —C(═O)—(PEG)-C(═O)N($R^5$)—($C_1$-$C_{12}$ alkyldiyl)-.

6. The macromolecule-supported compound of claim 5 wherein $R^5$ is H and $C_1$-$C_{12}$ alkyldiyl is $-CH_2-$.

7. The macromolecule-supported compound of claim 1 wherein PEG has the formula: $-(CH_2CH_2O)_n-(CH_2)_m-$; where m is 2 and n is 10.

8. The macromolecule-supported compound of claim 1 wherein $X^2$—$R^2$ is $-CH_2CH_2CH_3$, and $X^3$—$R^3$ is $-OCH_2CH_3$.

9. The macromolecule-supported compound of claim 1 wherein the macromolecular support is an antibody construct.

10. A method for treating cancer comprising administering a therapeutically effective amount of a macromolecule-supported compound according to claim 1 or a composition comprising a plurality of the macromolecule-supported compounds to a subject in need thereof.

* * * * *